United States Patent
Achab et al.

(10) Patent No.: US 9,730,940 B2
(45) Date of Patent: Aug. 15, 2017

(54) PURINE INHIBITORS OF HUMAN PHOSPHATIDYLINOSITOL 3-KINASE DELTA

(71) Applicant: Merck Sharp & Dohme Corp., Rahway, NJ (US)

(72) Inventors: Abdelghani Abe Achab, Melrose, MA (US); Michael D. Altman, Needham, MA (US); Yongqi Deng, Newton, MA (US); Timothy Guzi, Sudbury, MA (US); Solomon Kattar, Wakefield, MA (US); Jason D. Katz, Newton, MA (US); Joey L. Methot, Westwood, MA (US); Hua Zhou, Acton, MA (US); Meredeth McGowan, Boston, MA (US); Matthew P. Christopher, Brookline, MA (US); Yudith Garcia, Brookline, MA (US); Neville John Anthony, Northborough, MA (US); Francesc Xavier Fradera Llinas, Brookline, MA (US); Kin Chiu Fong, Shanghai (CN); Xiansheng Leng, Shanghai (CN); Changwei Mu, Beijing (CN); Sixing Zhang, Beijing (CN); Rong Zhang, Beijing (CN)

(73) Assignee: Merck Sharp & Dohme, Rahway, NJ (US)

( * ) Notice: Subject to any disclaimer, the term of this patent is extended or adjusted under 35 U.S.C. 154(b) by 0 days.

(21) Appl. No.: 14/443,294

(22) PCT Filed: Nov. 15, 2013

(86) PCT No.: PCT/CN2013/001394
§ 371 (c)(1),
(2) Date: May 15, 2015

(87) PCT Pub. No.: WO2014/075392
PCT Pub. Date: May 22, 2014

(65) Prior Publication Data
US 2015/0353552 A1    Dec. 10, 2015

Related U.S. Application Data

(60) Provisional application No. 61/727,416, filed on Nov. 16, 2012.

(51) Int. Cl.
| | | |
|---|---|---|
| A61K 31/52 | (2006.01) | |
| C07D 473/00 | (2006.01) | |
| C07D 473/06 | (2006.01) | |
| C07D 473/30 | (2006.01) | |
| C07D 473/38 | (2006.01) | |
| C07D 519/00 | (2006.01) | |
| A61K 31/5377 | (2006.01) | |
| A61K 45/06 | (2006.01) | |

(52) U.S. Cl.
CPC .......... *A61K 31/52* (2013.01); *A61K 31/5377* (2013.01); *A61K 45/06* (2013.01); *C07D 473/00* (2013.01); *C07D 473/06* (2013.01); *C07D 473/30* (2013.01); *C07D 473/38* (2013.01); *C07D 519/00* (2013.01)

(58) Field of Classification Search
CPC .... A61K 31/52; C07D 473/00; C07D 473/06; C07D 473/30; C07D 473/38; C07D 519/00
See application file for complete search history.

(56) References Cited

U.S. PATENT DOCUMENTS 9,458,108 B2 * 10/2016 Claiborne ............ C07D 213/69

FOREIGN PATENT DOCUMENTS

| CN | 102838600 A | 12/2012 |
|---|---|---|
| EP | 421819 A1 | 4/1991 |
| WO | 1996006845 A1 | 3/1996 |
| WO | 0181346 | 11/2001 |
| WO | WO2004074278 A1 | 9/2004 |
| WO | WO2004111032 A1 | 12/2004 |
| WO | 2005105803 A1 | 11/2005 |
| WO | WO2008019124 A1 | 2/2008 |
| WO | WO2010005558 A2 | 1/2010 |

(Continued)

OTHER PUBLICATIONS

Ibrahim et al., 2010, caplus an 2010:740998.*

(Continued)

*Primary Examiner* — Sun Jae Yoo
(74) *Attorney, Agent, or Firm* — Patricia A. Shatynski; John C. Todaro

(57) ABSTRACT

The instant invention provides compounds of formula I which are PI3K-delta inhibitors, and as such are useful for the treatment of PI3K-delta-mediated diseases such as inflammation, asthma, COPD and cancer.

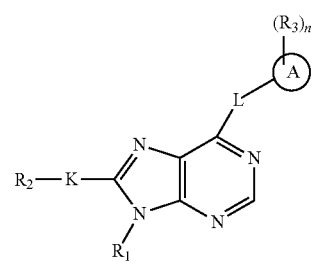

9 Claims, No Drawings

(56) References Cited

FOREIGN PATENT DOCUMENTS

| WO | WO2011075643 A1 | 6/2011 |
| WO | WO2012003264 A1 | 1/2012 |
| WO | WO2012004299 A1 | 1/2012 |
| WO | 2012037204 | 3/2012 |
| WO | WO2012037226 A1 | 3/2012 |

OTHER PUBLICATIONS

Temple et al., 1968, caplus an 1968:105159.*
Temple et al., Journal of Medicinal Chemistry, 1968, 11(1), 41-44.*
Hassan, et al., Some cyclization reactions of 6-mercaptopurone with expected biological activity, Asian Journal of Chemistry, 2010, pp. 689-698., vol. 22, No. 1.
Ibrahim, et al., Novel 8-arylated purines as glycogen synthase kinase, European journal of Medicinal Chemistry, 2010, pp. 3389-3393, vol. 45, No. 8.
Kochergin, Synthesis and some properties of 6-beta-oxoalkyl)aralkyl, heteralkyl, cycloalkyl)thiopurines, Khimiya Geterotsiklicheskikh, 1993, pp. 1548-1553, vol. 11.
Schabel, et al., Experimental evaluation of potential anticancer agents I. Qualtitative therapeutic evaluation of certain purine analogs, Cancer Research, 1961, pp. 690-699, vol. 21.
Smith, et al., Inhibition of purine ribonucleotide and phosphoribosyl pyrophosphate synthesis by 6-cyclopentylthio-9-hydroxynethylpurine and structurally related compounts., Cancer Research, 1941, pp. 463-467, vol. 34, No. 3.
Temple, et al., Lipid-Soluble Derivatives of 6-Mercaptopurine, J. Med. Chem., 1968, pp. 41-44, vol. 11, No. 1.
CAS-109292-91-3.
CAS-1347497-11-3.
CAS-1348555-71-4.
CAS-1349793-28-7.
De Lilt et al., Synthesis & biological evaluation of disubstituted N6-cyclopentyladenine analogues: the search for a neutral antagonist with high affinity for the adenosine Al receptor, Bioorganic & Medicinal Chemistry, 2004, pp. 139-149, vol. 12.
Jorda et al., Anti-leishmanial activity of disubstituted purines and related pyrazolo[4,3-d]pyrimidines, Bioorganic & Medicinal Chemistry Letters, 2011, pp. 4233-4237, vol. 21.
Macmillan et al., Fundamental Relationships between Structure, Reactivity, and Biological Activity for the Duocarmycins and CC-1065, J. Med. Chem., 2009, pp. 5771-5780, vol. 52.
Borrmann et al, "Structure-Activity Relationships of Adenine and Deazaadenine Derivatives as Ligands for Adenine Receptors, a New Purinergic Receptor Family." Journal of Medicinal Chemistry, 2009,52(19), 5974-5989.

* cited by examiner

PURINE INHIBITORS OF HUMAN PHOSPHATIDYLINOSITOL 3-KINASE DELTA

CROSS REFERENCE TO RELATED APPLICATIONS

This application is a U.S. National Phase application under 35 U.S.C. §371 of PCT Application No. PCT/CN2013/001394, filed Nov. 15, 2013 which claims priority under 35 U.S.C. §119(e) from U.S. Provisional Application Ser. No. 61/727,416, filed on Nov. 16, 2012.

BACKGROUND OF THE INVENTION

Compounds are provided that inhibit phosphatidylinositol 3-kinase delta isoform (PI3K-delta) activity, including compounds that selectively inhibit PI3K-delta activity. The invention provides methods of using PI3K-delta inhibitory compounds to inhibit PI3K-delta mediated processes in vitro and in vivo.

Methods of inhibiting PI3K-delta activity, and methods of treating diseases, such as disorders of immunity and inflammation, in which PI3K-delta plays a role in leukocyte function are disclosed. Methods of using PI3K-delta inhibitory compounds to inhibit cancer cell growth or proliferation are also provided. Preferably, the methods employ active agents that selectively inhibit PI3K-delta, while not significantly inhibiting activity of other PI3K isoforms.

SUMMARY OF THE INVENTION

The present invention provides novel compounds which are inhibitors of phosphoinosititde 3-kinases delta (PI3K-delta). The invention also provides a method for the treatment and prevention of PI3K-delta-mediated diseases and disorders using the novel compounds, as well as pharmaceutical compositions containing the compounds.

DETAILED DESCRIPTION OF THE INVENTION

The present invention provides compounds of formula I or pharmaceutically acceptable salts or stereoisomers thereof:

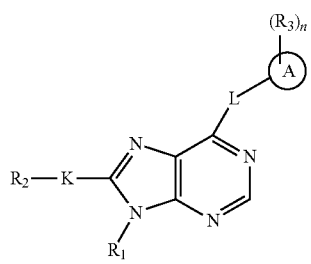

I $R^1$ is selected from hydrogen, $C_{1-5}$alkyl, $C_{3-12}$cycloalkyl, $C_{1-5}$heteroalkyl, and $C_{3-12}$heterocycloalkyl, wherein $R^1$ is optionally substituted by 0, 1, 2, 3, or 4 groups independently selected from hydrogen, fluoro, chloro, methyl, amino, $OR^a$, $O(C=O)R^a$, $O(C=O)OR^a$ and $NH(C=O)R^a$;

$R^a$ is independently selected from hydrogen, $C_{1-10}$alkyl, $C_{1-10}$heteroalkyl, aryl, $C_{3-13}$cycloalkyl, $C_{3-12}$heterocycloalkyl, and heteroaryl;

$R^2$ is selected from hydrogen, halogen, $C_{1-10}$alkyl, $C_{3-12}$cycloalkyl, $C_{3-12}$heterocycloalkyl, $C_{1-10}$ heteroalkyl, $C_{2-10}$alkynyl, aryl, iodo, and heteroaryl, wherein $R^2$ is substituted with 0, 1, 2, 3, or 4 $R^3$ substituents;

n is 0, 1, 2, 3, or 4;

A is $C_{3-12}$ cycloalkyl, $C_{3-12}$heterocycloalkyl, and $C_{6-12}$spirocyclyl;

L is selected from O, S, $SO_2$, and $-CH_2$;

K is selected from a bond, NH, O, C(O), $CH_2$, $N((C_{1-5})$alkyl$)_{1-2}$, $-C(O)N(R^b)-(CH_2)_m$, S, $SO_2$, and $C_{2-10}$ alkynylene;

$R^b$ is H or $C_{1-10}$ alkyl;

m is 0, 1, 2, or 3;

$R^3$ is independently selected from:
halogen,
$C_{1-10}$ alkyl(oxy)$_{0-1}$(carbonyl)$_{0-1}C_{0-10}$ alkyl,
$C_{2-10}$ alkenyl(oxy)$_{0-1}$(carbonyl)$_{0-1}C_{0-10}$ alkyl,
$C_{1-10}$ heteroalkyl(oxy)$_{0-1}$(carbonyl)$_{0-1}C_{0-10}$ alkyl,
aryl $C_{0-10}$ alkyl(oxy)$_{0-1}$(carbonyl)$_{0-1}C_{0-10}$ alkyl,
aryl $C_{2-10}$ alkynyl(oxy)$_{0-1}$(carbonyl)$_{0-1}C_{0-10}$ alkyl,
$C_{3-12}$ cycloalkyl$C_{0-10}$ alkyl(oxy)$_{0-1}$(carbonyl)$_{0-1}C_{0-10}$ alkyl,
heteroaryl $C_{0-10}$ alkyl(oxy)$_{0-1}$(carbonyl)$_{0-1}C_{0-10}$ alkyl,
$(C_{3-12})$heterocycloalkyl $C_{0-10}$ alkyl(oxy)$_{0-1}$(carbonyl)$_{0-1}C_{0-10}$ alkyl,
$C_{1-10}$ alkyl(carbonyl)$_{0-1}$oxy$C_{0-10}$ alkyl,
$C_{1-10}$ heteroalkyl(carbonyl)$_{0-1}$oxy$C_{0-10}$ alkyl,
$C_{1-10}$ heteroalkyl(carbonyl)$_{0-1}$oxy$C_{0-10}$ alkyl,
aryl $C_{0-10}$ alkyl(carbonyl)$_{0-1}$oxy$C_{0-10}$ alkyl,
$(C_{3-12})$cycloalkyl $C_{0-10}$ alkyl(carbonyl)$_{0-1}$oxy$C_{0-10}$ alkyl,
heteroaryl$C_{0-10}$ alkyl(carbonyl)$_{0-1}$oxy$C_{0-10}$ alkyl,
$(C_{3-12})$heterocycloalkyl $C_{0-10}$ alkyl(carbonyl)$_{0-1}$oxy$C_{0-10}$ alkyl,
$((C_{0-10})$alkyl$)_{1-2}$aminocarbonyloxy,
$(C_{0-10})$heteroalkylaminocarbonyloxy,
aryl$(C_{0-10})$alkylaminocarbonyloxy,
$(C_{3-12})$cycloalkyl$(C_{0-10})$alkylaminocarbonyloxy,
heteroaryl$(C_{0-10})$alkylaminocarbonyloxy,
$(C_{3-12})$heterocycloalkyl$(C_{0-10})$alkylaminocarbonyloxy,
$C_{1-10}$ alkylamino(carbonyl)$_{0-1}C_{0-10}$ alkyl,
$(C_{1-10})$heteroalkylamino(carbonyl)$_{0-1}C_{0-10}$ alkyl,
$C_{3-12}$ cycloalkyl $C_{0-10}$ alkylamino(carbonyl)$_{0-1}C_{0-10}$ alkyl,
aryl $C_{0-10}$alkylamino(carbonyl)$_{0-1}C_{0-10}$ alkyl,
heteroaryl$C_{0-10}$alkylamino(carbonyl)$_{0-1}C_{0-10}$ alkyl,
$(C_{3-12})$heterocycloalkyl$C_{0-10}$alkylamino(carbonyl)$_{0-1}C_{0-10}$ alkyl,
$C_{1-10}$ alkyl(oxy)$_{0-1}$(carbonyl)$_{0-1}$amino$C_{0-10}$ alkyl,
$C_{1-10}$ heteroalkyl(oxy)$_{0-1}$(carbonyl)$_{0-1}$amino$C_{0-10}$ alkyl,
$C_{3-12}$ cycloalkyl $C_{0-10}$ alkyl(oxy)$_{0-1}$(carbonyl)$_{0-1}$amino$C_{0-10}$ alkyl,
aryl $C_{0-10}$ alkyl(oxy)$_{0-1}$(carbonyl)$_{0-1}$amino$C_{0-10}$ alkyl,
heteroaryl $C_{0-10}$ alkyl(oxy)$_{0-1}$(carbonyl)$_{0-1}$amino$C_{0-10}$ alkyl,
$(C_{3-12})$heterocycloalkyl $C_{0-10}$ alkyl(oxy)$_{0-1}$-(carbonyl)$_{0-1}$amino$C_{0-10}$ alkyl,
$-CO_2(C_{0-10}$ alkyl),
$-(C_{0-10}$ alkyl)$CO_2H$,
Oxo (=O);
$C_{1-10}$ alkylS(O)$_{1-2}$,
$C_{1-10}$ heteroalkyl S(O)$_{1-2}$,
$(C_{3-12})$cycloalkylS(O)$_{1-2}$,
$(C_{3-12})$cycloheteroalkylS(O)$_{1-2}$,
heteroarylS(O)$_{1-2}$,
arylS(O)$_{1-2}$,
$-SO_2N(C_{0-6}$ alkyl)$_{0-2}$, $C_{0-6}$ alkyl(amino)$_{0-1}$S(O)$_{1-2}$amino,
$C_{1-10}$ heteroalkyl(amino)$_{0-1}$S(O)$_{1-2}$amino,
$(C_{3-12})$cycloalkyl(amino)$_{0-1}$S(O)$_{1-2}$amino,
$(C_{3-12})$cycloheteroalkyl(amino)$_{0-1}$S(O)$_{1-2}$amino,
heteroaryl(amino)$_{0-1}$S(O)$_{1-2}$amino,
aryl(amino)$_{0-1}$S(O)$_{1-2}$amino,
—SO$_2$CF$_3$,
—SO$_2$CF$_2$H,
—Si(C$_{0-6}$ alkyl)$_3$,
amino,
(C$_{0-10}$ alkyl)$_{1-2}$ amino,
C$_{1-4}$acylamino C$_{0-10}$ alkyl,
hydroxy,
(C$_{1-10}$ alkyl)OH,
C$_{0-10}$ alkylalkoxyl,
cyano,
C$_{1-6}$alkylcyano, and
C$_{1-6}$haloalkyl;

wherein $R^3$ is each substituted with 0, 1, 2, 3, or 4 $R^4$ substituents and each $R^4$ is independently selected from:
halogen,
C$_{1-10}$ alkyl(oxy)$_{0-1}$(carbonyl)$_{0-1}$C$_{0-10}$ alkyl,
C$_{1-10}$ heteroalkyl(oxy)$_{0-1}$(carbonyl)$_{0-1}$C$_{0-10}$ alkyl,
aryl C$_{0-10}$ alkyl(oxy)$_{0-1}$(carbonyl)$_{0-1}$C$_{0-10}$ alkyl,
aryl C$_{2-10}$ alkynyl(oxy)$_{0-1}$(carbonyl)$_{0-1}$C$_{0-10}$ alkyl,
$(C_{3-12})$cycloalkyl C$_{0-10}$ alkyl(oxy)$_{0-1}$(carbonyl)$_{0-1}$C$_{0-10}$ alkyl,
heteroaryl C$_{0-10}$ alkyl(oxy)$_{0-1}$(carbonyl)$_{0-1}$C$_{0-10}$ alkyl,
$(C_{3-12})$heterocycloalkyl C$_{0-10}$ alkyl(oxy)$_{0-1}$(carbonyl)$_{0-1}$C$_{0-10}$ alkyl,
C$_{1-10}$ alkyl(carbonyl)$_{0-1}$oxyC$_{0-10}$ alkyl,
C$_{1-10}$ heteroalkyl(carbonyl)$_{0-1}$oxyC$_{0-10}$ alkyl,
aryl C$_{0-10}$ alkyl(carbonyl)$_{0-1}$oxyC$_{0-10}$ alkyl,
$(C_{3-12})$cycloalkyl C$_{0-10}$ alkyl(carbonyl)$_{0-1}$oxyC$_{0-10}$ alkyl,
heteroarylC$_{0-10}$ alkyl(carbonyl)$_{0-1}$oxyC$_{0-10}$ alkyl,
$(C_{3-12})$heterocycloalkyl C$_{0-10}$ alkyl(carbonyl)$_{0-1}$oxyC$_{0-10}$ alkyl,
((C$_{0-10}$)alkyl)$_{1-2}$aminocarbonyloxy,
aryl (C$_{0-10}$)alkylaminocarbonyloxy,
$(C_{3-12})$cycloalkyl(C$_{0-10}$)alkylaminocarbonyloxy,
heteroaryl(C$_{0-10}$)alkylaminocarbonyloxy,
$(C_{3-12})$heterocycloalkyl(C$_{0-10}$)alkylaminocarbonyloxy,
C$_{1-10}$ alkylaminocarbonylC$_{0-10}$ alkyl,
$(C_{3-12})$cycloalkyl C$_{0-10}$ alkylaminocarbonylC$_{0-10}$ alkyl,
aryl C$_{0-10}$ alkylaminocarbonylC$_{0-10}$ alkyl,
heteroaryl C$_{0-10}$ alkylaminocarbonylC$_{0-10}$ alkyl,
$(C_{3-12})$heterocycloalkyl C$_{0-10}$ alkylaminocarbonylC$_{0-10}$ alkyl,
C$_{1-10}$ alkyl(oxy)$_{0-1}$(carbonyl)$_{0-1}$aminoC$_{0-10}$ alkyl,
$(C_{3-12})$cycloalkyl C$_{0-10}$ alkyl(oxy)$_{0-1}$(carbonyl)$_{0-1}$aminoC$_{0-10}$ alkyl,
aryl C$_{0-10}$ alkyl(oxy)$_{0-1}$(carbonyl)$_{0-1}$aminoC$_{0-10}$ alkyl,
heteroaryl C$_{0-10}$ alkyl(oxy)$_{0-1}$(carbonyl)$_{0-1}$aminoC$_{0-10}$ alkyl,
$(C_{3-12})$heterocycloalkyl C$_{0-10}$ alkyl(oxy)$_{0-1}$(carbonyl)$_{0-1}$aminoC$_{0-10}$ alkyl,
—CO$_2$(C$_{0-10}$ alkyl),
—(C$_{0-10}$ alkyl)CO$_2$H,
Oxo (=O),
C$_{1-10}$ alkylS(O)$_{1-2}$,
C$_{1-10}$ heteroalkyl S(O)$_{1-2}$,
$(C_{3-12})$cycloalkylS(O)$_{1-2}$,
$(C_{3-12})$cycloheteroalkylS(O)$_{1-2}$,
heteroarylS(O)$_{1-2}$,
arylS(O)$_{1-2}$,
C$_{0-6}$ alkyl(amino)$_{0-1}$S(O)$_{1-2}$amino,
C$_{1-10}$ heteroalkyl(amino)$_{0-1}$S(O)$_{1-2}$amino,
$(C_{3-12})$cycloalkyl(amino)$_{0-1}$S(O)$_{1-2}$amino,
$(C_{3-12})$cycloheteroalkyl(amino)$_{0-1}$S(O)$_{1-2}$amino,
heteroaryl(amino)$_{0-1}$S(O)$_{1-2}$amino,
aryl(amino)$_{0-1}$S(O)$_{1-2}$amino,
—SO$_2$N(C$_{1-6}$alkyl)$_{1-2}$,
—SO$_2$C$_{1-6}$alkyl,
—SO$_2$CF$_3$,
—SO$_2$CF$_2$H,
amino,
(C$_{0-10}$ alkyl)$_{1-2}$ amino,
-(oxy)$_{0-1}$(carbonyl)$_{0-1}$N(C$_{0-10}$ alkyl)$_{1-2}$,
hydroxy,
(C$_{1-10}$ alkyl)OH,
C$_{1-10}$ alkoxy,
cyano, and
C$_{1-6}$haloalkyl;

$R^4$ is substituted with 0, 1, 2, or 3 $R^5$ substituents and each $R^5$ substituent is independently selected from hydroxy, (C$_{1-6}$)alkyl, (C$_{1-6}$)alkoxy, (C$_{1-10}$ alkyl)OH, halogen, CO$_2$H, —(C$_{0-6}$)alkylCN, —O(C=O)C$_1$-C$_6$ alkyl, —(C=O)OC$_1$-C$_6$ alkyl, NO$_2$, trifluoromethoxy, trifluoroethoxy, trifluoromethyl, trifluoroethyl, —N—C(O)O (C$_{0-6}$)alkyl, C$_{1-10}$ alkylsulfonyl, C$_{1-10}$ heteroalkyl, aryl, $(C_{3-12})$cycloalkyl, heteroaryl, $(C_{3-12})$heterocycloalkyl, C$_{1-10}$ heteroalkylsulfonyl, oxo (O=), $(C_{3-12})$cycloalkylsulfonyl, $(C_{3-12})$cycloheteroalkylsulfonyl, heteroarylsulfonyl, arylsulfonyl, aminosulfonyl, —SO$_2$N(C$_{1-6}$ alkyl)$_{1-2}$, —SO$_2$C$_{1-6}$alkyl, —SO$_2$CF$_3$, —SO$_2$CF$_2$H, —C$_{1-10}$ alkylsulfinyl, —O$_{(0-1)}$(C$_{1-10}$)haloalkyl, amino (C$_{1-6}$alkyl)$_{0-2}$ and NH$_2$; and $R^5$ is substituted with 0, 1, or 2 $R^6$ substituents and each $R^6$ substituent is independently selected from hydroxy, (C$_{1-6}$)alkyl, (C$_{1-6}$)alkoxy, (C$_{1-10}$ alkyl)OH, halogen, CO$_2$H, —(C$_{0-6}$)alkylCN, —O(C=O)C$_1$-C$_6$ alkyl, —(C=O)OC$_1$-C$_6$ alkyl, NO$_2$, trifluoromethoxy, trifluoroethoxy, trifluoromethyl, trifluoroethyl, —N—C(O)O (C$_{0-6}$)alkyl, C$_{1-10}$ alkylsulfonyl, C$_{1-10}$heteroalkylsulfonyl, oxo (O=), $(C_{3-12})$cycloalkylsulfonyl, arylsulfonyl, aminosulfonyl, $(C_{3-12})$cycloheteroalkylsulfonyl, heteroarylsulfonyl, —SO$_2$N(C$_{1-6}$alkyl)$_{1-2}$, —SO$_2$C$_{1-6}$alkyl, —SO$_2$CF$_3$, —SO$_2$CF$_2$H, —O$_{(0-1)}$(C$_{1-10}$)haloalkyl, amino (C$_{1-6}$alkyl)$_{0-2}$ and NH$_2$.

Representative compounds of the instant invention include, but are not limited to, the following compounds and their pharmaceutically acceptable salts and their stereoisomers thereof:

tert-butyl-3-{[8-(1-ethyl-5-methyl-1H-pyrazol-4-yl)-9-methyl-9H-purin-6-yl]oxy}pyrrolidine-1-carboxylate;
8-(1-ethyl-5-methyl-1H-pyrazol-4-yl)-9-methyl-6-[pyrrolidin-3-yloxy]-9H-purine;
tert-butyl-3-{[9-ethyl-8-(2-methylpyrimidin-5-yl)-9H-purin-6-yl]oxy}pyrrolidine-1-carboxylate;
2-methylpropyl-3-{[8-(1-ethyl-5-methyl-1H-pyrazol-4-yl)-9-methyl-9H-purin-6-yl]oxy}pyrrolidine-1-carboxylate;
naphthalen-2-yl-3-{[8-(1-ethyl-5-methyl-1H-pyrazol-4-yl)-9-methyl-9H-purin-6-yl]oxy}pyrrolidine-1-carboxylate;
benzyl-3-{[8-(1-ethyl-5-methyl-1H-pyrazol-4-yl)-9-methyl-9H-purin-6-yl]oxy}pyrrolidine-1-carboxylate;
4-methylphenyl-3-{[8-(1-ethyl-5-methyl-1H-pyrazol-4-yl)-9-methyl-9H-purin-6-yl]oxy}pyrrolidine-1-carboxylate;
phenyl-3-{[8-(1-ethyl-5-methyl-1H-pyrazol-4-yl)-9-methyl-9H-purin-6-yl]oxy}pyrrolidine-1-carboxylate;
2,2-dimethylpropyl-3-{[8-(1-ethyl-5-methyl-1H-pyrazol-4-yl)-9-methyl-9H-purin-6-yl]oxy}pyrrolidine-1-carboxylate;

3-(trifluoromethyl)phenyl-3-{[8-(1-ethyl-5-methyl-1H-pyrazol-4-yl)-9-methyl-9H-purin-6-yl]oxy}pyrrolidine-1-carboxylate;
4-methoxyphenyl-3-{[8-(1-ethyl-5-methyl-1H-pyrazol-4-yl)-9-methyl-9H-purin-6-yl]oxy}pyrrolidine-1-carboxylate;
tert-butyl 4-{[8-(1-ethyl-5-methyl-1H-pyrazol-3-yl)-9-methyl-9H-purin-6-yl]oxy}piperidine-1-carboxylate;
tert-butyl-3-{[8-(6-methoxy-5-methylpyridin-3-yl)-9-methyl-9H-purin-6-yl]oxy}pyrrolidine-1-carboxylate;
tert-butyl-3-{[9-methyl-8-(2-methylpyrimidin-5-yl)-9H-purin-6-yl]oxy}pyrrolidine-1-carboxylate;
tert-butyl-3-({9-methyl-8-[4-(1H-pyrazol-1-yl)phenyl]-9H-purin-6-yl}oxy)pyrrolidine-1-carboxylate;
tert-butyl-3-{[8-(1,3-dimethyl-1H-pyrazol-4-yl)-9-methyl-9H-purin-6-yl]oxy}pyrrolidine-1-carboxylate;
tert-butyl-3-{[8-(1,2-dimethyl-1H-imidazol-5-yl)-9-methyl-9H-purin-6-yl]oxy}pyrrolidine-1-carboxylate;
tert-butyl-3-{[8-(4-hydroxyphenyl)-9-methyl-9H-purin-6-yl]oxy}pyrrolidine-1-carboxylate;
tert-butyl-3-{[9-methyl-8-(1H-pyrazol-4-yl)-9H-purin-6-yl]oxy}pyrrolidine-1-carboxylate;
tert-butyl-3-({8-[6-(dimethylamino)pyridin-3-yl]-9-methyl-9H-purin-6-yl}oxy)pyrrolidine-1-carboxylate;
tert-butyl-3-{[9-methyl-8-(2-methyl-1H-indol-7-yl)-9H-purin-6-yl]oxy}pyrrolidine-1-carboxylate;
tert-butyl-3-[(9-methyl-8-pyrazolo[1,5-a]pyrimidin-3-yl-9H-purin-6-yl)oxy]pyrrolidine-1-carboxylate;
tert-butyl-3-({8-[4-(acetylamino)phenyl]-9-methyl-9H-purin-6-yl}oxy)pyrrolidine-1-carboxylate;
tert-butyl-3-{[9-methyl-8-(6-morpholin-4-ylpyridin-3-yl)-9H-purin-6-yl]oxy}pyrrolidine-1-carboxylate;
tert-butyl-3-({8-[4-(1H-imidazol-1-yl)phenyl]-9-methyl-9H-purin-6-yl}oxy)pyrrolidine-1-carboxylate;
tert-butyl-3-{[9-methyl-8-(3-methyl-1H-pyrazol-4-yl)-9H-purin-6-yl]oxy}pyrrolidine-1-carboxylate;
tert-butyl-3-{[9-methyl-8-(6-pyrrolidin-1-ylpyridin-3-yl)-9H-purin-6-yl]oxy}pyrrolidine-1-carboxylate;
tert-butyl-3-[(8-isoquinolin-4-yl-9-methyl-9H-purin-6-yl)oxy]pyrrolidine-1-carboxylate;
tert-butyl-3-{[8-(1H-indazol-5-yl)-9-methyl-9H-purin-6-yl]oxy}pyrrolidine-1-carboxylate;
tert-butyl 4-((8-(1-ethyl-5-methyl-1H-pyrazol-4-yl)-9-methyl-9H-purin-6-yl)oxy)-2-methylpyrrolidine-1-carboxylate;
tert-butyl 3-((8-(3-methoxycyclobutyl)-9-methyl-9H-purin-6-yl)oxy)pyrrolidine-1-carboxylate;
tert-butyl 3-((9-methyl-9H-purin-6-yl)oxy)pyrrolidine-1-carboxylate;
tert-butyl 3-((9-methyl-8-(3-methyl-1H-pyrazolo[3,4-b]pyridin-5-yl)-9H-purin-6-yl)oxy)pyrrolidine-1-carboxylate;
tert-butyl-3-{[9-ethyl-8-(6-methoxy-5-methylpyridin-3-yl)-9H-purin-6-yl]oxy}pyrrolidine-1-carboxylate;
tert-butyl-3-{[8-(2-tert-butyl-1,3-thiazol-5-yl)-9-ethyl-9H-purin-6-yl]oxy}pyrrolidine-1-carboxylate;
methyl-3-{[8-(1-ethyl-5-methyl-1H-pyrazol-4-yl)-9-methyl-9H-purin-6-yl]oxy}pyrrolidine-1-carboxylate;
ethyl-3-{[8-(1-ethyl-5-methyl-1H-pyrazol-4-yl)-9-methyl-9H-purin-6-yl]oxy}pyrrolidine-1-carboxylate;
1-methylethyl-3-{[8-(1-ethyl-5-methyl-1H-pyrazol-4-yl)-9-methyl-9H-purin-6-yl]oxy}pyrrolidine-1-carboxylate;
tert-butyl-3-{[8-(2-tert-butyl-1,3-thiazol-5-yl)-9-methyl-9H-purin-6-yl]oxy}pyrrolidine-1-carboxylate;
tert-butyl 3-((8-(1-ethyl-5-methyl-1H-pyrazol-4-yl)-9-methyl-9H-purin-6-yl)oxy)azetidine-1-carboxylate;
tert-butyl 3-((8-(1-ethyl-5-methyl-1H-pyrazol-4-yl)-9-methyl-9H-purin-6-yl)oxy)piperidine-1-carboxylate;
8-(1-ethyl-5-methyl-1H-pyrazol-4-yl)-9-methyl-6-{[1-(phenylcarbonyl)pyrrolidin-3-yl]oxy}-9H-purine;
6-{[1-(cyclopentylcarbonyl)pyrrolidin-3-yl]oxy}-8-(1-ethyl-5-methyl-1H-pyrazol-4-yl)-9-methyl-9H-purine;
8-(1-ethyl-5-methyl-1H-pyrazol-4-yl)-9-methyl-6-{[1-(naphthalen-2-ylcarbonyl)pyrrolidin-3-yl]oxy}-9H-purine;
6-{[1-(cyclohexylcarbonyl)pyrrolidin-3-yl]oxy}-8-(1-ethyl-5-methyl-1H-pyrazol-4-yl)-9-methyl-9H-purine;
8-(1-ethyl-5-methyl-1H-pyrazol-4-yl)-6-{[1-(methoxyacetyl)pyrrolidin-3-yl]oxy}-9-methyl-9H-purine;
8-(1-ethyl-5-methyl-1H-pyrazol-4-yl)-9-methyl-6-{[1-(tetrahydro-2H-pyran-4-ylacetyl)pyrrolidin-3-yl]oxy}-9H-purine;
8-(1-ethyl-5-methyl-1H-pyrazol-4-yl)-9-methyl-6-{[1-(1,3-oxazol-5-ylcarbonyl)pyrrolidin-3-yl]oxy}-9H-purine;
(3-((8-(1-ethyl-5-methyl-1H-pyrazol-4-yl)-9-methyl-9H-purin-6-yl)oxy)pyrrolidin-1-yl)(tetrahydro-2H-pyran-4-yl)methanone;
8-(1-ethyl-5-methyl-1H-pyrazol-4-yl)-9-methyl-6-({1-[(4-methyltetrahydro-2H-pyran-4-yl)carbonyl]pyrrolidin-3-yl}oxy)-9H-purine;
8-(1-ethyl-5-methyl-1H-pyrazol-3-yl)-9-methyl-6-{[1-(tetrahydro-2H-pyran-4-ylcarbonyl)piperidin-4-yl]oxy}-9H-purine;
8-(1-ethyl-5-methyl-1H-pyrazol-3-yl)-9-methyl-6-{[1-(phenylcarbonyl)piperidin-4-yl]oxy}-9H-purine;
6-{[1-(cyclopentylcarbonyl)piperidin-4-yl]oxy}-8-(1-ethyl-5-methyl-1H-pyrazol-3-yl)-9-methyl-9H-purine;
8-(1-ethyl-5-methyl-1H-pyrazol-3-yl)-9-methyl-6-[(1-propanoylpiperidin-4-yl)oxy]-9H-purine;
3-[3-{[8-(1-ethyl-5-methyl-1H-pyrazol-4-yl)-9-methyl-9H-purin-6-yl]oxy}pyrrolidin-1-yl]-3-oxopropanenitrile;
6-{[1-(cyclopropylcarbonyl)pyrrolidin-3-yl]oxy}-8-(1-ethyl-5-methyl-1H-pyrazol-4-yl)-9-methyl-9H-purine;
8-(1-ethyl-5-methyl-1H-pyrazol-4-yl)-9-methyl-6-{[1-(tetrahydrofuran-2-ylcarbonyl)pyrrolidin-3-yl]oxy}-9H-purine;
8-(1-ethyl-5-methyl-1H-pyrazol-4-yl)-9-methyl-6-{(1-[(5-methylisoxazol-3-yl)carbonyl]pyrrolidin-3-yl}oxy)-9H-purine;
1-{2-[3-{[8-(1-ethyl-5-methyl-1H-pyrazol-4-yl)-9-methyl-9H-purin-6-yl]oxy}pyrrolidin-1-yl]-2-oxoethyl}pyrrolidin-2-one;
8-(1-ethyl-5-methyl-1H-pyrazol-4-yl)-9-methyl-6-{[1-(naphthalen-1-ylcarbonyl)pyrrolidin-3-yl]oxy}-9H-purine;
8-(1-ethyl-5-methyl-1H-pyrazol-4-yl)-9-methyl-6-{[1-{[4-(4-methylpiperazin-1-yl)phenyl]carbonyl}pyrrolidin-3-yl]oxy}-9H-purine;
8-(1-ethyl-5-methyl-1H-pyrazol-4-yl)-9-methyl-6-{[1-(pyridin-3-ylcarbonyl)pyrrolidin-3-yl]oxy}-9H-purine;
8-(1-ethyl-5-methyl-1H-pyrazol-4-yl)-9-methyl-6-{[1-propanoylpyrrolidin-3-yl]oxy}-9H-purine;
6-({1-[(2,2-dimethyltetrahydro-2H-pyran-4-yl)carbonyl]pyrrolidin-3-yl}oxy)-8-(1-ethyl-5-methyl-1H-pyrazol-4-yl)-9-methyl-9H-purine;
9-ethyl-8-(2-methylpyrimidin-5-yl)-6-{[1-propanoylpyrrolidin-3-yl]oxy}-9H-purine;
9-ethyl-8-(2-methylpyrimidin-5-yl)-6-{[1-(tetrahydro-2H-pyran-4-ylcarbonyl)pyrrolidin-3-yl]oxy}-9H-purine;
8-(1-ethyl-5-methyl-1H-pyrazol-4-yl)-9-methyl-6-({-1-[(2-methyl-1,3-oxazol-4-yl)carbonyl]pyrrolidin-3-yl}oxy)-9H-purine;

6-({1-[(2,5-dimethyl-1,3-oxazol-4-yl)carbonyl]pyrrolidin-3-yl}oxy)-8-(1-ethyl-5-methyl-1H-pyrazol-4-yl)-9-methyl-9H-purine;

8-(1-ethyl-5-methyl-1H-pyrazol-4-yl)-9-methyl-6-{[1-(1,2,5-oxadiazol-3-ylcarbonyl)pyrrolidin-3-yl]oxy}-9H-purine;

8-(1-ethyl-5-methyl-1H-pyrazol-4-yl)-9-methyl-6-{[1-{[3-(1-methylethyl)-1H-pyrazol-5-yl]carbonyl}pyrrolidin-3-yl]oxy}-9H-purine;

8-(1-ethyl-5-methyl-1H-pyrazol-4-yl)-9-methyl-6-{[1-{[1-(1-methylethyl)-1H-pyrazol-4-yl]carbonyl}pyrrolidin-3-yl]oxy}-9H-purine;

8-(1-ethyl-5-methyl-1H-pyrazol-4-yl)-6-{[1-(isoxazol-5-ylcarbonyl)pyrrolidin-3-yl]oxy}-9-methyl-9H-purine;

8-(1-ethyl-5-methyl-1H-pyrazol-4-yl)-9-methyl-6-{[1-(1H-pyrazol-5-ylcarbonyl)pyrrolidin-3-yl]oxy}-9H-purine;

8-(1-ethyl-5-methyl-1H-pyrazol-4-yl)-9-methyl-6-{[1-(pyrazolo[1,5-a]pyridin-3-ylcarbonyl)pyrrolidin-3-yl]oxy}-9H-purine;

8-(1-ethyl-5-methyl-1H-pyrazol-4-yl)-9-methyl-6-({1-[(4-methyl-1,2,5-oxadiazol-3-yl)carbonyl]pyrrolidin-3-yl}oxy)-9H-purine;

8-(1-ethyl-5-methyl-1H-pyrazol-4-yl)-9-methyl-6-({1-[(1-methyl-1H-pyrazol-5-yl)carbonyl]pyrrolidin-3-yl}oxy)-9H-purine;

8-(1-ethyl-5-methyl-1H-pyrazol-4-yl)-9-methyl-6-({1-[(1-methyl-1H-pyrazol-3-yl)carbonyl]pyrrolidin-3-yl}oxy)-9H-purine;

6-({1-[(1,3-dimethyl-1H-pyrazol-5-yl)carbonyl]pyrrolidin-3-yl}oxy)-8-(1-ethyl-5-methyl-1H-pyrazol-4-yl)-9-methyl-9H-purine;

8-(1-ethyl-5-methyl-1H-pyrazol-4-yl)-9-methyl-6-({1-[(1-methyl-1H-imidazol-2-yl)carbonyl]pyrrolidin-3-yl}oxy)-9H-purine;

8-(1-ethyl-5-methyl-1H-pyrazol-4-yl)-9-methyl-6-{[1-(1H-1,2,3-triazol-4-ylcarbonyl)pyrrolidin-3-yl]oxy}-9H-purine;

8-(1-ethyl-5-methyl-1H-pyrazol-4-yl)-9-methyl-6-{[1-(pyrazolo[1,5-a]pyrimidin-3-ylcarbonyl)pyrrolidin-3-yl]oxy}-9H-purine;

8-(1-ethyl-5-methyl-1H-pyrazol-4-yl)-9-methyl-6-{[1-(5,6,7,8-tetrahydro[1,2,4]triazolo[4,3-a]pyridin-3-ylcarbonyl)pyrrolidin-3-yl]oxy}-9H-purine;

8-(1-ethyl-5-methyl-1H-pyrazol-4-yl)-9-methyl-6-{[1-{[3-(trifluoromethyl)-1H-pyrazol-4-yl]carbonyl}pyrrolidin-3-yl]oxy}-9H-purine;

8-(1-ethyl-5-methyl-1H-pyrazol-4-yl)-9-methyl-6-({1-[(1-methyl-1H-1,2,3-triazol-4-yl)carbonyl]pyrrolidin-3-yl}oxy)-9H-purine;

8-(1-ethyl-5-methyl-1H-pyrazol-4-yl)-6-{[1-(imidazo[1,2-a]pyrimidin-2-ylcarbonyl)pyrrolidin-3-yl]oxy}-9-methyl-9H-purine;

8-(1-ethyl-5-methyl-1H-pyrazol-4-yl)-9-methyl-6-({1-[(5-methyl-1,2,3-thiadiazol-4-yl)carbonyl]pyrrolidin-3-yl}oxy)-9H-purine;

6-({1-[(7-chloro[1,2,4]triazolo[1,5-a]pyridin-2-yl)carbonyl]pyrrolidin-3-yl}oxy)-8-(1-ethyl-5-methyl-1H-pyrazol-4-yl)-9-methyl-9H-purine;

8-(1-ethyl-5-methyl-1H-pyrazol-4-yl)-9-methyl-6-({1-[(4-methyl-1H-pyrazol-5-yl)carbonyl]pyrrolidin-3-yl}oxy)-9H-purine;

5-{[3-{[8-(1-ethyl-5-methyl-1H-pyrazol-4-yl)-9-methyl-9H-purin-6-yl]oxy}pyrrolidin-1-yl]carbonyl}-N,N-dimethyl-1,3,4-oxadiazol-2-amine;

2-(3-{[3-{[8-(1-ethyl-5-methyl-1H-pyrazol-4-yl)-9-methyl-9H-purin-6-yl]oxy}pyrrolidin-1-yl]carbonyl}-1,2,4-oxadiazol-5-yl)propan-2-ol;

8-(1-ethyl-5-methyl-1H-pyrazol-4-yl)-9-methyl-6-({1-[(3-methylisoxazol-4-yl)carbonyl]pyrrolidin-3-yl}oxy)-9H-purine;

8-(1-ethyl-5-methyl-1H-pyrazol-4-yl)-9-methyl-6-{[1-{[1-(1-methylethyl)-1H-pyrazol-5-yl]carbonyl}pyrrolidin-3-yl]oxy}-9H-purine;

8-(1-ethyl-5-methyl-1H-pyrazol-4-yl)-9-methyl-6-({1-[(6-methylpyridin-3-yl)carbonyl]pyrrolidin-3-yl}oxy)-9H-purine;

8-(1-ethyl-5-methyl-1H-pyrazol-4-yl)-6-{[1-(4H-furo[3,2-b]pyrrol-5-ylcarbonyl)pyrrolidin-3-yl]oxy}-9-methyl-9H-purine;

8-(1-ethyl-5-methyl-1H-pyrazol-4-yl)-9-methyl-6-{[1-{[1-methyl-3-(trifluoromethyl)-1H-pyrazol-4-yl]carbonyl}pyrrolidin-3-yl]oxy}-9H-purine;

8-(1-ethyl-5-methyl-1H-pyrazol-4-yl)-9-methyl-6-({1-[(2-methylpyridin-4-yl)carbonyl]pyrrolidin-3-yl}oxy)-9H-purine;

8-(1-ethyl-5-methyl-1H-pyrazol-4-yl)-9-methyl-6-({1-[(5-methyl-1,3-oxazol-4-yl)carbonyl]pyrrolidin-3-yl}oxy)-9H-purine;

6-({{(1-[(2,4-dimethyl-1,3-oxazol-5-yl)carbonyl]pyrrolidin-3-yl}oxy)-8-(1-ethyl-5-methyl-1H-pyrazol-4-yl)-9-methyl-9H-purine;

6-({{(1-[(1,5-dimethyl-1H-pyrazol-3-yl)carbonyl]pyrrolidin-3-yl}oxy)-8-(1-ethyl-5-methyl-1H-pyrazol-4-yl)-9-methyl-9H-purine;

6-({1-[(5-cyclopropylisoxazol-4-yl)carbonyl]pyrrolidin-3-yl}oxy)-8-(1-ethyl-5-methyl-1H-pyrazol-4-yl)-9-methyl-9H-purine;

8-(1-ethyl-5-methyl-1H-pyrazol-4-yl)-9-methyl-6-{[1-{[1-methyl-3-(trifluoromethyl)-1H-pyrazol-5-yl]carbonyl}pyrrolidin-3-yl]oxy}-9H-purine;

4-{[3-{[8-(1-ethyl-5-methyl-1H-pyrazol-4-yl)-9-methyl-9H-purin-6-yl]oxy}pyrrolidin-1-yl]carbonyl}-1-methylpyrrolidin-2-one;

8-(1-ethyl-5-methyl-1H-pyrazol-4-yl)-6-({1-[(1-ethyl-5-methyl-1H-pyrazol-4-yl)carbonyl]pyrrolidin-3-yl}oxy)-9-methyl-9H-purine;

8-(1-ethyl-5-methyl-1H-pyrazol-4-yl)-9-methyl-6-{[1-(pyridin-4-ylcarbonyl)pyrrolidin-3-yl]oxy}-9H-purine;

8-(1-ethyl-5-methyl-1H-pyrazol-4-yl)-9-methyl-6-({1-[(5-methylisoxazol-4-yl)carbonyl]pyrrolidin-3-yl}oxy)-9H-purine;

8-(1-ethyl-5-methyl-1H-pyrazol-4-yl)-9-methyl-6-{[1-(pyridin-2-ylcarbonyl)pyrrolidin-3-yl]oxy}-9H-purine;

8-(1-ethyl-5-methyl-1H-pyrazol-4-yl)-9-methyl-6-({1-[(1-methyl-1H-pyrrol-2-yl)carbonyl]pyrrolidin-3-yl}oxy)-9H-purine;

6-({1-[(5-ethylisoxazol-4-yl)carbonyl]pyrrolidin-3-yl}oxy)-8-(1-ethyl-5-methyl-1H-pyrazol-4-yl)-9-methyl-9H-purine;

8-(1-ethyl-5-methyl-1H-pyrazol-4-yl)-9-methyl-6-({1-[(4-methylisoxazol-5-yl)carbonyl]pyrrolidin-3-yl}oxy)-9H-purine;

8-(1-ethyl-5-methyl-1H-pyrazol-4-yl)-6-{[1-(1H-imidazo[1,2-b]pyrazol-7-ylcarbonyl)pyrrolidin-3-yl]oxy}-9-methyl-9H-purine;

8-(1-ethyl-5-methyl-1H-pyrazol-4-yl)-9-methyl-6-({1-[(4-methyl-1,3-oxazol-5-yl)carbonyl]pyrrolidin-3-yl}oxy)-9H-purine;

8-(1-ethyl-5-methyl-1H-pyrazol-4-yl)-9-methyl-6-{[1-(1H-pyrazol-4-ylcarbonyl)pyrrolidin-3-yl]oxy}-9H-purine;

8-(1-ethyl-5-methyl-1H-pyrazol-4-yl)-9-methyl-6-({1-[(1-methyl-1H-imidazol-5-yl)carbonyl]pyrrolidin-3-yl}oxy)-9H-purine;

6-({1-[(3,5-dimethylisoxazol-4-yl)carbonyl]pyrrolidin-3-yl}oxy)-8-(1-ethyl-5-methyl-1H-pyrazol-4-yl)-9-methyl-9H-purine;

8-(1-ethyl-5-methyl-1H-pyrazol-4-yl)-9-methyl-6-({1-[(5-methyl-1H-pyrazol-3-yl)carbonyl]pyrrolidin-3-yl}oxy)-9H-purine;

6-({(1-[(3-tert-butyl-1-methyl-1H-pyrazol-5-yl)carbonyl]pyrrolidin-3-yl}oxy)-8-(1-ethyl-5-methyl-1H-pyrazol-4-yl)-9-methyl-9H-purine;

4-{[3-{[8-(1-ethyl-5-methyl-1H-pyrazol-4-yl)-9-methyl-9H-purin-6-yl]oxy}pyrrolidin-1-yl]carbonyl}-1-(1-methylethyl)pyrrolidin-2-one;

8-(1-ethyl-5-methyl-1H-pyrazol-4-yl)-9-methyl-6-({1-[(1,3,5-trimethyl-1H-pyrazol-4-yl)carbonyl]pyrrolidin-3-yl}oxy)-9H-purine;

8-(1-ethyl-5-methyl-1H-pyrazol-4-yl)-9-methyl-6-({1-[(1,2,5-trimethyl-1H-pyrrol-3-yl)carbonyl]pyrrolidin-3-yl}oxy)-9H-purine;

8-(1-ethyl-5-methyl-1H-pyrazol-4-yl)-9-methyl-6-({1-[(1-methyl-1H-pyrazol-4-yl)carbonyl]pyrrolidin-3-yl}oxy)-9H-purine;

8-(1-ethyl-5-methyl-1H-pyrazol-4-yl)-9-methyl-6-({1-[(5-methyl-1,3,4-oxadiazol-2-yl)carbonyl]pyrrolidin-3-yl}oxy)-9H-purine;

2-(5-{[3-{[8-(1-ethyl-5-methyl-1H-pyrazol-4-yl)-9-methyl-9H-purin-6-yl]oxy}pyrrolidin-1-yl]carbonyl}-1,2,4-oxadiazol-3-yl)propan-2-ol;

8-(1-ethyl-5-methyl-1H-pyrazol-4-yl)-9-methyl-6-{[1-(1H-pyrrolo[3,2-b]pyridin-2-ylcarbonyl)pyrrolidin-3-yl]oxy}-9H-purine;

6-{[1-(6,7-dihydro-5H-pyrrolo[1,2-d]tetrazol-5-ylcarbonyl)pyrrolidin-3-yl]oxy}-8-(1-ethyl-5-methyl-1H-pyrazol-4-yl)-9-methyl-9H-purine;

6-{[1-(5,6-dihydro-4H-pyrrolo[1,2-b]pyrazol-2-ylcarbonyl)pyrrolidin-3-yl]oxy}-8-(1-ethyl-5-methyl-1H-pyrazol-4-yl)-9-methyl-9H-purine;

6-({1-[(2-ethyl-4-methyl-1,3-oxazol-5-yl)carbonyl]pyrrolidin-3-yl}oxy)-8-(1-ethyl-5-methyl-1H-pyrazol-4-yl)-9-methyl-9H-purine;

8-(1-ethyl-5-methyl-1H-pyrazol-4-yl)-9-methyl-6-{[1-{[5-(1-methylethyl)isoxazol-4-yl]carbonyl}pyrrolidin-3-yl]oxy}-9H-purine;

8-(1-ethyl-5-methyl-1H-pyrazol-4-yl)-9-methyl-6-{[1-(1,3-oxazol-4-ylcarbonyl)pyrrolidin-3-yl]oxy}-9H-purine;

1-(3-((9-ethyl-8-(6-methoxy-5-methylpyridin-3-yl)-9H-purin-6-yl)oxy)pyrrolidin-1-yl)propan-1-one;

1-(3-((8-(1-ethyl-5-methyl-1H-pyrazol-4-yl)-9-methyl-9H-purin-6-yl)oxy)pyrrolidin-1-yl)ethanone;

1-(3-((8-(1-ethyl-5-methyl-1H-pyrazol-4-yl)-9-methyl-9H-purin-6-yl)oxy)pyrrolidin-1-yl)-2-methylpropan-1-one;

1-(3-((8-(1-ethyl-5-methyl-1H-pyrazol-4-yl)-9-methyl-9H-purin-6-yl)oxy)pyrrolidin-1-yl)-2,2-dimethylpropan-1-one;

1-(3-((9-ethyl-8-(1-ethyl-5-methyl-1H-pyrazol-4-yl)-9H-purin-6-yl)oxy)pyrrolidin-1-yl)propan-1-one;

1-(3-((8-(6-methoxy-5-methylpyridin-3-yl)-9-methyl-9H-purin-6-yl)oxy)pyrrolidin-1-yl)propan-1-one;

1-(3-((8-(2-(tert-butyl)thiazol-5-yl)-9-ethyl-9H-purin-6-yl)oxy)pyrrolidin-1-yl)propan-1-one;

1-(3-((8-(2-(tert-butyl)thiazol-5-yl)-9-methyl-9H-purin-6-yl)oxy)pyrrolidin-1-yl)propan-1-one;

1-(3-((9-cyclopropyl-8-(1-ethyl-5-methyl-1H-pyrazol-4-yl)-9H-purin-6-yl)oxy)pyrrolidin-1-yl)propan-1-one;

1-(3-((8-(1H-indazol-6-yl)-9-methyl-9H-purin-6-yl)oxy)pyrrolidin-1-yl)propan-1-one;

1-(3-((9-methyl-8-(6-(trifluoromethyl)pyridin-3-yl)-9H-purin-6-yl)oxy)pyrrolidin-1-yl)propan-1-one;

1-(3-((9-methyl-8-(1H-pyrrolo[2,3-b]pyridin-5-yl)-9H-purin-6-yl)oxy)pyrrolidin-1-yl)propan-1-one;

1-(3-((8-(1H-indol-6-yl)-9-methyl-9H-purin-6-yl)oxy)pyrrolidin-1-yl)propan-1-one;

1-(3-((8-(1H-indazol-5-yl)-9-methyl-9H-purin-6-yl)oxy)pyrrolidin-1-yl)propan-1-one;

1-(3-((8-(6-methoxy-5-(trifluoromethyl)pyridin-3-yl)-9-methyl-9H-purin-6-yl)oxy)pyrrolidin-1-yl)propan-1-one;

1-(3-((8-(1H-indol-5-yl)-9-methyl-9H-purin-6-yl)oxy)pyrrolidin-1-yl)propan-1-one;

1-(3-((9-methyl-8-(6-methylpyridin-3-yl)-9H-purin-6-yl)oxy)pyrrolidin-1-yl)propan-1-one;

8-(1-ethyl-5-methyl-1H-pyrazol-4-yl)-6-{[1-(ethylsulfonyl)pyrrolidin-3-yl]oxy}-9-methyl-9H-purine;

8-(1-ethyl-5-methyl-1H-pyrazol-4-yl)-9-methyl-6-({1-[(1-methylethyl)sulfonyl]pyrrolidin-3-yl}oxy)-9H-purine;

8-(1-ethyl-5-methyl-1H-pyrazol-4-yl)-9-methyl-6-({1-[(trifluoromethyl)sulfonyl]pyrrolidin-3-yl}oxy)-9H-purine;

8-(1-ethyl-5-methyl-1H-pyrazol-4-yl)-9-methyl-6-{[1-(phenylsulfonyl)pyrrolidin-3-yl]oxy}-9H-purine;

8-(1-ethyl-5-methyl-1H-pyrazol-4-yl)-9-methyl-6-({1-[(1-methyl-1H-imidazol-4-yl)sulfonyl]pyrrolidin-3-yl}oxy)-9H-purine;

8-(1-ethyl-5-methyl-1H-pyrazol-4-yl)-9-methyl-6-{[1-(naphthalen-2-ylsulfonyl)pyrrolidin-3-yl]oxy}-9H-purine;

6-{[1-(biphenyl-4-ylsulfonyl)pyrrolidin-3-yl]oxy}-8-(1-ethyl-5-methyl-1H-pyrazol-4-yl)-9-methyl-9H-purine;

N-cyclohexyl-3-{[8-(1-ethyl-5-methyl-1H-pyrazol-4-yl)-9-methyl-9H-purin-6-yl]oxy}pyrrolidine-1-carboxamide;

3-{[8-(1-ethyl-5-methyl-1H-pyrazol-4-yl)-9-methyl-9H-purin-6-yl]oxy}-N-(3-methylphenyl)pyrrolidine-1-carboxamide;

3-{[8-(1-ethyl-5-methyl-1H-pyrazol-4-yl)-9-methyl-9H-purin-6-yl]oxy}-N-(1-methylethyl)pyrrolidine-1-carboxamide;

3-{[8-(1-ethyl-5-methyl-1H-pyrazol-4-yl)-9-methyl-9H-purin-6-yl]oxy}-N-(1,1,3,3-tetramethylbutyl)pyrrolidine-1-carboxamide;

3-{[8-(1-ethyl-5-methyl-1H-pyrazol-4-yl)-9-methyl-9H-purin-6-yl]oxy}-N-[(1R)-1-phenylethyl]pyrrolidine-1-carboxamide;

ethyl N-{[3-{[8-(1-ethyl-5-methyl-1H-pyrazol-4-yl)-9-methyl-9H-purin-6-yl]oxy}pyrrolidin-1-yl]carbonyl}alaninate;

N-ethyl-3-((8-(1-ethyl-5-methyl-1H-pyrazol-4-yl)-9-methyl-9H-purin-6-yl)oxy)pyrrolidine-1-carboxamide;

8-(1-ethyl-5-methyl-1H-pyrazol-4-yl)-9-methyl-6-{[1-(1-phenylethyl)pyrrolidin-3-yl]oxy}-9H-purine;

6-{[1-(cyclohexylmethyl)pyrrolidin-3-yl]oxy}-8-(1-ethyl-5-methyl-1H-pyrazol-4-yl)-9-methyl-9H-purine;

4-{[3-{[8-(1-ethyl-5-methyl-1H-pyrazol-4-yl)-9-methyl-9H-purin-6-yl]oxy}pyrrolidin-1-yl]methyl}-N,N-dimethylaniline;

8-(1-ethyl-5-methyl-1H-pyrazol-4-yl)-9-methyl-6-{[1-(1H-pyrrol-2-ylmethyl)pyrrolidin-3-yl]oxy}-9H-purine;

8-(1-ethyl-5-methyl-1H-pyrazol-4-yl)-9-methyl-6-{[1-pyrimidin-2-ylpyrrolidin-3-yl]oxy}-9H-purine;

8-(1-ethyl-5-methyl-1H-pyrazol-4-yl)-9-methyl-6-{[1-(6-methylthieno[2,3-d]pyrimidin-4-yl)pyrrolidin-3-yl]oxy}-9H-purine;

8-(1-ethyl-5-methyl-1H-pyrazol-4-yl)-9-methyl-6-{[1-thieno[3,2-c]pyridin-4-ylpyrrolidin-3-yl]oxy}-9H-purine;

8-(1-ethyl-5-methyl-1H-pyrazol-4-yl)-9-methyl-6-{[1-thieno[3,2-d]pyrimidin-4-ylpyrrolidin-3-yl]oxy}-9H-purine;

8-(1-ethyl-5-methyl-1H-pyrazol-4-yl)-9-methyl-6-({1-[4-(trifluoromethyl)pyridin-2-yl]pyrrolidin-3-yl}oxy)-9H-purine;

8-[3-{[8-(1-ethyl-5-methyl-1H-pyrazol-4-yl)-9-methyl-9H-purin-6-yl]oxy}pyrrolidin-1-yl][1,2,4]triazolo[4,3-a]pyrazine;

8-(1-ethyl-5-methyl-1H-pyrazol-4-yl)-9-methyl-6-{[1-pyridin-2-ylpyrrolidin-3-yl]oxy}-9H-purine;

1-[3-{[8-(1-ethyl-5-methyl-1H-pyrazol-4-yl)-9-methyl-9H-purin-6-yl]oxy}pyrrolidin-1-yl]phthalazine;

8-(1-ethyl-5-methyl-1H-pyrazol-4-yl)-9-methyl-6-({1-[6-(4-methyl-1H-pyrazol-1-yl)pyrimidin-4-yl]pyrrolidin-3-yl}oxy)-9H-purine;

8-(1-ethyl-5-methyl-1H-pyrazol-4-yl)-6-{[1-(4-furan-2-ylpyrimidin-2-yl)pyrrolidin-3-yl]oxy}-9-methyl-9H-purine;

8-(1-ethyl-5-methyl-1H-pyrazol-4-yl)-9-methyl-6-{[1-(6-methylpyrazin-2-yl)pyrrolidin-3-yl]oxy}-9H-purine;

6-{[1-(5,6-dimethylthieno[2,3-d]pyrimidin-4-yl)pyrrolidin-3-yl]oxy}-8-(1-ethyl-5-methyl-1H-pyrazol-4-yl)-9-methyl-9H-purine;

8-(1-ethyl-5-methyl-1H-pyrazol-4-yl)-9-methyl-6-{[1-thieno[2,3-d]pyrimidin-4-ylpyrrolidin-3-yl]oxy}-9H-purine;

4-[3-{[8-(1-ethyl-5-methyl-1H-pyrazol-4-yl)-9-methyl-9H-purin-6-yl]oxy}pyrrolidin-1-yl]-1-methyl-1H-pyrazolo[3,4-d]pyrimidine;

8-(1-ethyl-5-methyl-1H-pyrazol-4-yl)-9-methyl-6-({1-[6-(1H-pyrazol-1-yl)pyrimidin-4-yl]pyrrolidin-3-yl}oxy)-9H-purine;

(3-((8-(1-ethyl-5-methyl-1H-pyrazol-4-yl)-9-methyl-9H-purin-6-yl)oxy)cyclopentyl)(morpholino)methanone;

tert-butyl [3-{[8-(1-ethyl-5-methyl-1H-pyrazol-4-yl)-9-methyl-9H-purin-6-yl]oxy}cyclopentyl]carbamate;

tert-butyl [3-{[8-(1-ethyl-5-methyl-1H-pyrazol-4-yl)-9-methyl-9H-purin-6-yl]oxy}cyclopentyl]carbamate;

N-[3-{[8-(1-ethyl-5-methyl-1H-pyrazol-4-yl)-9-methyl-9H-purin-6-yl]oxy}cyclopentyl]tetrahydro-2H-pyran-4-carboxamide;

1-[3-{[8-(1-ethyl-5-methyl-1H-pyrazol-4-yl)-9-methyl-9H-purin-6-yl]oxy}cyclopentyl]-1,3-dihydro-2H-imidazo[4,5-b]pyridin-2-one;

tert-butyl 3-((8-(1-ethyl-5-methyl-1H-pyrazol-4-yl)-9-methyl-9H-purin-6-yl)thio)pyrrolidine-1-carboxylate;

tert-butyl 3-((8-(1-ethyl-5-methyl-1H-pyrazol-4-yl)-9-methyl-9H-purin-6-yl)sulfonyl)pyrrolidine-1-carboxylate;

(3-((8-(1-ethyl-5-methyl-1H-pyrazol-4-yl)-9-methyl-9H-purin-6-yl)thio)pyrrolidin-1-yl)(tetrahydro-2H-pyran-4-yl)methanone;

1-(3-((8-(1-ethyl-5-methyl-1H-pyrazol-4-yl)-9-methyl-9H-purin-6-yl)thio)pyrrolidin-1-yl)propan-1-one;

(3-((8-(1-ethyl-5-methyl-1H-pyrazol-4-yl)-9-methyl-9H-purin-6-yl)sulfonyl)pyrrolidin-1-yl)(tetrahydro-2H-pyran-4-yl)methanone;

1-(3-((8-(1-ethyl-5-methyl-1H-pyrazol-4-yl)-9-methyl-9H-purin-6-yl)sulfonyl)pyrrolidin-1-yl)propan-1-one;

cyclopropyl(3-((8-(1-ethyl-5-methyl-1H-pyrazol-4-yl)-9-methyl-9H-purin-6-yl)thio)pyrrolidin-1-yl)methanone;

ethyl 3-((8-(1-ethyl-5-methyl-1H-pyrazol-4-yl)-9-methyl-9H-purin-6-yl)thio)pyrrolidine-1-carboxylate;

isobutyl 3-((8-(1-ethyl-5-methyl-1H-pyrazol-4-yl)-9-methyl-9H-purin-6-yl)thio)pyrrolidine-1-carboxylate;

(3-((8-(1-ethyl-5-methyl-1H-pyrazol-4-yl)-9-methyl-9H-purin-6-yl)thio)pyrrolidin-1-yl)(1-methyl-1H-pyrazol-3-yl)methanone;

(3-((8-(1-ethyl-5-methyl-1H-pyrazol-4-yl)-9-methyl-9H-purin-6-yl)thio)pyrrolidin-1-yl)(2-methyloxazol-4-yl)methanone;

8-(1-ethyl-5-methyl-1H-pyrazol-4-yl)-9-methyl-6-((1-(pyrimidin-4-yl)pyrrolidin-3-yl)thio)-9H-purine;

4-(3-((8-(1-ethyl-5-methyl-1H-pyrazol-4-yl)-9-methyl-9H-purin-6-yl)thio)pyrrolidin-1-yl)thieno[2,3-d]pyrimidine;

tert-butyl 3-((8-(1-ethyl-5-methyl-1H-pyrazol-4-yl)-9-methyl-9H-purin-6-yl)methyl)pyrrolidine-1-carboxylate;

(3-((8-(1-ethyl-5-methyl-1H-pyrazol-4-yl)-9-methyl-9H-purin-6-yl)methyl)pyrrolidin-1-yl)(tetrahydro-2H-pyran-4-yl)methanone;

1-(3-((8-(1-ethyl-5-methyl-1H-pyrazol-4-yl)-9-methyl-9H-purin-6-yl)methyl)pyrrolidin-1-yl)propan-1-one;

Ethyl 3-{[9-ethyl-8-(2-methylpyrimidin-5-yl)-9H-purin-6-yl]oxy}pyrrolidine-1-carboxylate;

Tert-butyl 3-{[9-ethyl-8-(2-methylpyrimidin-5-yl)-9H-purin-6-yl]oxy}-4-fluoropyrrolidine-1-carboxylate;

Benzyl 3-ethyl-4-{[9-ethyl-8-(2-methylpyrimidin-5-yl)-9H-purin-6-yl]oxy}pyrrolidine-1-carboxylate;

Tert-butyl 3-{[9-ethyl-8-(2-methylpyrimidin-5-yl)-9H-purin-6-yl]oxy}-4-hydroxypyrrolidine-1-carboxylate;

Tert-butyl 4-{[9-ethyl-8-(2-methylpyrimidin-5-yl)-9H-purin-6-yl]oxy}-3,3-difluoropyrrolidine-1-carboxylate;

Tert-butyl-3-{[9-ethyl-8-(2-methylpyrimidin-5-yl)-9H-purin-6-yl]oxy}-2-methylpyrrolidine-1-carboxylate;

2-(dimethylamino)ethyl-3-{[9-ethyl-8-(2-methylpyrimidin-5-yl)-9H-purin-6-yl]oxy}pyrrolidine-1-carboxylate;

2-(dimethylamino)propyl-3-{[9-ethyl-8-(2-methylpyrimidin-5-yl)-9H-purin-6-yl]oxy}pyrrolidine-1-carboxylate;

Tert-butyl-3-({8-[6-(difluoromethoxy)pyridin-3-yl]-9-ethyl-9H-purin-6-yl}oxy)pyrrolidine-1-carboxylate;

6-{[-1-(cyclopropylcarbonyl)-2-methylpyrrolidin-3-yl]oxy}-9-ethyl-8-(2-methylpyrimidin-5-yl)-9H-purine;

6-{[-1-(cyclopropylcarbonyl)-4,4-difluoropyrrolidin-3-yl]oxy}-9-ethyl-8-(2-methylpyrimidin-5-yl)-9H-purine;

1-(cyclopropylcarbonyl)-4-{[9-ethyl-8-(2-methylpyrimidin-5-yl)-9H-purin-6-yl]oxy}pyrrolidin-3-ol;

2-{[(3S)-3-{[9-ethyl-8-(2-methylpyrimidin-5-yl)-9H-purin-6-yl]oxy}pyrrolidin-1-yl]carbonyl}cyclopentanamine;

6-{[1-(azetidin-3-ylcarbonyl)pyrrolidin-3-yl]oxy}-9-ethyl-8-(2-methylpyrimidin-5-yl)-9H-purine;

2-{[3-{[9-ethyl-8-(2-methylpyrimidin-5-yl)-9H-purin-6-yl]oxy}pyrrolidin-1-yl]carbonyl}cyclopentanamine;

6-({1-[-1-azabicyclo[2.2.1]hept-3-ylcarbonyl]pyrrolidin-3-yl}oxy)-9-ethyl-8-(2-methylpyrimidin-5-yl)-9H-purine;

6-{[1-(cyclobutylcarbonyl)pyrrolidin-3-yl]oxy}-8-(1-ethyl-5-methyl-1H-pyrazol-4-yl)-9-methyl-9H-purine;

6-({{1-[(3,3-difluorocyclobutyl)carbonyl]pyrrolidin-3-yl}oxy)-8-(1-ethyl-5-methyl-1H-pyrazol-4-yl)-9-methyl-9H-purine;

6-{[1-(cyclopropylcarbonyl)pyrrolidin-3-yl]oxy}-9-ethyl-8-(2-methylpyrimidin-5-yl)-9H-purine;

9-ethyl-6-({1-[(2-methylcyclopropyl)carbonyl]pyrrolidin-3-yl}oxy)-8-(2-methylpyrimidin-5-yl)-9H-purine;

9-ethyl-6-({1-[(1-methyl-1H-pyrazol-3-yl)carbonyl]pyrrolidin-3-yl}oxy)-8-(2-methylpyrimidin-5-yl)-9H-purine;

6-({1-[bicyclo[2.2.1]hept-2-ylcarbonyl]pyrrolidin-3-yl}oxy)-9-ethyl-8-(2-methylpyrimidin-5-yl)-9H-purine;

1-[3-{[9-ethyl-8-(2-methylpyrimidin-5-yl)-9H-purin-6-yl]oxy}pyrrolidin-1-yl]-3-methyl-1-oxobutan-2-amine;

1-{[3-{[9-ethyl-8-(2-methylpyrimidin-5-yl)-9H-purin-6-yl]oxy}pyrrolidin-1-yl]carbonyl}cyclobutanamine;

9-ethyl-8-(2-methylpyrimidin-5-yl)-6-{[1-(tetrahydrofuran-3-ylcarbonyl)pyrrolidin-3-yl]oxy}-9H-purine;

4-[3-{[9-ethyl-8-(2-methylpyrimidin-5-yl)-9H-purin-6-yl]oxy}pyrrolidin-1-yl]-2-methyl-4-oxobutan-2-amine;

6-{[1-(cyclopropylcarbonyl)-4-methoxypyrrolidin-3-yl]oxy}-9-ethyl-8-(2-methylpyrimidin-5-yl)-9H-purine;
9-ethyl-6-{[1-(3-methylbut-2-enoyl)pyrrolidin-3-yl]oxy}-8-(2-methylpyrimidin-5-yl)-9H-purine;
9-ethyl-6-({1-[(-methylcyclobutyl)carbonyl]pyrrolidin-3-yl}oxy)-8-(2-methylpyrimidin-5-yl)-9H-purine;
6-({1-[(2,3-dimethylcyclopropyl)carbonyl]pyrrolidin-3-yl}oxy)-9-ethyl-8-(2-methylpyrimidin-5-yl)-9H-purine;
9-ethyl-8-(2-methylpyrimidin-5-yl)-6-{[spiro[2.4]hept-1-ylcarbonyl)pyrrolidin-3-yl]oxy}-9H-purine;
6-{[1-{[2-(difluoromethyl)cyclopropyl]carbonyl}pyrrolidin-3-yl]oxy}-9-ethyl-8-(2-methylpyrimidin-5-yl)-9H-purine;
6-({1-[(2,2-dimethylcyclopropyl)carbonyl]pyrrolidin-3-yl}oxy)-9-ethyl-8-(2-methylpyrimidin-5-yl)-9H-purine;
9-ethyl-6-({1-[(3-methylcyclobutyl)carbonyl]pyrrolidin-3-yl}oxy)-8-(2-methylpyrimidin-5-yl)-9H-purine;
{[(3S)-3-{[9-ethyl-8-(2-methylpyrimidin-5-yl)-9H-purin-6-yl]oxy}pyrrolidin-1-yl]carbonyl}cyclopropyl)methanol;
9-ethyl-6-{[1-{[2-(fluoromethyl)cyclopropyl]carbonyl}pyrrolidin-3-yl]oxy}-8-(2-methylpyrimidin-5-yl)-9H-purine;
9-ethyl-6-({(3S)-1-[(2-fluorocyclopropyl)carbonyl]pyrrolidin-3-yl}oxy)-8-(2-methylpyrimidin-5-yl)-9H-purine;
9-ethyl-8-(2-methylpyrimidin-5-yl)-6-{[1-(1,3-oxazol-4-ylcarbonyl)pyrrolidin-3-yl]oxy}-9H-purine;
6-{[1-(cyclopropylcarbonyl)-4-fluoropyrrolidin-3-yl]oxy}-9-ethyl-8-(2-methylpyrimidin-5-yl)-9H-purin;
cyclopropyl(2-((9-ethyl-8-(2-methylpyrimidin-5-yl)-9H-purin-6-yl)oxy)-7-azabicyclo[2.2.1]heptan-7-yl)methanone;
6-{[1-(cyclopropylcarbonyl)-3-methylpyrrolidin-3-yl]oxy}-9-ethyl-8-(2-methylpyrimidin-5-yl)-9H-purin;
6-{[1-(cyclopropylcarbonyl)pyrrolidin-3-yl]oxy}-9-ethyl-8-[4-(trifluoromethoxy)phenyl]-9H-purine;
6-{[1-(cyclopropylcarbonyl)pyrrolidin-3-yl]oxy}-9-ethyl-8-(6-methoxypyridin-3-yl)-9H-purine;
6-{[1-(cyclopropylcarbonyl)pyrrolidin-3-yl]oxy}-9-ethyl-8-(2-methoxypyridin-4-yl)-9H-purine;
6-{[1-(cyclopropylcarbonyl)pyrrolidin-3-yl]oxy}-9-ethyl-8-[6-(trifluoromethyl)pyridin-3-yl]-9H-purine;
6-{[1-(cyclopropylcarbonyl)pyrrolidin-3-yl]oxy}-9-ethyl-8-[4-(trifluoromethyl)phenyl]-9H-purine;
6-{[1-(cyclopropylcarbonyl)pyrrolidin-3-yl]oxy}-8-[6-(difluoromethoxy)pyridin-3-yl]-9-ethyl-9H-purine;
3-fluoro-5-(9-methyl-6-{[1-propanoylpyrrolidin-3-yl]oxy}-9H-purin-8-yl)phenol;
9-methyl-8-(3-methyl-1H-pyrazolo[3,4-b]pyridin-5-yl)-6-{[1-propanoylpyrrolidin-3-yl]oxy}-9H-purine;
9-methyl-8-(1-phenyl-1H-pyrazol-4-yl)-6-{[1-propanoylpyrrolidin-3-yl]oxy}-9H-purine;
9-methyl-8-(5-methyl-1-phenyl-1H-pyrazol-4-yl)-6-{[1-propanoylpyrrolidin-3-yl]oxy}-9H-purine;
8-(1-ethyl-5-methyl-1H-pyrazol-4-yl)-6-{[1-propanoylpyrrolidin-3-yl]oxy}-9H-purine;
N-[3-fluoro-5-(9-methyl-6-{[(3S)-1-propanoylpyrrolidin-3-yl]oxy}-9H-purin-8-yl)phenyl]methanesulfonamide;
5-(9-methyl-6-{[1-propanoylpyrrolidin-3-yl]oxy}-9H-purin-8-yl)pyridin-3-amine;
8-(1-tert-butyl-1H-pyrazol-4-yl)-9-methyl-6-{[1-propanoylpyrrolidin-3-yl]oxy}-9H-purine;
8-(6-chloropyridin-3-yl)-9-methyl-6-{[1-propanoylpyrrolidin-3-yl]oxy}-9H-purine;
8-(1-ethyl-5-methyl-1H-pyrazol-4-yl)-6-{[1-propanoylpyrrolidin-3-yl]oxy}-9-propyl-9H-purine;
8-(2-methylpyrimidin-5-yl)-6-{[1-propanoylpyrrolidin-3-yl]oxy}-9-propyl-9H-purine;
9-methyl-8-(2-methylpyrimidin-5-yl)-6-{[1-propanoylpyrrolidin-3-yl]oxy}-9H-purine;
9-(2,2-difluoroethyl)-8-(1-ethyl-5-methyl-1H-pyrazol-4-yl)-6-{[1-propanoylpyrrolidin-3-yl]oxy}-9H-purine;
8-(5,6-dihydro-4H-pyrrolo[1,2-b]pyrazol-3-yl)-9-methyl-6-{[1-propanoylpyrrolidin-3-yl]oxy}-9H-purine;
6-{[1-(cyclopropylcarbonyl)pyrrolidin-3-yl]oxy}-9-ethyl-8-(5-methyl-1-phenyl-1H-pyrazol-4-yl)-9H-purine;
6-{[1-(cyclopropylcarbonyl)pyrrolidin-3-yl]oxy}-9-ethyl-8-(3-fluoro-4-methoxyphenyl)-9H-purine;
6-{[1-(cyclopropylcarbonyl)pyrrolidin-3-yl]oxy}-9-ethyl-8-(1H-pyrrolo[2,3-b]pyridin-5-yl)-9H-purine;
6-{[1-(cyclopropylcarbonyl)pyrrolidin-3-yl]oxy}-9-ethyl-8-[6-methoxy-5-(trifluoromethyl)pyridin-3-yl]-9H-purine;
6-{[1-(cyclopropylcarbonyl)pyrrolidin-3-yl]oxy}-9-ethyl-8-(2-methoxypyrimidin-5-yl)-9H-purine;
8-(5-chloro-6-methoxypyridin-3-yl)-6-{[1-(cyclopropylcarbonyl)pyrrolidin-3-yl]oxy}-9-ethyl-9H-purine;
6-{[1-(cyclopropylcarbonyl)pyrrolidin-3-yl]oxy}-8-(2,4-dimethylpyrimidin-5-yl)-9-ethyl-9H-purine;
6-{[1-(cyclopropylcarbonyl)pyrrolidin-3-yl]oxy}-9-ethyl-8-(5-fluoro-6-methoxypyridin-3-yl)-9H-purine;
8-iodo-9-methyl-6-{[1-propanoylpyrrolidin-3-yl]oxy}-9H-purine;
8-(3-fluoro-4-methoxyphenyl)-9-methyl-6-{[1-propanoylpyrrolidin-3-yl]oxy}-9H-purine;
8-(6-methoxypyridin-3-yl)-9-methyl-6-{[1-propanoylpyrrolidin-3-yl]oxy}-9H-purine;
8-(5-fluoro-6-methoxypyridin-3-yl)-9-methyl-6-{[1-propanoylpyrrolidin-3-yl]oxy}-9H-purine;
8-[4-methoxy-3-(trifluoromethyl)phenyl]-9-methyl-6-{[1-propanoylpyrrolidin-3-yl]oxy}-9H-purine;
8-(4-methoxy-3-methylphenyl)-9-methyl-6-{[1-propanoylpyrrolidin-3-yl]oxy}-9H-purine;
2-methoxy-5-(9-methyl-6-{[1-propanoylpyrrolidin-3-yl]oxy}-9H-purin-8-yl)pyridine-3-carbonitrile;
N-[2-methoxy-5-(9-methyl-6-{[1-propanoylpyrrolidin-3-yl]oxy}-9H-purin-8-yl)pyridin-3-yl]methanesulfonamide;
9-methyl-8-[4-(methylsulfonyl)phenyl]-6-{[1-propanoylpyrrolidin-3-yl]oxy}-9H-purine;
9-methyl-6-{[1-propanoylpyrrolidin-3-yl]oxy}-8-(4,5,6,7-tetrahydropyrazolo[1,5-a]pyridin-3-yl)-9H-purine;
N-[5-(6-{[1-(cyclopropylcarbonyl)pyrrolidin-3-yl]oxy}-9-ethyl-9H-purin-8-yl)-2-methoxypyridin-3-yl]methanesulfonamide;
5-(6-{[1-(cyclopropylcarbonyl)pyrrolidin-3-yl]oxy}-9-ethyl-9H-purin-8-yl)-2-methoxypyridine-3-carbonitrile;
6-{[1-(cyclopropylcarbonyl)pyrrolidin-3-yl]oxy}-9-ethyl-8-[2-(trifluoromethyl)pyrimidin-5-yl]-9H-purine;
5-(6-{[1-(cyclopropylcarbonyl)pyrrolidin-3-yl]oxy}-9-ethyl-9H-purin-8-yl)-3-(trifluoromethyl)pyridin-2-amine;
5-(6-{[1-(cyclopropylcarbonyl)pyrrolidin-3-yl]oxy}-9-ethyl-9H-purin-8-yl)-N,N-dimethylpyrimidin-2-amine;
6-{[1-(cyclopropylcarbonyl)-4-ethylpyrrolidin-3-yl]oxy}-9-ethyl-8-(2-methylpyrimidin-5-yl)-9H-purine;
6-{[1-(cyclopropylcarbonyl)pyrrolidin-3-yl]oxy}-9-ethyl-8-(5-methoxypyridin-2-yl)-9H-purine;
6-{[1-(cyclopropylcarbonyl)pyrrolidin-3-yl]oxy}-9-ethyl-8-(6-methoxy-5-methylpyridin-3-yl)-9H-purine;
9-ethyl-8-(6-methoxypyridin-3-yl)-6-{[1-(2-methylpropanoyl)pyrrolidin-3-yl]oxy}-9H-purine;
6-({1-[(3,3-difluorocyclobutyl)carbonyl]pyrrolidin-3-yl}oxy)-9-ethyl-8-(6-methoxypyridin-3-yl)-9H-purine;
9-ethyl-8-(6-methoxypyridin-3-yl)-6-{[1-(tetrahydro-2H-pyran-4-ylcarbonyl)pyrrolidin-3-yl]oxy}-9H-purine;

6-{[1-(cyclopropylcarbonyl)pyrrolidin-3-yl]oxy}-9-ethyl-8-(5-fluoro-6-methoxypyridin-3-yl)-9H-purine;
9-ethyl-8-(5-fluoro-6-methoxypyridin-3-yl)-6-{[1-(2-methylpropanoyl)pyrrolidin-3-yl]oxy}-9H-purine;
6-({1-[(3,3-difluorocyclobutyl)carbonyl]pyrrolidin-3-yl}oxy)-9-ethyl-8-(5-fluoro-6-methoxypyridin-3-yl)-9H-purine;
9-ethyl-8-(5-fluoro-6-methoxypyridin-3-yl)-6-{[1-(tetrahydro-2H-pyran-4-ylcarbonyl)pyrrolidin-3-yl]oxy}-9H-purine;
9-ethyl-8-(5-fluoro-6-methoxypyridin-3-yl)-6-({1-[(1-methyl-1H-pyrazol-3-yl)carbonyl]pyrrolidin-3-yl}oxy)-9H-purine;
9-ethyl-8-(5-fluoro-6-methoxypyridin-3-yl)-6-({1-[(1-methyl-1H-imidazol-5-yl)carbonyl]pyrrolidin-3-yl}oxy)-9H-purine;
6-{[1-(cyclopropylcarbonyl)pyrrolidin-3-yl]oxy}-9-ethyl-8-(4,5,6,7-tetrahydropyrazolo[1,5-a]pyridin-3-yl)-9H-purine;
9-ethyl-6-{[1-(2-methylpropanoyl)pyrrolidin-3-yl]oxy}-8-(4,5,6,7-tetrahydropyrazolo[1,5-a]pyridin-3-yl)-9H-purine;
(3-((9-ethyl-8-(1-ethyl-5-methyl-1H-pyrazol-4-yl)-9H-purin-6-yl)oxy)pyrrolidin-1-yl)(tetrahydro-2H-pyran-4-yl)methanone;
6-{[1-(cyclopropylcarbonyl)-4,4-dimethylpyrrolidin-3-yl]oxy}-9-ethyl-8-(2-methylpyrimidin-5-yl)-9H-purine;
6-{[5-(cyclopropylcarbonyl)-5-azaspiro[2.4]hept-7-yl]oxy}-9-ethyl-8-(2-methylpyrimidin-5-yl)-9H-purine;
6-{[1-(cyclopropylcarbonyl)-4-methylpyrrolidin-3-yl]oxy}-9-ethyl-8-(2-methylpyrimidin-5-yl)-9H-purine;
Cyclopropyl([3-(difluoromethyl)-4-((9-ethyl-8-(2-methylpyrimidin-5-yl)-9H-purin-6-yl)oxy)pyrrolidin-1-yl)methanone;
Cyclopropyl(3-((9-ethyl-8-(2-methylpyrimidin-5-yl)-9H-purin-6-yl)oxy)-4-(fluoromethyl)pyrrolidin-1-yl)methanone;
9-ethyl-6-((1-(ethylsulfonyl)pyrrolidin-3-yl)oxy)-8-(2-methylpyrimidin-5-yl)-9H-purine;
N-ethyl-3-{[9-ethyl-8-(2-methylpyrimidin-5-yl)-9H-purin-6-yl]oxy}pyrrolidine-1-carboxamide;
N-ethyl-3-{[9-ethyl-8-(2-methylpyrimidin-5-yl)-9H-purin-6-yl]oxy}-N-methylpyrrolidine-1-carboxamide;
N-cyclopropyl-3-{[9-ethyl-8-(2-methylpyrimidin-5-yl)-9H-purin-6-yl]oxy}-N-methylpyrrolidine-1-carboxamide;
6-{[1-(azetidin-1-ylcarbonyl)pyrrolidin-3-yl]oxy}-9-ethyl-8-(2-methylpyrimidin-5-yl)-9H-purine;
4-{[9-ethyl-8-(2-methylpyrimidin-5-yl)-9H-purin-6-yl]oxy}-N-methyl-N-phenylpiperidine-1-carboxamide;
9-ethyl-6-({1-[(3-methoxyazetidin-1-yl)carbonyl]pyrrolidin-3-yl}oxy)-8-(2-methylpyrimidin-5-yl)-9H-purine;
6-({1-[(3,3-difluoroazetidin-1-yl)carbonyl]pyrrolidin-3-yl}oxy)-9-ethyl-8-(2-methylpyrimidin-5-yl)-9H-purine;
9-ethyl-6-({(3S)-1-[(methylazetidin-1-yl)carbonyl]pyrrolidin-3-yl}oxy)-8-(2-methylpyrimidin-5-yl)-9H-purine;
3-{[9-ethyl-8-(2-methylpyrimidin-5-yl)-9H-purin-6-yl]oxy}-N-methyl-N-phenylpyrrolidine-1-carboxamide;
(1-{[3-{[9-ethyl-8-(2-methylpyrimidin-5-yl)-9H-purin-6-yl]oxy}pyrrolidin-1-yl]carbonyl}pyrrolidin-3-yl)methanol;
6-({1-[(3,3-dimethylpyrrolidin-1-yl)carbonyl]pyrrolidin-3-yl}oxy)-9-ethyl-8-(2-methylpyrimidin-5-yl)-9H-purine;
1-{[3-{[9-ethyl-8-(2-methylpyrimidin-5-yl)-9H-purin-6-yl]oxy}pyrrolidin-1-yl]carbonyl}-3-methylpyrrolidin-3-ol;
9-ethyl-6-({1-[(3-methoxy-3-methylazetidin-1-yl)carbonyl]pyrrolidin-3-yl}oxy)-8-(2-methylpyrimidin-5-yl)-9H-purine;
6-{[1-(3-azabicyclo[3.1.0]hex-3-ylcarbonyl)pyrrolidin-3-yl]oxy}-9-ethyl-8-(2-methylpyrimidin-5-yl)-9H-purine;
9-ethyl-8-(2-methylpyrimidin-5-yl)-6-{[1-(piperidin-1-ylcarbonyl)pyrrolidin-3-yl]oxy}-9H-purine;
6-({1-[(7-azabicyclo[2.2.1]hept-7-ylcarbonyl]pyrrolidin-3-yl}oxy)-9-ethyl-8-(2-methylpyrimidin-5-yl)-9H-purine;
1-{[3-{[9-ethyl-8-(2-methylpyrimidin-5-yl)-9H-purin-6-yl]oxy}pyrrolidin-1-yl]carbonyl}azetidin-3-ol;
6-({1-[(3,3-difluoropyrrolidin-1-yl)carbonyl]pyrrolidin-3-yl}oxy)-9-ethyl-8-(2-methylpyrimidin-5-yl)-9H-purine;
9-ethyl-6-({1-[(3-fluoroazetidin-1-yl)carbonyl]pyrrolidin-3-yl}oxy)-8-(2-methylpyrimidin-5-yl)-9H-purine;
(3-((9-ethyl-8-(6-(trifluoromethyl)pyridin-3-yl)-9H-purin-6-yl)oxy)pyrrolidin-1-yl)(3-methoxyazetidin-1-yl)methanone;
8-(1-ethyl-5-methyl-1H-pyrazol-4-yl)-9-methyl-6-((1-propylpyrrolidin-3-yl)oxy)-9H-purine;
6-((1-benzyl-4,4-dimethylpyrrolidin-3-yl)oxy)-9-ethyl-8-(2-methylpyrimidin-5-yl)-9H-purine;
9-ethyl-6-{[1-(2-methylphenyl)pyrrolidin-3-yl]oxy}-8-(2-methylpyrimidin-5-yl)-9H-purine;
9-ethyl-8-(2-methylpyrimidin-5-yl)-6-{[1-pyridin-2-ylpyrrolidin-3-yl]oxy}-9H-purine;
9-ethyl-6-{[1-(4-methylpyridin-2-yl)pyrrolidin-3-yl]oxy}-8-(2-methylpyrimidin-5-yl)-9H-purine;
9-ethyl-8-(2-methylpyrimidin-5-yl)-6-{[1-phenylpyrrolidin-3-yl]oxy}-9H-purine;
9-ethyl-6-{[1-(4-fluorophenyl)pyrrolidin-3-yl]oxy}-8-(2-methylpyrimidin-5-yl)-9H-purine;
9-ethyl-6-{[1-(3-fluorophenyl)pyrrolidin-3-yl]oxy}-8-(2-methylpyrimidin-5-yl)-9H-purine;
9-ethyl-8-(2-methylpyrimidin-5-yl)-6-{[1-(1,3-thiazol-2-yl)pyrrolidin-3-yl]oxy}-9H-purine;
9-ethyl-8-(2-methylpyrimidin-5-yl)-6-{[1-pyrimidin-5-ylpyrrolidin-3-yl]oxy}-9H-purine;
9-ethyl-8-(2-methylpyrimidin-5-yl)-6-{[1-pyridin-3-ylpyrrolidin-3-yl]oxy}-9H-purine;
6-{[1-(1,2-benzisoxazol-6-yl)pyrrolidin-3-yl]oxy}-9-ethyl-8-(2-methylpyrimidin-5-yl)-9H-purine;
9-ethyl-8-(2-methylpyrimidin-5-yl)-6-{[1-pyrazin-2-ylpyrrolidin-3-yl]oxy}-9H-purine;
9-ethyl-8-(2-methylpyrimidin-5-yl)-6-{[1-pyridin-2-ylpiperidin-3-yl]oxy}-9H-purine;
tert-butyl (3-{[9-ethyl-8-(2-methylpyrimidin-5-yl)-9H-purin-6-yl]oxy}cyclobutyl)carbamate;
N-(4-{[9-ethyl-8-(2-methylpyrimidin-5-yl)-9H-purin-6-yl]oxy}cyclohexyl)propanamide;
N-(4-{[9-ethyl-8-(2-methylpyrimidin-5-yl)-9H-purin-6-yl]oxy}cyclohexyl)cyclopropanecarboxamide;
N-(3-{[9-ethyl-8-(2-methylpyrimidin-5-yl)-9H-purin-6-yl]oxy}cyclopentyl)tetrahydro-2H-pyran-4-carboxamide;
N-(3-{[9-ethyl-8-(2-methylpyrimidin-5-yl)-9H-purin-6-yl]oxy}cyclobutyl)ethanesulfonamide;
8-(2,3-dimethylphenoxy)-9-methyl-6-{[1-propanoylpyrrolidin-3-yl]oxy}-9H-purine;
8-(3-fluoro-5-methoxyphenoxy)-9-methyl-6-{[1-propanoylpyrrolidin-3-yl]oxy}-9H-purine;
9-methyl-8-[(2-methylpyrimidin-5-yl)oxy]-6-{[1-propanoylpyrrolidin-3-yl]oxy}-9H-purine;
8-(3-fluoro-4-methoxyphenoxy)-9-methyl-6-{[1-propanoylpyrrolidin-3-yl]oxy}-9H-purine;
Tert-butyl-3-({9-ethyl-8-[methyl(2-methylpropyl)amino]-9H-purin-6-yl}oxy)pyrrolidine-1-carboxylate;
Tert-butyl-3-({9-ethyl-8-[(2-hydroxyethyl)(methyl)amino]-9H-purin-6-yl}oxy)pyrrolidine-1-carboxylate;
Tert-butyl-3-({9-ethyl-8-[3-(methylsulfonyl)pyrrolidin-1-yl]-9H-purin-6-yl}oxy)pyrrolidine-1-carboxylate;

Tert-butyl-3-{[9-ethyl-8-(4-methylpiperidin-1-yl)-9H-purin-6-yl]oxy}pyrrolidine-1-carboxylate;
Tert-butyl-3-{[9-ethyl-8-(4-phenylpiperidin-1-yl)-9H-purin-6-yl]oxy}pyrrolidine-1-carboxylate;
Tert-butyl-3-({9-ethyl-8-[(2-methoxyethyl)(methyl)amino]-9H-purin-6-yl}oxy)pyrrolidine-1-carboxylate;
Tert-butyl-3-({9-ethyl-8-[methyl(1-methylethyl)amino]-9H-purin-6-yl}oxy)pyrrolidine-1-carboxylate;
Tert-butyl-3-{[9-ethyl-8-(3-methylpyrrolidin-1-yl)-9H-purin-6-yl]oxy}pyrrolidine-1-carboxylate;
8-(3,6-dihydro-2H-pyran-4-yl)-9-ethyl-6-{[1-propanoylpyrrolidin-3-yl]oxy}-9H-purine;
8-cyclopropyl-9-methyl-6-{[1-propanoylpyrrolidin-3-yl]oxy}-9H-purine;
9-ethyl-8-(2-methylpropyl)-6-{[1-propanoylpyrrolidin-3-yl]oxy}-9H-purine;
9-methyl-8-(2-methylpropyl)-6-{[1-propanoylpyrrolidin-3-yl]oxy}-9H-purine;
8-(difluoromethyl)-9-ethyl-6-{[1-propanoylpyrrolidin-3-yl]oxy}-9H-purine;
9-ethyl-6-{[1-propanoylpyrrolidin-3-yl]oxy}-8-(trifluoromethyl)-9H-purine;
9-methyl-6-{[1-propanoylpyrrolidin-3-yl]oxy}-8-(trifluoromethyl)-9H-purine;
Tert-butyl-3-({9-ethyl-8-[(2,2,2-trifluoroethyl)carbamoyl]-9H-purin-6-yl}oxy)pyrrolidine-1-carboxylate;
9-ethyl-6-((1-(3-methoxyazetidine-1-carbonyl)pyrrolidin-3-yl)oxy)-N-(2,2,2-trifluoroethyl)-9H-purine-8-carboxamide;
Tert-butyl-3-({8-[(cyclopropylmethyl)carbamoyl]-9-ethyl-9H-purin-6-yl}oxy)pyrrolidine-1-carboxylate;
Tert-butyl-3-{[8-(cyclohexylcarbamoyl)-9-ethyl-9H-purin-6-yl]oxy}pyrrolidine-1-carboxylate; and
Tert-butyl-3-{[9-ethyl-8-(ethylcarbamoyl)-9H-purin-6-yl]oxy}pyrrolidine-1-carboxylate.

The invention also encompasses pharmaceutical compositions containing a compound of formula I, and methods for treatment or prevention of PI3K-delta mediated diseases using compounds of formula I.

One aspect of the present invention is to provide compounds that can inhibit the biological activity of human PI3K-delta. Another aspect of the invention is to provide methods of selectively modulating human PI3K-delta activity and thereby promoting medical treatment of diseases mediated by PI3K-delta dysfunction.

In one embodiment of the invention, the compounds of formula I inhibit PI3K-delta activity in biochemical and cell-based assays and to exhibit therapeutic activity in medical conditions in which PI3K-delta activity is excessive or undesirable.

The invention is described using the following definitions unless otherwise indicated.

"Acyl" means a —C(O)R radical Where R is optionally substituted alkyl, alkenyl, cycloalkyl, heterocycloalkyl, aryl heteroaryl, etc.

"Acylamino" means a —NRR' radical where R is H, OH, or alkoxy and R' is acyl, as defined herein.

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or $CH_3$, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. The term "alkylene" refers to both branched- and straight-chain saturated aliphatic hydrocarbon groups, including all isomers, having the specified number of carbons, and having two terminal end chain attachments. For illustration, the term "unsubstituted A-$C_4$alkylene-B" represents A-$CH_2$—$CH_2$—$CH_2$—$CH_2$—B. The term "alkoxy" represents a linear or branched alkyl group of indicated number of carbon atoms attached through an oxygen bridge.

The term "alkyl" refers to an aliphatic hydrocarbon group which may be straight or branched and having the indicated number of carbon atoms. Non-limiting examples of alkyl groups include methyl, ethyl, propyl, isopropyl, butyl, s- and t-butyl, pentyl, hexyl, and the like.

The term "heteroalkyl" refers to an alkyl group where 1, 2, or 3 of the carbon atoms are each independently replaced by a heteroatom independently selected from N, O, or S.

"Alkenyl" refers to an aliphatic hydrocarbon group containing at least one carbon-carbon double bond and which may be straight or branched and having the indicated number of carbon atoms. Preferably alkenyl contains one carbon to carbon double bond, and up to four nonaromatic carbon-carbon double bonds may be present. Examples of alkenyl groups include ethenyl, propenyl, n-butenyl, 2-methyl-1-butenyl, 3-methylbut-2-enyl, n-pentenyl, octenyl and decenyl.

"Alkynyl" refers to an aliphatic hydrocarbon group containing at least one carbon-carbon triple bond and which may be straight or branched and having the indicated number of carbon atoms. Non-limiting examples of suitable alkynyl groups include ethynyl, propynyl, 2-butynyl and 3-methylbutynyl.

"Alkoxy" refers to an alkyl-O— group in which the alkyl group is as described above. $C_{1-6}$alkoxy, for example, includes methoxy, ethoxy, propoxy, isopropoxy, and the like. "Alkoxyalkyl" refers to an alkyl group as described above in which one or more (in particular 1 to 3) hydrogen atoms have been replaced by alkoxy groups. Examples include $CH_2OCH_3$, $CH_2CH_2OCH_3$ and $CH(OCH_3)CH_3$.

"Aminoalkyl" refers to an alkyl group as described above in which one hydrogen atom has been replaced by an amino, monoalkylamino or dialkylamino group. Examples include $CH_2NH_2$, $CH_2CH_2NHCH_3$ and $CH(N(CH_3)_2)CH_3$.

The term "$C_0$" as employed in expressions such as "$C_{0-6}$ alkyl" means a direct covalent bond; or when the term appears at the terminus of a substituent, $C_{0-6}$ alkyl means hydrogen or $C_{1-6}$alkyl. Similarly, when an integer defining the presence of a certain number of atoms in a group is equal to zero, it means that the atoms adjacent thereto are connected directly by a bond. For example, in the structure

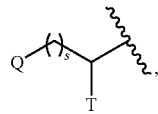

wherein s is an integer equal to zero, 1 or 2, the structure is

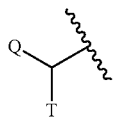

when s is zero.

The term "C$_{3-8}$ cycloalkyl" (or "C$_3$-C$_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "C$_{3-7}$ cycloalkyl", "C$_{3-6}$ cycloalkyl", "C$_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "aryl" refers to aromatic mono- and polycarbocyclic ring systems, wherein the individual carbocyclic rings in the polyring systems are fused or attached to each other via a single bond. Suitable aryl groups include phenyl, naphthyl, 2,3-dihydro-1H-indenyl, and biphenyl.

"Carboxy" refers to the functional group —C(O)OR, for example: ethylcarboxy is

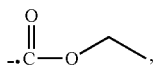

phenylcarboxy is

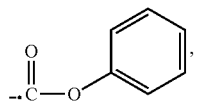

and cyclopropycarboxy is

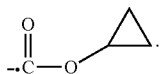

"Carboxyalkyl" refers to an alkyl group substituted with at least one, specifically one or two, —C(O)OH group(s).

The term "carbocycle" (and variations thereof such as "carbocyclic" or "carbocyclyl") as used herein, unless otherwise indicated, refers to (i) a C$_3$ to C$_8$ monocyclic, saturated or unsaturated ring or (ii) a C$_7$ to C$_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a C$_7$ to C$_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with C$_{1-6}$ alkyl, C$_{1-6}$ alkenyl, C$_{1-6}$ alkynyl, aryl, halogen, NH$_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

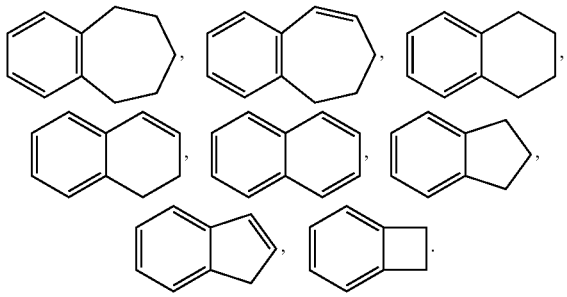

"Cyanoalkyl" refers to an alkyl group as described above in which one hydrogen atom has been replaced by a cyano group. Examples include CH$_2$CN, CH$_2$CH$_2$CN and CH(CN)CH$_3$.

"Cycloalkyl" means a carbocyclic ring system having 3 to 12 ring carbon atoms; said ring system may be (a) a monocyclic saturated carbocycle optionally fused to a benzene or a partially unsaturated carbocycle, or (b) a bicyclic saturated carbocycle. For a bicyclic system, within either (a) or (b), the rings are fused across two adjacent ring carbon atoms (e.g., decalin), at one ring carbon atom (e.g., spiro[2.2]pentane), or are bridged groups (e.g., norbornane). Additional examples within the above meaning include, but are not limited to, cyclopropane, cyclobutane, cyclopentane, cyclohexane, perhydroindan, decalin, spiro[4.5]decane, bicyclo[2.2.2]octane, and the like.

"Heterocycloalkyl" refers to a "cycloalkyl" wherein one or more of the carbon atoms are replaced by at least one heteroatom, such as for example, 1 to 4 heteroatoms selected from nitrogen, oxygen, and sulfur. Non-limiting examples of heterocycloalkyl include azabicyclo[2.2.1]heptyl, piperidinyl, pyrrolidinyl, and azetidinyl.

"Haloalkyl" refers to an alkyl group as described above wherein one or more (in particular 1 to 5) hydrogen atoms have been replaced by halogen atoms, with up to complete substitution of all hydrogen atoms with halo groups. C$_{1-6}$haloalkyl, for example, includes —CF$_3$, —CF$_2$CF$_3$, CHFCH$_3$, and the like.

"Heterocycle", "heterocyclic" or "heterocyclyl" represents a monocyclic or bicyclic 3-12 membered ring system in which at least one ring is non-aromatic (saturated or partially unsaturated) and containing at least one heteroatom selected from O, S and N. In a bicyclic ring system, the second ring may be a heteroaryl, heterocycle or a saturated, partially unsaturated or aromatic carbocycle, and the point (s) of attachment to the rest of the molecule may be on either ring. "Heterocyclyl" therefore includes heteroaryls, as well as dihydro and tetrahydro analogs thereof. Attachment of a heterocyclyl substituent can occur via a carbon atom or via a heteroatom.

Examples of heterocycles (heterocyclyl) include, but are not limited to, azetidinyl, pyrrolidinyl, piperidinyl, piperazinyl, morpholinyl, thiamorpholinyl, tetrahydrofuranyl, dihydrofuranyl, tetrahydrothienyl, tetrahydropyranyl, dihydropyranyl, dihydroimidazolyl, dihydroindolyl, 1,2,3,4-tetrahydroisoquinolinyl, 5,6,7,8-tetrahydroimidazo[1,2-a]pyrazine, 2,3-dihydrobenzofuranyl, benzo-1,4-dioxanyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

Saturated heterocyclics form a subset of the heterocycles; i.e., the terms "saturated heterocyclic and heterocycloalkyl" generally refers to a heterocycle as defined above in which the entire ring system (whether mono- or poly-cyclic) is saturated. The term "saturated heterocyclic ring" refers to a 3- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, azetidinyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl)

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. For a bicyclic heteroaryl only one of the rings need to be heteroaromatic, the second ring may be a heteroaromatic or an aromatic, saturated, or partially unsaturated carbocycle, and the point(s) of attachment to the rest of the molecule may be on either ring. In the case of substituted heteroaryl rings containing at least one nitrogen atom (e.g., pyridine), such substitutions can be those resulting in N-oxide formation. Examples of heteroaryl include, but are not limited to, furanyl, thienyl (or thiophenyl), pyrrolyl, imidazolyl, pyrazolyl, oxazolyl, thiazolyl, isoxazolyl, isothiazolyl, triazolyl, oxadiazolyl, thiadiazolyl, tetrazolyl, pyridyl, pyrimidinyl, pyrazinyl, pyridazinyl, triazinyl, quinolinyl, isoquinolinyl, naphthyridinyl, benzothienyl, benzofuranyl, benzimidazole, benzpyrazolyl, indolyl, isoindolyl, indolizinyl, indazolyl, purinyl, quinolizinyl, phthalazinyl, quinoxalinyl, quinazolinyl, benzoxazolyl, benzisoxazolyl, 5,6,7,8-tetrahydroquinolinyl, imidazo[1,2-a]pyridinyl, imidazo[1,2-a]-pyrimidinyl, 5,6-dihydropyrrolo[1,2-b]pyrazolyl, pyrrolo[3,2-c]pyridinyl, pyrrolo[2,3-b]pyridinyl, thieno[2,3-b]pyrrolyl, furopyridine and thienopyridine.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e.,

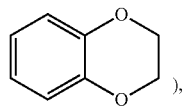), imidazo(2,1-b)(1,3)thiazole, (i.e.,

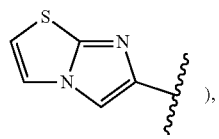 [SMILES: *c1cn2ccsc2n1]), and benzo-1,3-dioxolyl (i.e.,

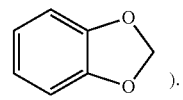).

In certain contexts herein,

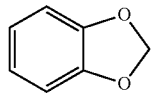

is alternatively referred to as phenyl having as a substituent methylenedioxy attached to two adjacent carbon atoms.

"Heteroalicyclic" group refers to a monocyclic or fused ring of 3 to 12 ring atoms containing one, or more heteroatoms in the ring.

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

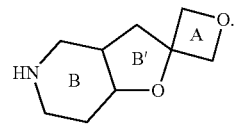

In one embodiment, all rings of the spirocyclyl system are saturated. In another embodiment, the individual rings of the spirocyclyl system are selected from both saturated and unsaturated rings.

For example a heteroalicyclic spirocyclyl or "spiroheterocyclic ring," as used herein, refers to a bicyclic heterocyclic ring as defined above wherein the two rings are joined through a common ring carbon atom. In one embodiment, a spiroheterocyclic ring is a 3- to 12-membered ring system containing one to three heteroatoms, e.g., one to two heteroatoms, selected from the group consisting of N and O. Non-limiting examples of spiroheterocyclic rings include 1,9-diazaspiro[5.5]undecane; 2,8-diazaspiro[5.5]undecane; 2,8-diazaspiro[4.5]decane; 1,7-diazaspiro[4.4]nonane; 1,7-diazaspiro[4.5]decane; 2,7-diazaspiro[4.5]decane, 1-oxa-8-azaspiro[5.5]undecane; 2-oxa-7-azaspiro[4.5]decane; 1-oxa-7-azaspiro[4.5]decane; 1,4-dioxa-7-azaspiro[4.5]decane; 1,4-dioxa-8-azaspiro[4.5]decane, azaspiro[2.4]heptyl, and 1,4-dioxaspiro[4.5]decane.

Non-limiting examples of a carbocyclic spirocyclyl systems comprising include: spiro[2.2]pentane, spiro[cylclobutane-1,2'-indene], spiro[2.4]heptyl, spiro[4.4]nonane, and spiro[4.5]decane.

"Hydroxyalkyl" refers to an alkyl group as described above in which one or more (in particular 1 to 3) hydrogen atoms have been replaced by hydroxy groups. Examples include $CH_2OH$, $CH_2CHOH$ and $CHOHCH_3$.

"Alkylene," "alkenylene," "alkynylene," "cycloalkylene," "arylene," "heteroarylene," and "heterocyclylene" refer to a divalent radical obtained by the removal of one hydrogen atom from an alkyl, alkenyl, alkynyl, cycloalkyl, aryl, heteroaryl, and heterocyclyl group, respectively, each of which is as defined above.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

The term "oxy" means an oxygen (O) atom. The term "thio" means a sulfur (S) atom. The term "oxo" means "=O". The term "carbonyl" means "C=O."

Structural representations of compounds having substituents terminating with a methyl group may display the terminal methyl group either using the characters "$CH_3$", e.g. "—$CH_3$" or using a straight line representing the presence of the methyl group, e.g. "——", i.e.,

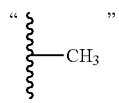

and

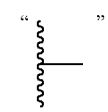

have equivalent meanings.

For variable definitions containing terms having repeated terms, e.g., $(CR^iR^j)_r$, where r is the integer 2, $R^i$ is a defined variable, and $R^j$ is a defined variable, the value of $R^i$ may differ in each instance in which it occurs, and the value of $R^j$ may differ in each instance in which it occurs. For example, if $R^i$ and $R^j$ are independently selected from the group consisting of methyl, ethyl, propyl and butyl, then $(CR^iR^j)_2$ can be

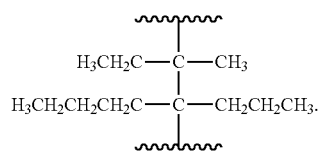

In one embodiment of the invention, $R^1$ is selected from hydrogen, $C_{1-5}$alkyl, and $C_{3-12}$ cycloalkyl, wherein $R^1$ is optionally substituted by 0, 1, 2, 3, or 4 groups independently selected from hydrogen, fluoro, chloro, methyl, amino, $OR^a$, $O(C=O)R^a$, $O(C=O)OR^a$ and $NH(C=O)R^a$. In a variant of this invention, $R^1$ is selected from $C_{1-5}$alkyl and $C_{3-12}$ cycloalkyl.

In a further embodiment of the invention, $R^1$ is selected from hydrogen, methyl, ethyl, propyl, butyl, pentyl, cyclopropyl, cyclobutyl, and cyclopentyl. In a variant of this embodiment, $R^1$ is hydrogen, methyl, ethyl, propyl, or cyclopropyl, optionally substituted by 0, 1, 2, 3, or 4 groups independently selected from hydrogen, fluoro, chloro, methyl, amino, $OR^a$, $O(C=O)R^a$, $O(C=O)OR^a$ and $NH(C=O)R^a$.

In one embodiment, optionally substituted $R^1$ is selected from hydrogen, methyl, ethyl, propyl, cyclopropyl, trifluoroethyl, and difluoroethyl.

In another embodiment, $R^1$ is $C_{1-5}$heteroalkyl or $C_{3-12}$heterocycloalkyl.

In one embodiment of the invention, $R^a$ is selected from hydrogen, $C_{1-10}$alkyl, $C_{1-10}$ heteroalkyl, aryl, $C_{3-12}$cycloalkyl, $C_{3-12}$heterocycloalkyl, and heteroaryl. In a variant of this embodiment, $R^a$ is selected from hydrogen, $C_{1-10}$alkyl, and $C_{1-10}$ heteroalkyl. In another variant, $R^a$ is hydrogen or $C_{1-10}$alkyl. In a variant of this embodiment, $R^a$ is hydrogen, methyl, ethyl, or propyl.

In one embodiment of the invention, $R^2$ is selected from hydrogen, $C_{1-10}$alkyl, $C_{3-12}$ cycloalkyl, $(C_{3-12})$ heterocycloalkyl, $C_{1-10}$ heteroalkyl, $C_{2-10}$ alkynyl, aryl, iodo, and heteroaryl, wherein $R^2$ is substituted with 0, 1, 2, 3, or 4 independently selected $R^3$.

In another embodiment of the invention, $R^2$ is selected from $C_{1-10}$alkyl, $C_{3-8}$ cycloalkyl, $(C_{3-8})$ heterocycloalkyl, $C_{1-10}$ heteroalkyl, $C_{2-10}$ alkynyl, aryl, iodo, and heteroaryl, optionally substituted with one or more $R^3$.

In another embodiment, $R^2$ is selected from hydrogen, $C_{1-10}$alkyl, $C_{3-12}$ cycloalkyl, $(C_{3-12})$ heterocycloalkyl, aryl, iodo, and heteroaryl, optionally substituted with one or more $R^3$.

In one embodiment, $R^2$ is selected from cyclopropyl, isobutyl, 2-methylpropyl, methyl, ethyl, iodo, pyridazinyl, pyrimidinyl, pyrazinyl, pyridinyl, pyrrolidinyl, piperidinyl, ethoxycarbonyl, cyclohexyl, phenyl, quinazolinyl, isoquinolinyl, pyrazolyl, imidazolyl, indolyl, indazolyl, thiazolyl, pyrazolo[1,5-a]pyrimidinyl, 3,6-dihydro-2H-pyranyl, 1H-pyrrolo[2,3-b]pyridinyl, cyclobutyl, hydrogen, 1H-pyrazolo[3,4-b]pyridinyl], pyrrolo[2,3-b]pyridinyl, benzimidazolyl, morpholinyl, 4,5,6,7,-tetrahydropyrazolo[1,5-a]

pyridinyl, 5,6-dihydro-4H-pyrrolo[1,2-b]pyrazolyl, wherein $R^2$ is substituted with 0, 1, 2, 3, or 4 independently selected $R^3$.

In one variant of this embodiment, $R^2$ is selected from cyclopropyl, isobutyl, 2-methylpropyl, methyl, ethyl, iodo, pyrimidinyl, pyridinyl, pyrrolidinyl, piperidinyl, ethoxycarbonyl, cyclohexyl, phenyl, isoquinolinyl, pyrazolyl, imidazolyl, indolyl, indazolyl, thiazolyl, pyrazolo[1,5-a]pyrimidinyl, 3,6-dihydro-2H-pyranyl, 1H-pyrrolo[2,3-b]pyridinyl, cyclobutyl, hydrogen, 1H-pyrazolo[3,4-b]pyridinyl], pyrrolo[2,3-b]pyridinyl, 4,5,6,7,-tetrahydropyrazolo[1,5-a]pyridinyl, and 5,6-dihydro-4H-pyrrolo[1,2-b]pyrazolyl, wherein $R^2$ is substituted with 0, 1, 2, 3, or 4 independently selected $R^3$.

In a variant of this embodiment, $R^2$ is selected from cyclopropyl, 2-methylpropyl, methyl, ethyl, iodo, pyrimidinyl, pyridinyl, pyrrolidinyl, piperidinyl, cyclohexyl, phenyl, isoquinolinyl, pyrazolyl, imidazolyl, indolyl, indazolyl, thiazolyl, pyrazolo[1,5-a]pyrimidinyl, 3,6-dihydro-2H-pyranyl, cyclobutyl, hydrogen, 1H-pyrazolo[3,4-b]pyridinyl], pyrrolo[2,3-b]pyridinyl, 4,5,6,7,-tetrahydropyrazolo[1,5-a]pyridinyl, and 5,6-dihydro-4H-pyrrolo[1,2-b]pyrazolyl, wherein $R^2$ is substituted with 0, 1, 2, 3, or 4 independently selected $R^3$.

In one embodiment, A is selected from $C_{3-12}$ cycloalkyl, and $(C_{3-12})$heterocycloalkyl.

In one embodiment, A is $(C_{6-12})$spirocyclic. In a variant of this embodiment the rings of the spirocyclyl system are saturated.

In one embodiment, A is selected from pyrrolidinyl, piperidinyl, cyclobutyl, cyclohexyl, azaspiro[2.4]hept-2-yl, azabicyclo[2.2.1]heptanyl, azetidinyl, and cyclopentyl. In a variant of this embodiment, A is selected from pyrrolidinyl, piperidinyl, cyclobutyl, cyclohexyl, azaspiro[2.4]heptyl, azabicyclo[2.2.1]heptyl, and cyclopentyl. In yet another embodiment, A is selected from pyrrolidinyl, piperidinyl, azetidinyl, and cyclopentyl. In a variant of this embodiment A is pyrrolidinyl.

In one embodiment of the invention, L is O, S, $SO_2$, and $CH_2$.

In another embodiment, L is O. In yet another embodiment, L is S or $SO_2$. In yet another embodiment of the invention, L is $CH_2$.

In one embodiment of the invention, K is selected from a bond. In another embodiment of the invention, K is selected from bond, NH, O, C(O), $CH_2$, $N((C_{1-5})alkyl)_{1-2}$, —C(O)N($R^b$)—$(CH_2)_m$, S, $SO_2$, and $C_{2-10}$ alkynylene, wherein $R^b$ is H or $C_{1-10}$ alkyl and m is 0, 1, 2, or 3.

In another embodiment of the invention, K is selected from a bond, O, —N($(C_{1-5})$alkyl)$_{1-2}$-, $C_{2-10}$ alkynylene, and C(O)N($R^b$)—$(CH_2)_m$—, where $R^b$ is H, methyl, or ethyl, and m is 0 or 1. In a variant of this embodiment, K is selected from a bond, —O—, —N(CH$_3$)—, —N(C$_3$H$_7$)—, ethynyl, —C(O)NH— and —C(O)NH—CH$_2$—.

In one embodiment, $R^3$ is independently selected from: halogen, $C_{1-10}$ alkyl(oxy)$_{0-1}$(carbonyl)$_{0-1}C_{0-10}$ alkyl, $C_{2-10}$ alkenyl(oxy)$_{0-1}$(carbonyl)$_{0-1}C_{0-10}$ alkyl, $C_{1-10}$ heteroalkyl(oxy)$_{0-1}$(carbonyl)$_{0-1}C_{0-10}$ alkyl, aryl $C_{0-10}$ alkyl(oxy)$_{0-1}$(carbonyl)$_{0-1}C_{0-10}$ alkyl, $C_{3-12}$ cycloalkyl$C_{0-10}$ alkyl(oxy)$_{0-1}$(carbonyl)$_{0-1}$ $C_{0-10}$alkyl, heteroaryl$C_{0-10}$alkyl(oxy)$_{0-1}$(carbonyl)$_{0-1}C_{0-10}$ alkyl, $(C_{3-12})$heterocycloalkyl $C_{0-10}$ alkyl(oxy)$_{0-1}$(carbonyl)$_{0-1}C_{0-10}$ alkyl, $C_{1-10}$ alkylamino(carbonyl)$_{0-1}C_{0-10}$ alkyl, $(C_{1-10})$heteroalkylamino(carbonyl)$_{0-1}C_{0-10}$ alkyl, $C_{3-12}$ cycloalkyl $C_{0-10}$ alkylamino(carbonyl)$_{0-1}C_{0-10}$ alkyl, aryl $C_{0-10}$alkylamino(carbonyl)$_{0-1}C_{0-10}$ alkyl, heteroaryl$C_{0-10}$alkylamino(carbonyl)$_{0-1}C_{0-10}$ alkyl, $(C_{3-12})$heterocycloalkyl$C_{1-10}$alkylamino(carbonyl)$_{0-1}C_{0-10}$ alkyl, $C_{1-10}$ alkyl(oxy)$_{0-1}$(carbonyl)$_{0-1}$aminoC$_{0-10}$ alkyl, $C_{1-10}$ heteroalkyl(oxy)$_{0-1}$(carbonyl)$_{0-1}$aminoC$_{0-10}$ alkyl, $C_{3-12}$ cycloalkyl $C_{0-10}$ alkyl (oxy)$_{0-1}$(carbonyl)$_{0-1}$aminoC$_{0-10}$ alkyl, aryl $C_{0-10}$ alkyl (oxy)$_{0-1}$(carbonyl)$_{0-1}$aminoC$_{0-10}$ alkyl, heteroaryl $C_{0-10}$ alkyl(oxy)$_{0-1}$(carbonyl)$_{0-1}$aminoC$_{0-10}$ alkyl, $(C_{3-12})$heterocycloalkyl $C_{0-10}$ alkyl(oxy)$_{0-1}$(carbonyl)$_{0-1}$aminoC$_{0-10}$ alkyl, —CO$_2$(C$_{0-10}$ alkyl), —(C$_{0-10}$ alkyl)CO$_2$H, Oxo(=O); $C_{1-10}$alkylS(O)$_{1-2}$, heteroarylS(O)$_{1-2}$, arylS(O)$_{1-2}$, C$_{0-6}$ alkyl(amino)$_{0-1}$S(O)$_{1-2}$amino, $C_{1-10}$ heteroalkyl(amino)$_{0-1}$S(O)$_{1-2}$amino, $(C_{3-12})$cycloalkyl(amino)$_{0-1}$S(O)$_{1-2}$amino, $(C_{3-12})$cycloheteroalkyl(amino)$_{0-1}$S(O)$_{1-2}$amino, heteroaryl(amino)$_{0-1}$S(O)$_{1-2}$amino, $C_{1-10}$heteroalkylS(O)$_{1-2}$, $(C_{3-12})$cycloalkylS(O)$_{1-2}$, $(C_{3-12})$cycloheteroalkylS(O)$_{1-2}$, heteroarylS(O)$_{1-2}$, arylS(O)$_{1-2}$, —SO$_2$N(C$_{0-6}$ alkyl)$_{0-2}$, —SO$_2$CF$_3$, amino, (C$_{0-10}$ alkyl)$_{1-2}$ amino, hydroxy, (C$_{1-10}$ alkyl)OH, C$_{0-10}$ alkylalkoxy, cyano, C$_{1-6}$alkylcyano, and C$_{1-6}$haloalkyl; wherein $R^3$ is each substituted with 0, 1, 2, 3, or 4 substituents, $R^4$.

In one embodiment, $R^3$ is independently selected from: In one embodiment, $R^3$ is independently selected from: halogen, $C_{1-10}$ alkyl(oxy)$_{0-1}$(carbonyl)$_{0-1}C_{0-10}$ alkyl, $C_{2-10}$ alkenyl(oxy)$_{0-1}$(carbonyl)$_{0-1}C_{0-10}$ alkyl, aryl $C_{0-10}$ alkyl(oxy)$_{0-1}$(carbonyl)$_{0-1}C_{0-10}$ alkyl, $C_{3-12}$ cycloalkyl$C_{0-10}$ alkyl(oxy)$_{0-1}$(carbonyl)$_{0-1}C_{0-10}$ alkyl, heteroaryl$C_{0-10}$alkyl (oxy)$_{0-1}$(carbonyl)$_{0-1}C_{0-10}$ alkyl, $(C_{3-12})$heterocycloalkyl $C_{0-10}$ alkyl(oxy)$_{0-1}$(carbonyl)$_{0-1}C_{0-10}$ alkyl, $C_{1-10}$ alkylamino(carbonyl)$_{0-1}C_{0-10}$ alkyl, $C_{3-12}$ cycloalkyl $C_{0-10}$ alkylamino(carbonyl)$_{0-1}C_{0-10}$ alkyl, aryl $C_{0-10}$alkylamino(carbonyl)$_{0-1}C_{0-10}$ alkyl, $C_{1-10}$ alkyl(oxy)$_{0-1}$(carbonyl)$_{0-1}$aminoC$_{0-10}$ alkyl, $C_{3-12}$ cycloalkyl $C_{0-10}$ alkyl(oxy)$_{0-1}$(carbonyl)$_{0-1}$aminoC$_{0-10}$ alkyl, heteroaryl $C_{0-10}$ alkyl(oxy)$_{0-1}$(carbonyl)$_{0-1}$aminoC$_{0-10}$ alkyl, $(C_{3-12})$heterocycloalkyl $C_{0-10}$ alkyl(oxy)$_{0-1}$(carbonyl)$_{0-1}$aminoC$_{0-10}$ alkyl, Oxo (=O); $C_{1-10}$alkylS(O)$_{1-2}$, heteroarylS(O)$_{1-2}$, arylS(O)$_{1-2}$, C$_{0-6}$ alkyl(amino)$_{0-1}$S(O)$_{1-2}$amino, —SO$_2$CF$_3$, amino, (C$_{0-10}$ alkyl)$_{1-2}$ amino, hydroxy, (C$_{1-10}$ alkyl)OH, C$_{0-10}$ alkylalkoxy, cyano, and C$_{1-6}$haloalkyl; wherein $R^3$ is each substituted with 0, 1, 2, 3, or 4 substituents, $R^4$.

In one embodiment, $R^3$ is independently selected from: fluoro, chloro, methyl, ethyl, propyl, methoxy, pyrazolyl, thiazolyl, benzisoxazolyl, pyrazinyl, cyclopropyl, pyridinyl, cyclopropylmethyl, hydroxy, oxo (=O), dimethylamino, morpholinyl, imidazolyl, pyrrolidinyl, piperidinyl, tert-butyl, trifluoromethyl, methoxymethyl, isobutylcarboxy, tert-butylcarboxy, phenylcarboxy, hydrogen, methylpropylcarboxy, ethoxycarbonyl, napthalenylcarboxy, benzylcarboxy, isobutylcarboxy, 2,2,-dimethylpropylcarboxy, methylcarboxy, ethylcarboxy, methylethylcarboxy, cyclopentylcarbonyl, cyclobutylcarbonyl, spiro[2.4]heptylcarbonyl, imidazolylcarbonyl, ethylcarbonyl, methylethylcarbonyl, propyloxycarbonyl, phenylcarbonyl, piperidinylcarbonyl, napthalenylcarbonyl, cyclohexylcarbonyl, methylcarbonyl, (tetrahydro-2H-pyran-4-ylmethyl)carbonyl, tetrahydro-2H-pyran-4-ylcarbonyl, oxazolylcarbonyl, pyridinylcarbonyl, cyclopropylcarbonyl, pyrrolidinylmethylcarbonyl, azetidinylcarbonyl, tetrahydropyranylcarbonyl, tetrahydropyranylcarbonylamino, cyclopropylaminocarbonyl, tetrahydrofuranylcarbonyl, isoxazolylcarbonyl, pyrrolindinylmethylcarbonyl, pyrazolo[1,5-a]pyridinylcarbonyl, pyrazolo[1,5-a]pyrimidinylcarbonyl, triazolylcarbonyl, 1,2,3-triazolylcarbonyl, imidazo[1,2-a]pyrimidinylcarbonyl, thiadiazolylcarbonyl, 1,2,3-thiadiazolylcarbonyl, furo[3,2-b]pyrrolylcarbonyl, pyrazolylcarbonyl, pyrrolindinylcarbonyl, hydroxymethyl, fluoromethyl, pyrrolylcarbonyl, imidazo[1,2-b]pyrazolylcarbonyl, pyrrolo[3,2-b]pyridinylcarbonyl, pyrrolo[1,2-d]tetrazolylcarbonyl, oxadiazolylcarbonyl, 1,2,5-oxadiaxolylcarbonyl, 1,3,4-oxadiazolylcarbonyl, 1,2,4-oxadiazolylcarbonyl, pyrrolo[1,2-b]pyrazolylcarbonyl, ethylcarbonyl, tert-butylcarbonyl, azetidinylpropyloxycarbonyl, trifluoromethylsulfonyl, ethylsulfonyl, methylsulfonyl, ethylsulfonylamino, methylsulfonylamino, (methylethyl)sulfonyl, phenylsulfonyl, imidazolylsulfonyl, naphthalenylsulfonyl, 5,6,7,8-tetrahydro[1,2,4]triazolo[4,3-a]pyridinylcarbonyl, [1,2,4]triazolo-[1,5-a]pyridinylcarbonyl, acetylamino, azabicyclo[3.1.0]hexylcarbonyl, azabicyclo[2.2.1]heptylcarbonyl, methylethylaminocarbonyl, cyclohexylaminocarbonyl, phenylaminocarbonyl, 1-phenylethylaminocarbonyl, dimethylethylaminocarbonyl, tetramethylbutylaminocarbonyl, benzylaminocarbonyl, ethylaminocarbonyl, oxazolylcarbonylamino, dimethylpropylcarbonylamino, methylcarbonylamino, bicyclo[2.2.1]heptylcarbonyl, propylaminocarbonyl, isopropylcarbonylamino, benzyl, phenyl, benzoxycarbonyl, cyclohexylmethyl, phenylmethyl, 1-phenylethyl, pyrrolylmethyl, pyrimidinyl, thieno[2,3-d]pyrimidinyl, thieno[3,2-c]pyridinyl, difluoromethyl, [1,2,4]triazolo[4.3-a]pyrazinyl, phthalazinyl, pyrazolo[3,4-d]pyrimidinyl, morpholinylcarbonyl, tert-butylaminocarbonyl, tert-butyloxycarbonylamino, 2-methylpropylcarbonyl, (2-methylprop-1-ene)carbonyl, ethylcarbonylamino, cyclopropylcarbonylamino, cyano, (methylamino)methyl, tetrahydro-2H-pyranylcarbonylamino, imidazo[4,5-b]pyridinyl, 1,3-dihydro-2H-imidazo[4,5-b]pyridinyl, pyranylcarbonyl, amino, hydroxyisopropyl, 2-hydroxypropyl, and isobutylcarbonyl; wherein $R^3$ is each substituted with 0, 1, 2, 3, or 4 substituents, $R^4$.

In yet another embodiment, $R^3$ is independently selected from: fluoro, chloro, methyl, ethyl, propyl, methoxy, pyrazolyl, thiazolyl, benzisoxazolyl, pyrazinyl, cyclopropyl, pyridinyl, hydroxy, oxo (=O), dimethylamino, morpholinyl, pyrrolidinyl, tert-butyl, trifluoromethyl, methoxymethyl, isobutylcarboxy, tert-butylcarboxy, phenylcarboxy, hydrogen, methylpropylcarboxy, ethoxycarbonyl, napthalenylcarboxy, benzylcarboxy, isobutylcarboxy, 2,2,-dimethylpropylcarboxy, methylcarboxy, ethylcarboxy, methylethylcarboxy, cyclopentylcarbonyl, cyclobutylcarbonyl, spiro[2.4]heptylcarbonyl, imidazolylcarbonyl, ethylcarbonyl, methylethylcarbonyl, propyloxycarbonyl, phenylcarbonyl, piperidinylcarbonyl, napthalenylcarbonyl, cyclohexylcarbonyl, methylcarbonyl, (tetrahydro-2H-pyran-4-ylmethyl)carbonyl, tetrahydro-2H-pyran-4-ylcarbonyl, oxazolylcarbonyl, cyclopropylcarbonyl, pyridinylcarbonyl, pyrrolidinylmethylcarbonyl, azetidinylcarbonyl, tetrahydropyranylcarbonyl, tetrahydropyranylcarbonylamino, cyclopropylaminocarbonyl, tetrahydrofuranylcarbonyl, isoxazolylcarbonyl, pyrazolo[1,5-a]pyridinylcarbonyl, triazolylcarbonyl, 1,2,3-triazolylcarbonyl, imidazo[1,2-a]pyrimidinylcarbonyl, thiadiazolylcarbonyl, 1,2,3-thiadiazolylcarbonyl, furo[3,2-b]pyrrolylcarbonyl, pyrazolylcarbonyl, pyrrolindinylcarbonyl, hydroxymethyl, fluoromethyl, pyrrolylcarbonyl, imidazo[1,2-b]pyrazolylcarbonyl, pyrrolo[3,2-b]pyridinyl, pyrrolo[1,2-d]tetrazolylcarbonyl, oxadiazolylcarbonyl, 1,2,5-oxadiaxolylcarbonyl, 1,3,4-oxadiazolylcarbonyl, 1,2,4-oxadiazolylcarbonyl, pyrrolo[1,2-b]pyrazolylcarbonyl, ethylcarbonyl, trifluoromethylsulfonyl, ethylsulfonyl, methylsulfonyl, ethylsulfonylamino, methylsulfonylamino, (methylethyl)sulfonyl, phenylsulfonyl, imidazolylsulfonyl, naphthalenylsulfonyl, 5,6,7,8-tetrahydro[1,2,4]triazolo[4,3-a]pyridinylcarbonyl, [1,2,4]triazolo-[1,5-a]pyridinylcarbonyl, acetylamino, azabicyclo[3.1.0]hexylcarbonyl, azabicyclo[2.2.1]heptylcarbonyl, methylethylaminocarbonyl, cyclohexylaminocarbonyl, phenylaminocarbonyl, tetramethylbutylaminocarbonyl, benzylaminocarbonyl, ethylaminocarbonyl, methylcarbonylamino, bicyclo[2.2.1]heptylcarbonyl, phenyl, cyclohexylmethyl, phenylmethyl, 1-phenylethyl, pyrrolylmethyl, pyrimidinyl, thieno[2,3-d]pyrimidinyl, thieno[3,2-c]pyridinyl, difluoromethyl, [1,2,4]triazolo[4.3-a]pyrazinyl, phthalazinyl, pyrazolo[3,4-d]pyrimidinyl, morpholinylcarbonyl, tert-butylaminocarbonyl, tert-butyloxycarbonylamino, 2-methylpropylcarbonyl, (2-methylprop-1-ene)carbonyl, cyclopropylcarbonylamino, cyano, tetrahydro-2H-pyranylcarbonylamino, imidazo[4,5-b]pyridinyl, 1,3-dihydro-2H-imidazo[4,5-b]pyridinyl, amino, and isobutylcarbonyl; wherein $R^3$ is each substituted with 0, 1, 2, 3, or 4 substituents, $R^4$.

In one embodiment of the invention, $R^4$ is independently selected from: halogen, $C_{1-10}$ alkyl(oxy)$_{0-1}$(carbonyl)$_{0-1}$ $C_{0-10}$ alkyl, $C_{1-10}$ heteroalkyl(oxy)$_{0-1}$(carbonyl)$_{0-1}$$C_{0-10}$ alkyl, aryl $C_{0-10}$ alkyl(oxy)$_{0-1}$(carbonyl)$_{0-1}$$C_{0-10}$ alkyl, $C_{3-12}$ cycloalkyl $C_{0-10}$ alkyl(oxy)$_{0-1}$(carbonyl)$_{0-1}$$C_{0-10}$ alkyl, heteroaryl $C_{0-10}$ alkyl(oxy)$_{0-1}$(carbonyl)$_{0-1}$$C_{0-10}$ alkyl, $C_{3-12}$heterocycloalkyl $C_{0-10}$ alkyl(oxy)$_{0-1}$(carbonyl)$_{0-1}$$C_{0-10}$ alkyl, $C_{1-10}$ alkyl(carbonyl)$_{0-1}$oxy$C_{0-10}$ alkyl, $C_{1-10}$ heteroalkyl(carbonyl)$_{0-1}$oxy$C_{0-10}$ alkyl, aryl $C_{0-10}$ alkyl(carbonyl)$_{0-1}$oxy$C_{0-10}$ alkyl, $C_{3-12}$cycloalkyl $C_{0-10}$ alkyl(carbonyl)$_{0-1}$oxy$C_{0-10}$ alkyl, heteroaryl$C_{0-10}$ alkyl(carbonyl)$_{0-1}$oxy$C_{0-10}$ alkyl, $C_{3-12}$heterocycloalkyl $C_{0-10}$ alkyl(carbonyl)$_{0-10}$oxy$C_{0-10}$ alkyl, $C_{1-10}$ alkyl(oxy)$_{0-1}$(carbonyl)$_{0-1}$amino$C_{0-10}$ alkyl, $(C_{3-12})$cycloalkyl $C_{0-10}$ alkyl(oxy)$_{0-1}$(carbonyl)$_{0-1}$amino$C_{0-10}$ alkyl, aryl $C_{0-10}$ alkyl(oxy)$_{0-1}$(carbonyl)$_{0-1}$amino$C_{0-10}$ alkyl, heteroaryl $C_{0-10}$ alkyl(oxy)$_{0-1}$(carbonyl)$_{0-1}$amino$C_{0-10}$ alkyl, $(C_{3-12})$heterocycloalkyl $C_{0-10}$ alkyl(oxy)$_{0-1}$(carbonyl)$_{0-1}$amino$C_{0-10}$ alkyl, $C_{1-10}$ alkylaminocarbonyl$C_{0-10}$ alkyl, $C_{3-12}$ cycloalkyl $C_{0-10}$ alkylaminocarbonyl$C_{0-10}$ alkyl, aryl $C_{0-10}$ alkylaminocarbonyl$C_{0-10}$ alkyl, heteroaryl $C_{0-10}$ alkylaminocarbonyl$C_{0-10}$ alkyl, $C_{3-12}$heterocycloalkyl $C_{0-10}$ alkylaminocarbonyl$C_{0-10}$ alkyl, —$CO_2(C_{0-10}$ alkyl), —$(C_{0-10}$ alkyl)$CO_2$H, Oxo (=O), $C_{1-10}$ alkylS(O)$_{1-2}$, $C_{1-10}$ heteroalkyl S(O)$_{1-2}$, $C_{3-12}$cycloalkylS(O)$_{1-2}$, $C_{3-12}$cycloheteroalkylS(O)$_{1-2}$, heteroarylS(O)$_{1-2}$, arylS(O)$_{1-2}$, —$SO_2N(C_{1-6}$alkyl)$_{1-2}$, —$SO_2C_{1-6}$alkyl, —$SO_2CF_3$, amino, $(C_{0-10}$ alkyl)$_{1-2}$ amino, $(C_{1-10}$ alkyl)OH, $C_{1-10}$ alkoxy, cyano, and $C_{1-6}$haloalkyl; wherein $R^4$ is substituted with 0, 1, 2, or 3 $R^5$.

In one embodiment of the invention, $R^4$ is independently selected from: halogen, $C_{1-10}$ alkyl(oxy)$_{0-1}$(carbonyl)$_{0-1}$ $C_{0-10}$ alkyl, aryl $C_{0-10}$ alkyl(oxy)$_{0-1}$(carbonyl)$_{0-1}$$C_{0-10}$ alkyl, $C_{3-12}$ cycloalkyl $C_{0-10}$ alkyl(oxy)$_{0-1}$(carbonyl)$_{0-1}$$C_{0-10}$ alkyl, heteroaryl $C_{0-10}$ alkyl(oxy)$_{0-1}$(carbonyl)$_{0-1}$$C_{0-10}$ alkyl, $C_{3-12}$heterocycloalkyl $C_{0-10}$ alkyl(oxy)$_{0-1}$(carbonyl)$_{0-1}$$C_{0-10}$ alkyl, $C_{1-10}$ alkyl(oxy)$_{0-1}$(carbonyl)$_{0-1}$amino$C_{0-10}$ alkyl, Oxo (=O)), —$SO_2C_{1-6}$alkyl, amino, $(C_{0-10}$ alkyl)$_{1-2}$ amino, $(C_{1-10}$ alkyl)OH, $C_{1-10}$ alkoxy, cyano, and $C_{1-6}$haloalkyl; wherein $R^4$ is substituted with 0, 1, 2, or 3 $R^5$.

In another embodiment of the invention, $R^4$ is selected from: halogen, methyl, methoxy, cyano, Oxo (=O), piperazinyl, isopropyl, dimethylamino, propanol, methylethyl, propyl, trifluoromethyl, cyclopropyl, ethyl, phenyl, pyrazolyl, furanyl, tert-butyl, and ethyloxycarbonyl.

In another embodiment of the invention, $R^4$ is selected from: methyl, trifluoromethyl, methoxy, dimethylamino, fluoro, cyano, oxo, piperazinyl, methylethyl, chloro, hydroxypropyl, cyclopropyl, ethyl, tert-butyl, difluormethyl, hydroxymethyl, fluoromethyl, phenyl, ethylcarboxy, pyrazolyl, and furanyl; wherein $R^4$ is substituted with 0, 1, 2, or 3 $R^5$.

In one embodiment, $R^5$ is independently selected from hydroxy, $(C_{1-6})$alkyl, $(C_{1-6})$alkoxy, $(C_{1-10}$ alkyl)OH, halogen, $CO_2$H, —$(C_{0-6})$alkylCN, $NO_2$, trifluoromethyl, trifluoroethyl, $C_{1-10}$ alkylsulfonyl, $C_{1-10}$ heteroalkyl, aryl, $C_{3-12}$ cycloalkyl, heteroaryl, $(C_{3-12})$heterocycloalkyl, oxo (O=), $-O_{(0-1)}(C_{1-10})$haloalkyl, and amino$(C_{1-6}$alkyl$)_{0-2}$.

In another embodiment of the invention, $R^5$ is selected from $-O(C=O)C_1-C_6$ alkyl, $-(C=O)OC_1-C_6$ alkyl, trifluoromethoxy, trifluoroethoxy, $-N=C(O)O(C_{0-6})$alkyl, $C_{1-10}$ heteroalkylsulfonyl, $(C_{3-12})$cycloalkylsulfonyl, $(C_{3-12})$ cycloheteroalkylsulfonyl, heteroarylsulfonyl, arylsulfonyl, aminosulfonyl, $-SO_2N(C_{1-6}$alkyl$)_{1-2}$, $-SO_2C_{1-6}$alkyl, $-SO_2CF_3$, $-SO_2CF_2H$, $-C_{1-10}$alkylsulfinyl, and $NH_2$.

In one embodiment, $R^5$ is selected from hydroxy, $(C_{1-6})$ alkyl, $(C_{1-6})$alkoxy, $(C_{1-10}$ alkyl$)$OH, halogen, $CO_2H$, $-(C_{0-6})$alkylCN, $NO_2$, trifluoromethyl, trifluoroethyl, oxo (O=), $-O_{(0-1)}(C_{1-10})$haloalkyl, and amino$(C_{1-6}$alkyl$)_{0-2}$. In one variant of the invention, $R^5$ is selected from hydroxy, methyl, ethyl, propyl, methoxy, ethoxy, cyano, fluoro, and chloro. In yet another variant of the invention, $R^5$ is selected from methyl and fluoro.

In one embodiment of the invention, $R^6$ is selected from hydroxy, $(C_{1-6})$alkyl, $(C_{1-6})$alkoxy, $(C_{1-10}$ alkyl$)$OH, halogen, $CO_2H$, trifluoromethyl, trifluoroethyl, oxo (O=), $-SO_2N(C_{1-6}$alkyl$)_{1-2}$, $-SO_2C_{1-6}$alkyl, $-SO_2CF_3$, $-O_{(0-1)}(C_{1-10})$haloalkyl, amino$(C_{1-6}$alkyl$)_{0-2}$ and amino.

In one embodiment of the invention, $R^6$ is selected from hydroxy, $(C_{1-6})$alkyl, $(C_{1-6})$alkoxy, halogen, $CO_2H$, trifluoromethyl, trifluoroethyl, oxo (O=), and amino.

One embodiment of the invention comprises the compounds of formula I or pharmaceutically acceptable salts or stereoisomers thereof:

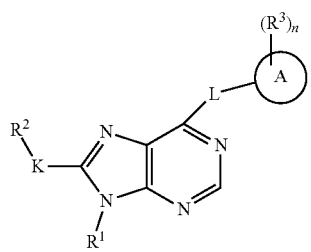

I $R^1$ is selected from hydrogen, $C_{1-5}$alkyl, $C_{3-5}$cycloalkyl, $C_{1-5}$heteroalkyl, and $C_{3-5}$heterocycloalkyl, wherein $R^1$ is optionally substituted by 0, 1, 2, 3, or 4 groups independently selected from hydrogen, fluoro, chloro, methyl, amino, $OR^a$, $O(C=O)R^a$, $O(C=O)OR^a$ and $NH(C=O)R^a$; $R^a$ is independently selected from hydrogen, $C_{1-10}$alkyl, $C_{1-10}$heteroalkyl, aryl, cycloalkyl, heterocycloalkyl, and heteroaryl;
$R^2$ is selected from hydrogen, $C_{1-10}$alkyl, $C_{3-8}$ cycloalkyl, $C_{3-8}$heterocycloalkyl, $C_{1-10}$ heteroalkyl, $C_{2-10}$alkynyl, aryl, and heteroaryl, wherein $R^2$ is substituted with 0, 1, 2, 3, or 4 $R^3$ substituents;
n is 0, 1, 2, 3, or 4;
A is $C_{3-12}$ cycloalkyl, $C_{3-12}$heterocycloalkyl, and $C_{6-12}$spirocyclyl;
L is selected from O, S, $SO_2$, and $-CH_2$;
K is selected from a bond, NH, O, C(O), $CH_2$, $N(C_{1-5})$alkyl, S, $SO_2$, and $C_{2-10}$ alkynylene;
$R^3$ is independently selected from:
  halogen,
  $C_{1-10}$ alkyl(oxy)$_{0-1}$(carbonyl)$_{0-1}C_{0-10}$ alkyl,
  $C_{1-10}$ heteroalkyl(oxy)$_{0-1}$(carbonyl)$_{0-1}C_{0-10}$ alkyl,
  aryl $C_{0-10}$ alkyl(oxy)$_{0-1}$(carbonyl)$_{0-1}C_{0-10}$ alkyl,
  aryl $C_{2-10}$ alkynyl(oxy)$_{0-1}$(carbonyl)$_{0-1}C_{0-10}$ alkyl,
  $C_{3-8}$ cycloalkyl$C_{0-10}$ alkyl(oxy)$_{0-1}$(carbonyl)$_{0-1}$ $C_{0-10}$ alkyl,
  heteroaryl $C_{0-10}$ alkyl(oxy)$_{0-1}$(carbonyl)$_{0-1}C_{0-10}$ alkyl,
  $(C_{3-8})$heterocycloalkyl $C_{0-10}$ alkyl(oxy)$_{0-1}$(carbonyl)$_{0-1}$ $C_{0-10}$ alkyl,
  $C_{1-10}$ alkyl(carbonyl)$_{0-1}$oxy$C_{0-10}$ alkyl,
  $C_{1-10}$ heteroalkyl(carbonyl)$_{0-1}$oxy$C_{0-10}$ alkyl,
  $C_{1-10}$ heteroalkyl(carbonyl)$_{0-1}$oxy$C_{0-10}$ alkyl,
  aryl $C_{0-10}$ alkyl(carbonyl)$_{0-1}$oxy$C_{0-10}$ alkyl,
  $(C_{3-8})$cycloalkyl $C_{0-10}$ alkyl(carbonyl)$_{0-1}$ oxy$C_{0-10}$ alkyl,
  heteroaryl$C_{0-10}$ alkyl(carbonyl)$_{0-1}$oxy$C_{0-10}$ alkyl,
  $(C_{3-8})$heterocycloalkyl $C_{0-10}$ alkyl(carbonyl)$_{0-1}$oxy$C_{0-10}$ alkyl,
  $((C_{0-10})$alkyl$)_{1-2}$aminocarbonyloxy,
  $(C_{0-10})$heteroalkylamminocarbonyloxy,
  aryl$(C_{0-10})$alkylaminocarbonyloxy,
  $(C_{3-8})$cycloalkyl$(C_{0-10})$alkylaminocarbonyloxy,
  heteroaryl$(C_{0-10})$alkylaminocarbonyloxy,
  $(C_{3-8})$heterocycloalkyl$(C_{0-10})$alkylaminocarbonyloxy,
  $C_{1-10}$ alkylamino(carbonyl)$_{0-1}C_{0-10}$ alkyl,
  $(C_{1-10})$heteroalkylamino(carbonyl)$_{0-1}C_{0-10}$ alkyl,
  $C_{3-8}$ cycloalkyl $C_{0-10}$ alkylamino(carbonyl)$_{0-1}C_{0-10}$ alkyl,
  aryl $C_{0-10}$alkylamino(carbonyl)$_{0-1}C_{0-10}$ alkyl,
  heteroaryl$C_{0-10}$alkylamino(carbonyl)$_{0-1}C_{0-10}$ alkyl,
  $(C_{3-8})$heterocycloalkyl$C_{0-10}$alkylamino(carbonyl)$_{0-1}C_{0-10}$ alkyl,
  $C_{1-10}$ alkyl(oxy)$_{0-1}$(carbonyl)$_{0-1}$amino$C_{0-10}$ alkyl,
  $C_{1-10}$ heteroalkyl(oxy)$_{0-1}$(carbonyl)$_{0-1}$amino $C_{0-10}$ alkyl,
  $C_{3-8}$ cycloalkyl $C_{0-10}$ alkyl(oxy)$_{0-1}$(carbonyl)$_{0-1}$ amino$C_{0-10}$ alkyl,
  aryl $C_{0-10}$ alkyl(oxy)$_{0-1}$(carbonyl)$_{0-1}$amino$C_{0-10}$ alkyl,
  heteroaryl $C_{0-10}$ alkyl(oxy)$_{0-1}$(carbonyl)$_{0-1}$amino$C_{0-10}$ alkyl,
  $(C_{3-8})$heterocycloalkyl $C_{0-10}$ alkyl(oxy)$_{0-1}$(carbonyl)$_{0-1}$ amino$C_{0-10}$ alkyl,
  $-CO_2(C_{0-10}$ alkyl$)$,
  $-(C_{0-10}$ alkyl$)CO_2H$,
  Oxo (=O);
  $C_{1-10}$ alkylS(O)$_{1-2}$,
  $C_{1-10}$ heteroalkyl S(O)$_{1-2}$,
  $(C_{3-8})$cycloalkylS(O)$_{1-2}$,
  $(C_{3-8})$cycloheteroalkylS(O)$_{1-2}$,
  heteroarylS(O)$_{1-2}$,
  arylS(O)$_{1-2}$,
  $-SO_2N(C_{0-6}$ alkyl$)_{0-2}$,
  $C_{0-6}$ alkyl(amino)$_{0-1}$S(O)$_{1-2}$amino,
  $C_{1-10}$ heteroalkyl(amino)$_{0-1}$S(O)$_{1-2}$amino,
  $(C_{3-8})$cycloalkyl(amino)$_{0-1}$S(O)$_{1-2}$amino,
  $(C_{3-8})$cycloheteroalkyl(amino)$_{0-1}$S(O)$_{1-2}$amino,
  heteroaryl(amino)$_{0-1}$S(O)$_{1-2}$amino,
  aryl(amino)$_{0-1}$S(O)$_{1-2}$amino,
  $-SO_2CF_3$,
  $-SO_2CF_2H$,
  $-Si(C_{0-6}$ alkyl$)_3$,
  amino,
  $(C_{0-10}$ alkyl$)_{1-2}$ amino,
  $C_{1-4}$acylamino $C_{0-10}$ alkyl,
  hydroxyl,
  $(C_{1-10}$ alkyl$)$OH,
  $C_{0-10}$ alkylalkoxyl,
  cyano,
  $C_{1-6}$alkylcyano, and
  $C_{1-6}$haloalkyl;
wherein $R^3$ is each substituted with 0, 1, 2, 3, or 4 $R^4$ substituents and each $R^4$ is independently selected from:
  halogen,
  $C_{1-10}$ alkyl(oxy)$_{0-1}$(carbonyl)$_{0-1}C_{0-10}$ alkyl, $C_{1-10}$ heteroalkyl(oxy)$_{0-1}$(carbonyl)$_{0-1}C_{0-10}$ alkyl,
aryl $C_{0-10}$ alkyl(oxy)$_{0-1}$(carbonyl)$_{0-1}C_{0-10}$ alkyl,
aryl $C_{2-10}$ alkynyl(oxy)$_{0-1}$(carbonyl)$_{0-1}$ $C_{0-10}$ alkyl,
$C_{3-8}$ cycloalkyl $C_{0-10}$ alkyl(oxy)$_{0-1}$(carbonyl)$_{0-1}C_{0-10}$ alkyl,
heteroaryl $C_{0-10}$ alkyl(oxy)$_{0-1}$(carbonyl)$_{0-1}C_{0-10}$ alkyl,
$(C_{3-8})$heterocycloalkyl $C_{0-10}$ alkyl(oxy)$_{0-1}$(carbonyl)$_{0-1}$ $C_{0-10}$ alkyl,
$C_{1-10}$ alkyl(carbonyl)$_{0-1}$oxy$C_{0-10}$ alkyl,
$C_{1-10}$ heteroalkyl(carbonyl)$_{0-1}$oxy$C_{0-10}$ alkyl,
aryl $C_{0-10}$ alkyl(carbonyl)$_{0-1}$oxy$C_{0-10}$ alkyl,
$(C_{3-8})$cycloalkyl $C_{0-10}$ alkyl(carbonyl)$_{0-1}$oxy$C_{0-10}$ alkyl,
heteroaryl$C_{0-10}$ alkyl(carbonyl)$_{0-1}$oxy$C_{0-10}$ alkyl,
$(C_{3-8})$heterocycloalkyl $C_{0-10}$ alkyl(carbonyl)$_{0-1}$oxy$C_{0-10}$ alkyl,
$((C_{0-10})$alkyl$)_{1-2}$aminocarbonyloxy,
aryl$(C_{0-10})$alkylaminocarbonyloxy,
$(C_{3-8})$cycloalkyl$(C_{0-10})$alkylaminocarbonyloxy,
heteroaryl$(C_{0-10})$alkylaminocarbonyloxy,
$(C_{3-8})$heterocycloalkyl$(C_{0-10})$alkylaminocarbonyloxy,
$C_{1-10}$ alkylaminocarbonyl$C_{0-10}$ alkyl,
$C_{3-8}$ cycloalkyl $C_{0-10}$ alkylaminocarbonyl$C_{0-10}$ alkyl,
aryl $C_{0-10}$ alkylaminocarbonyl$C_{0-10}$ alkyl,
heteroaryl $C_{0-10}$ alkylaminocarbonyl$C_{0-10}$ alkyl,
$(C_{3-8})$heterocycloalkyl $C_{0-10}$ alkylaminocarbonyl$C_{0-10}$ alkyl,
$C_{1-10}$ alkyl(oxy)$_{0-1}$(carbonyl)$_{0-1}$amino$C_{0-10}$ alkyl,
$C_{3-8}$ cycloalkyl $C_{0-10}$ alkyl(oxy)$_{0-1}$(carbonyl)$_{0-1}$ amino$C_{0-10}$ alkyl,
aryl $C_{0-10}$ alkyl(oxy)$_{0-1}$(carbonyl)$_{0-1}$amino$C_{0-10}$ alkyl,
heteroaryl $C_{0-10}$ alkyl(oxy)$_{0-1}$(carbonyl)$_{0-1}$amino$C_{0-10}$ alkyl,
$(C_{3-8})$heterocycloalkyl $C_{0-10}$ alkyl(oxy)$_{0-1}$(carbonyl)$_{0-1}$ amino$C_{0-10}$ alkyl,
—CO$_2$($C_{0-10}$ alkyl),
—($C_{0-10}$ alkyl)CO$_2$H,
Oxo (=O),
$C_{1-10}$ alkylS(O)$_{1-2}$,
$C_{1-10}$ heteroalkyl S(O)$_{1-2}$,
$(C_{3-8})$cycloalkylS(O)$_{1-2}$,
$(C_{3-8})$cycloheteroalkylS(O)$_{1-2}$,
heteroarylS(O)$_{1-2}$,
arylS(O)$_{1-2}$,
$C_{0-6}$ alkyl(amino)$_{0-1}$S(O)$_{1-2}$amino,
$C_{1-10}$ heteroalkyl(amino)$_{0-1}$S(O)$_{1-2}$amino,
$(C_{3-8})$cycloalkyl(amino)$_{0-1}$S(O)$_{1-2}$amino,
$(C_{3-8})$cycloheteroalkyl(amino)$_{0-1}$S(O)$_{1-2}$amino,
heteroaryl(amino)$_{0-1}$S(O)$_{1-2}$amino,
aryl(amino)$_{0-1}$S(O)$_{1-2}$amino,
—SO$_2$N($C_{1-6}$alkyl)$_{1-2}$,
—SO$_2$C$_{1-6}$alkyl,
—SO$_2$CF$_3$,
—SO$_2$CF$_2$H,
amino,
$(C_{0-10}$ alkyl)$_{1-2}$ amino,
-(oxy)$_{0-1}$(carbonyl)$_{0-1}$N($C_{0-10}$ alkyl)$_{1-2}$,
hydroxy,
($C_{1-10}$ alkyl)OH,
$C_{1-10}$ alkoxy,
cyano, and
$C_{1-6}$haloalkyl;
$R^4$ is substituted with 0, 1, 2, or 3 $R^5$ substituents and each $R^5$ substituent is independently selected from hydroxy, $(C_{1-6})$alkyl, $(C_{1-6})$alkoxy, $(C_{1-10}$ alkyl)OH, halogen, CO$_2$H, —$(C_{0-6})$alkylCN, —O(C=O)C$_1$-C$_6$ alkyl, —(C=O)OC$_1$-C$_6$ alkyl, NO$_2$, trifluoromethoxy, trifluoroethoxy, trifluoromethyl, trifluoroethyl, —N—C(O)O(C$_{0-6}$)alkyl, $C_{1-10}$ alkylsulfonyl, $C_{1-10}$ heteroalkyl, aryl, $C_{3-8}$ cycloalkyl, heteroaryl, $(C_{3-8})$heterocycloalkyl, $C_{1-10}$ heteroalkylsulfonyl, oxo (O=), $(C_{3-8})$cycloalkylsulfonyl, $(C_{3-8})$cycloheteroalkylsulfonyl, heteroarylsulfonyl, arylsulfonyl, aminosulfonyl, —SO$_2$N(C$_{1-6}$alkyl)$_{1-2}$, —SO$_2$C$_{1-6}$alkyl, —SO$_2$CF$_3$, —SO$_2$CF$_2$H, —$C_{1-10}$ alkylsulfinyl, —O$_{(0-1)}$(C$_{1-10}$)haloalkyl, amino($C_{1-6}$alkyl)$_{0-2}$ and NH$_2$; and $R^5$ is substituted with 0, 1, or 2 $R^6$ substituents and each $R^6$ substituent is independently selected from hydroxy, $(C_{1-6})$alkyl, $(C_{1-6})$alkoxy, $(C_{1-10}$ alkyl)OH, halogen, CO$_2$H, —$(C_{0-6})$alkylCN, —O(C=O)C$_1$-C$_6$ alkyl, —(C=O)OC$_1$-C$_6$ alkyl, NO$_2$, trifluoromethoxy, trifluoroethoxy, trifluoromethyl, trifluoroethyl, —N—C(O)O(C$_{0-6}$)alkyl, $C_{1-10}$ alkylsulfonyl, $C_{1-10}$ heteroalkylsulfonyl, oxo (O=), $(C_{3-8})$cycloalkylsulfonyl, $(C_{3-8})$cycloheteroalkylsulfonyl, heteroarylsulfonyl, arylsulfonyl, aminosulfonyl, —SO$_2$N(C$_{1-6}$alkyl)$_{1-2}$, —SO$_2$C$_{1-6}$alkyl, —SO$_2$CF$_3$, —SO$_2$CF$_2$H, —O$_{(0-1)}$(C$_{1-10}$)haloalkyl, amino(C$_{1-6}$alkyl)$_{0-2}$ and NH$_2$.

Another embodiment of the invention includes compounds of formula II or pharmaceutically acceptable salts or stereoisomers thereof:

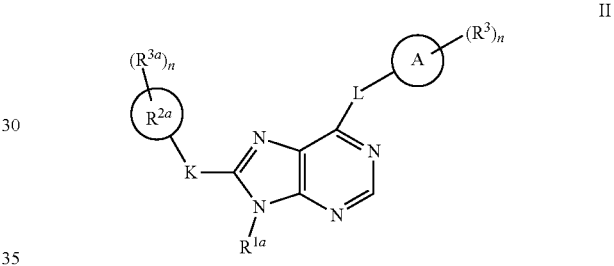

II $R^{1a}$ is selected from hydrogen, methyl, ethyl, propyl, butyl, pentyl, cyclopropyl, cyclobutyl, and cyclopentyl, wherein $R^{1a}$ is optionally substituted by 0, 1, 2, 3, or 4 groups independently selected from fluoro, chloro, methyl and amino;

$R^{2a}$ is selected from hydrogen, halogen, $C_{1-10}$alkyl, $C_{3-12}$ cycloalkyl, $C_{3-12}$heterocycloalkyl, $C_{1-10}$ heteroalkyl, $C_{2-10}$alkynyl, aryl, iodo, and heteroaryl, wherein $R^{2a}$ is substituted with 0, 1, 2, 3, or 4 $R^{3a}$ substituents;

n is 0, 1, 2, 3, or 4;

A is selected from pyrrolidinyl, piperidinyl, cyclobutyl, cyclohexyl, azaspiro[2.4]hept-2-yl, azabicyclo[2.2.1]heptanyl, azetidinyl, and cyclopentyl;

L is selected from O, S, SO$_2$, and —CH$_2$;

K is selected from a bond, NH, O, C(O), CH$_2$, N((C$_{1-5}$)alkyl)$_{1-2}$, —C(O)N(R$^b$)—(CH$_2$)$_m$, S, SO$_2$, and C$_{2-10}$ alkynylene;

$R^b$ is H or $C_{1-10}$ alkyl;

m is 0, 1, 2, or 3;

$R^{3a}$ is independently selected from: fluoro, chloro, methyl, ethyl, methoxy, pyrazolyl, hydroxyl, dimethylamino, morpholinyl, pyrrolidinyl, tert-butyl, methylsulfonyl, trifluoromethyl, phenyl, hydroxymethyl, cyclopropyl, imidazolyl, methylsulfonylamino, acetylamino, methylcarbonylamino, cyano, and amino, wherein $R^{3a}$ is each substituted with 0, 1, 2, 3, or 4 $R^4$ substituents and each $R^4$ is independently selected from: halogen, methyl, ethyl, hydroxy, and amino;

$R^3$ is independently selected from:
halogen,
$C_{1-10}$ alkyl(oxy)$_{0-1}$(carbonyl)$_{0-1}C_{0-10}$ alkyl, $C_{2-10}$ alkenyl(oxy)$_{0-1}$(carbonyl)$_{0-1}C_{0-10}$ alkyl,
$C_{1-10}$ heteroalkyl(oxy)$_{0-1}$(carbonyl)$_{0-1}C_{0-10}$ alkyl,
aryl $C_{0-10}$ alkyl(oxy)$_{0-1}$(carbonyl)$_{0-1}C_{0-10}$ alkyl,
$C_{3-12}$ cycloalkyl$C_{0-10}$ alkyl(oxy)$_{0-1}$(carbonyl)$_{0-1}C_{0-10}$alkyl,
heteroaryl$C_{0-10}$alkyl(oxy)$_{0-1}$(carbonyl)$_{0-1}$ $C_{0-10}$ alkyl,
$(C_{3-12})$heterocycloalkyl $C_{0-10}$ alkyl(oxy)$_{0-1}$(carbonyl)$_{0-1}$ $C_{0-10}$ alkyl,
$C_{1-10}$ alkylamino(carbonyl)$_{0-1}C_{0-10}$ alkyl,
$(C_{1-10})$heteroalkylamino(carbonyl)$_{0-1}C_{0-10}$ alkyl,
$C_{3-12}$ cycloalkyl $C_{0-10}$ alkylamino(carbonyl)$_{0-1}C_{0-10}$ alkyl,
aryl $C_{0-10}$ alkylamino(carbonyl)$_{0-1}C_{0-10}$ alkyl,
heteroaryl$C_{0-1}$alkylamino(carbonyl)$_{0-1}C_{0-10}$ alkyl,
$(C_{3-12})$heterocycloalkyl$C_{0-10}$alkylamino(carbonyl)$_{0-1}$ $C_{0-10}$ alkyl,
$C_{1-10}$ alkyl(oxy)$_{0-1}$(carbonyl)$_{0-1}$amino$C_{0-10}$ alkyl,
$C_{1-10}$ heteroalkyl(oxy)$_{0-1}$(carbonyl)$_{0-1}$amino$C_{0-10}$ alkyl,
$C_{3-12}$ cycloalkyl $C_{0-10}$ alkyl(oxy)$_{0-1}$(carbonyl)$_{0-1}$ amino$C_{0-10}$ alkyl,
aryl $C_{0-10}$ alkyl(oxy)$_{0-1}$(carbonyl)$_{0-1}$amino$C_{0-10}$ alkyl,
heteroaryl $C_{0-10}$ alkyl(oxy)$_{0-1}$(carbonyl)$_{0-1}$amino$C_{0-10}$ alkyl,
$(C_{3-12})$heterocycloalkyl $C_{0-10}$ alkyl(oxy)$_{0-1}$(carbonyl)$_{0-1}$ amino$C_{0-10}$ alkyl,
—$CO_2(C_{0-10}$ alkyl),
—$(C_{0-10}$ alkyl)$CO_2H$,
Oxo (=O),
$C_{1-10}$alkylS(O)$_{1-2}$,
heteroarylS(O)$_{1-2}$,
arylS(O)$_{1-2}$,
$C_{0-6}$ alkyl(amino)$_{0-1}$S(O)$_{1-2}$amino,
$C_{1-10}$ heteroalkyl(amino)$_{0-1}$S(O)$_{1-2}$amino,
$(C_{3-12})$cycloalkyl(amino)$_{0-1}$S(O)$_{1-2}$amino,
$(C_{3-12})$cycloheteroalkyl(amino)$_{0-1}$S(O)$_{1-2}$amino,
heteroaryl(amino)$_{0-1}$S(O)$_{1-2}$amino,
$C_{1-10}$heteroalkylS(O)$_{1-2}$, $(C_{3-12})$cycloalkylS(O)$_{1-2}$,
$(C_{3-12})$cycloheteroalkylS(O)$_{1-2}$,
heteroarylS(O)$_{1-2}$, arylS(O)$_{1-2}$,
—$SO_2N(C_{0-6}$ alkyl)$_{0-2}$,
—$SO_2CF_3$, amino,
$(C_{0-10}$ alkyl)$_{1-2}$ amino,
hydroxy,
$(C_{1-10}$ alkyl)OH,
$C_{0-10}$ alkylalkoxy,
cyano,
$C_{1-6}$alkylcyano, and
$C_{1-6}$haloalkyl; wherein $R^3$ is each substituted with 0, 1, 2, 3, or 4 substituents, $R^4$;
$R^4$ is independently selected from:
halogen,
$C_{1-10}$ alkyl(oxy)$_{0-1}$(carbonyl)$_{0-1}C_{0-10}$ alkyl,
aryl $C_{0-10}$ alkyl(oxy)$_{0-1}$(carbonyl)$_{0-1}C_{0-10}$ alkyl,
$C_{3-12}$ cycloalkyl $C_{0-10}$ alkyl(oxy)$_{0-1}$(carbonyl)$_{0-1}C_{0-10}$ alkyl,
heteroaryl $C_{0-10}$ alkyl(oxy)$_{0-1}$(carbonyl)$_{0-1}C_{0-10}$ alkyl,
$C_{3-12}$heterocycloalkyl $C_{0-10}$ alkyl(oxy)$_{0-1}$(carbonyl)$_{0-1}$ $C_{0-10}$ alkyl,
$C_{1-10}$ alkyl(oxy)$_{0-1}$(carbonyl)$_{0-1}$amino$C_{0-10}$ alkyl,
Oxo (=O),
—$SO_2C_{1-6}$alkyl,
amino,
$(C_{0-10}$ alkyl)$_{1-2}$ amino,
$(C_{1-10}$ alkyl)OH,
$C_{1-10}$ alkoxy,
cyano, and
$C_{1-6}$haloalkyl; wherein $R^4$ is substituted with 0, 1, 2, or 3 $R^5$;
$R^5$ is independently selected from hydroxy, $(C_{1-6})$alkyl, $(C_{1-6})$alkoxy, halogen, $CO_2H$, —$(C_{0-6})$alkylCN, $NO_2$, trifluoromethoxy, trifluoroethoxy, trifluoromethyl, trifluoroethyl, oxo (O=), —$O_{(0-1)}(C_{1-10})$haloalkyl, amino$(C_{1-6}$alkyl)$_{0-2}$ and $NH_2$; and $R^5$ is substituted with 0, 1, or 2 $R^6$ substituents;
$R^6$ is independently selected from hydroxy, methyl, halogen, oxo (O=) and $NH_2$.

In one embodiment, $R^{2a}$ is selected from cyclopropyl, isobutyl, 2-methylpropyl, methyl, ethyl, iodo, pyridazinyl, pyrimidinyl, pyrazinyl, pyridinyl, pyrrolidinyl, piperidinyl, ethoxycarbonyl, cyclohexyl, phenyl, quinazolinyl, isoquinolinyl, pyrazolyl, imidazolyl, indolyl, indazolyl, thiazolyl, pyrazolo[1,5-a]pyrimidinyl, 3,6-dihydro-2H-pyranyl, 1H-pyrrolo[2,3-b]pyridinyl, cyclobutyl, hydrogen, 1H-pyrazolo[3,4-b]pyridinyl, pyrrolo[2,3-b]pyridinyl, benzimidazolyl, morpholinyl, 4,5,6,7,-tetrahydropyrazolo[1,5-a]pyridinyl, 5,6-dihydro-4H-pyrrolo[1,2-b]pyrazolyl, wherein $R^2$ is substituted with 0, 1, 2, 3, or 4 independently selected $R^3$.

In one embodiment, $R^3$ is independently selected from: fluoro, chloro, methyl, ethyl, propyl, methoxy, pyrazolyl, thiazolyl, benzisoxazolyl, pyrazinyl, cyclopropyl, pyridinyl, hydroxy, oxo (=O), dimethylamino, morpholinyl, pyrrolidinyl, tert-butyl, trifluoromethyl, methoxymethyl, isobutylcarboxy, tert-butylcarboxy, phenylcarboxy, hydrogen, methylpropylcarboxy, ethoxycarbonyl, napthalenylcarboxy, benzylcarboxy, isobutylcarboxy, 2,2,-dimethylpropylcarboxy, methylcarboxy, ethylcarboxy, methylethylcarboxy, cyclopentylcarbonyl, cyclobutylcarbonyl, spiro[2.4]heptylcarbonyl, imidazolylcarbonyl, ethylcarbonyl, methylethylcarbonyl, propyloxycarbonyl, phenylcarbonyl, piperidinylcarbonyl, napthalenylcarbonyl, cyclohexylcarbonyl, methylcarbonyl, (tetrahydro-2H-pyran-4-ylmethyl)carbonyl, tetrahydro-2H-pyran-4-ylcarbonyl, oxazolylcarbonyl, pyridinylcarbonyl, cyclopropylcarbonyl, pyrrolidinylmethylcarbonyl, azetidinylcarbonyl, tetrahydropyranylcarbonyl, tetrahydropyranylcarbonylamino, cyclopropylaminocarbonyl, tetrahydrofuranylcarbonyl, isoxazolylcarbonyl, pyrazolo[1,5-a]pyridinylcarbonyl, triazolylcarbonyl, 1,2,3-triazolylcarbonyl, imidazo[1,2-a]pyrimidinylcarbonyl, thiadiazolylcarbonyl, 1,2,3-thiadiazolylcarbonyl, furo[3,2-b]pyrrolylcarbonyl, pyrazolylcarbonyl, pyrrolindinylcarbonyl, hydroxymethyl, fluoromethyl, pyrrolylcarbonyl, imidazo[1,2-b]pyrazolylcarbonyl, pyrrolo[3,2-b]pyridinylcarbonyl, pyrrolo[1,2-d]tetrazolylcarbonyl, oxadiazolylcarbonyl, 1,2,5-oxadiaxolylcarbonyl, 1,3,4-oxadiazolylcarbonyl, 1,2,4-oxadiazolylcarbonyl, pyrrolo[1,2-b]pyrazolylcarbonyl, ethylcarbonyl, trifluoromethylsulfonyl, ethylsulfonyl, methylsulfonyl, ethylsulfonylamino, methylsulfonylamino, (methylethyl)sulfonyl, phenylsulfonyl, imidazolylsulfonyl, naphthalenylsulfonyl, 5,6,7,8-tetrahydro[1,2,4]triazolo[4,3-a]pyridinylcarbonyl, [1,2,4]triazolo-[1,5-a]pyridinylcarbonyl, acetylamino, azabicyclo[3.1.0]hexylcarbonyl, azabicyclo[2.2.1]heptylcarbonyl, methylethylaminocarbonyl, cyclohexylaminocarbonyl, phenylaminocarbonyl, tetramethylbutylaminocarbonyl, benzylaminocarbonyl, ethylaminocarbonyl, methylcarbonylamino, bicyclo[2.2.1]heptylcarbonyl, phenyl, cyclohexylmethyl, phenylmethyl, 1-phenylethyl, pyrrolylmethyl, pyrimidinyl, thieno[2,3-d]pyrimidinyl, thieno[3,2-c]pyridinyl, difluoromethyl, [1,2,4]triazolo[4.3-a]pyrazinyl, phthalazinyl, pyrazolo[3,4-d]pyrimidinyl, morpholinylcarbonyl, tert-butylaminocarbonyl, tert-butyloxycarbonylamino, 2-methylpropylcarbonyl, (2-methylprop-1-ene)

carbonyl, cyclopropylcarbonylamino, cyano, tetrahydro-2H-pyranylcarbonylamino, imidazo[4,5-b]pyridinyl, 1,3-dihydro-2H-imidazo[4,5-b]pyridinyl, amino, and isobutylcarbonyl; wherein $R^3$ is each substituted with 0, 1, 2, 3, or 4 substituents, $R^4$.

In another embodiment, $R^4$ is selected from: methyl, trifluoromethyl, methoxy, dimethylamino, fluoro, cyano, oxo, piperazinyl, methylethyl, chloro, hydroxypropyl, cyclopropyl, ethyl, tert-butyl, difluormethyl, hydroxymethyl, fluoromethyl, phenyl, ethylcarboxy, pyrazolyl, and furanyl; wherein $R^4$ is substituted with 0, 1, 2, or 3 $R^5$.

In one embodiment, $R^5$ is independently selected from hydroxy, $(C_{1-6})$alkyl, $(C_{1-6})$alkoxy, halogen, $CO_2H$, —$(C_{0-6})$alkylCN, trifluoromethyl, trifluoroethyl, oxo (O=), —$O_{(0-1)}(C_{1-10})$haloalkyl, amino$(C_{1-6}$alkyl$)_{0-2}$ and $NH_2$. In another variant, $R^5$ is independently, methyl or fluoro.

In a particular embodiment of the invention the compound of formula 1 is selected from:
8-(1-ethyl-5-methyl-1H-pyrazol-4-yl)-9-methyl-6-{[1-(tetrahydro-2H-pyran-4-ylcarbonyl)pyrrolidin-3-yl]oxy}-9H-purine;
8-(1-ethyl-5-methyl-1H-pyrazol-4-yl)-9-methyl-6-{[1-(1,3-oxazol-4-ylcarbonyl)pyrrolidin-3-yl]oxy}-9H-purine;
6-{[1-(cyclopropylcarbonyl)-2-methylpyrrolidin-3-yl]oxy}-9-ethyl-8-(2-methylpyrimidin-5-yl)-9H-purine;
6-{[1-(cyclobutylcarbonyl)pyrrolidin-3-yl]oxy}-8-(1-ethyl-5-methyl-1H-pyrazol-4-yl)-9-methyl-9H-purine;
6-({1-[(3,3-difluorocyclobutyl)carbonyl]pyrrolidin-3-yl}oxy)-8-(1-ethyl-5-methyl-1H-pyrazol-4-yl)-9-methyl-9H-purine;
6-{[1-(cyclopropylcarbonyl)pyrrolidin-3-yl]oxy}-9-ethyl-8-(2-methylpyrimidin-5-yl)-9H-purine;
9-ethyl-6-({1-[(1-methyl-1H-pyrazol-3-yl)carbonyl]pyrrolidin-3-yl}oxy)-8-(2-methylpyrimidin-5-yl)-9H-purine;
6-{[1-{[2-(difluoromethyl)cyclopropyl]carbonyl}pyrrolidin-3-yl]oxy}-9-ethyl-8-(2-methylpyrimidin-5-yl)-9H-purine;
9-ethyl-6-{[1-{[2-(fluoromethyl)cyclopropyl]carbonyl}pyrrolidin-3-yl]oxy}-8-(2-methylpyrimidin-5-yl)-9H-purine;
9-ethyl-6-({1-[(2-fluorocyclopropyl)carbonyl]pyrrolidin-3-yl}oxy)-8-(2-methylpyrimidin-5-yl)-9H-purine;
9-ethyl-8-(2-methylpyrimidin-5-yl)-6-{[1-(1,3-oxazol-4-ylcarbonyl)pyrrolidin-3-yl]oxy}-9H-purine;
6-{[1-(cyclopropylcarbonyl)-4-fluoropyrrolidin-3-yl]oxy}-9-ethyl-8-(2-methylpyrimidin-5-yl)-9H-purine;
6-{[1-(cyclopropylcarbonyl)pyrrolidin-3-yl]oxy}-9-ethyl-8-[6-(trifluoromethyl)pyridin-3-yl]-9H-purine;
6-{[1-(cyclopropylcarbonyl)pyrrolidin-3-yl]oxy}-9-ethyl-8-[4-(trifluoromethyl)phenyl]-9H-purine;
6-{[1-(cyclopropylcarbonyl)pyrrolidin-3-yl]oxy}-9-ethyl-8-(5-methyl-1-phenyl-1H-pyrazol-4-yl)-9H-purine;
2-methoxy-5-(9-methyl-6-{[1-propanoylpyrrolidin-3-yl]oxy}-9H-purin-8-yl)pyridine-3-carbonitrile;
9-methyl-6-{[1-propanoylpyrrolidin-3-yl]oxy}-8-(4,5,6,7-tetrahydropyrazolo[1,5-a]pyridin-3-yl)-9H-purine;
5-(6-{[1-(cyclopropylcarbonyl)pyrrolidin-3-yl]oxy}-9-ethyl-9H-purin-8-yl)-2-methoxypyridine-3-carbonitrile;
5-(6-{[1-(cyclopropylcarbonyl)pyrrolidin-3-yl]oxy}-9-ethyl-9H-purin-8-yl)-3-(trifluoromethyl)pyridin-2-amine;
9-ethyl-8-(1-ethyl-5-methyl-1H-pyrazol-4-yl)-6-{[1-(tetrahydro-2H-pyran-4-ylcarbonyl)pyrrolidin-3-yl]oxy}-9H-purine;
6-{[1-(cyclopropylcarbonyl)-4,4-dimethylpyrrolidin-3-yl]oxy}-9-ethyl-8-(2-methylpyrimidin-5-yl)-9H-purine;
6-{[5-(cyclopropylcarbonyl)-5-azaspiro[2.4]hept-7-yl]oxy}-9-ethyl-8-(2-methylpyrimidin-5-yl)-9H-purine;
6-{[1-(cyclopropylcarbonyl)-4-methylpyrrolidin-3-yl]oxy}-9-ethyl-8-(2-methylpyrimidin-5-yl)-9H-purine;
6-{[1-(azetidin-1-ylcarbonyl)pyrrolidin-3-yl]oxy}-9-ethyl-8-(2-methylpyrimidin-5-yl)-9H-purine;
9-ethyl-6-({1-[(3-methoxyazetidin-1-yl)carbonyl]pyrrolidin-3-yl}oxy)-8-(2-methylpyrimidin-5-yl)-9H-purine;
6-({1-[(3,3-difluoroazetidin-1-yl)carbonyl]pyrrolidin-3-yl}oxy)-9-ethyl-8-(2-methylpyrimidin-5-yl)-9H-purine; and
9-ethyl-6-({1-[(3-methoxyazetidin-1-yl)carbonyl]pyrrolidin-3-yl}oxy)-8-[6-(trifluoromethyl)pyridin-3-yl]-9H-purine;
or pharmaceutically acceptable salts or stereoisomers thereof.

In a variant of this embodiment, the compound is selected from:
8-(1-ethyl-5-methyl-1H-pyrazol-4-yl)-9-methyl-6-{[1-(tetrahydro-2H-pyran-4-ylcarbonyl)pyrrolidin-3-yl]oxy}-9H-purine;
8-(1-ethyl-5-methyl-1H-pyrazol-4-yl)-9-methyl-6-{[1-(1,3-oxazol-4-ylcarbonyl)pyrrolidin-3-yl]oxy}-9H-purine;
6-{[1-(cyclopropylcarbonyl)-2-methylpyrrolidin-3-yl]oxy}-9-ethyl-8-(2-methylpyrimidin-5-yl)-9H-purine;
6-{[1-(cyclopropylcarbonyl)pyrrolidin-3-yl]oxy}-9-ethyl-8-(2-methylpyrimidin-5-yl)-9H-purine;
9-ethyl-6-({1-[(1-methyl-1H-pyrazol-3-yl)carbonyl]pyrrolidin-3-yl}oxy)-8-(2-methylpyrimidin-5-yl)-9H-purine;
6-{[1-{[2-(difluoromethyl)cyclopropyl]carbonyl}pyrrolidin-3-yl]oxy}-9-ethyl-8-(2-methylpyrimidin-5-yl)-9H-purine;
9-ethyl-6-{[1-{[2-(fluoromethyl)cyclopropyl]carbonyl}pyrrolidin-3-yl]oxy}-8-(2-methylpyrimidin-5-yl)-9H-purine;
9-ethyl-6-({1-[(2-fluorocyclopropyl)carbonyl]pyrrolidin-3-yl}oxy)-8-(2-methylpyrimidin-5-yl)-9H-purine;
9-ethyl-8-(2-methylpyrimidin-5-yl)-6-{[1-(1,3-oxazol-4-ylcarbonyl)pyrrolidin-3-yl]oxy}-9H-purine;
6-{[1-(cyclopropylcarbonyl)-4-fluoropyrrolidin-3-yl]oxy}-9-ethyl-8-(2-methylpyrimidin-5-yl)-9H-purine;
6-{[1-(cyclopropylcarbonyl)-4-methylpyrrolidin-3-yl]oxy}-9-ethyl-8-(2-methylpyrimidin-5-yl)-9H-purine;
6-{[1-(azetidin-1-ylcarbonyl)pyrrolidin-3-yl]oxy}-9-ethyl-8-(2-methylpyrimidin-5-yl)-9H-purine;
9-ethyl-6-({1-[(3-methoxyazetidin-1-yl)carbonyl]pyrrolidin-3-yl}oxy)-8-(2-methylpyrimidin-5-yl)-9H-purine;
6-({1-[(3,3-difluoroazetidin-1-yl)carbonyl]pyrrolidin-3-yl}oxy)-9-ethyl-8-(2-methylpyrimidin-5-yl)-9H-purine; and
9-ethyl-6-({1-[(3-methoxyazetidin-1-yl)carbonyl]pyrrolidin-3-yl}oxy)-8-[6-(trifluoromethyl)pyridin-3-yl]-9H-purine;
or pharmaceutically acceptable salts or stereoisomers thereof.

In yet another variant of this embodiment, the compound of the invention is selected from:
6-({1-[(3,3-difluorocyclobutyl)carbonyl]pyrrolidin-3-yl}oxy)-8-(1-ethyl-5-methyl-1H-pyrazol-4-yl)-9-methyl-9H-purine;
2-methoxy-5-(9-methyl-6-{[1-propanoylpyrrolidin-3-yl]oxy}-9H-purin-8-yl)pyridine-3-carbonitrile;
9-methyl-6-{[1-propanoylpyrrolidin-3-yl]oxy}-8-(4,5,6,7-tetrahydropyrazolo[1,5-a]pyridin-3-yl)-9H-purine;
5-(6-{[1-(cyclopropylcarbonyl)pyrrolidin-3-yl]oxy}-9-ethyl-9H-purin-8-yl)-2-methoxypyridine-3-carbonitrile;
5-(6-{[1-(cyclopropylcarbonyl)pyrrolidin-3-yl]oxy}-9-ethyl-9H-purin-8-yl)-3-(trifluoromethyl)pyridin-2-amine;

9-ethyl-8-(1-ethyl-5-methyl-1H-pyrazol-4-yl)-6-{[1-(tetrahydro-2H-pyran-4-ylcarbonyl)pyrrolidin-3-yl]oxy}-9H-purine;

6-{[1-(cyclopropylcarbonyl)-4,4-dimethylpyrrolidin-3-yl]oxy}-9-ethyl-8-(2-methylpyrimidin-5-yl)-9H-purine;

6-{[5-(cyclopropylcarbonyl)-5-azaspiro[2.4]hept-7-yl]oxy}-9-ethyl-8-(2-methylpyrimidin-5-yl)-9H-purine;

6-{[1-(cyclopropylcarbonyl)pyrrolidin-3-yl]oxy}-9-ethyl-8-(2-methylpyrimidin-5-yl)-9H-purine;

6-{[1-(cyclopropylcarbonyl)pyrrolidin-3-yl]oxy}-9-ethyl-8-[4-(trifluoromethyl)phenyl]-9H-purine;

9-ethyl-6-({1-[(3-methoxyazetidin-1-yl)carbonyl]pyrrolidin-3-yl}oxy)-8-[6-(trifluoromethyl)pyridin-3-yl]-9H-purine;

9-ethyl-6-({1-[(3-methoxyazetidin-1-yl)carbonyl]pyrrolidin-3-yl}oxy)-8-(2-methylpyrimidin-5-yl)-9H-purine;

9-ethyl-8-(2-methylpyrimidin-5-yl)-6-{[1-(1,3-oxazol-4-ylcarbonyl)pyrrolidin-3-yl]oxy}-9H-purine;

or pharmaceutically acceptable salts or stereoisomers thereof.

"Patient" for the purposes of the present invention includes humans and other animals, particularly mammals and other organisms. Thus the methods are applicable to both human therapy and beterinary applications.

"Mammal" means humans and other mammalian animals.

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, and pharmaceutically acceptable excipients.

The term "optionally substituted" means "unsubstituted or substituted," and therefore, the generic structural formulas described herein encompasses compounds containing the specified optional substituent as well as compounds that do not contain the optional substituent.

Each variable is independently defined each time it occurs within the generic structural formula definitions. For example, when there is more than one substituent for aryl/heteroaryl, each substituent is independently selected at each occurrence, and each substituent can be the same or different from the other(s). As another example, for the group —(CR$^3$R$^3$)$_2$—, each occurrence of the two R$^3$ groups may be the same or different. As used herein, unless explicitly stated to the contrary, each reference to a specific compound of the present invention or a generic formula of compounds of the present invention is intended to include the compound(s) as well as pharmaceutically acceptable salts thereof.

Optical Isomers-Diastereomers-Geometric Isomers-Tautomers

Compounds of formula I contain one or more asymmetric centers and can thus occur as racemates and racemic mixtures, single enantiomers, diastereomeric mixtures and individual diastereomers. The present invention is meant to comprehend all such isomeric forms of the compounds of formula I, either as single species or mixtures thereof.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of formula I.

Specific embodiments of the present invention include a compound which is selected from the group consisting of the subject compounds of the Examples herein or a pharmaceutically acceptable salt thereof.

The compounds of the present invention may contain one or more asymmetric centers and can thus occur as "stereoisomers" including racemates and racemic mixtures, enantiomeric mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the scope of this invention. The present invention is meant to comprehend all such isomeric forms of these compounds. When bonds to the chiral carbon are depicted as straight lines in the Formulas of the invention, it is understood that both the (R) and (S) configurations of the chiral carbon, and hence both enantiomers and mixtures thereof, are embraced within the Formula. For example, Formula I shows the structure of the class of compounds without specific stereochemistry. When the compounds of the present invention contain one chiral center, the term "stereoisomer" includes both enantiomers and mixtures of enantiomers, such as the specific 50:50 mixture referred to as racemic mixtures.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

In the present application when a particular stereomeric compound is named using an "and" in the stereomeric designation, for example, (S and R)-tert-butyl 3-((8-(1-ethyl-5-methyl-1H-pyrazol-4-yl)-9-methyl-9H-purin-6-yl)oxy)piperidine-1-carboxylate, the "and" indicates a racemic mixture of the enantiomers. That is, the individual enantiomers were not individually isolated.

When the stereomeric nomenclature includes "or", for example, (S or R)-tert-butyl 3-((8-(1-ethyl-5-methyl-1H-pyrazol-4-yl)-9-methyl-9H-purin-6-yl)oxy)piperidine-1-carboxylate, the "or" indicates that chiral resolution of racemate into individual enantiomers was accomplished but the actual optical activity of the specific enantiomer was not determined.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound can be obtained by stereoselective synthesis using optically pure starting materials or reagents of known configuration by methods well known in the art.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, unless otherwise specified, references to the compound of formula I, subsets thereof, embodiments thereof, as well as specific compounds are meant to also include the pharmaceutically acceptable salts.

Furthermore, some of the crystalline forms for compounds of the present invention may exist as polymorphs and as such all forms are intended to be included in the present invention.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—$(C_1$-$C_2)$alkylamino$(C_2$-$C_3)$alkyl (such as β-dimethylaminoethyl), carbamoyl-$(C_1$-$C_2)$alkyl, N,N-di $(C_1$-$C_2)$alkylcarbamoyl-(C1-C2)alkyl and piperidino-, pyrrolidino- or morpholino$(C_2$-$C_3)$alkyl, and the like.

Similarly, if a compound of Formula (I) contains an alcohol functional group, a prodrug can be formed by the replacement of the hydrogen atom of the alcohol group with a group such as, for example, $(C_1$-$C_6)$alkanoyloxymethyl, 1-(($C_1$-$C_6)$alkanoyloxy)ethyl, 1-methyl-1-(($C_1$-$C_6)$alkanoyloxy)ethyl, $(C_1$-$C_6)$alkoxycarbonyloxymethyl, N—$(C_1$-$C_6)$ alkoxycarbonylaminomethyl, succinoyl, $(C_1$-$C_6)$alkanoyl, α-amino$(C_1$-$C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$-$C_6)$alkyl$)_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1$-$C_{10})$ alkyl, $(C_3$-$C_7)$cycloalkyl, benzyl, or R-carbonyl is a natural α-aminoacyl or natural α-aminoacyl, —$C(OH)C(O)OY^1$ wherein $Y^1$ is H, $(C_1$-$C_6)$alkyl or benzyl, —$C(OY^2)Y^3$ wherein $Y^2$ is $(C_1$-$C_4)$ alkyl and $Y^3$ is $(C_1$-$C_6)$alkyl, carboxy $(C_1$-$C_5)$alkyl, amino$(C_1$-$C_4)$alkyl or mono-N— or di-N,N—$(C_1$-$C_6)$alkylaminoalkyl, —$C(Y^4)Y^5$ wherein $Y^4$ is H or methyl and $Y^5$ is mono-N— or di-N,N—$(C_1$-$C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Tech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Labelled Compounds

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Additionally, the present invention is meant to include in compounds of generic Formula I, all suitable replacements of sp3 orbital carbons to sp3 Si as can readily be envisioned by one of ordinary skill in the art.

Utilities

Compounds of the Invention have activity for PI3K-delta. Compounds of this invention have been tested using the assays described in the Biological Examples and have been determined to be inhibitors of PI3K-delta. Suitable in vitro assays for measuring PI3K-delta activity and the inhibition thereof by compounds are known in the art. For further details of an in vitro assay for measuring PI3K-delta see the Biological Examples herein. Cell-based assays for measurement of in vitro efficacy in treatment of cancer are known in the art. In addition, assays are described in the Biological Examples provided herein.

Suitable in vivo models for cancer are known to those of ordinary skill in the art. See for example, international patent application published as WO 2012/037226 for further details of in vivo models for prostate adenocarcinoma, glioblastoma, lung carcinoma, and melanoma. Following the examples disclosed herein, as well as that disclosed in the art, a person of ordinary skill in the art can determine the activity of a compound of this invention.

Compounds of Formula I are useful for treating diseases, including autoimmune disorders, inflammatory diseases, and cancers, which are listed below.

Cancers: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma, prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplasia syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma.

Autoimmune diseases: Hashimoto's thyroiditis, systemic lupus erythematosus (SLE), Goodpasture's syndrome, pemphigus, receptor autoimmune diseases, Basedow's disease (Graves' disease), myasthernia gravis, insulin resistant diseases, autoimmune hemolytic anemia, autoimmune thrombocytopenic purpura, autoimmune encephalomyelitis, rheumatism, rheumatoid arthritis, scleroderma, mixed connective tissue disease, polymyositis, pernicious anemia, idiopathic Addison's disease, some types of infertility, glomerulonephritis, bullous pemphigus, Sjogren's syndrome, some types of diabetes, adrenergic agent resistance, chronic active hepatitis, primary biliary cirrhosis, endocrine failure, vitiligo, angiitis, post-cardiac surgery syndrome, urticaria, atopic dermatiti and multiple sclerosis, autoimmune polyglandular disease (also known as autoimmune polyglandular syndrome), autoimmune alopecia; pernicious anemia; vitiligo; autoimmune hypopituatarism, and Guillain-Barre syndrome.

Inflammatory Diseases: asthma, allergic rhinitis, psoriasis, inflammatory arthritis, rheumatoid arthritis, psoriatic arthritis or osteoarthritis, irritable bowel syndrome, ulcerative colitis, Crohn's disease, respiratory allergies (asthma, hay fever, allergic rhinitis) or skin allergies, scleracierma, mycosis fungoides, acute inflammatory responses (such as acute respiratory distress syndrome and ishchemia/reperfusion injury), dermatomyositis, alopecia greata, chronic actinic dermatitis, eczema, Behcet's disease, Pustulosis palmoplanteris, Pyoderma gangrenum, Sezary's syndrome, atopic dermatitis, systemic sclerosis, and morphea.

Central Nervous System Disorders: multiple sclerosis, schizophrenia

Thus, in one embodiment, the invention provides a method of inhibiting PI3K-delta comprising contacting the PI3K-delta with an effective amount of a compound as disclosed herein.

In one embodiment, the compounds of the instant invention are selective PI3K-delta inhibitors relative to PI3K-alpha. The determination of relative selectivity for a given compound of PI3K-delta inhibition is defined as the relative ratio of the (PI3K-alpha $IC_{50}$ value/PI3K-delta $IC_{50}$ value) is at least 2. In yet another embodiment, for a given compound, the relative ratios of the (PI3K-alpha $IC_{50}$ value/PI3K-delta $IC_{50}$ value) is at least 4.

In another embodiment, the invention provides a method of treating a PI3K-delta modulated disease comprising administering to a mammal in need of such treatment a therapeutically effective amount of a compound as disclosed herein.

In another embodiment, the invention provides a method of treating cancer disease mediated by PI3K-delta comprising administering to a mammal in need of such treatment a therapeutically effective amount of a compound as disclosed herein.

Compounds of the invention are also useful as inhibitors of PI3K-delta in vivo for studying the in vivo role of PI3K-delta in biological processes, including the diseases described herein. Accordingly, the invention also comprises a method of inhibiting PI3K-delta in vivo comprising administering a compound or composition of the invention to a mammal.

Accordingly, another aspect of the present invention provides a method for the treatment or prevention of a PI3K-delta mediated disease or disorder comprising administering to a mammal in need thereof a therapeutically effective amount of a compound of formula I. In one embodiment such diseases include asthma and rheumatoid arthritis.

Another aspect of the present invention provides for the use of a compound of formula I in the manufacture of a medicament for the treatment or prevention of a PI3K-delta mediated diseases or disorder.

Dose Ranges

The magnitude of prophylactic or therapeutic dose of a compound of formula I will, of course, vary with the nature and the severity of the condition to be treated and with the particular compound of formula I and its route of administration. It will also vary according to a variety of factors including the age, weight, general health, sex, diet, time of administration, rate of excretion, drug combination and response of the individual patient. In general, the daily dose from about 0.001 milligram of active agent per kilogram body weight of a mammal (mg/kg) to about 100 mg/kg, typically, between 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.01 mg to 10 g of active agent compounded with an appropriate and convenient amount of carrier material which may vary from about 5 to about 99.95 percent of the total composition. Dosage unit forms will generally contain between from about 0.1 mg to about 0.4 g of an active ingredient, typically 0.5 mg, 1 mg, 2 mg, 5 mg, 10 mg, 25 mg, 50 mg, 100 mg, 200 mg, 400 mg, or 500 mg.

If formulated as a fixed dose, such combination products employ the compounds of this invention within the dosage range described above and the other pharmaceutically acceptable agent(s) when a combination formulation is inappropriate.

The final dosage regimen will be determined by the attending physician in view of good medical practice, considering various factors that modify the action of drugs, e.g., the agent's specific activity, the identity and severity of the disease state, the responsiveness of the patient, the age, condition, body weight, sex, and diet of the patient, and the severity of any infection. Additional factors that can be taken into account include time and frequency of administration, drug combinations, reaction sensitivities, and tolerance/response to therapy. Further refinement of the dosage appropriate for treatment involving any of the formulations mentioned herein is done routinely by the skilled practitioner without undue experimentation, especially in light of the dosage information and assays disclosed, as well as the pharmacokinetic data observed in human clinical trials. Appropriate dosages can be ascertained through use of established assays for determining concentration of the agent in a body fluid or other sample together with dose response data.

The frequency of dosing will depend on the pharmacokinetic parameters of the agent and the route of administration. Dosage and administration are adjusted to provide sufficient levels of the active moiety or to maintain the desired effect. Accordingly, the pharmaceutical compositions can be administered in a single dose, multiple discrete doses, continuous infusion, sustained release depots, or combinations thereof, as required to maintain desired minimum level of the agent. Short-acting pharmaceutical compositions (i.e., short half-life) can be administered once a day or more than once a day (e.g., two, three, or four times a day). Long acting pharmaceutical compositions might be administered every 3 to 4 days, every week, or once every two weeks. Pumps, such as subcutaneous, intraperitoneal, or subdural pumps, can be preferred for continuous infusion.

Pharmaceutical Compositions

Another aspect of the present invention provides pharmaceutical compositions comprising a compound of formula I with a pharmaceutically acceptable carrier. For the treatment of any of the prostanoid mediated diseases compounds of formula I may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Additional excipients, for example sweetening, flavoring and coloring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage forms for inhaled administration may conveniently be formulated as aerosols or dry powders. For compositions suitable and/or adapted for inhaled administration, it is preferred that the active substance is in a particle-size-reduced form, and more preferably the size-reduced form is obtained or obtainable by micronization.

In one embodiment the medicinal preparation is adapted for use with a pressurized metered dose inhaler (pMDI) which releases a metered dose of medicine upon each actuation. The formulation for pMDIs can be in the form of solutions or suspensions in halogenated hydrocarbon propellants. The type of propellant being used in pMDIs is being shifted to hydrofluoroalkanes (HFAs), also known as hydrofluorocarbons (HFCs). In particular, 1,1,1,2-tetrafluoroethane (HFA 134a) and 1,1,1,2,3,3,3-heptafluoropropane (HFA 227) are used in several currently marketed pharmaceutical inhalation products. The composition may include other pharmaceutically acceptable excipients for inhalation use such as ethanol, oleic acid, polyvinylpyrrolidone and the like.

Pressurized MDIs typically have two components. Firstly, there is a canister component in which the drug particles are stored under pressure in a suspension or solution form. Secondly, there is a receptacle component used to hold and actuate the canister. Typically, a canister will contain multiple doses of the formulation, although it is possible to have single dose canisters as well. The canister component typically includes a valve outlet from which the contents of the canister can be discharged. Aerosol medication is dispensed from the pMDI by applying a force on the canister component to push it into the receptacle component thereby opening the valve outlet and causing the medication particles to be conveyed from the valve outlet through the receptacle component and discharged from an outlet of the receptacle. Upon discharge from the canister, the medication particles are "atomized", forming an aerosol. It is intended that the patient coordinate the discharge of aerosolized medication with his or her inhalation, so that the medication particles are entrained in the patient's aspiratory flow and conveyed to the lungs. Typically, pMDIs use propellants to pressurize the contents of the canister and to propel the medication particles out of the outlet of the receptacle component. In pMDIs, the formulation is provided in a liquid or suspension form, and resides within the container along with the propellant. The propellant can take a variety of forms. For example, the propellant can comprise a compressed gas or liquefied gas.

In another embodiment the medicinal preparation is adapted for use with a dry powder inhaler (DPI). The inhalation composition suitable for use in DPIs typically comprises particles of the active ingredient and particles of a pharmaceutically acceptable carrier. The particle size of the active material may vary from about 0.1 μm to about 10 μm; however, for effective delivery to the distal lung, at least 95 percent of the active agent particles are 5 μm or smaller. Each of the active agent can be present in a concentration of 0.01-99%. Typically however, each of the active agents is present in a concentration of about 0.05 to 50%, more typically about 0.2-20% of the total weight of the composition.

As noted above, in addition to the active ingredients, the inhalable powder preferably includes pharmaceutically acceptable carrier, which may be composed of any pharmacologically inert material or combination of materials which is acceptable for inhalation. Advantageously, the carrier particles are composed of one or more crystalline sugars; the carrier particles may be composed of one or more sugar alcohols or polyols. Preferably, the carrier particles are particles of dextrose or lactose, especially lactose. In embodiments of the present invention which utilize conventional dry powder inhalers, such as the Handihaler, Rotohaler, Diskhaler, Twisthaler and Turbohaler, the particle size of the carrier particles may range from about 10 microns to about 1000 microns. In certain of these embodiments, the particle size of the carrier particles may range from about 20 microns to about 120 microns. In certain other embodiments, the size of at least 90% by weight of the carrier particles is less than 1000 microns and preferably lies between 60 microns and 1000 microns. The relatively large size of these carrier particles gives good flow and entrainment characteristics. Where present, the amount of carrier particles will generally be up to 95%, for example, up to 90%, advantageously up to 80% and preferably up to 50% by weight based on the total weight of the powder. The amount of any fine excipient material, if present, may be up to 50% and advantageously up to 30%, especially up to 20%, by weight, based on the total weight of the powder. The powder may optionally contain a performance modifier such as L-leucine or another amino acid, and/or metals salts of stearic acid such as magnesium or calcium stearate.

Compounds of formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

In certain embodiments, a compound of Formula I is combined in a pharmaceutical combination formulation, or dosing regimen as combination therapy, with one or more other therapeutic agent that has anti-inflammatory or anti-hyperproliferative properties or that is useful for treating an inflammation, immune-response disorder, or hyperproliferative disorder (e.g., cancer). The other therapeutic agent of the pharmaceutical combination formulation or dosing regimen preferably has complementary activities to the compound of Formula I such that they do not adversely affect each other. Such agents are suitably present in combination in amounts that are effective for the purpose intended.

In one embodiment of the invention, the compound of Formula I, or a stereoisomer, tautomer, or pharmaceutically acceptable salt or prodrug thereof, may be co-administered with one or more other therapeutic agents for the treatment and prevention of PI3Kdelta mediated diseases. Thus in another aspect the present invention provides pharmaceutical compositions for treating PI3Kdelta mediated diseases comprising a therapeutically effective amount of a compound of formula I and one or more other therapeutic agents.

In one embodiment for example, for the treatment of the inflammatory diseases rheumatoid arthritis, psoriasis, inflammatory bowel disease, COPD, asthma and allergic rhinitis a compound of formula I may be combined with other therapeutic agents such as: (1) TNF-α inhibitors such as Remicade® and Enbrel®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including low dose methotrexate, lefunomide, ciclesonide, hydroxychloroquine, d-penicillamine, auranofin or parenteral or oral gold; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast; (8) antihistaminic H1 receptor antagonists such as cetirizine, loratadine, desloratadine, fexofenadine, astemizole, azelastine, and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclidinium bromide, glycopyrrolate, pirenzepine, and telenzepine; (11) β-adrenoceptor agonists such as metaproterenol, isoproterenol, isoprenaline, albuterol, salbutamol, formoterol, salmeterol, terbutaline, orciprenaline, bitolterol mesylate, and pirbuterol, or methylxanthines including theophylline and aminophylline, sodium cromoglycate; (12) insulin-like growth factor type I (IGF-1) mimetic; (13) inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate.

In another embodiment of the invention, the compounds of Formula I, or a stereoisomer, tautomer, or pharmaceutically acceptable salt or prodrug thereof, may be employed alone or in combination with other therapeutic agents for the treatment of hyperproliferative disorders (e.g., cancer) including standard chemotherapy regimens, and anti-CD20 monoclonal antibodies, rituximab, bendamustine, ofatumumab, fludarabine, lenalidomide, and/or bortezomib.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active therapeutic agents simultaneously exert their biological activities.

SCHEMES AND EXAMPLES

The abbreviations used herein have the following tabulated meanings. Abbreviations not tabulated below have their meanings as commonly used unless specifically stated otherwise.

| | |
|---|---|
| ACN | acetonitrile |
| AcOH | acetic acid |
| BAST | N,N-bis(2-methoxyethyl)aminosulfur trifluoride |
| 9-BBN | 9-borabicyclo[3.3.1]nonane |
| Boc | tert-butoxycarbamate |
| CDI | carbonyldiimidazole |
| DCM | dichloromethane |
| DEA | diethylamine |
| DIPEA | diisopropylethylamine |
| DMA | dimethylacetamide |
| DMF | dimethylformamide |
| DMSO | dimethyl sulfoxide |
| EDC | 1-ethyl-3-(3-dimethylaminopropyl)carbodiimide |
| EI | electron ionization |
| EtOAc | ethyl acetate |
| HATU | 2-(1H-7-azabenzotriazol-1-yl)-1,1,3,3-tetramethyl uronium hexafluorophosphate methanaminium |
| HOBt | N-hydroxybenzotriazole |
| HPLC | high performance liquid chromatography |
| LC/MS | liquid chromatography coupled to mass spectrometer |
| MeCN | acetonitrile |
| mCPBA | meta-chloroperoxybenzoic acid |
| MeOH | methanol |
| MS | mass spectrum (data) |
| NMM | N-methylmorpholine |
| NMR | nuclear magnetic resonance (data) |
| $Pd_2$(dppf) | 1,1'-bis(diphenylphosphino)ferrocene-palladium(II)dichloride |
| RT | room temperature |
| Si-DPP Pd | SiliaCat® DPP-Pd is a unique diphenylphosphine palladium (II) heterogeneous catalysts made from a leach-resistant organoceramic matrix. Sold by Silicycle; Cat#R390-100. |
| T3P | propyl phosphonic anhydride |
| TEA | triethylamine |
| TFA | trifluoroacetic acid |
| THF | tetrahydrofuran |

Methods of Synthesis

The compounds of the present invention can be prepared according to the following general schemes using appropriate materials, and are further exemplified by the subsequent specific examples. The compounds illustrated in the examples are not to be construed as forming the only genus that is considered as the invention. The illustrative Examples below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of the instant invention herein above.

Those skilled in the art will readily understand that known variations of the conditions and processes of the following preparative procedures can be used to prepare these compounds. The invention will now be illustrated in the following non-limiting Examples in which, unless otherwise stated:

All reactions were stirred (mechanically, stir bar/stir plate, or shaken) and conducted under an inert atmosphere of nitrogen or argon unless specifically stated otherwise.

All temperatures are degrees Celsius (° C.) unless otherwise noted. Ambient temperature is 15-25° C.

Most compounds were purified by reverse-phase preparative HPLC, MPLC on silica gel, recrystallization and/or intermediate Gen-1 by addition of a primary amine followed by cyclization. For example, oxidative cyclization with an aldehyde would yield the corresponding purine. Next, Gen-1 was elaborated to Gen-2 by addition of the appropriate carbon, oxygen or sulfur-based nucleophile. For example, reaction with a pyrrolidinol would yield the corresponding oxygen-linked compound where L is oxygen and the A ring is a pyrrolidine.

In a modified route, the cyclic ring A was introduced first. In this case, reaction of 4,6-dichloro-5-nitropyrimidine with a primary amine followed by addition of ring A via L would yield Gen-3. Using the above-mentioned example, reaction of a pyrrolidinol would yield Gen-3 having an oxygen linker L. Finally, the nitro group of Gen-3 was reduced; for example by hydrogenation with hydrogen and palladium on carbon. The aminopyrimidine intermediate was finally converted to Gen-2 using chemistry similar to that used to prepare Gen-1.

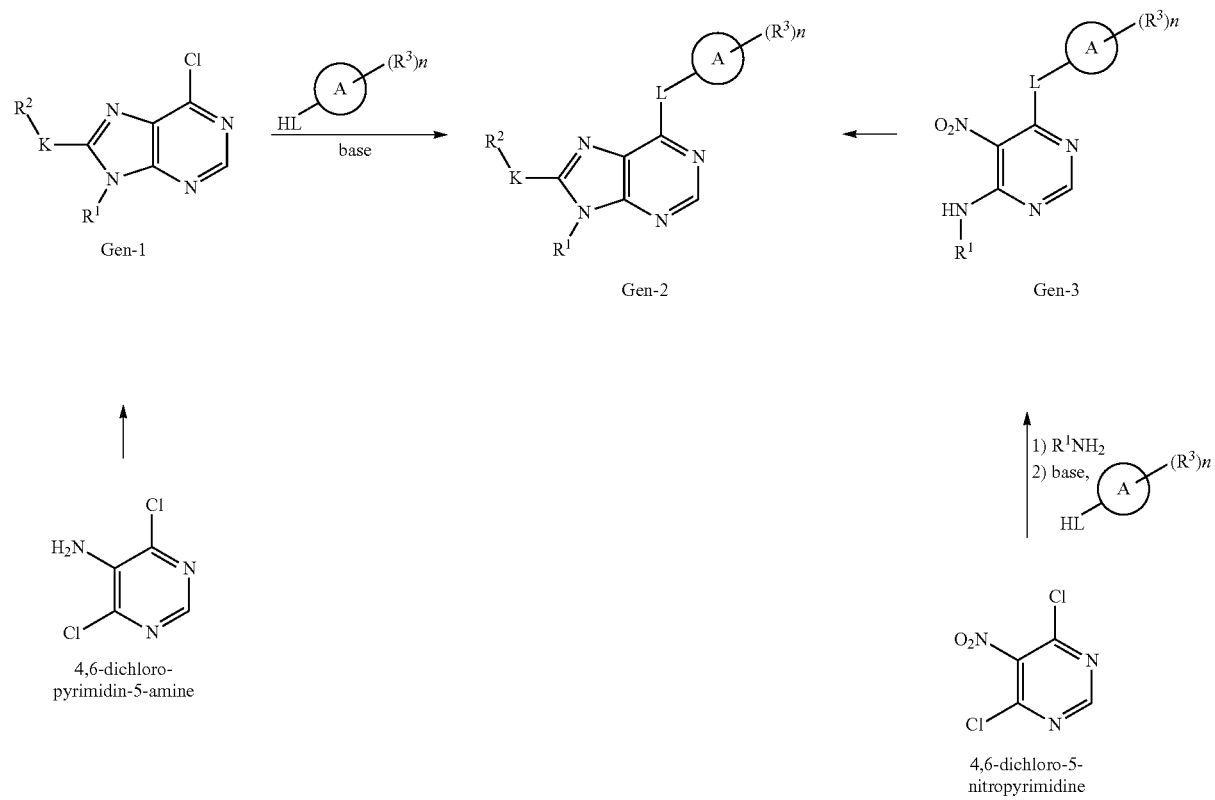

swish (suspension in a solvent followed by filtration of the solid). The course of the reactions was followed by thin layer chromatography (TLC) and/or LCMS and/or NMR and reaction times are given for illustration only.

All end products were analyzed by NMR and LCMS.

Intermediates were analyzed by NMR and/or TLC and/or LCMS.

General Synthetic Schemes

Several synthetic routes were employed in the syntheses of the compounds described herein. In one approach, 4,6-dichloropyrimidine-5-amine was elaborated to a common On occasion, ring A was incorporated into the structure bearing a protective group, forming an intermediate such as Gen-4. The protective group was removed and functionalized with diverse $R^3$ to arrive and the final compounds (designated Gen-2). For example, a Boc protective group could be removed by treatment with dilute acid. The A ring bearing the protective group could also be introduced very early in the sequence, proceeding via Gen-5 in a manner analogous to the preparation of Gen-3 above.

Examples of these general synthetic approaches can be found in the descriptions of the syntheses of several examples enclosed herein.

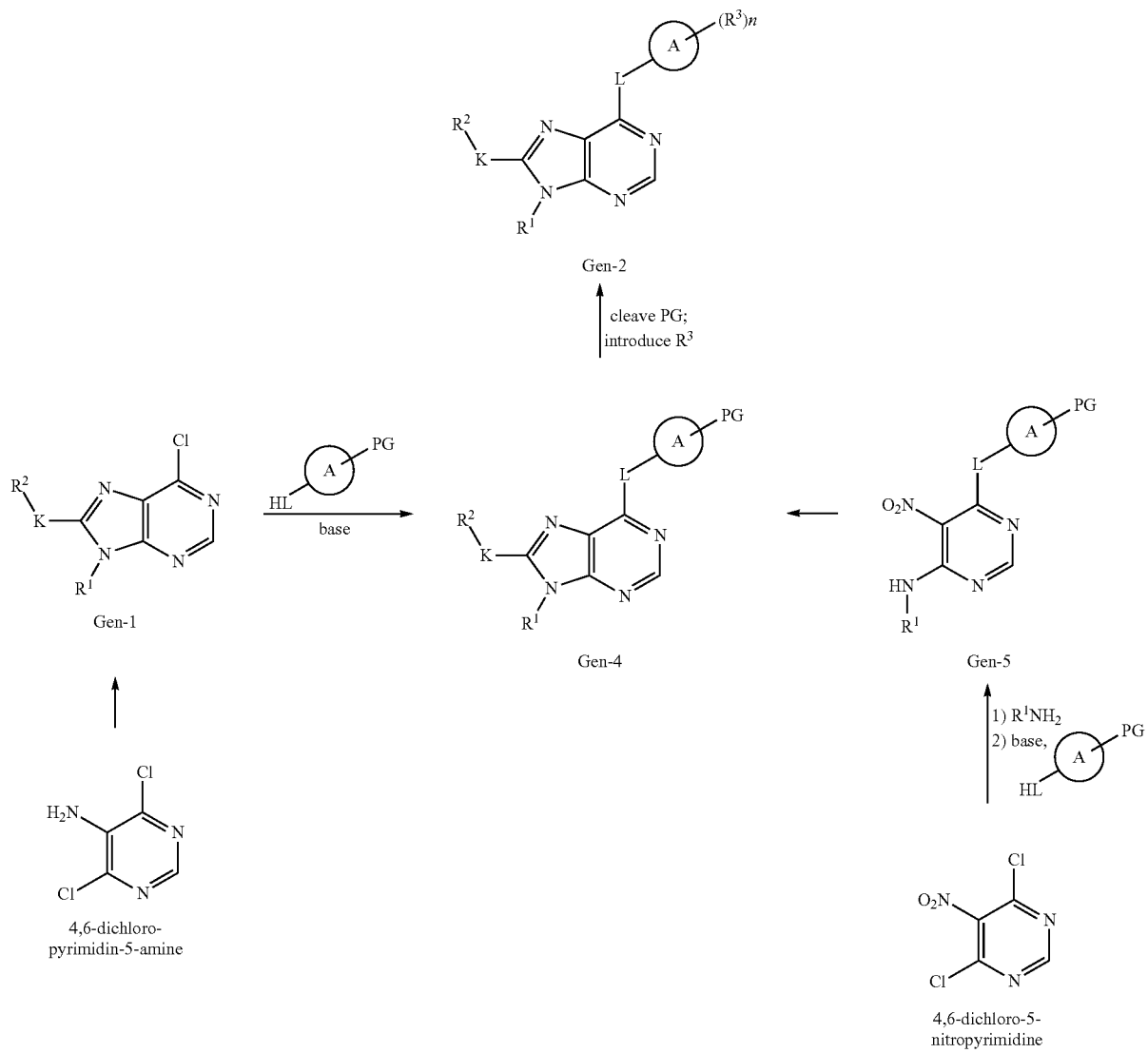

An alternative approach to intermediate Gen-1 was alkylation of 6-chloropurine followed by iodination at the 8-position. Introduction of K—R² gave Gen-1, examples would include introduction of aromatics employing a Suzuki reaction, addition of alcohols, phenols, amines, anilines, and carbonylation to obtain amides. Alternatively, the chloroiodopurine intermediate can be reacted with ring A to provide Gen-6 and further elaborated to Gen-2 via introduction of K—R².

Ring A can be introduced fully elaborated with (R³)n attached, or introduced with a protective group (such as Gen-4 or Gen-7). Later, deprotection can be followed by addition of R³. Examples include amide formation with carboxylic acids or acid chlorides, alkylation, arylation via base-mediated SNAr or palladium-mediated, or carbamate and urea formation.

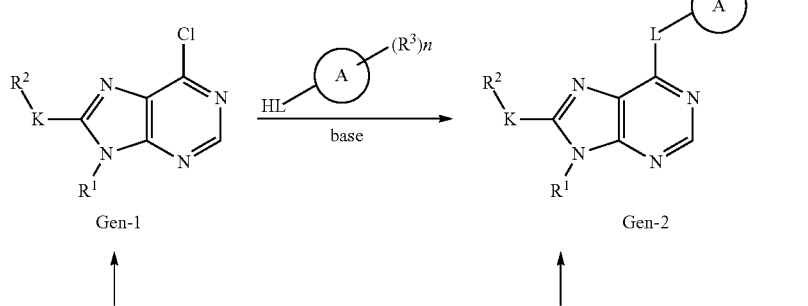

-continued
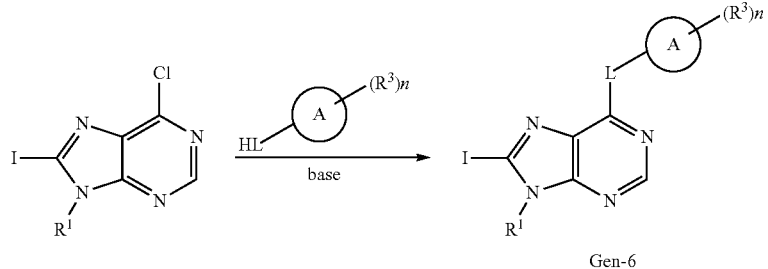
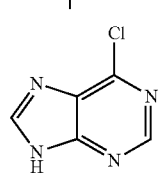
6-chloro-9H-purine
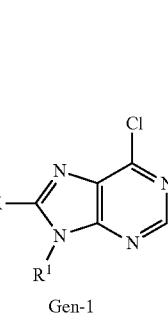
Gen-1
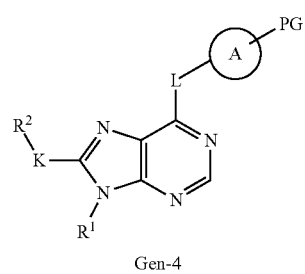
Gen-4
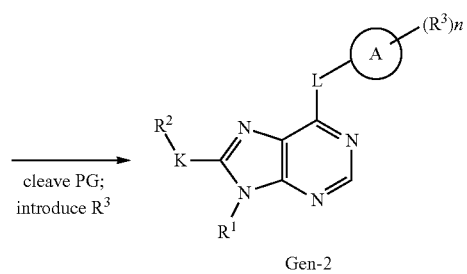
Gen-2
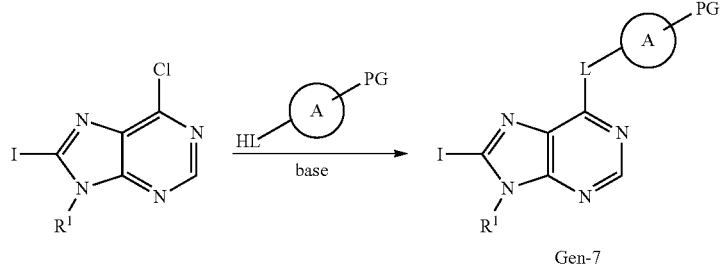
Gen-7
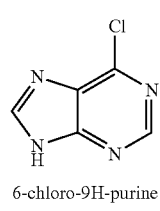
6-chloro-9H-purine

Compound Examples of Table 1

Example 1—Preparation of Compound 1-1

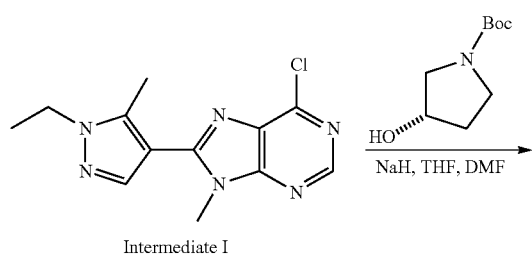

Intermediate I

Intermediate I, 6-chloro-8-(1-ethyl-5-methyl-1H-pyrazol-4-yl)-9-methyl-9H-purine, was made in a manner described in the published international application, WO 12/037266, incorporated by reference herein, disclosing the preparation of heterocyclyl-substituted purine derivatives as inhibitors of PI3K-delta for the treatment of cancer.

A solution of (S)-tert-butyl 3-hydroxypyrrolidine-1-carboxylate (5.00 g, 26.7 mmol) in 50 mL of THF was treated with a 60% suspension of sodium hydride in mineral oil (1.6 g, 40 mmol). The suspension was stirred for 10 min, then a mixture of Intermediate I (7.40 g, 26.7 mmol) in 20 mL of DMF was added. The reaction mixture was stirred overnight, then diluted with EtOAc and washed with 1 N NaOH, water, dried (Na$_2$SO$_4$), filtered and concentrated. The residue was purified by chromatography on SiO$_2$ (0-30% MeOH/DCM gradient) to provide 1-1. $^1$H NMR (600 MHz, DMSO-d$_6$) δ 8.46 (s, 1H), 7.96 (s, 1H), 5.79 (d, 1H), 4.15 (q, J=8.2 Hz, 2H), 3.81 (s, 3H), 3.65 (m, 1H), 3.45 (m, 1H), 3.35 (m, 1H), 3.29 (m, 1H), 2.53 (s, 3H), 2.30-2.10 (m, 2H), 1.36 (m, 9H), 1.32 (t, J=9.1 Hz, 3H); MS (EI) Calc'd for C$_{21}$H$_{30}$N$_7$O$_3$ [M+H]$^+$, 428. found 428.

Example 1A—Preparation of Intermediate IV and 1-3

Convergent Approach to Intermediate IV

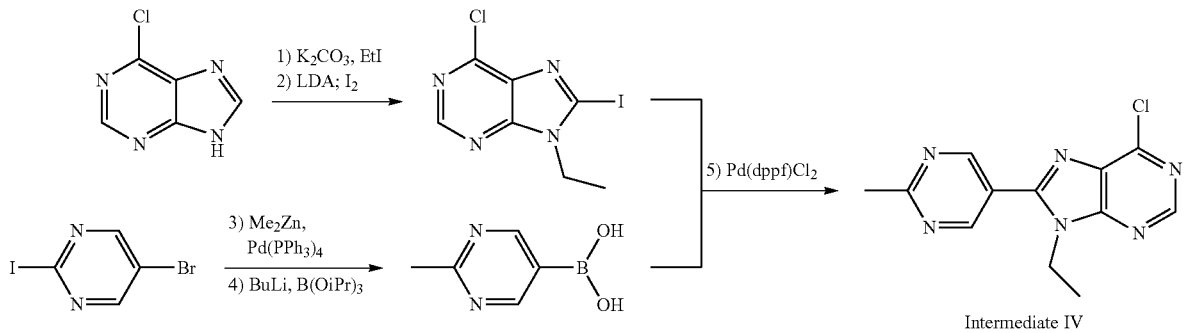

-continued

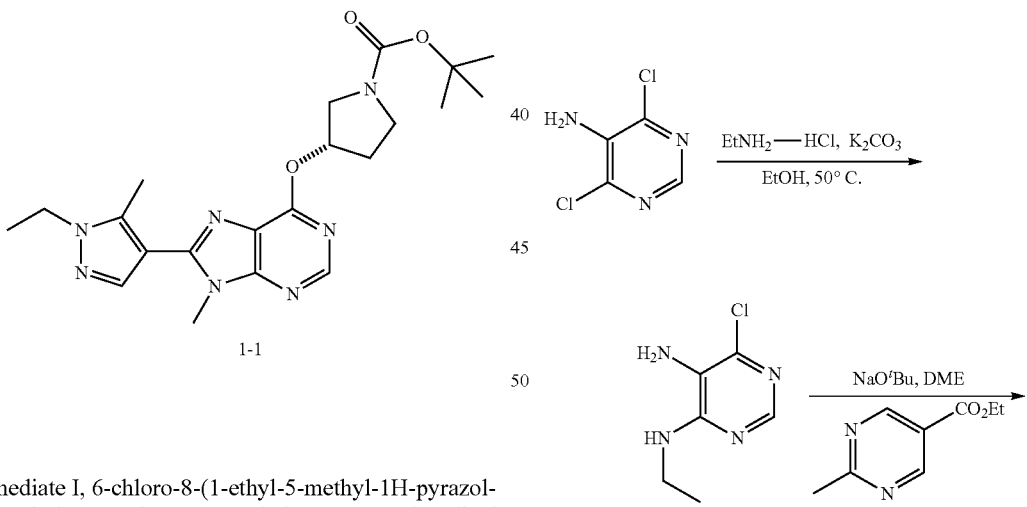

1-1

Linear Approach to Intermediate IV

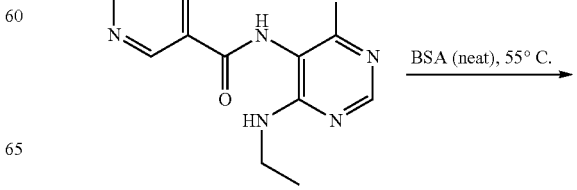

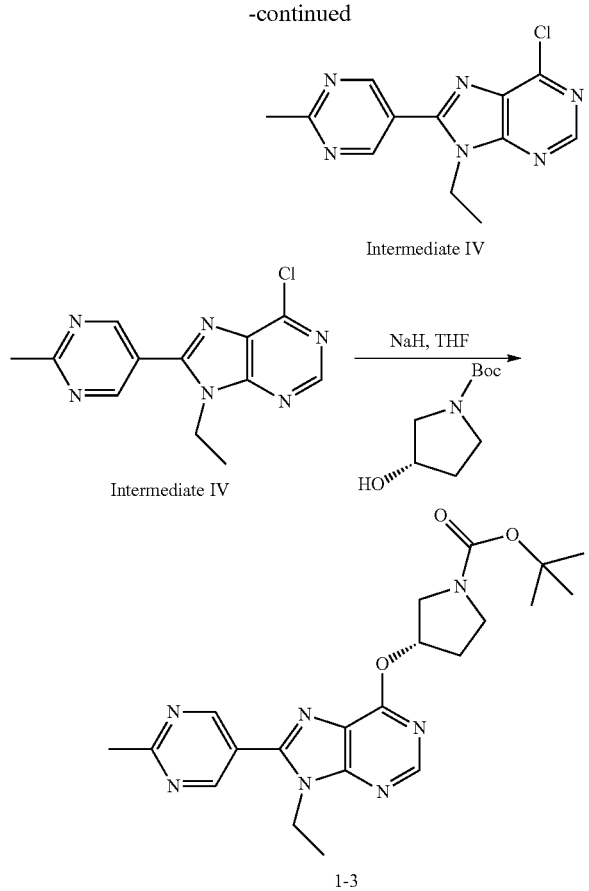

Convergent Approach to Intermediate IV

Steps 1 and 2: Preparation of
6-chloro-9-ethyl-8-iodo-9H-purine

Into a 10-L 4-neck round-bottom flask was placed a solution of 6-chloro-9H-purine (500 g, 3.24 mol), iodoethane (1009 g, 6.47 mol) and potassium carbonate (447 g, 3.23 mol) in DMSO (5 L). The resulting solution was stirred overnight at room temperature. It was then diluted with brine and extracted with 3×1.5 L of ethyl acetate. The organic extracts were combined, dried over anhydrous magnesium sulfate and concentrated under vacuum. The residue was applied onto a silica gel column and eluted with ethyl acetate/petroleum ether (1:2) providing 6-chloro-9-ethyl-9H-purine.

Into a 10-L 4-neck round-bottom flask purged and maintained with an inert atmosphere of nitrogen was placed a solution of diisopropylamine (200 g, 1.98 mol) in THF (1.2 L). This was followed by addition of 2.5 M n-BuLi (736 mL, 1.40 equiv) at −78° C. After stirring for 30 min, a solution of 6-chloro-9-ethyl-9H-purine (240 g, 1.31 mol) in THF (1.2 L) was added dropwise with stirring at −78° C. The resulting solution was stirred for 5 min at −78° C., followed by addition of a solution of I$_2$ (467 g, 1.84 mol) in THF (1.2 L) at −78° C. The resulting solution was stirred for an additional 10 min at −78° C., then quenched by the addition of 200 mL of aqueous NH$_4$Cl. The organic layer was washed with 2×1.5 L of aqueous Na$_2$S$_2$O$_3$, dried over anhydrous magnesium sulfate and concentrated under vacuum. The obtained solid was washed with 2×200 mL of ethyl ether to give 6-chloro-9-ethyl-8-iodo-9H-purine.

Steps 3 and 4: Preparation of
(2-methylpyrimidin-5-yl)boronic acid

Into a 10-L 4-neck round-bottom flask purged and maintained with an inert atmosphere of nitrogen was placed a solution of 5-bromo-2-iodopyrimidine (590 g, 2.07 mol) in THF (3 L). This was followed by dropwise addition of 1 M solution of dimethyl zinc (3.11 L, 3.11 mol) with stirring at 0° C. To this was added Pd(PPh$_3$)$_4$ (120 g, 104 mmol). The resulting solution was stirred for 3 h at 0° C., then quenched by the addition of 600 mL of aqueous NH$_4$Cl. The resulting solution was extracted with 2×1.5 L of ethyl acetate. The organic extracts were combined, dried over anhydrous magnesium sulfate and concentrated under vacuum. The residue was applied onto a silica gel column and eluted with ethyl acetate/petroleum ether (1:50) to provide 5-bromo-2-methylpyrimidine.

Into a 10-L 4-neck round-bottom flask purged and maintained with an inert atmosphere of nitrogen was placed a solution of 5-bromo-2-methylpyrimidine (184 g, 1.06 mol) and B(i-PrO)$_3$ (240 g, 1.28 mol) in THF/toluene (3/3 L). This was followed by the dropwise addition of a 2.5 M solution of n-BuLi (510 mL, 1.28 mol) with stirring at −78° C. The resulting solution was stirred for 1 h at −78° C., then quenched by the addition of 200 mL of aqueous NH$_4$CL. The organic phase was dried and concentrated under vacuum. The aqueous phase was adjusted to pH 4 with AcOH. The solid was collected by filtration and dried in an oven under reduced pressure providing (2-methylpyrimidin-5-yl)boronic acid.

Step 5: Preparation of 6-chloro-9-ethyl-8-(2-methyl-pyrimidin-5-yl)-9H-purine

Into a 5-L 4-neck round-bottom flask purged and maintained with an inert atmosphere of nitrogen was placed a solution of 6-chloro-9-ethyl-8-iodo-9H-purine (242 g, 784 mmol), (2-methylpyrimidin-5-yl)boronic acid (108 g, 783 mmol), potassium carbonate (162 g, 1.17 mol) and Pd(dppf)Cl$_2$-DCM (32 g, 39 mmol) in dioxane (2.4 L) and water (480 mL). The resulting solution was stirred overnight at 90° C. The reaction mixture was cooled to room temperature, then extracted with 2×1.5 L of ethyl acetate. The organic extracts were combined, dried over anhydrous magnesium sulfate and concentrated under vacuum. The residue was applied onto a silica gel column and eluted with petroleum ether/dichloromethane/ethyl acetate (5:1:1) providing 6-chloro-9-ethyl-8-(2-methylpyrimidin-5-yl)-9H-purine (Intermediate IV). $^1$H NMR (300 MHz, CDCl$_3$) δ 9.12 (s, 2H), 8.80 (s, 1H), 4.46 (q, J=7.2 Hz, 2H), 2.89 (s, 3H), 1.57-1.51 (t, J=7.2 Hz, 3H). MS (EI) Calc'd for C$_{12}$H$_{12}$N$_6$Cl [M+H]$^+$, 275. found, 275.

Linear Approach to Intermediate IV

A mixture of 4,6-dichloropyrimidin-5-amine (20.0 g, 122 mmol), ethanamine hydrochloride (19.9 g, 243 mmol), potassium carbonate (50.7 g, 367 mmol) in ethanol (100 mL) was heated to 50° C. for 39 hr. After cooling to room temperature, the reaction mixture was diluted with DCM (750 mL) and then filtered. The cake was washed with DCM (250 mL). The combined filtrate was concentrated to dryness to provide 6-chloro-N4-ethylpyrimidine-4,5-diamine. MS (EI) Calc'd for C$_6$H$_{10}$ClN$_4$ [M+H]$^+$, 173. found, 173.

To a mixture of 6-chloro-N4-ethylpyrimidine-4,5-diamine (16.4 g, 91 mmol) and ethyl-2-methylpyrimidine-5-carboxylate (15 g, 90 mmol) in 50 mL of DME, a slurry of sodium tert-butoxide (9.1 g, 92 mmol) in DME (25 mL) was added. The reaction mixture was stirred at 40-20° C. for 2 hr and then quenched by adding 75 mL of water and 75 mL of EtOAc. The reaction mixture was extracted with EtOAc (75 mL×2). The aqueous layer was charged with acetic acid (5.3 mL, 92 mmol) and a slurry was formed. The solid was collected by filtration and washed with 75 mL of 1:1 DME/water and dried in a vacuum at 35° C. overnight to provide N-(4-chloro-6-(ethylamino)pyrimidin-5-yl)-2-methylpyrimidine-5-carboxamide. MS (EI) Calc'd for $C_{12}H_{14}ClN_6O$ [M+H]$^+$, 293. found, 293.

To trimethylsilyl N-(trimethylsilyl)acetimidate (BSA, 22 mL, 91 mmol), N-(4-chloro-6-(ethylamino)pyrimidin-5-yl)-2-methylpyrimidine-5-carboxamide (5.0 g, 17 mmol) was added in portions. The reaction solution was heated to 55° C. for 1 hr and then cooled to room temperature. The formed solid was collected by filtration and washed with heptane (15 mL). The solid was dried in a vacuum at 50° C. overnight to provide 6-chloro-9-ethyl-8-(2-methylpyrimidin-5-yl)-9H-purine. MS (EI) Calc'd for $C_{12}H_{12}ClN_6$ [M+H]$^+$, 275. found, 275.

Preparation of 1-3

To a solution of (S)-tert-butyl 3-hydroxypyrrolidine-1-carboxylate (5.7 g, 30 mmol) in THF (80 mL), 60% NaH in mineral oil (2.0 g, 50 mmol) was added. The mixture was stirred at 0° C. for 30 min, then Intermediate IV (7.0 g, 26 mmol) was added. The solution was stirred at 20° C. for 15 h, then cooled, diluted with water (10 mL) and extracted with ethyl acetate (2×10 mL). The combined were concentrated under reduced pressure to give 1-3. MS (EI) Calc'd for $C_{21}H_{28}N_7O_3$ [M+H]$^+$, 426. found 426.

Example 1B—Preparation of 1-44

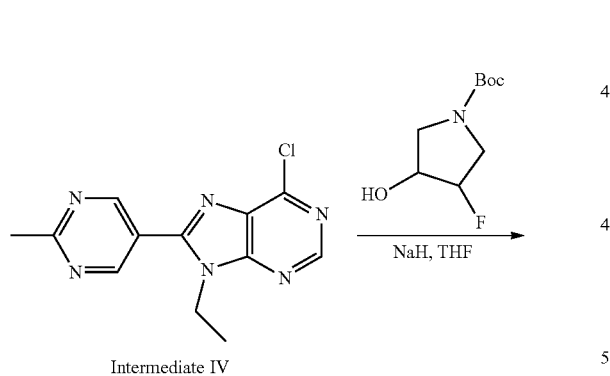

To a solution of rac-trans-tert-butyl 3-fluoro-4-hydroxypyrrolidine-1-carboxylate (0.5 g, 2.44 mmol) in THF (10 mL) was added a 60% suspension of NaH in mineral oil (0.13 g, 3.2 mmol), the mixture was stirred at 0° C. for 30 min, then Intermediate IV added (0.45 g, 1.6 mmol). The mixed solution was stirred at 20° C. for 20 h. The mixture was cooled, water (10 mL) was added and the mixture was extracted with ethyl acetate (2×10 mL). The combined organic extracts were concentrated under reduced pressure to give 1-44. $^1$H NMR (400 MHz, CD$_3$OD) δ 9.13 (s, 2H), 8.63 (s, 1H), 5.96-5.94 (m, 1H), 5.46-5.34 (m, 1H), 4.50-4.45 (m, 2H), 3.88-3.74 (m, 4H), 2.83 (s, 3H), 1.50-1.46 (m, 12H). MS (EI) Calc'd for $C_{21}H_{27}FN_7O_3$ [M+H]$^+$, 444. found, 444.

Example 2—Preparation of Compound 1-2

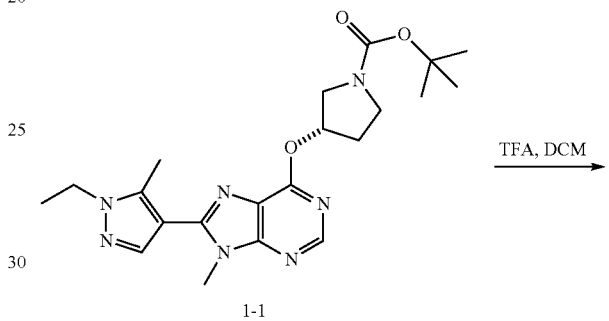

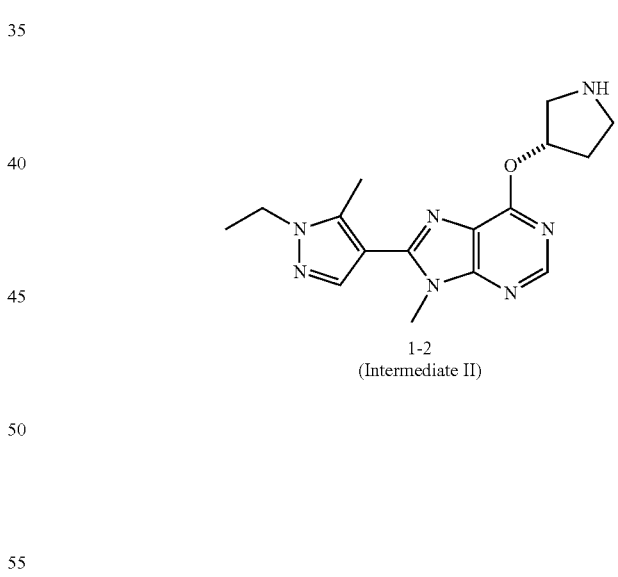

A solution of 1-1 (4.55 g, 10.6 mmol) in 50 mL of DCM was treated with 5 mL of TFA and stirred for 1 hour. The incomplete reaction was then retreated with 5 mL of TFA. After stirring for an additional 1 hour, the reaction mixture was concentrated to dryness. The oily residue was dissolved in 4:1 DCM:MeOH and washed with saturated NaHCO$_3$, dried (Na$_2$SO$_4$), and concentrated to provide 1-2; Intermediate II. $^1$H NMR (600 MHz, DMSO-d$_6$) δ 8.43 (s, 1H), 7.96 (1H), 5.65 (m, 1H), 4.15 (q, J=7.3 Hz, 2H), 3.80 (s, 3H), 3.15-3.12 (m, 2H), 2.93-2.89 (m, 2H), 2.78 (m, 1H), 2.54 (s, 3H), 2.08 (m, 1H), 1.85 (m, 1H), 1.33 (t, J=7.3 Hz, 3H); MS (EI) Calc'd for $C_{16}H_{22}N_7O$ [M+H]$^+$, 328. found 328.

Example 3—Preparation of Compound 1-10

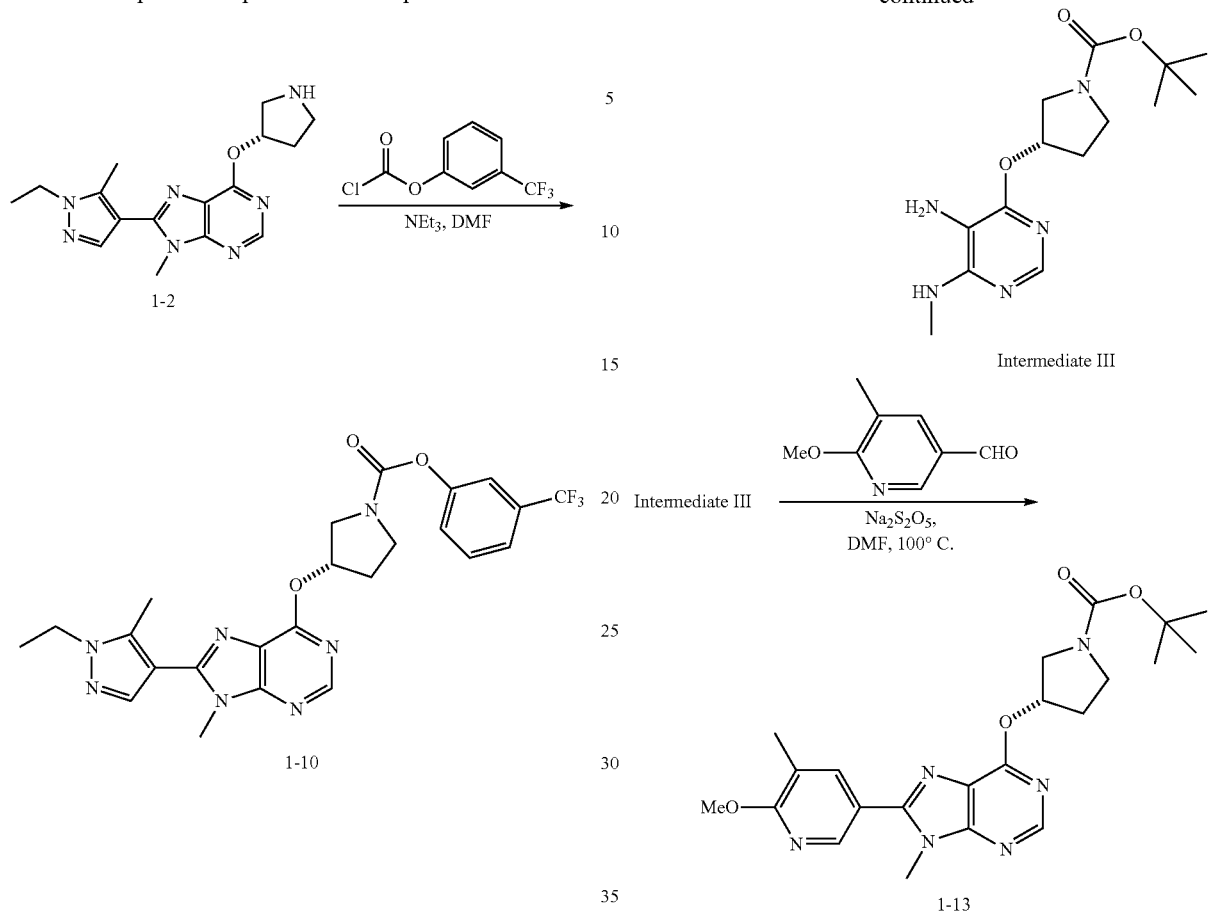

A solution of 1-2 (25 mg, 0.076 mmol) in 1 mL of DMF was added to a reaction vial containing 3-(trifluoromethyl) phenyl carbonochloridate (24 mg, 0.10 mmol). Triethylamine was added (0.021 mL, 0.15 mmol) and the reaction stirred overnight at room temperature. The mixture was filtered, washing the filter with DMSO (1 mL). The filtrate was purified by reverse phase HPLC, and the purified fraction concentrated under reduced pressure to yield 1-10 as the TFA salt. $^1$H NMR (600 MHz, DMSO-$d_6$) δ 8.49 (s, 1H), 7.97 (d, J=2.1 Hz, 1H), 7.55-7.53 (m, 4H), 5.90 (m, 1H), 4.15 (q, J=7.3 Hz, 2H), 3.82 (s, 3H), 3.82-3.60 (m, 3H), 2.55 (s, 3H), 2.47 (m, 1H), 2.36-2.30 (m, 2H), 1.33 (t, J=7.2 Hz, 3H); MS (EI) Calc'd. for $C_{24}H_{25}F_3N_7O_3$ [M+H]$^+$, 516. found 516.

Example 4—Preparation of Compound 1-13

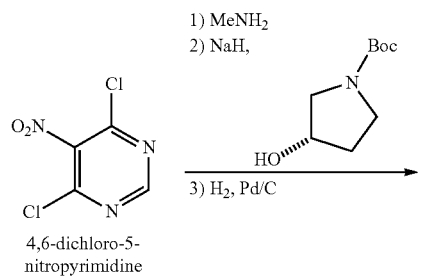

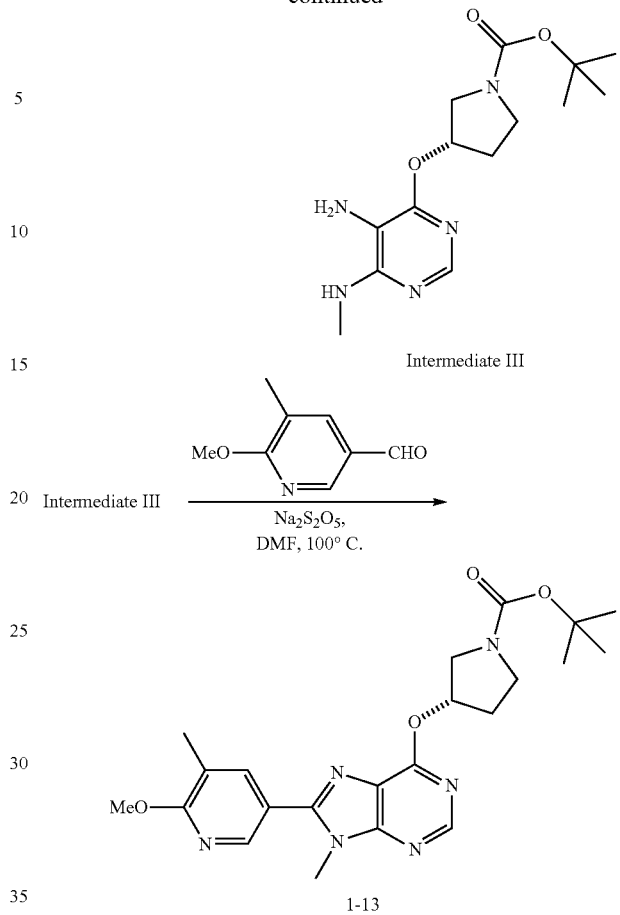

Step 1: Preparation of Intermediate III

A solution of 4,6-dichloro-5-nitropyrimidine (2.00 g, 10.3 mmol) in 20 mL of THF was cooled to −78° C. and treated with i-Pr$_2$NEt (2.00 mL, 11.5 mmol) followed dropwise by a 33% solution of methanamine in ethanol (1.30 mL, 10.9 mmol). The mixture was stirred for 60 min, and allowed to warm to RT. LC/MS analysis indicated good conversion to the desired intermediate; 6-chloro-N-methyl-5-nitropyrimidin-4-amine. Concentrated to dryness to remove ethanol, then redissolved in THF and concentrated again to remove traces of ethanol. MS (EI) Calc'd for $C_5H_6ClN_4O_2$ [M+H]$^+$, 189. found 189.

In a separate flask, (S)-tert-butyl 3-((6-(methylamino)-5-nitropyrimidin-4-yl)oxy)pyrrolidine-1-carboxylate (1.50 g, 4.42 mmol) was dissolved in THF (20 mL) and treated with a 60% mineral oil suspension of sodium hydride (1.30 g, 32.5 mmol). The reaction was stirred for 20 min. Next, the above intermediate in THF was added and the reaction stirred at RT. After stirring for 30 min, LC/MS analysis indicated product was formed. Diluted with EtOAc and washed with water, dried (Na$_2$SO$_4$) and concentrated. Purified the residue by chromatography on SiO$_2$ (0-50% EtOAc/DCM), to provide (S)-tert-butyl 3-((6-(methylamino)-5-nitropyrimidin-4-yl)oxy)pyrrolidine-1-carboxylate. MS (EI) Calc'd for $C_{14}H_{22}N_5O_5$ [M+H]$^+$, 340. found 340.

A suspension of (S)-tert-butyl 3-((6-(methylamino)-5-nitropyrimidin-4-yl)oxy)pyrrolidine-1-carboxylate (1.50 g, 4.42 mmol), Pd/C (0.235 g, 0.221 mmol) in ethyl acetate (10 mL) was placed under vacuum and purged with hydrogen three times. The suspension was vigorously stirred overnight under an atmosphere of hydrogen (balloon).

Filtered reaction mixture through a pad of celite and concentrated. Purified the resulting residue by chromatography on SiO$_2$ (0-20% MeOH/DCM, then 0-100% EtOAc/DCM gradients) to provide the desired product; Intermediate III. $^1$H NMR (600 MHz, DMSO-d$_6$) δ 7.70 (s, 1H), 6.18 (s, 1H), 5.37 (m, 1H), 4.05 (s, 2H), 3.51 (m, 1H), 3.40 (m, 2H), 3.32 (m, 1H), 2.82-2.81 (m, 3H), 2.13-1.95 (m, 2H), 1.36-1.34 (m, 9H); MS (EI) Calc'd for C$_{14}$H$_{24}$N$_5$O$_3$ [M+H]$^+$, 310. found 310.

Step 2: Preparation of 1-13

A solution of intermediate III (25 mg, 0.081 mmol) in 1 mL of DMF was treated with 6-methoxy-5-methylnicotinaldehyde (25 mg, 0.17 mmol) followed by sodium metabisulfite (30 mg, 0.16 mmol). The reaction mixture was heated to 100° C. and stirred for 6 hours. Cooled to RT. Filtered and purified by reverse phase chromatography to provide the TFA salt of the desired product. $^1$H NMR (600 MHz, DMSO-d$_6$) δ 8.52 (m, 2H), 8.06 (s, 1H), 5.80 (d, 1H), 3.95 (s, 3H), 3.86 (s, 3H), 3.62 (m, 1H), 3.50-3.44 (m, 2H), 3.38-3.33 (m, 1H), 2.46 (s, 3H), 2.25-2.15 (m, 2H), 1.38-1.36 (m, 9H); MS (EI) Calc'd for C$_{22}$H$_{29}$N$_6$O$_4$ [M+H]$^+$, 441. found 441.

Example 4A—Preparation of 1-43

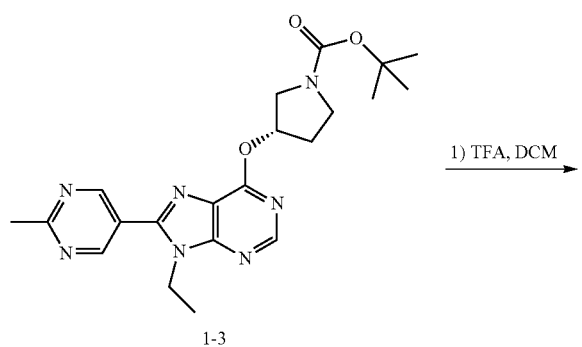

1-3

1) TFA, DCM

2) ClCO$_2$Et, NEt$_3$, DCM

Intermediate V

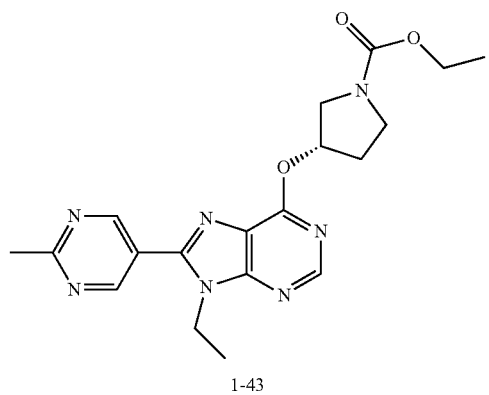

1-43

To a solution of (S)-tert-butyl 3-(9-ethyl-8-(2-methylpyrimidin-5-yl)-9H-purin-6-yloxy)pyrrolidine-1-carboxylate (1-3) (9 g, 21 mmol) in DCM (100 mL) was added TFA (25 mL) and the reaction stirred at 20° C. for 2 h. The mixture was cooled, aqueous sodium hydrogen carbonate (saturated, 100 mL) was added and the mixture extracted with dichloromethane (2×100 mL). The combined organic extracts were concentrated under reduced pressure to give (S)-9-ethyl-8-(2-methylpyrimidin-5-yl)-6-(pyrrolidin-3-yloxy)-9H-purine (Intermediate V). MS (EI) Calc'd for C$_{16}$H$_{20}$N$_7$O [M+H]$^+$, 326. found, 326.

To a solution of Intermediate V (50 mg, 0.15 mmol) in DCM (3 mL) was added TEA (0.04 mL, 0.3 mmol) and ethyl chloroformate (0.04 mL, 0.3 mmol). The resulting mixture was stirred at room temperature for 1 h. The reaction was concentrated to give a residue which was purified by preparative HPLC (MeCN/water with 10 mM aqueous NH$_4$HCO$_3$ modifier) to afford 1-43. $^1$H NMR (400 MHz, DMSO) δ 9.15 (s, 2H), 8.62 (s, 1H), 5.86 (s, 1H), 4.38 (q, J=7.2 Hz, 2H), 4.13-3.97 (m, 2H), 3.78-3.39 (m, 4H), 2.75 (s, 3H), 2.35-2.20 (m, 2H), 1.34 (t, J=7.2 Hz, 3H), 1.22-1.15 (m, 3H). MS (EI) Calc'd for C$_{19}$H$_{24}$N$_7$O$_3$ [M+H]$^+$, 398. found, 398.

Example 4B—Preparation of 1-47

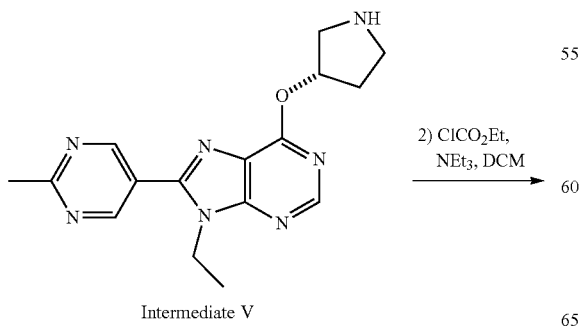

1) Dess-Martin Reagent

2) BAST, DCM

3) H$_2$, Pd(OH)$_2$/C

4) Intermediate IV, NaH, THF

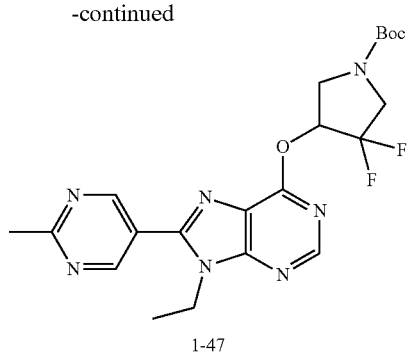

1-47

Steps 1 and 2: Preparation of tert-Butyl 4-(benzyloxy)-3,3-difluoropyrrolidine-1-carboxylate A mixture of rac-trans-tert-butyl 3-(benzyloxy)-4-hydroxypyrrolidine-1-carboxylate (prepared as described in WO 1999/64399) (100 mg, 0.34 mmol) in DCM (10 mL) was treated with the Dess-Martin reagent (430 mg, 1 mmol) and stirred RT for 2 h. The reaction mixture was diluted with DCM (20 mL), washed with aq. $NaHCO_3$ (10 mL) and aq. $Na_2SO_3$ (10 mL), then dried ($Na_2SO_4$), filtered, and concentrated. The residue was purified by chromatography on $SiO_2$ (ethyl acetate/petroleum ether 1:10) to give tert-butyl 3-(benzyloxy)-4-oxopyrrolidine-1-carboxylate. MS (EI) Calc'd for $C_{16}H_{22}NO_4$ $[M+H]^+$, 292. found, 292.

A mixture of rac-tert-butyl 3-(benzyloxy)-4-oxopyrrolidine-1-carboxylate (200 mg, 0.69 mmol) in DCM (20 mL) was treated with bis(2-methoxyethyl)aminosulfur trifluoride (BAST) (460 mg, 2 mmol) and stirred for 15 h at RT. The mixture was washed with aq. $NaHCO_3$ (20 mL) and concentrated, then purified by chromatography on $SiO_2$ (ethyl acetate/petroleum ether 1:10) to give rac-tert-butyl 4-(benzyloxy)-3,3-difluoropyrrolidine-1-carboxylate. MS (EI) Calc'd for $C_{16}H_{22}F_2NO_3$ $[M+H]^+$, 314. found, 314.

Steps 3 and 4: Preparation of 1-47

A suspension of rac-tert-butyl 4-(benzyloxy)-3,3-difluoropyrrolidine-1-carboxylate (50 mg, 0.16 mmol) and 10% Pd(OH)$_2$/C (10 mg) in MeOH (10 mL) and stirred under an atmosphere of $H_2$ for 15 h at RT. The mixture was filtered and concentrated to give rac-tert-butyl 3,3-difluoro-4-hydroxypyrrolidine-1-carboxylate. MS (EI) Calc'd for $C_9H_{16}F_2NO_3$ $[M+H]^+$, 224. found, 224.

A mixture of Intermediate IV (37 mg, 0.13 mmol), rac-tert-butyl 3,3-difluoro-4-hydroxypyrrolidine-1-carboxylate (30 mg, 0.13 mmol) in THF (3 mL) was treated with a 60% suspension of NaH in mineral oil (11 mg, 0.27 mmol) and stirred at RT for 15 h. Water (0.5 mL) was added and mixture concentrated to dryness. The residue was purified by chromatography on $SiO_2$ (MeOH/DCM 1:10) to give 1-47. $^1$H NMR (400 MHz, CD$_3$OD) δ 9.03 (s, 2H), 8.52 (s, 1H), 6.05-5.90 (m, 1H), 4.39-4.34 (m, 2H), 3.87-3.66 (m, 4H), 2.72 (s, 3H), 1.38-1.30 (m, 12H). MS (EI) Calc'd for $C_{21}H_{26}F_2N_7O_3$ $[M+H]^+$, 462. found, 462.

Example 4C—Preparation of 1-49

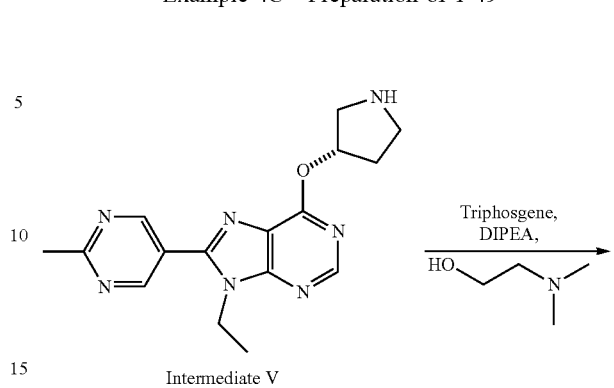

To a stirred solution of Intermediate V (100 mg, 0.307 mmol) in DCM (20 mL) at 0° C. was added DIPEA (0.107 mL, 0.615 mmol) followed by dropwise addition of triphosgene (36.5 mg, 0.123 mmol). The resulting mixture was stirred at RT for 1 h, then treated with 2-(dimethylamino)ethanol (23 mg, 0.26 mmol) at 0° C. The resulting mixture was stirred at RT for another 1 h and cooled, water (10 mL) was added and the mixture extracted with DCM (2×30 mL). The combined organic extracts were washed with water, brine, dried (Na$_2$SO$_4$), filtered and concentrated under reduced pressure. The residue was purified by reverse phase chromatography to give 1-49. $^1$H NMR (400 MHz, CD$_3$OD) δ 9.14 (s, 2H), 8.61 (s, 1H), 6.03-5.97 (m, 1H), 4.47 (q, J=7.2 Hz, 2H), 4.31-4.20 (m, 2H), 3.88-3.62 (m, 4H), 2.84 (s, 3H), 2.78-2.66 (m, 2H), 2.42-2.32 (m, 8H), 1.48 (t, J=7.2 Hz, 3H); MS (EI) Calc'd for $C_{21}H_{29}N_8O_3$ $[M+H]^+$, 441. found, 441.

Example 4D—Preparation of 1-51

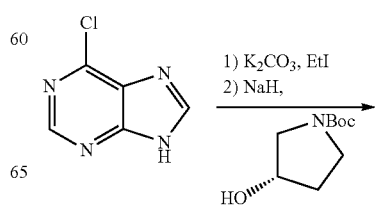

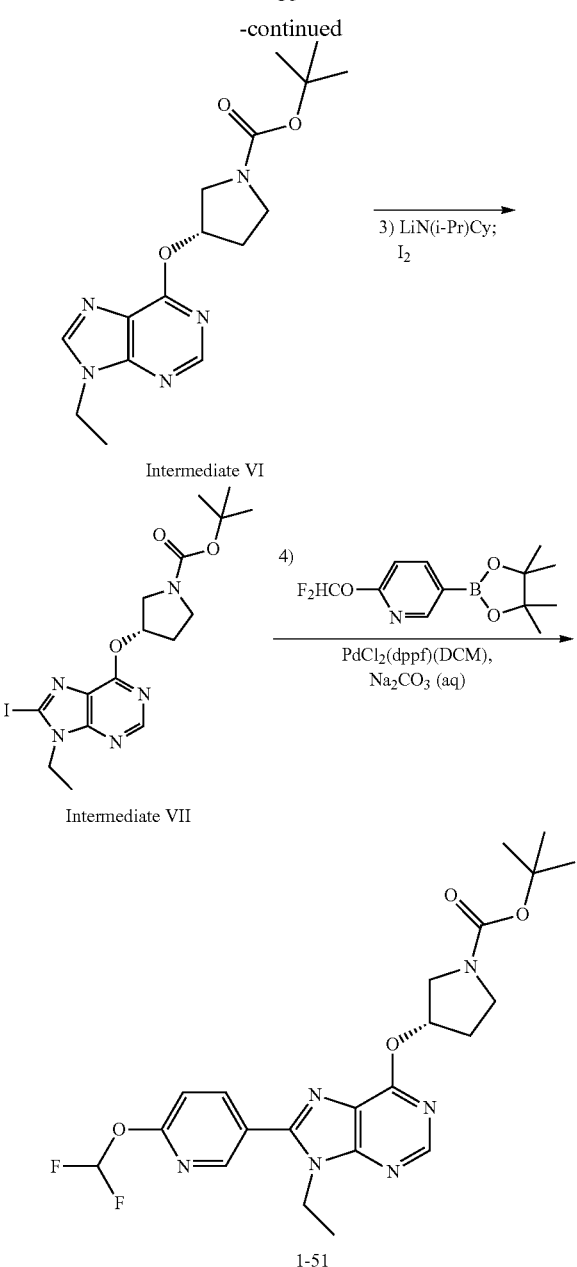

Steps 1, 2, and 3: Preparation of Intermediates VI and VII

Into a 5-L 4-neck round-bottom flask purged and maintained with an inert atmosphere of nitrogen was placed a solution of 6-chloro-9H-purine (150 g, 971 mmol) in DMSO (2 L) and potassium carbonate (202 g, 1.46 mol). This was followed by dropwise addition of iodoethane (228 g, 1.46 mol) with stirring at room temperature. The resulting solution was stirred overnight at room temperature, then quenched by addition of 2 L of water. The resulting solution was extracted with 3×1 L of dichloromethane. The organic extracts were combined, dried over anhydrous sodium sulfate and concentrated. The residue was purified by chromatography on SiO$_2$ (EtOAc/hexane; 1:1) providing 6-chloro-9-ethyl-9H-purine.

Into a 3-L 4-neck round-bottom flask purged and maintained with an inert atmosphere of nitrogen was placed a suspension of 60% sodium hydride in mineral oil (18.5 g, 462 mmol) in THF (500 mL). This was followed by the dropwise addition of a solution of tert-butyl (3S)-3-hydroxypyrrolidine-1-carboxylate (72 g, 385 mmol) in THF (540 mL) with stirring at 0° C. The resulting solution was stirred for 15 minutes at room temperature. To this was added 6-chloro-9-ethyl-9H-purine (70 g, 383 mmol) in several batches at room temperature. The resulting solution was allowed to stir overnight at room temperature. The reaction was then quenched by the addition of 500 mL of water and extracted with 6×300 mL of ethyl acetate. The organic extracts were combined, dried over anhydrous sodium sulfate and concentrated. The residue was purified by chromatography on SiO$_2$ (DCM/MeOH; 20:1) providing tert-butyl (3S)-3-[(9-ethyl-9H-purin-6-yl)oxy]pyrrolidine-1-carboxylate (Intermediate VI).

Into a 5-L 4-neck round-bottom flask purged and maintained with an inert atmosphere of nitrogen was placed a solution of HN(iPr)Cy (44.8 g, 318 mmol) in THF (1.4 L). This was followed by dropwise addition of 2.4 N n-BuLi (126 mL) with stirring at −78° C., and the resulting solution stirred for 30 minutes at −78° C. To this was added dropwise a solution of tert-butyl (3S)-3-[(9-ethyl-9H-purin-6-yl)oxy]pyrrolidine-1-carboxylate (70 g, 210 mmol) in THF (700 mL) with stirring at −78° C. After stirring for an additional 30 minutes at −78° C., the mixture was treated with a solution of iodine (80.5 g, 317 mmol) in THF (420 mL) at −78° C. The resulting solution was stirred for an additional 1 hour at −78° C., then quenched by the addition of 500/1000 mL of aq. NH$_4$Cl (500 mL) and aq. Na$_2$SO$_3$ (1000 mL). The resulting solution was extracted with 2×500 mL of ethyl acetate, the organic extracts were combined, dried over anhydrous sodium sulfate and concentrated. The residue was purified by chromatography on SiO$_2$ (EtOAc/petroleum ether, 1:1) giving tert-butyl (3S)-3-[(8-iodo-9-methyl-9H-purin-6-yl)oxy]pyrrolidine-1-carboxylate (Intermediate VII). $^1$H NMR (400 MHz, CDCl$_3$) δ 8.59-8.39 (d, 1H), 5.99-5.75 (s, 1H), 4.45-4.15 (m, 2H), 3.90-3.40 (m, 4H), 2.45-2.15 (m, 2H), 1.70-1.45 (m, 12H). MS (EI) Calc'd for C$_{16}$H$_{22}$IN$_5$O$_3$ [M+H]$^+$, 460. found, 460.

Step 4: Preparation of 1-51

A vial was charged with Intermediate VII (140 mg, 0.305 mmol), 2-(difluoromethoxy)-5-(4,4,5,5-tetramethyl-1,3,2-dioxaborolan-2-yl)pyridine (83 mg, 0.31 mmol), and PdCl$_2$(dppf)-DCM (22 mg, 0.030 mmol). The flask was vacuum/backfilled with argon three times. Dioxane (3 mL) was added, followed by 2 N Na$_2$CO$_3$ (0.11 mL, 0.22 mmol). The vial was heated at 85° C. for 16 hours, filtered through a plug of silica gel and washed with DCM and MeOH. Concentration and purification by reverse phase chromatography gave the TFA salt of 1-51. $^1$H NMR (400 MHz, DMSO-d$_6$) δ 8.67 (s, 1H), 8.55 (s, 1H), 8.34-8.32 (d, 1H), 7.30-7.28 (d, 1H), 5.81 (s, 1H), 4.32-4.29 (m, 2H), 3.49-3.45 (m, 4H), 2.45-2.15 (m, 2H), 1.37-1.35 (m, 9H), 1.29-1.26 (m, 4H). MS (EI) Calc'd for C$_{22}$H$_{27}$F$_2$N$_6$O$_4$ [M+H]$^+$, 477. found, 477.

Compounds 1-4 through 1-9, 1-11, 1-36 through 1-38 were prepared in an analogous fashion as described for Example 3 using the corresponding chloroformate reagent and Intermediate II.

Compounds 1-12, 1-40 to 1-42 were prepared in an analogous fashion as described for Example 1 using the corresponding alcohol and Intermediate I.

Compounds 1-14 to 1-35 and 1-39 were prepared in an analogous fashion as described for Example 4 using the corresponding aldehyde (paraformaldeyde was used for compound 1-32).

Compound 1-45 was prepared in an analogous fashion as described for Example 1A; substituting (S)-tert-butyl 3-hydroxypyrrolidine-1-carboxylate for benzyl 3-ethyl-4-hydroxypyrrolidine-1-carboxylate (prepared via the route outlined in *J. Med. Chem.* 2010, 53, 6730-6746).

Compound 1-46 was prepared in an analogous fashion as described for Example 1A; substituting (S)-tert-butyl 3-hydroxypyrrolidine-1-carboxylate for cis-tert-butyl 3,4-dihydroxypyrrolidine-1-carboxylate (prepared via the route outlined in WO 2005/014582 A1).

Compound 1-48 was prepared in an analogous fashion as described for Example 1A; substituting (S)-tert-butyl 3-hydroxypyrrolidine-1-carboxylate for (2R,3R)-tert-butyl 3-hydroxy-2-methylpyrrolidine-1-carboxylate (prepared via the route outlined in *Tetrahedron Lett.* 2011, 52, 5036-5038 and WO 2009/013211 A2).

Compound 1-50 was prepared in an analogous fashion as described for Example 4C from Intermediate V.

TABLE 1

| Compound | Structure | Compound Name | MS [M + H]$^+$ |
|---|---|---|---|
| 1-1 | 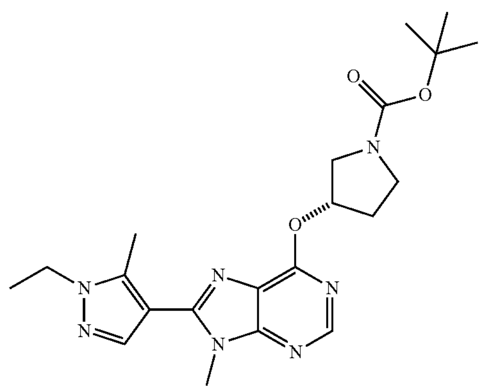 | tert-butyl (3S)-3-{[8-(1-ethyl-5-methyl-1H-pyrazol-4-yl)-9-methyl-9H-purin-6-yl]oxy}pyrrolidine-1-carboxylate | Calc'd 428, found 428 |
| 1-2 | 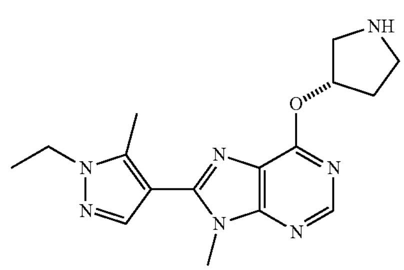 | 8-(1-ethyl-5-methyl-1H-pyrazol-4-yl)-9-methyl-6-[(3S)-pyrrolidin-3-yloxy]-9H-purine | Calc'd 328, found 328 |
| 1-3 | 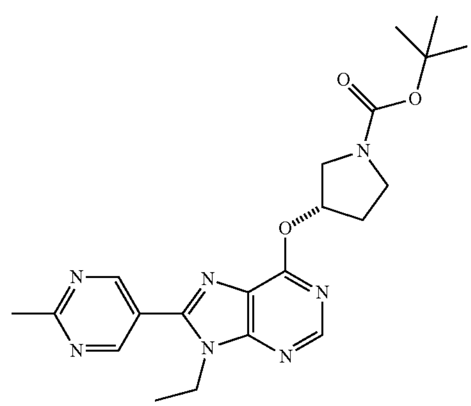 | tert-butyl (3S)-3-{[9-ethyl-8-(2-methylpyrimidin-5-yl)-9H-purin-6-yl]oxy}pyrrolidine-1-carboxylate | Calc'd 426, found 426 |

TABLE 1-continued

| Compound | Structure | Compound Name | MS [M + H]+ |
|---|---|---|---|
| 1-4 | 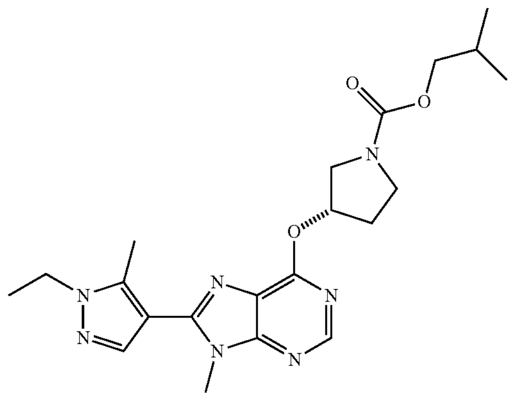 | 2-methylpropyl (3S)-3-{[8-(1-ethyl-5-methyl-1H-pyrazol-4-yl)-9-methyl-9H-purin-6-yl]oxy}pyrrolidine-1-carboxylate | Calc'd 428, found 428 |
| 1-5 | 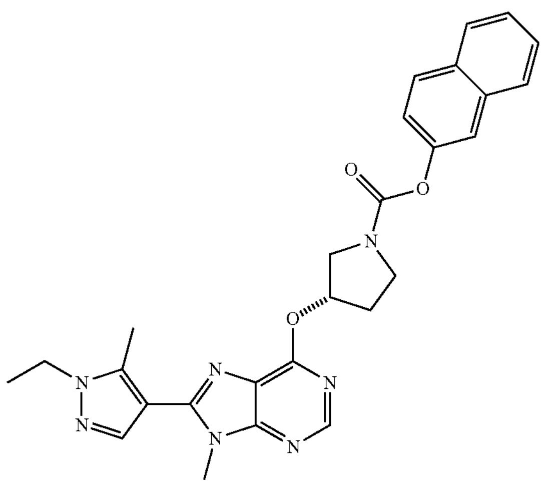 | naphthalen-2-yl (3S)-3-{[8-(1-ethyl-5-methyl-1H-pyrazol-4-yl)-9-methyl-9H-purin-6-yl]oxy}pyrrolidine-1-carboxylate | Calc'd 498, found 498 |
| 1-6 | 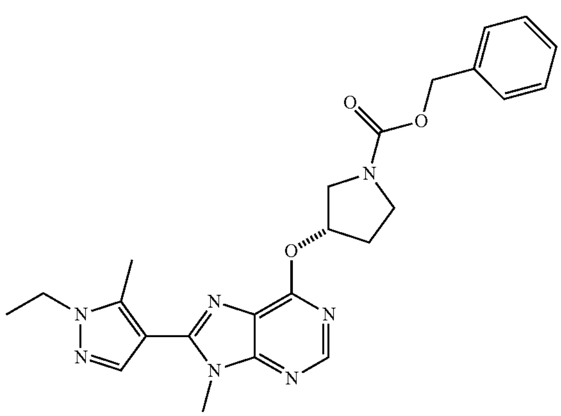 | benzyl (3S)-3-{[8-(1-ethyl-5-methyl-1H-pyrazol-4-yl)-9-methyl-9H-purin-6-yl]oxy}pyrrolidine-1-carboxylate | Calc'd 462, found 462 |

TABLE 1-continued

| Compound | Structure | Compound Name | MS [M + H]+ |
|---|---|---|---|
| 1-7 | 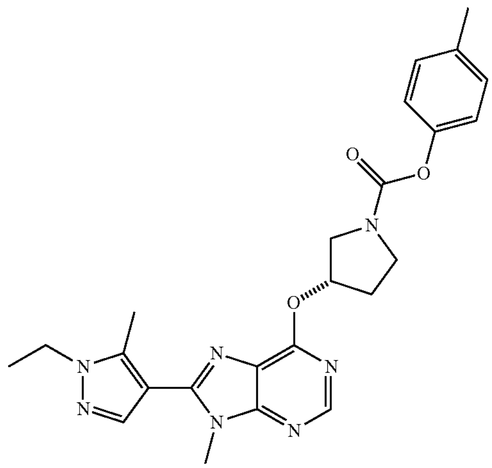 | 4-methylphenyl (3S)-3-{[8-(1-ethyl-5-methyl-1H-pyrazol-4-yl)-9-methyl-9H-purin-6-yl]oxy}pyrrolidine-1-carboxylate | Calc'd 462, found 462 |
| 1-8 | 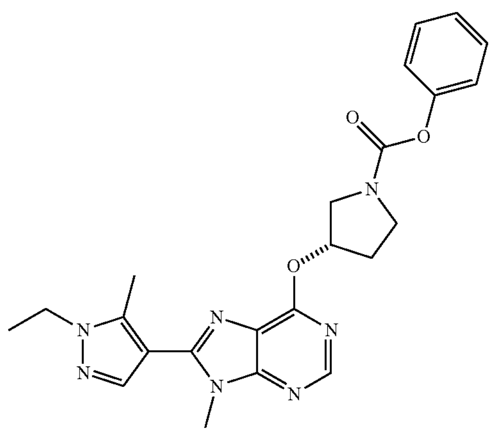 | phenyl (3S)-3-{[8-(1-ethyl-5-methyl-1H-pyrazol-4-yl)-9-methyl-9H-purin-6-yl]oxy}pyrrolidine-1-carboxylate | Calc'd 448, found 448 |
| 1-9 | 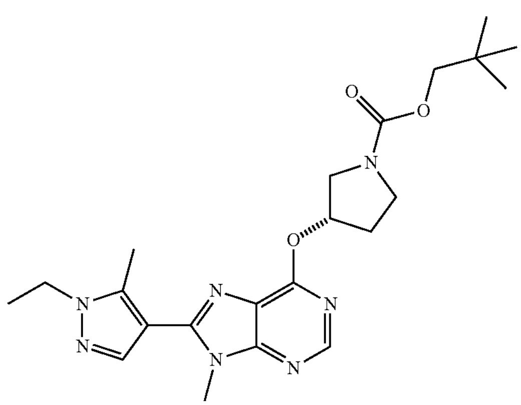 | 2,2-dimethylpropyl (3S)-3-{[8-(1-ethyl-5-methyl-1H-pyrazol-4-yl)-9-methyl-9H-purin-6-yl]oxy}pyrrolidine-1-carboxylate | Calc'd 442, found 442 |

TABLE 1-continued

| Compound | Structure | Compound Name | MS [M + H]+ |
|---|---|---|---|
| 1-10 | 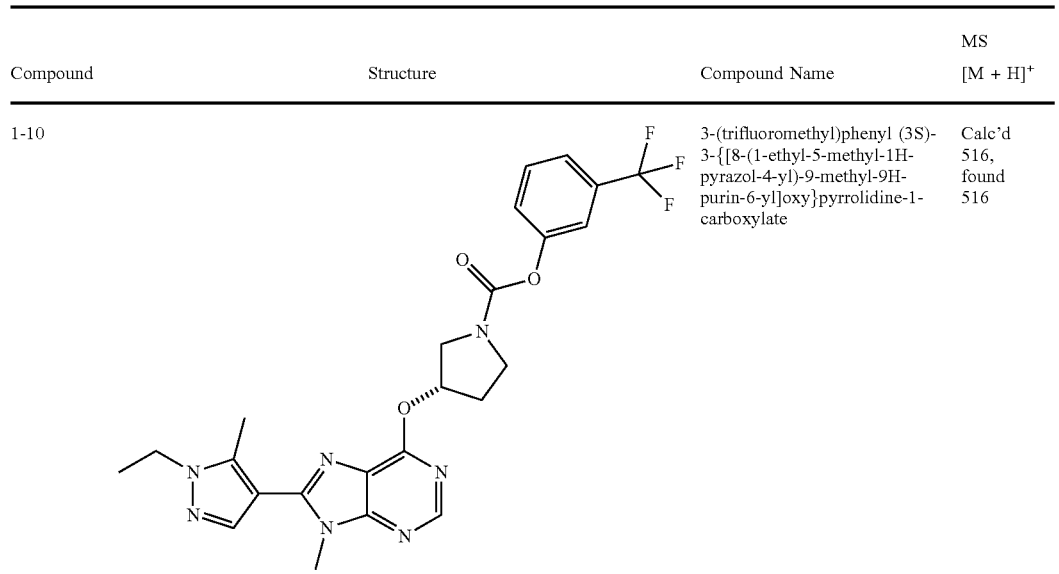 | 3-(trifluoromethyl)phenyl (3S)-3-{[8-(1-ethyl-5-methyl-1H-pyrazol-4-yl)-9-methyl-9H-purin-6-yl]oxy}pyrrolidine-1-carboxylate | Calc'd 516, found 516 |
| 1-11 | 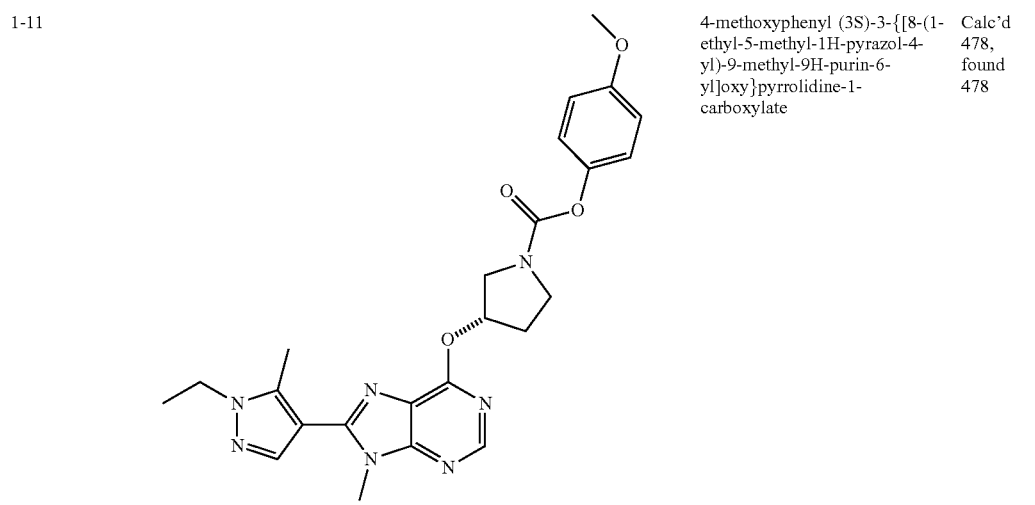 | 4-methoxyphenyl (3S)-3-{[8-(1-ethyl-5-methyl-1H-pyrazol-4-yl)-9-methyl-9H-purin-6-yl]oxy}pyrrolidine-1-carboxylate | Calc'd 478, found 478 |
| 1-12 | 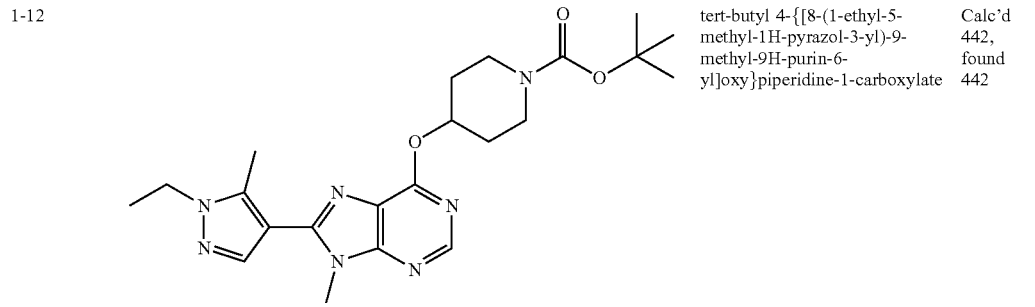 | tert-butyl 4-{[8-(1-ethyl-5-methyl-1H-pyrazol-3-yl)-9-methyl-9H-purin-6-yl]oxy}piperidine-1-carboxylate | Calc'd 442, found 442 |

TABLE 1-continued

| Compound | Structure | Compound Name | MS [M + H]+ |
|---|---|---|---|
| 1-13 | 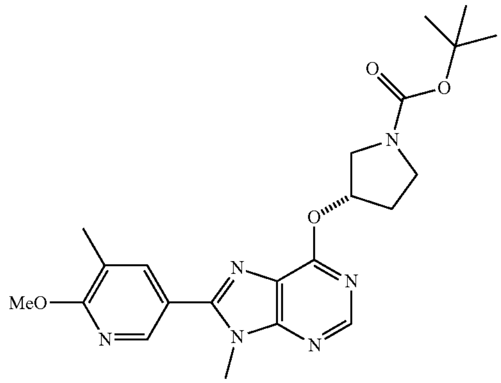 | tert-butyl (3S)-3-{[8-(6-methoxy-5-methylpyridin-3-yl)-9-methyl-9H-purin-6-yl]oxy}pyrrolidine-1-carboxylate | Calc'd 441, found 441 |
| 1-14 | 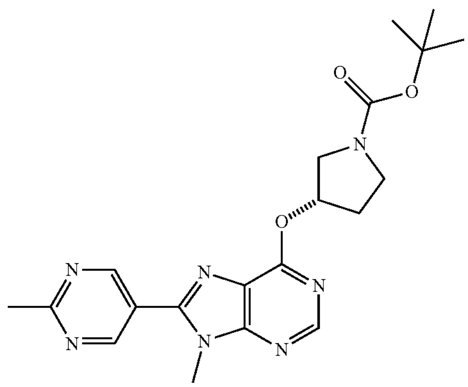 | terl-butyl (3S)-3-{[9-methyl-8-(2-methylpyrimidin-5-yl)-9H-purin-6-yl]oxy}pyrrolidine-1-carboxylate | Calc'd 412, found 412 |
| 1-15 | 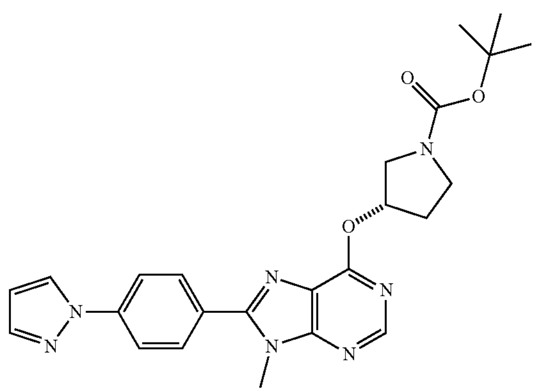 | tert-butyl (3S)-3-({9-methyl-8-[4-(1H-pyrazol-1-yl)phenyl]-9H-purin-6-yl}oxy)pyrrolidine-1-carboxylate | Calc'd 462, found 462 |
| 1-16 | 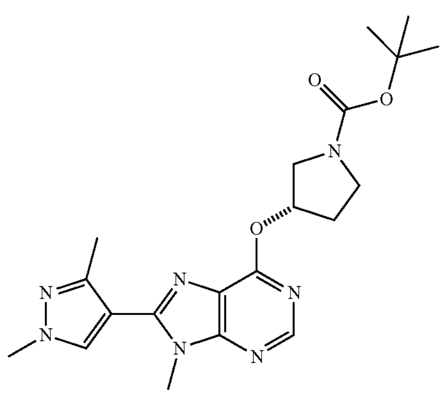 | tert-butyl (3S)-3-{[8-(1,3-dimethyl-1H-pyrazol-4-yl)-9-methyl-9H-purin-6-yl]oxy}pyrrolidine-1-carboxylate | Calc'd 414, found 414 |

TABLE 1-continued

| Compound | Structure | Compound Name | MS [M + H]+ |
|---|---|---|---|
| 1-17 | 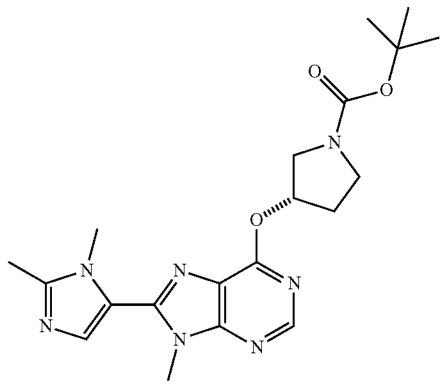 | tert-butyl (3S)-3-{[8-(1,2-dimethyl-1H-imidazol-5-yl)-9-methyl-9H-purin-6-yl]oxy}pyrrolidine-1-carboxylate | Calc'd 414, found 414 |
| 1-18 | 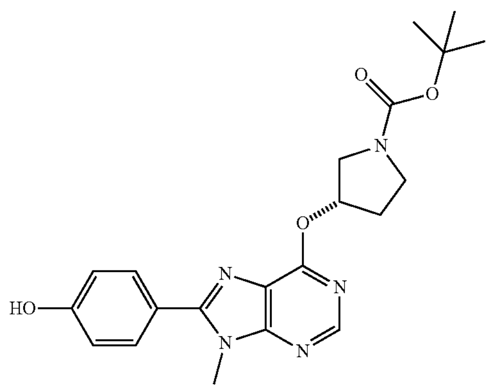 | tert-butyl (3S)-3-{[8-(4-hydroxyphenyl)-9-methyl-9H-purin-6-yl]oxy}pyrrolidine-1-carboxylate | Calc'd 412, found 412 |
| 1-19 | 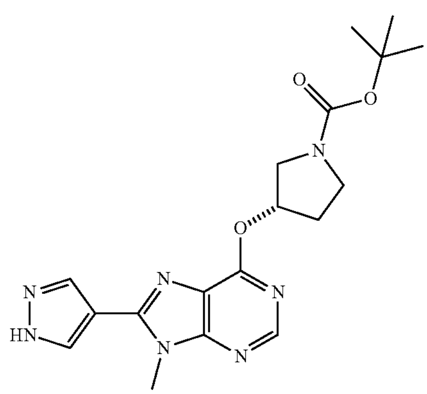 | tert-butyl (3S)-3-{[9-methyl-8-(1H-pyrazol-4-yl)-9H-purin-6-yl]oxy}pyrrolidine-1-carboxylate | Calc'd 386, found 386 |
| 1-20 | 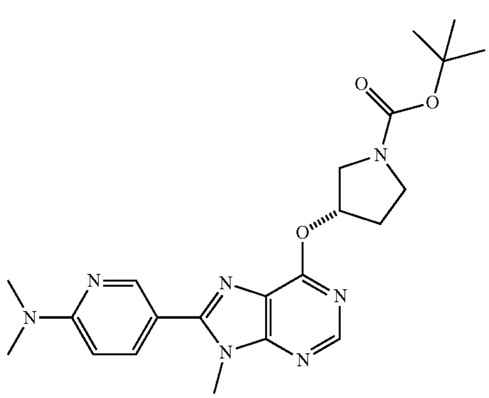 | tert-butyl (3S)-3-{[8-(6-(dimethylamino)pyridin-3-yl]-9-methyl-9H-purin-6-yl}oxy)pyrrolidine-1-carboxylate | Calc'd 440, found 440 |

TABLE 1-continued

| Compound | Structure | Compound Name | MS [M + H]+ |
|---|---|---|---|
| 1-21 | 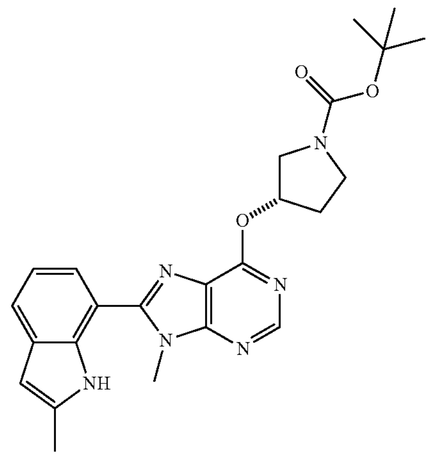 | tert-butyl (3S)-3-{[9-methyl-8-(2-methyl-1H-indol-7-yl)-9H-purin-6-yl]oxy}pyrrolidine-1-carboxylate | Calc'd 449, found 449 |
| 1-22 | 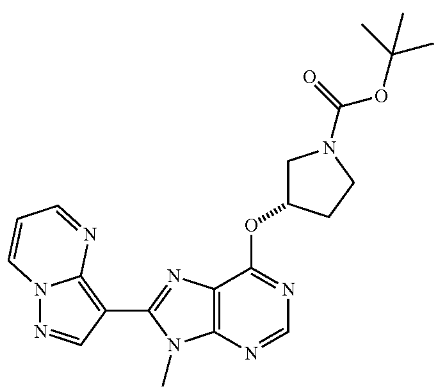 | tert-butyl (3S)-3-[(9-methyl-8-pyrazolo[1,5-a]pyrimidin-3-yl-9H-purin-6-yl)oxy]pyrrolidine-1-carboxylate | Calc'd 437, found 437 |
| 1-23 | 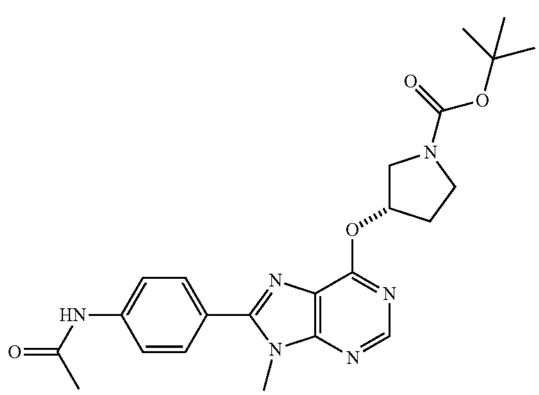 | tert-butyl (3S)-3-({8-[4-(acetylamino)phenyl]-9-methyl-9H-purin-6-yl}oxy)pyrrolidine-1-carboxylate | Calc'd 453, found 453 |

TABLE 1-continued

| Compound | Structure | Compound Name | MS [M + H]+ |
|---|---|---|---|
| 1-24 | 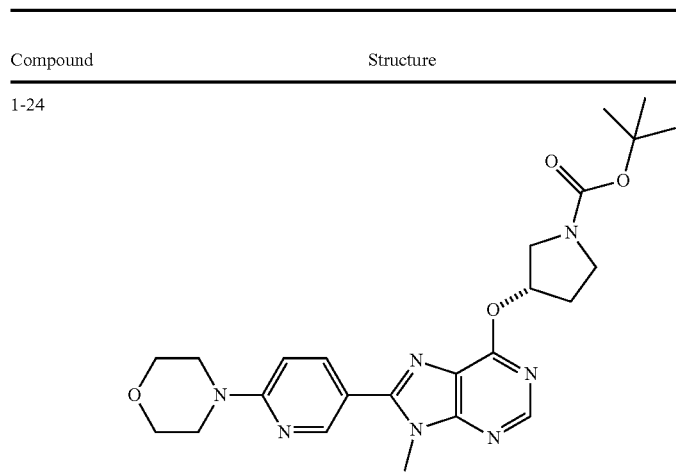 | tert-butyl (3S)-3-{[9-methyl-8-(6-morpholin-4-ylpyridin-3-yl)-9H-purin-6-yl]oxy}pyrrolidine-1-carboxylate | Calc'd 482, found 482 |
| 1-25 | 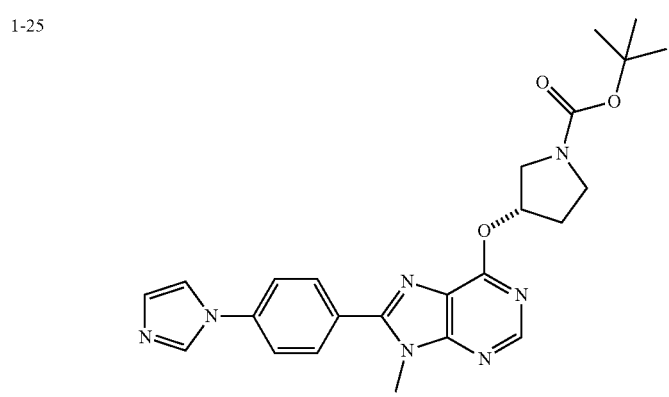 | tert-butyl (3S)-3-({8-[4-(1H-imidazol-1-yl)phenyl]-9-methyl-9H-purin-6-yl}oxy)pyrrolidine-1-carboxylate | Calc'd 462, found 462 |
| 1-26 | 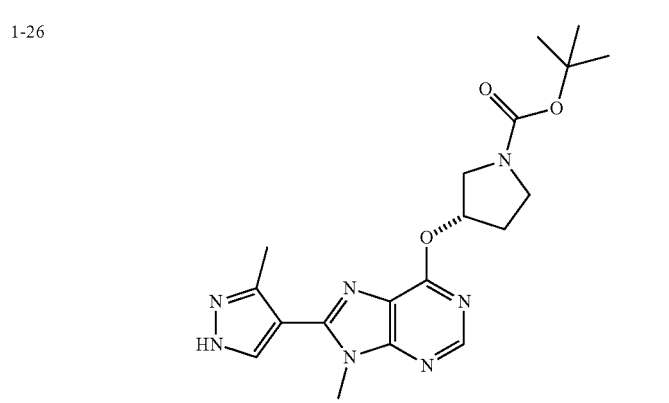 | tert-butyl (3S)-3-{[9-methyl-8-(3-methyl-1H-pyrazol-4-yl)-9H-purin-6-yl]oxy}pyrrolidine-1-carboxylate | Calc'd 400, found 400 |
| 1-27 | 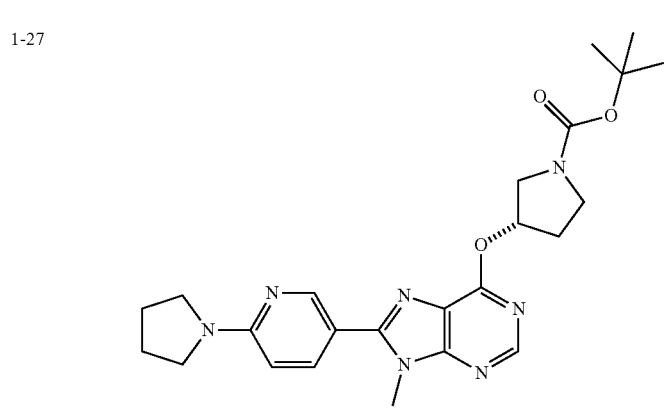 | tert-butyl (3S)-3-{[9-methyl-8-(6-pyrrolidin-1-ylpyridin-3-yl)-9H-purin-6-yl]oxy}pyrrolidine-1-carboxylate | Calc'd 466, found 466 |

TABLE 1-continued

| Compound | Structure | Compound Name | MS [M + H]+ |
|---|---|---|---|
| 1-28 | 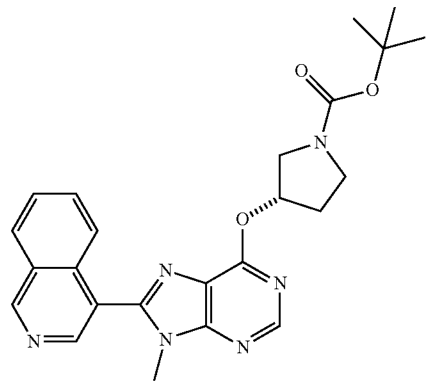 | tert-butyl (3S)-3-[(8-isoquinolin-4-yl-9-methyl-9H-purin-6-yl)oxy]pyrrolidine-1-carboxylate | Calc'd 447, found 447 |
| 1-29 | 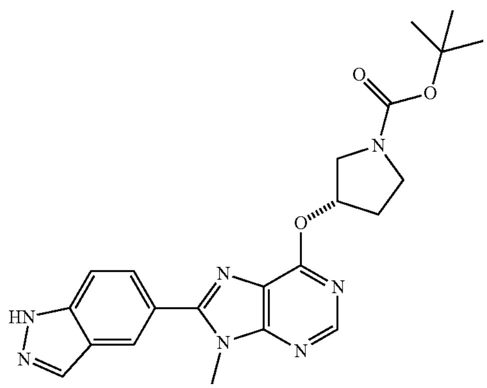 | tert-butyl (3S)-3-{[8-(1H-indazol-5-yl)-9-methyl-9H-purin-6-yl]oxy}pyrrolidine-1-carboxylate | Calc'd 436, found 436 |
| 1-30 | 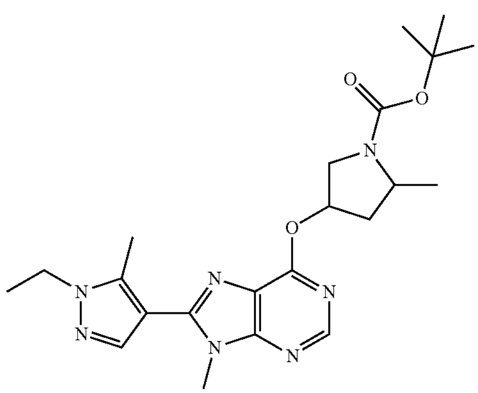 [SMILES: CCn1ncc(-c2nc3c(OC4CC(C)N(C(=O)OC(C)(C)C)C4)ncnc3n2C)c1C] | tert-butyl 4-((8-(1-ethyl-5-methyl-1H-pyrazol-4-yl)-9-methyl-9H-purin-6-yl)oxy)-2-methylpyrrolidine-1-carboxylate | Calc'd 442, found 442 |
| 1-31 | 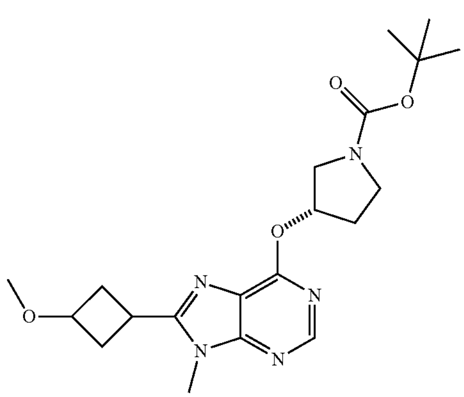 | (S)-tert-butyl 3-((8-(3-methoxycyclobutyl)-9-methyl-9H-purin-6-yl)oxy)pyrrolidine-1-carboxylate | Calc'd 404, found 404 |

TABLE 1-continued

| Compound | Structure | Compound Name | MS [M + H]+ |
|---|---|---|---|
| 1-32 | 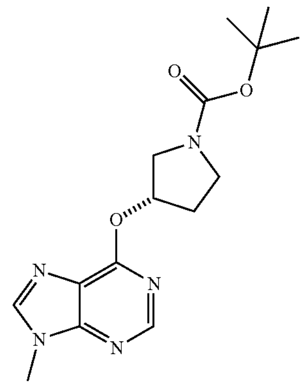 | (S)-tert-butyl 3-((9-methyl-9H-purin-6-yl)oxy)pyrrolidine-1-carboxylate | Calc'd 320, found 320 |
| 1-33 | 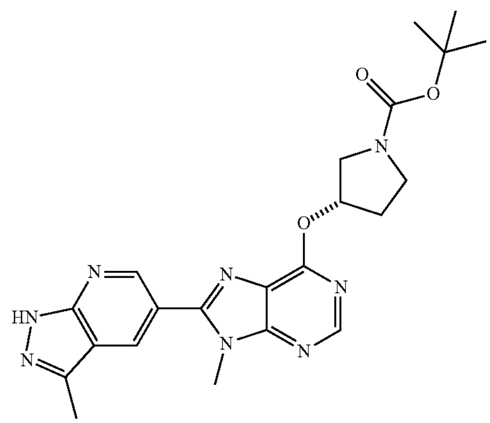 | (S)-tert-butyl 3-((9-methyl-8-(3-methyl-1H-pyrazolo[3,4-b]pyridin-5-yl)-9H-purin-6-yl)oxy}pyrrolidine-1-carboxylate | Calc'd 451, found 451 |
| 1-34 | 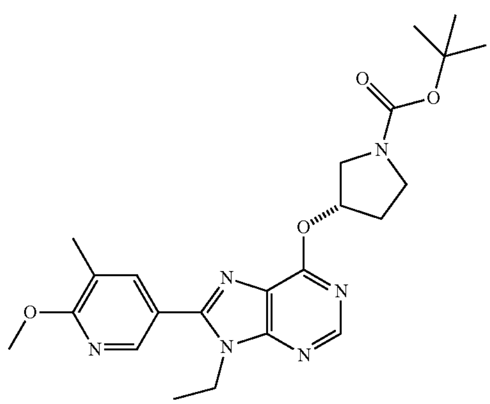 | tert-butyl (3S)-3-{[9-ethyl-8-(6-methoxy-5-methylpyridin-3-yl)-9H-purin-6-yl]oxy}pyrrolidine-1-carboxylate | Calc'd 455, found 455 |
| 1-35 | 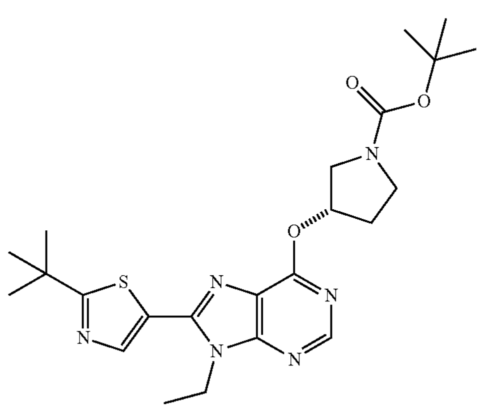 | tert-butyl (3S)-3-{[8-(2-tert-butyl-1,3-thiazol-5-yl)-9-ethyl-9H-purin-6-yl]oxy}pyrrolidine-1-carboxylate | Calc'd 473, found 473 |

TABLE 1-continued

| Compound | Structure | Compound Name | MS [M + H]+ |
|---|---|---|---|
| 1-36 | 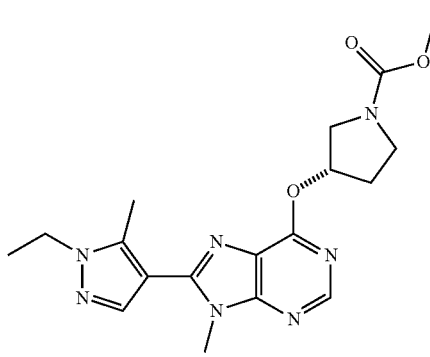 | methyl (3S)-3-{[8-(1-ethyl-5-methyl-1H-pyrazol-4-yl)-9-methyl-9H-purin-6-yl]oxy}pyrrolidine-1-carboxylate | Calc'd 386, found 386 |
| 1-37 | 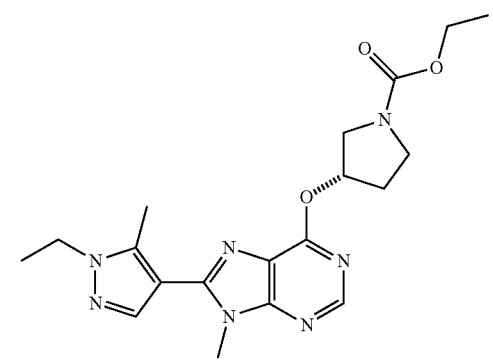 | ethyl (3S)-3-{[8-(1-ethyl-5-methyl-1H-pyrazol-4-yl)-9-methyl-9H-purin-6-yl]oxy}pyrrolidine-1-carboxylate | Calc'd 400, found 400 |
| 1-38 | 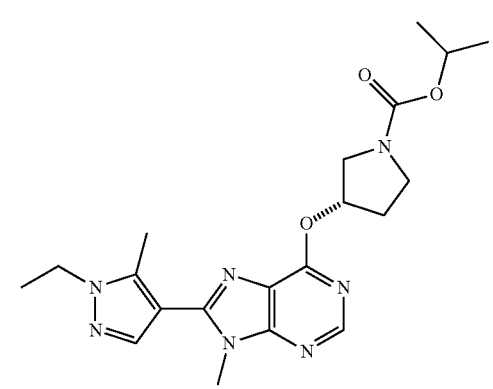 | 1-methylethyl (3S)-3-{[8-(1-ethyl-5-methyl-1H-pyrazol-4-yl)-9-methyl-9H-purin-6-yl]oxy}pyrrolidine-1-carboxylate | Calc'd 414, found 414 |
| 1-39 | 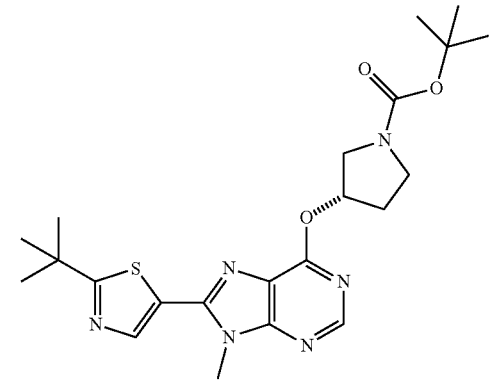 | tert-butyl (3S)-3-{[8-(2-tert-butyl-1,3-thiazol-5-yl)-9-methyl-9H-purin-6-yl]oxy}pyrrolidine-1-carboxylate | Calc'd 459, found 459 |

TABLE 1-continued

| Compound | Structure | Compound Name | MS [M + H]+ |
|---|---|---|---|
| 1-40 | 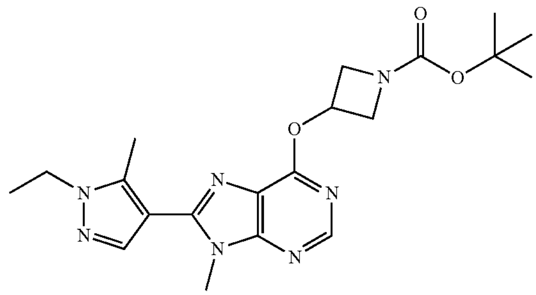 [SMILES: CCn1ncc(-c2nc3c(OC4CN(C(=O)OC(C)(C)C)C4)ncnc3n2C)c1C] | tert-butyl 3-((8-(1-ethyl-5-methyl-1H-pyrazol-4-yl)-9-methyl-9H-purin-6-yl)oxy)azetidine-1-carboxylate | Calc'd 414, found 414 |
| 1-41 | 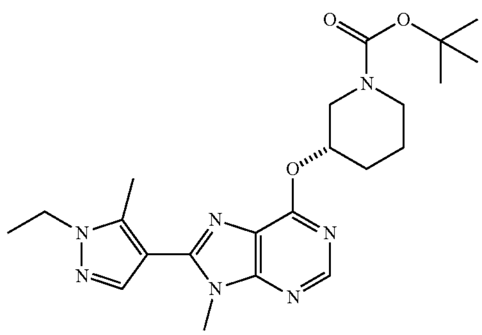 | (S)-tert-butyl 3-((8-(1-ethyl-5-methyl-1H-pyrazol-4-yl)-9-methyl-9H-purin-6-yl)oxy)piperidine-1-carboxylate | Calc'd 442, found 442 |
| 1-42 | 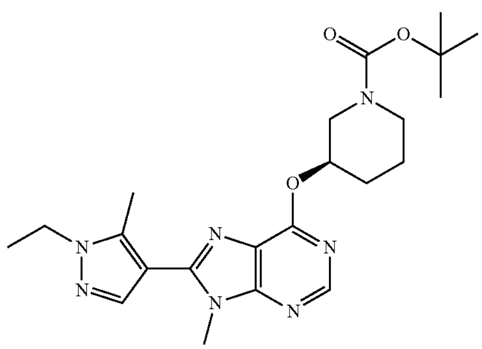 [SMILES: CCn1ncc(-c2nc3c(O[C@@H]4CCCN(C(=O)OC(C)(C)C)C4)ncnc3n2C)c1C] | (R)-tert-butyl 3-((8-(1-ethyl-5-methyl-1H-pyrazol-4-yl)-9-methyl-9H-purin-6-yl)oxy)piperidine-1-carboxylate | Calc'd 442, found 442 |
| 1-43 | 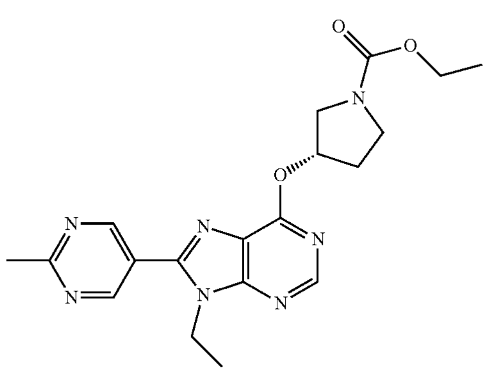 [SMILES: CCOC(=O)N1CC[C@H](Oc2ncnc3c2nc(-c2cnc(C)nc2)n3CC)C1] | (S)-ethyl 3-{[9-ethyl-8-(2-methylpyrimidin-5-yl)-9H-purin-6-yl]oxy}pyrrolidine-1-carboxylate | Calc'd 398, found 398 |

TABLE 1-continued

| Compound | Structure | Compound Name | MS [M + H]+ |
|---|---|---|---|
| 1-44 | 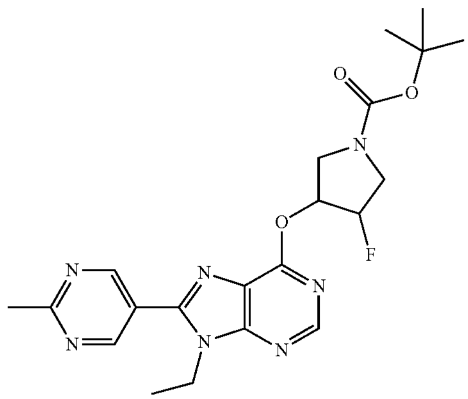 [SMILES: CCn1c(-c2cnc(C)nc2)nc2c(OC3CN(C(=O)OC(C)(C)C)CC3F)ncnc21] | [(3S,4S) and (3R,4R)]-tert-butyl 3-{[9-ethyl-8-(2-methylpyrimidin-5-yl)-9H-purin-6-yl]oxy}-4-fluoropyrrolidine-1-carboxylate | Calc'd 444, found 444 |
| 1-45 | 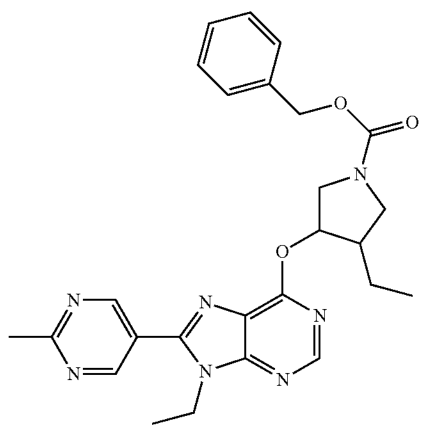 [SMILES: CCC1CN(C(=O)OCc2ccccc2)CC1Oc1ncnc2c1nc(-c1cnc(C)nc1)n2CC] | [(3S,4R) and (3R,4S)]-benzyl 3-ethyl-4-{[9-ethyl-8-(2-methylpyrimidin-5-yl)-9H-purin-6-yl]oxy}pyrrolidine-1-carboxylate | Calc'd 488, found 488 |
| 1-46 | 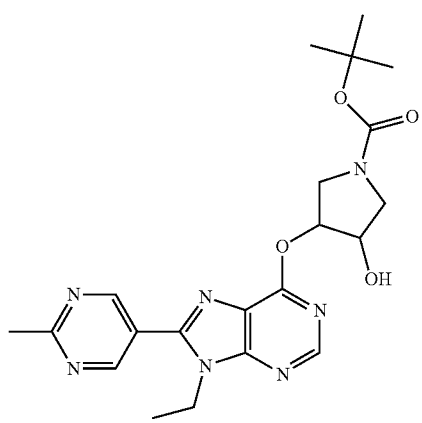 [SMILES: CCn1c(-c2cnc(C)nc2)nc2c(OC3CN(C(=O)OC(C)(C)C)CC3O)ncnc21] | [(3S,4S) and (3R,4R)]-tert-butyl 3-{[9-ethyl-8-(2-methylpyrimidin-5-yl)-9H-purin-6-yl]oxy}-4-hydroxypyrrolidine-1-carboxylate | Calc'd 442, found 442 |
| 1-47 | 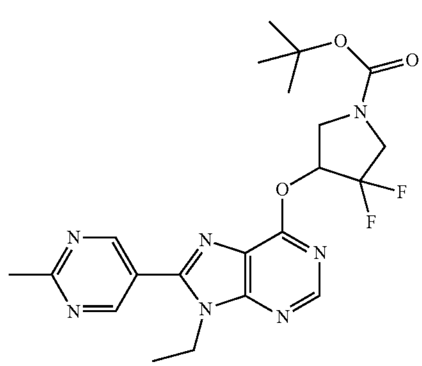 [SMILES: CCn1c(-c2cnc(C)nc2)nc2c(OC3CN(C(=O)OC(C)(C)C)CC3(F)F)ncnc21] | (4S and 4R)-tert-butyl 4-{[9-ethyl-8-(2-methylpyrimidin-5-yl)-9H-purin-6-yl]oxy}-3,3-difluoropyrrolidine-1-carboxylate | Calc'd 462, found 462 |

TABLE 1-continued

| Compound | Structure | Compound Name | MS [M + H]+ |
|---|---|---|---|
| 1-48 | 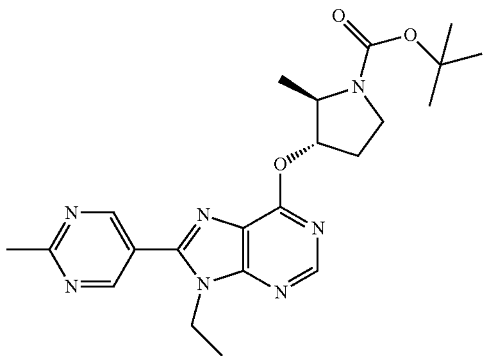 [SMILES: CCn1c(-c2cnc(C)nc2)nc2c(O[C@H]3CCN(C(=O)OC(C)(C)C)[C@@H]3C)ncnc21] | tert-butyl (2R,3S)-3-{[9-ethyl-8-(2-methylpyrimidin-5-yl)-9H-purin-6-yl]oxy}-2-methylpyrrolidine-1-carboxylate | Calc'd 440, found 440 |
| 1-49 | 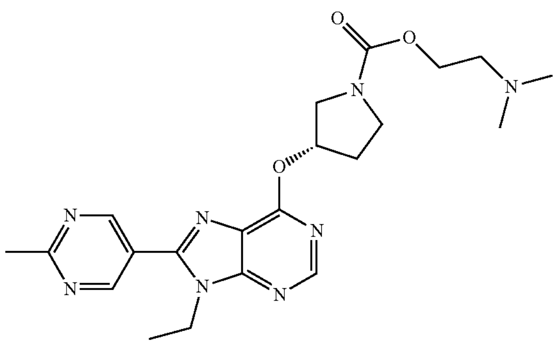 | 2-(dimethylamino)ethyl (3S)-3-{[9-ethyl-8-(2-methylpyrimidin-5-yl)-9H-purin-6-yl]oxy}pyrrolidine-1-carboxylate | Calc'd 441, found 441 |
| 1-50 | 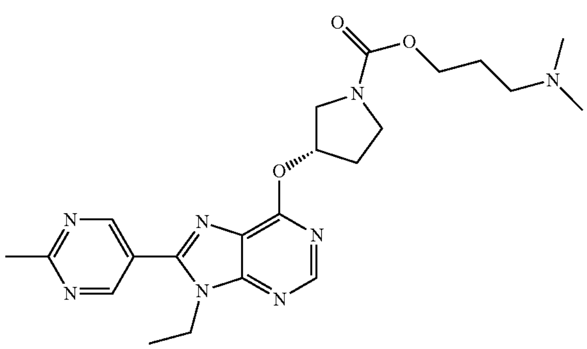 | 2-(dimethylamino)propyl (3S)-3-{[9-ethyl-8-(2-methylpyrimidin-5-yl)-9H-purin-6-yl]oxy}pyrrolidine-1-carboxylate | Calc'd 455, found 455 |
| 1-51 | 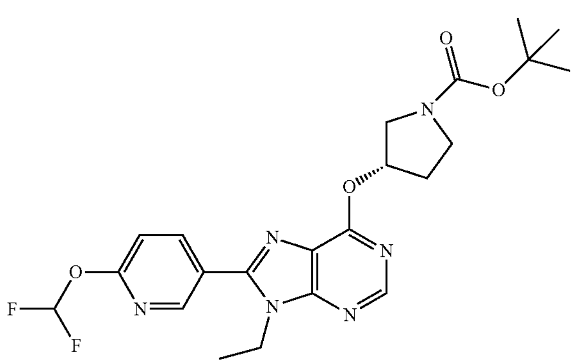 [SMILES: CCn1c(-c2ccc(OC(F)F)nc2)nc2c(O[C@H]3CCN(C(=O)OC(C)(C)C)C3)ncnc21] | tert-butyl (3S)-3-({8-[6-(difluoromethoxy)pyridin-3-yl]-9-ethyl-9H-purin-6-yl}oxy)pyrrolidine-1-carboxylate | Calc'd 477, found 477 |

Compound Examples of Table 2

Example 5—Preparation of Compound 2-2

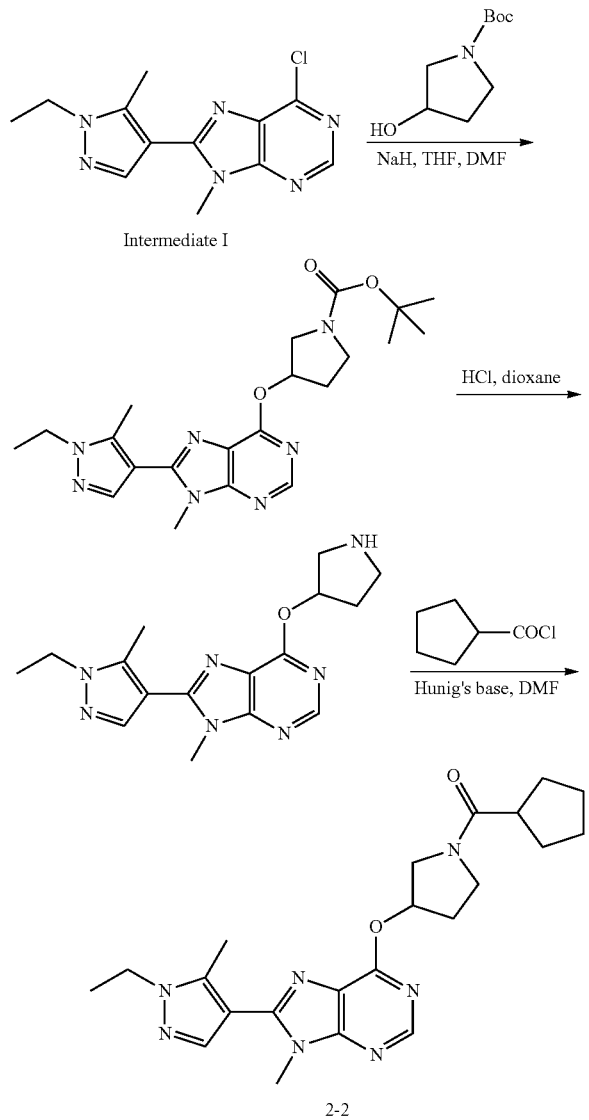

2-2

Step 1: Preparation of tert-butyl 3-((8-(1-ethyl-5-methyl-1H-pyrazol-4-yl)-9-methyl-9H-purin-6-yl)oxy)pyrrolidine-1-carboxylate A solution of tert-butyl 3-hydroxypyrrolidine-1-carboxylate (1.00 g, 5.34 mmol) in 10 mL of THF was treated with a 60% suspension of sodium hydride in mineral oil (250 mg, 6.25 mmol). The mixture was stirred for 10 min, then a mixture of Intermediate I (350 mg, 1.27 mmol) in 10 mL of DMF was added. The reaction mixture was stirred overnight, diluted with EtOAc and washed with 1 N NaOH, water, dried (Na$_2$SO$_4$), filtered and concentrated. The oily residue was purified by chromatography on SiO$_2$ (0-30% MeOH/DCM) to provide the title compound. MS (EI) Calc'd for C$_{21}$H$_{30}$N$_7$O$_3$ [M+H]$^+$, 428. found 428.

Step 2: Preparation of 8-(1-ethyl-5-methyl-1H-pyrazol-4-yl)-9-methyl-6-(pyrrolidin-3-yloxy)-9H-purine A solution of tert-butyl 3-((8-(1-ethyl-5-methyl-1H-pyrazol-4-yl)-9-methyl-9H-purin-6-yl)oxy)pyrrolidine-1-carboxylate (1.50 g, 3.51 mmol) in 10 mL of dioxane was treated with a 4 M solution of HCl in dioxane (4.0 mL, 16 mmol). The reaction mixture was stirred until LC/MS analysis indicated complete conversion to the deprotected amine. The mixture was concentrated to dryness to provide the HCl salt of 8-(1-ethyl-5-methyl-1H-pyrazol-4-yl)-9-methyl-6-(pyrrolidin-3-yloxy)-9H-purine. MS (EI) Calc'd for C$_{16}$H$_{22}$N$_7$O [M+H]$^+$, 328. found 328.

Step 3: Preparation of cyclopentyl(3-((8-(1-ethyl-5-methyl-1H-pyrazol-4-yl)-9-methyl-9H-purin-6-yl)oxy)pyrrolidin-1-yl)methanone A solution of the HCl salt of 8-(1-ethyl-5-methyl-1H-pyrazol-4-yl)-9-methyl-6-(pyrrolidin-3-yloxy)-9H-purine (40 mg, 0.10 mmol) in 1 mL of DMF was treated with triethylamine (0.070 mL, 0.50 mmol) followed by cyclopentyl carbonyl chloride (25 mg, 0.19 mmol). The mixture was stirred overnight, filtered and purified by reverse phase chromatography to provide the TFA salt of 2-2 after lyophilization of the appropriate LC fraction. $^1$H NMR (600 MHz, DMSO-d$_6$) δ 8.47 (s, 1H), 7.97 (s, 1H), 5.88-5.80 (m, 1H), 4.15 (q, J=7.3 Hz, 2H), 3.85-3.37 (m, 4H), 3.81 (m, 3H), 2.80 (m, 1H), 2.53 (m, 3H), 2.35-2.14 (m, 2H), 1.75 (m, 2H), 1.65-1.55 (m, 4H), 1.50-1.42 (m, 2H), 1.32 (t, J=7.0 Hz, 3H); MS (EI) Calc'd for C$_{22}$H$_{30}$N$_7$O$_2$ [M+H]$^+$, 424. found 424.

Example 6—Preparation of Compound 2-39

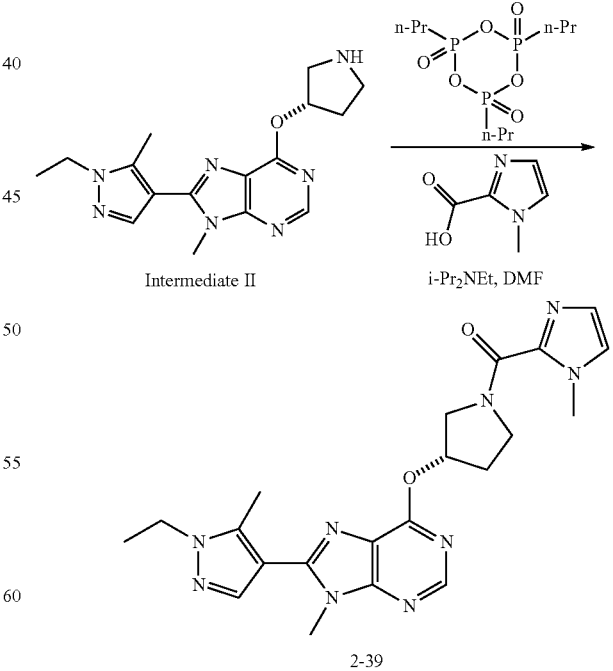

2-39

A solution of Intermediate II (30 mg, 0.092 mmol) and 1-methyl-1H-imidazole-2-carboxylic acid (14 mg, 0.11 mmol) in 1 mL of DMF was treated at 0° C. with i-Pr$_2$NEt (0.10 mL, 0.57 mmol) and propane phosphonic acid anhydride (T3P; 0.11 mL, 0.25 mmol). The vial was sealed and stirred at room temperature overnight. The reaction mixture was filtered, washing the filter with DMSO (1 mL). The crude product dissolved in 2 mL of DMSO/DMF was purified by reverse phase HPLC. The desired fraction was concentrated under reduced pressure to yield 2-39. $^1$H NMR (600 MHz, DMSO-$d_6$) δ 8.48 (m, 1H), 7.96 (m, 1H), 7.28 (m, 1H), 6.96 (m, 1H), 5.88 (s, 1H), 4.14 (q, J=7.2 Hz, 2H), 3.82 (s, 3H), 3.80 (s, 3H), 4.00-3.60 (m, 4H), 2.53-2.52 (m, 3H), 2.35-2.20 (m, 2H), 1.32 (t, J=7.3 Hz, 3H); MS (EI) Calc'd for $C_{21}H_{26}N_9O_2$ [M+H]$^+$, 436. found 436.

Example 6A—Preparation of 2-15

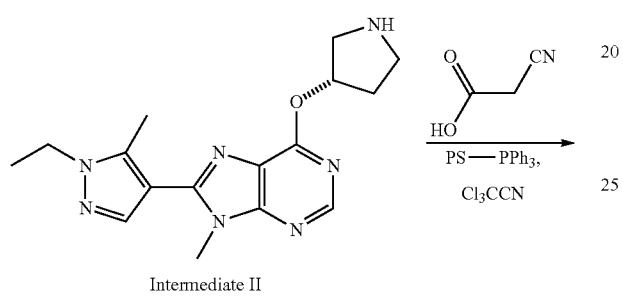

Intermediate II

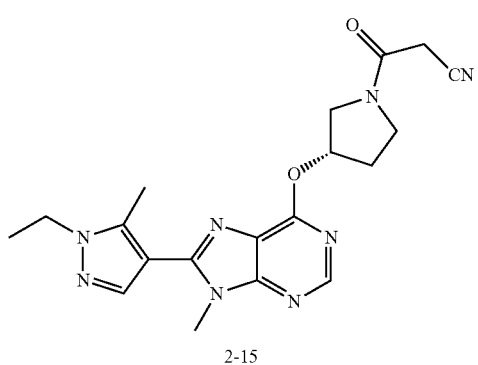

2-15

A mixture containing Intermediate II (25 mg, 0.076 mmol), 2-cyanoacetic acid (9 mg, 0.1 mmol), PS-Triphenylphosphine (119 mg, 0.229 mmol) and trichloroacetonitrile (0.038 mL, 0.38 mmol) in acetonitrile (1.5 mL) was heated to 150° C. for 10 min. Once cool, the mixture was filtered and the residue washed with DMSO (1.5 mL). The combined organic extracts was subjected to purification by reverse phase chromatography to provide the TFA salt of 2-15. $^1$H NMR (600 MHz, DMSO-$d_6$) δ 8.47 (s, 1H), 7.97 (m, 1H), 5.85 (m, 1H), 4.14 (q, J=7.0 Hz, 2H), 4.00 (m, 2H), 3.82 (m, 3H), 3.88-3.54 (m, 4H), 2.53 (m, 3H), 2.33-2.19 (m, 2H), 1.33 (t, J=7.0 Hz, 3H). MS (EI) Calc'd for $C_{19}H_{23}N_8O_2$ [M+H]$^+$, 395. found, 395.

Example 7

Preparation of Compound 2-88

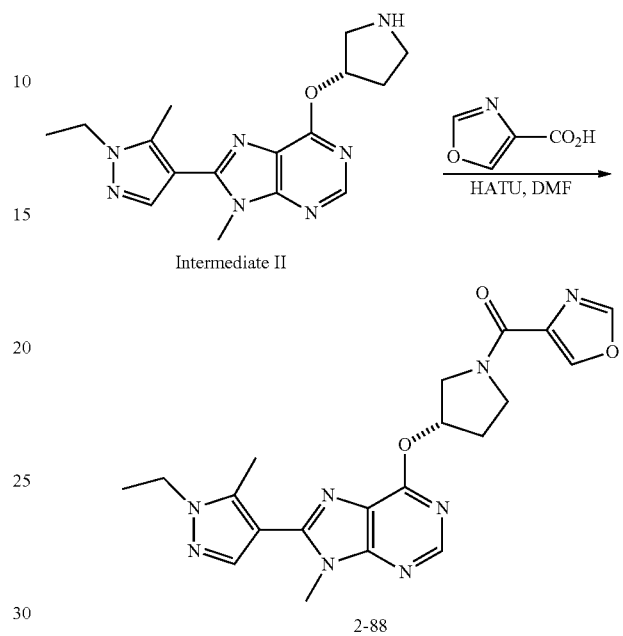

A solution of Intermediate II (100 mg, 0.305 mmol) in 2 mL of DMF was treated with oxazole-4-carboxylic acid (100 mg, 0.884 mmol) and HATU (2-(1H-7-azabenzotriazol-1-yl)-1,1,3,3-tetramethyl uronium hexafluorophosphate methanaminium; 200 mg, 0.526 mmol). The reaction mixture was stirred overnight, then diluted with DCM and washed with sat'd NaHCO$_3$, dried (Na$_2$SO$_4$) and concentrated. Purification by reverse phase chromatography followed by lyophilization of the desired fraction provided the TFA salt of 2-88. $^1$H NMR (600 MHz, DMSO-$d_6$) δ 8.64-8.61 (m, 1H), 8.48-8.47 (m, 1H), 8.44 (s, 1H), 7.96 (s, 1H), 5.88 (m, 1H), 4.21 (m, 1H), 4.14 (q, J=7.3 Hz, 2H), 4.10 (m, 1H), 3.95-3.60 (m, 2H), 3.81-3.80 (m, 3H), 2.52 (s, 3H), 2.35-2.20 (m, 2H), 1.32 (t, J=7.4 Hz, 3H); MS (EI) Calc'd for $C_{20}H_{23}N_8O_3$ [M+H]$^+$, 423. found 423.

Example 7A—Preparation of 2-107

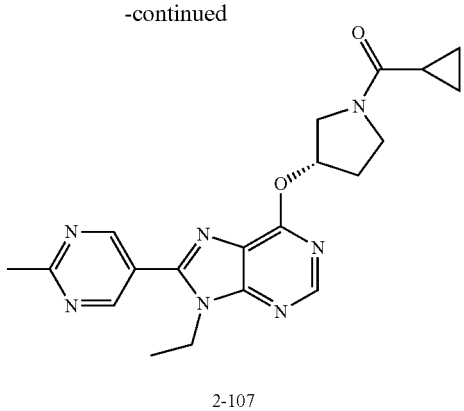

2-107

To a solution of cyclopropanecarboxylic acid (27 mg, 0.31 mmol) in N,N-dimethylformamide (2 mL) was added HATU (88 mg, 0.23 mmol) and 4-methylmorpholine (0.034 mL, 0.31 mmol). The mixed solution was stirred at 20° C. for 15 min, then (S)-9-ethyl-8-(2-methylpyrimidin-5-yl)-6-(pyrrolidin-3-yloxy)-9H-purine (Intermediate V) (50 mg, 0.15 mmol) was added, and the solution was stirred at 20° C. for 15 h. The mixture was cooled, water (10 mL) was added and the mixture was extracted with ethyl acetate (2×10 mL). The combined organic extracts were concentrated under reduced pressure. The residue was purified by preparative reverse phase HPLC, eluting with acetonitrile/water with 0.05% TFA, to give 2-107. $^1$H NMR (400 MHz, DMSO) δ 9.23 (s, 2H), 8.56 (s, 1H), 5.87-5.98 (m, 1H), 4.37-4.36 (m, 2H), 4.08-3.70 (m, 2H), 3.67-3.39 (m, 2H), 2.76 (s, 3H), 2.51-2.24 (m, 2H), 1.84-1.75 (m, 1H), 1.36-1.34 (m, 3H), 0.67-0.57 (m, 4H). MS (EI) Calc'd for $C_{20}H_{24}N_7O_2$ [M+H]$^+$, 394. found, 394.

Example 7B—Preparation of 2-137 and 2-138

To a solution of 1-44 (0.17 g, 0.38 mmol) in MeOH (2 mL) was added 4 N HCl in dioxane (1 mL). The mixture was stirred at RT for 2 hours, then concentrated under reduced pressure to give the hydrochloride salt. MS (EI) Calc'd for $C_{16}H_{19}FN_7O$ [M+H]$^+$, 344. found, 344. This intermediate was dissolved in dichloromethane (2 mL) and treated with triethylamine (0.2 mL, 1.4 mmol) followed by cyclopropylcarbonyl chloride (44 mg, 0.42 mmol). The mixed solution was stirred at 20° C. for 0.5 hours, concentrated to dryness and the residue purified by preparative reverse phase HPLC eluting with acetonitrile/water with 10 mM NH$_4$HCO$_3$ to give a mixture of 2-137 and 2-138. The racemic mixture was then resolved by chiral column chromatography using the following conditions: Column AD-H 4.6×250 mm 5 um, CO$_2$/EtOH (0.1% DEA), Column Temperature 40° C. Compound 2-137 eluted at 3.8 min, while its enantiomer 2-138 eluted at 5.1 min.

Compound 2-137: $^1$H NMR (400 MHz, CD$_3$OD) δ 9.20 (s, 2H), 8.66 (m, 1H), 6.11-6.00 (m, 1H), 5.60-5.39 (m, 1H), 4.51-4.46 (m, 2H), 4.29-3.90 (m, 4H), 2.84 (s, 3H), 1.88-1.85 (m, 1H), 1.50-1.47 (m, 3H), 1.00-0.90 (m, 4H). MS (EI) Calc'd for $C_{20}H_{23}FN_7O_2$ [M+H]$^+$, 412. found, 412.

Compound 2-138: $^1$H NMR (400 MHz, CD$_3$OD) δ 9.14 (s, 2H), 8.68-8.64 (m, 1H), 6.13-5.99 (m, 1H), 5.61-5.38 (m, 1H), 4.52-4.45 (m, 2H), 4.32-3.88 (m, 4H), 2.84 (s, 3H), 1.89-1.81 (m, 1H), 1.51-1.46 (m, 3H), 1.01-0.84 (m, 4H). MS (EI) Calc'd for $C_{20}H_{23}FN_7O_2$ M+H]$^+$, 412. found, 412.

Example 7C—Preparation of 2-139 and 2-140

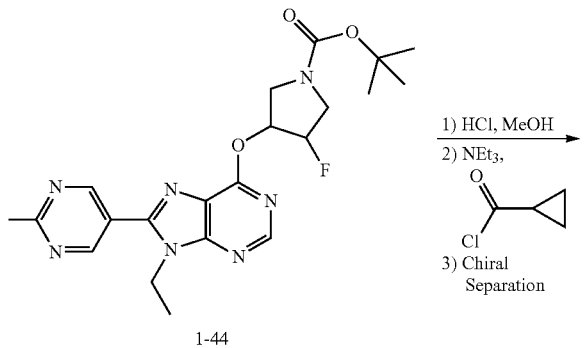

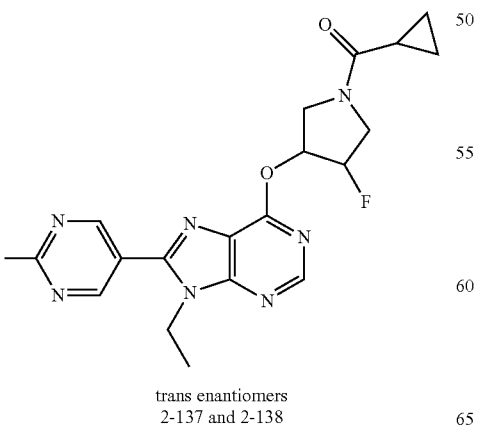

trans enantiomers
2-137 and 2-138

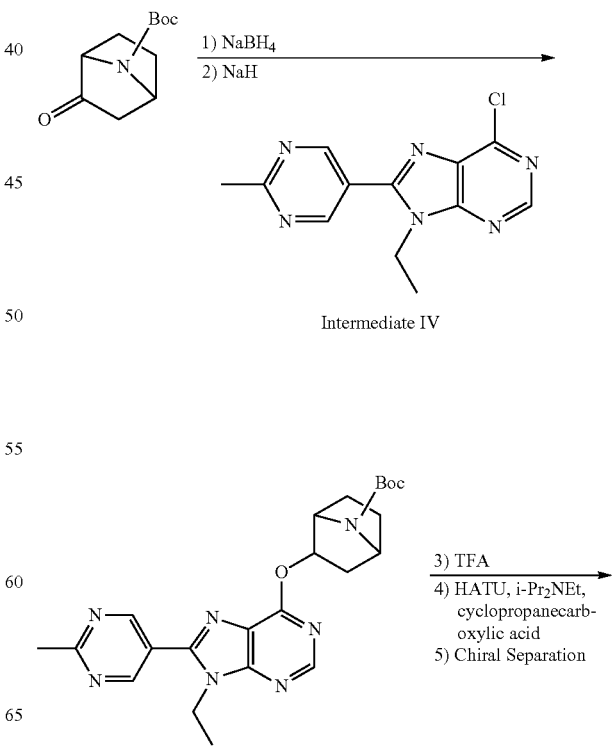

-continued

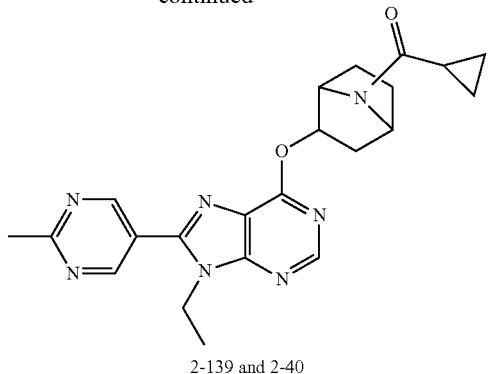

2-139 and 2-40

Steps 1 and 2: Preparation of tert-butyl 2-((9-ethyl-8-(2-methylpyrimidin-5-yl)-9H-purin-6-yl)oxy)-7-azabicyclo[2.2.1]heptane-7-carboxylate To a solution of rac-tert-butyl 2-oxo-7-azabicyclo[2.2.1]heptane-7-carboxylate (500 mg, 2.37 mmol; a synthesis of this bicycle is described in WO 2005/000806) in MeOH (4.7 mL) at 0° C. was added sodium borohydride (134 mg, 3.55 mmol) in several portions. The reaction mixture was stirred at 0° C. for 1 hr and warmed to room temperature and continuously stirred overnight. The mixture was quenched with saturated aq. ammonium chloride aqueous solution and the methanol was evaporated under reduced pressure. The resulting aqueous residue was extracted with $CH_2Cl_2$ (3×), and the combined organic extracts were dried over sodium sulfate, filtered, and concentrated to give rac-tert-butyl 2-hydroxy-7-azabicyclo[2.2.1]heptane-7-carboxylate as a mixture of diastereomers which was used without further purification.

To a solution of rac-tert-butyl 2-hydroxy-7-azabicyclo[2.2.1]heptane-7-carboxylate (243 mg, 1.14 mmol) in THF (9 mL) was added a 60% suspension of NaH in mineral oil (150 mg, 3.75 mmol). The reaction was stirred at 0° C. for 30 min, after which Intermediate IV (250 mg, 0.91 mmol) was added. The reaction was allowed to warm to RT and was stirred for 15 h. The reaction was then quenched with water (10 mL) and extracted with ethyl acetate (2×10 mL). The combined organic extracts were dried over sodium sulfate, filtered, and evaporated under reduced pressure. The residue was purified by chromatography on silica gel (30 to 100% ethyl acetate/hexanes) to provide rac-tert-butyl 2-((9-ethyl-8-(2-methylpyrimidin-5-yl)-9H-purin-6-yl)oxy)-7-azabicyclo[2.2.1]heptane-7-carboxylate. MS (EI) Calc'd for $C_{23}H_{30}N_7O_3$ [M+H]$^+$, 452. found, 452.

Steps 3, 4 and 5: Preparation of Enantiomers 2-139 and 2-140

A flask was charged with rac-tert-butyl 2-((9-ethyl-8-(2-methylpyrimidin-5-yl)-9H-purin-6-yl)oxy)-7-azabicyclo[2.2.1]heptane-7-carboxylate (323 mg, 0.715 mmol) and DCM (2 mL). To this solution was added TFA (0.50 mL). The reaction was stirred at RT for 5.5 h, then the solvent was removed in vacuo and the residue placed under high vacuum for 3 hours to afford rac-6-(7-azabicyclo[2.2.1]heptan-2-yloxy)-9-ethyl-8-(2-methylpyrimidin-5-yl)-9H-purine, TFA salt which was used without further purification. MS (EI) Calc'd for $C_{19}H_{21}N_7O$ [M+H]$^+$, 352. found, 352.

To a vial were added rac-6-(7-azabicyclo[2.2.1]heptan-2-yloxy)-9-ethyl-8-(2-methylpyrimidin-5-yl)-9H-purine, TFA (0.333 g, 0.715 mmol), cyclopropanecarboxylic acid (0.068 mL, 0.86 mmol), HATU (0.299 g, 0.787 mmol), DMF (4.77 mL) and i-Pr$_2$NEt (1.0 mL, 5.7 mmol). The mixture was stirred at RT for 16 hours. The mixture was then diluted with EtOAc and water, and then extracted with EtOAc (2×). The combined organic extracts were dried with brine, magnesium sulfate, filtered, and concentrated. The residue was purified by chromatography on silica gel (0-20% EtOAc to 10:1:1:1 EtOAc/MeOH/Acetone/water in EtOAc) to provide cyclopropyl((1R,2S,4S and 1S,2R,4S)-2-((9-ethyl-8-(2-methylpyrimidin-5-yl)-9H-purin-6-yl)oxy)-7-azabicyclo[2.2.1]heptan-7-yl)methanone. This racemic mixture was then separated by chiral SFC using a Chiralpak, AD-H, 21×250 (mm) column eluting with 25% MeOH in $CO_2$ at a flow rate of 70 mL/min to provide 2-139 (retention time 4.75 min) and 2-140 (retention time 7.85 min). Compounds 2-139 and 2-140 are cyclopropyl([(1R,2R,4S) or (1S,2S,4R)]-2-((9-ethyl-8-(2-methylpyrimidin-5-yl)-9H-purin-6-yl)oxy)-7-azabicyclo[2.2.1]heptan-7-yl)methanone.

Compound 2-139: $^1$H NMR (500 MHz, DMSO-d$_6$) δ 9.14 (s, 2H), 8.60 (s, 1H), 5.51-5.28 (m, 1H), 5.06-4.83 (m, 1H), 4.71-4.41 (m, 1H), 4.36 (q, J=7.2 Hz, 2H), 2.74 (s, 3H), 2.40-2.02 (m, 1H), 1.99-1.37 (m, 6H), 1.33 (t, J=7.2 Hz, 3H), 0.79-0.65 (m, 4H). MS (EI) Calc'd for $C_{22}H_{26}N_7O_2$ [M+H]$^+$, 420. found, 420.

Compound 2-140: $^1$H NMR (500 MHz, DMSO-d$_6$) δ 9.14 (s, 2H), 8.60 (s, 1H), 5.51-5.28 (m, 1H), 5.06-4.83 (m, 1H), 4.71-4.41 (m, 1H), 4.36 (q, J=7.0 Hz, 2H), 2.74 (s, 3H), 2.40-2.02 (m, 1H), 1.99-1.37 (m, 6H), 1.33 (t, J=7.0 Hz, 3H), 0.79-0.65 (m, 4H). MS (EI) Calc'd for $C_{22}H_{26}N_7O_2$ [M+H]$^+$, 420. found, 420.

Example 7D—Preparation of 2-147

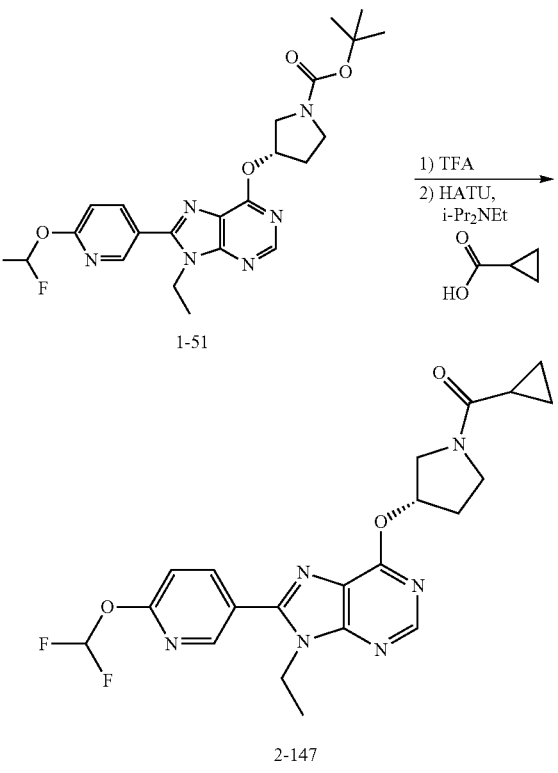

2-147

To a solution of 1-51 (35 mg, 0.073 mmol) in DCM (2 mL) was added TFA (0.11 mL, 1.5 mmol). The mixture was stirred for 16 h at ambient temperature. Then the reaction was concentrated under reduced pressure to afford (S)-8-(6-(difluoromethoxy)pyridin-3-yl)-9-ethyl-6-(pyrrolidin-3-yloxy)-9H-purine, TFA. MS (EI) Calc'd for $C_{17}H_{19}F_2N_6O_2$ [M+H]$^+$, 377. found, 377.

To a vial were added (S)-8-(6-(difluoromethoxy)pyridin-3-yl)-9-ethyl-6-(pyrrolidin-3-yloxy)-9H-purine, TFA (40 mg, 0.11 mmol)cyclopropanecarboxylic acid (0.008 mL, 0.1 mmol), HATU (49 mg, 0.13 mmol) and DIEA (0.11 mL, 0.64 mmol) in DMF (1 mL). The mixture was stirred for 16 hours at 25° C., then filtered and purified by reverse phase HPLC to afford 2-147 as the TFA salt. $^1$H NMR (400 MHz, CD$_3$OD): δ 8.67 (s, 1H), 8.55 (s, 1H), 8.34-8.32 (m, 1H), 7.65 (m, 1H), 7.30-7.28 (m, 1H), 6.05-5.95 (m, 1H), 4.41-4.38 (m, 2H), 4.12-3.55 (m, 4H), 2.50-2.35 (m, 2H), 1.85-1.75 (m, 1H), 1.41 (t, 3H), 0.92-0.77 (m, 4H). MS (EI) Calc'd for $C_{21}H_{23}F_2N_6O_3$ [M+H]$^+$, 445. found, 445.

Compounds 2-1, 2-2, 2-8, 2-9, 2-11 through 2-14, and 2-90 through 2-93 were prepared in an analogous fashion as described for Example 5 from the corresponding acid chloride and Intermediate II.

Compounds 2-4 and 2-5 were prepared in an analogous fashion as described for Example 7 from the corresponding carboxylic acid and Intermediate II, substituting HATU reagent for EDC and HOBt.

Compounds 2-6, 2-7, 2-10 were prepared in an analogous fashion as described for Example 7 from the corresponding carboxylic acid and Intermediate II.

Compounds 2-16 through 2-23 were prepared in an analogous fashion as described for Example 6A from the corresponding carboxylic acid and substituted pyrrolidine.

Compound 2-24 was prepared in an analogous fashion as described for Example 7 from the corresponding carboxylic acid and substituted pyrrolidine, and racemic mixture then resolved by chiral column chromatography using the following conditions: Column AS-H 2.1×250 mm 5 um, Flow Rate 70 mL/min, 6 min run time, Mobile Phase 15% MeOH, 85% $C_{O2}$ (with 0.25% dimethylethylamine), Wavelength 220 nm, 0.25 mL Injections of an 80 mg/mL MeOH solution. Compound 2-24 eluted at 4.8 min, while the enantiomer eluted at 3.8 min.

Compounds 2-25 and 2-26 were prepared in an analogous fashion as described for Example 5 from the corresponding acid chloride and Intermediate V.

Compounds 2-27 through 2-87 were prepared in an analogous fashion as described for Example 6 from the corresponding carboxylic acid and substituted pyrrolidine.

Compound 2-89 was prepared from compound 1-34 in an analogous fashion as described for Example 5.

Compound 2-94 was prepared from compound 1-13 in an analogous fashion as described for Example 5.

Compound 2-95 was prepared from compound 1-35 in an analogous fashion as described for Example 5.

Compound 2-96 was prepared from compound 1-39 in an analogous fashion as described for Example 5.

Compound 2-97 was prepared in an analogous fashion as described for Example 5 from the corresponding acid chloride and substituted pyrrolidine.

Compound 2-98 was prepared from compound 1-48 in an analogous fashion as described for Example 5.

Compound 2-99 was prepared in an analogous fashion from 1-47 as described for Example 5, and the racemic mixture then resolved by chiral column chromatography using the following conditions: Column AY-H 4.6×250 mm 5 um, CO$_2$ Flow Rate 2.55, Co-Solvent MeOH:ACN=1:1 (0.1% DEA), Co-Solvent Flow Rate 0.45, Column Temperature 40° C. Compound 2-99 eluted at 23.0 min, while the enantiomer eluted at 11.8 min.

Compound 2-100 was prepared in an analogous fashion from 1-46 as described for Example 5, and the racemic mixture then resolved by chiral column chromatography using the following conditions: Column AD-H 4.6×250 mm 5 um, CO$_2$ Flow Rate 2.55, Co-Solvent MeOH:ACN=1:1 (0.1% DEA), Co-Solvent Flow Rate 0.45, Column Temperature 40° C. Compound 2-100 eluted at 7.1 min, while the enantiomer eluted at 15.2 min.

Compounds 2-101 to 2-104 were prepared in an analogous fashion as described for Example 6 from Intermediate V and the corresponding carboxylic acid.

Compounds 2-105 and 2-106 were prepared in an analogous fashion as described for Example 7 from Intermediate II and the corresponding carboxylic acid.

Compounds 2-107 to 2-116, 2-121 to 2-123, 2-128, 2-129, 2-136 were prepared in an analogous fashion as described for Example 7A from Intermediate V and the corresponding carboxylic acid.

Compounds 2-117 to 2-120 were prepared in an analogous fashion as described for Example 7A from Intermediate V and the corresponding carboxylic acid, and the racemic mixture then resolved by chiral column chromatography using the following conditions: Thar SFC Prep 80, Column ChiralPak OJ-H 20×250 mm 5 um, Flow Rate 70 g/min, Mobile Phase CO$_2$/EtOH 90/10 (0.1% DEA), Back Pressure 100 bar, Wavelength 214 nm, Column Temperature 35° C., Cycle Time 7.6 min, 14 mg per injection as a 20 mg/mL MeOH solution. Retention times for 2-117, 2-118, 2-119 and 2-120 were 4.07, 4.18, 5.51 and 6.64 min, respectively.

Compounds 2-124 and 2-125 were prepared in an analogous fashion as described for Example 7A from Intermediate V and the corresponding carboxylic acid, and the racemic mixture then resolved by chiral column chromatography using the following conditions: Column OZ-H 4.6×250 mm 5 um, CO$_2$ Flow Rate 1.95, Co-Solvent MeOH (0.1% DEA), Co-Solvent Flow Rate 1.05, Column Temperature 40° C. Compound 2-124 eluted at 4.5 min, while its enantiomer 2-125 eluted at 3.9 min.

Compounds 2-126 and 2-127 were prepared in an analogous fashion as described for Example 7A from Intermediate V and the corresponding carboxylic acid, and the racemic mixture then resolved by chiral column chromatography using the following conditions: Column OZ-H 4.6×250 mm 5 um, CO$_2$ Flow Rate 1.95, Co-Solvent MeOH (0.1% DEA), Co-Solvent Flow Rate 1.05, Column Temperature 40° C. Compound 2-126 eluted at 2.8 min, while its enantiomer 2-127 eluted at 4.7 min.

Compounds 2-130 and 2-131 were prepared in an analogous fashion as described for Example 7A from Intermediate V and the corresponding carboxylic acid, and the racemic mixture then resolved by chiral column chromatography using the following conditions: Column OZ-H 4.6×250 mm 5 um, CO$_2$ Flow Rate 1.95, Co-Solvent MeOH (0.1% DEA), Co-Solvent Flow Rate 1.05, Column Temperature 40° C. Compound 2-130 eluted at 4.4 min, while its enantiomer 2-131 eluted at 6.0 min.

Compounds 2-132 and 2-133 were prepared in an analogous fashion as described for Example 7A from Intermediate V and the corresponding carboxylic acid, and the racemic mixture then resolved by chiral column chromatography using the following conditions: Column OZ-H 4.6×250 mm 5 um, CO$_2$ Flow Rate 1.95, Co-Solvent MeOH (0.1% DEA), Co-Solvent Flow Rate 1.05, Column Temperature 40° C. Compound 2-132 eluted at 4.2 min, while its enantiomer 2-133 eluted at 6.9 min.

Compounds 2-134 and 2-135 were prepared in an analogous fashion as described for Example 7A from Intermediate V and the corresponding carboxylic acid, and the racemic mixture then resolved by chiral column chromatography using the following conditions: Column OZ-H 4.6×250 mm 5 um, $CO_2$ Flow Rate 1.95, Co-Solvent MeOH (0.1% DEA), Co-Solvent Flow Rate 1.05, Column Temperature 40° C. Compound 2-134 eluted at 3.4 min, while its enantiomer 2-135 eluted at 5.1 min.

Compound 2-141 was prepared in an analogous fashion as described for Example 7A substituting N-Boc-3-hydroxypyrrolidine for N-Boc-3-hydroxy-3-methylpyrrolidine.

Compound 2-142 to 2-146 was prepared in an analogous fashion as described for Example 7D (compound 2-147).

TABLE 2

| Compound | Structure | Compound Name | MS [M + H]$^+$ |
|---|---|---|---|
| 2-1 | 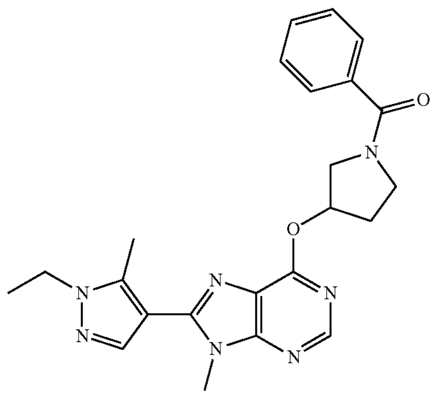 [SMILES: CCn1ncc(-c2nc3c(OC4CCN(C(=O)c5ccccc5)C4)ncnc3n2C)c1C] | 8-(1-ethyl-5-methyl-1H-pyrazol-4-yl)-9-methyl-6-{[1-(phenylcarbonyl)pyrrolidin-3-yl]oxy}-9H-purine | Calc'd 432, found 432 |
| 2-2 | 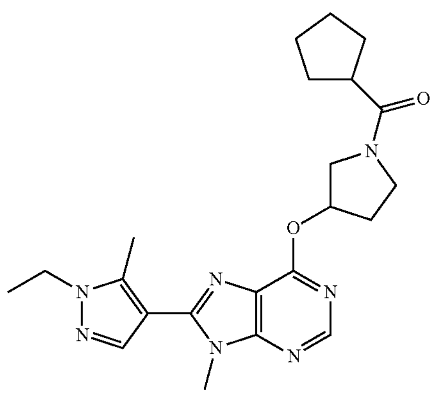 [SMILES: CCn1ncc(-c2nc3c(OC4CCN(C(=O)C5CCCC5)C4)ncnc3n2C)c1C] | 6-{[1-(cyclopentylcarbonyl)pyrrolidin-3-yl]oxy}-8-(1-ethyl-5-methyl-1H-pyrazol-4-yl)-9-methyl-9H-purine | Calc'd 424, found 424 |
| 2-3 | 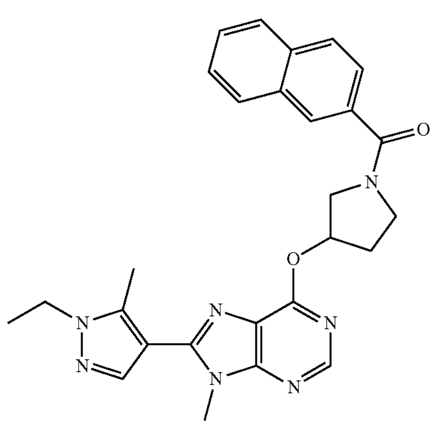 [SMILES: CCn1ncc(-c2nc3c(OC4CCN(C(=O)c5ccc6ccccc6c5)C4)ncnc3n2C)c1C] | 8-(1-ethyl-5-methyl-1H-pyrazol-4-yl)-9-methyl-6-{[1-(naphthalen-2-ylcarbonyl)pyrrolidin-3-yl]oxy}-9H-purine | Calc'd 482, found 482 |

TABLE 2-continued

| Compound | Structure | Compound Name | MS [M + H]+ |
|---|---|---|---|
| 2-4 | 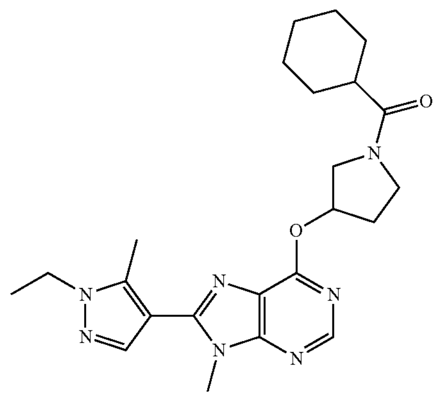 [SMILES: CCn1ncc(-c2nc3c(OC4CCN(C(=O)C5CCCCC5)C4)ncnc3n2C)c1C] | 6-{[1-(cyclohexylcarbonyl)pyrrolidin-3-yl]oxy}-8-(1-ethyl-5-methyl-1H-pyrazol-4-yl)-9-methyl-9H-purine | Calc'd 438, found 438 |
| 2-5 | 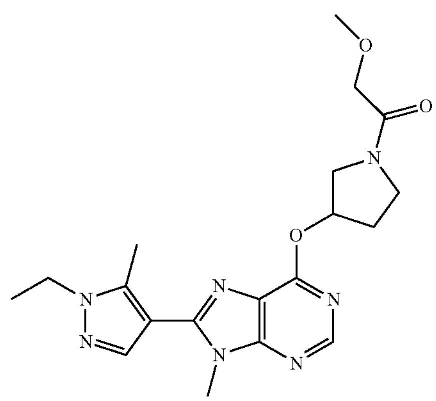 [SMILES: CCn1ncc(-c2nc3c(OC4CCN(C(=O)COC)C4)ncnc3n2C)c1C] | 8-(1-ethyl-5-methyl-1H-pyrazol-4-yl)-6-{[1-(methoxyacetyl)pyrrolidin-3-yl]oxy}-9-methyl-9H-purine | Calc'd 400, found 400 |
| 2-6 | 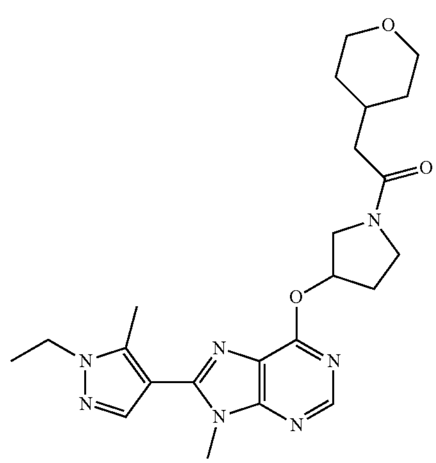 [SMILES: CCn1ncc(-c2nc3c(OC4CCN(C(=O)CC5CCOCC5)C4)ncnc3n2C)c1C] | 8-(1-ethyl-5-methyl-1H-pyrazol-4-yl)-9-methyl-6-{[1-(tetrahydro-2H-pyran-4-ylacetyl)pyrrolidin-3-yl]oxy}-9H-purine | Calc'd 454, found 454 |

TABLE 2-continued

| Compound | Structure | Compound Name | MS [M + H]+ |
|---|---|---|---|
| 2-7 | 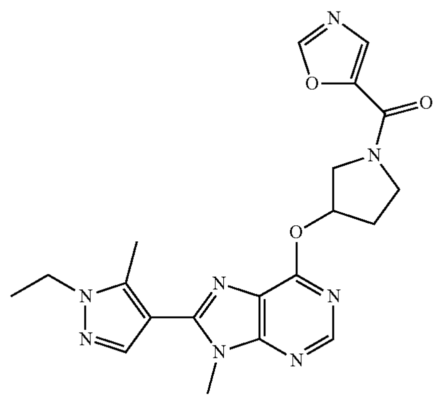 [SMILES: CCn1ncc(-c2nc3c(OC4CCN(C(=O)c5cnco5)C4)ncnc3n2C)c1C] | 8-(1-ethyl-5-methyl-1H-pyrazol-4-yl)-9-methyl-6-{[1-(1,3-oxazol-5-ylcarbonyl)pyrrolidin-3-yl]oxy}-9H-purine | Calc'd 423, found 423 |
| 2-8 | 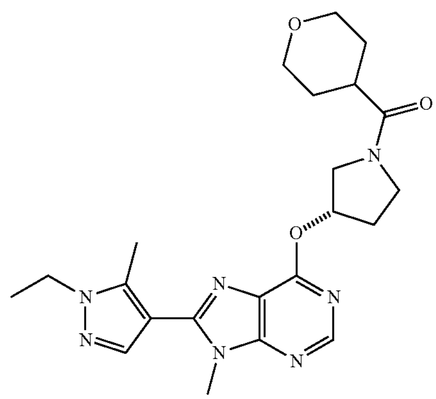 | (S)-(3-((8-(1-ethyl-5-methyl-1H-pyrazol-4-yl)-9-methyl-9H-purin-6-yl)oxy)pyrrolidin-1-yl)(tetrahydro-2H-pyran-4-yl)methanone | Calc'd 440, found 440 |
| 2-9 | 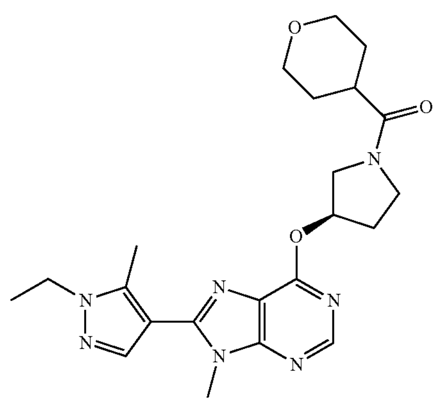 [SMILES: CCn1ncc(-c2nc3c(O[C@@H]4CCN(C(=O)C5CCOCC5)C4)ncnc3n2C)c1C] | (R)-(3-((8-(1-ethyl-5-methyl-1H-pyrazol-4-yl)-9-methyl-9H-purin-6-yl)oxy)pyrrolidin-1-yl)(tetrahydro-2H-pyran-4-yl)methanone | Calc'd 440, found 440 |
| 2-10 | 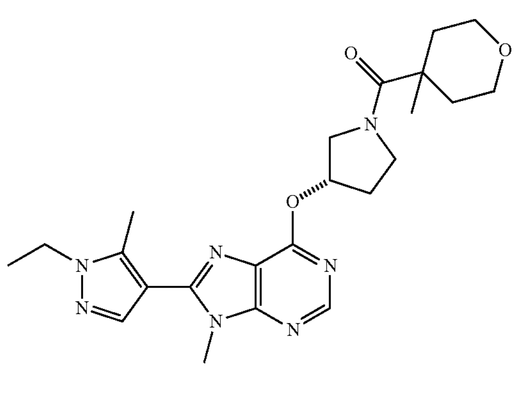 | 8-(1-ethyl-5-methyl-1H-pyrazol-4-yl)-9-methyl-6-({(3S)-1-[(4-methyltetrahydro-2H-pyran-4-yl)carbonyl]pyrrolidin-3-yl}oxy)-9H-purine | Calc'd 454, found 454 |

TABLE 2-continued

| Compound | Structure | Compound Name | MS [M + H]+ |
|---|---|---|---|
| 2-11 | 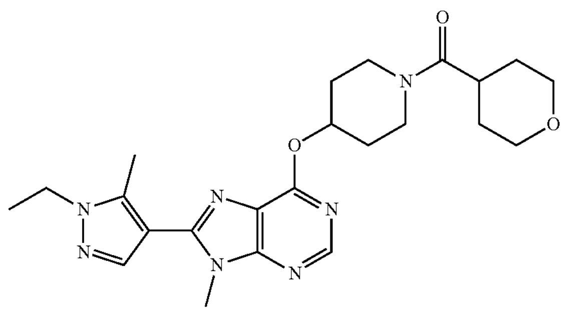 [SMILES: CCn1ncc(-c2nc3c(OC4CCN(C(=O)C5CCOCC5)CC4)ncnc3n2C)c1C] | (4-((8-(1-ethyl-5-methyl-1H-pyrazol-4-yl)-9-methyl-9H-purin-6-yl)oxy)piperidin-1-yl)(tetrahydro-2H-pyran-4-yl)methanone | Calc'd 454, found 454 |
| 2-12 | 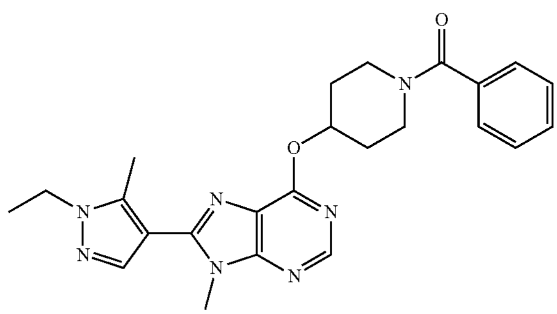 [SMILES: CCn1ncc(-c2nc3c(OC4CCN(C(=O)c5ccccc5)CC4)ncnc3n2C)c1C] | (4-((8-(1-ethyl-5-methyl-1H-pyrazol-4-yl)-9-methyl-9H-purin-6-yl)oxy)piperidin-1-yl)(phenyl)methanone | Calc'd 446, found 446 |
| 2-13 | 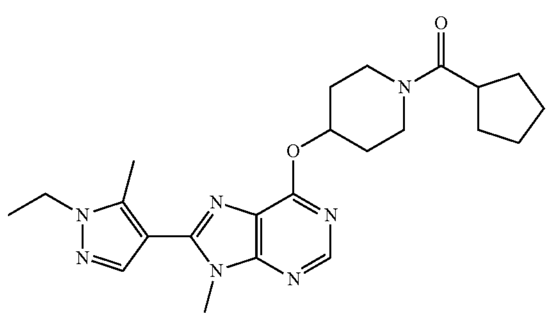 [SMILES: CCn1ncc(-c2nc3c(OC4CCN(C(=O)C5CCCC5)CC4)ncnc3n2C)c1C] | cyclopentyl(4-((8-(1-ethyl-5-methyl-1H-pyrazol-4-yl)-9-methyl-9H-purin-6-yl)oxy)piperidin-1-yl)methanone | Calc'd 438, found 438 |
| 2-14 | 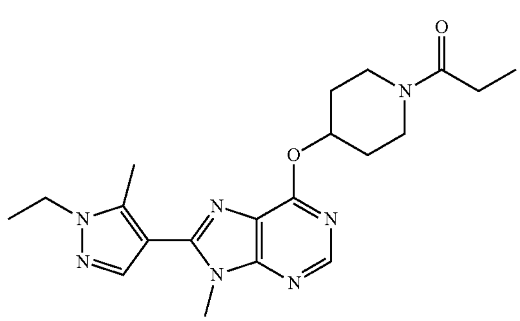 [SMILES: CCC(=O)N1CCC(Oc2ncnc3c2nc(-c2cnn(CC)c2C)n3C)CC1] | 1-(4-((8-(1-ethyl-5-methyl-1H-pyrazol-4-yl)-9-methyl-9H-purin-6-yl)oxy)piperidin-1-yl)propan-1-one | Calc'd 398, found 398 |

TABLE 2-continued

| Compound | Structure | Compound Name | MS [M + H]+ |
|---|---|---|---|
| 2-15 | 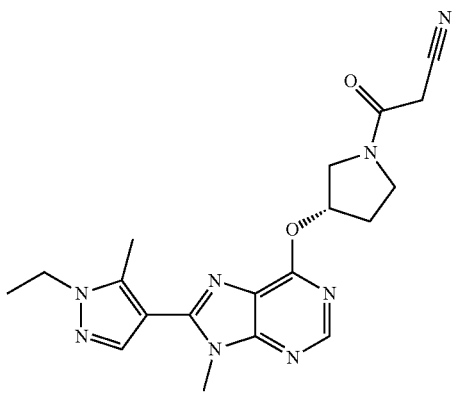 [SMILES: CCn1ncc(-c2nc3c(O[C@H]4CCN(C(=O)CC#N)C4)ncnc3n2C)c1C] | 3-[(3S)-3-{[8-(1-ethyl-5-methyl-1H-pyrazol-4-yl)-9-methyl-9H-purin-6-yl]oxy}pyrrolidin-1-yl]-3-oxopropanenitrile | Calc'd 395, found 395 |
| 2-16 | 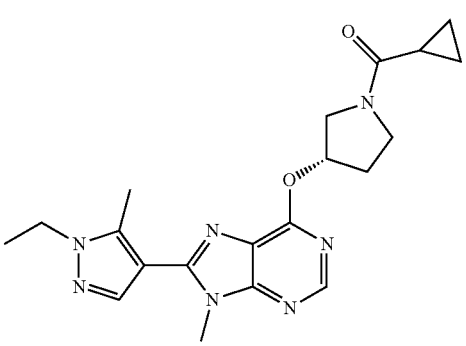 [SMILES: CCn1ncc(-c2nc3c(O[C@H]4CCN(C(=O)C5CC5)C4)ncnc3n2C)c1C] | 6-{[(3S)-1-(cyclopropylcarbonyl)pyrrolidin-3-yl]oxy}-8-(1-ethyl-5-methyl-1H-pyrazol-4-yl)-9-methyl-9H-purine | Calc'd 396, found 396 |
| 2-17 | 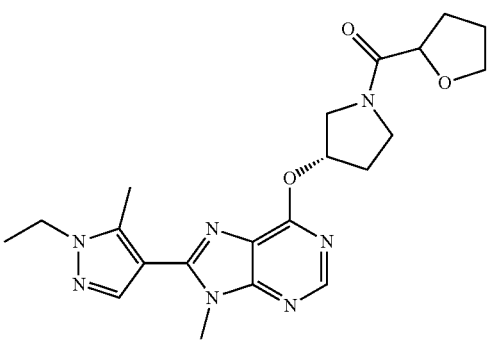 [SMILES: CCn1ncc(-c2nc3c(O[C@H]4CCN(C(=O)C5CCCO5)C4)ncnc3n2C)c1C] | 8-(1-ethyl-5-methyl-1H-pyrazol-4-yl)-9-methyl-6-{[(3S)-1-(tetrahydrofuran-2-ylcarbonyl)pyrrolidin-3-yl]oxy}-9H-purine | Calc'd 426, found 426 |
| 2-18 | 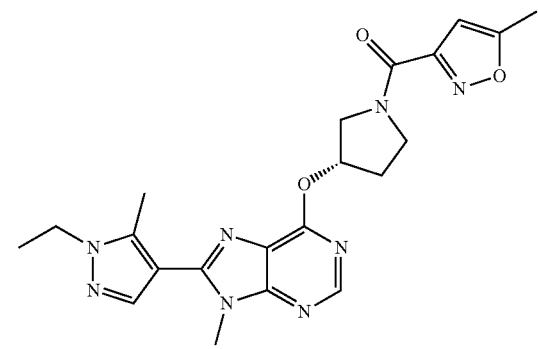 [SMILES: CCn1ncc(-c2nc3c(O[C@H]4CCN(C(=O)c5cc(C)on5)C4)ncnc3n2C)c1C] | 8-(1-ethyl-5-methyl-1H-pyrazol-4-yl)-9-methyl-6-({(3S)-1-[(5-methylisoxazol-3-yl)carbonyl]pyrrolidin-3-yl}oxy)-9H-purine | Calc'd 437, found 437 |

TABLE 2-continued

| Compound | Structure | Compound Name | MS [M + H]+ |
|---|---|---|---|
| 2-19 | 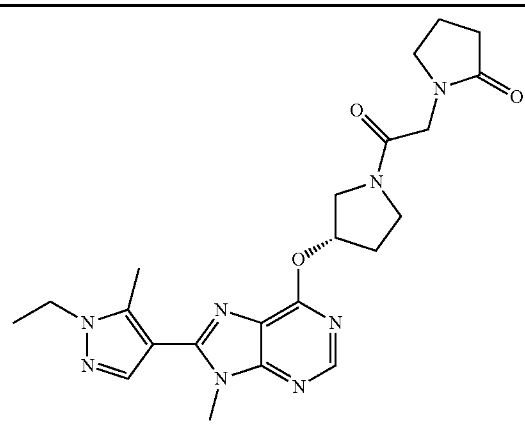 | 1-{2-[(3S)-3-{[8-(1-ethyl-5-methyl-1H-pyrazol-4-yl)-9-methyl-9H-purin-6-yl]oxy}pyrrolidin-1-yl]-2-oxoethyl}pyrrolidin-2-one | Calc'd 453, found 453 |
| 2-20 | 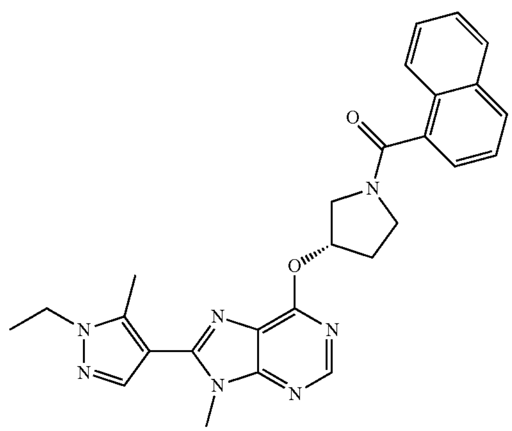 [SMILES: CCn1ncc(-c2nc3c(O[C@H]4CCN(C(=O)c5cccc6ccccc56)C4)ncnc3n2C)c1C] | 8-(1-ethyl-5-methyl-1H-pyrazol-4-yl)-9-methyl-6-{[(3S)-1-(naphthalen-1-ylcarbonyl)pyrrolidin-3-yl]oxy}-9H-purine | Calc'd 482, found 482 |
| 2-21 | 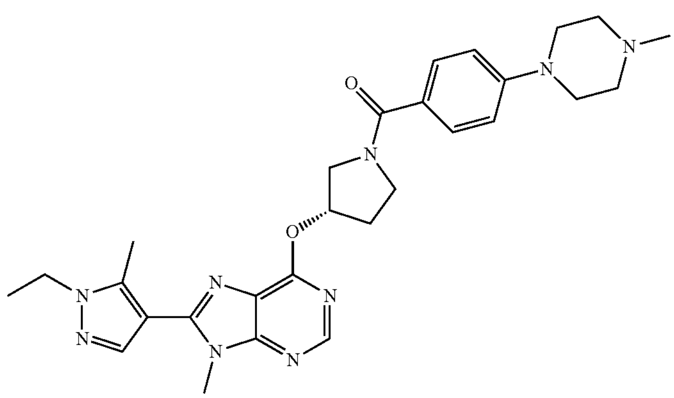 [SMILES: CCn1ncc(-c2nc3c(O[C@H]4CCN(C(=O)c5ccc(N6CCN(C)CC6)cc5)C4)ncnc3n2C)c1C] | 8-(1-ethyl-5-methyl-1H-pyrazol-4-yl)-9-methyl-6-{[(3S)-1-{[4-(4-methylpiperazin-1-yl)phenyl]carbonyl}pyrrolidin-3-yl]oxy}-9H-purine | Calc'd 530, found 530 |
| 2-22 | 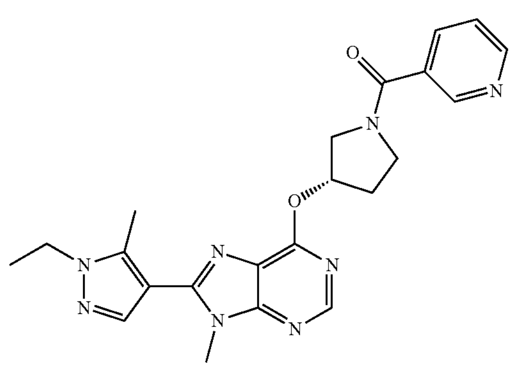 [SMILES: CCn1ncc(-c2nc3c(O[C@H]4CCN(C(=O)c5cccnc5)C4)ncnc3n2C)c1C] | 8-(1-ethyl-5-methyl-1H-pyrazol-4-yl)-9-methyl-6-{[(3S)-1-(pyridin-3-ylcarbonyl)pyrrolidin-3-yl]oxy}-9H-purine | Calc'd 433, found 433 |

TABLE 2-continued

| Compound | Structure | Compound Name | MS [M + H]+ |
|---|---|---|---|
| 2-23 | 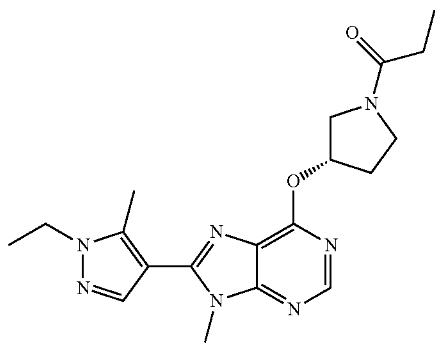 [SMILES: CCC(=O)N1CC[C@H](Oc2ncnc3c2nc(-c2cnn(CC)c2C)n3C)C1] | 8-(1-ethyl-5-methyl-1H-pyrazol-4-yl)-9-methyl-6-{[(3S)-1-propanoylpyrrolidin-3-yl]oxy}-9H-purine | Calc'd 384, found 384 |
| 2-24 | 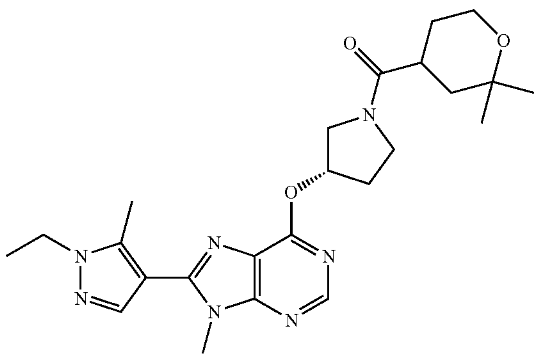 [SMILES: CCn1ncc(-c2nc3c(O[C@H]4CCN(C(=O)C5CCOC(C)(C)C5)C4)ncnc3n2C)c1C] | 6-({(3S)-1-[(2,2-dimethyltetrahydro-2H-pyran-4-yl)carbonyl]pyrrolidin-3-yl}oxy)-8-(1-ethyl-5-methyl-1H-pyrazol-4-yl)-9-methyl-9H-purine | Calc'd 468, found 468 |
| 2-25 | 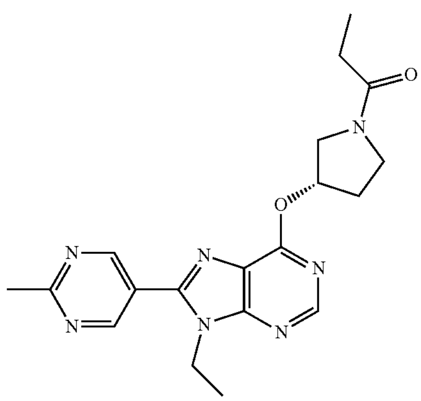 [SMILES: CCC(=O)N1CC[C@H](Oc2ncnc3c2nc(-c2cnc(C)nc2)n3CC)C1] | 9-ethyl-8-(2-methylpyrimidin-5-yl)-6-{[(3S)-1-propanoylpyrrolidin-3-yl]oxy}-9H-purine | Calc'd 382, found 382 |
| 2-26 | 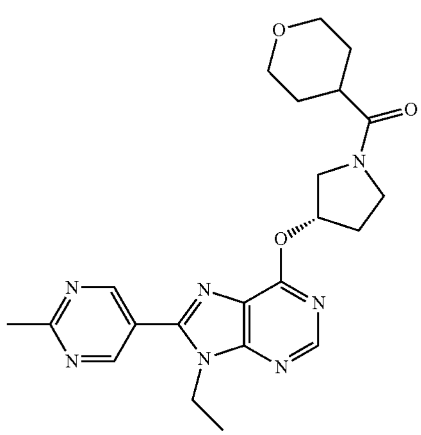 [SMILES: CCn1c(-c2cnc(C)nc2)nc2c(O[C@H]3CCN(C(=O)C4CCOCC4)C3)ncnc21] | 9-ethyl-8-(2-methylpyrimidin-5-yl)-6-{[(3S)-1-(tetrahydro-2H-pyran-4-ylcarbonyl)pyrrolidin-3-yl]oxy}-9H-purine | Calc'd 438, found 438 |

TABLE 2-continued

| Compound | Structure | Compound Name | MS [M + H]+ |
|---|---|---|---|
| 2-27 | 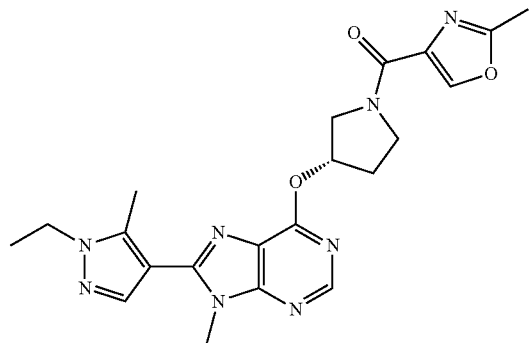 [SMILES: CCn1ncc(-c2nc3c(O[C@H]4CCN(C(=O)c5coc(C)n5)C4)ncnc3n2C)c1C] | 8-(1-ethyl-5-methyl-1H-pyrazol-4-yl)-9-methyl-6-({(3S)-1-[(2-methyl-1,3-oxazol-4-yl)carbonyl]pyrrolidin-3-yl}oxy)-9H-purine | Calc'd 437, found 437 |
| 2-28 | 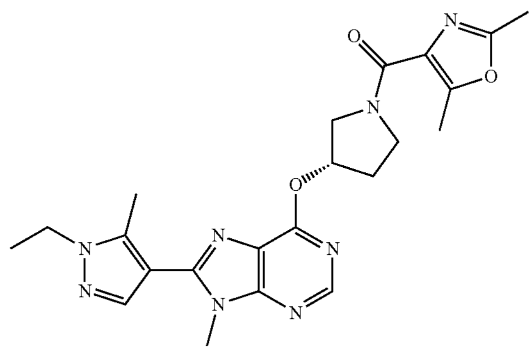 [SMILES: CCn1ncc(-c2nc3c(O[C@H]4CCN(C(=O)c5nc(C)oc5C)C4)ncnc3n2C)c1C] | 6-({(3S)-1-[(2,5-dimethyl-1,3-oxazol-4-yl)carbonyl]pyrrolidin-3-yl}oxy)-8-(1-ethyl-5-methyl-1H-pyrazol-4-yl)-9-methyl-9H-purine | Calc'd 451, found 451 |
| 2-29 | 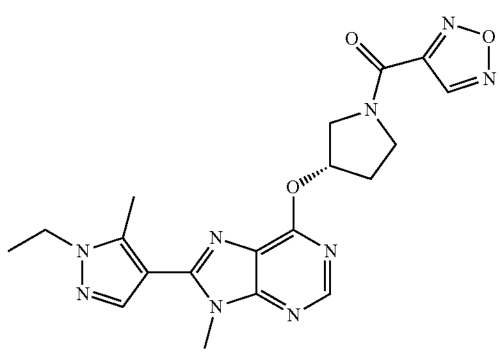 [SMILES: CCn1ncc(-c2nc3c(O[C@H]4CCN(C(=O)c5cnon5)C4)ncnc3n2C)c1C] | 8-(1-ethyl-5-methyl-1H-pyrazol-4-yl)-9-methyl-6-{[(3S)-1-(1,2,5-oxadiazol-3-ylcarbonyl)pyrrolidin-3-yl]oxy}-9H-purine | Calc'd 424, found 424 |
| 2-30 | 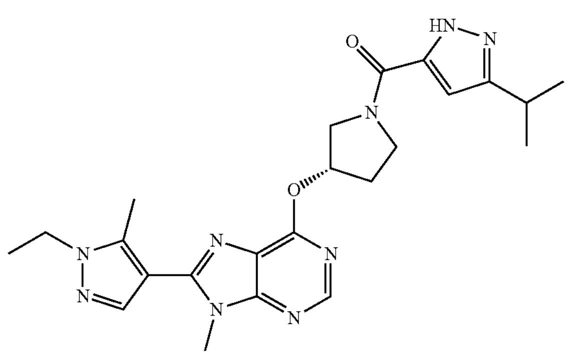 [SMILES: CCn1ncc(-c2nc3c(O[C@H]4CCN(C(=O)c5cc(C(C)C)n[nH]5)C4)ncnc3n2C)c1C] | 8-(1-ethyl-5-methyl-1H-pyrazol-4-yl)-9-methyl-6-{[(3S)-1-{[3-(1-methylethyl)-1H-pyrazol-5-yl]carbonyl}pyrrolidin-3-yl]oxy}-9H-purine | Calc'd 464, found 464 |

TABLE 2-continued

| Compound | Structure | Compound Name | MS [M + H]+ |
|---|---|---|---|
| 2-31 | 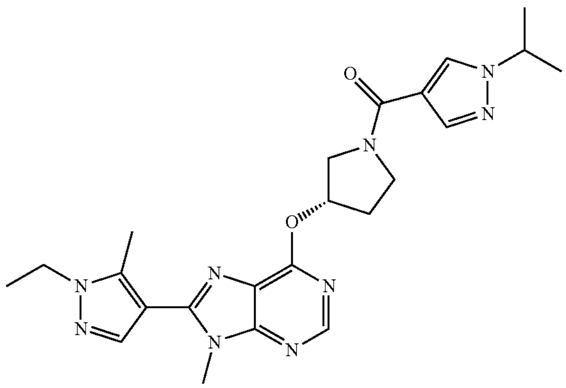 [SMILES: CCn1ncc(-c2nc3c(O[C@H]4CCN(C(=O)c5cnn(C(C)C)c5)C4)ncnc3n2C)c1C] | 8-(1-ethyl-5-methyl-1H-pyrazol-4-yl)-9-methyl-6-{[(3S)-1-{[1-(1-methylethyl)-1H-pyrazol-4-yl]carbonyl}pyrrolidin-3-yl]oxy}-9H-purine | Calc'd 464, found 464 |
| 2-32 | 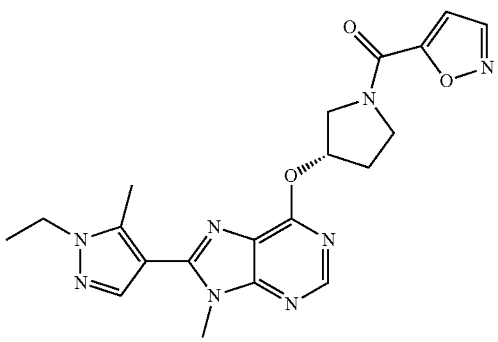 [SMILES: CCn1ncc(-c2nc3c(O[C@H]4CCN(C(=O)c5ccno5)C4)ncnc3n2C)c1C] | 8-(1-ethyl-5-methyl-1H-pyrazol-4-yl)-6-{[(3S)-1-(isoxazol-5-ylcarbonyl)pyrrolidin-3-yl]oxy}-9-methyl-9H-purine | Calc'd 423, found 423 |
| 2-33 | 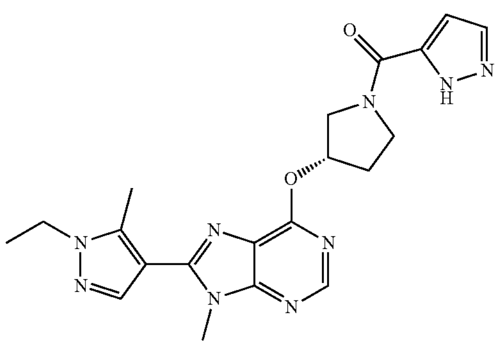 [SMILES: CCn1ncc(-c2nc3c(O[C@H]4CCN(C(=O)c5ccn[nH]5)C4)ncnc3n2C)c1C] | 8-(1-ethyl-5-methyl-1H-pyrazol-4-yl)-9-methyl-6-{[(3S)-1-(1H-pyrazol-5-ylcarbonyl)pyrrolidin-3-yl]oxy}-9H-purine | Calc'd 422, found 422 |
| 2-34 | 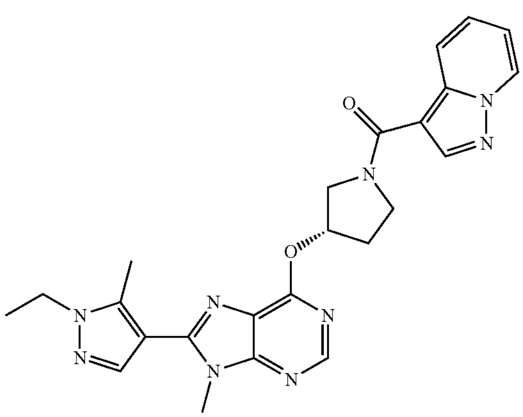 [SMILES: CCn1ncc(-c2nc3c(O[C@H]4CCN(C(=O)c5cnn6ccccc56)C4)ncnc3n2C)c1C] | 8-(1-ethyl-5-methyl-1H-pyrazol-4-yl)-9-methyl-6-{[(3S)-1-(pyrazolo[1,5-a]pyridin-3-ylcarbonyl)pyrrolidin-3-yl]oxy}-9H-purine | Calc'd 472, found 472 |

TABLE 2-continued

| Compound | Structure | Compound Name | MS [M + H]+ |
|---|---|---|---|
| 2-35 | 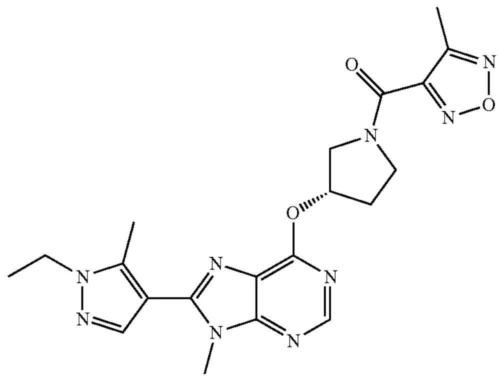 [SMILES: CCn1ncc(-c2nc3c(O[C@H]4CCN(C(=O)c5nonc5C)C4)ncnc3n2C)c1C] | 8-(1-ethyl-5-methyl-1H-pyrazol-4-yl)-9-methyl-6-({(3S)-1-[(4-methyl-1,2,5-oxadiazol-3-yl)carbonyl]pyrrolidin-3-yl}oxy)-9H-purine | Calc'd 438, found 438 |
| 2-36 | 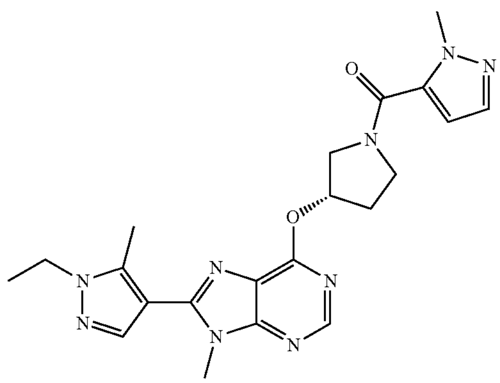 [SMILES: CCn1ncc(-c2nc3c(O[C@H]4CCN(C(=O)c5ccnn5C)C4)ncnc3n2C)c1C] | 8-(1-ethyl-5-methyl-1H-pyrazol-4-yl)-9-methyl-6-({(3S)-1-[(1-methyl-1H-pyrazol-5-yl)carbonyl]pyrrolidin-3-yl}oxy)-9H-purine | Calc'd 436, found 436 |
| 2-37 | 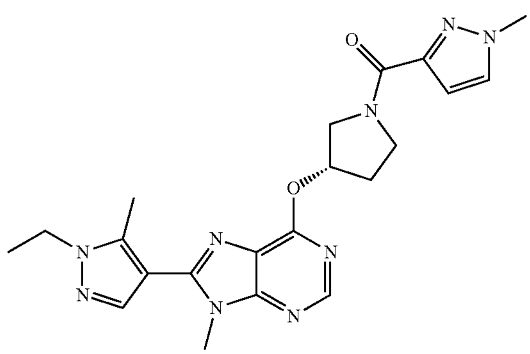 [SMILES: CCn1ncc(-c2nc3c(O[C@H]4CCN(C(=O)c5ccn(C)n5)C4)ncnc3n2C)c1C] | 8-(1-ethyl-5-methyl-1H-pyrazol-4-yl)-9-methyl-6-({(3S)-1-[(1-methyl-1H-pyrazol-3-yl)carbonyl]pyrrolidin-3-yl}oxy)-9H-purine | Calc'd 436, found 436 |
| 2-38 | 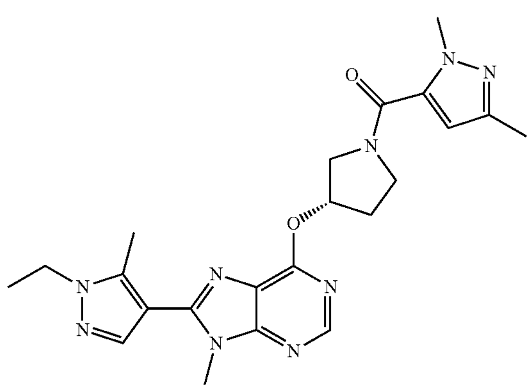 [SMILES: CCn1ncc(-c2nc3c(O[C@H]4CCN(C(=O)c5cc(C)nn5C)C4)ncnc3n2C)c1C] | 6-({(3S)-1-[(1,3-dimethyl-1H-pyrazol-5-yl)carbonyl]pyrrolidin-3-yl}oxy)-8-(1-ethyl-5-methyl-1H-pyrazol-4-yl)-9-methyl-9H-purine | Calc'd 450, found 450 |

TABLE 2-continued

| Compound | Structure | Compound Name | MS [M + H]+ |
|---|---|---|---|
| 2-39 | 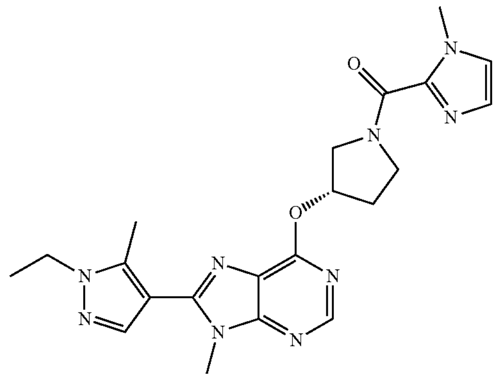 [SMILES: CCn1ncc(-c2nc3c(O[C@H]4CCN(C(=O)c5nccn5C)C4)ncnc3n2C)c1C] | 8-(1-ethyl-5-methyl-1H-pyrazol-4-yl)-9-methyl-6-({(3S)-1-[(1-methyl-1H-imidazol-2-yl)carbonyl]pyrrolidin-3-yl}oxy)-9H-purine | Calc'd 436, found 436 |
| 2-40 | 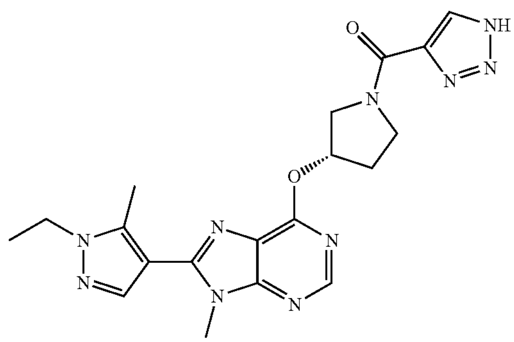 [SMILES: CCn1ncc(-c2nc3c(O[C@H]4CCN(C(=O)c5c[nH]nn5)C4)ncnc3n2C)c1C] | 8-(1-ethyl-5-methyl-1H-pyrazol-4-yl)-9-methyl-6-{[(3S)-1-(1H-1,2,3-triazol-4-ylcarbonyl)pyrrolidin-3-yl]oxy}-9H-purine | Calc'd 423, found 423 |
| 2-41 | 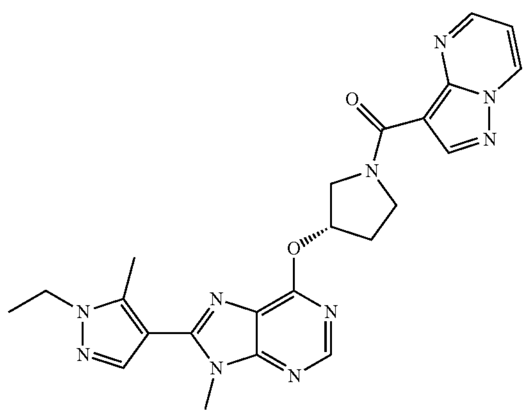 [SMILES: CCn1ncc(-c2nc3c(O[C@H]4CCN(C(=O)c5cnn6cccnc56)C4)ncnc3n2C)c1C] | 8-(1-ethyl-5-methyl-1H-pyrazol-4-yl)-9-methyl-6-{[(3S)-1-(pyrazolo[1,5-a]pyrimidin-3-ylcarbonyl)pyrrolidin-3-yl]oxy}-9H-purine | Calc'd 473, found 473 |
| 2-42 | 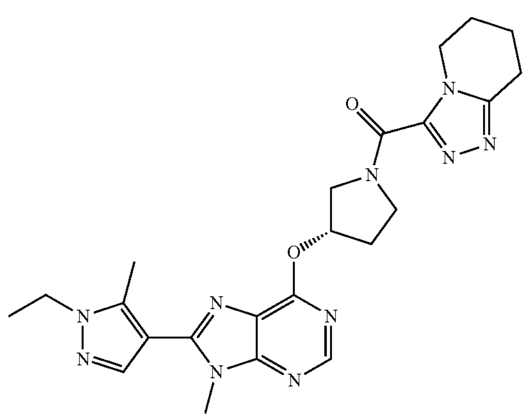 [SMILES: CCn1ncc(-c2nc3c(O[C@H]4CCN(C(=O)c5nnc6n5CCCC6)C4)ncnc3n2C)c1C] | 8-(1-ethyl-5-methyl-1H-pyrazol-4-yl)-9-methyl-6-{[(3S)-1-(5,6,7,8-tetrahydro[1,2,4]triazolo[4,3-a]pyridin-3-ylcarbonyl)pyrrolidin-3-yl]oxy}-9H-purine | Calc'd 477, found 477 |

TABLE 2-continued

| Compound | Structure | Compound Name | MS [M + H]+ |
|---|---|---|---|
| 2-43 | 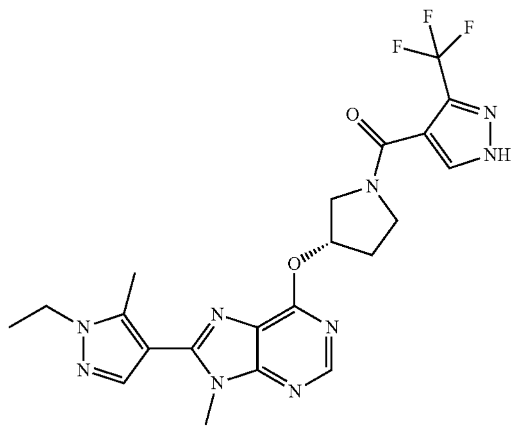 [SMILES: CCn1ncc(-c2nc3c(O[C@H]4CCN(C(=O)c5c[nH]nc5C(F)(F)F)C4)ncnc3n2C)c1C] | 8-(1-ethyl-5-methyl-1H-pyrazol-4-yl)-9-methyl-6-{[(3S)-1-{[3-(trifluoromethyl)-1H-pyrazol-4-yl]carbonyl}pyrrolidin-3-yl]oxy}-9H-purine | Calc'd 490, found 490 |
| 2-44 | 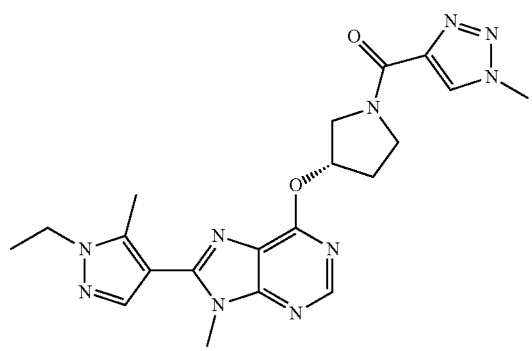 [SMILES: CCn1ncc(-c2nc3c(O[C@H]4CCN(C(=O)c5cn(C)nn5)C4)ncnc3n2C)c1C] | 8-(1-ethyl-5-methyl-1H-pyrazol-4-yl)-9-methyl-6-({(3S)-1-[(1-methyl-1H-1,2,3-triazol-4-yl)carbonyl]pyrrolidin-3-yl}oxy)-9H-purine | Calc'd 437, found 437 |
| 2-45 | 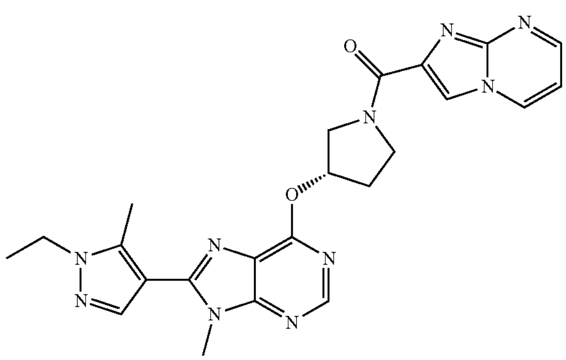 [SMILES: CCn1ncc(-c2nc3c(O[C@H]4CCN(C(=O)c5cn6cccnc6n5)C4)ncnc3n2C)c1C] | 8-(1-ethyl-5-methyl-1H-pyrazol-4-yl)-6-{[(3S)-1-(imidazo[1,2-a]pyrimidin-2-ylcarbonyl)pyrrolidin-3-yl]oxy}-9-methyl-9H-purine | Calc'd 473, found 473 |
| 2-46 | 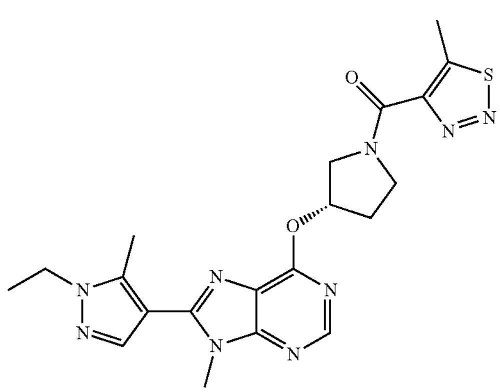 [SMILES: CCn1ncc(-c2nc3c(O[C@H]4CCN(C(=O)c5nnsc5C)C4)ncnc3n2C)c1C] | 8-(1-ethyl-5-methyl-1H-pyrazol-4-yl)-9-methyl-6-({(3S)-1-[(5-methyl-1,2,3-thiadiazol-4-yl)carbonyl]pyrrolidin-3-yl}oxy)-9H-purine | Calc'd 454, found 454 |

TABLE 2-continued

| Compound | Structure | Compound Name | MS [M + H]+ |
|---|---|---|---|
| 2-47 | 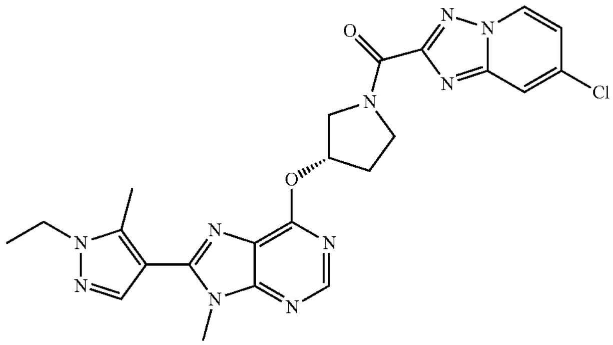 [SMILES: CCn1ncc(-c2nc3c(O[C@H]4CCN(C(=O)c5nc6cc(Cl)ccn6n5)C4)ncnc3n2C)c1C] | 6-({(3S)-1-[(7-chloro[1,2,4]triazolo[1,5-a]pyridin-2-yl)carbonyl]pyrrolidin-3-yl}oxy)-8-(1-ethyl-5-methyl-1H-pyrazol-4-yl)-9-methyl-9H-purine | Calc'd 507, found 507 |
| 2-48 | 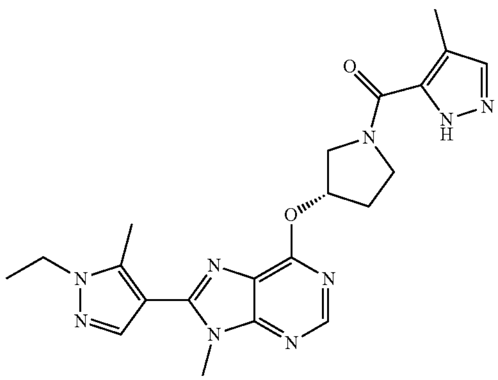 [SMILES: CCn1ncc(-c2nc3c(O[C@H]4CCN(C(=O)c5[nH]ncc5C)C4)ncnc3n2C)c1C] | 8-(1-ethyl-5-methyl-1H-pyrazol-4-yl)-9-methyl-6-({(3S)-1-[(4-methyl-1H-pyrazol-5-yl)carbonyl]pyrrolidin-3-yl}oxy)-9H-purine | Calc'd 436, found 436 |
| 2-49 | 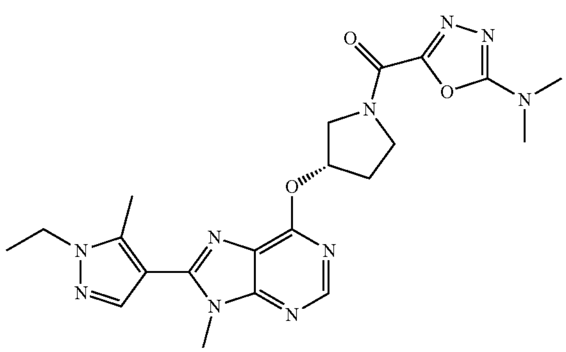 [SMILES: CCn1ncc(-c2nc3c(O[C@H]4CCN(C(=O)c5nnc(N(C)C)o5)C4)ncnc3n2C)c1C] | 5-{[(3S)-3-{[8-(1-ethyl-5-methyl-1H-pyrazol-4-yl)-9-methyl-9H-purin-6-yl]oxy}pyrrolidin-1-yl]carbonyl}-N,N-dimethyl-1,3,4-oxadiazol-2-amine | Calc'd 467, found 467 |
| 2-50 | 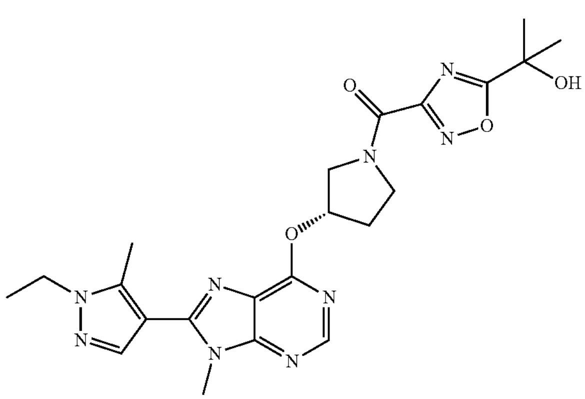 [SMILES: CCn1ncc(-c2nc3c(O[C@H]4CCN(C(=O)c5noc(C(C)(C)O)n5)C4)ncnc3n2C)c1C] | 2-(3-{[(3S)-3-{[8-(1-ethyl-5-methyl-1H-pyrazol-4-yl)-9-methyl-9H-purin-6-yl]oxy}pyrrolidin-1-yl]carbonyl}-1,2,4-oxadiazol-5-yl)propan-2-ol | Calc'd 482, found 482 |

TABLE 2-continued

| Compound | Structure | Compound Name | MS [M + H]+ |
|---|---|---|---|
| 2-51 | 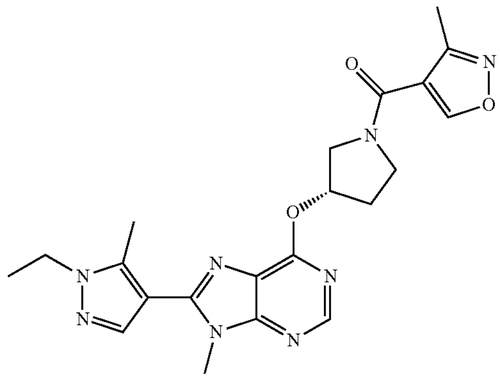 [SMILES: CCn1ncc(-c2nc3c(O[C@H]4CCN(C(=O)c5conc5C)C4)ncnc3n2C)c1C] | 8-(1-ethyl-5-methyl-1H-pyrazol-4-yl)-9-methyl-6-({(3S)-1-[(3-methylisoxazol-4-yl)carbonyl]pyrrolidin-3-yl}oxy)-9H-purine | Calc'd 437, found 437 |
| 2-52 | 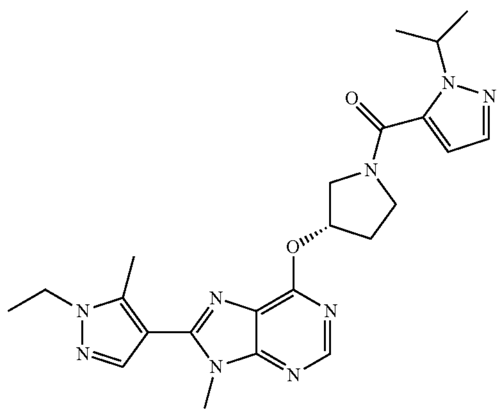 [SMILES: CCn1ncc(-c2nc3c(O[C@H]4CCN(C(=O)c5ccnn5C(C)C)C4)ncnc3n2C)c1C] | 8-(1-ethyl-5-methyl-1H-pyrazol-4-yl)-9-methyl-6-{[(3S)-1-{[1-(1-methylethyl)-1H-pyrazol-5-yl]carbonyl}pyrrolidin-3-yl]oxy}-9H-purine | Calc'd 464, found 464 |
| 2-53 | 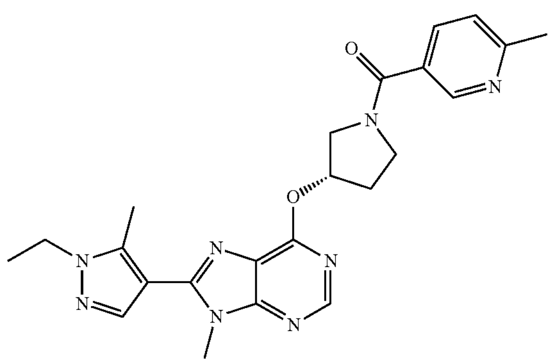 [SMILES: CCn1ncc(-c2nc3c(O[C@H]4CCN(C(=O)c5ccc(C)nc5)C4)ncnc3n2C)c1C] | 8-(1-ethyl-5-methyl-1H-pyrazol-4-yl)-9-methyl-6-({(3S)-1-[(6-methylpyridin-3-yl)carbonyl]pyrrolidin-3-yl}oxy)-9H-purine | Calc'd 447, found 447 |
| 2-54 | 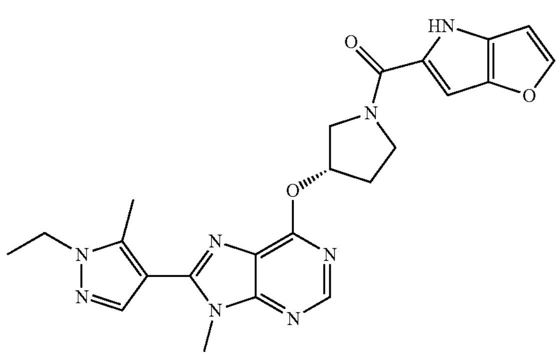 [SMILES: CCn1ncc(-c2nc3c(O[C@H]4CCN(C(=O)c5cc6occc6[nH]5)C4)ncnc3n2C)c1C] | 8-(1-ethyl-5-methyl-1H-pyrazol-4-yl)-6-{[(3S)-1-(4H-furo[3,2-b]pyrrol-5-ylcarbonyl)pyrrolidin-3-yl]oxy}-9-methyl-9H-purine | Calc'd 461, found 461 |

TABLE 2-continued

| Compound | Structure | Compound Name | MS [M + H]+ |
|---|---|---|---|
| 2-55 | 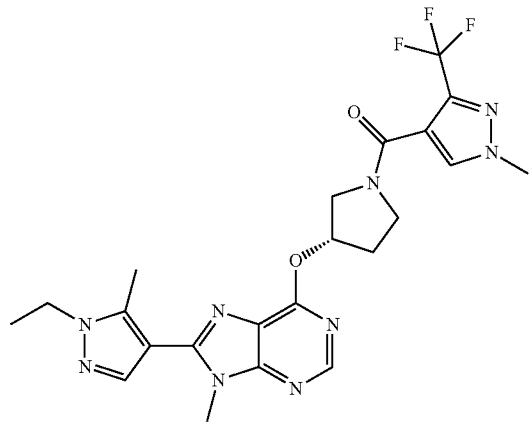 [SMILES: CCn1ncc(-c2nc3c(O[C@H]4CCN(C(=O)c5cn(C)nc5C(F)(F)F)C4)ncnc3n2C)c1C] | 8-(1-ethyl-5-methyl-1H-pyrazol-4-yl)-9-methyl-6-{[(3S)-1-{[1-methyl-3-(trifluoromethyl)-1H-pyrazol-4-yl]carbonyl}pyrrolidin-3-yl]oxy}-9H-purine | Calc'd 504, found 504 |
| 2-56 | 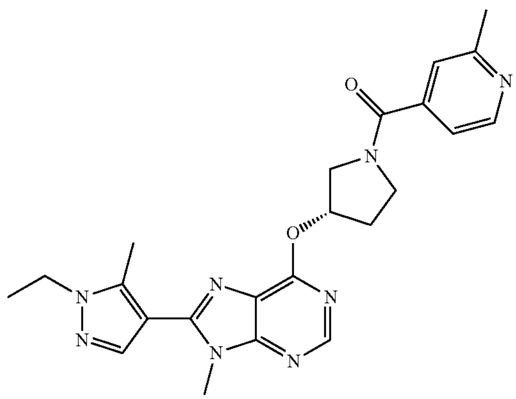 [SMILES: CCn1ncc(-c2nc3c(O[C@H]4CCN(C(=O)c5ccnc(C)c5)C4)ncnc3n2C)c1C] | 8-(1-ethyl-5-methyl-1H-pyrazol-4-yl)-9-methyl-6-({(3S)-1-[(2-methylpyridin-4-yl)carbonyl]pyrrolidin-3-yl}oxy)-9H-purine | Calc'd 447, found 447 |
| 2-57 | 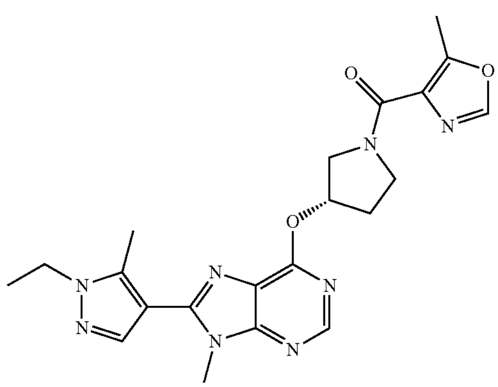 [SMILES: CCn1ncc(-c2nc3c(O[C@H]4CCN(C(=O)c5ncoc5C)C4)ncnc3n2C)c1C] | 8-(1-ethyl-5-methyl-1H-pyrazol-4-yl)-9-methyl-6-({(3S)-1-[(5-methyl-1,3-oxazol-4-yl)carbonyl]pyrrolidin-3-yl}oxy)-9H-purine | Calc'd 437, found 437 |
| 2-58 | 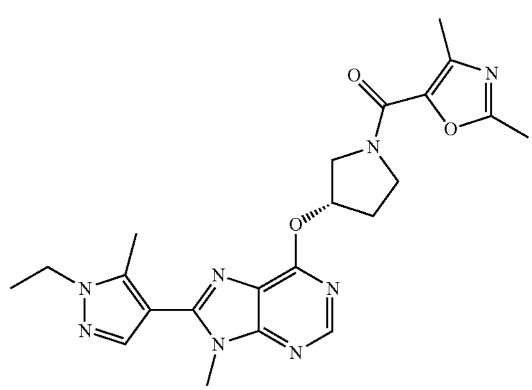 [SMILES: CCn1ncc(-c2nc3c(O[C@H]4CCN(C(=O)c5oc(C)nc5C)C4)ncnc3n2C)c1C] | 6-({(3S)-1-[(2,4-dimethyl-1,3-oxazol-5-yl)carbonyl]pyrrolidin-3-yl}oxy)-8-(1-ethyl-5-methyl-1H-pyrazol-4-yl)-9-methyl-9H-purine | Calc'd 451, found 451 |

TABLE 2-continued

| Compound | Structure | Compound Name | MS [M + H]+ |
|---|---|---|---|
| 2-59 | 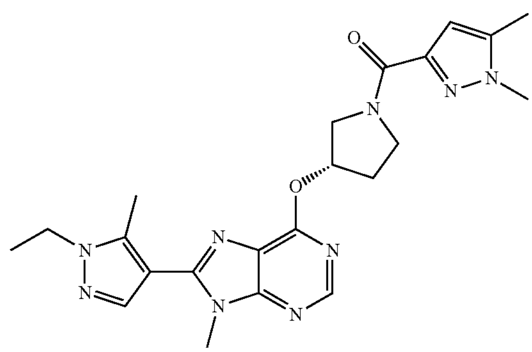 [SMILES: CCn1ncc(-c2nc3c(O[C@H]4CCN(C(=O)c5cc(C)n(C)n5)C4)ncnc3n2C)c1C] | 6-({(3S)-1-[(1,5-dimethyl-1H-pyrazol-3-yl)carbonyl]pyrrolidin-3-yl}oxy)-8-(1-ethyl-5-methyl-1H-pyrazol-4-yl)-9-methyl-9H-purine | Calc'd 450, found 450 |
| 2-60 | 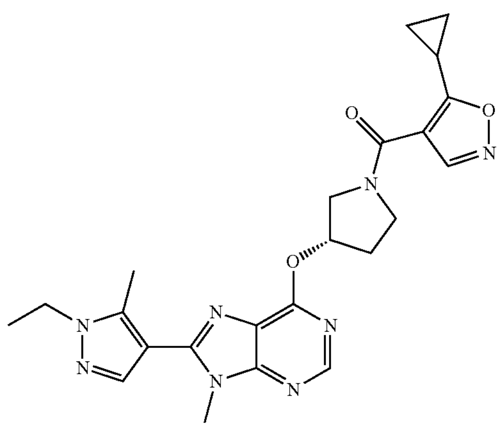 [SMILES: CCn1ncc(-c2nc3c(O[C@H]4CCN(C(=O)c5cnoc5C5CC5)C4)ncnc3n2C)c1C] | 6-({(3S)-1-[(5-cyclopropylisoxazol-4-yl)carbonyl]pyrrolidin-3-yl}oxy)-8-(1-ethyl-5-methyl-1H-pyrazol-4-yl)-9-methyl-9H-purine | Calc'd 463, found 463 |
| 2-61 | 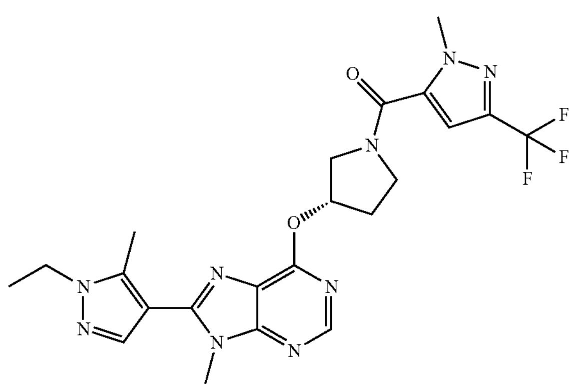 [SMILES: CCn1ncc(-c2nc3c(O[C@H]4CCN(C(=O)c5cc(C(F)(F)F)nn5C)C4)ncnc3n2C)c1C] | 8-(1-ethyl-5-methyl-1H-pyrazol-4-yl)-9-methyl-6-{[(3S)-1-{[1-methyl-3-(trifluoromethyl)-1H-pyrazol-5-yl]carbonyl}pyrrolidin-3-yl]oxy}-9H-purine | Calc'd 504, found 504 |
| 2-62 | 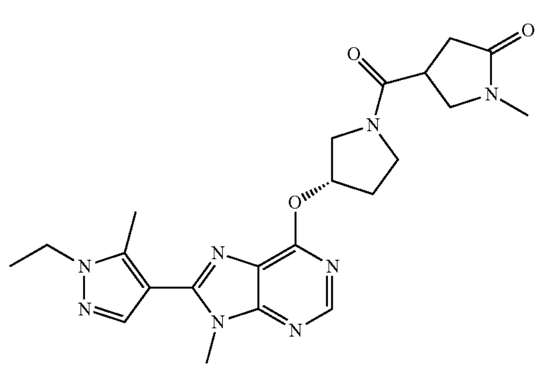 [SMILES: CCn1ncc(-c2nc3c(O[C@H]4CCN(C(=O)C5CC(=O)N(C)C5)C4)ncnc3n2C)c1C] | 4-{[(3S)-3-{[8-(1-ethyl-5-methyl-1H-pyrazol-4-yl)-9-methyl-9H-purin-6-yl]oxy}pyrrolidin-1-yl]carbonyl}-1-methylpyrrolidin-2-one | Calc'd 453, found 453 |

TABLE 2-continued

| Compound | Structure | Compound Name | MS [M + H]+ |
|---|---|---|---|
| 2-63 | 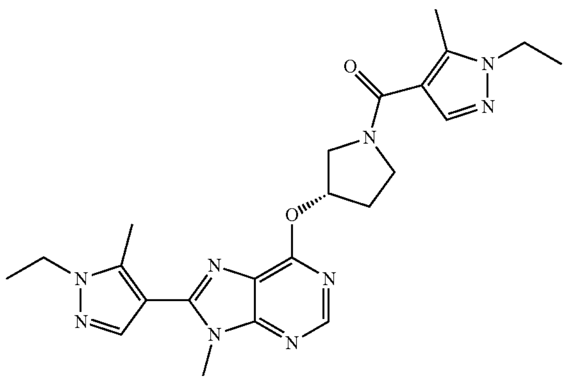 [SMILES: CCn1ncc(C(=O)N2CC[C@H](Oc3ncnc4c3nc(-c3cnn(CC)c3C)n4C)C2)c1C] | 8-(1-ethyl-5-methyl-1H-pyrazol-4-yl)-6-({(3S)-1-[(1-ethyl-5-methyl-1H-pyrazol-4-yl)carbonyl]pyrrolidin-3-yl}oxy)-9-methyl-9H-purine | Calc'd 464, found 464 |
| 2-64 | 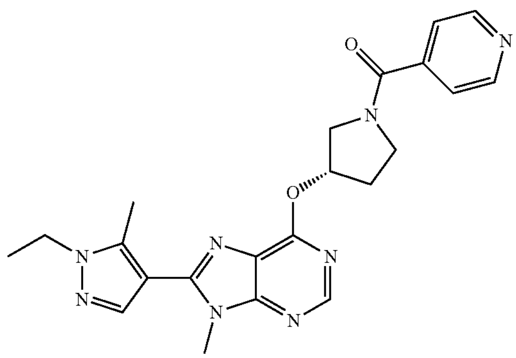 [SMILES: CCn1ncc(-c2nc3c(O[C@H]4CCN(C(=O)c5ccncc5)C4)ncnc3n2C)c1C] | 8-(1-ethyl-5-methyl-1H-pyrazol-4-yl)-9-methyl-6-{[(3S)-1-(pyridin-4-ylcarbonyl)pyrrolidin-3-yl]oxy}-9H-purine | Calc'd 433, found 433 |
| 2-65 | 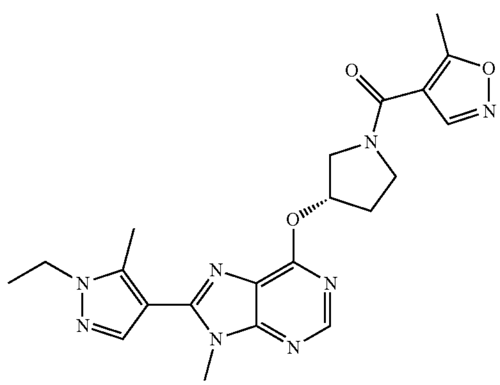 [SMILES: CCn1ncc(-c2nc3c(O[C@H]4CCN(C(=O)c5cnoc5C)C4)ncnc3n2C)c1C] | 8-(1-ethyl-5-methyl-1H-pyrazol-4-yl)-9-methyl-6-({(3S)-1-[(5-methylisoxazol-4-yl)carbonyl]pyrrolidin-3-yl}oxy)-9H-purine | Calc'd 437, found 437 |
| 2-66 | 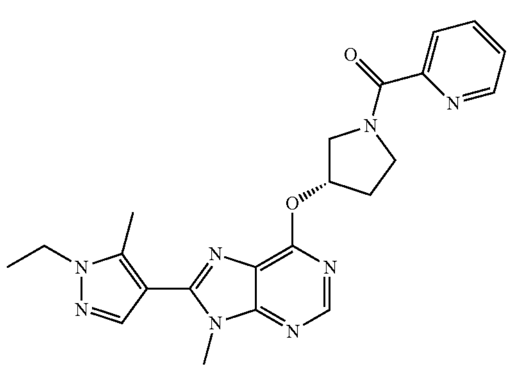 [SMILES: CCn1ncc(-c2nc3c(O[C@H]4CCN(C(=O)c5ccccn5)C4)ncnc3n2C)c1C] | 8-(1-ethyl-5-methyl-1H-pyrazol-4-yl)-9-methyl-6-{[(3S)-1-(pyridin-2-ylcarbonyl)pyirolidin-3-yl]oxy}-9H-purine | Calc'd 433, found 433 |

TABLE 2-continued

| Compound | Structure | Compound Name | MS [M + H]+ |
|---|---|---|---|
| 2-67 | 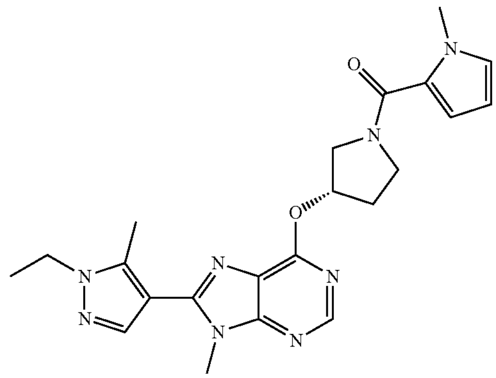 [SMILES: CCn1ncc(-c2nc3c(O[C@H]4CCN(C(=O)c5cccn5C)C4)ncnc3n2C)c1C] | 8-(1-ethyl-5-methyl-1H-pyrazol-4-yl)-9-methyl-6-({(3S)-1-[(1-methyl-1H-pyrrol-2-yl)carbonyl]pyrrolidin-3-yl}oxy)-9H-purine | Calc'd 435, found 435 |
| 2-68 | 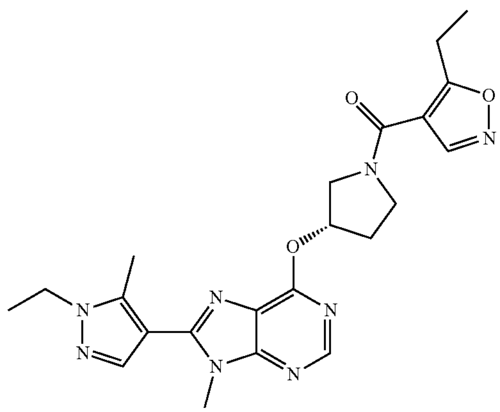 [SMILES: CCc1oncc1C(=O)N1CC[C@H](Oc2ncnc3c2nc(-c2cnn(CC)c2C)n3C)C1] | 6-({(3S)-1-[(5-ethylisoxazol-4-yl)carbonyl]pyrrolidin-3-yl}oxy)-8-(1-ethyl-5-methyl-1H-pyrazol-4-yl)-9-methyl-9H-purine | Calc'd 451, found 451 |
| 2-69 | 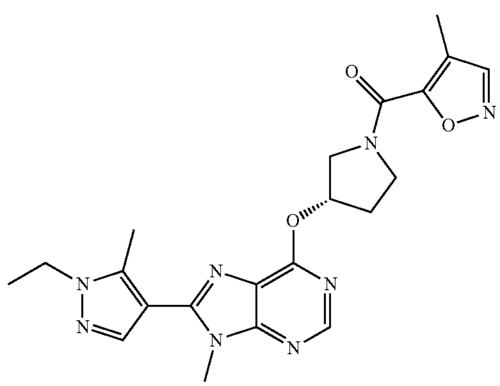 [SMILES: CCn1ncc(-c2nc3c(O[C@H]4CCN(C(=O)c5oncc5C)C4)ncnc3n2C)c1C] | 8-(1-ethyl-5-methyl-1H-pyrazol-4-yl)-9-methyl-6-({(3S)-1-[(4-methylisoxazol-5-yl)carbonyl]pyrrolidin-3-yl}oxy)-9H-purine | Calc'd 437, found 437 |
| 2-70 | 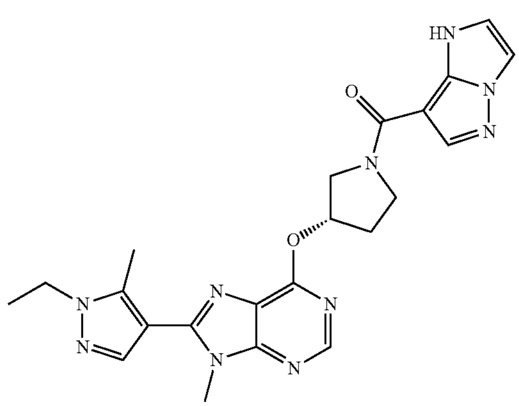 [SMILES: CCn1ncc(-c2nc3c(O[C@H]4CCN(C(=O)c5cnn6cc[nH]c56)C4)ncnc3n2C)c1C] | 8-(1-ethyl-5-methyl-1H-pyrazol-4-yl)-6-{[(3S)-1-(1H-imidazo[1,2-b]pyrazol-7-ylcarbonyl)pyrrolidin-3-yl]oxy}-9-methyl-9H-purine | Calc'd 461, found 461 |

TABLE 2-continued

| Compound | Structure | Compound Name | MS [M + H]+ |
|---|---|---|---|
| 2-71 | 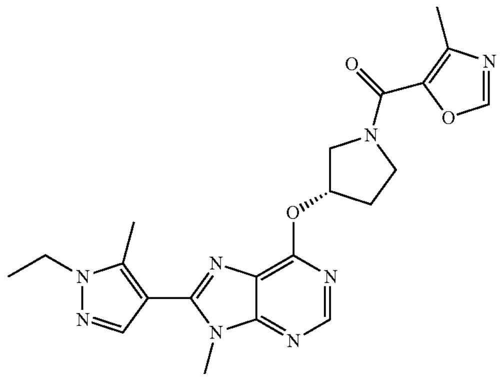 [SMILES: CCn1ncc(-c2nc3c(O[C@H]4CCN(C(=O)c5ocnc5C)C4)ncnc3n2C)c1C] | 8-(1-ethyl-5-methyl-1H-pyrazol-4-yl)-9-methyl-6-({(3S)-1-[(4-methyl-1,3-oxazol-5-yl)carbonyl]pyrrolidin-3-yl}oxy)-9H-purine | Calc'd 437, found 437 |
| 2-72 | 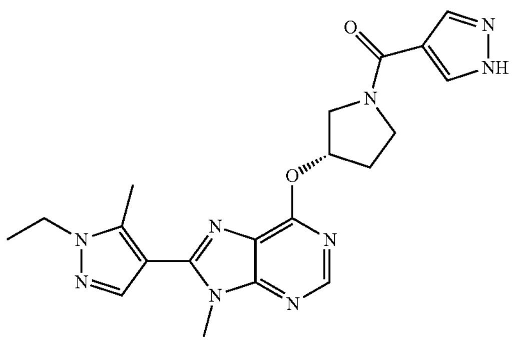 [SMILES: CCn1ncc(-c2nc3c(O[C@H]4CCN(C(=O)c5cn[nH]c5)C4)ncnc3n2C)c1C] | 8-(1-ethyl-5-methyl-1H-pyrazol-4-yl)-9-methyl-6-{[(3S)-1-(1H-pyrazol-4-ylcarbonyl)pyrrolidin-3-yl]oxy}-9H-purine | Calc'd 422, found 422 |
| 2-73 | 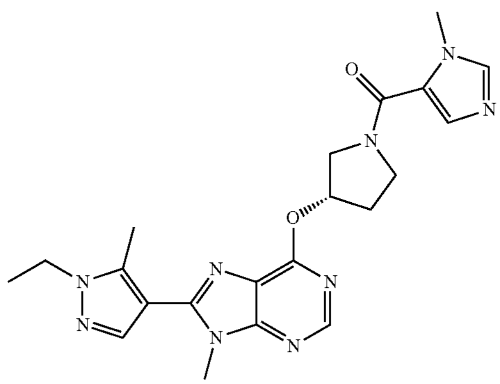 [SMILES: CCn1ncc(-c2nc3c(O[C@H]4CCN(C(=O)c5cncn5C)C4)ncnc3n2C)c1C] | 8-(1-ethyl-5-methyl-1H-pyrazol-4-yl)-9-methyl-6-({(3S-1-[(1-methyl-1H-imidazol-5-yl)carbonyl]pyrrolidin-3-yl}oxy)-9H-purine | Calc'd 436, found 436 |
| 2-74 | 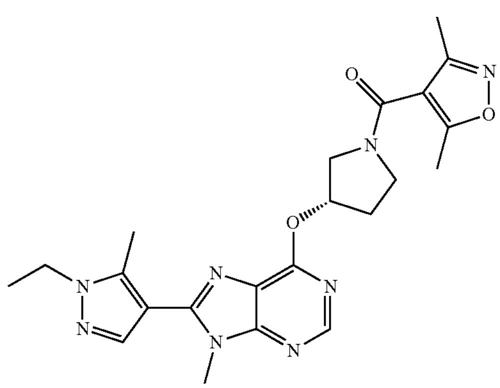 [SMILES: CCn1ncc(-c2nc3c(O[C@H]4CCN(C(=O)c5c(C)noc5C)C4)ncnc3n2C)c1C] | 6-({(3S)-1-[(3,5-dimethylisoxazol-4-yl)carbonyl]pyrrolidin-3-yl}oxy)-8-(1-ethyl-5-methyl-1H-pyrazol-4-yl)-9-methyl-9H-purine | Calc'd 451, found 451 |

TABLE 2-continued

| Compound | Structure | Compound Name | MS [M + H]+ |
|---|---|---|---|
| 2-75 | 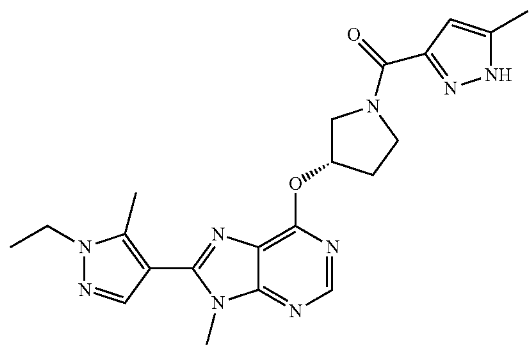 [SMILES: CCn1ncc(-c2nc3c(O[C@H]4CCN(C(=O)c5cc(C)[nH]n5)C4)ncnc3n2C)c1C] | 8-(1-ethyl-5-methyl-1H-pyrazol-4-yl)-9-methyl-6-({(3S)-1-[(5-methyl-1H-pyrazol-3-yl)carbonyl]pyrrolidin-3-yl}oxy)-9H-purine | Calc'd 436, found 436 |
| 2-76 | 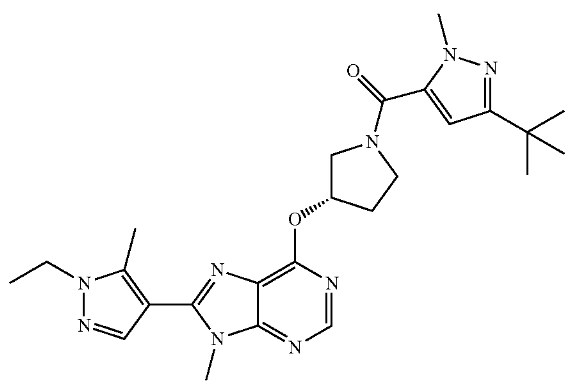 [SMILES: CCn1ncc(-c2nc3c(O[C@H]4CCN(C(=O)c5cc(C(C)(C)C)nn5C)C4)ncnc3n2C)c1C] | 6-({(3S)-1-[(3-tert-butyl-1-methyl-1H-pyrazol-5-yl)carbonyl]pyrrolidin-3-yl}oxy)-8-(1-ethyl-5-methyl-1H-pyrazol-4-yl)-9-methyl-9H-purine | Calc'd 492, found 492 |
| 2-77 | 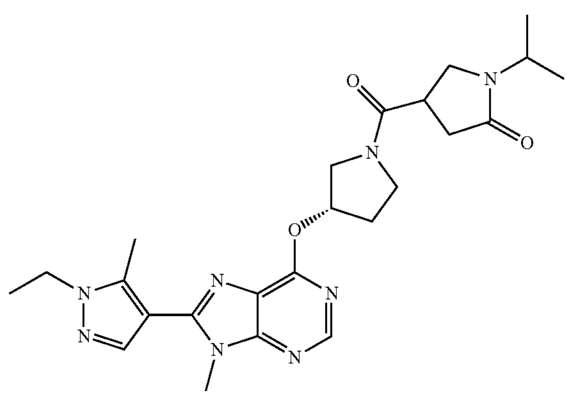 [SMILES: CCn1ncc(-c2nc3c(O[C@H]4CCN(C(=O)C5CC(=O)N(C(C)C)C5)C4)ncnc3n2C)c1C] | 4-{[(3S)-3-{[8-(1-ethyl-5-methyl-1H-pyrazol-4-yl)-9-methyl-9H-purin-6-yl]oxy}pyrrolidin-1-yl]carbonyl}-1-(1-methylethyl)pyrrolidin-2-one | Calc'd 481, found 481 |
| 2-78 | 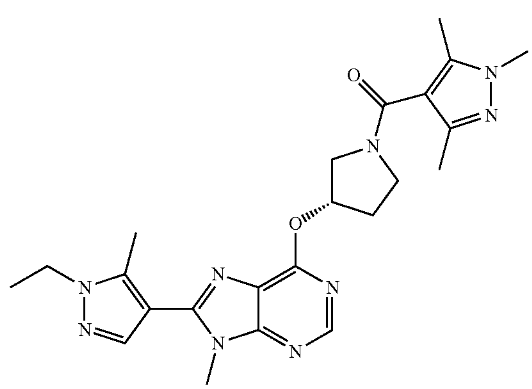 [SMILES: CCn1ncc(-c2nc3c(O[C@H]4CCN(C(=O)c5c(C)nn(C)c5C)C4)ncnc3n2C)c1C] | 8-(1-ethyl-5-methyl-1H-pyrazol-4-yl)-9-methyl-6-({(3S)-1-[(1,3,5-trimethyl-1H-pyrazol-4-yl)carbonyl]pyrrolidin-3-yl}oxy)-9H-purine | Calc'd 464, found 464 |

TABLE 2-continued

| Compound | Structure | Compound Name | MS [M + H]+ |
|---|---|---|---|
| 2-79 | 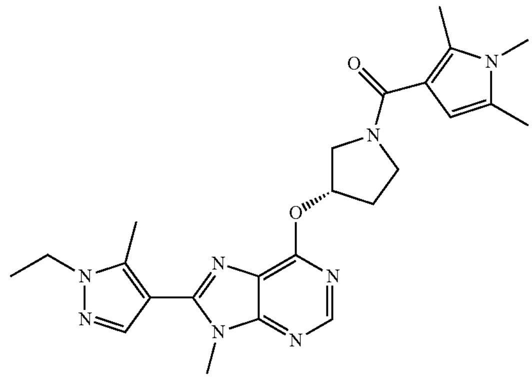 [SMILES: CCn1ncc(-c2nc3c(O[C@H]4CCN(C(=O)c5cc(C)n(C)c5C)C4)ncnc3n2C)c1C] | 8-(1-ethyl-5-methyl-1H-pyrazol-4-yl)-9-methyl-6-({(3S)-1-[(1,2,5-trimethyl-1H-pyrrol-3-yl)carbonyl]pyrrolidin-3-yl}oxy)-9H-purine | Calc'd 463, found 463 |
| 2-80 | 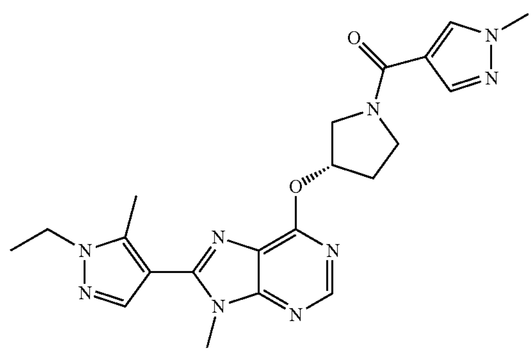 [SMILES: CCn1ncc(-c2nc3c(O[C@H]4CCN(C(=O)c5cnn(C)c5)C4)ncnc3n2C)c1C] | 8-(1-ethyl-5-methyl-1H-pyrazol-4-yl)-9-methyl-6-({(3S)-1-[(1-methyl-1H-pyrazol-4-yl)carbonyl]pyrrolidin-3-yl}oxy)-9H-purine | Calc'd 436, found 436 |
| 2-81 | 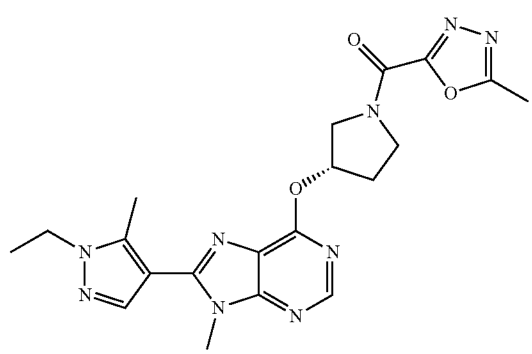 [SMILES: CCn1ncc(-c2nc3c(O[C@H]4CCN(C(=O)c5nnc(C)o5)C4)ncnc3n2C)c1C] | 8-(1-ethyl-5-methyl-1H-pyrazol-4-yl)-9-methyl-6-({(3S)-1-[(5-methyl-1,3,4-oxadiazol-2-yl)carbonyl]pyrrolidin-3-yl}oxy)-9H-purine | Calc'd 438, found 438 |
| 2-82 | 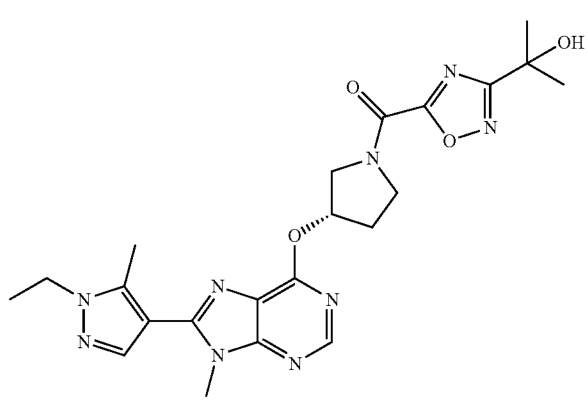 [SMILES: CCn1ncc(-c2nc3c(O[C@H]4CCN(C(=O)c5nc(C(C)(C)O)no5)C4)ncnc3n2C)c1C] | 2-(5-{[(3S)-3-{[8-(1-ethyl-5-methyl-1H-pyrazol-4-yl)-9-methyl-9H-purin-6-yl]oxy}pyrrolidin-1-yl]carbonyl}-1,2,4-oxadiazol-3-yl)propan-2-ol | Calc'd 482, found 482 |

TABLE 2-continued

| Compound | Structure | Compound Name | MS [M + H]+ |
|---|---|---|---|
| 2-83 | 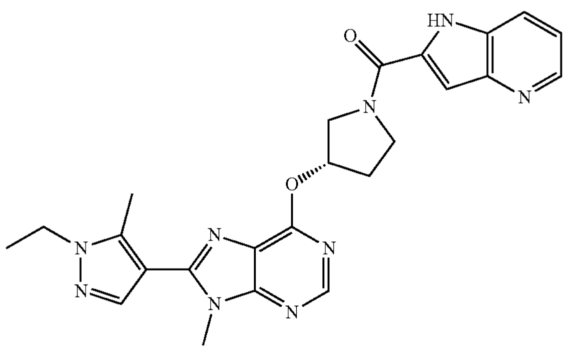 [SMILES: CCn1ncc(-c2nc3c(O[C@H]4CCN(C(=O)c5cc6ncccc6[nH]5)C4)ncnc3n2C)c1C] | 8-(1-ethyl-5-methyl-1H-pyrazol-4-yl)-9-methyl-6-{[(3S)-1-(1H-pyrrolo[3,2-b]pyridin-2-ylcarbonyl)pyrrolidin-3-yl]oxy}-9H-purine | Calc'd 472, found 472 |
| 2-84 | 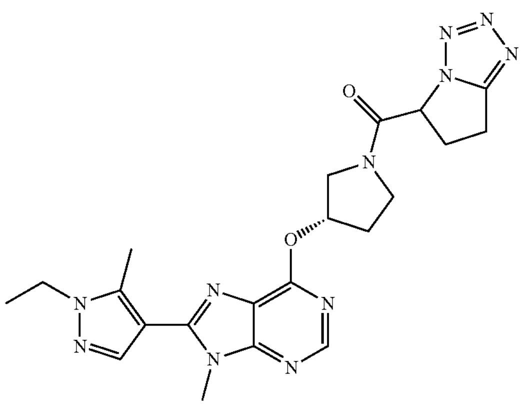 [SMILES: CCn1ncc(-c2nc3c(O[C@H]4CCN(C(=O)C5CCc6nnnn65)C4)ncnc3n2C)c1C] | 6-{[(3S)-1-(6,7-dihydro-5H-pyrrolo[1,2-d]tetrazol-5-ylcarbonyl)pyrrolidin-3-yl]oxy}-8-(1-ethyl-5-methyl-1H-pyrazol-4-yl)-9-methyl-9H-purine (non-preferred name) | Calc'd 464, found 464 |
| 2-85 | 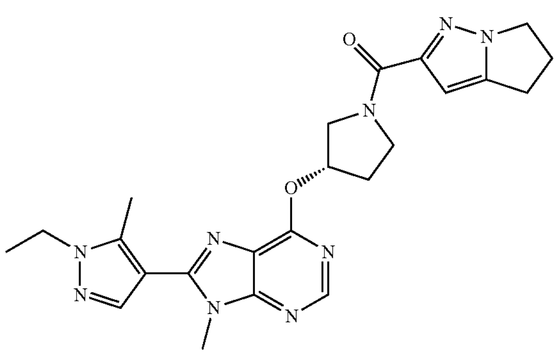 [SMILES: CCn1ncc(-c2nc3c(O[C@H]4CCN(C(=O)c5cc6n(n5)CCC6)C4)ncnc3n2C)c1C] | 6-{[(3S)-1-(5,6-dihydro-4H-pyrrolo[1,2-b]pyrazol-2-ylcarbonyl)pyrrolidin-3-yl]oxy}-8-(1-ethyl-5-methyl-1H-pyrazol-4-yl)-9-methyl-9H-purine | Calc'd 462, found 462 |
| 2-86 | 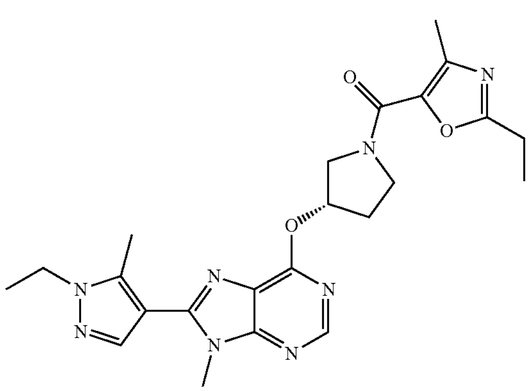 [SMILES: CCc1nc(C)c(C(=O)N2CC[C@H](Oc3ncnc4c3nc(-c3cnn(CC)c3C)n4C)C2)o1] | 6-({(3S)-1-[(2-ethyl-4-methyl-1,3-oxazol-5-yl)carbonyl]pyrrolidin-3-yl}oxy)-8-(1-ethyl-5-methyl-1H-pyrazol-4-yl)-9-methyl-9H-purine | Calc'd 465, found 465 |

TABLE 2-continued

| Compound | Structure | Compound Name | MS [M + H]+ |
|---|---|---|---|
| 2-87 | 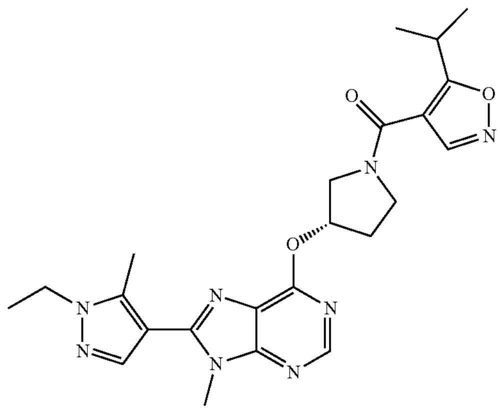 [SMILES: CCn1ncc(-c2nc3c(O[C@H]4CCN(C(=O)c5cnoc5C(C)C)C4)ncnc3n2C)c1C] | 8-(1-ethyl-5-methyl-1H-pyrazol-4-yl)-9-methyl-6-{[(3S)-1-{[5-(1-methylethyl)isoxazol-4-yl]carbonyl}pyrrolidin-3-yl]oxy}-9H-purine | Calc'd 465, found 465 |
| 2-88 | 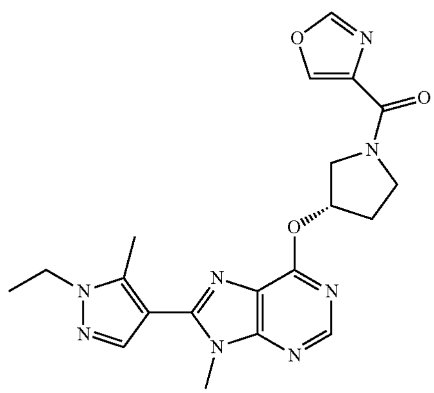 [SMILES: CCn1ncc(-c2nc3c(O[C@H]4CCN(C(=O)c5cocn5)C4)ncnc3n2C)c1C] | 8-(1-ethyl-5-methyl-1H-pyrazol-4-yl)-9-methyl-6-{[(3S)-1-(1,3-oxazol-4-ylcarbonyl)pyrrolidin-3-yl]oxy}-9H-purine | Calc'd 423, found 423 |
| 2-89 | 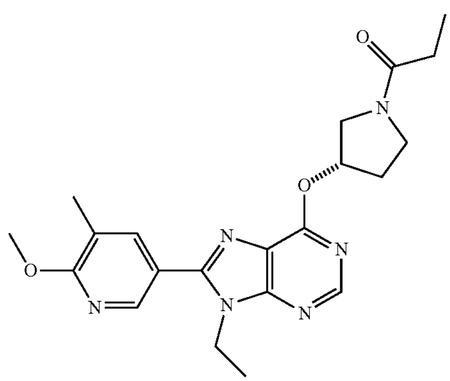 | (S)-1-(3-((9-ethyl-8-(6-methoxy-5-methylpyridin-3-yl)-9H-purin-6-yl)oxy)pyrrolidin-1-yl)propan-1-one | Calc'd 411, found 411 |
| 2-90 | 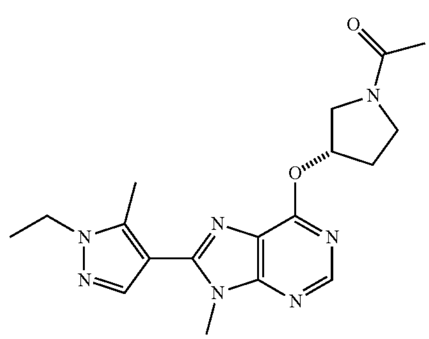 | (S)-1-(3-((8-(1-ethyl-5-methyl-1H-pyrazol-4-yl)-9-methyl-9H-purin-6-yl)oxy)pyrrolidin-1-yl)ethanone | Calc'd 370, found 370 |

TABLE 2-continued

| Compound | Structure | Compound Name | MS [M + H]+ |
|---|---|---|---|
| 2-91 | 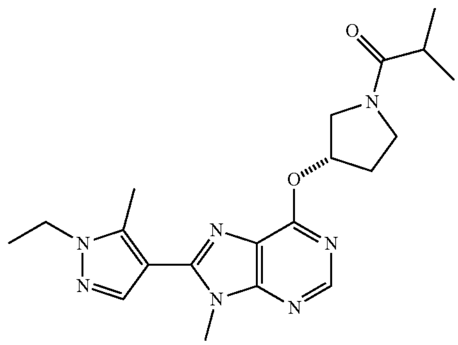 | (S)-1-(3-((8-(1-ethyl-5-methyl-1H-pyrazol-4-yl)-9-methyl-9H-purin-6-yl)oxy)pyrrolidin-1-yl)-2-methylpropan-1-one | Calc'd 398, found 398 |
| 2-92 | 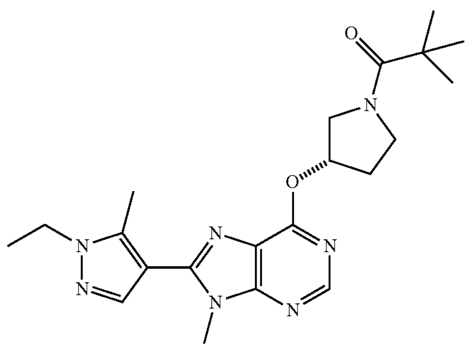 | (S)-1-(3-((8-(1-ethyl-5-methyl-1H-pyrazol-4-yl)-9-methyl-9H-purin-6-yl)oxy)pyrrolidin-1-yl)-2,2-dimethylpropan-1-one | Calc'd 412, found 412 |
| 2-93 | 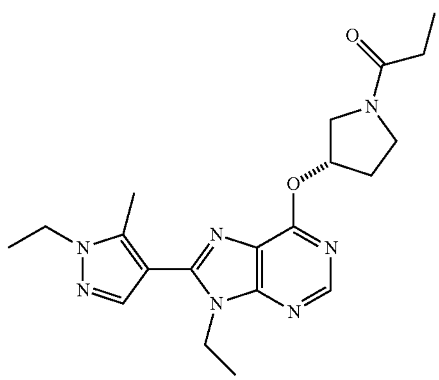 | (S)-1-(3-((9-ethyl-8-(1-ethyl-5-methyl-1H-pyrazol-4-yl)-9H-purin-6-yl)oxy)pyrrolidin-1-yl)propan-1-one | Calc'd 398, found 398 |
| 2-94 | 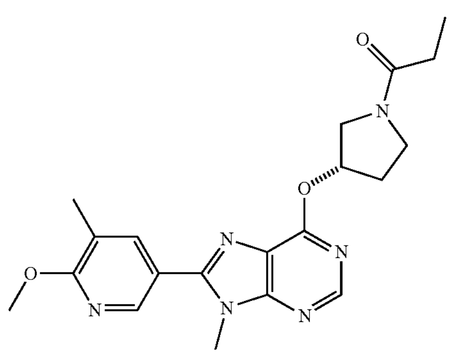 | (S)-1-(3-((8-(6-methoxy-5-methylpyridin-3-yl)-9-methyl-9H-purin-6-yl)oxy)pyrrolidin-1-yl)propan-1-one | Calc'd 397, found 397 |

TABLE 2-continued

| Compound | Structure | Compound Name | MS [M + H]+ |
|---|---|---|---|
| 2-95 | 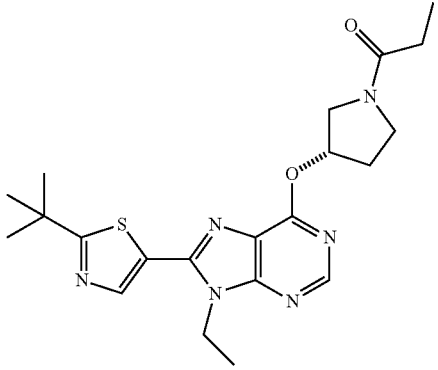 | (S)-1-(3-((8-(2-(tert-butyl)thiazol-5-yl)-9-ethyl-9H-purin-6-yl)oxy)pyrrolidin-1-yl)propan-1-one | Calc'd 429, found 429 |
| 2-96 | 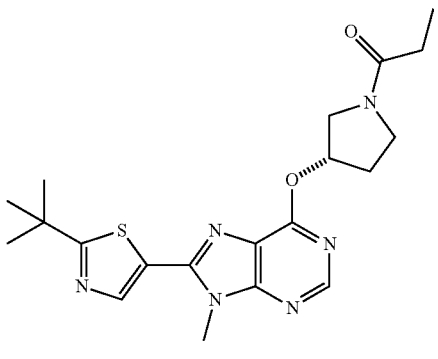 | (S)-1-(3-((8-(2-(tert-butyl)thiazol-5-yl)-9-methyl-9H-purin-6-yl)oxy)pyrrolidin-1-yl)propan-1-one | Calc'd 415, found 415 |
| 2-97 | 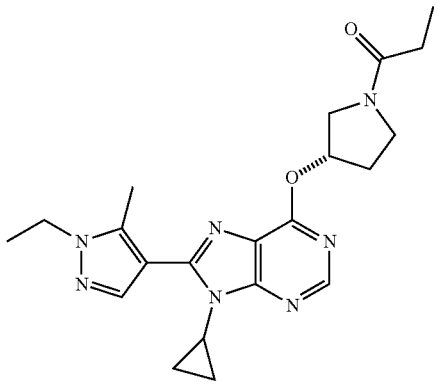 | (S)-1-(3-((9-cyclopropyl-8-(1-ethyl-5-methyl-1H-pyrazol-4-yl)-9H-purin-6-yl)oxy)pyrrolidin-1-yl)propan-1-one | Calc'd 410, found 410 |
| 2-98 | 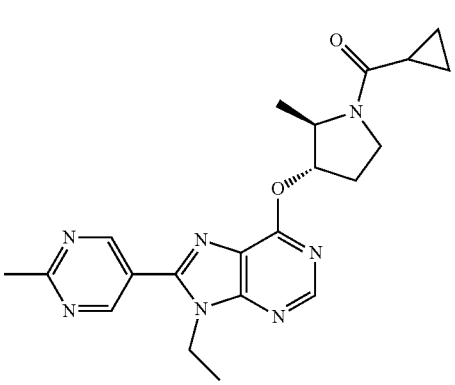 [SMILES: CCn1c(-c2cnc(C)nc2)nc2c(O[C@H]3CCN(C(=O)C4CC4)[C@@H]3C)ncnc21] | 6-{[(2R,3S)-1-(cyclopropylcarbonyl)-2-methylpyrrolidin-3-yl]oxy}-9-ethyl-8-(2-methylpyrimidin-5-yl)-9H-purine | Calc'd 408, found 408 |

TABLE 2-continued

| Compound | Structure | Compound Name | MS [M + H]+ |
|---|---|---|---|
| 2-99 | 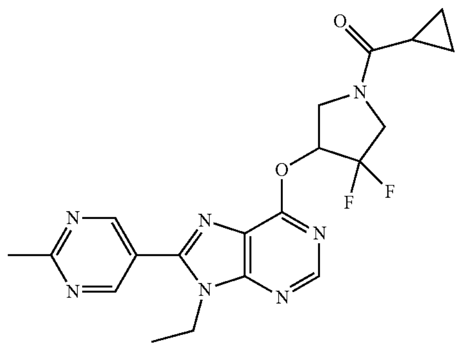 [SMILES: CCn1c(-c2cnc(C)nc2)nc2c(OC3CN(C(=O)C4CC4)CC3(F)F)ncnc21] | 6-{[1-(cyclopropylcarbonyl)-4,4-difluoropyrrolidin-3-yl]oxy}-9-ethyl-8-(2-methylpyrimidin-5-yl)-9H-purine | Calc'd 430, found 430 |
| 2-100 | 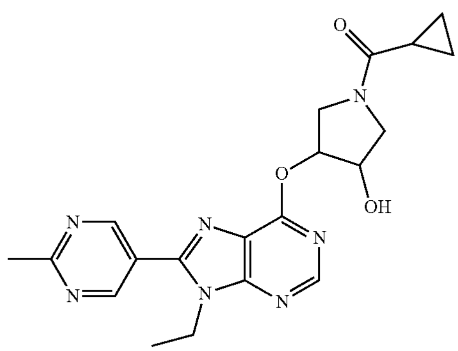 [SMILES: CCn1c(-c2cnc(C)nc2)nc2c(OC3CN(C(=O)C4CC4)CC3O)ncnc21] | [(3R,4R) or (3S,4S)]-trans-1-(cyclopropylcarbonyl)-4-{[9-ethyl-8-(2-methylpyrimidin-5-yl)-9H-purin-6-yl]oxy}pyrrolidin-3-ol | Calc'd 410, found 410 |
| 2-101 | 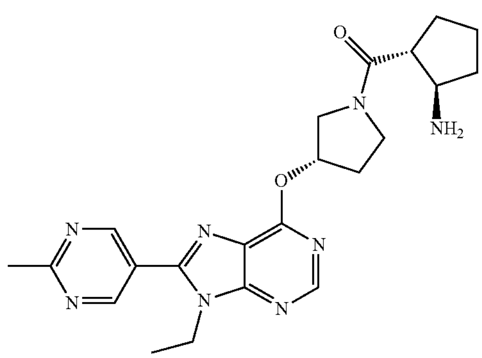 [SMILES: CCn1c(-c2cnc(C)nc2)nc2c(O[C@H]3CCN(C(=O)[C@@H]4CCC[C@H]4N)C3)ncnc21] | (1R,2R)-2-{[(3S)-3-{[9-ethyl-8-(2-methylpyrimidin-5-yl)-9H-purin-6-yl]oxy}pyrrolidin-1-yl]carbonyl}cyclopentanamine | Calc'd 437, found 437 |
| 2-102 | 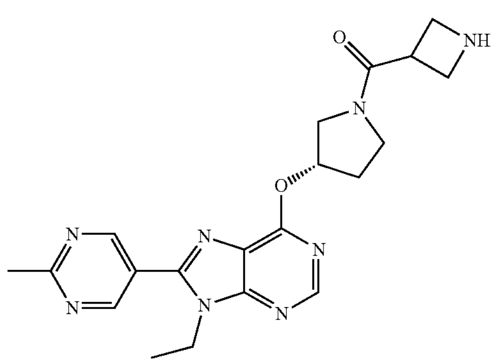 [SMILES: CCn1c(-c2cnc(C)nc2)nc2c(O[C@H]3CCN(C(=O)C4CNC4)C3)ncnc21] | 6-{[(3S)-1-(azetidin-3-ylcarbonyl)pyrrolidin-3-yl]oxy}-9-ethyl-8-(2-methylpyrimidin-5-yl)-9H-purine | Calc'd 409, found 409 |

TABLE 2-continued

| Compound | Compound Name | MS [M + H]+ |
|---|---|---|
| 2-103 | (1R,2S)-2-{[(3S)-3-{[9-ethyl-8-(2-methylpyrimidin-5-yl)-9H-purin-6-yl]oxy}pyrrolidin-1-yl]carbonyl}cyclopentanamine | Calc'd 437, found 437 |
| 2-104 | 6-({(3S)-1-[(3S,4R)-1-azabicyclo[2.2.1]hept-3-ylcarbonyl]pyrrolidin-3-yl}oxy)-9-ethyl-8-(2-methylpyrimidin-5-yl)-9H-purine | Calc'd 449, found 449 |
| 2-105 | 6-{[(3S)-1-(cyclobutylcarbonyl)pyrrolidin-3-yl]oxy}-8-(1-ethyl-5-methyl-1H-pyrazol-4-yl)-9-methyl-9H-purine | Calc'd 410, found 410 |
| 2-106 | 6-({(3S)-1-[(3,3-difluorocyclobutyl)carbonyl]pyrrolidin-3-yl}oxy)-8-(1-ethyl-5-methyl-1H-pyrazol-4-yl)-9-methyl-9H-purine | Calc'd 446, found 446 |

TABLE 2-continued

| Compound | Structure | Compound Name | MS [M + H]+ |
|---|---|---|---|
| 2-107 | 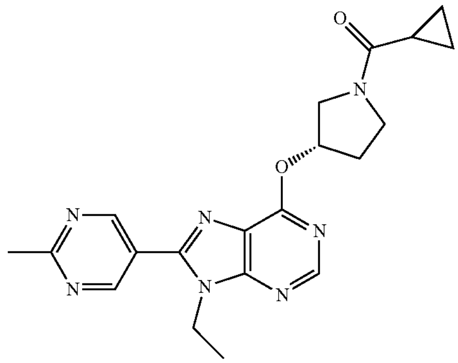 [SMILES: CCn1c(-c2cnc(C)nc2)nc2c(O[C@H]3CCN(C(=O)C4CC4)C3)ncnc21] | 6-{[(3S)-1-(cyclopropylcarbonyl)pyrrolidin-3-yl]oxy}-9-ethyl-8-(2-methylpyrimidin-5-yl)-9H-purine | Calc'd 394, found 394 |
| 2-108 | 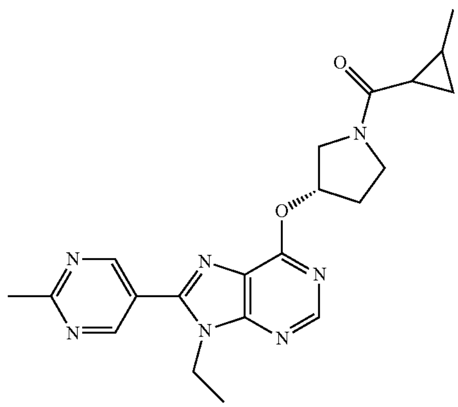 | 9-ethyl-6-({(3S)-1-[(2-methylcyclopropyl)carbonyl]pyrrolidin-3-yl}oxy)-8-(2-methylpyrimidin-5-yl)-9H-purine | Calc'd 408, found 408 |
| 2-109 | 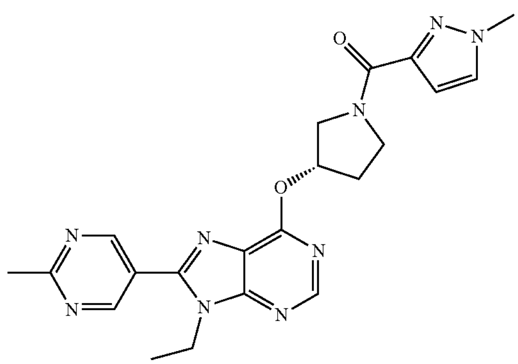 | 9-ethyl-6-({(3S)-1-[(1-methyl-1H-pyrazol-3-yl)carbonyl]pyrrolidin-3-yl}oxy)-8-(2-methylpyrimidin-5-yl)-9H-purine | Calc'd 434, found 434 |
| 2-110 | 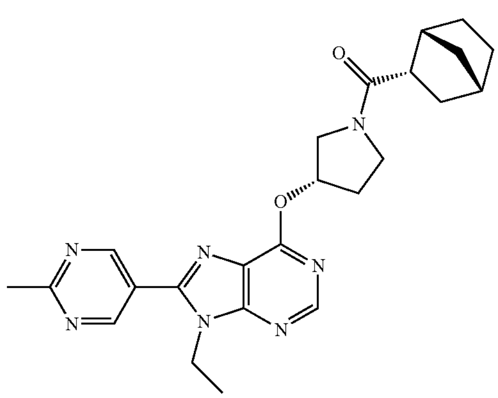 [SMILES: CCn1c(-c2cnc(C)nc2)nc2c(O[C@H]3CCN(C(=O)[C@H]4C[C@H]5CC[C@@H]4C5)C3)ncnc21] | 6-({(3S)-1-[(1R,2S,4S)-bicyclo[2.2.1]hept-2-ylcarbonyl]pyrrolidin-3-yl}oxy)-9-ethyl-8-(2-methylpyrimidin-5-yl)-9H-purine | Calc'd 448, found 448 |

TABLE 2-continued
| Compound | Structure | Compound Name | MS [M + H]+ |
|---|---|---|---|
| 2-111 | 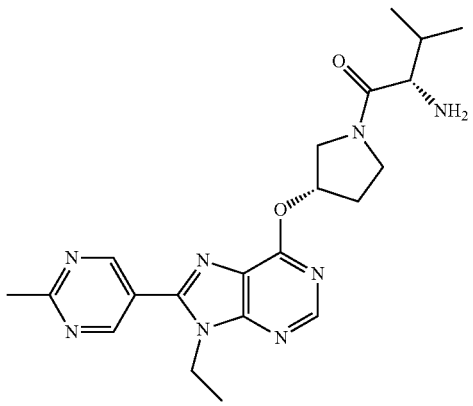 [SMILES: CCn1c(-c2cnc(C)nc2)nc2c(O[C@H]3CCN(C(=O)[C@@H](N)C(C)C)C3)ncnc21] | (2S)-1-[(3S)-3-{[9-ethyl-8-(2-methylpyrimidin-5-yl)-9H-purin-6-yl]oxy}pyrrolidin-1-yl]-3-methyl-1-oxobutan-2-amine | Calc'd 425, found 425 |
| 2-112 | 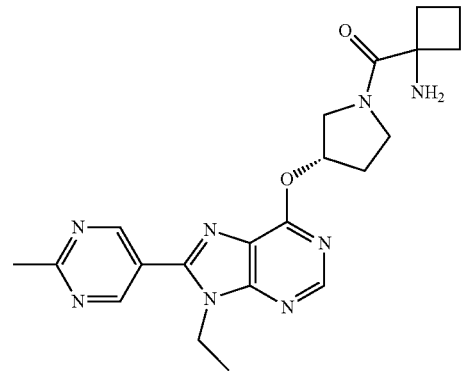 [SMILES: CCn1c(-c2cnc(C)nc2)nc2c(O[C@H]3CCN(C(=O)C4(N)CCC4)C3)ncnc21] | 1-{[(3S)-3-{[9-ethyl-8-(2-methylpyrimidin-5-yl)-9H-purin-6-yl]oxy}pyrrolidin-1-yl]carbonyl}cyclobutanamine | Calc'd 423, found 423 |
| 2-113 | 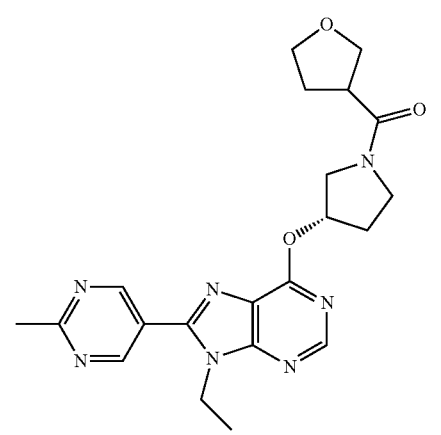 [SMILES: CCn1c(-c2cnc(C)nc2)nc2c(O[C@H]3CCN(C(=O)C4CCOC4)C3)ncnc21] | 9-ethyl-8-(2-methylpyrimidin-5-yl)-6-{[(3S)-1-(tetrahydrofuran-3-ylcarbonyl)pyrrolidin-3-yl]oxy}-9H-purine | Calc'd 424, found 424 |

TABLE 2-continued

| Compound | Structure | Compound Name | MS [M + H]+ |
|---|---|---|---|
| 2-114 | 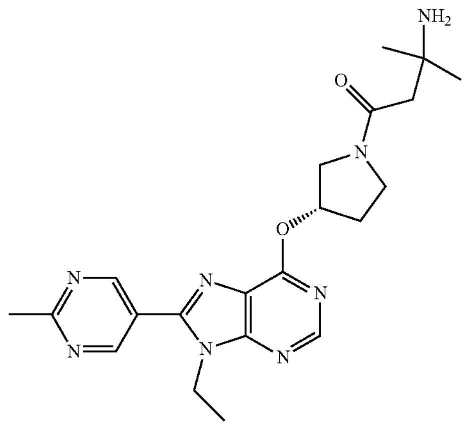 [SMILES: CCn1c(-c2cnc(C)nc2)nc2c(O[C@H]3CCN(C(=O)CC(C)(C)N)C3)ncnc21] | 4-[(3S)-3-{[9-ethyl-8-(2-methylpyrimidin-5-yl)-9H-purin-6-yl]oxy}pyrrolidin-1-yl]-2-methyl-4-oxobutan-2-amine | Calc'd 425, found 425 |
| 2-115 | 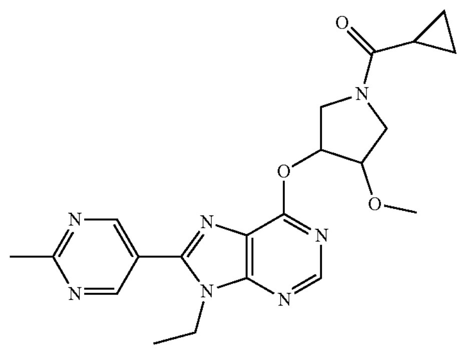 | [(3S,4S) or (3R,4R)]-trans-6-{[1-(cyclopropylcarbonyl)-4-triethoxypyrrolidin-3-yl]oxy}-9-ethyl-8-(2-methylpyrimidin-5-yl)-9H-purine | Calc'd 424, found 424 |
| 2-116 | 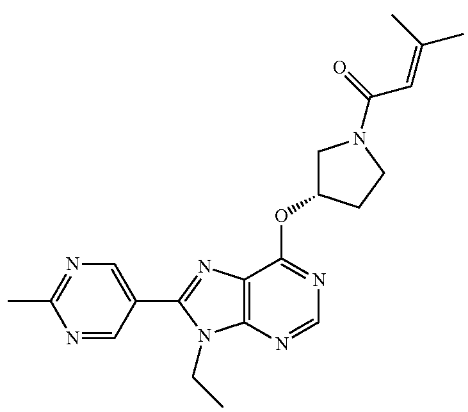 [SMILES: CCn1c(-c2cnc(C)nc2)nc2c(O[C@H]3CCN(C(=O)C=C(C)C)C3)ncnc21] | 9-ethyl-6-{[(3S)-1-(3-methylbut-2-enoyl)pyrrolidin-3-yl]oxy}-8-(2-methylpyrimidin-5-yl)-9H-purine | Calc'd 408, found 408 |
| 2-117 | 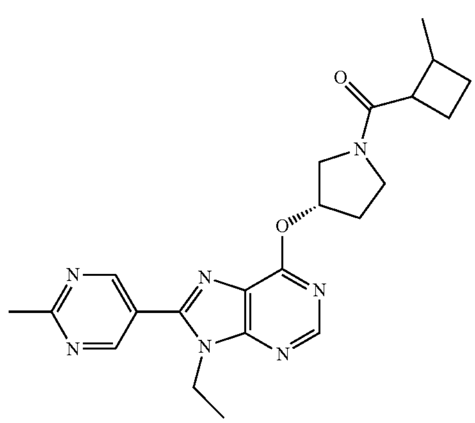 [SMILES: CCn1c(-c2cnc(C)nc2)nc2c(O[C@H]3CCN(C(=O)C4CCC4C)C3)ncnc21] | 9-ethyl-6-({(3S)-1-[([(1R,2S) or (1R,2R) or (1S,2R) or (1S,2S)]-methylcyclobutyl)carbonyl]pyrrolidin-3-yl}oxy)-8-(2-methylpyrimidin-5-yl)-9H-purine | Calc'd 422, found 422 |

TABLE 2-continued

| Compound | Structure | Compound Name | MS [M + H]+ |
|---|---|---|---|
| 2-118 | 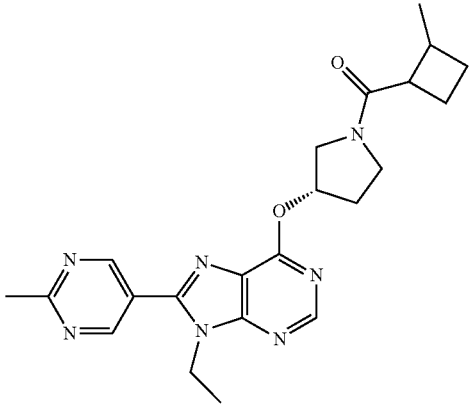 [SMILES: CCn1c(-c2cnc(C)nc2)nc2c(O[C@H]3CCN(C(=O)C4CCC4C)C3)ncnc21] | 9-ethyl-6-({(3S)-1-[[[(1R,2S) or (1R,2R) or (1S,2R) or (1S,2S)]-methylcyclobutyl)carbonyl]pyrrolidin-3-yl}oxy)-8-(2-methylpyrimidin-5-yl)-9H-purine | Calc'd 422, found 422 |
| 2-119 | 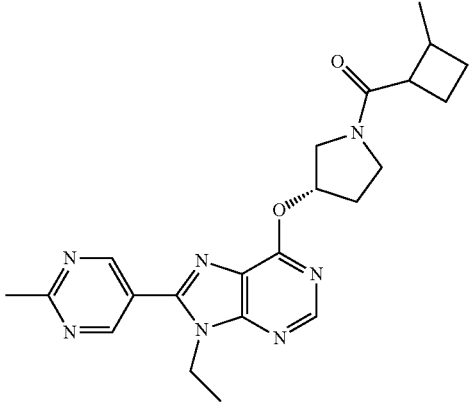 [SMILES: CCn1c(-c2cnc(C)nc2)nc2c(O[C@H]3CCN(C(=O)C4CCC4C)C3)ncnc21] | 9-ethyl-6-({(3S)-1-[[[(1R,2S) or (1R,2R) or (1S,2R) or (1S,2S)]-methyl]cyclobutyl)carbonyl]pyrrolidin-3-yl}oxy)-8-(2-methylpyrimidin-5-yl)-9H-purine | Calc'd 422, found 422 |
| 2-120 | 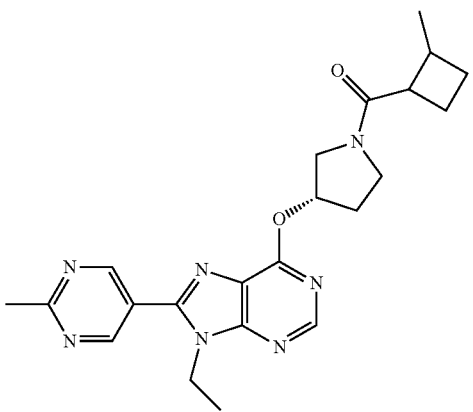 [SMILES: CCn1c(-c2cnc(C)nc2)nc2c(O[C@H]3CCN(C(=O)C4CCC4C)C3)ncnc21] | 9-ethyl-6-({(3S)-1-[[[(1R,2S) or (1R,2R) or (1S,2R) or (1S,2S)]-methylcyclobutyl)carbonyl]pyrrolidin-3-yl}oxy)-8-(2-methylpyrimidin-5-yl)-9H-purine | Calc'd 422, found 422 |

TABLE 2-continued

| Compound | Structure | Compound Name | MS [M + H]+ |
|---|---|---|---|
| 2-121 | 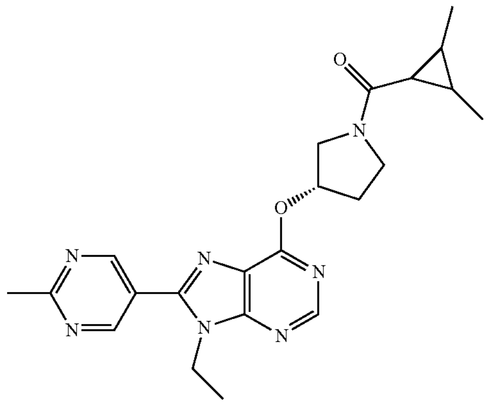 | 6-({(3S)-1-[(2S,3S)-(2,3-dimethylcyclopropyl)carbonyl]pyrrolidin-3-yl}oxy)-9-ethyl-8-(2-methylpyrimidin-5-yl)-9H-purine | Calc'd 422, found 422 |
| 2-122 | 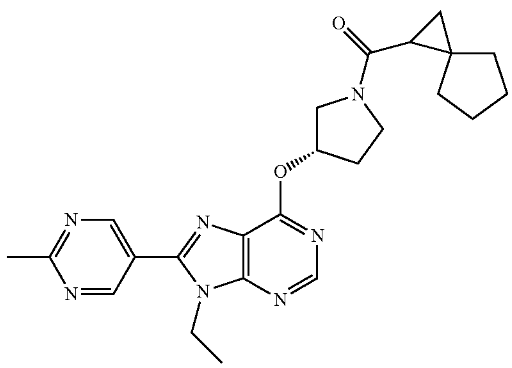 [SMILES: CCn1c(-c2cnc(C)nc2)nc2c(O[C@H]3CCN(C(=O)C4CC45CCCC5)C3)ncnc21] | 9-ethyl-8-(2-methylpyrimidin-5-yl)-6-{[(3S)-1-((R or S)-spiro[2.4]hept-1-ylcarbonyl)pyrrolidin-3-yl]oxy}-9H-purine | Calc'd 448, found 448 |
| 2-123 | 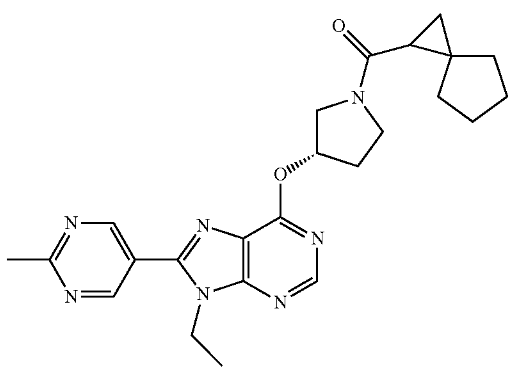 [SMILES: CCn1c(-c2cnc(C)nc2)nc2c(O[C@H]3CCN(C(=O)C4CC45CCCC5)C3)ncnc21] | 9-ethyl-8-(2-methylpyrimidin-5-yl)-6-{[(3S)-1-((R or S)-spiro[2.4]hept-1-ylcarbonyl)pyrrolidin-3-yl]oxy}-9H-purine | Calc'd 448, found 448 |
| 2-124 | 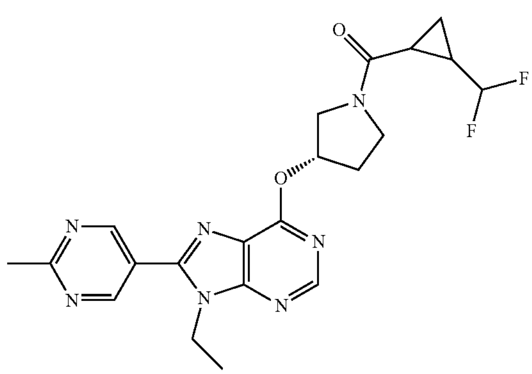 [SMILES: CCn1c(-c2cnc(C)nc2)nc2c(O[C@H]3CCN(C(=O)C4CC4C(F)F)C3)ncnc21] | 6-{[(3S)-{(1S,2S)- or (1R,2R)-[2-(difluoromethyl)cyclopropyl]carbonyl}pyrrolidin-3-yl]oxy}-9-ethyl-8-(2-methylpyrimidin-5-yl)-9H-purine | Calc'd 444, found 444 |

TABLE 2-continued

| Compound | Structure | Compound Name | MS [M + H]+ |
|---|---|---|---|
| 2-125 | 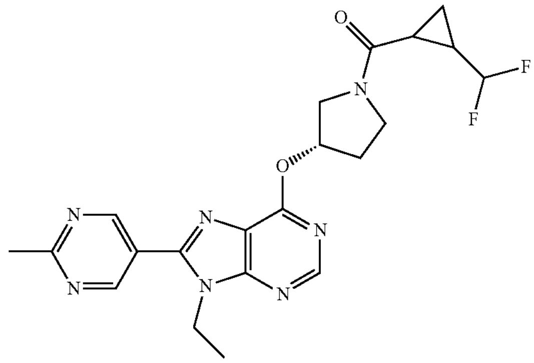 [SMILES: CCn1c(-c2cnc(C)nc2)nc2c(O[C@H]3CCN(C(=O)C4CC4C(F)F)C3)ncnc21] | 6-{[(3S)-1-{(1S,2S)- or (1R,2R)-[2-(difluoromethyl)cyclopropyl]carbonyl}pyrrolidin-3-yl]oxy}-9-ethyl-8-(2-methylpyrimidin-5-yl)-9H-purine | Calc'd 444, found 444 |
| 2-126 | 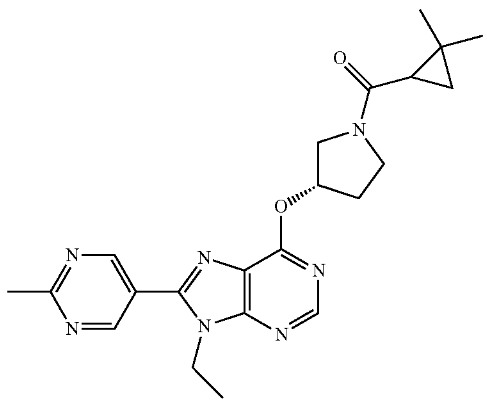 | 6-({(3S)-1-[S- or R-(2,2-dimethylcyclopropyl)carbonyl]pyrrolidin-3-yl}oxy)-9-ethyl-8-(2-methylpyrimidin-5-yl)-9H-purine | Calc'd 422, found 422 |
| 2-127 | 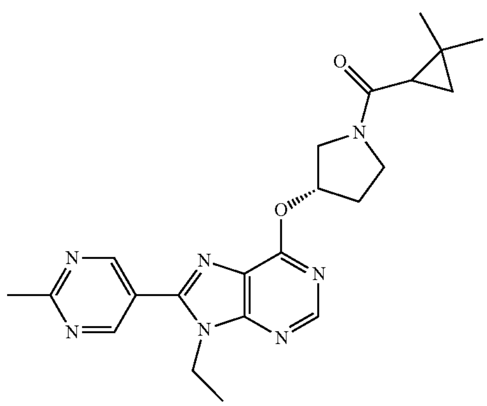 | 6-({(3S)-1-[S- or R-(2,2-dimethylcyclopropyl)carbonyl]pyrrolidin-3-yl}oxy)-9-ethyl-8-(2-methylpyrimidin-5-yl)-9H-purine | Calc'd 422, found 422 |
| 2-128 | 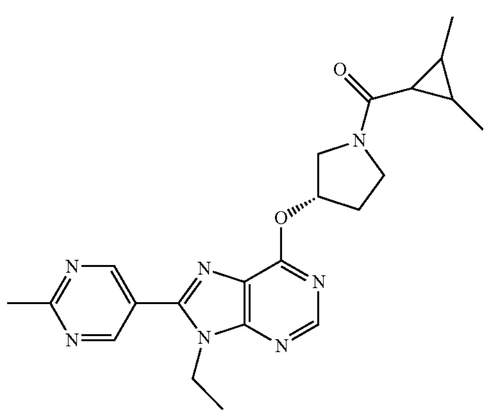 | 6-({(3S)-1-[((2S,3R)-(2,3-dimethylcyclopropyl)carbonyl]pyrrolidin-3-yl}oxy)-9-ethyl-8-(2-methylpyrimidin-5-yl)-9H-purine | Calc'd 422, found 422 |

TABLE 2-continued

| Compound | Structure | Compound Name | MS [M + H]+ |
|---|---|---|---|
| 2-129 | 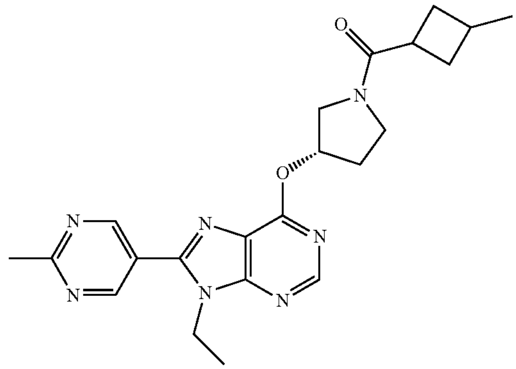 | 9-ethyl-6-({(3S)-1-[(3-methylcyclobutyl)carbonyl]pyrrolidin-3-yl}oxy)-8-(2-methylpyrimidin-5-yl)-9H-purine | Calc'd 422, found 422 |
| 2-130 | 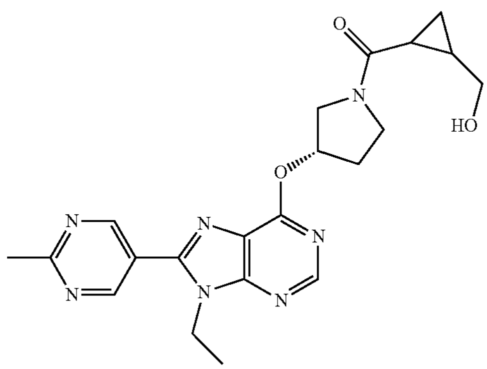 [SMILES: CCn1c(-c2cnc(C)nc2)nc2c(O[C@H]3CCN(C(=O)C4CC4CO)C3)ncnc21] | (1S,2S)- or (1R,2R)-{[(3S)-3-{[9-ethyl-8-(2-methylpyrimidin-5-yl)-9H-purin-6-yl]oxy}pyrrolidin-1-yl]carbonyl}cyclopropyl)methanol | Calc'd 424, found 424 |
| 2-131 | 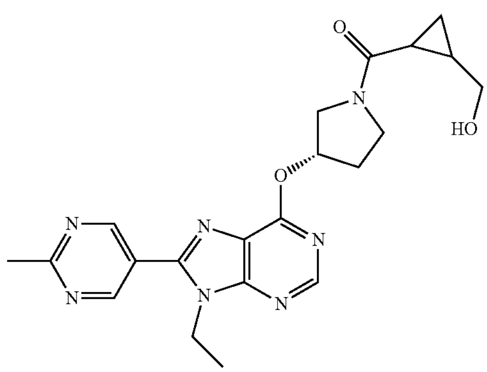 [SMILES: CCn1c(-c2cnc(C)nc2)nc2c(O[C@H]3CCN(C(=O)C4CC4CO)C3)ncnc21] | (1S,2S)- or (1R,2R)-{[(3S)-3-{[9-ethyl-8-(2-methylpyrimidin-5-yl)-9H-purin-6-yl]oxy}pyrrolidin-1-yl]carbonyl}cyclopropyl)methanol | Calc'd 424, found 424 |
| 2-132 | 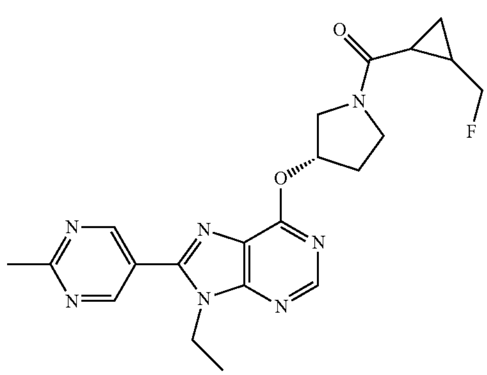 [SMILES: CCn1c(-c2cnc(C)nc2)nc2c(O[C@H]3CCN(C(=O)C4CC4CF)C3)ncnc21] | 9-ethyl-6-{[(3S)-1-{[(1S,2S)- or (1R,2R)-2-(fluoromethyl)cyclopropyl]carbonyl}pyrrolidin-3-yl]oxy}-8-(2-methylpyrimidin-5-yl)-9H-purine | Calc'd 426, found 426 |

TABLE 2-continued

| Compound | Structure | Compound Name | MS [M + H]+ |
|---|---|---|---|
| 2-133 | 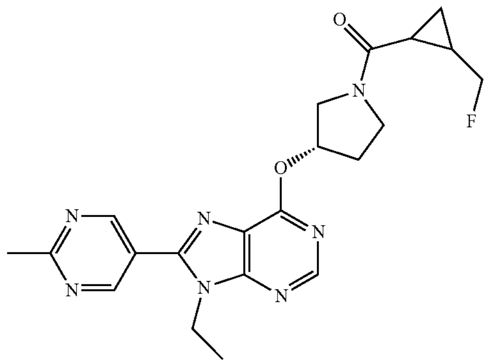 [SMILES: CCn1c(-c2cnc(C)nc2)nc2c(O[C@H]3CCN(C(=O)C4CC4CF)C3)ncnc21] | 9-ethyl-6-{[(3S)-1-{[(1S,2S)- or (1R,2R)-2-(fluoromethyl)cyclopropyl]carbonyl}pyrrolidin-3-yl]oxy}-8-(2-methylpyrimidin-5-yl)-9H-purine | Calc'd 426, found 426 |
| 2-134 | 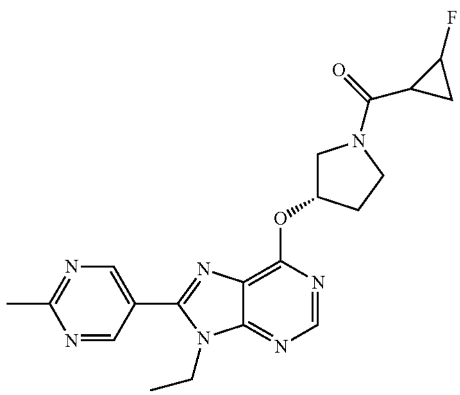 [SMILES: CCn1c(-c2cnc(C)nc2)nc2c(O[C@H]3CCN(C(=O)C4CC4F)C3)ncnc21] | 9-ethyl-6-(((3S)-1-[((1R,2R)- or (1S,2S)-2-fluorocyclopropyl)carbonyl]pyrrolidin-3-yl}oxy)-8-(2-methylpyrimidin-5-yl)-9H-purine | Calc'd 412, found 412 |
| 2-135 | 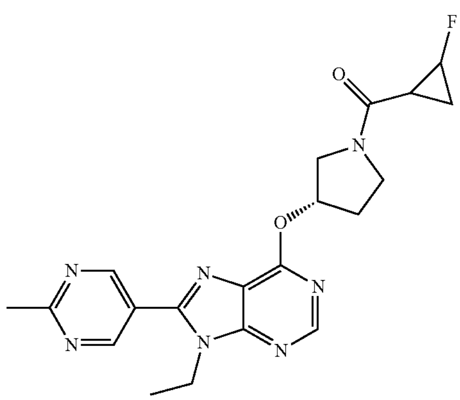 [SMILES: CCn1c(-c2cnc(C)nc2)nc2c(O[C@H]3CCN(C(=O)C4CC4F)C3)ncnc21] | 9-ethyl-6-({(3S)-1-[((1R,2R)- or (1S,2S)-2-fluorocyclopropyl)carbonyl]pyrrolidin-3-yl}oxy)-8-(2-methylpyrimidin-5-yl)-9H-purine | Calc'd 412, found 412 |
| 2-136 | 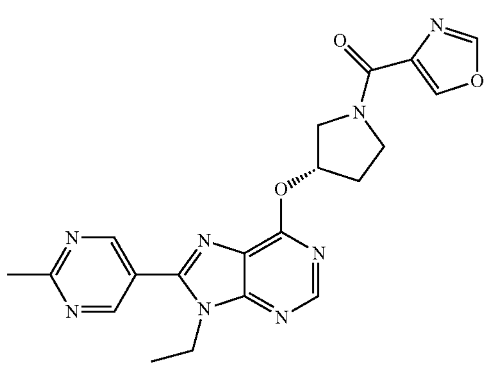 [SMILES: CCn1c(-c2cnc(C)nc2)nc2c(O[C@H]3CCN(C(=O)c4cocn4)C3)ncnc21] | 9-ethyl-8-(2-methylpyrimidin-5-yl)-6-{[(3S)-1-(1,3-oxazol-4-ylcarbonyl)pyrrolidin-3-yl]oxy}-9H-purine | Calc'd 421, found 421 |

TABLE 2-continued

| Compound | Structure | Compound Name | MS [M + H]+ |
|---|---|---|---|
| 2-137 | 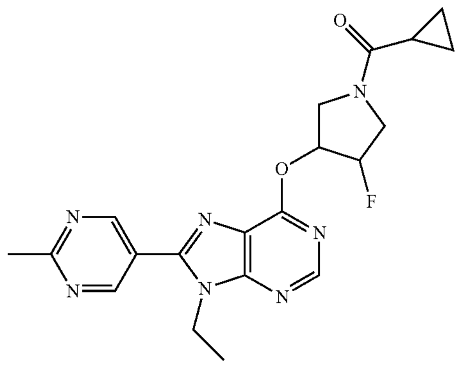 [SMILES: CCn1c(-c2cnc(C)nc2)nc2c(OC3CN(C(=O)C4CC4)CC3F)ncnc21] | 6-{[1-(cyclopropylcarbonyl)-(3S,4S)- or (3R,4R)-4-fluoropyrrolidin-3-yl]oxy}-9-ethyl-8-(2-methylpyrimidin-5-yl)-9H-purine | Calc'd 412, found 412 |
| 2-138 | 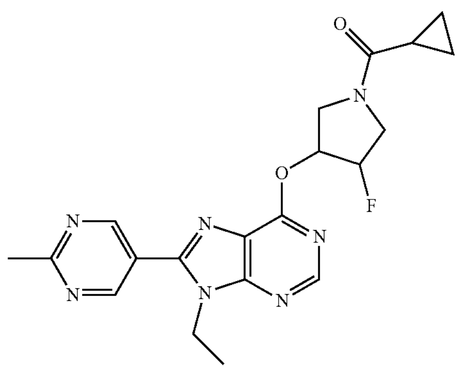 [SMILES: CCn1c(-c2cnc(C)nc2)nc2c(OC3CN(C(=O)C4CC4)CC3F)ncnc21] | 6-{[1-(cyclopropylcarbonyl)-(3S,4S)- or (3R,4R)-4-fluoropyrrolidin-3-yl]oxy}-9-ethyl-8-(2-methylpyrimidin-5-yl)-9H-purine | Calc'd 412, found 412 |
| 2-139 | 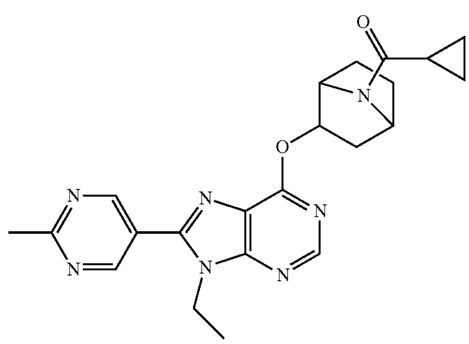 [SMILES: CCn1c(-c2cnc(C)nc2)nc2c(OC3CC4CCC3N4C(=O)C3CC3)ncnc21] | cyclopropyl([(1R,2R,4S) or (1S,2S,4R)]-2-((9-ethyl-8-(2-methylpyrimidin-5-yl)-9H-purin-6-yl)oxy)-7-azabicyclo[2.2.1]heptan-7-yl)methanone | Calc'd 420, found 420 |
| 2-140 | 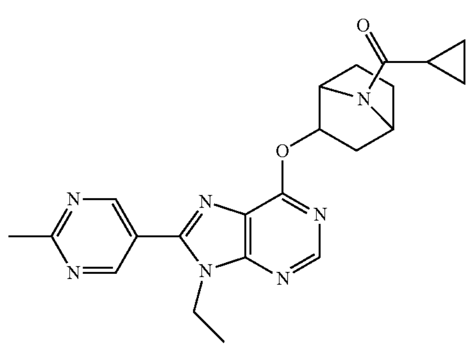 [SMILES: CCn1c(-c2cnc(C)nc2)nc2c(OC3CC4CCC3N4C(=O)C3CC3)ncnc21] | cyclopropyl([(1R,2R,4S) or (1S,2S,4R)]-2-((9-ethyl-8-(2-methylpyrimidin-5-yl)-9H-purin-6-yl)oxy)-7-azabicyclo[2.2.1]heptan-7-yl)methanone | Calc'd 420, found 420 |

TABLE 2-continued

| Compound | Structure | Compound Name | MS [M + H]+ |
|---|---|---|---|
| 2-141 | 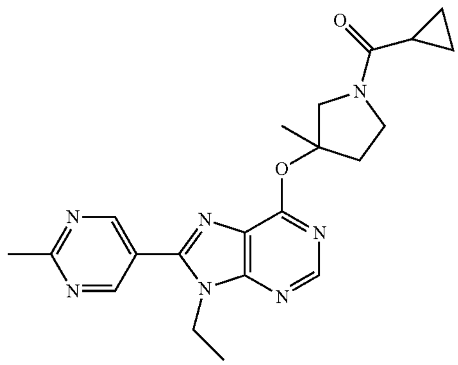 [SMILES: CCn1c(-c2cnc(C)nc2)nc2c(OC3(C)CCN(C(=O)C4CC4)C3)ncnc21] | 6-{[1-(cyclopropylcarbonyl)-3-methylpyrrolidin-3-yl]oxy}-9-ethyl-8-(2-methylpyrimidin-5-yl)-9H-purine | Calc'd 408, found 408 |
| 2-142 | 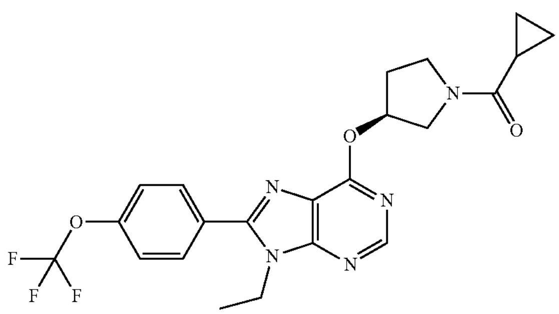 [SMILES: CCn1c(-c2ccc(OC(F)(F)F)cc2)nc2c(O[C@H]3CCN(C(=O)C4CC4)C3)ncnc21] | 6-{[(3S)-1-(cyclopropylcarbonyl)pyrrolidin-3-yl]oxy}-9-ethyl-8-[4-(trifluoromethoxy)phenyl]-9H-purine | Calc'd 462, found 462 |
| 2-143 | 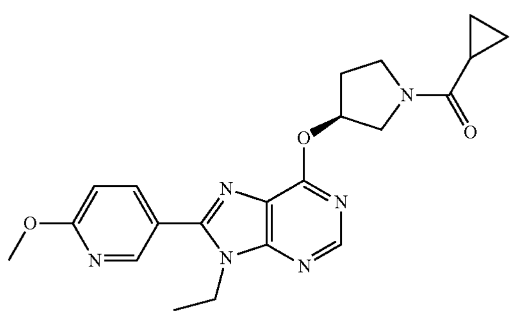 [SMILES: CCn1c(-c2ccc(OC)nc2)nc2c(O[C@H]3CCN(C(=O)C4CC4)C3)ncnc21] | 6-{[(3S)-1-(cyclopropylcarbonyl)pyrrolidin-3-yl]oxy}-9-ethyl-8-(6-methoxypyridin-3-yl)-9H-purine | Calc'd 409, found 409 |
| 2-144 | 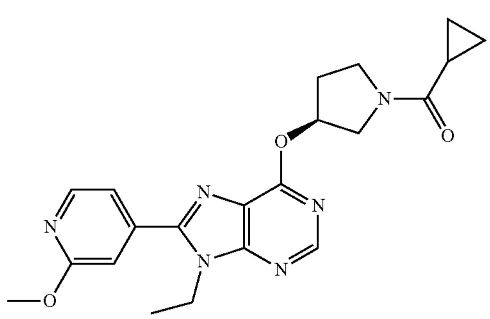 [SMILES: CCn1c(-c2ccnc(OC)c2)nc2c(O[C@H]3CCN(C(=O)C4CC4)C3)ncnc21] | 6-{[(3S)-1-(cyclopropylcarbonyl)pyrrolidin-3-yl]oxy}-9-ethyl-8-(2-methoxypyridin-4-yl)-9H-purine | Calc'd 409, found 409 |

TABLE 2-continued

| Compound | Structure | Compound Name | MS [M + H]+ |
|---|---|---|---|
| 2-145 | 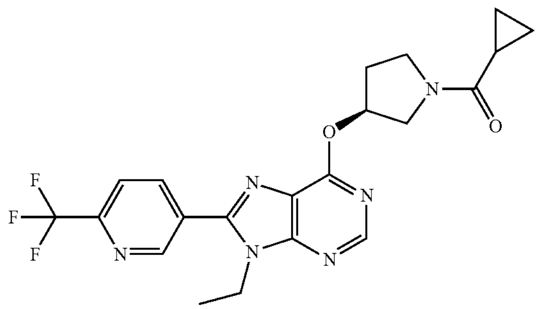 [SMILES: CCn1c(-c2ccc(C(F)(F)F)nc2)nc2c(O[C@H]3CCN(C(=O)C4CC4)C3)ncnc21] | 6-{[(3S)-1-(cyclopropylcarbonyl)pyrrolidin-3-yl]oxy}-9-ethyl-8-[6-(trifluoromethyl)pyridin-3-yl]-9H-purine | Calc'd 447, found 447 |
| 2-146 | 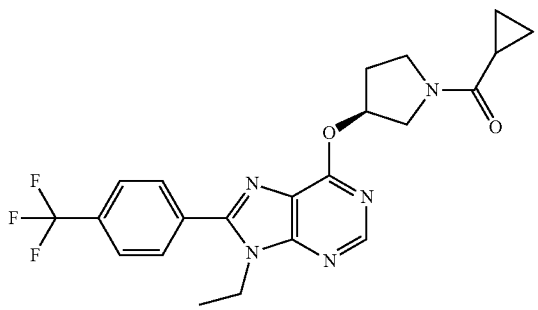 [SMILES: CCn1c(-c2ccc(C(F)(F)F)cc2)nc2c(O[C@H]3CCN(C(=O)C4CC4)C3)ncnc21] | 6-{[(3S)-1-(cyclopropylcarbonyl)pyrrolidin-3-yl]oxy}-9-ethyl-8-[4-(trifluoromethyl)phenyl]-9H-purine | Calc'd 446, found 446 |
| 2-147 | 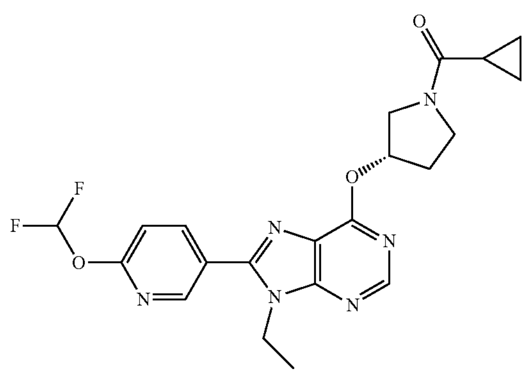 [SMILES: CCn1c(-c2ccc(OC(F)F)nc2)nc2c(O[C@H]3CCN(C(=O)C4CC4)C3)ncnc21] | 6-{[(3S)-1-(cyclopropylcarbonyl)pyrrolidin-3-yl]oxy}-8-[6-(difluoromethoxy)pyridin-3-yl]-9-ethyl-9H-purine | Calc'd 445, found 445 |

Compound Examples of Table 3

Example 8—Preparation of Compound 3-2

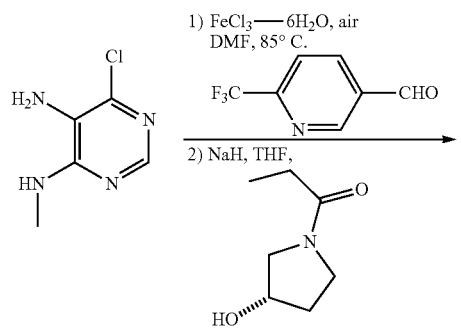

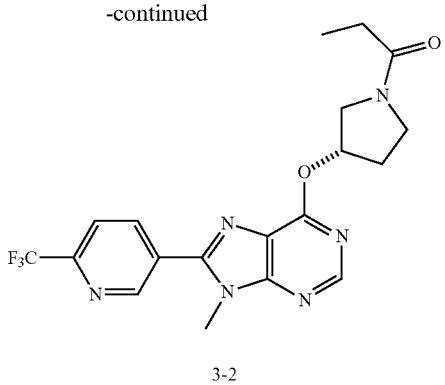

A solution of 6-chloro-$N^4$-methylpyrimidine-4,5-diamine (300 mg, 1.89 mmol) in 1 mL of DMF was treated with iron(III) trichloride hexahydrate (204 mg, 0.756 mmol) followed by 6-(trifluoromethyl)nicotinaldehyde (364 mg, 2.08 mmol). The reaction mixture was warmed to 85° C. with air bubbling through reaction mixture and stirred for 48 hours. After this time, cooled to room temperature and water (30 mL) was added, extracted with DCM (30 mL×2), dried with Na₂SO₄, filtered and concentrated in vacuo. The residue was purified by chromatography on SiO₂ (1:60 to 1:40 MeOH/DCM) to provide 6-chloro-9-methyl-8-(6-(trifluoromethyl)pyridin-3-yl)-9H-purine. MS (EI) Calc'd for $C_{12}H_8ClF_3N_5$ [M+H]⁺, 314. found, 314.

A solution of (S)-1-(3-hydroxypyrrolidin-1-yl)propan-1-one (10 mg, 0.070 mmol) in 1 mL of dry THF was treated at 0° C. with a 60% suspension of sodium hydride in mineral oil (3.0 mg, 0.77 mmol). The reaction was stirred at RT for 10 min, then treated with 6-chloro-9-methyl-8-(6-(trifluoromethyl)pyridin-3-yl)-9H-purine (20 mg, 0.064 mmol) and stirred overnight. The reaction was quenched with methanol (10 mL) and concentrated. The residue was purified by chromatography on SiO₂ (MeOH-DCM 1:30) to give 3-2. ¹H NMR (400 MHz, CDCl₃) δ 9.20 (s, 1H), 8.62-8.60 (m, 1H), 8.48-8.40 (m, 1H), 7.92-7.90 (m, 1H), 5.98 (s, 1H), 4.04-4.02 (m, 3H), 4.00-3.97 (m, 1H), 3.90-3.80 (m, 2H), 3.74-3.60 (m, 1H), 2.50-2.31 (m, 4H), 1.21-1.16 (m, 3H); MS (EI) Calc'd for $C_{19}H_{20}F_3N_6O_2$ [M+H]⁺, 421. found, 421.

Example 8A—Preparation of 3-31

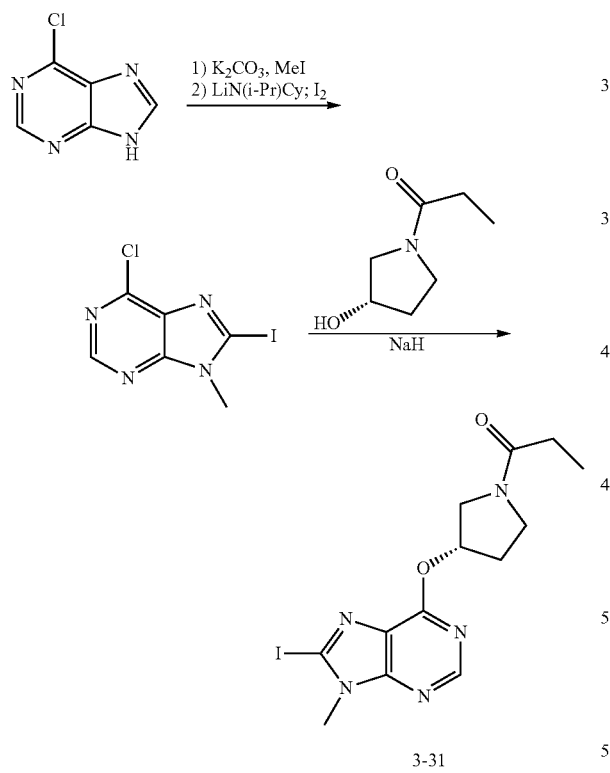

A mixture of 6-chloro-9H-purine (15.0 g, 97.4 mmol), DMSO (200 mL) and K₂CO₃ (20.2 g, 146 mmol) was treated dropwise with CH₃I (20.7 g, 146 mmol) and stirred at RT overnight. Water (500 mL) was added and the resulting mixture was extracted with DCM (2×500 mL). The combined organic extracts were washed with brine, dried with Na₂SO₄, filtered and concentrated. The crude material was purified by column chromatography (1:1 petroleum ether/ethyl acetate) to give 6-chloro-9-methyl-9H-purine. MS (EI) Calc'd for $C_6H_6ClN_4$ [M+H]⁺, 169. found, 169.

A mixture of N-isopropylcyclohexanamine (1.9 g, 13 mmol) in THF (30 mL) was cooled to −78° C., then n-BuLi (5.3 mL, 2.5 M, 13 mmol) was added dropwise and stirred at −78° C. for 10 min. Next, a solution of 6-chloro-9-methyl-9H-purine (1.5 g, 8.9 mmol) in THF (10 mL) was added dropwise and stirred for 15 min at −78° C. To this mixture, a solution of I2 (3.4 g, 13 mmol) in THF (10 mL) was added dropwise and the resulting mixture stirred for 1 h at −78° C. The reaction was quenched by the addition of aqueous NH₄Cl (20 mL). Aqueous Na₂SO₃ (10 mL) was added and the precipitate was filtered. The filtrate was dried with Na₂SO₄, filtered and concentrated to give 6-chloro-8-iodo-9-methyl-9H-purine. MS (EI) Calc'd for $C_6H_5ClIN_4$ [M+H]⁺, 295. found, 295.

A solution of (S)-1-(3-hydroxypyrrolidin-1-yl)propan-1-one (60 mg, 0.4 mmol) in THF (3 mL) was treated with a 60% suspension of NaH in mineral oil (24 mg, 1 mmol). The resulting mixture was stirred for 30 minutes at 0° C. and 6-chloro-8-iodo-9-methyl-9H-purine (100 mg, 0.34 mmol) was added. The reaction was stirred at room temperature for 15 h. The reaction mixture then was diluted with water (10 mL) and extracted with ethyl acetate (10 mL). The combined organic extracts was dried over Na₂SO₄, filtered and concentrated. The residue was purified by chromatography on SiO₂ (DCM/MeOH: 20/1) to afford 3-31. MS (EI) Calc'd for $C_{13}H_{17}IN_5O_2$ [M+H]⁺, 402. found, 402.

Example 8B—Preparation of 3-32

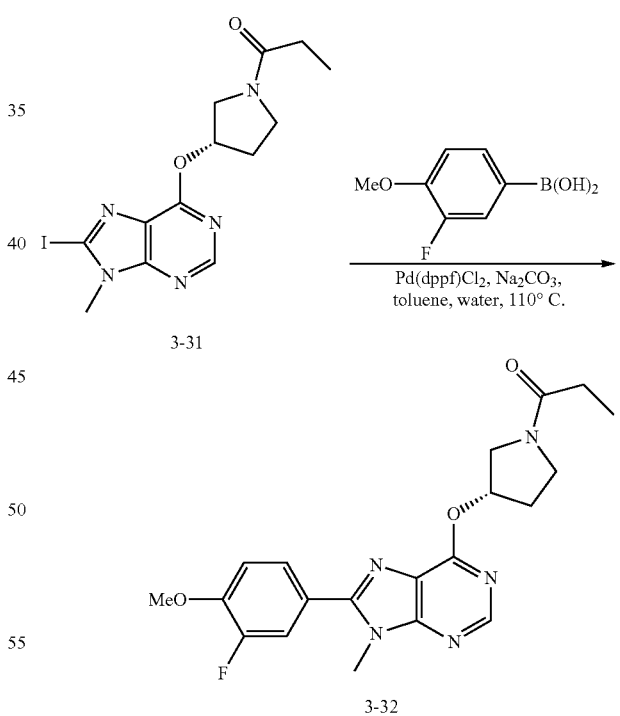

A solution of 3-31 (80 mg, 0.20 mmol) in toluene (2 mL) and water (0.2 mL) was treated with 3-fluoro-4-methoxyphenylboronic acid (68 mg, 0.4 mmol), Pd(dppf)Cl₂ (16 mg, 0.02 mmol), and Na₂CO₃ (64 mg, 0.6 mmol). The mixture was stirred at 110° C. for 15 h, diluted with water (10 mL) and extracted with ethyl acetate (10 mL). The combined organic extracts were dried over Na₂SO₄, filtered and concentrated. The residue was purified by reverse phase HPLC (MeCN/water with 10 mM aqueous NH₄HCO₃ modifier) to afford 3-32. ¹H NMR (400 MHz, DMSO-d₆) δ 8.56 (s, 1H), 7.68-7.65 (m, 2H), 7.36-7.32 (m, 1H), 6.04-6.00 (m, 1H), 4.02-3.92 (m, 6H), 3.89-3.76 (m, 4H), 2.48-2.35 (m, 4H), 1.17-1.11 (m, 3H). MS (EI) Calc'd for $C_{20}H_{23}FN_5O_3$ [M+H]⁺, 400. found, 400.

Example 8C

Preparation of 3-46 and 3-47

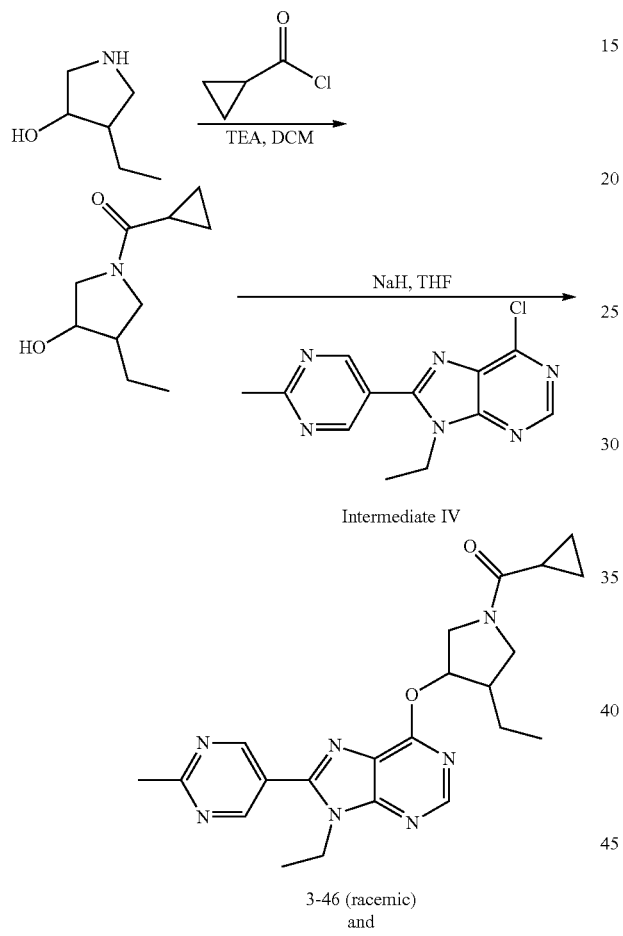

3-46 (racemic) and
3-47 (nonracemic)

A mixture of rac-trans-4-ethylpyrrolidin-3-ol (100 mg, 0.87 mmol) (prepared as described in *J. Med. Chem.*, 2010, 53, 6730-6746), cyclopropanecarbonyl chloride (94 mg, 0.90 mmol), triethylamine (0.14 mL, 1.50 mmol) in DCM (5 mL) was stirred at 25° C. for 3 h. After completion, water was added, and the mixture extracted with EtOAc (5 mL×3) and concentrated. The resulting solid was washed with ether (15 mL×3) to afford rac-cyclopropyl(3-ethyl-4-hydroxypyrrolidin-1-yl)methanone. MS (EI) Calc'd for $C_{10}H_{18}NO_2$ [M+H]⁺, 184. found, 184.

To a stirred solution of rac-trans-cyclopropyl(3-ethyl-4-hydroxypyrrolidin-1-yl)methanone (100 mg, 0.55 mmol) in THF (25 mL) was added sodium hydride (28 mg, 0.70 mmol, 60% on mineral) at 0° C., then Intermediate IV (137 mg, 0.50 mmol) was added. After addition, the resulting mixture was stirred at 25° C. for 15 h. The solvent was evaporated under reduced pressure, water (2 mL) was added and the mixture extracted with DCM (40 mL×2). The combined organic extracts were washed with water (5 mL), dried (Na₂SO₄), filtered and concentrated to give the crude product as a yellow oil. Chromatography on silica gel (DCM:MeOH=10:1) gave 3-46. MS (EI) Calc'd for $C_{22}H_{28}N_7O_2$ [M+H]⁺, 422. found, 422.

The racemic compound was separated by chiral column chromatography using the following conditions: AS-H (4.6× 250 mm, 5 um), CO₂ Flow Rate: 2.25, Co-Solvent: MeOH (0.5% DEA), Co-Solvent Flow Rate: 0.75, Column Temperature: 40.1° C.; to afford 3-47 eluting at 3.6 min and its enantiomer at 2.5 min. Data for 3-47: ¹H NMR (CD₃OD, 400 MHz) δ 9.11 (s, 2H), 8.59 (s, 1H), 5.78-5.71 (m, 1H), 4.45-4.43 (m, 2H), 4.30-4.46 (m, 4H), 2.81 (s, 3H), 2.58-2.45 (m, 1H), 1.86-1.66 (m, 2H), 1.47-1.43 (m, 4H), 1.12-1.05 (m, 3H), 0.88-0.93 (m, 4H). MS (EI) Calc'd for $C_{22}H_{28}N_7O_2$ [M+H]⁺, 422. found, 422.

Example 8D—Preparation of 3-48

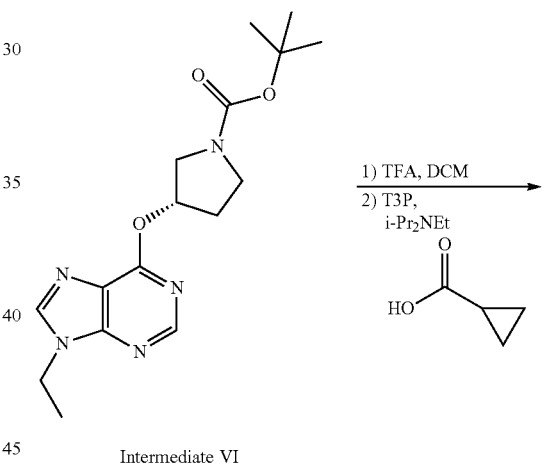

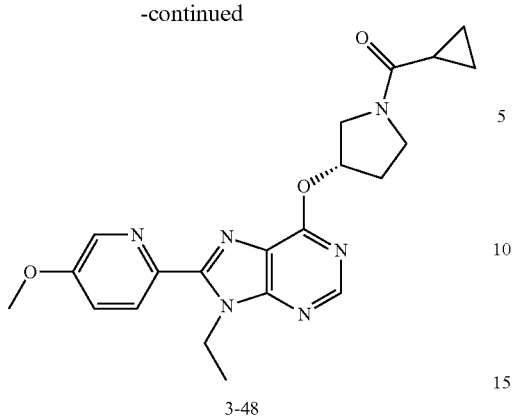

3-48

(S)-9-ethyl-6-(pyrrolidin-3-yloxy)-9H-purine was prepared from Intermediate VI in a fashion analogous to that described for Intermediate II (Example 2) using TFA in DCM. MS (EI) Calc'd for $C_{11}H_{16}N_5O$ [M+H]+ 234. found 234.

Next, conversion of (S)-9-ethyl-6-(pyrrolidin-3-yloxy)-9H-purine to (S)-cyclopropyl(3-((9-ethyl-9H-purin-6-yl)oxy)pyrrolidin-1-yl)methanone was completed in a fashion analogous to the preparation of 2-39 (Example 6) using propane phosphonic acid anhydride (T3P), i-$Pr_2NEt$ and cyclopropanecarbonic acid. MS (EI) Calc'd for $C_{15}H_{20}N_5O_2$ [M+H]$^+$, 302. found, 302.

Sealed tube #1 containing palladium (II) acetate (0.003 g, 0.013 mmol) and butyl-1-adamantylphosphine (0.0095 g, 0.027 mmol) in degassed dioxane (0.15 mL) was purged with argon and heated to 50° C. for 30 minutes. Sealed tube #2 was prepared by combining 2-chloro-5-methoxypyridine (0.019 g, 0.13 mmol), (S)-cyclopropyl(3-((9-ethyl-9H-purin-6-yl)oxy)pyrrolidin-1-yl)methanone (0.020 g, 0.13 mmol), pivalic acid (0.009 g, 0.086 mmol), and cesium fluoride (0.030 g, 0.20 mmol) in degassed dioxane (0.4 mL). The palladium acetate-butyl-1-adamantylphosphine mixture was then added to sealed tube #2, the reaction tube purged with argon, sealed and warmed to 110° C. for 12 hours. The reaction was cooled, diluted with DCM (4.0 mL) and water (4.0 mL) and was partioned using a separatory funnel. The organic extracts were collected and concentrated in vacuo and the residue was taken up in DMSO (1.0 mL), filtered and purified by reverse phase preparative HPLC to afford the TFA salt of 3-48. $^1$H NMR (600 MHz, DMSO-$d_6$) δ 8.53 (d, J=5.2 Hz, 1H); 8.44 (d, J=2.7 Hz, 1H); 8.29 (d, J=8.8 Hz, 1H); 7.56 (d, J=9.0 Hz, 1H); 5.93-5.81 (m, 1H); 4.77-4.76 (m, 2H); 4.06-3.78 (m, 5H); 3.66-3.65 (m, 1H); 3.60-3.36 (m, 1H); 2.39-2.21 (m, 2H); 1.82-1.72 (m, 1H); 1.33 (t, J=6.9 Hz, 3H); 0.74-0.68 (m, 4H). MS (EI) Calc'd for $C_{21}H_{24}N_6O_3$ [M+H]$^+$, 409. found, 409.

Example 4E—Preparation of 3-49

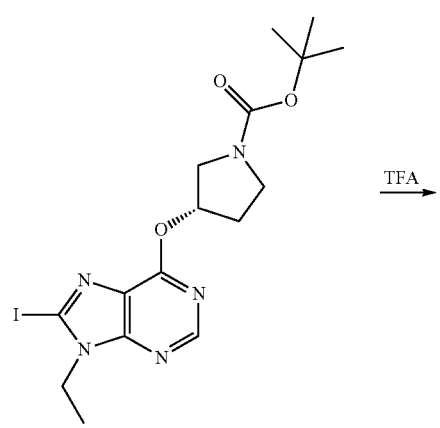

Intermediate VII

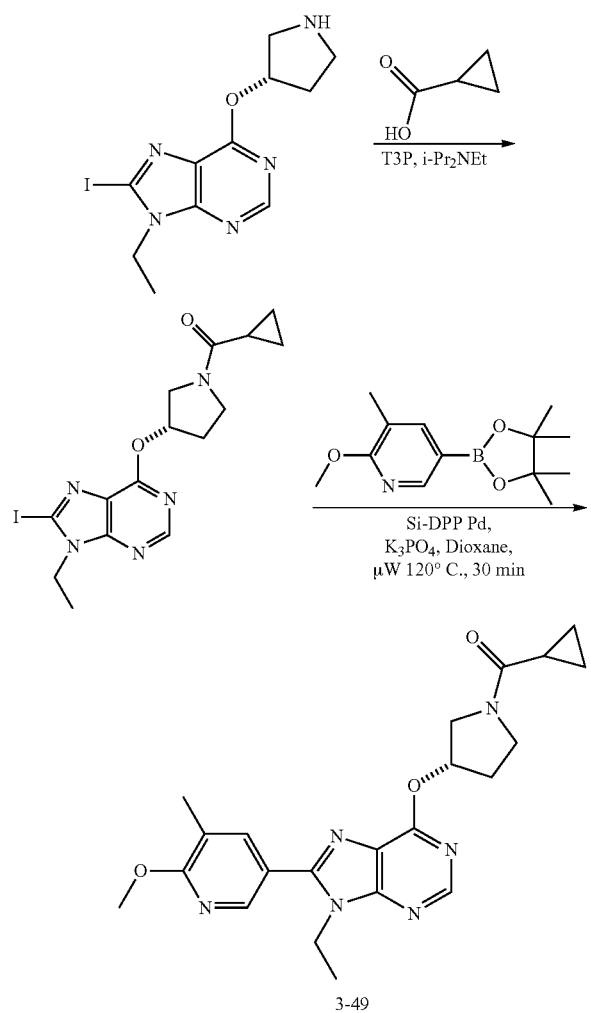

3-49

A solution of (S)-tert-butyl 3-((9-ethyl-8-iodo-9H-purin-6-yl)oxy)pyrrolidine-1-carboxylate; Intermediate VII (0.3 g, 0.65 mmol) in DCM (8.0 mL) was treated dropwise with TFA (2.0 mL, 26 mmol). The reaction was stirred at ambient temperature for 3 hours and concentrated to afford (S)-9- ethyl-8-iodo-6-(pyrrolidin-3-yloxy)-9H-purine, TFA as a crude oil. MS (EI) Calc'd for $C_{11}H_{15}N_5O$ [M+H]$^+$, 360. found, 360.

A reaction vessel was charged with (S)-9-ethyl-8-iodo-6-(pyrrolidin-3-yloxy)-9H-purine, TFA (0.030 g, 0.063 mmol) and cyclopropanecarboxylic acid (0.017 g, 0.20 mmol). Next were added DMF (1.1 mL) and DIEA (0.10 mL, 0.57 mmol) and the reaction was allowed to stir for 5 minutes. Next was added propylphosphonic anhydride (T3P) solution (0.10 mL, 50% w/w in DMF). The reaction vessel was capped and stirred at ambient temperature for 12 hours. The reaction was diluted with water (5.0 mL) and was extracted with DCM (2×5 mL) using a separatory funnel. The collected organic extracts were dried over magnesium sulfate, filtered, and concentrated to afford (S)-cyclopropyl(3-((9-ethyl-8-iodo-9H-purin-6-yl)oxy)pyrrolidin-1-yl)methanone which was used without further purification. MS (EI) Calc'd for $C_{15}H_{19}IN_5O_2$ [M+H]$^+$, 428. found, 428.

To a microwave vial were added (S)-cyclopropyl(3-((9-ethyl-8-iodo-9H-purin-6-yl)oxy)pyrrolidin-1-yl)methanone (0.027 g, 0.063 mmol), 3-methyl-2-methoxy-5-(4,4,5,5-tetramethyl-1,3,2-dioxaborolan-2-yl)pyridine (0.038 g, 0.15 mmol), potassium phosphate tribasic (0.053 g, 0.35 mmol), Si-DPP Pd (0.050 g, 0.013 mmol, 0.26 mmol/g; available from Silicycle Cat#R390-100), dioxane (1.0 mL), and water (0.30 mL). The reaction vial was sealed and irradiated in the microwave for 30 minutes at 120° C. The reaction was diluted with water (2.0 mL) and extracted with DCM (5.0 mL) using a phase separator SPE cartridge. The collected eluent was concentrated in vacuo, the residue was taken up in DMSO (1.0 mL), filtered and purified by reverse phase preparative HPLC to afford the TFA salt of 3-49. $^1$H NMR (500 MHz, DMSO-d$_6$) δ 8.56 (d, 1H), 8.44 (s, 1H), 8.01 (s, 1H), 5.89 (d, 1H), 4.37-4.33 (m, 2H), 3.97 (s, 3H), 3.88-3.74 (m, 1H), 3.66 (s, 1H), 3.60-3.38 (m, 1H), 2.43-2.14 (m, 3H), 2.24 (s, 3H), 1.83-1.73 (m, 1H), 1.31 (m, 3H), 0.75-0.66 (m, 4H). MS ESI calc'd. for $C_{22}H_{27}N_6O_3$ [M+H]$^+$ 423. found 423.

Example 8F—Preparation of 3-66 and 3-67

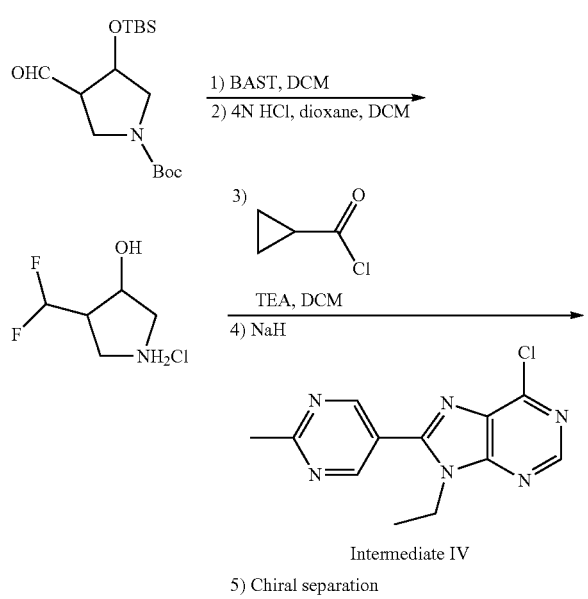

5) Chiral separation

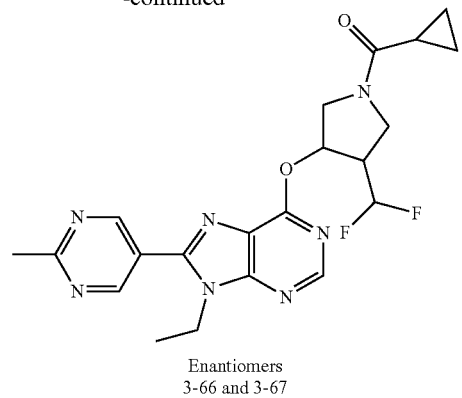

Enantiomers
3-66 and 3-67

Steps 1 and 2: Synthesis of 4-(difluoromethyl)pyrrolidin-3-ol, HCl salt

To a mixture of rac-trans-tert-butyl 3-((tert-butyldimethylsilyl)oxy)-4-formylpyrrolidine-1-carboxylate (procedure see *J. Am. Chem. Soc.* 2008, 130, 2166-2167; 100 mg, 0.30 mmol) in DCM (3 mL) was added BAST (0.17 mL, 0.90 mmol) and the reaction stirred for 15 h at RT. Next, aqueous sodium hydrogen carbonate (saturated, 3 mL) was added and the mixture was extracted with DCM (2×3 mL). The combined organic extracts were washed with brine (saturated, 3 mL), dried (Na$_2$SO$_4$), filtered and concentrated. The residue was purified by chromatography on silica gel (30:1 petroleum ether/ethyl acetate) to give rac-trans-tert-butyl 3-((tert-butyldimethylsilyl)oxy)-4-(difluoromethyl)pyrrolidine-1-carboxylates a colorless oil. MS (EI) Calc'd for $C_{16}H_{32}F_2NO_3Si$ [M+H]$^+$, 352. found, 352. The oil was dissolved in DCM (2 mL) was treated with 4M HCl/1,4-dioxane (0.5 mL, 2.0 mmol) at RT, and stirred for 15 h. The solvent was removed to give 4-(difluoromethyl)pyrrolidin-3-ol, HCl salt which was used in the next step without further purification. MS (EI) Calc'd for $C_5H_{10}F_2NO$ [M+H]$^+$, 138. found, 138.

Steps 3-5: Synthesis of 3-66 and 3-67

A mixture of 4-(difluoromethyl)pyrrolidin-3-ol hydrochloride (35 mg, 0.20 mmol) in DCM (3 mL) was cooled to −5° C. and triethylamine (61 mg, 0.60 mmol) was added, then cyclopropanecarbonyl chloride (25 mg, 0.24 mmol) was added and the mixture was stirred at 0° C. for 2 h. MeOH (0.1 mL) was added, the mixture was stirred for 30 min at RT, then concentrated. The residue was washed with ether (20 mL), filtered, and the filtrate was concentrated to give rac-trans-cyclopropyl(3-(difluoromethyl)-4-hydroxypyrrolidin-1-yl)methanone as a yellow oil which was used in the next step without further purification. MS (EI) Calc'd for $C_9H_{14}F_2NO_2$ [M+H]$^+$, 206. found, 206.

To a mixture of rac-trans-cyclopropyl(3-(difluoromethyl)-4-hydroxypyrrolidin-1-yl)methanone (40 mg, 0.20 mmol), 6-chloro-9-ethyl-8-(2-methylpyrimidin-5-yl)-9H-purine (54 mg, 0.20 mmol) in THF (3 mL) was added 60% NaH (12 mg, 0.30 mmol), then the resulting mixture was stirred for 15 h. EtOAc (10 mL) was added, the mixture was washed with water (5 mL), dried (Na$_2$SO$_4$) and concentrated. The residue was purified by chromatography on SiO$_2$ (10:1 DCM/MeOH) to give racemic product. MS (EI) Calc'd for $C_{21}H_{24}F_2N_7O_2$ [M+H]$^+$, 444. found, 444. The material was resolved by chiral chromatography. Conditions: Column OJ-H 4.6×250 mm 5 um, $CO_2$ Flow Rate 2.55, Co-Solvent MeOH:ACN=1:1 (0.1% DEA), Co-Solvent Flow Rate 0.45, Column Temperature 40° C. Compound 3-66 eluted at 5.5 min, while compound 3-67 eluted at 7.9 min.

Characterization data for 3-66: $^1$H NMR (400 MHz, $CD_3OD$) δ 9.14 (s, 2H), 8.63-8.64 (m, 1H), 6.42-6.05 (m, 2H), 4.46 (q, J=7.2 Hz, 2H), 4.34-3.86 (m, 4H), 3.31-3.10 (m, 1H), 2.84 (s, 3H), 1.93-1.74 (m, 1H), 1.48 (t, J=7.2 Hz, 3H), 0.93-0.86 (m, 4H). MS (EI) Calc'd for $C_{21}H_{24}F_2N_7O_2$ [M+H]$^+$, 444. found, 444.

Characterization data for 3-67: $^1$H NMR (400 MHz, $CD_3OD$) δ 9.14 (s, 2H), 8.64-8.63 (m, 1H), 6.42-6.05 (m, 2H), 4.46 (q, J=7.2 Hz, 2H), 4.34-3.86 (m, 4H), 3.31-3.10 (m, 1H), 2.84 (s, 3H), 1.93-1.74 (m, 1H), 1.48 (t, J=7.2 Hz, 3H), 0.93-0.86 (m, 4H). MS (EI) Calc'd for $C_{21}H_{24}F_2N_7O_2$ [M+H]$^+$, 444. found, 444.

Example 8G—Preparation of 3-68 and 3-69

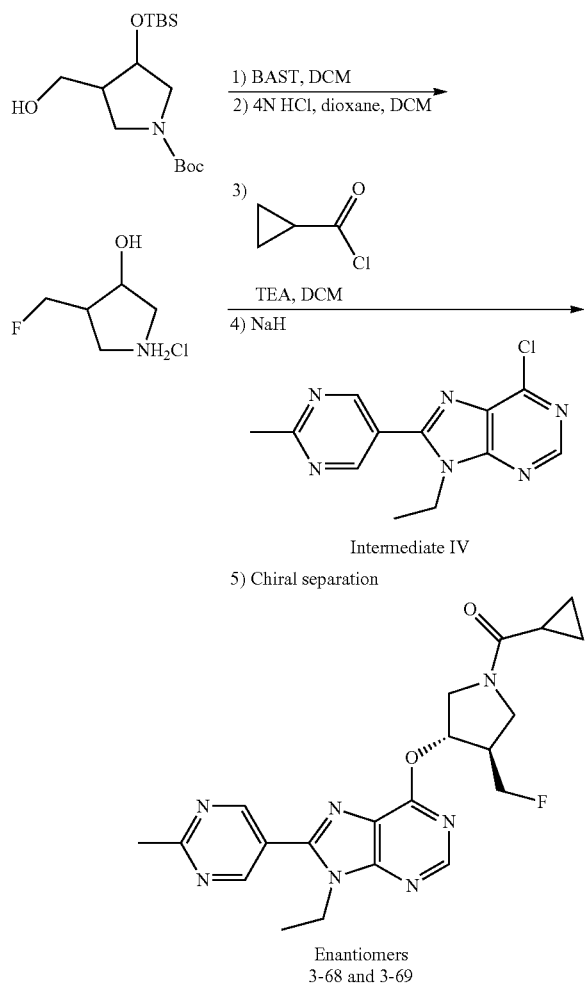

Steps 1 and 2: Preparation of 4-(fluoromethyl)pyrrolidin-3-ol, HCl

To a mixture of rac-trans-tert-butyl 3-((tert-butyldimethylsilyl)oxy)-4-(hydroxymethyl)pyrrolidine-1-carboxylate (50 mg, 0.15 mmol; for a synthesis of this material see *J. Am. Chem. Soc.*, 2008, 130, 2166-2167) in DCM (2 mL) was added BAST (0.056 mL, 0.30 mmol) and the mixture stirred for 15 h at RT. Next, the mixture was washed with saturated aq. $NaHCO_3$ (1 mL), dried ($Na_2SO_4$), filtered and concentrated. Finally, the residue was purified by chromatography on silica gel (10:1 petroleum ether/ethyl acetate) to give a colorless oil. The oil was then dissolved in DCM (3 mL), treated with 4 N HCl/1,4-dioxane (0.5 mL, 2.0 mmol) and stirred for 15 h at RT. The mixture was concentrated to give the title product; used in the next step without further purification. MS (EI) Calc'd for $C_5H_{11}FNO$ [M+H]$^+$, 120. found, 120.

Steps 3 to 5: Preparation of 3-68 and 3-69

A mixture of rac-trans-4-(fluoromethyl)pyrrolidin-3-ol hydrochloride (8 mg, 0.05 mmol), DCM (2 mL) and triethylamine (13 mg, 0.13 mmol) was cooled to 0° C. and cyclopropanecarbonyl chloride (6 mg, 0.06 mmol) was added. The mixture was stirred at 0° C. for 2 h, MeOH (0.1 mL) was added and warmed to RT. The reaction mixture was stirred for 10 min and concentrated to dryness. MS (EI) Calc'd for $C_9H_{15}FNO_2$ [M+H]$^+$, 188. found, 188. To a mixture of rac-trans-cyclopropyl(3-(fluoromethyl)-4-hydroxypyrrolidin-1-yl)methanone (8 mg, 0.04 mmol), 6-chloro-9-ethyl-8-(2-methylpyrimidin-5-yl)-9H-purine (12 mg, 0.044 mmol) in THF (2 mL) was added a 60% suspension of NaH in mineral oil (3 mg, 0.08 mmol) and the resulting mixture stirred for 15 h at RT. EtOAc (10 mL) was added, the mixture was washed with water (5 mL), dried ($Na_2SO_4$) and concentrated. The residue was purified by chromatogaphy on $SiO_2$ (10:1 DCM/MeOH) to give a mixture of 3-68 and 3-69. MS (EI) Calc'd for $C_{21}H_{25}FN_7O_2$ [M+H]$^+$, 426. found, 426.

The enantiomers were separated by chiral column chromatography using the following conditions: RegisCell 4.6× 250 mm 5 um, $CO_2$ Flow Rate 2.55, Co-Solvent 1:1 MeOH/ MeCN (with 0.1% DEA), Co-Solvent Flow Rate 0.45, Column Temperature 40° C. Compound 3-68 eluted at 5.3 min while compound 3-69 eluted at 6.7 min.

Characterization data for 3-68: $^1$H NMR (400 MHz, $CD_3OD$) δ 9.15 (s, 2H), 8.63-8.62 (m, 1H), 5.96-5.88 (m, 1H), 4.81-3.59 (m, 8H), 3.34-2.90 (m, 1H), 2.84 (s, 3H), 1.90-1.72 (m, 1H), 1.48 (t, J=7.2 Hz, 3H), 0.93-0.63 (m, 4H). MS (EI) Calc'd for $C_{21}H_{25}FN_7O_2$ [M+H]$^+$, 426. found, 426.

Characterization data for 3-69: $^1$H NMR (400 MHz, $CD_3OD$) δ 9.15 (s, 2H), 8.63-8.62 (m, 1H), 5.96-5.88 (m, 1H), 4.81-3.59 (m, 8H), 3.34-2.90 (m, 1H), 2.84 (s, 3H), 1.90-1.72 (m, 1H), 1.48 (t, J=7.2 Hz, 3H), 0.93-0.63 (m, 4H). MS (EI) Calc'd for $C_{21}H_{25}FN_7O_2$ [M+H]$^+$, 426. found, 426.

Compounds 3-1, 3-3 to 3-30 and 3-61 were prepared in an analogous fashion as described for Example 8 from a chlorodiaminopyrimidine and the corresponding aldehyde.

Compounds 3-33 to 3-45 were prepared in an analogous fashion as described for Example 8B from 3-31 and the corresponding boronic acid or boronic ester.

Compounds 3-50 to 3-60 were prepared in an analogous fashion as described for Example 8E (compound 3-49) using the appropriate boronic ester and carboxylic acid.

Compound 3-62 was prepared in an analogous fashion as described for Example 8C using 1-benzyl-4,4-dimethylpyrrolidin-3-ol as described in WO 2012/125893; then resolved using chiral column chromatography. Conditions: Column AS-H (4.6×250 mm, 5 um), $CO_2$ Flow Rate 2.25, Co- Solvent MeOH, Co-Solvent Flow Rate 0.75, Column Temperature 39.7° C. Compound 3-62 eluted at 2.2 min while its enantiomer eluted at 1.7 min.

Compounds 3-63 and 3-64 were prepared in an analogous fashion as described for Example 8C using 5-azaspiro[2.4]heptan-7-ol as described in WO 2009/61879; then resolved using chiral column chromatography. Conditions: Column AS-H (4.6×250 mm, 5 um), $CO_2$ Flow Rate 2.25, Co-Solvent MeOH (containing 0.5% DEA), Co-Solvent Flow Rate 0.75, Column Temperature 40.1° C. Compound 3-63 eluted at 1.9 min while 3-64 eluted at 2.7 min.

Compound 3-65 was prepared in an analogous fashion as described for Example 8C using commercially available trans-4-methylpyrrolidin-3-ol; then resolved using chiral column chromatography. Conditions: Column AS-H (4.6× 250 mm, 5 um), $CO_2$ Flow Rate 2.25, Co-Solvent MeOH (containing 0.5% DEA), Co-Solvent Flow Rate 0.75, Column Temperature 40.1° C. Compound 3-65 eluted at 3.6 min while its enantiomer eluted at 3.0 min.

TABLE 3

| Compound | Structure | Compound Name | MS [M + H]+ |
|---|---|---|---|
| 3-1 | 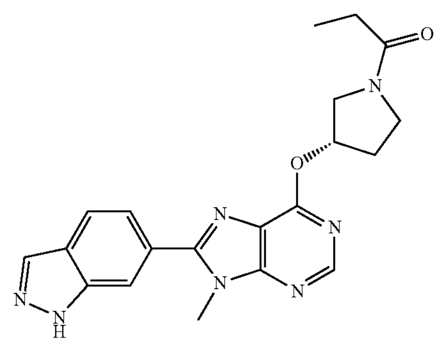 [SMILES: CCC(=O)N1CC[C@H](Oc2ncnc3c2nc(-c2ccc4cn[nH]c4c2)n3C)C1] | (S)-1-(3-((8-(1H-indazol-6-yl)-9-methyl-9H-purin-6-yl)oxy)pyrrolidin-1-yl)propan-1-one | Calc'd 392, found 392 |
| 3-2 | 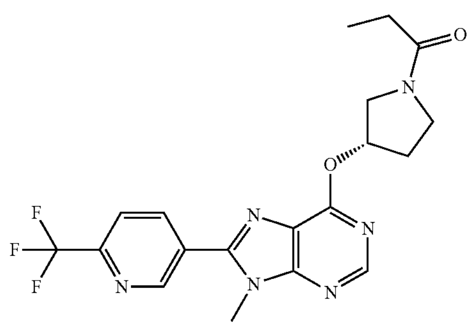 [SMILES: CCC(=O)N1CC[C@H](Oc2ncnc3c2nc(-c2ccc(C(F)(F)F)nc2)n3C)C1] | (S)-1-(3-((9-methyl-8-(6-(trifluoromethyl)pyridin-3-yl)-9H-purin-6-yl)oxy)pyrrolidin-1-yl)propan-1-one | Calc'd 421, found 421 |
| 3-3 | 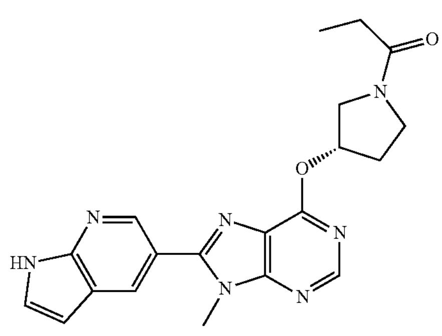 [SMILES: CCC(=O)N1CC[C@H](Oc2ncnc3c2nc(-c2cnc4[nH]ccc4c2)n3C)C1] | (S)-1-(3-((9-methyl-8-(1H-pyrrolo[2,3-b]pyridin-5-yl)-9H-purin-6-yl)oxy)pyrrolidin-1-yl)propan-1-one | Calc'd 392, found 392 |

TABLE 3-continued

| Compound | Structure | Compound Name | MS [M + H]+ |
|---|---|---|---|
| 3-4 | 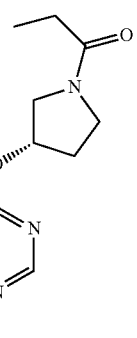 | (S)-1-(3-((8-(1H-indol-6-yl)-9-methyl-9H-purin-6-yl)oxy)pyrrolidin-1-yl)propan-1-one | Calc'd 391, found 391 |
| 3-5 | 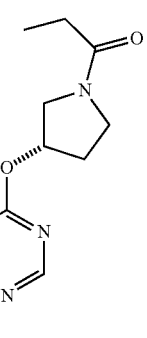 | (S)-1-(3-((8-(1H-indazol-5-yl)-9-methyl-9H-purin-6-yl)oxy)pyrrolidin-1-yl)propan-1-one | Calc'd 392, found 392 |
| 3-6 | 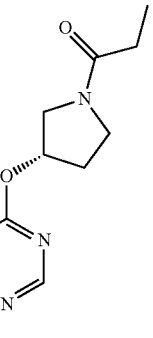 | (S)-1-(3-((8-(6-methoxy-5-(trifluoromethyl)pyridin-3-yl)-9-methyl-9H-purin-6-yl)oxy)pyrrolidin-1-yl)propan-1-one | Calc'd 451, found 451 |
| 3-7 | 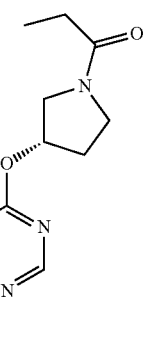 | (S)-1-(3-((8-(1H-indol-5-yl)-9-methyl-9H-purin-6-yl)oxy)pyrrolidin-1-yl)propan-1-one | Calc'd 391, found 391 |

TABLE 3-continued

| Compound | Structure | Compound Name | MS [M + H]⁺ |
|---|---|---|---|
| 3-8 | 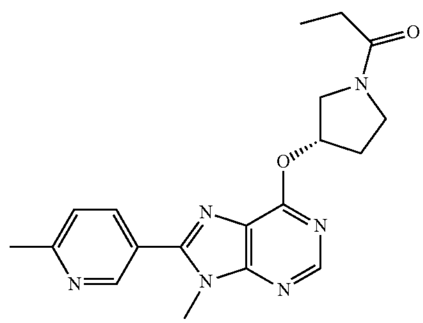 [SMILES: CCC(=O)N1CC[C@H](Oc2ncnc3c2nc(-c2ccc(C)nc2)n3C)C1] | (S)-1-(3-((9-methyl-8-(6-methylpyridin-3-yl)-9H-purin-6-yl)oxy)pyrrolidin-1-yl)propan-1-one | Calc'd 367, found 367 |
| 3-9 | 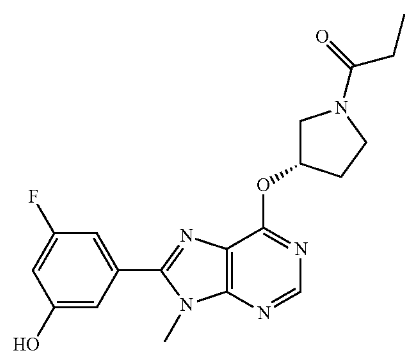 [SMILES: CCC(=O)N1CC[C@H](Oc2ncnc3c2nc(-c2cc(O)cc(F)c2)n3C)C1] | 3-fluoro-5-(9-methyl-6-{[(3S)-1-propanoylpyrrolidin-3-yl]oxy}-9H-purin-8-yl)phenol | Calc'd 386, found 386 |
| 3-10 | 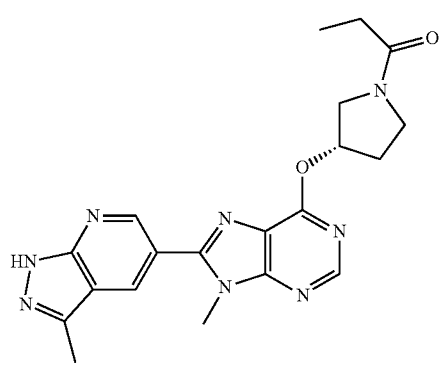 [SMILES: CCC(=O)N1CC[C@H](Oc2ncnc3c2nc(-c2cnc4[nH]nc(C)c4c2)n3C)C1] | 9-methyl-8-(3-methyl-1H-pyrazolo[3,4-b]pyridin-5-yl)-6-{[(3S)-1-propanoylpyrrolidin-3-yl]oxy}-9H-purine | Calc'd 407, found 407 |
| 3-11 | 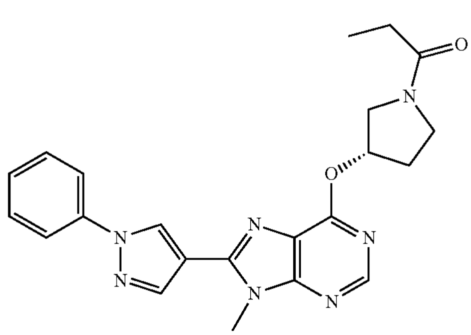 [SMILES: CCC(=O)N1CC[C@H](Oc2ncnc3c2nc(-c2cnn(-c4ccccc4)c2)n3C)C1] | 9-methyl-8-(1-phenyl-1H-pyrazol-4-yl)-6-{[(3S)-1-propanoylpyrrolidin-3-yl]oxy}-9H-purine | Calc'd 418, found 418 |

TABLE 3-continued

| Compound | Structure | Compound Name | MS [M + H]+ |
|---|---|---|---|
| 3-12 | 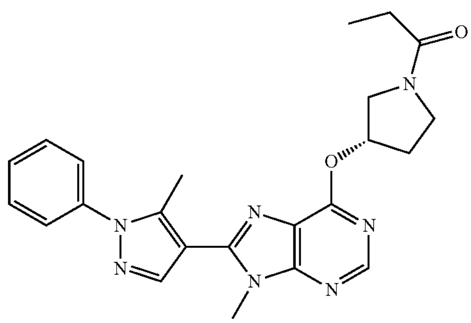 [SMILES: CCC(=O)N1CC[C@H](Oc2ncnc3c2nc(-c2cnn(-c4ccccc4)c2C)n3C)C1] | 9-methyl-8-(5-methyl-1-phenyl-1H-pyrazol-4-yl)-6-{[(3S)-1-propanoylpyrrolidin-3-yl]oxy}-9H-purine | Calc'd 432, found 432 |
| 3-13 | 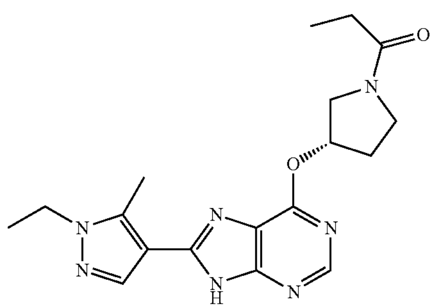 [SMILES: CCC(=O)N1CC[C@H](Oc2ncnc3[nH]c(-c4cnn(CC)c4C)nc23)C1] | 8-(1-ethyl-5-methyl-1H-pyrazol-4-yl)-6-{[(3S)-1-propanoylpyrrolidin-3-yl]oxy}-9H-purine | Calc'd 370, found 370 |
| 3-14 | 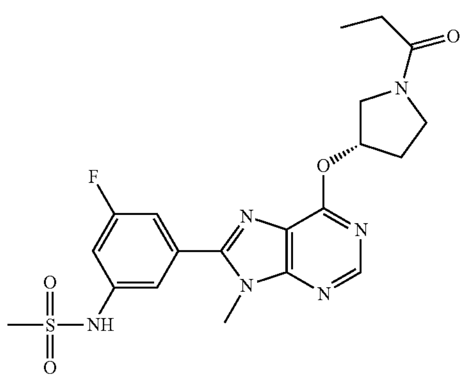 [SMILES: CCC(=O)N1CC[C@H](Oc2ncnc3c2nc(-c2cc(F)cc(NS(C)(=O)=O)c2)n3C)C1] | N-[3-fluoro-5-(9-methyl-6-{[(3S)-1-propanoylpyrrolidin-3-yl]oxy}-9H-purin-8-yl)phenyl]methanesulfonamide | Calc'd 463, found 463 |
| 3-15 | 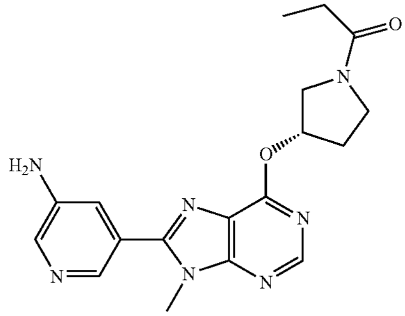 [SMILES: CCC(=O)N1CC[C@H](Oc2ncnc3c2nc(-c2cncc(N)c2)n3C)C1] | 5-(9-methyl-5-{[(3S)-1-propanoylpyrrolidin-3-yl]oxy}-9H-purin-8-yl)pyridin-3-amine | Calc'd 368, found 368 |

TABLE 3-continued

| Compound | Structure | Compound Name | MS [M + H]+ |
|---|---|---|---|
| 3-16 | 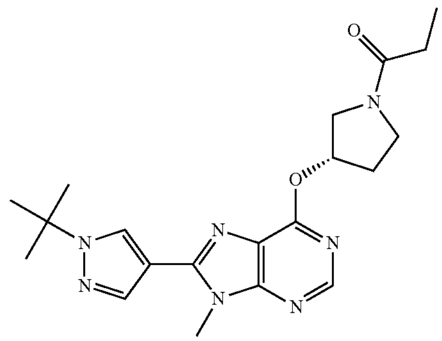 [SMILES: CCC(=O)N1CC[C@H](Oc2ncnc3c2nc(-c2cnn(C(C)(C)C)c2)n3C)C1] | 8-(1-tert-butyl-1H-pyrazol-4-yl)-9-methyl-6-{[(3S)-1-propanoylpyrrolidin-3-yl]oxy}-9H-purine | Calc'd 398, found 398 |
| 3-17 | 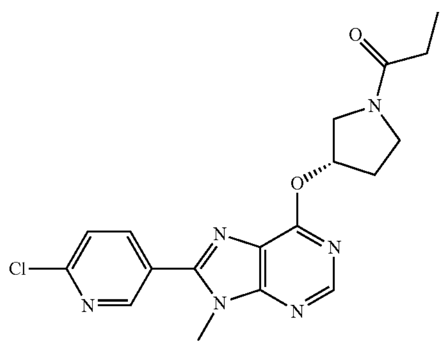 [SMILES: CCC(=O)N1CC[C@H](Oc2ncnc3c2nc(-c2ccc(Cl)nc2)n3C)C1] | 8-(6-chloropyridin-3-yl)-9-methyl-6-{[(3S)-1-propanoylpyrrolidin-3-yl]oxy}-9H-purine | Calc'd 387, found 387 |
| 3-18 | 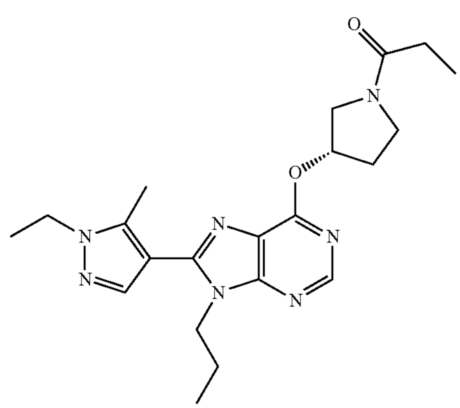 [SMILES: CCCn1c(-c2cnn(CC)c2C)nc2c(O[C@H]3CCN(C(=O)CC)C3)ncnc21] | 8-(1-ethyl-5-methyl-1H-pyrazol-4-yl)-6-{[(3S)-1-propanoylpyrrolidin-3-yl]oxy}-9-propyl-9H-purine | Calc'd 412, found 412 |
| 3-19 | 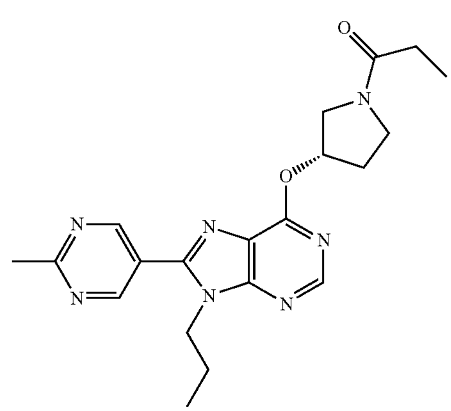 [SMILES: CCCn1c(-c2cnc(C)nc2)nc2c(O[C@H]3CCN(C(=O)CC)C3)ncnc21] | 8-(2-methylpyrimidin-5-yl)-6-{[(3S)-1-propanoylpyrrolidin-3-yl]oxy}-9-propyl-9H-purine | Calc'd 396, found 396 |

TABLE 3-continued

| Compound | Structure | Compound Name | MS [M + H]+ |
|---|---|---|---|
| 3-20 | 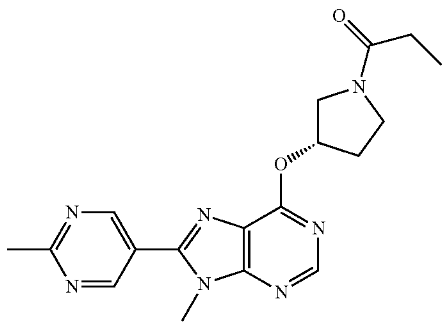 [SMILES: CCC(=O)N1CC[C@H](Oc2ncnc3c2nc(-c2cnc(C)nc2)n3C)C1] | 9-methyl-8-(2-methylpyrimidin-5-yl)-6-{[(3S)-1-propanoylpyrrolidin-3-yl]oxy}-9H-purine | Calc'd 368, found 368 |
| 3-21 | 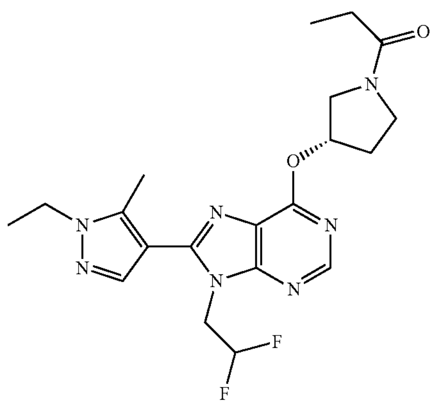 [SMILES: CCC(=O)N1CC[C@H](Oc2ncnc3c2nc(-c2cnn(CC)c2C)n3CC(F)F)C1] | 9-(2,2-difluoroethyl)-8-(1-ethyl-5-methyl-1H-pyrazol-4-yl)-6-{[(3S)-1-propanoylpyrrolidin-3-yl]oxy}-9H-purine | Calc'd 434, found 434 |
| 3-22 | 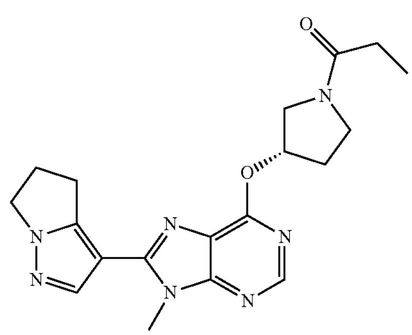 [SMILES: CCC(=O)N1CC[C@H](Oc2ncnc3c2nc(-c2cnn4c2CCC4)n3C)C1] | 8-(5,6-dihydro-4H-pyrrolo[1,2-b]pyrazol-3-yl)-9-methyl-6-{[(3S)-1-propanoylpyrrolidin-3-yl]oxy}-9H-purine | Calc'd 382, found 382 |
| 3-23 | 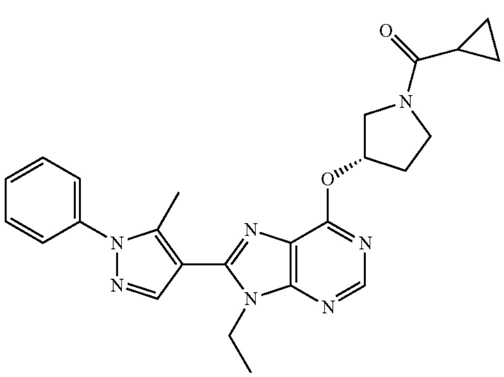 [SMILES: CCn1c(-c2cnn(-c3ccccc3)c2C)nc2c(O[C@H]3CCN(C(=O)C4CC4)C3)ncnc21] | 6-{[(3S)-1-(cyclopropylcarbonyl)pyrrolidin-3-yl]oxy}-9-ethyl-8-(5-methyl-1-phenyl-1H-pyrazol-4-yl)-9H-purine | Calc'd 458, found 458 |

TABLE 3-continued

| Compound | Structure | Compound Name | MS [M + H]+ |
|---|---|---|---|
| 3-24 | 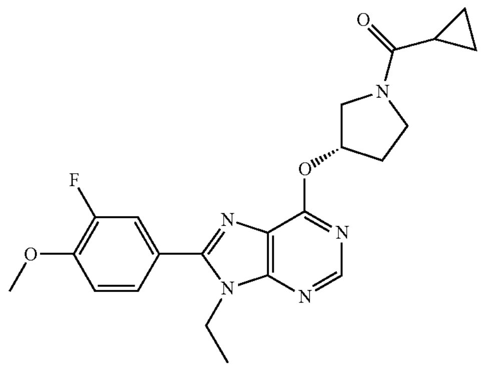 [SMILES: CCn1c(-c2ccc(OC)c(F)c2)nc2c(O[C@H]3CCN(C(=O)C4CC4)C3)ncnc21] | 6-{[(3S)-1-(cyclopropylcarbonyl)pyrrolidin-3-yl]oxy}-9-ethyl-8-(3-fluoro-4-methoxyphenyl)-9H-purine | Calc'd 426, found 426 |
| 3-25 | 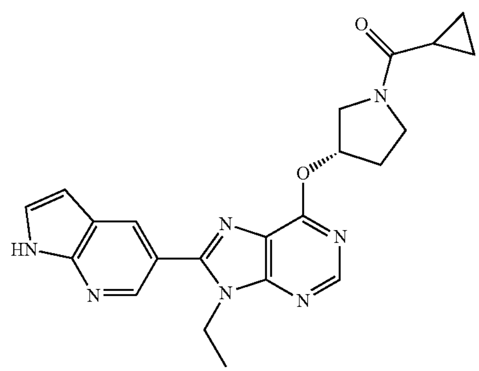 [SMILES: CCn1c(-c2cnc3[nH]ccc3c2)nc2c(O[C@H]3CCN(C(=O)C4CC4)C3)ncnc21] | 6-{[(3S)-1-(cyclopropylcarbonyl)pyrrolidin-3-yl]oxy}-9-ethyl-8-(1H-pyrrolo[2,3-b]pyridin-5-yl)-9H-purine | Calc'd 418, found 418 |
| 3-26 | 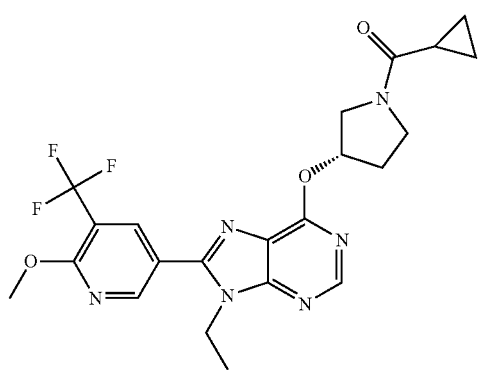 [SMILES: CCn1c(-c2cnc(OC)c(C(F)(F)F)c2)nc2c(O[C@H]3CCN(C(=O)C4CC4)C3)ncnc21] | 5-{[(3S)-1-(cyclopropylcarbonyl)pyrrolidin-3-yl]oxy}-9-ethyl-8-[6-methoxy-5-(trifluoromethyl)pyridin-3-yl]-9H-purine | Calc'd 477, found 477 |
| 3-27 | 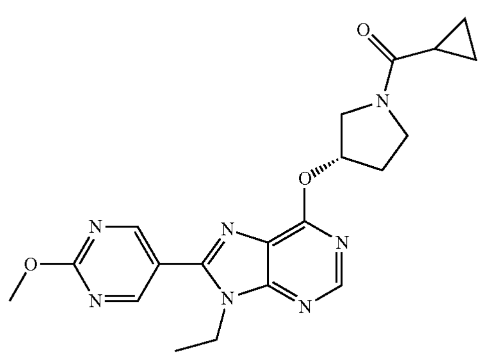 [SMILES: CCn1c(-c2cnc(OC)nc2)nc2c(O[C@H]3CCN(C(=O)C4CC4)C3)ncnc21] | 6-{[(3S)-1-(cyclopropylcarbonyl)pyrrolidin-3-yl]oxy}-9-ethyl-8-(2-methoxypyrimidin-5-yl)-9H-purine | Calc'd 410, found 410 |

TABLE 3-continued

| Compound | Structure | Compound Name | MS [M + H]+ |
|---|---|---|---|
| 3-28 | 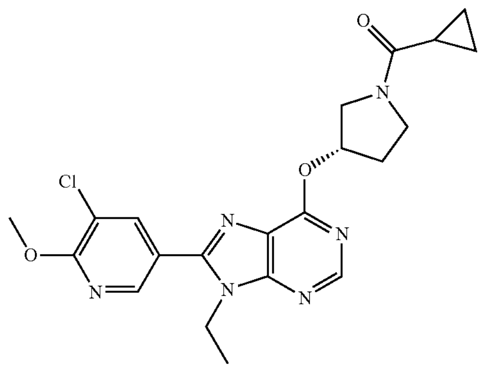 [SMILES: CCn1c(-c2cnc(OC)c(Cl)c2)nc2c(O[C@H]3CCN(C(=O)C4CC4)C3)ncnc21] | 8-(5-chloro-6-methoxypyridin-3-yl)-6-{[(3S)-1-(cyclopropylcarbonyl)pyrrolidin-3-yl]oxy}-9-ethyl-9H-purine | Calc'd 443, found 443 |
| 3-29 | 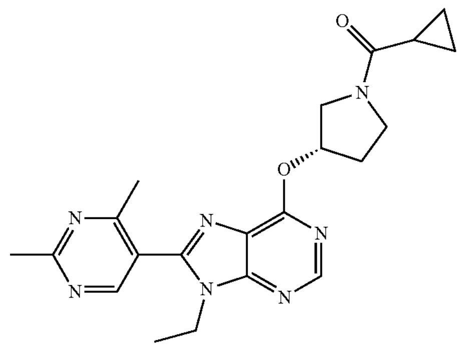 [SMILES: CCn1c(-c2cnc(C)nc2C)nc2c(O[C@H]3CCN(C(=O)C4CC4)C3)ncnc21] | 6-{[(3S)-1-(cyclopropylcarbonyl)pyrrolidin-3-yl]oxy}-8-(2,4-dimethylpyrimidin-5-yl)-9-ethyl-9H-purine | Calc'd 408, found 408 |
| 3-30 | 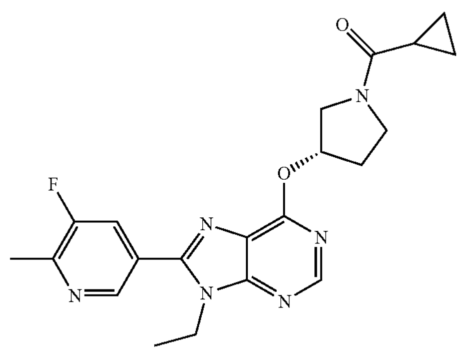 [SMILES: CCn1c(-c2cnc(C)c(F)c2)nc2c(O[C@H]3CCN(C(=O)C4CC4)C3)ncnc21] | 6-{[(3S)-1-(cyclopropylcarbonyl)pyrrolidin-3-yl]oxy}-9-ethyl-8-(5-fluoro-6-methylpyridin-3-yl)-9H-purine | Calc'd 411, found 411 |
| 3-31 | 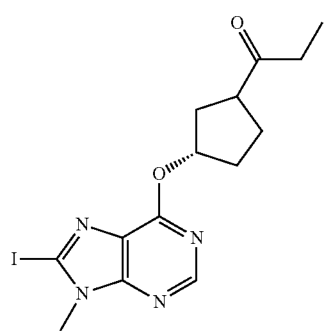 [SMILES: CCC(=O)C1CC[C@H](Oc2ncnc3c2nc(I)n3C)C1] | 8-iodo-9-methyl-6-{[(3S)-1-propanoylpyrrolidin-3-yl]oxy}-9H-purine | Calc'd 402, found 402 |

TABLE 3-continued

| Compound | Structure | Compound Name | MS [M + H]⁺ |
|---|---|---|---|
| 3-32 | 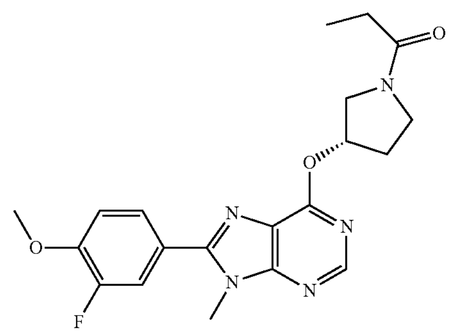 [SMILES: CCC(=O)N1CC[C@H](Oc2ncnc3c2nc(-c2ccc(OC)c(F)c2)n3C)C1] | 8-(3-fluoro-4-methoxyphenyl)-9-methyl-5-{[(3S)-1-propanoylpyrrolidin-3-yl]oxy}-9H-purine | Calc'd 400, found 400 |
| 3-33 | 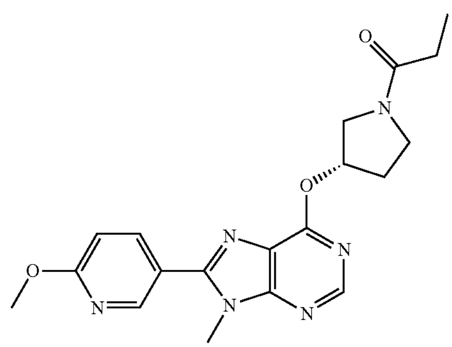 [SMILES: CCC(=O)N1CC[C@H](Oc2ncnc3c2nc(-c2ccc(OC)nc2)n3C)C1] | 8-(6-methoxypyridin-3-yl)-9-methyl-6-{[(3S)-1-propanoylpyrrolidin-3-yl]oxy}-9H-purine | Calc'd 383, found 383 |
| 3-34 | 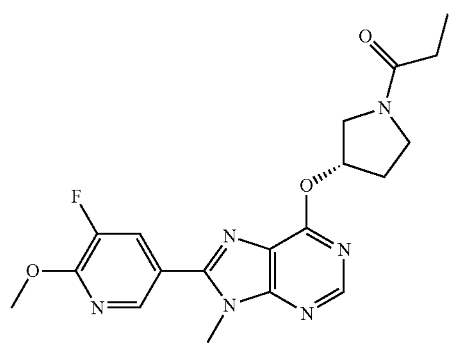 [SMILES: CCC(=O)N1CC[C@H](Oc2ncnc3c2nc(-c2cnc(OC)c(F)c2)n3C)C1] | 8-(5-fluoro-6-methoxypyridin-3-yl)-9-methyl-6-{[(3S)-1-propanoylpyrrolidin-3-yl]oxy}-9H-purine | Calc'd 401, found 401 |
| 3-35 | 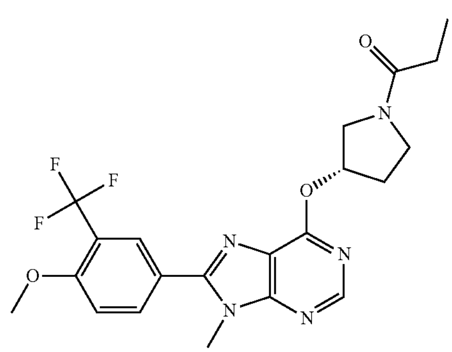 [SMILES: CCC(=O)N1CC[C@H](Oc2ncnc3c2nc(-c2ccc(OC)c(C(F)(F)F)c2)n3C)C1] | 8-[4-methoxy-3-(trifluoromethyl)phenyl]-9-methyl-6-{[(3S)-1-propanoylpyrrolidin-3-yl]oxy}-9H-purine | Calc'd 450, found 450 |

TABLE 3-continued

| Compound | Structure | Compound Name | MS [M + H]+ |
|---|---|---|---|
| 3-36 | 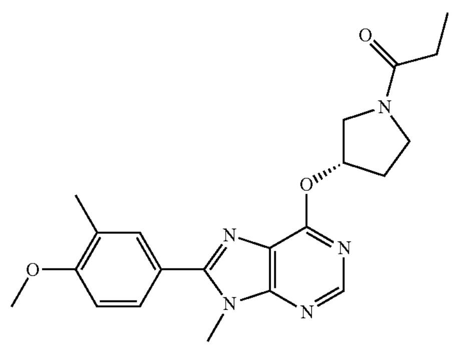 [SMILES: CCC(=O)N1CC[C@H](Oc2ncnc3c2nc(-c2ccc(OC)c(C)c2)n3C)C1] | 8-(4-methoxy-3-methylphenyl)-9-methyl-6-{[(3S)-1-propanoylpyrrolidin-3-yl]oxy}-9H-purine | Calc'd 396, found 396 |
| 3-37 | 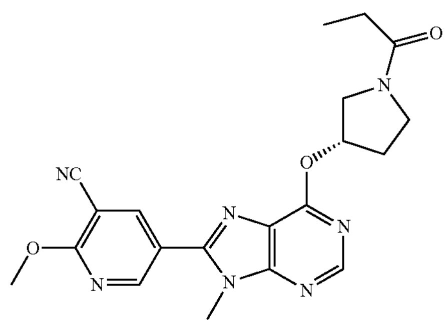 [SMILES: CCC(=O)N1CC[C@H](Oc2ncnc3c2nc(-c2cnc(OC)c(C#N)c2)n3C)C1] | 2-methoxy-5-(9-methyl-6-{[(3S)-1-propanoylpyrrolidin-3-yl]oxy}-9H-purin-8-yl)pyridine-3-carbonitrile | Calc'd 408, found 408 |
| 3-38 | 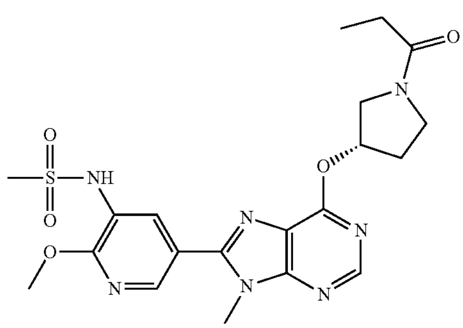 [SMILES: CCC(=O)N1CC[C@H](Oc2ncnc3c2nc(-c2cnc(OC)c(NS(C)(=O)=O)c2)n3C)C1] | N-[2-methoxy-5-(9-methyl-6-{[(3S)-1-propanoylpyrrolidin-3-yl]oxy}-9H-purin-8-yl)pyridin-3-yl]methanesulfonamide | Calc'd 476, found 476 |
| 3-39 | 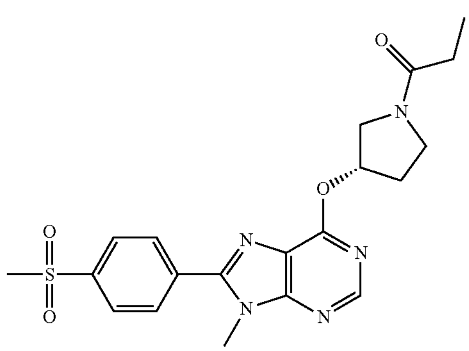 [SMILES: CCC(=O)N1CC[C@H](Oc2ncnc3c2nc(-c2ccc(S(C)(=O)=O)cc2)n3C)C1] | 9-methyl-8-[4-(methylsulfonyl)phenyl]-6-{[(3S)-1-propanoylpyrrolidin-3-yl]oxy}-9H-purine | Calc'd 430, found 430 |

TABLE 3-continued

| Compound | Structure | Compound Name | MS [M + H]+ |
|---|---|---|---|
| 3-40 | 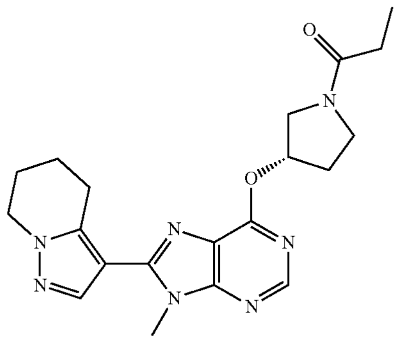 [SMILES: CCC(=O)N1CC[C@H](Oc2ncnc3c2nc(-c2cnn4c2CCCC4)n3C)C1] | 9-methyl-6-{[(3S)-1-propanoylpyrrolidin-3-yl]oxy}-8-(4,5,6,7-tetrahydropyrazolo[1,5-a]pyridin-3-yl)-9H-purine | Calc'd 396, found 396 |
| 3-41 | 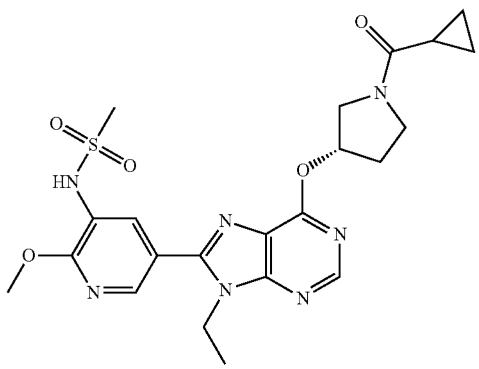 [SMILES: CCn1c(-c2cnc(OC)c(NS(C)(=O)=O)c2)nc2c(O[C@H]3CCN(C(=O)C4CC4)C3)ncnc21] | N-[5-(6-{[(3S)-1-(cyclopropylcarbonyl)pyrrolidin-3-yl]oxy}-9-ethyl-9H-purin-8-yl)-2-methoxypyridin-3-yl]methanesulfonamide | Calc'd 502, found 502 |
| 3-42 | 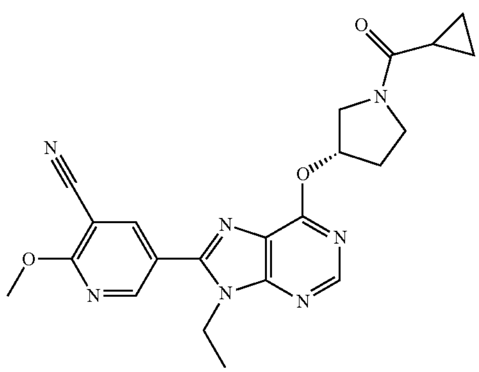 [SMILES: CCn1c(-c2cnc(OC)c(C#N)c2)nc2c(O[C@H]3CCN(C(=O)C4CC4)C3)ncnc21] | 5-(6-{[(3S)-1-(cyclopropylcarbonyl)pyrrolidin-3-yl]oxy}-9-ethyl-9H-purin-8-yl)-2-methoxypyridine-3-carbonitrile | Calc'd 434, found 434 |
| 3-43 | 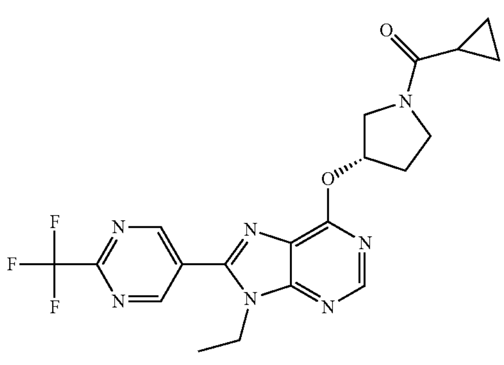 [SMILES: CCn1c(-c2cnc(C(F)(F)F)nc2)nc2c(O[C@H]3CCN(C(=O)C4CC4)C3)ncnc21] | 6-{[(3S)-1-(cyclopropylcarbonyl)pyrrolidin-3-yl]oxy}-9-ethyl-8-[2-(trifluoromethyl)pyrimidin-5-yl]-9H-purine | Calc'd 448, found 448 |

TABLE 3-continued

| Compound | Structure | Compound Name | MS [M + H]+ |
|---|---|---|---|
| 3-44 | 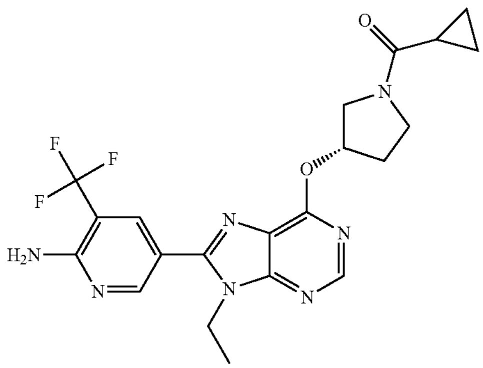 [SMILES: CCn1c(-c2cnc(N)c(C(F)(F)F)c2)nc2c(O[C@H]3CCN(C(=O)C4CC4)C3)ncnc21] | 5-(6-{[(3S)-1-(cyclopropylcarbonyl)pyrrolidin-3-yl]oxy}-9-ethyl-9H-purin-8-yl)-3-(trifluoromethyl)pyridin-2-amine | Calc'd 462, found 462 |
| 3-45 | 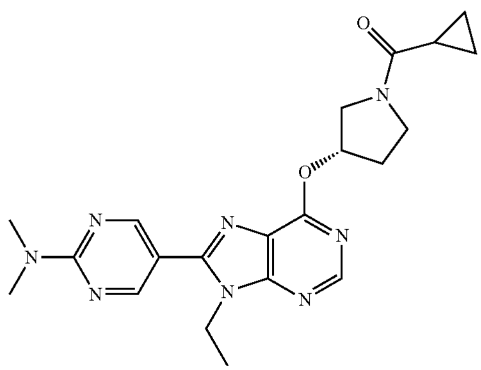 [SMILES: CCn1c(-c2cnc(N(C)C)nc2)nc2c(O[C@H]3CCN(C(=O)C4CC4)C3)ncnc21] | 5-(6-{[(3S)-1-(cyclopropylcarbonyl)pyrrolidin-3-yl]oxy}-9-ethyl-9H-purin-8-yl)-N,N-dimethylpyrimidin-2-amine | Calc'd 423, found 423 |
| 3-46 | 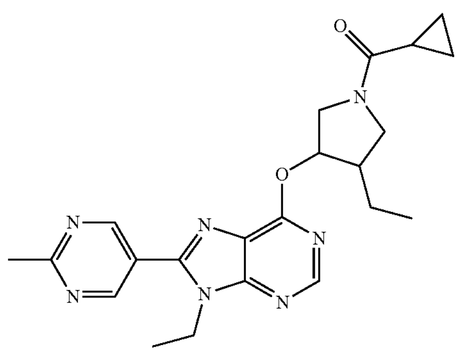 [SMILES: CCC1CN(C(=O)C2CC2)CC1Oc1ncnc2c1nc(-c1cnc(C)nc1)n2CC] | [3R,4S and 3S,4R]-6-{[1-(cyclopropylcarbonyl)-4-ethylpyrrolidin-3-yl]oxy}-9-ethyl-8-(2-methylpyrimidin-5-yl)-9H-purine | Calc'd 422, found 422 |
| 3-47 | 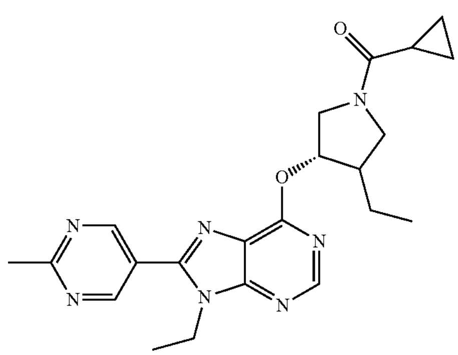 [SMILES: CCC1CN(C(=O)C2CC2)C[C@H]1Oc1ncnc2c1nc(-c1cnc(C)nc1)n2CC] | [3R,4S or 3S,4R]-6-{[1-(cyclopropylcarbonyl)-4-ethylpyrrolidin-3-yl]oxy}-9-ethyl-8-(2-methylpyrimidin-5-yl)-9H-purine | Calc'd 422, found 422 |

TABLE 3-continued

| Compound | Structure | Compound Name | MS [M + H]+ |
|---|---|---|---|
| 3-48 | 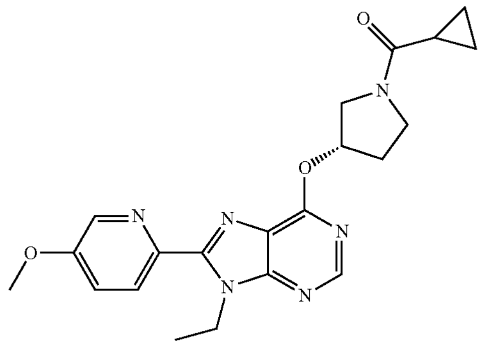 [SMILES: CCn1c(-c2ccc(OC)cn2)nc2c(O[C@H]3CCN(C(=O)C4CC4)C3)ncnc21] | 6-{[(3S)-1-(cyclopropylcarbonyl)pyrrolidin-3-yl]oxy}-9-ethyl-8-(5-methoxypyridin-2-yl)-9H-purine | Calc'd 409, found 409 |
| 3-49 | 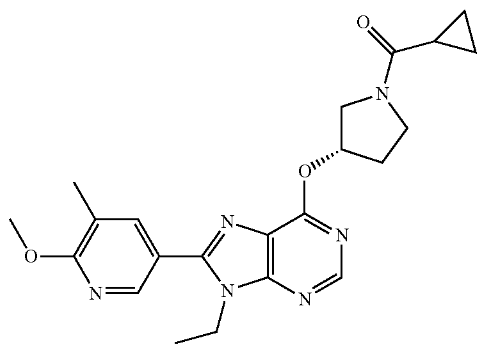 [SMILES: CCn1c(-c2cnc(OC)c(C)c2)nc2c(O[C@H]3CCN(C(=O)C4CC4)C3)ncnc21] | 6-{[(3S)-1-(cyclopropylcarbonyl)pyrrolidin-3-yl]oxy}-9-ethyl-8-(6-methoxy-5-methylpyridin-3-yl)-9H-purine | Calc'd 423, found 423 |
| 3-50 | 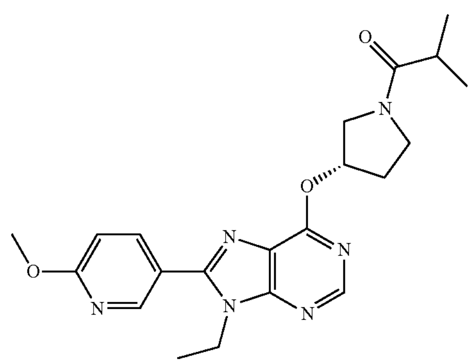 [SMILES: CCn1c(-c2ccc(OC)nc2)nc2c(O[C@H]3CCN(C(=O)C(C)C)C3)ncnc21] | 9-ethyl-8-(6-methoxypyridin-3-yl)-6-{[(3S)-1-(2-methylpropanoyl)pyrrolidin-3-yl]oxy}-9H-purine | Calc'd 411, found 411 |
| 3-51 | 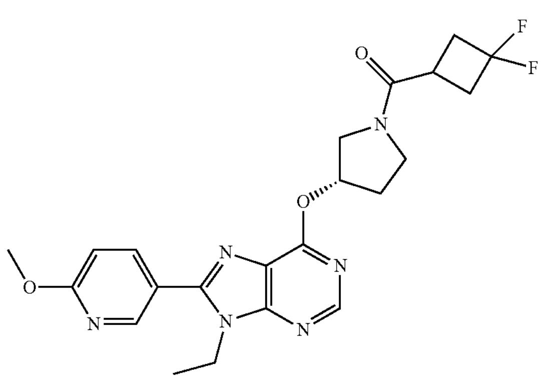 [SMILES: CCn1c(-c2ccc(OC)nc2)nc2c(O[C@H]3CCN(C(=O)C4CC(F)(F)C4)C3)ncnc21] | 6-({(3S)-1-[(3,3-difluorocyclobutyl)carbonyl]pyrrolidin-3-yl}oxy)-9-ethyl-8-(6-methoxypyridin-3-yl)-9H-purine | Calc'd 459, found 459 |

TABLE 3-continued

| Compound | Structure | Compound Name | MS [M + H]+ |
|---|---|---|---|
| 3-52 | 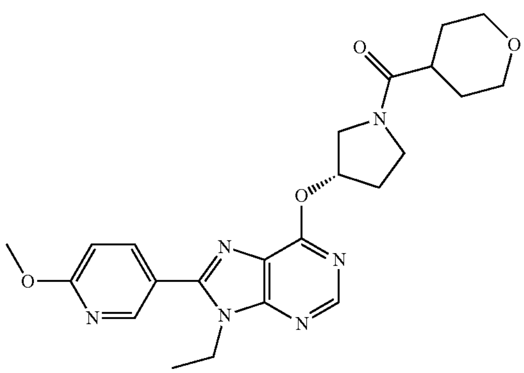 [SMILES: CCn1c(-c2ccc(OC)nc2)nc2c(O[C@H]3CCN(C(=O)C4CCOCC4)C3)ncnc21] | 9-ethyl-8-(6-methoxypyridin-3-yl)-6-{[(3S)-1-(tetrahydro-2H-pyran-4-ylcarbonyl)pyrrolidin-3-yl]oxy}-9H-purine | Calc'd 453, found 453 |
| 3-53 | 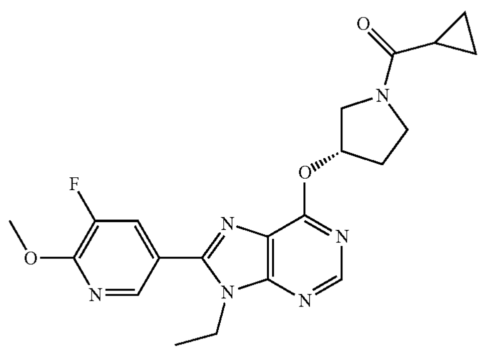 | 6-{[(3S)-1-(cyclopropylcarbonyl)pyrrolidin-3-yl]oxy}-9-ethyl-8-(5-fluoro-6-methoxypyridin-3-yl)-9H-purine | Calc'd 427, found 427 |
| 3-54 | 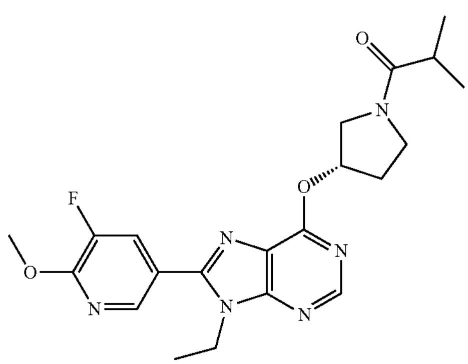 [SMILES: CCn1c(-c2cnc(OC)c(F)c2)nc2c(O[C@H]3CCN(C(=O)C(C)C)C3)ncnc21] | 9-ethyl-8-(5-fluoro-6-methoxypyridin-3-yl)-6-{[(3S)-1-(2-methylpropanoyl)pyrrolidin-3-yl]oxy}-9H-purine | Calc'd 429, found 429 |
| 3-55 | 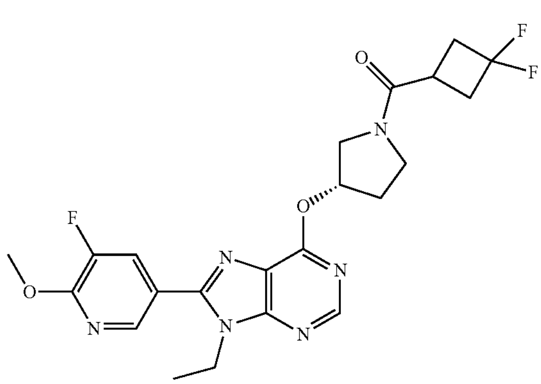 [SMILES: CCn1c(-c2cnc(OC)c(F)c2)nc2c(O[C@H]3CCN(C(=O)C4CC(F)(F)C4)C3)ncnc21] | 6-({(3S)-1-[(3,3-difluorocyclobutyl)carbonyl]pyrrolidin-3-yl}oxy)-9-ethyl-8-(5-fluoro-6-methoxypyridin-3-yl)-9H-purine | Calc'd 477, found 477 |

TABLE 3-continued

| Compound | Structure | Compound Name | MS [M + H]+ |
|---|---|---|---|
| 3-56 | 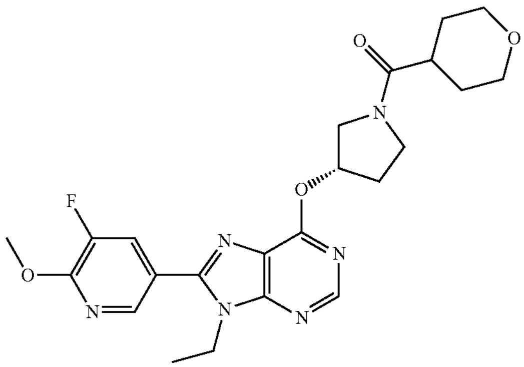 [SMILES: CCn1c(-c2cnc(OC)c(F)c2)nc2c(O[C@H]3CCN(C(=O)C4CCOCC4)C3)ncnc21] | 9-ethyl-8-(5-fluoro-6-methoxypyridin-3-yl)-6-{[(3S)-1-(tetrahydro-2H-pyran-4-ylcarbonyl)pyrrolidin-3-yl]oxy}-9H-purine | Calc'd 471, found 471 |
| 3-57 | 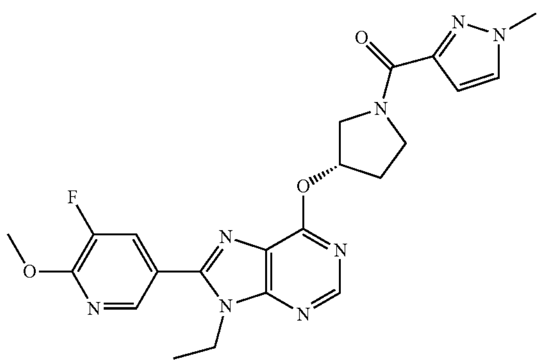 | 9-ethyl-8-(5-fluoro-6-methoxypyridin-3-yl)-6-({(3S)-1-[(1-methyl-1H-pyrazol-3-yl)carbonyl]pyrrolidin-3-yl}oxy)-9H-purine | Calc'd 467, found 467 |
| 3-58 | 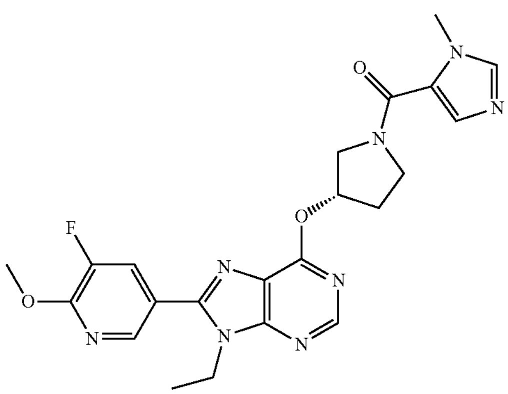 [SMILES: CCn1c(-c2cnc(OC)c(F)c2)nc2c(O[C@H]3CCN(C(=O)c4cncn4C)C3)ncnc21] | 9-ethyl-8-(5-fluoro-6-methoxypyridin-3-yl)-6-({(3S)-1-[(1-methyl-1H-imidazol-5-yl)carbonyl]pyrrolidin-3-yl}oxy)-9H-purine | Calc'd 467, found 467 |
| 3-59 | 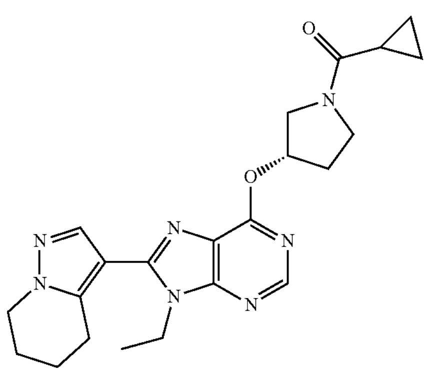 [SMILES: CCn1c(-c2cnn3c2CCCC3)nc2c(O[C@H]3CCN(C(=O)C4CC4)C3)ncnc21] | 6-{[(3S)-1-(cyclopropylcarbonyl)pyrrolidin-3-yl]oxy}-9-ethyl-8-(4,5,6,7-tetrahydropyrazolo[1,5-a]pyridin-3-yl)-9H-purine | Calc'd 422, found 422 |

TABLE 3-continued

| Compound | Structure | Compound Name | MS [M + H]+ |
|---|---|---|---|
| 3-60 | 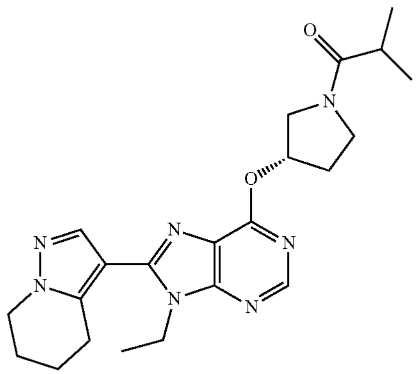 [SMILES: CCn1c(-c2cnn3c2CCCC3)nc2c(O[C@H]3CCN(C(=O)C(C)C)C3)ncnc21] | 9-ethyl-6-{[(3S)-1-(2-methylpropanoyl)pyrrolidin-3-yl]oxy}-8-(4,5,6,7-tetrahydropyrazolo[1,5-a]pyridin-3-yl)-9H-purine | Calc'd 424, found 424 |
| 3-61 | 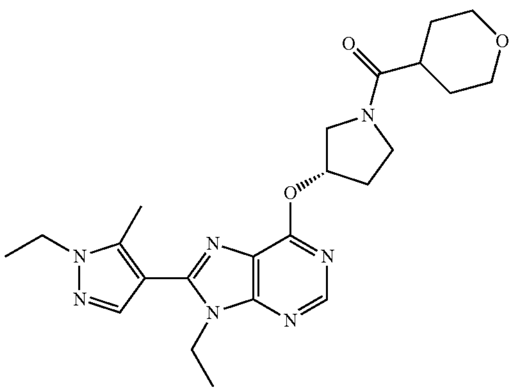 [SMILES: CCn1ncc(-c2nc3c(O[C@H]4CCN(C(=O)C5CCOCC5)C4)ncnc3n2CC)c1C] | (S)-(3-((9-ethyl-8-(1-ethyl-5-methyl-1H-pyrazol-4-yl)-9H-purin-6-yl)oxy)pyrrolidin-1-yl)(tetrahydro-2H-pyran-4-yl)methanone | Calc'd 454, found 454 |
| 3-62 | 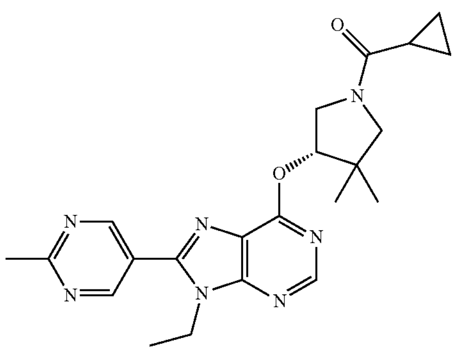 [SMILES: CCn1c(-c2cnc(C)nc2)nc2c(O[C@@H]3CN(C(=O)C4CC4)CC3(C)C)ncnc21] | racemic-6-{[1-(cyclopropylcarbonyl)-4,4-dimethylpyrrolidin-3-yl]oxy}-9-ethyl-8-(2-methylpyrimidin-5-yl)-9H-purine | Calc'd 422, found 422 |
| 3-63 | 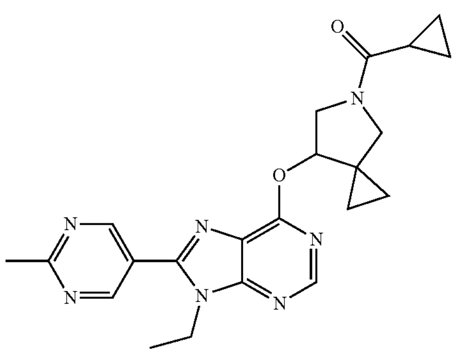 [SMILES: CCn1c(-c2cnc(C)nc2)nc2c(OC3CN(C(=O)C4CC4)CC34CC4)ncnc21] | (R— or S—)-6-{[5-(cyclopropylcarbonyl)-5-azaspiro[2.4]hept-7-yl]oxy}-9-ethyl-8-(2-methylpyrimidin-5-yl)-9H-purine | Calc'd 420, found 420 |

TABLE 3-continued

| Compound | Structure | Compound Name | MS [M + H]+ |
|---|---|---|---|
| 3-64 | 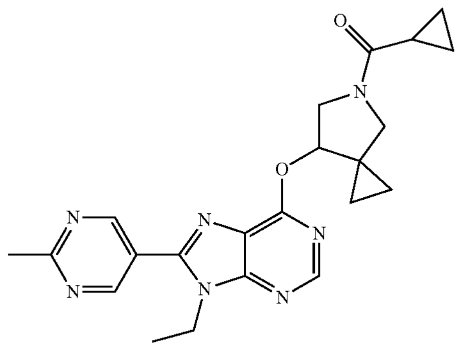 [SMILES: CCn1c(-c2cnc(C)nc2)nc2c(OC3CN(C(=O)C4CC4)CC34CC4)ncnc21] | (R— or S—)-6-{[5-(cyclopropylcarbonyl)-5-azaspiro[2.4]hept-7-yl]oxy}-9-ethyl-8-(2-methylpyrimidin-5-yl)-9H-purine | Calc'd 420, found 420 |
| 3-65 | 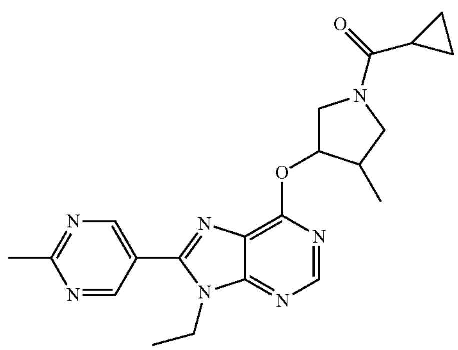 [SMILES: CCn1c(-c2cnc(C)nc2)nc2c(OC3CN(C(=O)C4CC4)CC3C)ncnc21] | [(3S,4R) or (3R,4S)]6-{[1-(cyclopropylcarbonyl)-4-methylpyrrolidin-3-yl]oxy}-9-ethyl-8-(2-methylpyrimidin-5-yl)-9H-purine | Calc'd 408, found 408 |
| 3-66 | 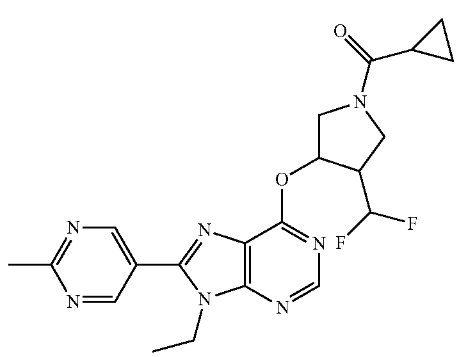 [SMILES: CCn1c(-c2cnc(C)nc2)nc2c(OC3CN(C(=O)C4CC4)CC3C(F)F)ncnc21] | cyclopropyl([(3R,4S) or (3S,4R)]-3-(difluoromethyl)-4-((9-ethyl-8-(2-methylpyrimidin-5-yl)-9H-purin-6-yl)oxy)pyrrolidin-1-yl)methanone | Calc'd 444, found 444 |

TABLE 3-continued

| Compound | Structure | Compound Name | MS [M + H]+ |
|---|---|---|---|
| 3-67 | 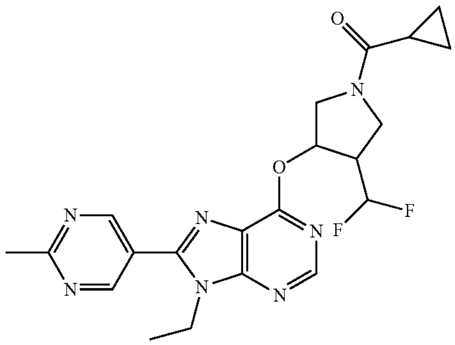 [SMILES: CCn1c(-c2cnc(C)nc2)nc2c(OC3CN(C(=O)C4CC4)CC3C(F)F)ncnc21] | cyclopropyl([[(3R,4S) or (3S,4R)]-3-(difluoromethyl)-4-((9-ethyl-8-(2-methylpyrimidin-5-yl)-9H-purin-6-yl)oxy)pyrrolidin-1-yl)methanone | Calc'd 444, found 444 |
| 3-68 | 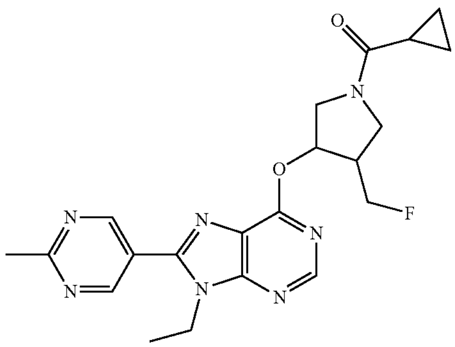 [SMILES: CCn1c(-c2cnc(C)nc2)nc2c(OC3CN(C(=O)C4CC4)CC3CF)ncnc21] | cyclopropyl([[(3S,4R) or (3R,4S)]-3-((9-ethyl-8-(2-methylpyrimidin-5-yl)-9H-purin-6-yl)oxy)-4-(fluoromethyl)pyrrolidin-1-yl)methanone | Calc'd 426, found 426 |
| 3-69 | 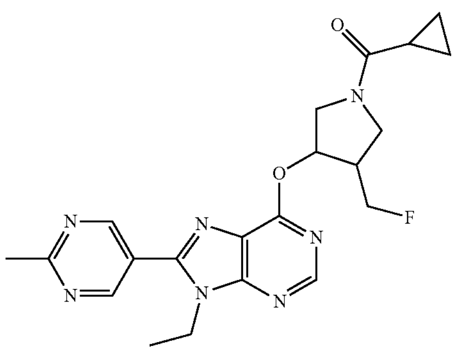 [SMILES: CCn1c(-c2cnc(C)nc2)nc2c(OC3CN(C(=O)C4CC4)CC3CF)ncnc21] | cyclopropyl([[(3S,4R) or (3R,4S)]-3-((9-ethyl-8-(2-methylpyrimidin-5-yl)-9H-purin-6-yl)oxy)-4-(fluoromethyl)pyrrolidin-1-yl)methanone | Calc'd 426, found 426 |

Compound Examples of Table 4

Example 9—Preparation of Compound 4-3

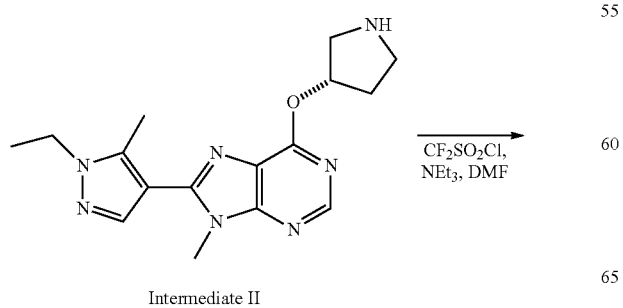

Intermediate II

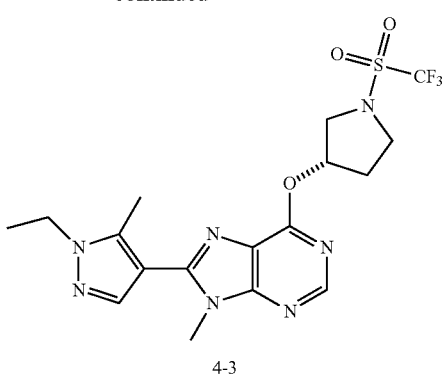

4-3

A solution of Intermediate II (25 mg, 0.076 mmol) and triethylamine (0.025 mL, 0.18 mmol) in 1.5 mL of DMF was added to a vial containing trifluoromethanesulfonyl chloride (17 mg, 0.10 mmol). The vial was stirred at room temperature for 2 hours, filtered, and the filter washed with 1.5 mL of DMSO. The filtrate containing the crude product in 3 mL of 1:1 DMSO/DMF was purified by reverse phase HPLC. The desired fraction was concentrated under reduced pressure to yield 4-3 as the TFA salt. $^1$H NMR (600 MHz, DMSO-$d_6$) δ 8.47 (s, 1H), 7.99 (s, 1H), 5.89 (s, 1H), 4.15 (q, J=7.3 Hz, 2H), 3.95 (d, J=11.8 Hz, 1H), 3.83 (s, 3H), 3.74-3.72 (m, 3H), 2.55 (s, 3H), 2.39-2.35 (m, 2H), 1.33 (t, J=7.24 Hz, 3H); MS (EI) Calc'd for $C_{17}H_{21}F_3N_7O_3S$ [M+H]$^+$, 460. found 460.

The compounds included in the Table 4 below were prepared in an analogous fashion to that of Example 9 using intermediate pyrrolidine and the corresponding sulfonyl chloride.

TABLE 4

| Compound | Structure | Compound Name | MS [M + H]$^+$ |
| --- | --- | --- | --- |
| 4-1 | 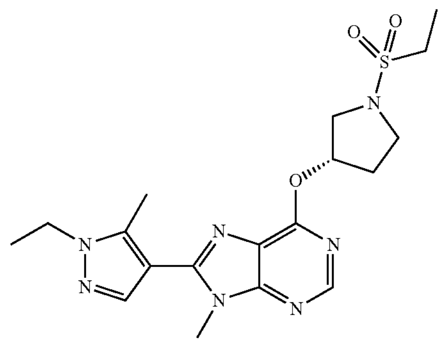 [SMILES: CCn1ncc(-c2nc3c(O[C@H]4CCN(S(=O)(=O)CC)C4)ncnc3n2C)c1C] | 8-(1-ethyl-5-methyl-1H-pyrazol-4-yl)-6-{[(3S)-1-(ethylsulfonyl)pyrrolidin-3-yl]oxy}-9-methyl-9H-purine | Calc'd 420, found 420 |
| 4-2 | 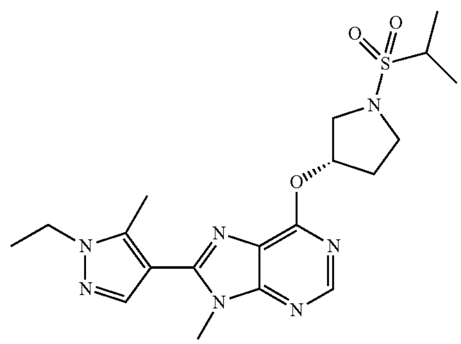 [SMILES: CCn1ncc(-c2nc3c(O[C@H]4CCN(S(=O)(=O)C(C)C)C4)ncnc3n2C)c1C] | 8-(1-ethyl-5-methyl-1H-pyrazol-4-yl)-9-methyl-6-({(3S)-1-[(1-methylethyl)sulfonyl]pyrrolidin-3-yl}oxy)-9H-purine | Calc'd 434, found 434 |
| 4-3 | 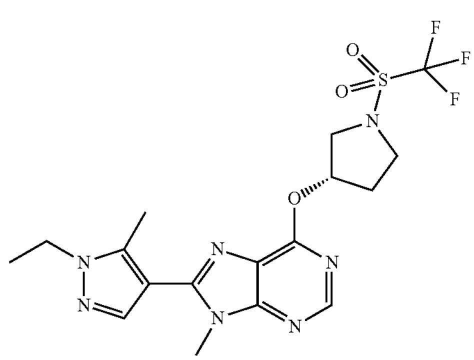 [SMILES: CCn1ncc(-c2nc3c(O[C@H]4CCN(S(=O)(=O)C(F)(F)F)C4)ncnc3n2C)c1C] | 8-(1-ethyl-5-methyl-1H-pyrazol-4-yl)-9-methyl-6-({(3S)-1-[(trifluoromethyl)sulfonyl]pyrrolidin-3-yl}oxy)-9H-purine | Calc'd 460, found 460 |

TABLE 4-continued

| Compound | Structure | Compound Name | MS [M + H]+ |
|---|---|---|---|
| 4-4 | 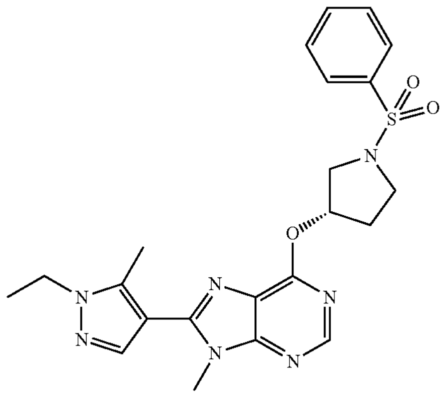 [SMILES: CCn1ncc(-c2nc3c(O[C@H]4CCN(S(=O)(=O)c5ccccc5)C4)ncnc3n2C)c1C] | 8-(1-ethyl-5-methyl-1H-pyrazol-4-yl)-9-methyl-6-{[(3S)-1-(phenylsulfonyl)pyrrolidin-3-yl]oxy}-9H-purine | Calc'd 468, found 468 |
| 4-5 | 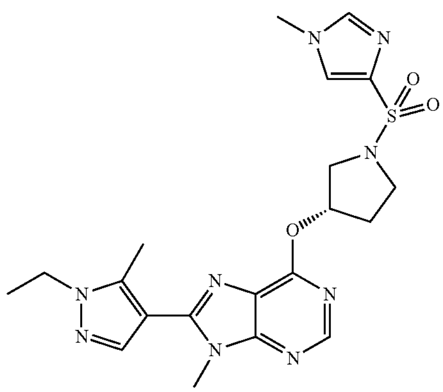 [SMILES: CCn1ncc(-c2nc3c(O[C@H]4CCN(S(=O)(=O)c5cn(C)cn5)C4)ncnc3n2C)c1C] | 8-(1-ethyl-5-methyl-1H-pyrazol-4-yl)-9-methyl-6-({(3S)-1-[(1-methyl-1H-imidazol-4-yl)sulfonyl]pyrrolidin-3-yl}oxy)-9H-purine | Calc'd 472, found 472 |
| 4-6 | 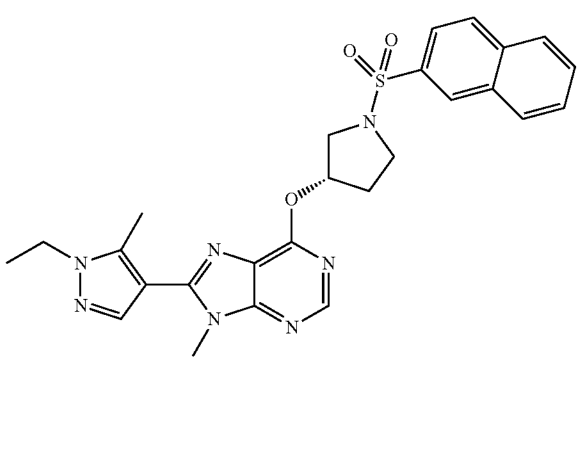 [SMILES: CCn1ncc(-c2nc3c(O[C@H]4CCN(S(=O)(=O)c5ccc6ccccc6c5)C4)ncnc3n2C)c1C] | 8-(1-ethyl-5-methyl-1H-pyrazol-4-yl)-9-methyl-6-{[(3S)-1-(naphthalen-2-ylsulfonyl)pyrrolidin-3-yl]oxy}-9H-purine | Calc'd 518, found 518 |

TABLE 4-continued

| Compound | Structure | Compound Name | MS [M + H]+ |
|---|---|---|---|
| 4-7 | 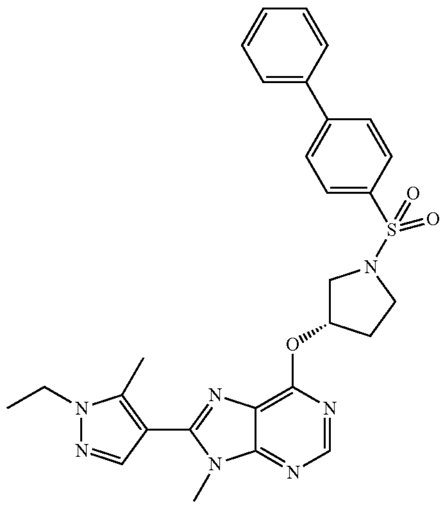 [SMILES: CCn1ncc(-c2nc3c(O[C@H]4CCN(S(=O)(=O)c5ccc(-c6ccccc6)cc5)C4)ncnc3n2C)c1C] | 6-{[(3S)-1-(biphenyl-4-ylsulfonyl)pyrrolidin-3-yl]oxy}-8-(1-ethyl-5-methyl-1H-pyrazol-4-yl)-9-methyl-9H-purine | Calc'd 544, found 544 |
| 4-8 | 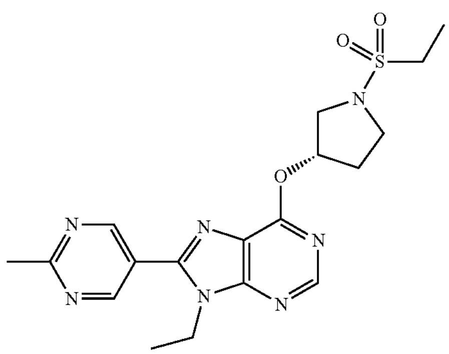 [SMILES: CCn1c(-c2cnc(C)nc2)nc2c(O[C@H]3CCN(S(=O)(=O)CC)C3)ncnc21] | (S)-9-ethyl-6-((1-(ethylsulfonyl)pyrrolidin-3-yl)oxy)-8-(2-methylpyrimidin-5-yl)-9H-purine | Calc'd 418, found 418 |

Compound Examples of Table 5

Example 10—Preparation of Compound 5-4

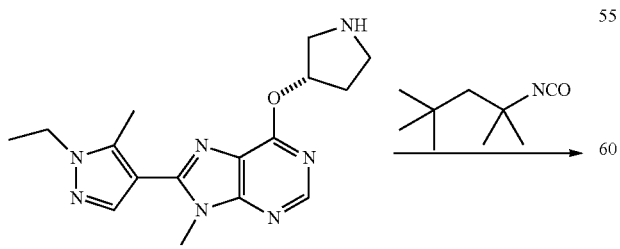

A solution of intermediate II (25 mg, 0.076 mmol) in 1.5 mL of DMF was added to a vial containing silicon polymer-supported DMAP (Si-DMAP; 294 mg, 0.229 mmol) and 2-isocyanato-2,4,4-trimethylpentane (16 mg, 0.10 mmol).

237

The vial was sealed and stirred overnight at room temperature. The reaction mixture was filtered, washing the filter with 1.5 mL of DMSO. The crude product dissolved in 3 mL of 1:1 DMSO/DMF was purified by reverse phase HPLC and the desired fraction concentrated under reduced pressure to yield 5-4 as the TFA salt. $^1$H NMR (600 MHz, DMSO-$d_6$) δ 8.46 (s, 1H), 7.97 (s, 1H), 5.79 (s, 1H), 4.15 (q, J=7.3 Hz, 2H), 3.81 (s, 3H), 3.61 (m, 1H), 3.52 (m, 1H), 3.41 (m, 1H), 2.54 (s, 3H), 2.48 (m, 1H), 2.23-2.16 (m, 2H), 1.65 (d, J=2.4 Hz, 2H), 1.33 (t, J=7.2 Hz, 3H), 1.26 (m, 6H), 0.90 (s, 9H); MS (EI) Calc'd for $C_{25}H_{39}N_8O_2$ [M+H]$^+$, 483. found 483.

Example 10A—Preparation of Compound 5-9

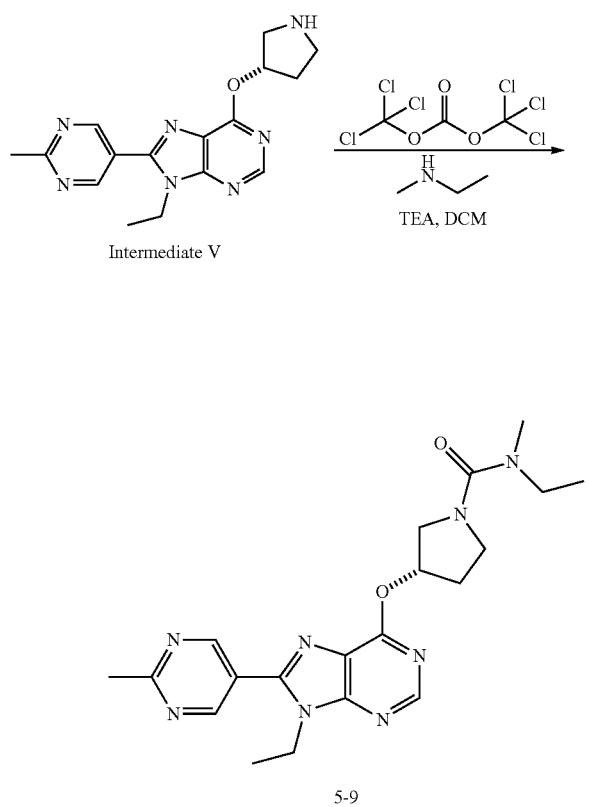

5-9

To a solution of N-methylethanamine (0.020 g, 0.34 mmol) and triethylamine (0.070 mL, 0.50 mmol) in DCM (5 mL) was added bis(trichloromethyl) carbonate (0.030 g, 0.10 mmol). The reaction was stirred at 20° C. for 0.5 h, then Intermediate V (0.080 g, 0.25 mmol) was added. The reaction was stirred at ambient temperature for 15 h, concentrated and purified by reverse phase chromatography (MeCN/water with 10 mM aqueous $NH_4HCO_3$ modifier) to afford 5-9. $^1$H NMR (400 MHz, $CD_3OD$) δ 9.13 (s, 2H), 8.60 (s, 1H), 5.96 (m, 1H), 4.46 (q, 2H), 3.98-3.94 (m, 1H), 3.79-3.77 (m, 1H), 3.69-3.66 (m, 1H), 3.58-3.57 (m, 1H), 3.27 (q, 2H), 2.84 (m, 6H), 2.34 (m, 2H), 1.47 (t, 3H), 1.17 (t, 3H). MS (EI) Calc'd for $C_{20}H_{27}N_8O_2$ [M+H]$^+$, 411. found 411.

238

Example 10B—Preparation of Compound 5-27

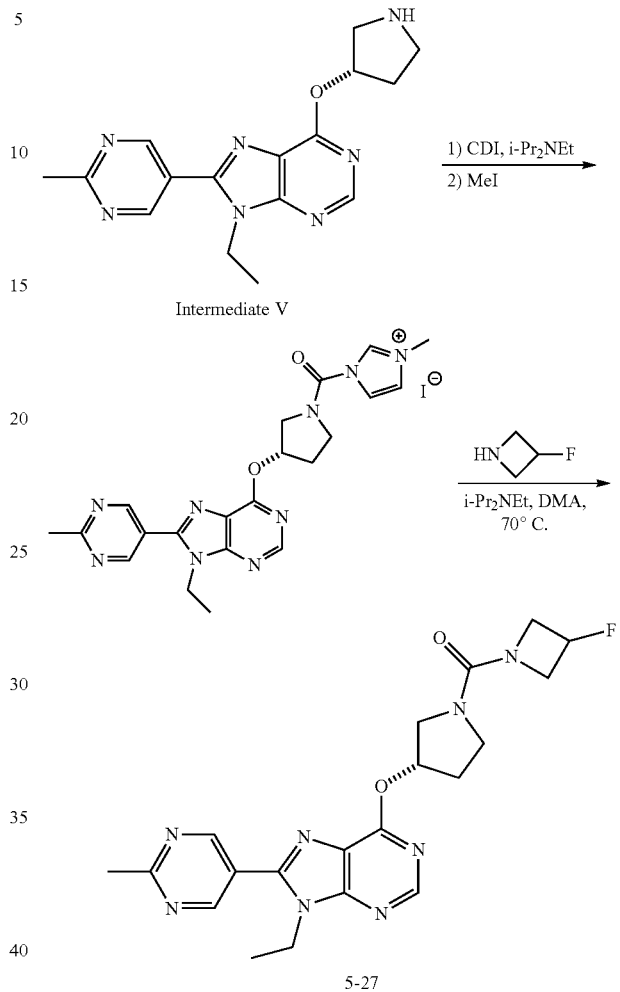

5-27

A solution of Intermediate V, HCl salt (0.25 g, 0.69 mmol) and CDI (0.22 g, 1.4 mmol) in THF (50 mL) was treated with i-Pr$_2$NEt (0.27 mL, 1.5 mmol) and heated to 75° C. for 12 hours. The reaction mixture was concentrated and the residue purified by chromatography on SiO$_2$ (0-10% MeOH/DCM) to afford (S)-(3-((9-ethyl-8-(2-methylpyrimidin-5-yl)-9H-purin-6-yl)oxy)pyrrolidin-1-yl)(1H-imidazol-1-yl)methanone. MS (EI) Calc'd for $C_{20}H_{22}N_9O_2$ [M+H]$^+$, 420. found, 420.

A solution of (S)-(3-((9-ethyl-8-(2-methylpyrimidin-5-yl)-9H-purin-6-yl)oxy)pyrrolidin-1-yl)(1H-imidazol-1-yl)methanone (0.25 g, 0.60 mmol) in acetonitrile (75 mL) was treated with iodomethane (0.15 mL, 2.4 mmol) and stirred for 12 hours at RT. The reaction was concentrated and triturated with ether (10 mL) overnight. The mixture was then filtered to afford (S)-1-(3-((9-ethyl-8-(2-methylpyrimidin-5-yl)-9H-purin-6-yl)oxy)pyrrolidine-1-carbonyl)-3-methyl-1H-imidazol-3-ium iodide. MS (EI) Calc'd for $C_{21}H_{24}N_9O_2$+[M+H]$^+$, 434. found, 434.

A mixture of (S)-1-(3-((9-ethyl-8-(2-methylpyrimidin-5-yl)-9H-purin-6-yl)oxy)pyrrolidine-1-carbonyl)-3-methyl-1H-imidazol-3-ium iodide (0.020 g, 0.046 mmol), 3-fluoroazetidine (0.011 g, 0.15 mmol), and DIEA (0.040 mL, 0.23 mmol) suspended in DMA (0.90 mL) was sealed and warmed to 70° C. for 8 h. The reaction was filtered and purified by reverse phase HPLC to afford the TFA salt of 5-27. $^1$H NMR (500 MHz, DMSO-d$_6$) δ 9.13 (s, 2H), 8.60 (s, 1H), 5.83 (s, 1H), 5.38-5.24 (m, 1H), 4.36 (q, 2H), 4.27-4.11 (m, 2H), 4.00-3.84 (m, 2H), 3.70 (dd, 1H), 3.55-3.39 (m, 3H), 2.74 (s, 3H), 2.28-2.17 (m, 2H), 1.32 (t, 3H). MS (EI) Calc'd for C$_{20}$H$_{24}$FN$_8$O$_2$ [M+H]$^+$, 427. found 427.

Example 10C—Preparation of Compound 5-12

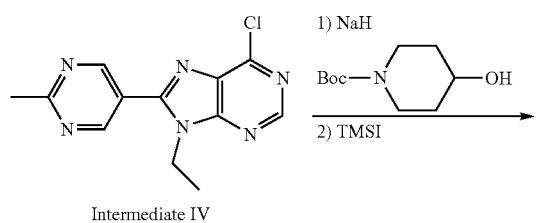

Intermediate IV

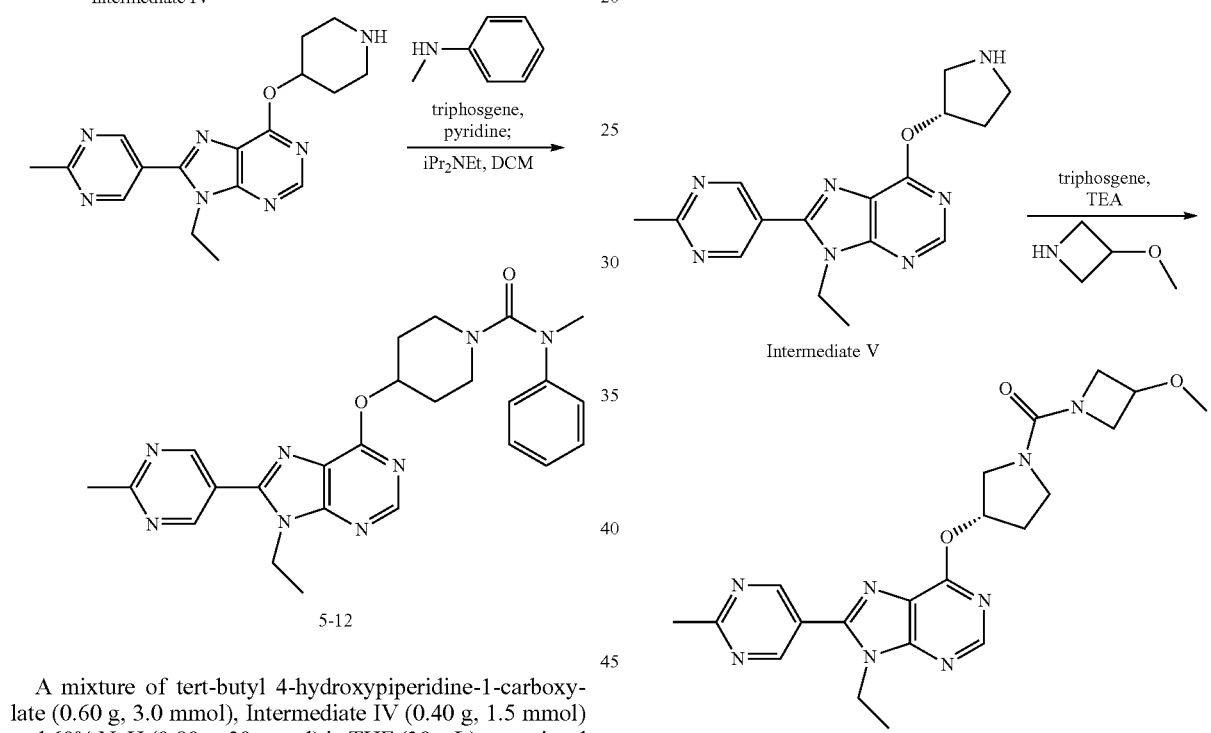

A mixture of tert-butyl 4-hydroxypiperidine-1-carboxylate (0.60 g, 3.0 mmol), Intermediate IV (0.40 g, 1.5 mmol) and 60% NaH (0.80 g, 20 mmol) in THF (30 mL) was stirred at ambient temperature for 18 h. The mixture was cooled, quenched with water (4.0 mL), and extracted with DCM (2×10 mL). The combined organic extracts were washed with brine (10 mL), dried over anhydrous Na$_2$SO$_4$, filtered and concentrated to afford tert-butyl 4-((9-ethyl-8-(2-methylpyrimidin-5-yl)-9H-purin-6-yl)oxy)piperidine-1-carboxylate as a crude residue. MS (EI) Calc'd for C$_{22}$H$_{30}$N$_7$O$_3$ [M+H]$^+$, 440. found, 440.

To a mixture of tert-butyl 4-((9-ethyl-8-(2-methylpyrimidin-5-yl)-9H-purin-6-yl)oxy) piperidine-1-carboxylate (0.10 g, 0.23 mmol) in DCM (5.0 mL) stirred at 0° C. was added TMSI (0.70 g, 3.5 mmol). The reaction was stirred for 2 hours and concentrated to afford a crude residue. MS (ESI) Calc'd for C$_{17}$H$_{22}$N$_7$O [M+H]$^+$, 340. found, 340.

To a mixture of Et$_3$N (1.0 mL, 7.5 mmol), N-methylaniline (0.40 g, 3.7 mmol) and toluene (30 mL) at 0° C. was added dropwise triphosgene (0.39 g, 1.3 mmol) in toluene (5.0 mL). The reaction was stirred for 2 h to afford methyl (phenyl)carbamic chloride as a crude solution. To a mixture of 9-ethyl-8-(2-methylpyrimidin-5-yl)-6-(piperidin-4-yloxy)-9H-purine, HI salt (0.10 g, 0.30 mmol), DIEA (0.15 mL, 0.88 mmol) in DCM (10 mL) at 0° C. was added methyl(phenyl)carbamic chloride in toluene (3.0 mL, 0.33 mmol, 0.11 M) dropwise. The mixture was stirred at ambient temperature for 18 h, diluted with DCM (30 mL), washed with aqueous NaHCO$_3$ (10 mL), dried over anhydrous Na$_2$SO$_4$, filtered and concentrated. The residue was purified by reverse phase HPLC (MeCN/water with 10 mM aqueous NH$_4$HCO$_3$ modifier) to give 5-12. $^1$H NMR (400 MHz, CDCl$_3$) δ 9.06 (s, 2H), 8.51 (s, 1H), 7.36-7.32 (m, 2H), 7.14-7.11 (m, 3H), 5.48 (m, 1H), 4.38 (q, J=7.2 Hz, 2H), 3.75-3.72 (m, 2H), 3.24 (s, 3H), 3.07-3.02 (m, 2H), 2.87 (s, 3H), 1.99-1.95 (m, 2H), 1.76-1.72 (m, 2H), 1.48 (t, J=7.2 Hz, 3H). MS (EI) Calc'd for C$_{25}$H$_{29}$N$_8$O$_2$ [M+H]$^+$, 473. found, 473.

Example 10D—Preparation of Compound 5-13

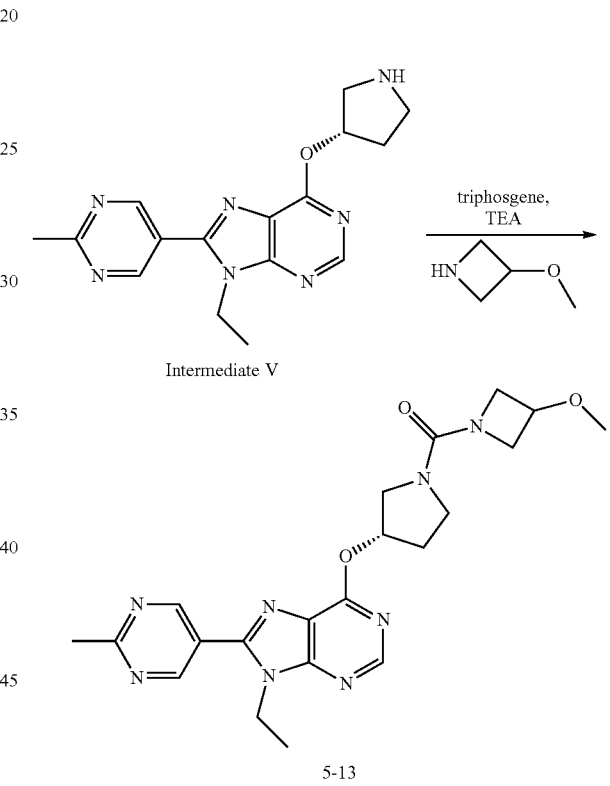

To a solution of 3-methoxyazetidine, HCl (0.020 g, 0.17 mmol) in DCM (3.3 mL) and TEA (0.092 mL, 0.66 mmol) in a vial was added triphosgene (0.030 g, 0.10 mmol). The solution was stirred at ambient temperature for 1 h. Simultaneously, in a separate vial, Intermediate V, HCl salt (0.060 g, 0.17 mmol) was suspended in DCM (0.50 mL) along with triethylamine (0.050 mL, 0.36 mmol). The solution was stirred at ambient temperature for 1 h, after which a suspension formed. This suspension was then added via syringe to the first vial and the reaction was stirred at ambient temperature for 16 h. The DCM was then evaporated under a stream of argon and the crude reaction mixture was then resuspened in DMF (1.0 mL). An additional portion of TEA (0.10 mL) was added, and the vial was heated to 50° C. for 72 h. The reaction vial was then cooled and diluted with DMSO (0.90 mL) and purified by reverse phase preparative HPLC to afford the TFA salt of 5-13. The TFA salt was then dissolved in methanol and eluted through a 1 g SiliPrep™ silicon-carbonate cartridge to afford neutral 5-13. ¹H NMR (500 MHz, DMSO-d$_6$) δ 9.13 (s, 2H), 8.59 (s, 1H), 5.82 (s, 1H), 4.35 (q, J=7.2 Hz, 2H), 4.17-4.04 (m, 2H), 4.04-3.92 (m, 1H), 3.78-3.61 (m, 3H), 3.53 (d, J=12.0 Hz, 1H), 3.49-3.37 (m, 2H), 3.16 (s, 3H), 2.74 (s, 3H), 2.31-2.11 (m, 2H), 1.32 (t, J=7.2 Hz, 3H). MS (EI) Calc'd for $C_{21}H_{27}N_8O_3$ [M+H]$^+$ 439. found 439.

Example 10E—Preparation of Compound 5-28

To a solution of Intermediate VII (500 mg, 1.1 mmol) in dioxane (20 mL) and water (0.5 mL) were added 5-(4,4,5,5-tetramethyl-1,3,2-dioxaborolan-2-yl)-2-(trifluoromethyl)pyridine (1.0 g, 3.7 mmol), potassium carbonate (964 mg, 7.0 mmol) and Pd(dppf)Cl$_2$ (174 mg, 0.213 mmol). The resulting mixture was stirred for 16 h at 80° C. The reaction mixture was quenched by the addition of water (30 mL), extracted with ethyl acetate (3×30 mL). The organic extracts were combined, dried over anhydrous sodium sulfate and filtered. The filtrate was concentrated under vacuum to give a residue, which was purified by silica gel column chroma-

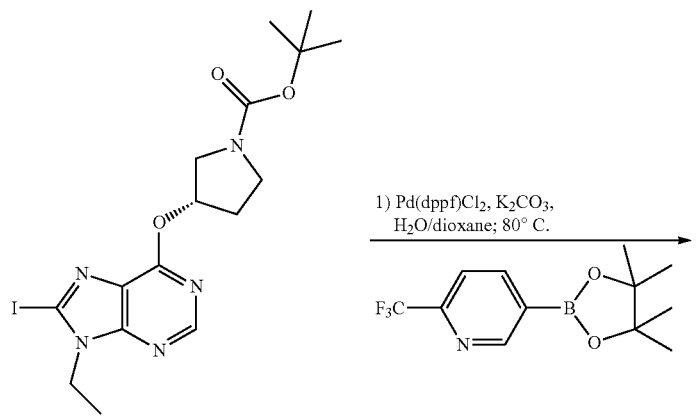

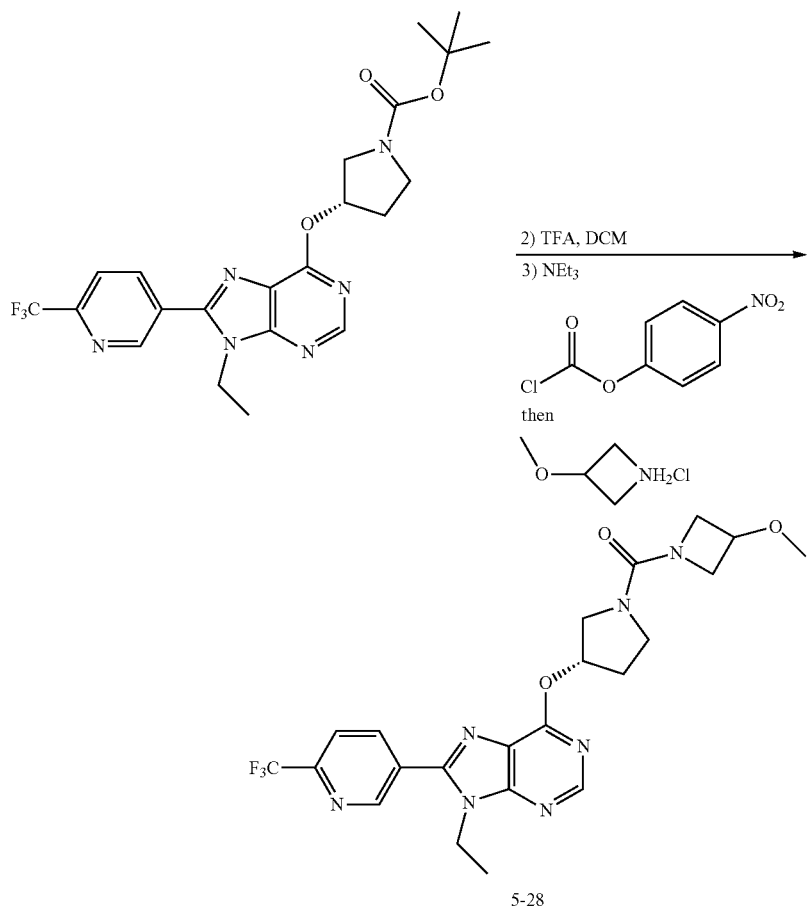

5-28 tography (25% ethyl acetate in petroleum ether) to afford (S)-tert-butyl 3-(9-ethyl-8-(6-(trifluoromethyl)pyridin-3-yl)-9H-purin-6-yloxy)pyrrolidine-1-carboxylate. MS (EI) Calc'd for $C_{22}H_{26}F_3N_6O_3$ [M+H]$^+$, 479. found, 479.

To a solution of(S)-tert-butyl 3-(9-ethyl-8-(6-(trifluoromethyl)pyridin-3-yl)-9H-purin-6-yloxy)pyrrolidine-1-carboxylate (500 mg, 1.05 mmol) in DCM (20 mL) was added trifluoroacetic acid (3 mL). The resulting solution was stirred for 1 h at ambient temperature. The reaction mixture was quenched by the addition of water (20 mL) and extracted with DCM (9×20 mL). The organic extracts were combined, dried over anhydrous sodium sulfate and filtered. The filtrate was concentrated under vacuum to afford (S)-9-ethyl-6-(pyrrolidin-3-yloxy)-8-(6-(trifluoromethyl)pyridin-3-yl)-9H-purine. MS (EI) Calc'd for $C_{17}H_{18}F_3N_6O$ [M+H]$^+$, 379. found, 379.

To a solution of (S)-9-ethyl-6-(pyrrolidin-3-yloxy)-8-(6-(trifluoromethyl)pyridin-3-yl)-9H-purine (100 mg, 0.26 mmol) in THF (15 mL) were added 4-nitrophenyl carbonochloridate (59 mg, 0.29 mmol) and triethylamine (40 mg, 0.40 mmol). The resulting mixture was stirred for 1 h at ambient temperature. Then 3-methoxyazetidine hydrochloride (163 mg, 1.32 mmol) and triethylamine (210 mg, 2.1 mmol) were added to the reaction mixture and the mixture was stirred for 2 days at 60° C. The reaction mixture was quenched by the addition of water (20 mL), and extracted with petroleum ether (3×30 mL). The organic extracts were combined, dried over anhydrous sodium sulfate and filtered. The filtrate was concentrated and was purified by Prep-TLC (30:1 DCM/MeOH) to afford 5-28. $^1$H NMR (300 MHz, DMSO-d$_6$) δ 9.22 (s, 1H), 8.64 (s, 1H), 8.58 (d, J=6.0 Hz, 1H), 8.16 (d, J=6.0 Hz, 1H), 5.85 (s, 1H), 4.42-4.38 (q, J=5.4 Hz, 2H), 4.13-4.09 (m, 2H), 4.07-4.00 (m, 1H), 3.76-3.71 (m, 3H), 3.69-3.66 (m, 1H), 3.58-3.48 (m, 2H), 3.18 (s, 3H), 2.28-2.23 (m, 2H), 1.37 (t, J=5.4 Hz, 3H). MS (EI) Calc'd for $C_{22}H_{25}F_3N_7O_3$ [M+H], 492. found, 492.

Compounds 5-1 to 5-3 and 5-5 to 5-7 were prepared in an analogous fashion as described for Example 10 from Intermediate II and the corresponding isocyanate.

Compound 5-8 was prepared in an analogous fashion as described for Example 10 from Intermediate V and the corresponding isocyanate.

Compounds 5-15 and 5-16 were prepared in an analogous fashion as described for Example 10D from the corresponding azetidine and pyrrolidine amines; the racemic mixture was then resolved by chiral column chromatography using the following conditions: Chiralpak column, IA, 21×250 mm, Flow Rate 70 mL/min, 8 min run time, Mobile Phase 40% MeOH in CO2, Wavelength 220 nm, 0.25 mL Injections of an 20 mg/mL MeOH solution. Compound 5-15 eluted at 3.4 min, while the enantiomer 5-16 eluted at 5.6 min.

Compound 5-8 was prepared in an analogous fashion as described in Example 10 using Intermediate V and the corresponding isocyanate.

Compounds 5-10 and 5-11 were prepared in an analogous fashion as described in Example 10A using Intermediate V and the corresponding amine.

Compounds 5-14 through 5-16 were prepared in an analogous fashion as described in Example 10D using Intermediate V and the corresponding amine.

Compounds 5-17 through 5-26 were prepared in an analogous fashion as described in Examples 10B using Intermediate V and the corresponding amine.

TABLE 5

| Compound | Structure | Compound Name | MS [M + H]$^+$ |
|---|---|---|---|
| 5-1 | 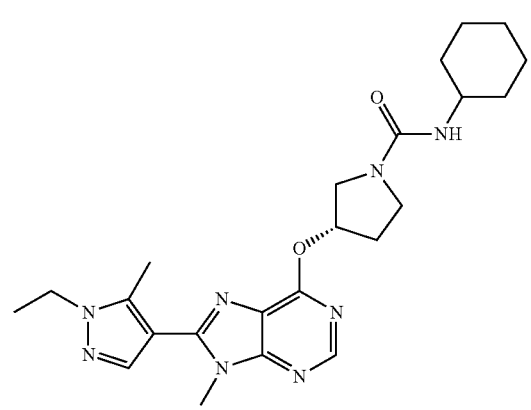 [SMILES: CCn1ncc(-c2nc3c(O[C@H]4CCN(C(=O)NC5CCCCC5)C4)ncnc3n2C)c1C] | (3S)-N-cyclohexyl-3-{[8-(1-ethyl-5-methyl-1H-pyrazol-4-yl)-9-methyl-9H-purin-6-yl]oxy}pyrrolidine-1-carboxamide | Calc'd 453, found 453 |

TABLE 5-continued

| Compound | Structure | Compound Name | MS [M + H]+ |
|---|---|---|---|
| 5-2 | 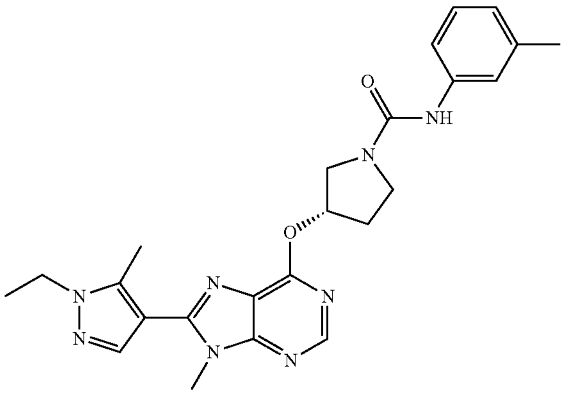 [SMILES: CCn1ncc(-c2nc3c(O[C@H]4CCN(C(=O)Nc5cccc(C)c5)C4)ncnc3n2C)c1C] | (3S)-3-{[8-(1-ethyl-5-methyl-1H-pyrazol-4-yl)-9-methyl-9H-purin-6-yl]oxy}-N-(3-methylphenyl)pyrrolidine-1-carboxamide | Calc'd 461, found 461 |
| 5-3 | 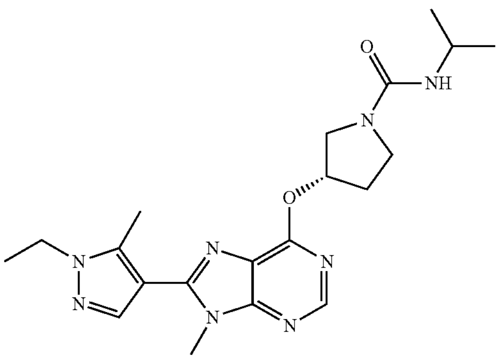 [SMILES: CCn1ncc(-c2nc3c(O[C@H]4CCN(C(=O)NC(C)C)C4)ncnc3n2C)c1C] | (3S)-3-{[8-(1-ethyl-5-methyl-1H-pyrazol-4-yl)-9-methyl-9H-purin-6-yl]oxy}-N-(1-methylethyl)pyrrolidine-1-carboxamide | Calc'd 413, found 413 |
| 5-4 | 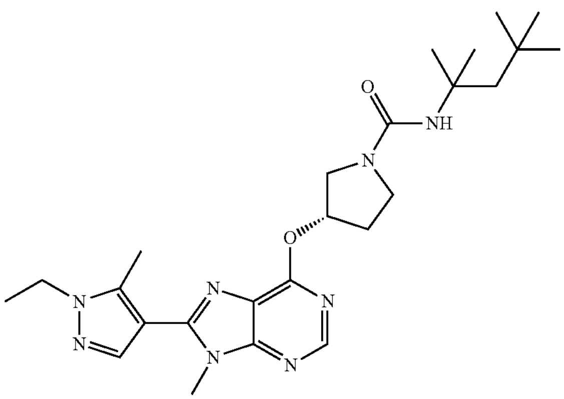 [SMILES: CCn1ncc(-c2nc3c(O[C@H]4CCN(C(=O)NC(C)(C)CC(C)(C)C)C4)ncnc3n2C)c1C] | (3S)-3-{[8-(1-ethyl-5-methyl-1H-pyrazol-4-yl)-9-methyl-9H-purin-6-yl]oxy}-N-(1,1,3,3-tetramethylbutyl)pyrrolidine-1-carboxamide | Calc'd 483, found 483 |
| 5-5 | 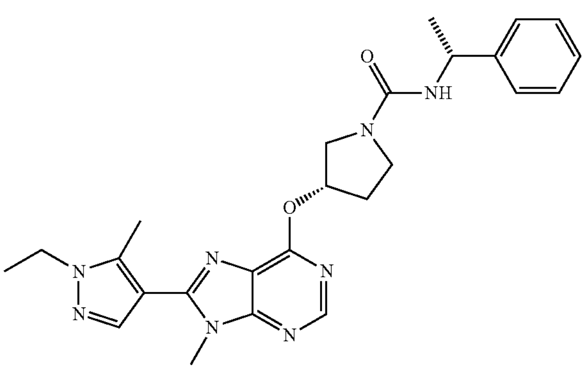 | (3S)-3-{[8-(1-ethyl-5-methyl-1H-pyrazol-4-yl)-9-methyl-9H-purin-6-yl]oxy}-N-[(1R)-1-phenylethyl]pyrrolidine-1-carboxamide | Calc'd 475, found 475 |

TABLE 5-continued

| Compound | Structure | Compound Name | MS [M + H]+ |
|---|---|---|---|
| 5-6 | 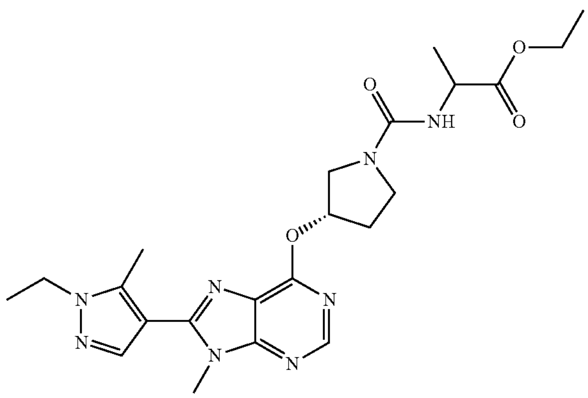 [SMILES: CCOC(=O)C(C)NC(=O)N1CC[C@H](Oc2ncnc3c2nc(-c2cnn(CC)c2C)n3C)C1] | ethyl N-{[(3S)-3-{[8-(1-ethyl-5-methyl-1H-pyrazol-4-yl)-9-methyl-9H-purin-6-yl]oxy}pyrrolidin-1-yl]carbonyl}alaninate | Calc'd 471, found 471 |
| 5-7 | 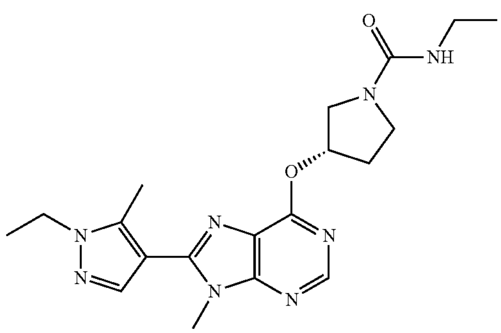 [SMILES: CCNC(=O)N1CC[C@H](Oc2ncnc3c2nc(-c2cnn(CC)c2C)n3C)C1] | (S)-N-ethyl-3-((8-(1-ethyl-5-methyl-1H-pyrazol-4-yl)-9-methyl-9H-purin-6-yl]oxy}pyrrolidine-1-carboxamide | Calc'd 399, found 399 |
| 5-8 | 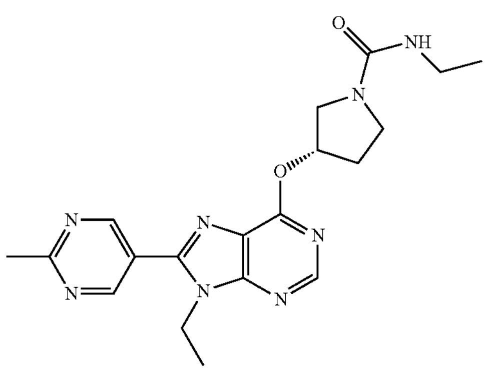 [SMILES: CCNC(=O)N1CC[C@H](Oc2ncnc3c2nc(-c2cnc(C)nc2)n3CC)C1] | (3S)-N-ethyl-3-{[9-ethyl-8-(2-methylpyrimidin-5-yl)-9H-purin-6-yl]oxy}pyrrolidine-1-carboxamide | Calc'd 397, found 397 |
| 5-9 | 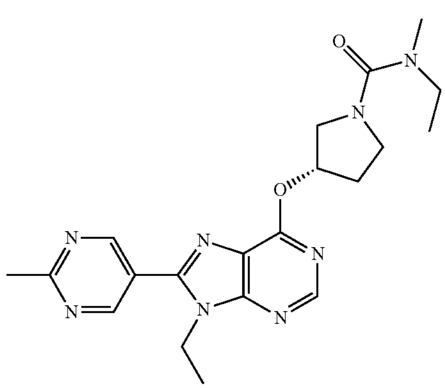 [SMILES: CCN(C)C(=O)N1CC[C@H](Oc2ncnc3c2nc(-c2cnc(C)nc2)n3CC)C1] | (3S)-N-ethyl-3-{[9-ethyl-8-(2-methylpyrimidin-5-yl)-9H-purin-6-yl]oxy}-N-methylpyrrolidine-1-carboxamide | Calc'd 411, found 411 |

TABLE 5-continued

| Compound | Structure | Compound Name | MS [M + H]+ |
|---|---|---|---|
| 5-10 | 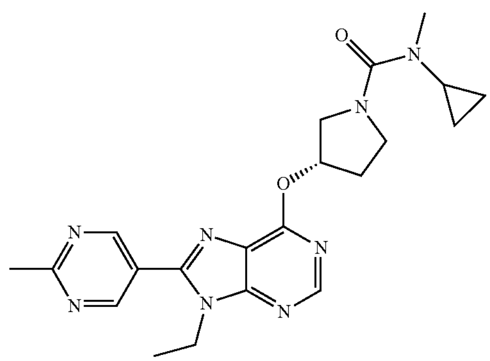 [SMILES: CCn1c(-c2cnc(C)nc2)nc2c(O[C@H]3CCN(C(=O)N(C)C4CC4)C3)ncnc21] | (3S)-N-cyclopropyl-3-{[9-ethyl-8-(2-methylpyrimidin-5-yl)-9H-purin-6-yl]oxy}-N-methylpyrrolidine-1-carboxamide | Calc'd 423, found 423 |
| 5-11 | 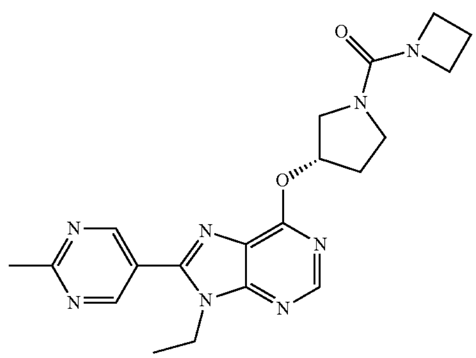 [SMILES: CCn1c(-c2cnc(C)nc2)nc2c(O[C@H]3CCN(C(=O)N4CCC4)C3)ncnc21] | 6-{[(3S)-1-(azetidin-1-ylcarbonyl)pyrrolidin-3-yl]oxy}-9-ethyl-8-(2-methylpyrimidin-5-yl)-9H-purine | Calc'd 409, found 409 |
| 5-12 | 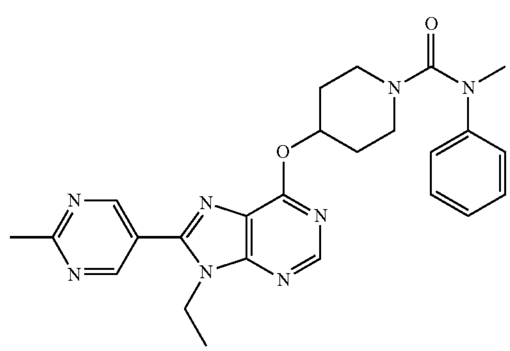 [SMILES: CCn1c(-c2cnc(C)nc2)nc2c(OC3CCN(C(=O)N(C)c4ccccc4)CC3)ncnc21] | 4-{[9-ethyl-8-(2-methylpyrimidin-5-yl)-9H-purin-6-yl]oxy}-N-methyl-N-phenylpiperidine-1-carboxamide | Calc'd 473, found 473 |
| 5-13 | 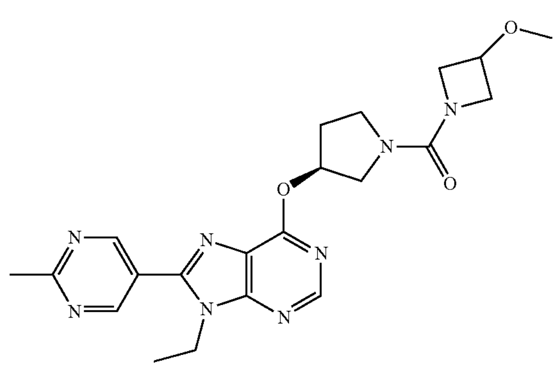 | 9-ethyl-6-({(3S)-1-[(3-methoxyazetidin-1-yl)carbonyl]pyrrolidin-3-yl}oxy)-8-(2-methylpyrimidin-5-yl)-9H-purine | Calc'd 439, found 439 |

TABLE 5-continued

| Compound | Structure | Compound Name | MS [M + H]+ |
|---|---|---|---|
| 5-14 | 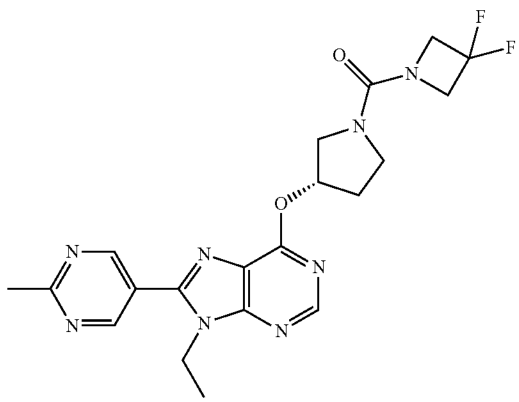 [SMILES: CCn1c(-c2cnc(C)nc2)nc2c(O[C@H]3CCN(C(=O)N4CC(F)(F)C4)C3)ncnc21] | 6-{[(3S)-1-[(3,3-difluoroazetidin-1-yl)carbonyl]pyrrolidin-3-yl}oxy)-9-ethyl-8-(2-methylpyrimidin-5-yl)-9H-purine | Calc'd 445, found 445 |
| 5-15 | 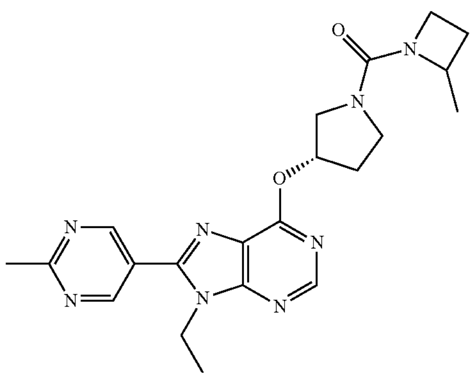 [SMILES: CCn1c(-c2cnc(C)nc2)nc2c(O[C@H]3CCN(C(=O)N4CCC4C)C3)ncnc21] | 9-ethyl-6-({(3S)-1-[((2R or 2S)-methylazetidin-1-yl)carbonyl]pyrrolidin-3-yl}oxy)-8-(2-methylpyrimidin-5-yl)-9H-purine | Calc'd 423, found 423 |
| 5-16 | 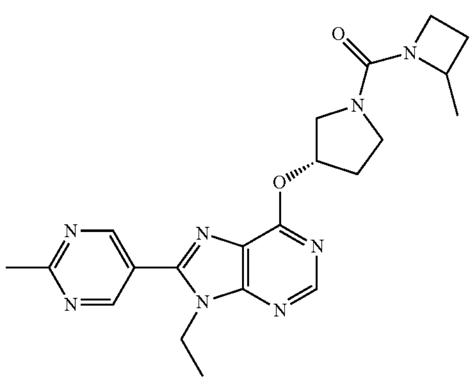 [SMILES: CCn1c(-c2cnc(C)nc2)nc2c(O[C@H]3CCN(C(=O)N4CCC4C)C3)ncnc21] | 9-ethyl-6-({(3S)-1-[((2R or 2S)-methylazetidin-1-yl)carbonyl]pyrrolidin-3-yl}oxy)-8-(2-methylpyrimidin-5-yl)-9H-purine | Calc'd 423, found 423 |
| 5-17 | 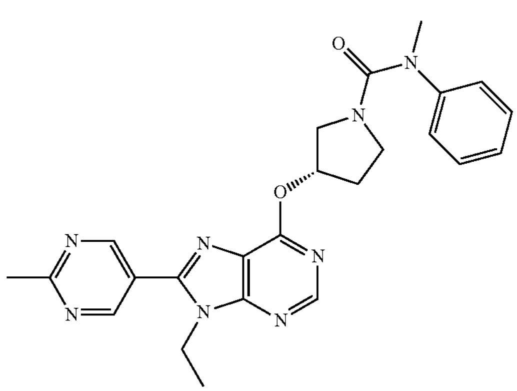 [SMILES: CCn1c(-c2cnc(C)nc2)nc2c(O[C@H]3CCN(C(=O)N(C)c4ccccc4)C3)ncnc21] | (3S)-3-{[9-ethyl-8-(2-methylpyrimidin-5-yl)-9H-purin-6-yl]oxy}-N-methyl-N-phenylpyrrolidine-1-carboxamide | Calc'd 459, found 459 |

TABLE 5-continued

| Compound | Structure | Compound Name | MS [M + H]+ |
|---|---|---|---|
| 5-18 | 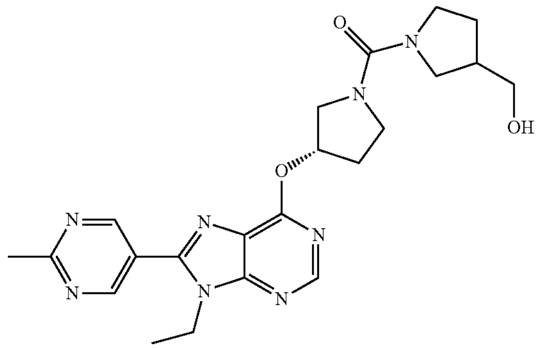 [SMILES: CCn1c(-c2cnc(C)nc2)nc2c(O[C@H]3CCN(C(=O)N4CCC(CO)C4)C3)ncnc21] | (1-{[(3S)-3-{[9-ethyl-8-(2-methylpyrimidin-5-yl)-9H-purin-6-yl]oxy}pyrrolidin-1-yl]carbonyl}pyrrolidin-3-yl)methanol | Calc'd 453, found 453 |
| 5-19 | 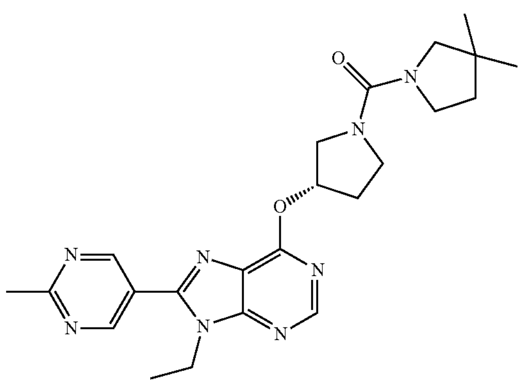 | 6-({(3S)-1-[(3,3-dimethylpyrrolidin-1-yl)carbonyl]pyrrolidin-3-yl}oxy)-9-ethyl-8-(2-methylpyrimidin-5-yl)-9H-purine | Calc'd 451, found 451 |
| 5-20 | 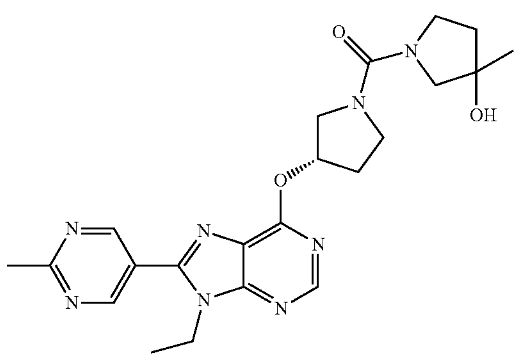 | 1-{[(3S)-3-{[9-ethyl-8-(2-methylpyrimidin-5-yl)-9H-purin-6-yl]oxy}pyrrolidin-1-yl]carbonyl}-3-methylpyrrolidin-3-ol | Calc'd 453, found 453 |
| 5-21 | 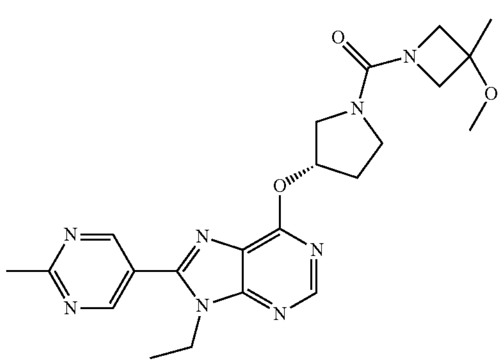 | 9-ethyl-6-({(3S)-1-[(3-methoxy-3-methylazetidin-1-yl)carbonyl]pyrrolidin-3-yl}oxy)-8-(2-methylpyrimidin-5-yl)-9H-purine | Calc'd 453, found 453 |

TABLE 5-continued

| Compound | Structure | Compound Name | MS [M + H]+ |
|---|---|---|---|
| 5-22 | 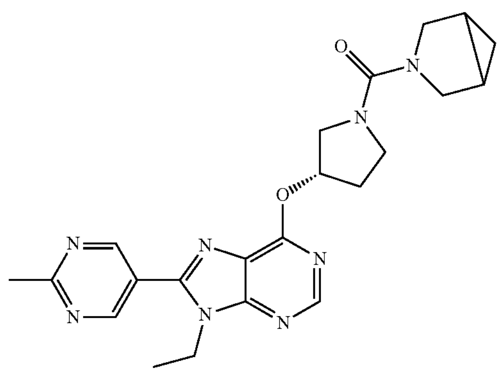 [SMILES: CCn1c(-c2cnc(C)nc2)nc2c(O[C@H]3CCN(C(=O)N4CC5CC5C4)C3)ncnc21] | 6-{[(3S)-1-(3-azabicyclo[3.1.0]hex-3-ylcarbonyl)pyrrolidin-3-yl]oxy}-9-ethyl-8-(2-methylpyrimidin-5-yl)-9H-purine | Calc'd 435, found 435 |
| 5-23 | 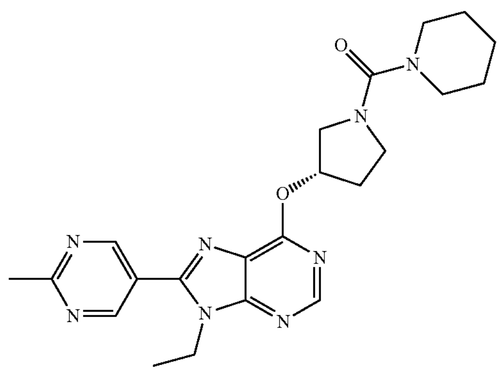 [SMILES: CCn1c(-c2cnc(C)nc2)nc2c(O[C@H]3CCN(C(=O)N4CCCCC4)C3)ncnc21] | 9-ethyl-8-(2-methylpyrimidin-5-yl)-6-{[(3S)-1-(piperidin-1-ylcarbonyl)pyrrolidin-3-yl]oxy}-9H-purine | Calc'd 437, found 437 |
| 5-24 | 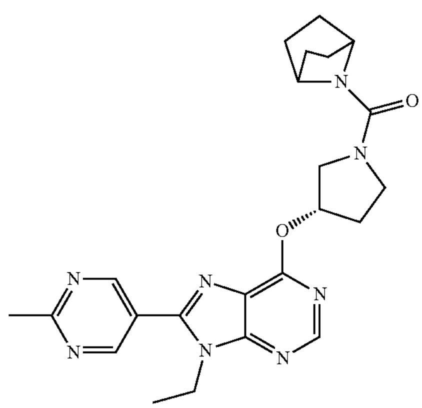 [SMILES: CCn1c(-c2cnc(C)nc2)nc2c(O[C@H]3CCN(C(=O)N4C5CCC4CC5)C3)ncnc21] | 6-({(3S)-1-[(7-azabicyclo[2.2.1]hept-7-ylcarbonyl]pyrrolidin-3-yl}oxy)-9-ethyl-8-(2-methylpyrimidin-5-yl)-9H-purine | Calc'd 449, found 449 |
| 5-25 | 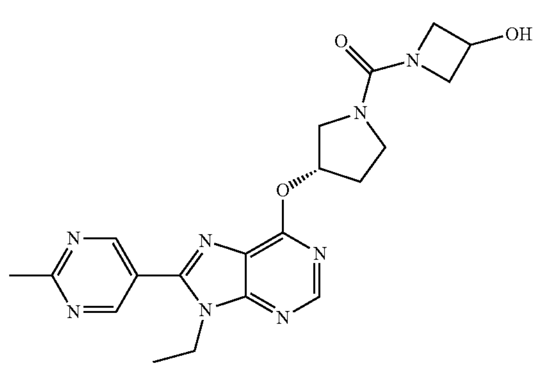 [SMILES: CCn1c(-c2cnc(C)nc2)nc2c(O[C@H]3CCN(C(=O)N4CC(O)C4)C3)ncnc21] | 1-{[(3S)-3-{[9-ethyl-8-(2-methylpyrimidin-5-yl)-9H-purin-6-yl]oxy}pyrrolidin-1-yl]carbonyl}azetidin-3-ol | Calc'd 425, found 425 |

TABLE 5-continued

| Compound | Structure | Compound Name | MS [M + H]+ |
|---|---|---|---|
| 5-26 | 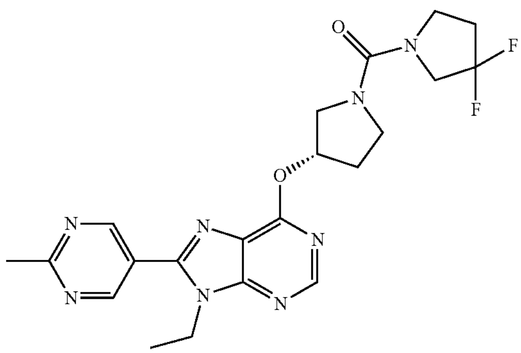 [SMILES: CCn1c(-c2cnc(C)nc2)nc2c(O[C@H]3CCN(C(=O)N4CCC(F)(F)C4)C3)ncnc21] | 6-({(3S)-1-[(3,3-difluoropyrrolidin-1-yl)carbonyl]pyrrolidin-3-yl}oxy)-9-ethyl-8-(2-methylpyrimidin-5-yl)-9H-purine | Calc'd 459, found 459 |
| 5-27 | 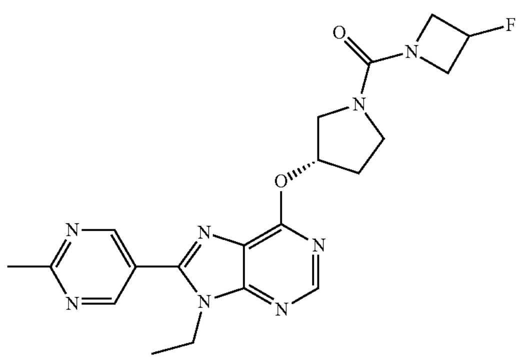 [SMILES: CCn1c(-c2cnc(C)nc2)nc2c(O[C@H]3CCN(C(=O)N4CC(F)C4)C3)ncnc21] | 9-ethyl-6-({(3S)-1-[(3-fluoroazetidin-1-yl)carbonyl]pyrrolidin-3-yl}oxy)-8-(2-methylpyrimidin-5-yl)-9H-purine | Calc'd 427, found 427 |
| 5-28 | 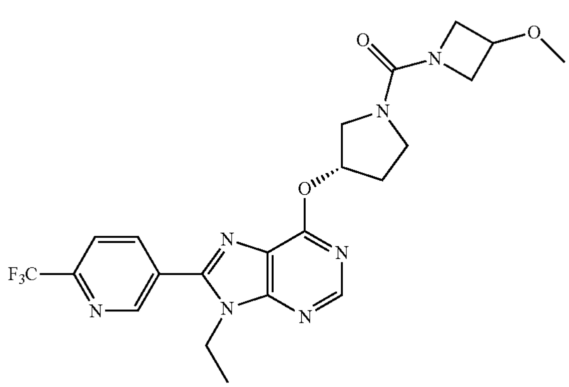 [SMILES: CCn1c(-c2ccc(C(F)(F)F)nc2)nc2c(O[C@H]3CCN(C(=O)N4CC(OC)C4)C3)ncnc21] | (S)-(3-((9-ethyl-8-(6-(trifluoromethyl)pyridin-3-yl)-9H-purin-6-yl)oxy)pyrrolidin-1-yl)(3-methoxyazetidin-1-yl)methanone | Calc'd 492, found 492 |

Compound Examples of Table 6

Example 11—Preparation of Compound 6-3

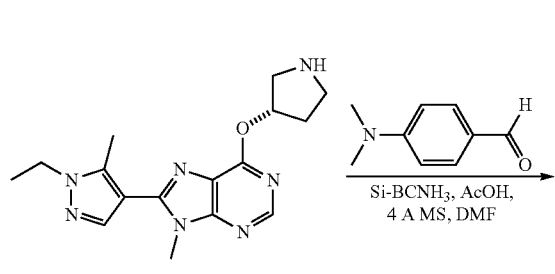

Intermediate II

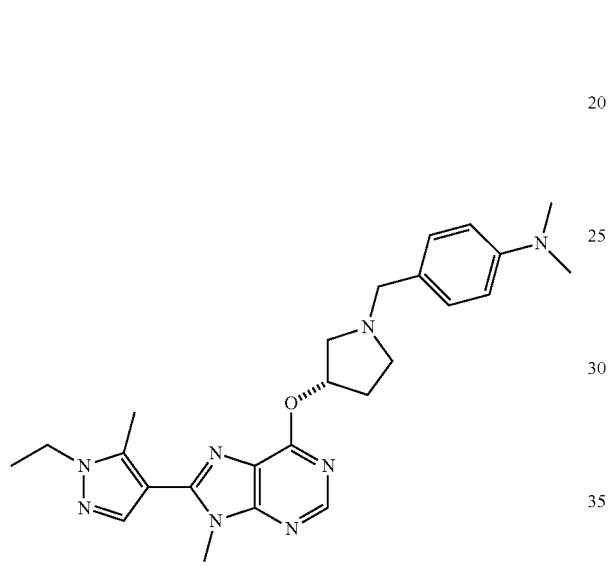

6-3

Example 11A—Preparation of Compound 6-5

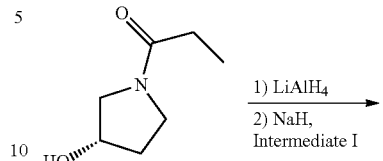

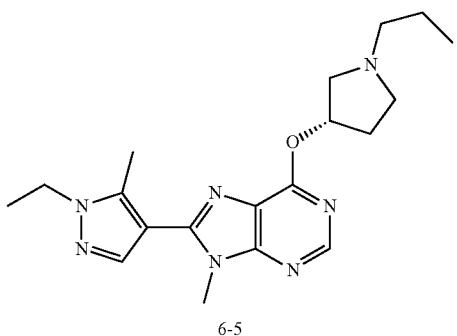

6-5

A solution of Intermediate II (25 mg, 0.076 mmol) in 1.5 mL of DMF was treated with AcOH (0.075 mL), 4-(dimethylamino)benzaldehyde (15 mg, 0.10 mmol) and powdered 3 angstrom molecular seives (75 mg). The vial was sealed and stirred overnight at 40° C. Next, Si-Cyanoborohydride (239 mg, 0.229 mmol) was added to the vial and the reaction mixture stirred again overnight at 40° C. The mixture was filtered, washing the filter with DMSO (1.5 mL). The crude product in 3 mL of 1:1 DMSO/DMF was purified by reverse phase HPLC. The desired fraction was concentrated under reduced pressure to yield compound 6-3 as the TFA salt. $^1$H NMR (600 MHz, DMSO-$d_6$) δ 8.48 (m, 1H), 8.00 (m, 1H), 7.29 (m, 2H), 6.69 (m, 2H), 5.86 (m, 1H), 4.32 (d, J=5.1 Hz, 1H), 4.24 (s, 1H), 4.15 (t, J=7.2 Hz, 2H), 3.84 (m, 3H), 3.85-3.20 (m, 4H), 2.88 (m, 6H), 2.50 (m, 3H), 2.75-2.20 (m, 2H), 1.33 (td, J=7.2, 2.3 Hz, 3H); MS (EI) Calc'd for $C_{25}H_{33}N_8O$ [M+H]$^+$, 461. found 461.

To a solution of (S)-1-(3-hydroxypyrrolidin-1-yl)propan-1-one (100 mg, 0.70 mmol) in THF (7 mL) was added LiAlH$_4$ (80 mg, 2.1 mmol) under N$_2$ pressure at 0° C. The resulting mixture was stirred for 15 h at room temperature. Water (0.1 mL), NaOH (0.1 mL, 4 M) and water (0.3 mL) were added and the reaction mixture filtered. The filtrate was concentrated to afford (S)-1-propylpyrrolidin-3-ol. MS (EI) Calc'd for $C_7H_{16}NO$ [M+H]$^+$, 130. found, 130.

To a solution of (S)-1-propylpyrrolidin-3-ol (90 mg, 0.70 mmol) in THF (10 mL) was added 60% NaH in mineral oil (60 mg, 2.4 mmol). The resulting mixture was stirred for 30 minutes at 0° C. and Intermediate I (240 mg, 0.86 mmol) was added. The reaction mixture was stirred at room temperature for 15 h, diluted with water (10 mL) and extracted with EtOAc (10 mL). The combined organic extracts was dried over Na$_2$SO$_4$, filtered and concentrated. The residue was purified with preparative HPLC (MeCN/water with 10 mM aqueous NH$_4$HCO$_3$ modifier) to afford 6-5. $^1$H NMR (400 MHz, DMSO-$d_6$) δ 8.50 (s, 1H), 7.95 (s, 1H), 5.81-5.78 (m, 1H), 4.30-4.25 (m, 2H), 3.90 (s, 3H), 3.33-3.13 (m, 1H), 2.96-2.87 (m, 2H), 2.67-2.46 (m, 7H), 2.18-2.16 (m, 1H), 1.62-1.46 (m, 5H), 0.96-0.94 (m, 3H). MS (EI) Calc'd for $C_{19}H_{28}N_7O$ [M+H]$^+$, 370. found, 370.

Compounds 6-1, 6-2, 6-4 were prepared in an analogous fashion as described for Example 11.

Compound 6-6 was prepared in an analogous fashion as described for Example 11A using Intermediate IV and 1-benzyl-4,4-dimethylpyrrolidin-3-ol; a preparation of which is described in WO 2012/125893.

TABLE 6

| Compound | Compound Name | MS [M + H]⁺ |
|---|---|---|
| 6-1 | 8-(1-ethyl-5-methyl-1H-pyrazol-4-yl)-9-methyl-6-{[(3S)-1-(1-phenylethyl)pyrrolidin-3-yl]oxy}-9H-purine | Calc'd 432, found 432 |
| 6-2 | 6-{[(3S)-1-(cyclohexylmethyl)pyrrolidin-3-yl]oxy}-8-(1-ethyl-5-methyl-1H-pyrazol-4-yl)-9-methyl-9H-purine | Calc'd 424, found 424 |
| 6-3 | 4-{[(3S)-3-{[8-(1-ethyl-5-methyl-1H-pyrazol-4-yl)-9-methyl-9H-purin-6-yl]oxy}pyrrolidin-1-yl]methyl}-N,N-dimethylaniline | Calc'd 461, found 461 |
| 6-4 | 8-(1-ethyl-5-methyl-1H-pyrazol-4-yl)-9-methyl-6-{[(3S)-1-(1H-pyrrol-2-ylmethyl)pyrrolidin-3-yl]oxy}-9H-purine | Calc'd 407, found 407 |

TABLE 6-continued

| Compound | Structure | Compound Name | MS [M + H]+ |
|---|---|---|---|
| 6-5 | 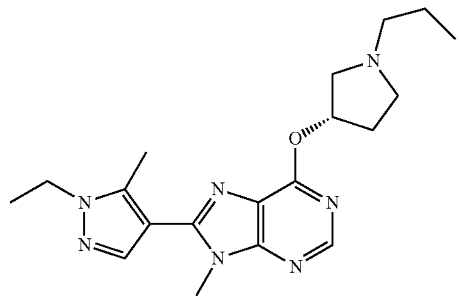 [SMILES: CCCN1CC[C@H](Oc2ncnc3c2nc(-c2cnn(CC)c2C)n3C)C1] | (S)-8-(1-ethyl-5-methyl-1H-pyrazol-4-yl)-9-methyl-6-((1-propylpyrrolidin-3-yl)oxy)-9H-purine | Calc'd 370, found 370 |
| 6-6 | 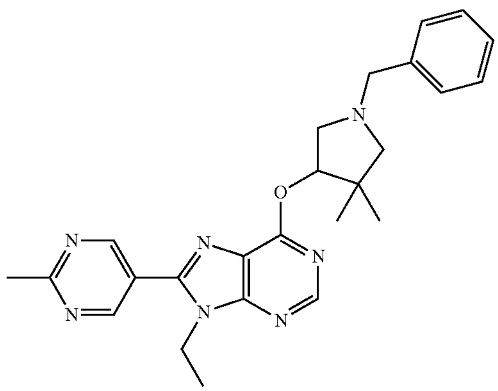 [SMILES: CCn1c(-c2cnc(C)nc2)nc2c(OC3CN(Cc4ccccc4)CC3(C)C)ncnc21] | 6-((1-benzyl-4,4-dimethylpyrrolidin-3-yl)oxy)-9-ethyl-8-(2-methylpyrimidin-5-yl)-9H-purine | Calc'd 444, found 444 |

Compound Examples of Table 7

Example 12—Preparation of 7-1

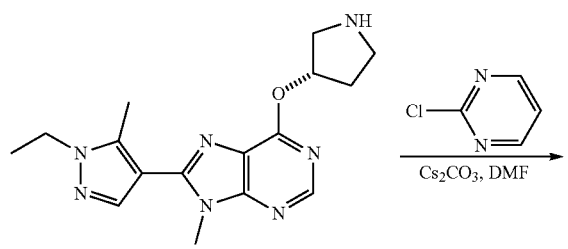

A solution of Intermediate II (30 mg, 0.092 mmol) in 1 mL of DMF was added to a vial containing 2-chloropyrimidine (23 mg, 0.20 mmol). Next, cesium carbonate (65 mg, 0.20 mmol) was added and the reaction warmed to 100° C. After stirring for 1 hour, LC/MS analysis indicated good conversion to the desired product. Filtered reaction mixture, diluted with DMSO and purified by reverse phase chromatography to provide the TFA salt of 7-1. $^1$H NMR (600 MHz, DMSO-$d_6$) δ 8.50 (s, 1H), 8.35 (m, 2H), 7.95 (s, 1H), 6.63 (t, J=4.7 Hz, 1H), 5.95 (m, 1H), 4.13 (q, J=7.5 Hz, 2H), 3.89 (dd, J=13.6, 4.9 Hz, 1H), 3.82 (m, 1H), 3.81 (s, 3H), 3.76 (m, 1H), 3.60 (m, 1H), 2.51 (s, 3H), 2.45-2.30 (m, 2H), 1.31 (t, J=6.9 Hz, 3H); MS (EI) Calc'd for $C_{20}H_{24}N_9O$ [M+H]+, 406. found 406.

Example 12A—Preparation of Compound 7-16

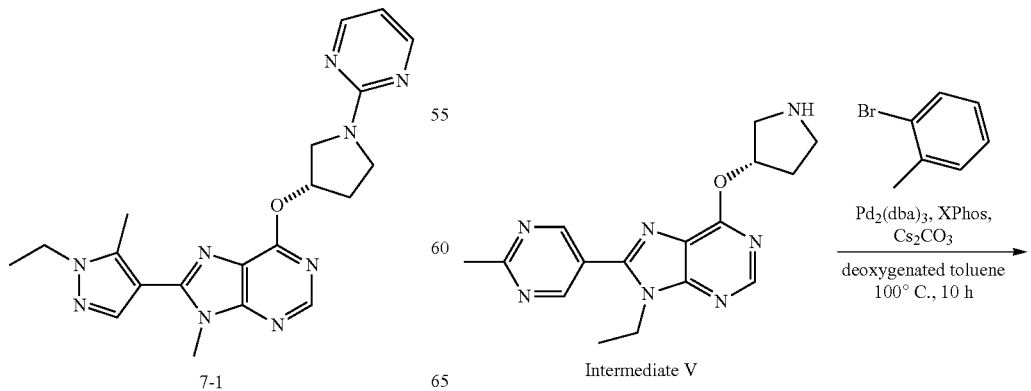

-continued

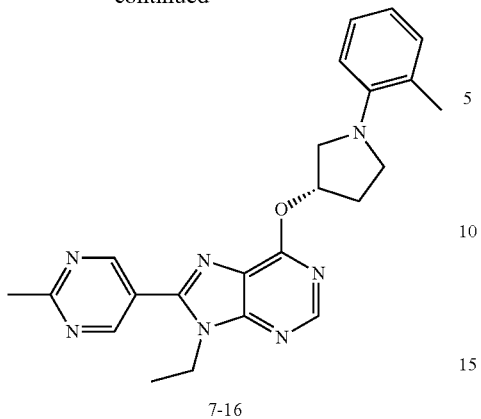

7-16

-continued

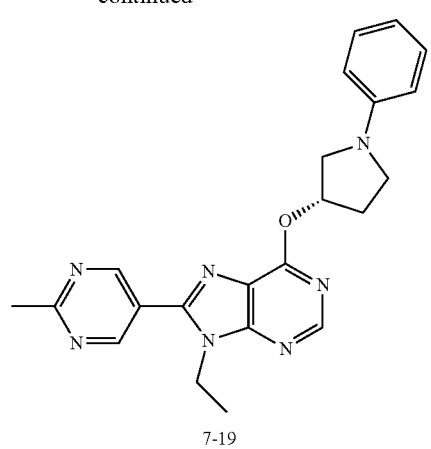

7-19

To a solution of Intermediate V (60 mg, 0.18 mmol) and 1-bromo-2-methylbenzene (63 mg, 0.37 mmol) in toluene (15 mL) were added Pd$_2$(dba)$_3$ (3 mg, 0.004 mmol), Cs$_2$CO$_3$ (21 mg, 0.060 mmol) and Xphos (2 mg, 0.004 mmol) at room temperature. The resulting mixture was stirred at 100° C. for 12 hours under an atmosphere of nitrogen, diluted with toluene (50 mL) and then washed with H$_2$O (3×50 mL). The organic layer was separated, washed with brine, dried over Na$_2$SO$_4$, filtered and concentrated. The crude product was purified by preparative reverse phase HPLC to provide the TFA salt of 7-16. $^1$H NMR (400 MHz, CD$_3$OD) δ 9.10 (s, 2H), 8.57 (s, 1H), 7.07 (t, J=7.6 Hz, 2H), 6.98-6.93 (m, 1H), 6.86-6.80 (m, 1H), 5.98-5.92 (m, 1H), 4.43 (q, J=7.2 Hz, 2H), 3.78-3.72 (m, 1H), 3.55-3.48 (m, 1H), 3.41-3.35 (m, 1H), 3.19-3.13 (m, 1H), 2.81 (s, 3H), 2.58-2.48 (m, 1H), 2.37-2.27 (m, 4H), 1.45 (t, J=7.2 Hz, 3H). MS (EI) Calc'd for C$_{23}$H$_{26}$N$_7$O [M+H]$^+$, 416. found, 416.

Example 12B—Preparation of Compound 7-19

To a tube were added Intermediate V, HCl (0.025 g, 0.069 mmol), chloro(2-dicyclohexylphosphino-2',4',6'-triisopropyl-1,1'-biphenyl)[2-(2'-amino-1,1'-biphenyl)]palladium(II) (0.0082 g, 0.0010 mmol), cesium carbonate (0.068 g, 0.21 mmol), bromobenzene (0.011 g, 0.069 mmol) and dioxane (0.70 mL). The reaction vessel was purged with argon, sealed and warmed to 90° C. for 8 hours. The reaction mixture was filtered and concentrated. The residue was taken up in DMSO (1.0 mL), filtered, then purified by reverse phase preparative HPLC (acetonitrile/water/NH$_4$OH modifier) to afford 7-19. $^1$H NMR (600 MHz, DMSO-d$_6$) δ 9.09 (s, 2H), 8.60 (s, 1H), 7.13 (t, 2H), 6.58 (t, 1H), 6.54 (d, 2H), 5.99 (s, 1H), 4.33 (q, 2H), 3.72 (dd, 1H), 3.47-3.44 (m, 1H), 3.43-3.37 (m, 2H), 2.70 (s, 3H), 2.44-2.39 (m, 1H), 2.32-2.30 (m, 1H), 1.29 (t, 3H). MS (EI) Calc'd. for C$_{22}$H$_{24}$N$_7$O [M+H]$^+$, 402. found, 402.

Example 12C—Preparation of Compound 7-27

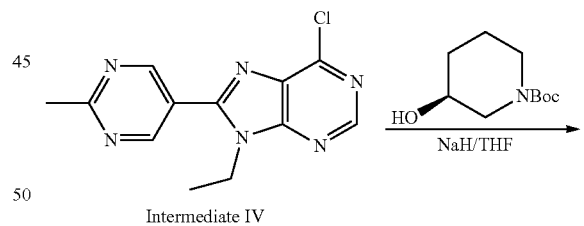

Intermediate IV

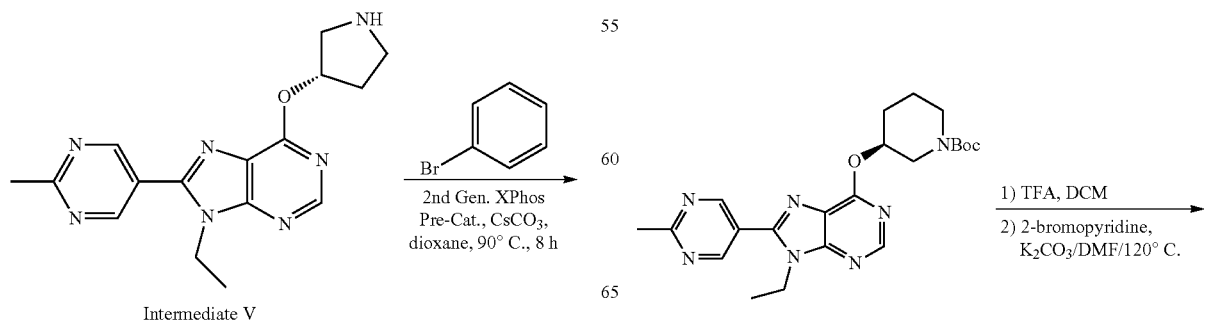

Intermediate V

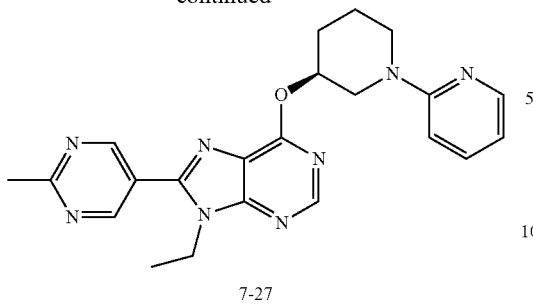

7-27

To a solution of (S)-tert-butyl 3-hydroxypiperidine-1-carboxylate (352 mg, 1.75 mmol in THF (20 mL) was added 60% sodium hydride in mineral oil (72 mg, 1.8 mmol) at 0° C. The resulting suspension was stirred at ambient temperature for 60 minutes before the addition of Intermediate IV (400 mg, 1.46 mmol). The mixture was stirred at ambient temperature for 15 hours and quenched with ice-water (100 mL), extracted with ethyl acetate (3×50 mL). The combined organic extracts were washed with saturated brine (2×50 mL), dried over sodium sulfate, filtered and concentrated under vacuum. The residue was purified by chromatography on silica gel (2%-5% ethyl acetate/hexane) to afford (S)-tert-butyl 3-(9-ethyl-8-(2-methylpyrimidin-5-yl)-9H-purin-6-yloxy)piperidine-1-carboxylate. MS (EI) Calc'd for $C_{22}H_{30}N_7O_3$ [M+H]$^+$, 440. found, 440.

To a solution of (S)-tert-butyl 3-(9-ethyl-8-(2-methylpyrimidin-5-yl)-9H-purin-6-yloxy)piperidine-1-carboxylate (500 mg, 1.14 mmol) in DCM (15 mL) was added trifluoroacetic acid (3 mL) at 10° C. The resulting solution was stirred at 25° C. for 1 h. The resulting mixture was concentrated and dissolved in water (15 mL), the pH was adjusted to 10 with saturated aqueous potassium carbonate. The resulting mixture was extracted with DCM (10×50 mL). The combined fractions were dried over anhydrous sodium sulfate, filtered and concentrated to afford (S)-9-ethyl-8-(2-methylpyrimidin-5-yl)-6-(piperidin-3-yloxy)-9H-purine. MS (EI) Calc'd for $C_{17}H_{22}N_7O$ [M+H]$^+$, 340. found, 340.

To a solution of (S)-9-ethyl-8-(2-methylpyrimidin-5-yl)-6-(piperidin-3-yloxy)-9H-purine (100 mg, 0.29 mmol) in DMF (2 mL) was added 2-bromopyridine (50 mg, 0.32 mmol) and potassium carbonate (61 mg, 0.44 mmol). The resulting mixture was stirred for 12 hours at 120° C. The reaction was cooled and quenched by the addition of water (100 mL), extracted with ethyl acetate (3×40 mL) and the organic extracts were combined, dried over anhydrous magnesium sulfate and filtered. The solvent was evaporated to give a residue which was purified by reverse phase HPLC (MeCN/water with 10 mM aqueous $NH_4HCO_3$ modifier) to afford 7-27. $^1$H NMR (300 MHz, DMSO-d$_6$) δ 9.17 (s, 2H), 8.63 (s, 1H), 8.07 (dd, J=1.6, 4.8 Hz, 1H), 7.55-7.50 (m, 1H), 6.90 (m, 1H), 6.62 (dd, J=5.2, 6.8 Hz, 1H), 5.47 (m, 1H), 4.41 (q, J=7.2 Hz, 2H), 4.23 (dd, J=3.6, 12.8 Hz, 1H), 3.90-3.80 (m, 1H), 3.57-3.52 (m, 1H), 3.39-3.31 (m, 1H), 2.78 (s, 3H), 2.22-2.12 (m, 1H), 1.94-1.90 (m, 2H), 1.68-1.67 (m, 1H), 1.37 (t, J=8.0 Hz, 3H). MS (EI) Calc'd for $C_{22}H_{25}N_8O$ [M+H]$^+$ 417. found, 417.

Compounds 7-2 to 7-15 were prepared in an analogous fashion as described for Example 12 using the corresponding aryl halide.

Compounds 7-17 and 7-18 were prepared in an analogous fashion as described for Example 12A using the corresponding aryl halide.

Compounds 7-20 to 7-26 were prepared in an analogous fashion as described for Example 12B using the corresponding aryl halide.

TABLE 7

| Compound | Structure | Compound Name | MS [M + H]$^+$ |
|---|---|---|---|
| 7-1 | 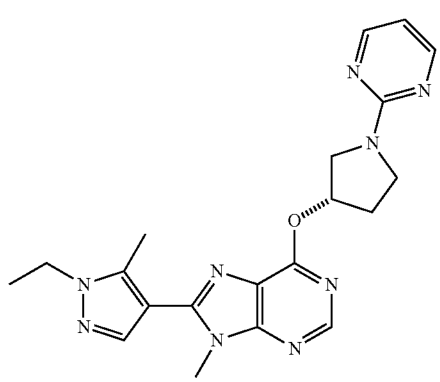 | 8-(1-ethyl-5-methyl-1H-pyrazol-4-yl)-9-methyl-6-{[(3S)-1-pyrimidin-2-ylpyrrolidin-3-yl]oxy}-9H-purine | Calc'd 406, found 406 |

TABLE 7-continued

| Compound | Structure | Compound Name | MS [M + H]+ |
|---|---|---|---|
| 7-2 | 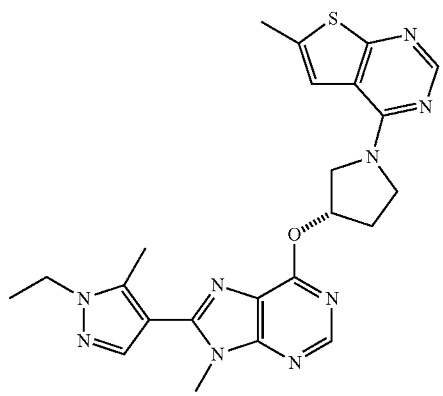 | 8-(1-ethyl-5-methyl-1H-pyrazol-4-yl)-9-methyl-6-{[(3S)-1-(6-methylthieno[2,3-d]pyrimidin-4-yl)pyrrolidin-3-yl]oxy}-9H-purine | Calc'd 476, found 476 |
| 7-3 | 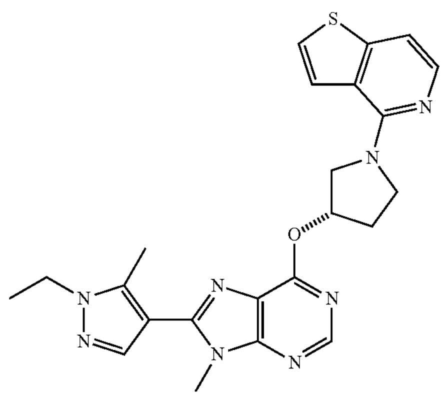 | 8-(1-ethyl-5-methyl-1H-pyrazol-4-yl)-9-methyl-6-{[(3S)-1-thieno[3,2-c]pyridin-4-ylpyrrolidin-3-yl]oxy}-9H-purine | Calc'd 461, found 461 |
| 7-4 | 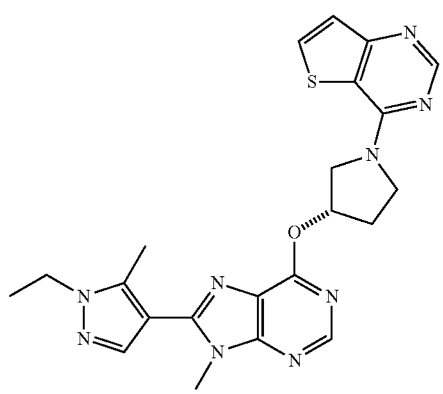 | 8-(1-ethyl-5-methyl-1H-pyrazol-4-yl)-9-methyl-6-{[(3S)-1-thieno[3,2-d]pyrimidin-4-ylpyrrolidin-3-yl]oxy}-9H-purine | Calc'd 462, found 462 |
| 7-5 | 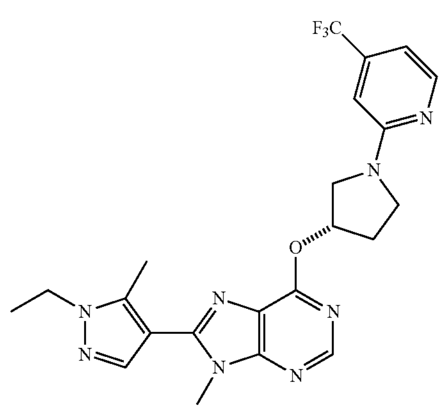 | 8-(1-ethyl-5-methyl-1H-pyrazol-4-yl)-9-methyl-6-({(3S)-1-[4-(trifluoromethyl)pyridin-2-yl]pyrrolidin-3-yl}oxy)-9H-purine | Calc'd 473, found 473 |

TABLE 7-continued

| Compound | Structure | Compound Name | MS [M + H]+ |
|---|---|---|---|
| 7-6 | 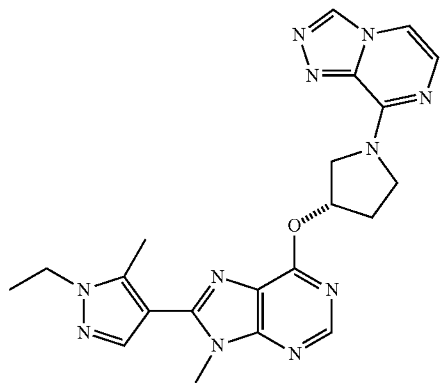 | 8-[(3S)-3-{[8-(1-ethyl-5-methyl-1H-pyrazol-4-yl)-9-methyl-9H-purin-6-yl]oxy}pyrrolidin-1-yl][1,2,4]triazolo[4,3-a]pyrazine | Calc'd 446, found 446 |
| 7-7 | 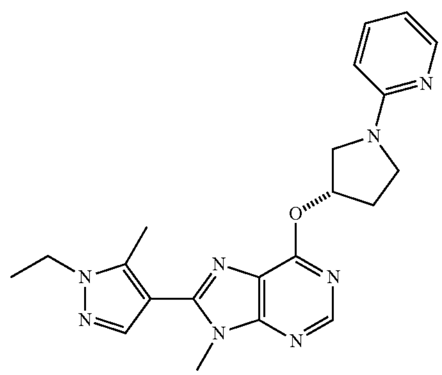 | 8-(1-ethyl-5-methyl-1H-pyrazol-4-yl)-9-methyl-6-{[(3S)-1-pyridin-2-ylpyrrolidin-3-yl]oxy}-9H-purine | Calc'd 405, found 405 |
| 7-8 | 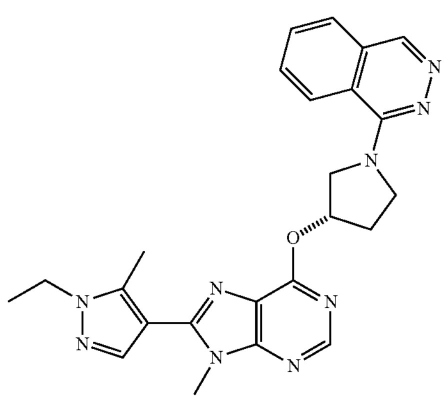 | 1-[(3S)-3-{[8-(1-ethyl-5-methyl-1H-pyrazol-4-yl)-9-methyl-9H-purin-6-yl]oxy}pyrrolidin-1-yl]phthalazine | Calc'd 456, found 456 |

TABLE 7-continued

| Compound | Structure | Compound Name | MS [M + H]+ |
|---|---|---|---|
| 7-9 | 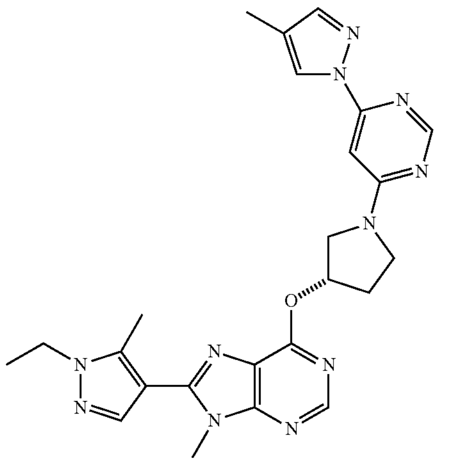 | 8-(1-ethyl-5-methyl-1H-pyrazol-4-yl)-9-methyl-6-({(3S)-1-[6-(4-methyl-1H-pyrazol-1-yl)pyrimidin-4-yl]pyrrolidin-3-yl}oxy)-9H-purine | Calc'd 486, found 486 |
| 7-10 | 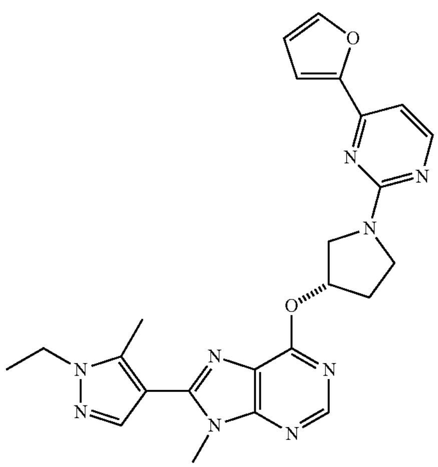 | 8-(1-ethyl-5-methyl-1H-pyrazol-4-yl)-6-{[(3S)-1-(4-furan-2-ylpyrimidin-2-yl)pyrrolidin-3-yl]oxy}-9-methyl-9H-purine | Calc'd 472, found 472 |
| 7-11 | 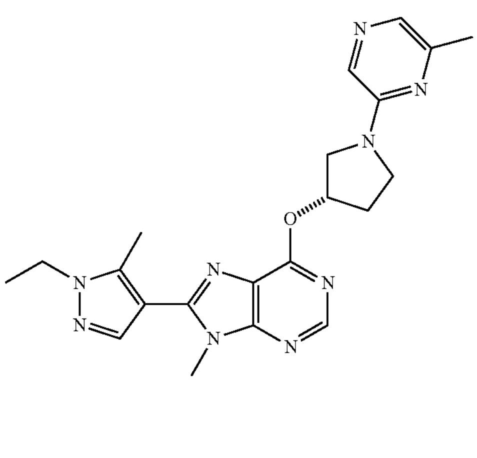 | 8-(1-ethyl-5-methyl-1H-pyrazol-4-yl)-9-methyl-6-{[(3S)-1-(6-methylpyrazin-2-yl)pyrrolidin-3-yl]oxy}-9H-purine | Calc'd 420, found 420 |

TABLE 7-continued

| Compound | Structure | Compound Name | MS [M + H]+ |
|---|---|---|---|
| 7-12 | 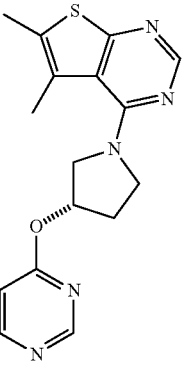 | 6-{[(3S)-1-(5,6-dimethylthieno[2,3-d]pyrimidin-4-yl)pyrrolidin-3-yl]oxy}-8-(1-ethyl-5-methyl-1H-pyrazol-4-yl)-9-methyl-9H-purine | Calc'd 490, found 490 |
| 7-13 | 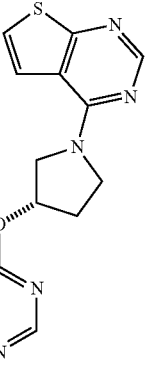 | 8-(1-ethyl-5-methyl-1H-pyrazol-4-yl)-9-methyl-6-{[(3S)-1-thieno[2,3-d]pyrimidin-4-ylpyrrolidin-3-yl]oxy}-9H-purine | Calc'd 462, found 462 |
| 7-14 | 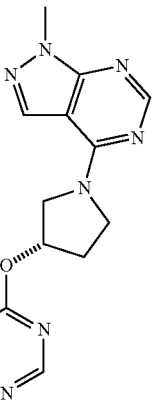 | 4-[(3S)-3-{[8-(1-ethyl-5-methyl-1H-pyrazol-4-yl)-9-methyl-9H-purin-6-yl]oxy}pyrrolidin-1-yl]-1-methyl-1H-pyrazolo[3,4-d]pyrimidine | Calc'd 460, found 460 |

TABLE 7-continued

| Compound | Structure | Compound Name | MS [M + H]+ |
|---|---|---|---|
| 7-15 | 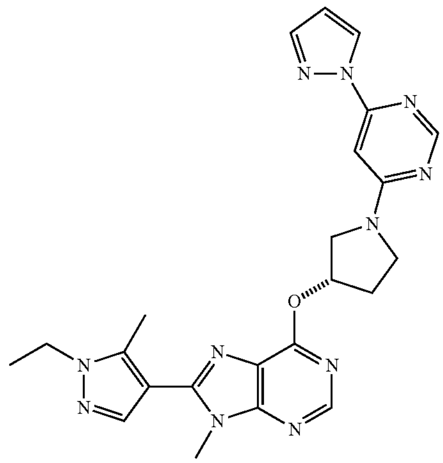 | 8-(1-ethyl-5-methyl-1H-pyrazol-4-yl)-9-methyl-6-({(3S)-1-[6-(1H-pyrazol-1-yl)pyrimidin-4-yl]pyrrolidin-3-yl}oxy)-9H-purine | Calc'd 472, found 472 |
| 7-16 | 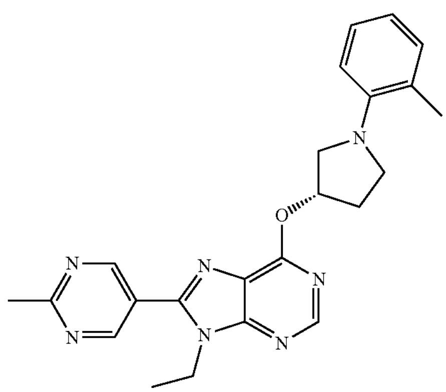 | 9-ethyl-6-{[(3S)-1-(2-methylphenyl)pyrrolidin-3-yl]oxy}-8-(2-methylpyrimidin-5-yl)-9H-purine | Calc'd 416, found 416 |
| 7-17 | 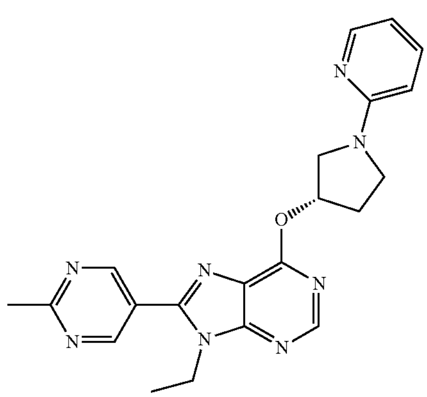 [SMILES: CCn1c(-c2cnc(C)nc2)nc2c(O[C@H]3CCN(c4ccccn4)C3)ncnc21] | 9-ethyl-8-(2-methylpyrimidin-5-yl)-6-{[(3S)-1-pyridin-2-ylpyrrolidin-3-yl]oxy}-9H-purine | Calc'd 403, found 403 |

TABLE 7-continued

| Compound | Structure | Compound Name | MS [M + H]+ |
|---|---|---|---|
| 7-18 | 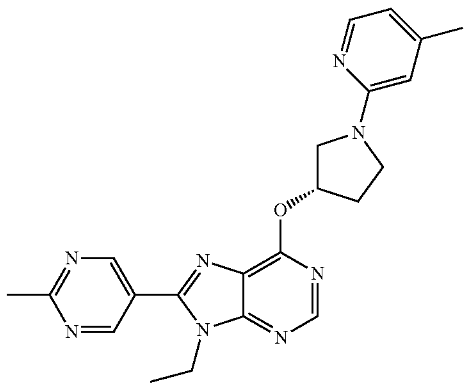 | 9-ethyl-6-{[(3S)-1-(4-methylpyridin-2-yl)pyrrolidin-3-yl]oxy}-8-(2-methylpyrimidin-5-yl)-9H-purine | Calc'd 417, found 417 |
| 7-19 | 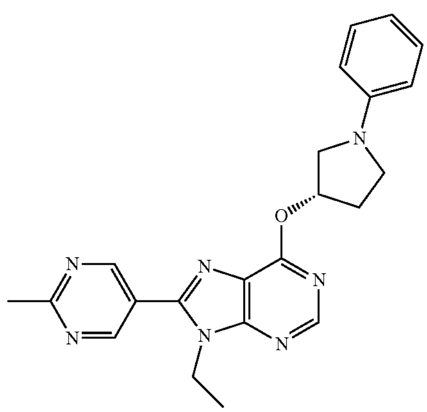 [SMILES: CCn1c(-c2cnc(C)nc2)nc2c(O[C@H]3CCN(c4ccccc4)C3)ncnc21] | 9-ethyl-8-(2-methylpyrimidin-5-yl)-6-{[(3S)-1-phenylpyrrolidin-3-yl]oxy}-9H-purine | Calc'd 402, found 402 |
| 7-20 | 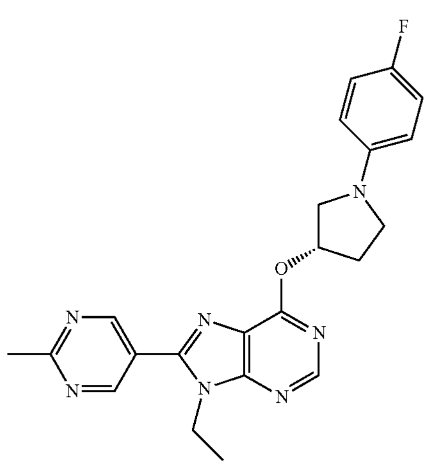 [SMILES: CCn1c(-c2cnc(C)nc2)nc2c(O[C@H]3CCN(c4ccc(F)cc4)C3)ncnc21] | 9-ethyl-6-{[(3S)-1-(4-fluorophenyl)pyrrolidin-3-yl]oxy}-8-(2-methylpyrimidin-5-yl)-9H-purine | Calc'd 420, found 420 |

TABLE 7-continued

| Compound | Compound Name | MS [M + H]+ |
|---|---|---|
| 7-21 | 9-ethyl-6-{[(3S)-1-(3-fluorophenyl)pyrrolidin-3-yl]oxy}-8-(2-methylpyrimidin-5-yl)-9H-purine | Calc'd 420, found 420 |
| 7-22 | 9-ethyl-8-(2-methylpyrimidin-5-yl)-6-{[(3S)-1-(1,3-thiazol-2-yl)pyrrolidin-3-yl]oxy}-9H-purine | Calc'd 409, found 409 |
| 7-23 | 9-ethyl-8-(2-methylpyrimidin-5-yl)-6-{[(3S)-1-pyrimidin-5-ylpyrrolidin-3-yl]oxy}-9H-purine | Calc'd 404, found 404 |
| 7-24 | 9-ethyl-8-(2-methylpyrimidin-5-yl)-6-{[(3S)-1-pyridin-3-ylprrolidin-3-yl]oxy}-9H-purine | Calc'd 403, found 403 |

TABLE 7-continued

| Compound | Structure | Compound Name | MS [M + H]+ |
|---|---|---|---|
| 7-25 | 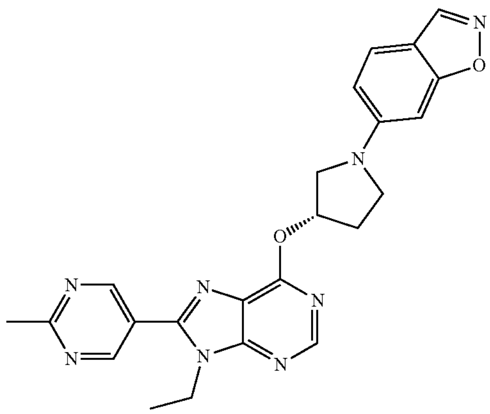 [SMILES: CCn1c(-c2cnc(C)nc2)nc2c(O[C@H]3CCN(c4ccc5cnoc5c4)C3)ncnc21] | 6-{[(3S)-1-(1,2-benzisoxazol-6-yl)pyrrolidin-3-yl]oxy}-9-ethyl-8-(2-methylpyrimidin-5-yl)-9H-purine | Calc'd 443, found 443 |
| 7-26 | 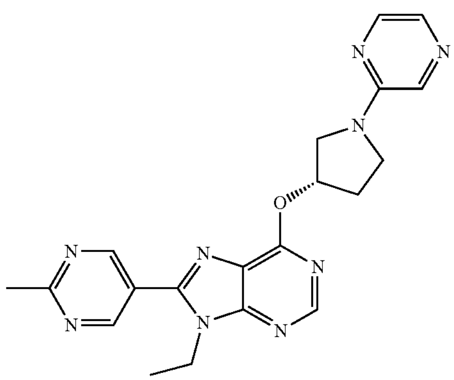 [SMILES: CCn1c(-c2cnc(C)nc2)nc2c(O[C@H]3CCN(c4cnccn4)C3)ncnc21] | 9-ethyl-8-(2-methylpyrimidin-5-yl)-6-{[(3S)-1-pyrazin-2-ylpyrrolidin-3-yl]oxy}-9H-purine | Calc'd 404, found 404 |
| 7-27 | 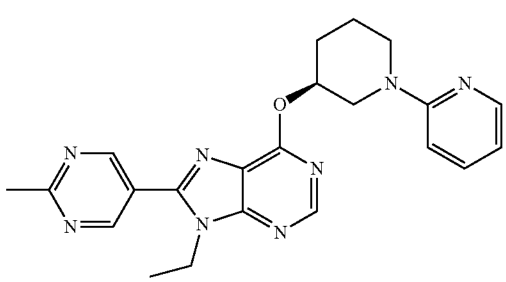 [SMILES: CCn1c(-c2cnc(C)nc2)nc2c(O[C@H]3CCCN(c4ccccn4)C3)ncnc21] | 9-ethyl-8-(2-methylpyrimidin-5-yl)-6-{[(3S)-1-pyridin-2-ylpiperidin-3-yl]oxy}-9H-purine | Calc'd 417, found 417 |

285
Compound Examples of Table 8

Example 13—Preparation of 8-1

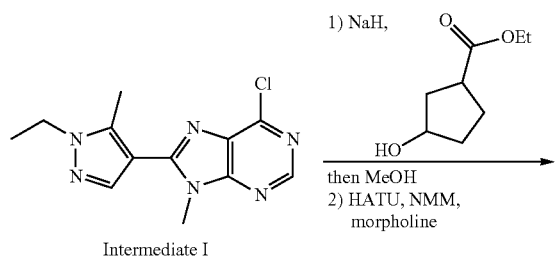

Intermediate I

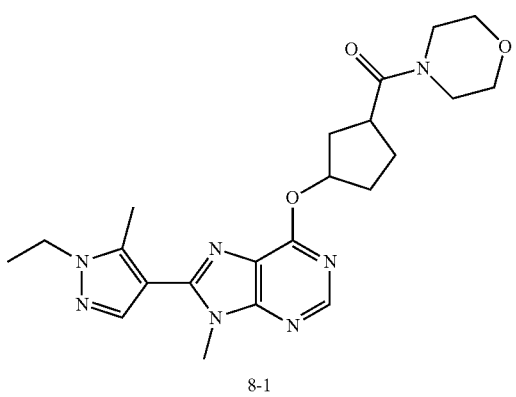

8-1

To a solution of ethyl 3-hydroxycyclopentanecarboxylate (100 mg, 0.65 mmol) in 5 mL of THF, a suspension of 60% NaH in mineral oil (40 mg, 0.98 mmol) was added at 0° C. and stirred at room temperature for 15 min. Next, Intermediate I was added (150 mg, 0.54 mmol) and the mixture stirred overnight. The reaction mixture was quenched with methanol (5 mL) and concentrated. Next, aqueous $NaHCO_3$ (10 mL) and ethyl acetate (10 mL) were added and separated. The aqueous layer was acidified by addition of 1 N aqueous HCL to pH~5 and extracted with DCM (three times 5 mL). The organic layer was washed with brine, dried over $Na_2SO_4$, filtered and concentrated to give an intermediate acid. MS (EI) Calc'd for $C_{18}H_{23}N_6O_3$ $[M+H]^+$, 371. found, 371.

This intermediate acid was dissolved in DMF (3 mL), treated with HATU (100 mg, 0.26 mmol) and stirred for 15 min. Next, morpholine (20 mg, 0.22 mmol) and 4-methylmorpholine (45 mg, 0.44 mmol) were added and the reaction mixture stirred overnight before being quenched with water (5 mL) and extracted with DCM (three time 5 mL). The organic layer was washed with brine, dried over $Na_2SO_4$, filtered and concentrated. The crude material was purified by reverse phase chromatography (water/MeCN with 0.05% TFA) to give the desired product; 8-1. $^1$H NMR (400 MHz, $CD_3OD$) δ 8.62 (s, 1H), 8.00 (s, 1H), 5.84-5.83 (m, 1H), 4.28 (q, J=4.8 Hz, 2H), 3.95 (s, 3H), 3.69-3.58 (m, 8H), 3.34-3.24 (m, 1H), 2.57-2.54 (m, 4H), 2.23-2.04 (m, 5H), 1.48 (t, J=4.8 Hz, 3H). MS (EI) Calc'd for $C_{22}H_{30}N_7O_3$ $[M+H]^+$, 440. found, 440.

The compounds included in the Table 8 below were prepared in an analogous fashion to that disclosed in Example 13.

TABLE 8

| Compound | Structure | Compound Name | MS [M + H]$^+$ |
|---|---|---|---|
| 8-1 | 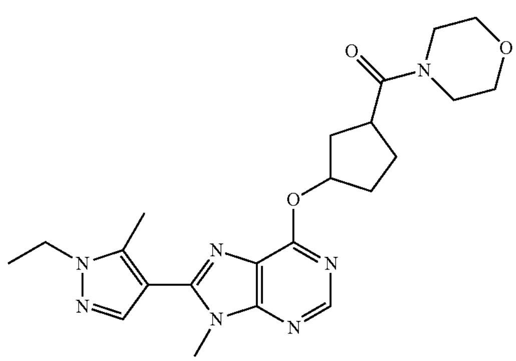 [SMILES: CCn1ncc(-c2nc3c(OC4CCC(C(=O)N5CCOCC5)C4)ncnc3n2C)c1C] | (3-((8-(1-ethyl-5-methyl-1H-pyrazol-4-yl)-9-methyl-9H-purin-6-yl)oxy)cyclopentyl)(morpholino)methanone | Calc'd 440, found 440 |

Compound Examples of Table 9

Example 14—Preparation of Compound 9-1

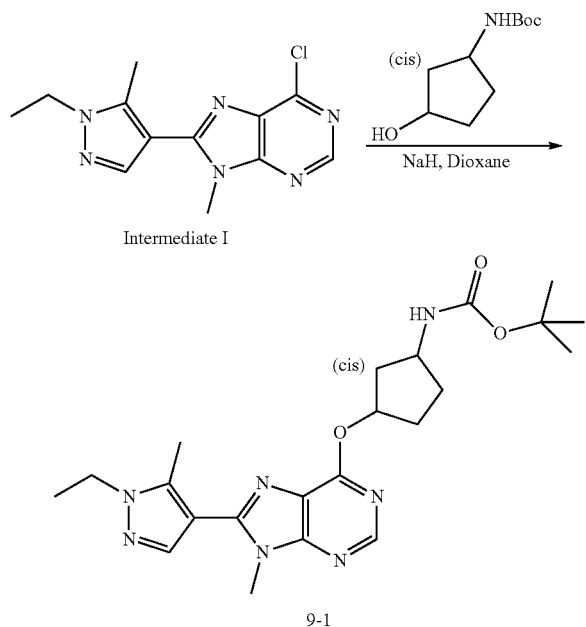

A solution of racemic cis-tert-butyl(3-hydroxycyclopentyl)carbamate (550 mg, 2.73 mmol) in 3 mL of dioxane was treated with a 60% suspension of sodium hydride in mineral oil (175 mg, 4.38 mmol). The suspension was stirred for 10 min, then treated with Intermediate I (800 mg, 2.89 mmol). The reaction mixture was stirred at RT overnight, then diluted with DCM and washed with sat'd NaHCO$_3$, dried (Na$_2$SO$_4$) and concentrated. Chromatography on SiO$_2$ (0-40% MeOH/DCM) gave the desired cis product 9-1 as a racemate. $^1$H NMR (600 MHz, DMSO-d$_6$) δ 8.42 (s, 1H), 7.96 (s, 1H), 6.93 (d, J=7.0 Hz, 1H), 5.55 (m, 1H), 4.15 (q, J=7.1 Hz, 2H), 3.80 (s, 3H), 2.55 (s, 3H), 2.45 (m, 1H), 2.02 (m, 1H), 1.88-1.83 (m, 2H), 1.68-1.58 (m, 2H), 1.33 (s, 9H), 1.33 (t, J=7.0 Hz, 3H); MS (EI) Calc'd for C$_{22}$H$_{32}$N$_7$O$_3$ [M+H]$^+$, 442. found 442.

Example 15—Preparation of Compound 9-3

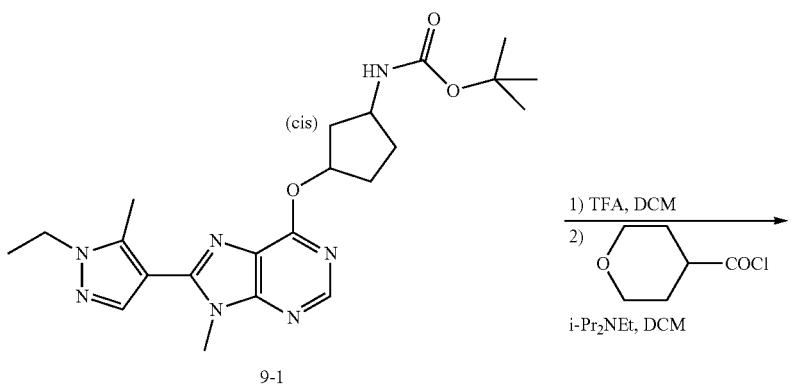

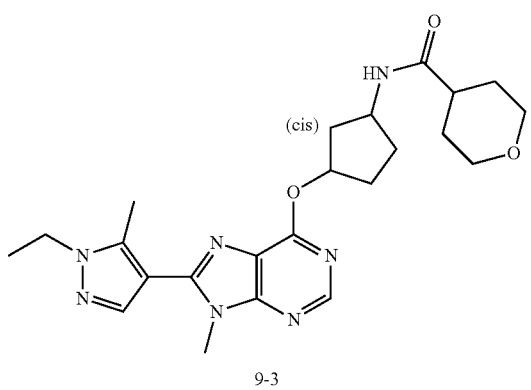

A solution of 9-1 (100 mg, 0.226 mmol) in 2 mL of DCM was treated with TFA (0.14 mL, 1.75 mmol) and stirred overnight. The reaction mixture was diluted with DCM and washed with sat'd NaHCO$_3$, dried (Na$_2$SO$_4$) and concentrated to dryness. The residue was dissolved in 2 mL of DCM and treated with i-Pr$_2$NEt (0.040 mL, 0.23 mmol) followed by tetrahydro-2H-pyran-4-carbonyl chloride (50 mg, 0.34 mmol). Stirred for 1 hour, diluted with DCM, washed with sat'd NaHCO$_3$, dried Na$_2$SO$_4$ and concentrated. Dissolved the residue in DMSO, filtered and purified by reverse phase purification (MeCN/water with TFA additive) followed by fraction concentration gave the TFA salt of 9-3. $^1$H NMR (600 MHz, DMSO-d$_6$) δ 8.43 (s, 1H), 7.96 (s, 1H), 7.83 (d, J=7.1 Hz, 1H), 5.58 (m, 1H), 4.15 (q, J=7.1 Hz, 2H), 4.03 (q, J=7.4 Hz, 1H), 3.80 (s, 3H), 3.75 (m, 4H), 3.20 (m, 2H), 2.54 (s, 3H), 2.27 (m, 1H), 2.04 (m, 1H), 1.95-1.85 (m, 2H), 1.70-1.60 (m, 1H), 1.55-1.45 (m, 4H), 1.33 (t, J=7.3 Hz, 3H); MS (EI) Calc'd for C$_{23}$H$_{32}$N$_7$O$_3$ [M+H]$^+$, 454. found 454.

Example 15A—Preparation of Compound 9-10

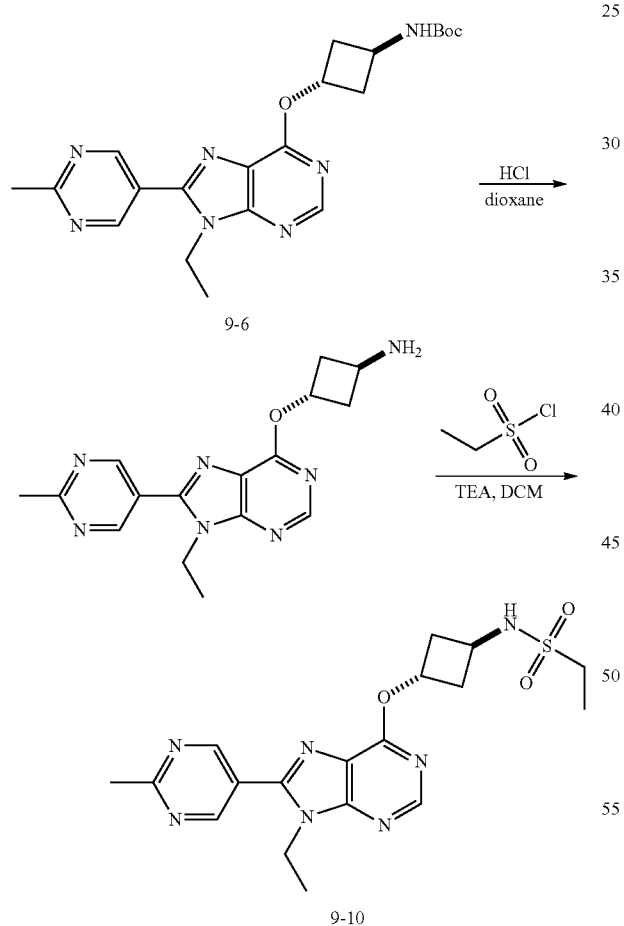

A mixture of 9-6 (170 mg, 0.400 mmol) and HCl in dioxane (4 M, 3 mL, 12 mmol) in MeOH (3 mL) was stirred and heated at 40° C. for 2 h. Solvent was removed under reduced pressure to give the HCl salt of trans-3-((9-ethyl-8-(2-methylpyrimidin-5-yl)-9H-purin-6 yl)oxy)cyclobutanamine.

To a mixture of the HCl salt of trans-3-((9-ethyl-8-(2-methylpyrimidin-5-yl)-9H-purin-6-yl)oxy)-cyclobutanamine (50 mg, 0.082 mmol) and TEA (0.1 mL, 0.72 mmol) in DCM (4 mL) was added ethanesulfonyl chloride (15 mg, 0.12 mmol) at 0° C. After addition, the resulting mixture was stirred for 4 h and slowly warmed to RT. The reaction mixture was concentrated and the residue purified by reverse phase HPLC (MeCN/water with 10 mM aqueous NH$_4$HCO$_3$ modifier) to give compound 9-10. $^1$H NMR (400 MHz, CD$_3$OD) δ 9.15 (s, 2H), 8.55 (s, 1H), 5.67-5.64 (m, 1H), 4.50-4.44 (m, 2H), 4.27-4.24 (m, 1H), 3.09-3.01 (m, 2H), 2.85 (s, 3H), 2.78-2.59 (m, 4H), 1.52-1.44 (m, 3H), 1.38-1.28 (m, 3H). MS (EI) Calc'd for C$_{18}$H$_{24}$N$_7$O$_3$S [M+H]$^+$, 418. found, 418.

Compound 16—Preparation of Compound 9-4

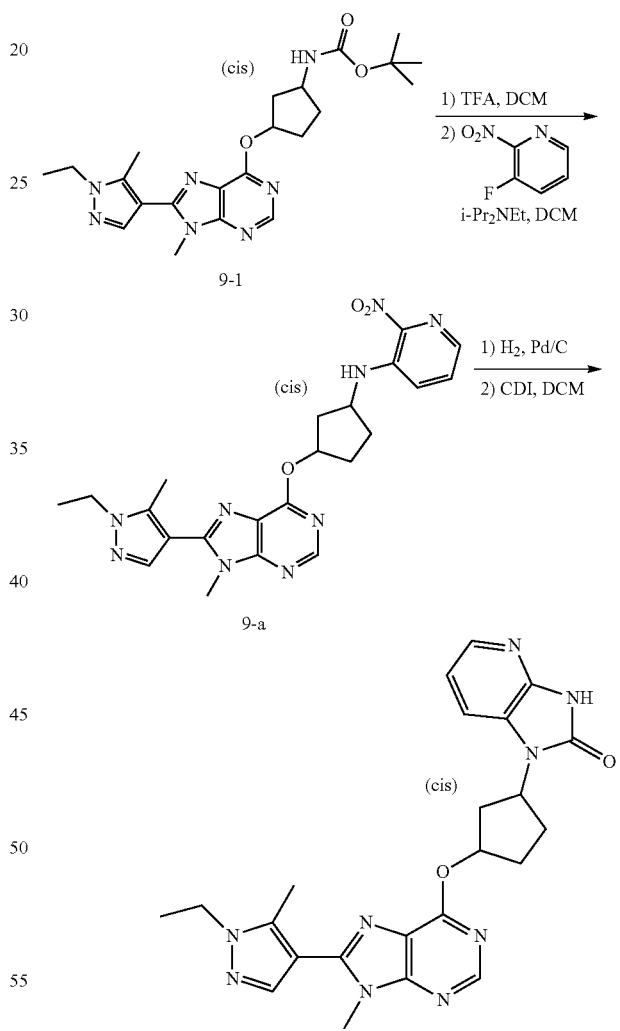

Step 1: Preparation of cis-N-(3-((8-(1-ethyl-5-methyl-1H-pyrazol-4-yl)-9-methyl-9H-purin-6-yl)oxy)cyclopentyl)-2-nitropyridin-3-amine A solution of racemic 9-1 (300 mg, 0.679 mmol) in 3 mL of DCM was treated with TFA (0.4 ml, 5.2 mmol) and stirred at RT overnight. Diluted reaction with DCM and washed with sat'd NaHCO₃, dried (Na₂SO₄) and concentrated. The residue was next dissolved in 3 mL of DCM and treated with i-Pr₂NEt (0.50 ml, 2.9 mmol) followed by 3-fluoro-2-nitropyridine (130 mg, 0.915 mmol). The reaction was stirred overnight at RT, then, recharged with additional i-Pr₂NEt (0.50 ml, 2.9 mmol) and 3-fluoro-2-nitropyridine (130 mg, 0.915 mmol). After stirring for 2 days, the reaction was diluted with DCM, washed with water, dried (Na₂SO₄), and concentrated. Chromatography on SiO₂ (0-30% MeOH/DCM gradient) gave the desired product, 9-a. MS (EI) Calc'd for C₂₂H₂₅N₉O₃ [M+H]⁺, 464. found 464.

Step 2: Preparation of cis-1-(3-((8-(1-Ethyl-5-methyl-1H-pyrazol-4-yl)-9-methyl-9H-purin-6-yl)oxy)cyclopentyl)-1H-imidazo[4,5-b]pyridin-2(3H)-one (9-4)

A mixture of cis-N-(3-((8-(1-ethyl-5-methyl-1H-pyrazol-4-yl)-9-methyl-9H-purin-6-yl)oxy)cyclopentyl)-2-nitropyridin-3-amine, 9-a, (225 mg, 0.485 mmol) in 3 mL of MeOH was treated with 10% Pd/C (50 mg, 0.047 mmol). The suspension was placed under vacuum and purged with hydrogen three times, and a hydrogen balloon was applied to the stirred reaction overnight. The suspension was filtered through Celite and concentrated filtrate to dryness. The residue was redissolved in 3 mL of DCM, treated with CDI (250 mg, 1.54 mmol) and stirred overnight, then the incomplete reaction was recharged with additional CDI (250 mg, 1.54 mmol) and again stirred overnight. The reaction mixture was cooled to RT, dissolved in DMSO and purified by reverse phase chromatography. Lyophilization of the desired fractions provided the TFA salt of the desired product 9-4. ¹H NMR (600 MHz, DMSO-d₆) δ 11.56 (s, 1H), 8.47 (s, 1H), 8.01 (s, 1H), 7.85 (m, 2H), 6.82 (m, 1H), 5.80 (m, 1H), 4.97 (m, 1H), 4.18 (q, J=7.3 Hz, 2H), 3.84 (s, 3H), 2.63 (s, 3H), 2.62 (m, 1H), 2.32 (m, 1H), 2.17-2.14 (m, 2H), 2.08 (m, 1H), 1.98 (m, 1H), 1.35 (t, J=7.4 Hz, 3H); MS (EI) Calc'd for C₂₃H₂₆N₉O₂ [M+H]⁺, 460. found 460.

Compounds 9-2, 9-5, 9-6 were prepared in an analogous fashion as described for Example 14.

Compounds 9-7 and 9-8 were prepared in an analogous fashion as described for Example 15.

Compound 9-9 was prepared in racemic form in an analogous fashion as described for Example 15 and the enantiomers were then separated by chiral column chromatography using the following conditions: Column: AD-H 4.6×250 mm 5 um, Co-Solvent:MeOH (0.1% DEA); Column Temperature: 40.8° C.; Co-Solvent Flow rate: 0.9. Compound 9-9 eluted at 4.24 min, while the enantiomer eluted at 6.61 min.

TABLE 9

| Compound | Structure | Compound Name | MS [M + H]⁺ |
|---|---|---|---|
| 9-1 | 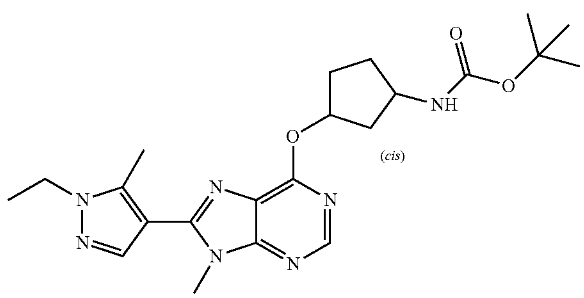 [SMILES: CCn1ncc(-c2nc3c(OC4CCC(NC(=O)OC(C)(C)C)C4)ncnc3n2C)c1C] | cis-tert-butyl [(1S,3R)-3-{[8-(1-ethyl-5-methyl-1H-pyrazol-4-yl)-9-methyl-9H-purin-6-yl]oxy}cyclopentyl]carbamate | Calc'd 442, found 442 |
| 9-2 | 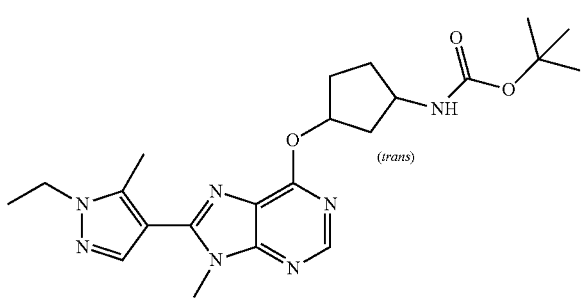 [SMILES: CCn1ncc(-c2nc3c(OC4CCC(NC(=O)OC(C)(C)C)C4)ncnc3n2C)c1C] | trans-tert-butyl [(1S,3S)-3-{[8-(1-ethyl-5-methyl-1H-pyrazol-4-yl)-9-methyl-9H-purin-6-yl]oxy}cyclopentyl]carbamate | Calc'd 442, found 442 |

TABLE 9-continued

| Compound | Structure | Compound Name | MS [M + H]+ |
|---|---|---|---|
| 9-3 | 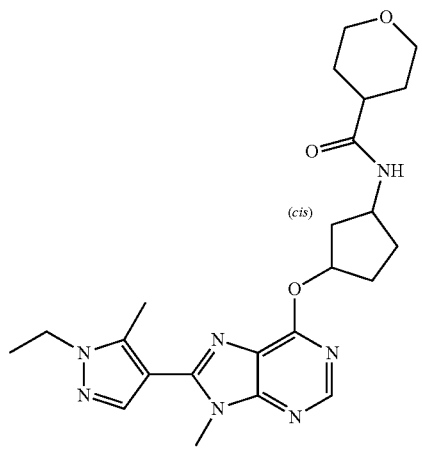 [SMILES: CCn1ncc(-c2nc3c(OC4CCC(NC(=O)C5CCOCC5)C4)ncnc3n2C)c1C] | cis-N-[(1S,3R)-3-{[8-(1-ethyl-5-methyl-1H-pyrazol-4-yl)-9-methyl-9H-purin-6-yl]oxy}cyclopentyl]tetrahydro-2H-pyran-4-carboxamide | Calc'd 454, found 454 |
| 9-4 | 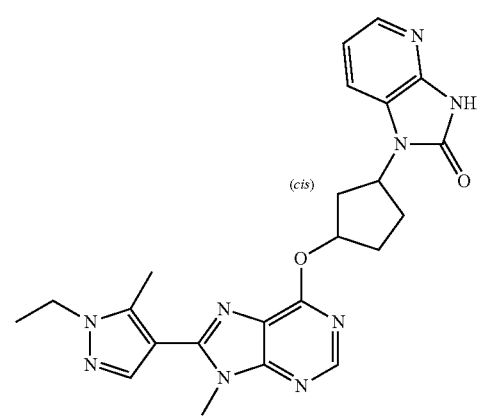 [SMILES: CCn1ncc(-c2nc3c(OC4CCC(n5c(=O)[nH]c6ncccc65)C4)ncnc3n2C)c1C] | cis-1-[(1S,3R)-3-{[8-(1-ethyl-5-methyl-1H-pyrazol-4-yl)-9-methyl-9H-purin-6-yl]oxy}cyclopentyl]-1,3-dihydro-2H-imidazo[4,5-b]pyridin-2-one | Calc'd 460, found 460 |
| 9-5 | 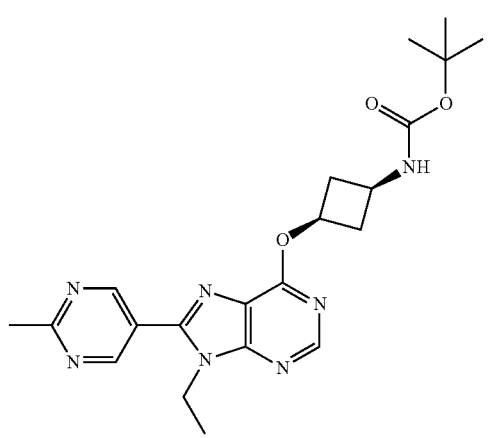 [SMILES: CCn1c(-c2cnc(C)nc2)nc2c(O[C@H]3C[C@@H](NC(=O)OC(C)(C)C)C3)ncnc21] | tert-butyl (cis-3-{[9-ethyl-8-(2-methylpyrimidin-5-yl)-9H-purin-6-yl]oxy}cyclobutyl)carbamate | Calc'd 426, found 426 |

TABLE 9-continued

| Compound | Structure | Compound Name | MS [M + H]+ |
|---|---|---|---|
| 9-6 | 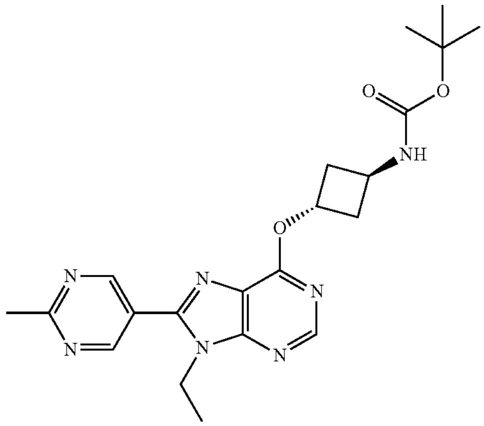 [SMILES: CCn1c(-c2cnc(C)nc2)nc2c(O[C@H]3C[C@H](NC(=O)OC(C)(C)C)C3)ncnc21] | tert-butyl (trans-3-{[9-ethyl-8-(2-methylpyrimidin-5-yl)-9H-purin-6-yl]oxy}cyclobutyl)carbamate | Calc'd 426, found 426 |
| 9-7 | 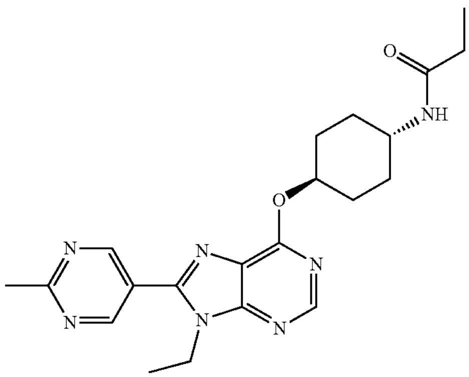 [SMILES: CCC(=O)N[C@H]1CC[C@H](Oc2ncnc3c2nc(-c2cnc(C)nc2)n3CC)CC1] | N-(trans-4-{[9-ethyl-8-(2-methylpyrimidin-5-yl)-9H-purin-6-yl]oxy}cyclohexyl)propanamide | Calc'd 410, found 410 |
| 9-8 | 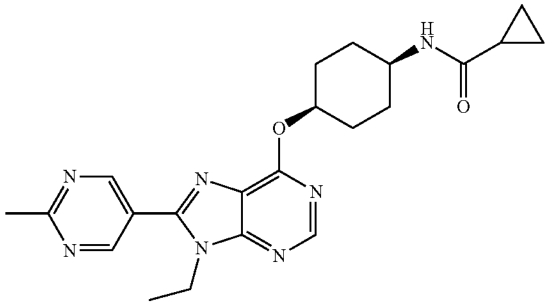 [SMILES: CCn1c(-c2cnc(C)nc2)nc2c(O[C@H]3CC[C@@H](NC(=O)C4CC4)CC3)ncnc21] | N-(cis-4-{[9-ethyl-8-(2-methylpyrimidin-5-yl)-9H-purin-6-yl]oxy}cyclohexyl)cyclopropane carboxamide | Calc'd 422, found 422 |
| 9-9 | 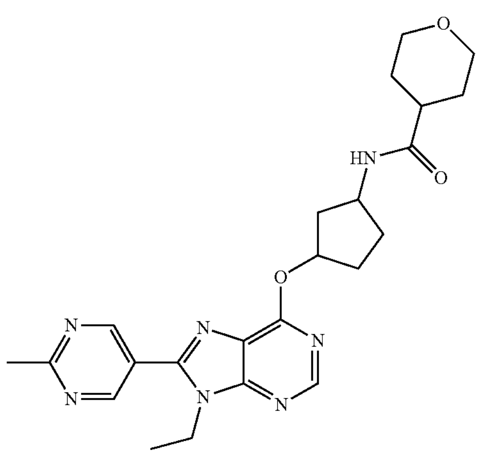 [SMILES: CCn1c(-c2cnc(C)nc2)nc2c(OC3CCC(NC(=O)C4CCOCC4)C3)ncnc21] | N-[(1S,3S) or (1R,3R)]-(3-{[9-ethyl-8-(2-methylpyrimidin-5-yl)-9H-purin-6-yl]oxy}cyclopentyl)tetrahydro-2H-pyran-4-carboxamide | Calc'd 452, found 452 |

TABLE 9-continued

| Compound | Structure | Compound Name | MS [M + H]+ |
|---|---|---|---|
| 9-10 | 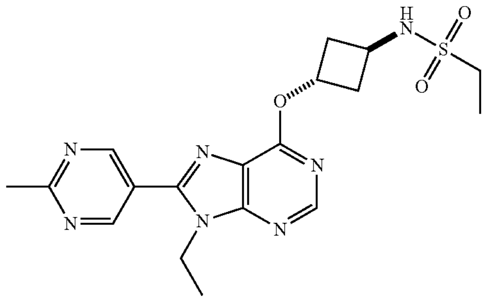 | trans-N-(3-{[9-ethyl-8-(2-methylpyrimidin-5-yl)-9H-purin-6-yl]oxy}cyclobutyl)ethanesulfonamide | Calc'd 418, found 418 |

Compound Examples of Table 10

Example 17—Preparation of Compound 10-1

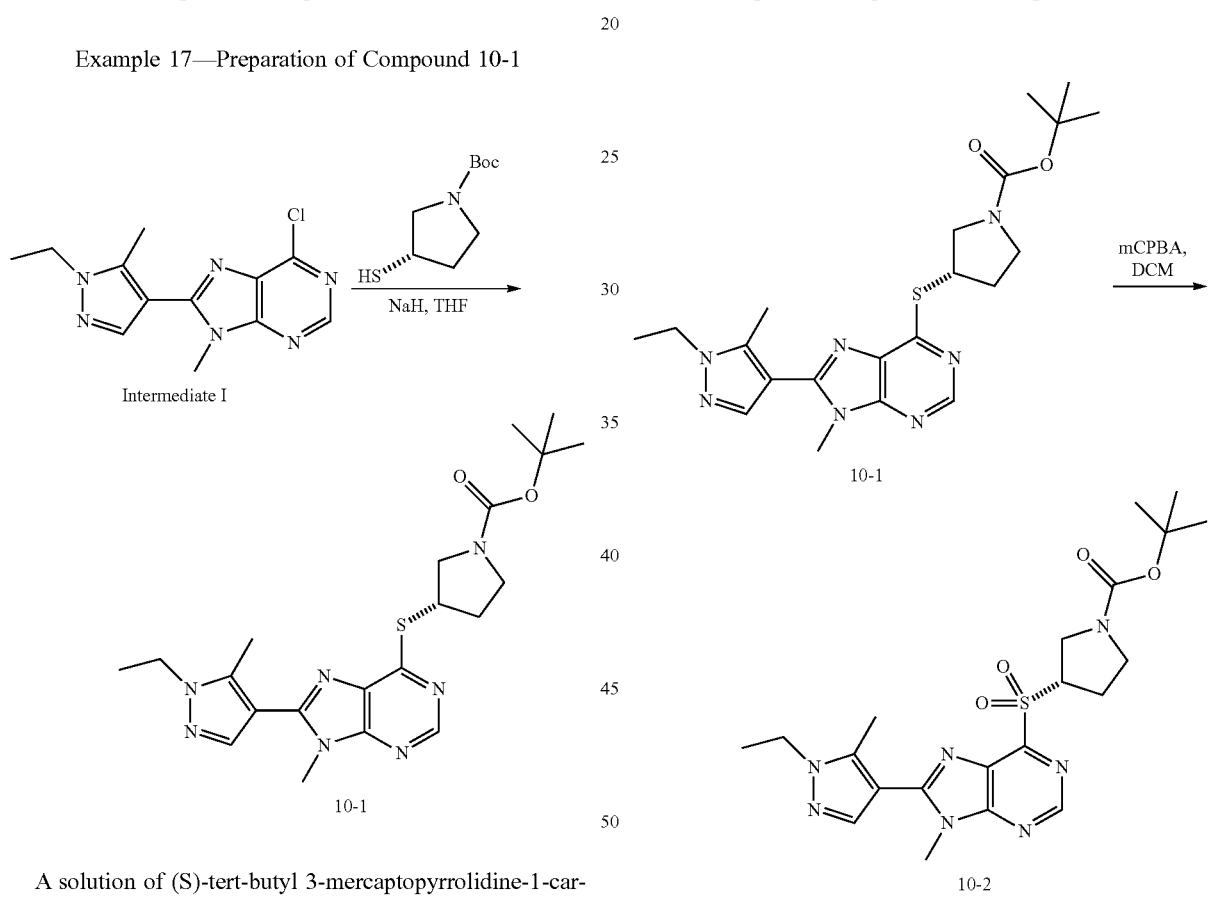

Example 18—Preparation of Compound 10-2

A solution of (S)-tert-butyl 3-mercaptopyrrolidine-1-carboxylate (1.1 g, 5.4 mmol) in 18 mL of THF was treated portionwise at 0° C. with a 60% suspension of sodium hydride in mineral oil (0.42 g, 11 mmol). The suspension was stirred for 15 min at room temperature, then Intermediate I (1.15 g, 4.20 mmol) was added. The reaction mixture was stirred overnight, quenched with 10 mL of methanol and concentrated. The crude mixture was purified by chromatography on $SiO_2$ (10% to 20% EtOAc/hexanes gradient) to provide 10-1. $^1$H NMR (400 MHz, CDCl$_3$) δ 8.70 (s, 1H), 7.84 (s, 1H), 4.75-4.65 (m, 1H), 4.23 (q, J=6.8 Hz, 2H), 4.10-4.00 (m, 1H), 3.94 (s, 3H), 3.60-3.40 (m, 3H), 2.68 (s, 3H), 2.51-2.48 (m, 1H), 2.20-2.10 (m, 1H), 1.51 (t, J=6.8 Hz, 3H), 1.48 (s, 9H); MS (EI) Calc'd for $C_{21}H_{30}N_7O_2S$ [M+H]+, 444. found 444.

A mixture of 10-1 (150 mg, 0.34 mmol) and mCPBA (150 mg, 0.85 mmol) in 5 mL of DCM was stirred at room temperature overnight. The reaction mixture was quenched with 2 M aqueous $Na_2SO_3$ (10 mL) and the organic layer was separated. The organic layer was washed with brine, dried over $Na_2SO_4$, filtered and concentrated. The crude material was purified by preparatory thin-layer chromatography on $SiO_2$ (25% EtOAc/hexane) to give 10-2. $^1$H NMR (400 MHz, CDCl$_3$) δ 9.03 (s, 1H), 7.97 (s, 1H), 4.75-4.62 (m, 1H), 4.27 (q, J=7.2 Hz, 2H), 4.08 (s, 3H), 4.00-3.49 (m, 4H), 2.78 (s, 3H), 2.70-2.30 (m, 2H), 1.52 (t, J=7.2 Hz, 3H), 1.45 (s, 9H); MS (EI) Calc'd for $C_{21}H_{30}N_7O_4S$ [M+H]+, 476. found, 476.

Example 19—Preparation of 10-4

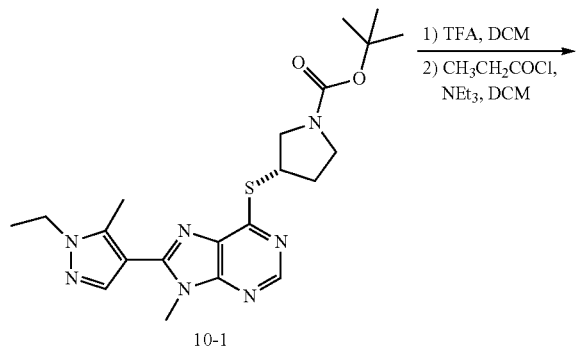

Example 20—Preparation of 10-6

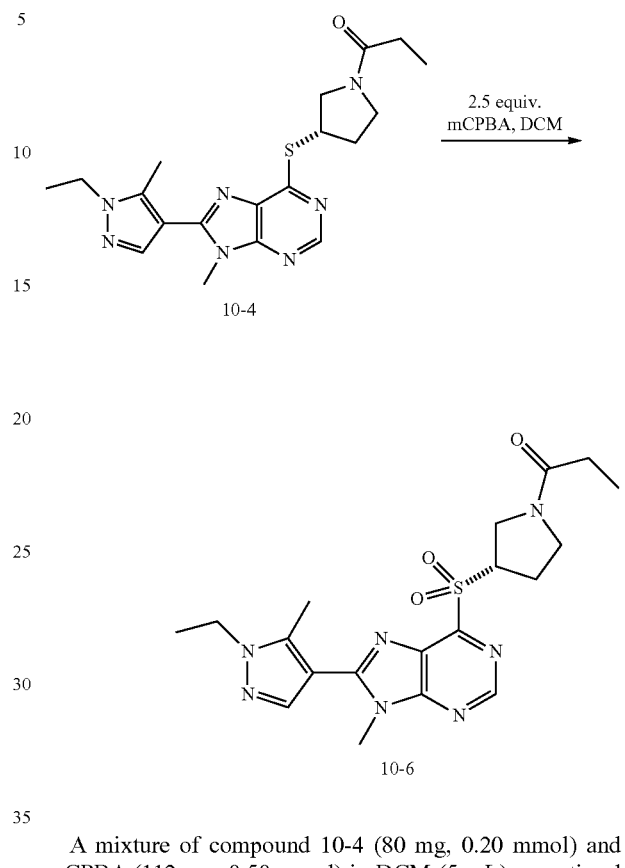

A solution of 10-1 (300 mg, 0.67 mmol) in 3 mL of DCM was treated with 1 mL of TFA at 0° C. The reaction was stirred at room temperature for 1 hour, then concentrated to give 8-(1-ethyl-5-methyl-1H-pyrazol-4-yl)-9-methyl-6-((S)-pyrrolidin-3-ylthio)-9H-purine as a TFA salt, 10-a. MS (EI) Calc'd for $C_{16}H_{22}N_7S$ [M+H]$^+$, 344. found, 344.

A solution of 8-(1-ethyl-5-methyl-1H-pyrazol-4-yl)-9-methyl-6-((S)-pyrrolidin-3-ylthio)-9H-purine TFA salt, 10-a, (70 mg, 0.20 mmol) in 3 mL of DCM was treated at 0° C. with propionyl chloride (28 mg, 0.22 mmol) and Et$_3$N (50 mg, 0.50 mmol). The resulting mixture was stirred at room temperature overnight, concentrated, and purified by reverse phase chromatography (MeCN/water with 0.05% TFA) to give 10-4. $^1$H NMR (400 MHz, DMSO-d$_6$) δ 8.70 (s, 1H), 8.07 (s, 1H), 4.70-4.60 (m, 1H), 4.20 (q, J=7.2 Hz, 2H), 4.10-3.90 (m, 1H), 3.89 (s, 3H), 3.65-3.40 (m, 3H), 2.51 (s, 3H), 2.55-2.40 (m, 1H), 2.30-2.20 (m, 2H), 2.20-1.90 (m, 1H), 1.38 (t, J=7.2 Hz, 3H), 1.10-0.90 (m, 3H); MS (EI) Calc'd for $C_{19}H_{26}N_7OS$ [M+H]$^+$, 400. found, 400.

A mixture of compound 10-4 (80 mg, 0.20 mmol) and mCPBA (112 mg, 0.50 mmol) in DCM (5 mL) was stirred at room temperature overnight. The reaction mixture was quenched with aqueous Na$_2$SO$_3$ (5 mL, 2 M) and the organic layer was separated. The organic layer was washed with brine, dried over Na$_2$SO$_4$, filtered and concentrated. The crude material was purified by prep-TLC (AcOEt/hexane: 10:30) to give 10-6. $^1$H NMR (400 MHz, DMSO-d$_6$) δ 9.06 (s, 1H), 8.20 (s, 1H), 4.70-4.60 (m, 1H), 4.20 (q, J=7.2 Hz, 2H), 3.99 (s, 3H), 3.85-3.30 (m, 4H), 2.70 (s, 3H), 2.50-2.20 (m, 4H), 1.38 (t, J=7.2 Hz, 3H), 0.97-0.90 (m, 3H); MS (EI) Calc'd for $C_{19}H_{26}N_7O_3S$ [M+H]f, 432. found, 432.

Compound 10-3 was prepared in a fashion analogous to Example 19.

Compounds 10-5 and 10-7 was prepared in a fashion analogous to Example 20.

Compounds 10-8 and 10-9 was prepared in a fashion analogous to Example 20, substituting the acid chloride reagent for the appropriate chloroformate reagent, Compounds 10-10 and 10-11 were prepared in a fashion analogous to Example 7, substituting Intermediate II for 8-(1-ethyl-5-methyl-1H-pyrazol-4-yl)-9-methyl-6-((S)-pyrrolidin-3-ylthio)-9H-purine and using the appropriate carboxylic acid.

Compounds 10-12 and 10-13 were prepared in a fashion analogous to Example 12, substituting the Intermediate II for 8-(1-ethyl-5-methyl-1H-pyrazol-4-yl)-9-methyl-6-((S)-pyrrolidin-3-ylthio)-9H-purine and using the appropriate aryl halide.

TABLE 10

| Compound | Structure | Compound Name | MS [M + H]+ |
|---|---|---|---|
| 10-1 | 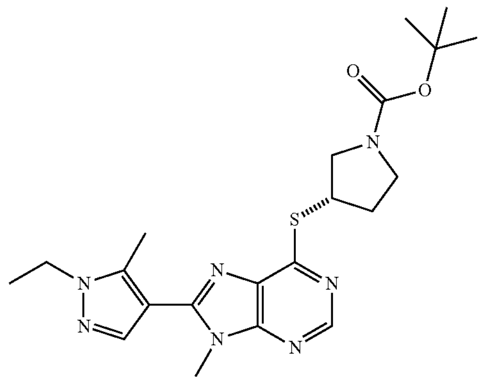 | (S)-tert-butyl 3-((8-(1-ethyl-5-methyl-1H-pyrazol-4-yl)-9-methyl-9H-purin-6-yl)thio)pyrrolidine-1-carboxylate | Calc'd 444, found 444 |
| 10-2 | 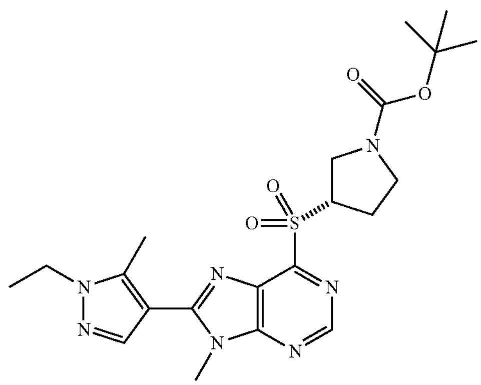 | (S)-tert-butyl 3-((8-(1-ethyl-5-methyl-1H-pyrazol-4-yl)-9-methyl-9H-purin-6-yl)sulfonyl)pyrrolidine-1-carboxylate | Calc'd 476, found 476 |
| 10-3 | 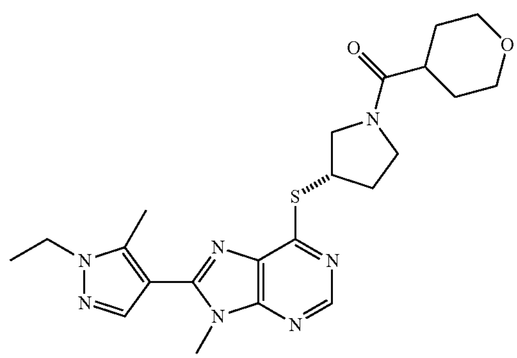 | (S)-(3-((8-(1-ethyl-5-methyl-1H-pyrazol-4-yl)-9-methyl-9H-purin-6-yl)thio)pyrrolidin-1-yl)(tetrahydro-2H-pyran-4-yl)methanone | Calc'd 456, found 456 |
| 10-4 | 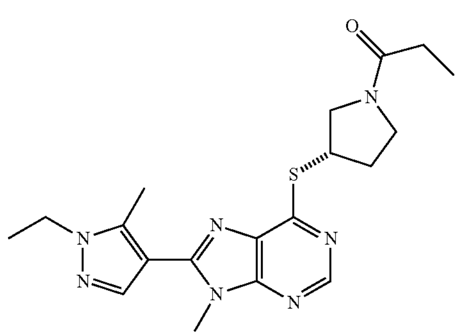 | (S)-1-(3-((8-(1-ethyl-5-methyl-1H-pyrazol-4-yl)-9-methyl-9H-purin-6-yl)thio)pyrrolidin-1-yl)propan-1-one | Calc'd 400, found 400 |

TABLE 10-continued

| Compound | Structure | Compound Name | MS [M + H]+ |
|---|---|---|---|
| 10-5 | 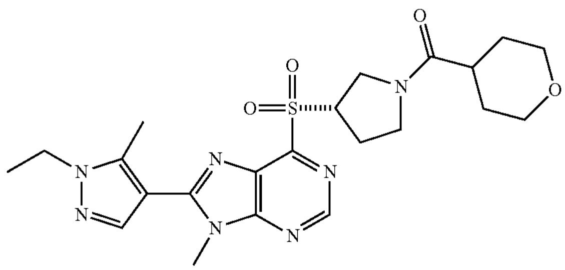 | (S)-(3-((8-(1-ethyl-5-methyl-1H-pyrazol-4-yl)-9-methyl-9H-purin-6-yl)sulfonyl)pyrrolidin-1-yl)(tetrahydro-2H-pyran-4-yl)methanone | Calc'd 488, found 488 |
| 10-6 | 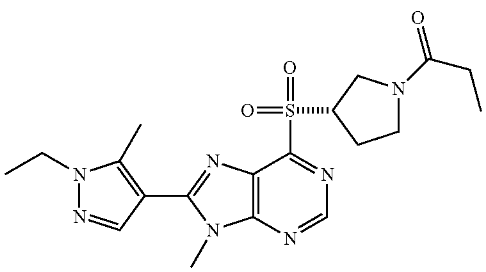 | (S)-1-(3-((8-(1-ethyl-5-methyl-1H-pyrazol-4-yl)-9-methyl-9H-purin-6-yl)sulfonyl)pyrrolidin-1-yl)propan-1-one | Calc'd 432, found 432 |
| 10-7 | 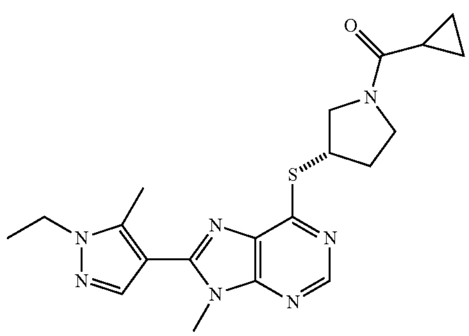 | (S)-cyclopropyl(3-((8-(1-ethyl-5-methyl-1H-pyrazol-4-yl)-9-methyl-9H-purin-6-yl)thio)pyrrolidin-1-yl)methanone | Calc'd 412, found 412 |
| 10-8 | 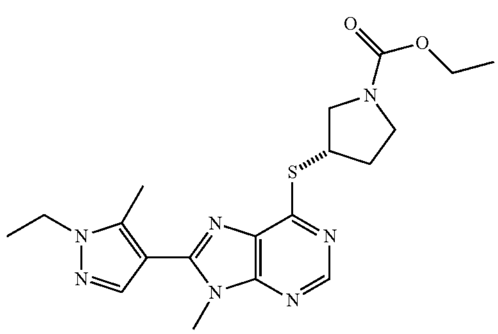 | (S)-ethyl 3-((8-(1-ethyl-5-methyl-1H-pyrazol-4-yl)-9-methyl-9H-purin-6-yl)thio)pyrrolidine-1-carboxylate | Calc'd 416, found 416 |
| 10-9 | 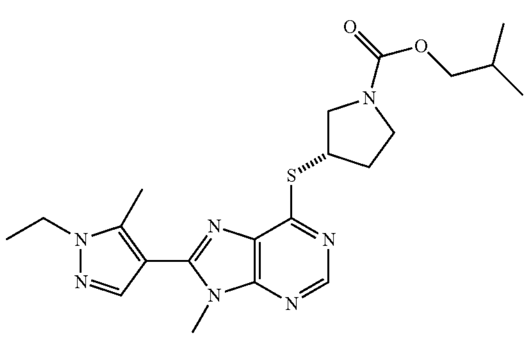 | (S)-isobutyl 3-((8-(1-ethyl-5-methyl-1H-pyrazol-4-yl)-9-methyl-9H-purin-6-yl)thio)pyrrolidine-1-carboxylate | Calc'd 444, found 444 |

TABLE 10-continued

| Compound | Structure | Compound Name | MS [M + H]+ |
|---|---|---|---|
| 10-10 | 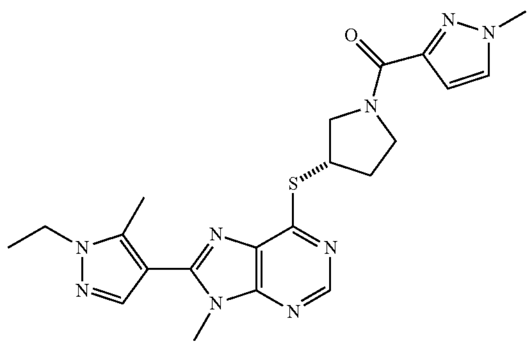 | (S)-(3-((8-(1-ethyl-5-methyl-1H-pyrazol-4-yl)-9-methyl-9H-purin-6-yl)thio)pyrrolidin-1-yl)(1-methyl-1H-pyrazol-3-yl)methanone | Calc'd 452, found 452 |
| 10-11 | 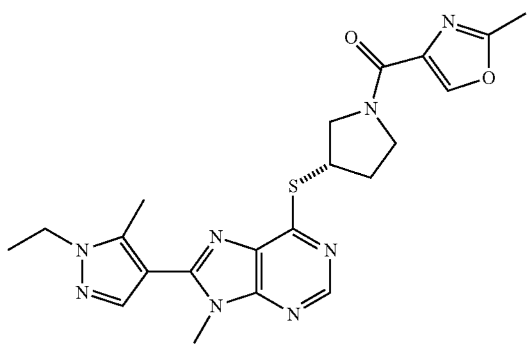 | (S)-(3-((8-(1-ethyl-5-methyl-1H-pyrazol-4-yl)-9-methyl-9H-purin-6-yl)thio)pyrrolidin-1-yl)(2-methyloxazol-4-yl)methanone | Calc'd 453, found 453 |
| 10-12 | 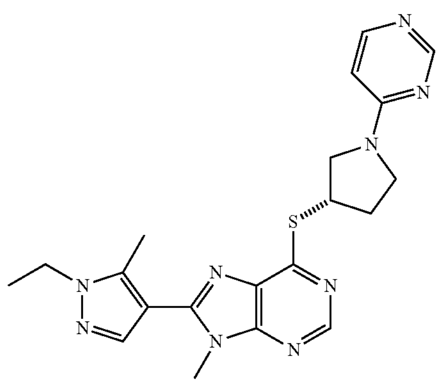 | (S)-8-(1-ethyl-5-methyl-1H-pyrazol-4-yl)-9-methyl-6-((1-(pyrimidin-4-yl)pyrrolidin-3-yl)thio)-9H-purine | Calc'd 422, found 422 |
| 10-13 | 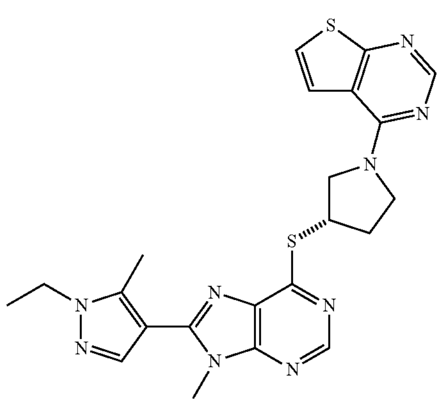 | (S)-4-(3-((8-(1-ethyl-5-methyl-1H-pyrazol-4-yl)-9-methyl-9H-purin-6-yl)thio)pyrrolidin-1-yl)thieno[2,3-d]pyrimidine | Calc'd 478, found 478 |

Compound Examples of Table 11

Example 21—Preparation of 11-1

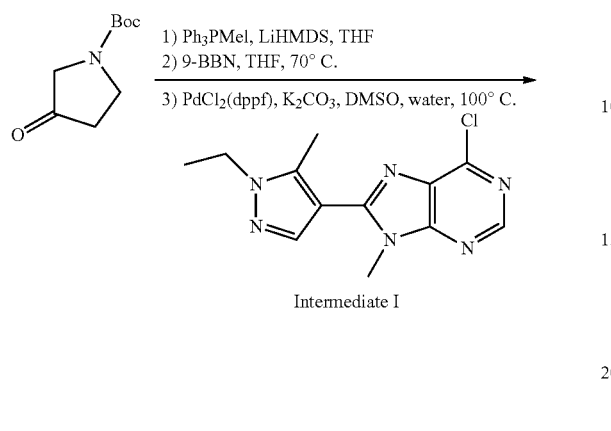

Intermediate I

To a suspension of methyltriphenylphosphonium iodide (10 g, 25 mmol) in toluene (150 mL) was added a 1.0 M THF solution of lithium hexamethyldisilazide (25 mL, 25 mmol). The mixture was stirred at room temperature for 2 h, then, added to a solution of tert-butyl-3-oxo-pyrrolidine-1-carboxylate (4.6 g, 25 mmol) in toluene (50 mL) at 0° C. over a period of 10 min. The ice bath was removed and the mixture was allowed to warm to room temperature. The mixture was then stirred at rt for overnight, diluted with petroleum ether (30 mL), filtered through a pad of silica gel, washed with petroleum ether and the filtrate was concentrated to give tert-butyl 3-methylenepyrrolidine-1-carboxylate: $^1$H-NMR (400 MHz, CDCl$_3$) δ 4.90 (s, 2H), 3.84 (s, 2H), 3.39 (t, J=6.8 Hz, 2H), 2.46 (t, J=6.8 Hz, 2H), 1.40 (s, 9H).

A solution of tert-butyl-3-methylenepyrrolidine-1-carboxylate (200 mg, 1.09 mmol) in dry THF (1 mL) under a nitrogen atmosphere was treated at 0° C. with a 0.5 M THF solution of 9-BBN (2.4 mL, 1.2 mmol). The mixture was heated at 70° C. for 2.5 h and was allowed to cool to room temperature. The solution was treated with Intermediate I (300 mg, 1.09 mmol), PdCl$_2$(dppf) (80 mg, 0.11 mmol), K$_2$CO$_3$ (300 mg, 2.19 mmol), water (1 mL) and DMSO (2 mL). The mixture was heated using microwave irradiation at 100° C. for 30 min, then purified by chromatography on SiO$_2$ (1:20 EtOAc/petroleum ether) to provide the desired compound 11-1. MS (EI) Calc'd for C$_{22}$H$_{32}$N$_7$O$_2$ [M+H]$^+$, 426. found, 426.

Example 22—Preparation of 11-2

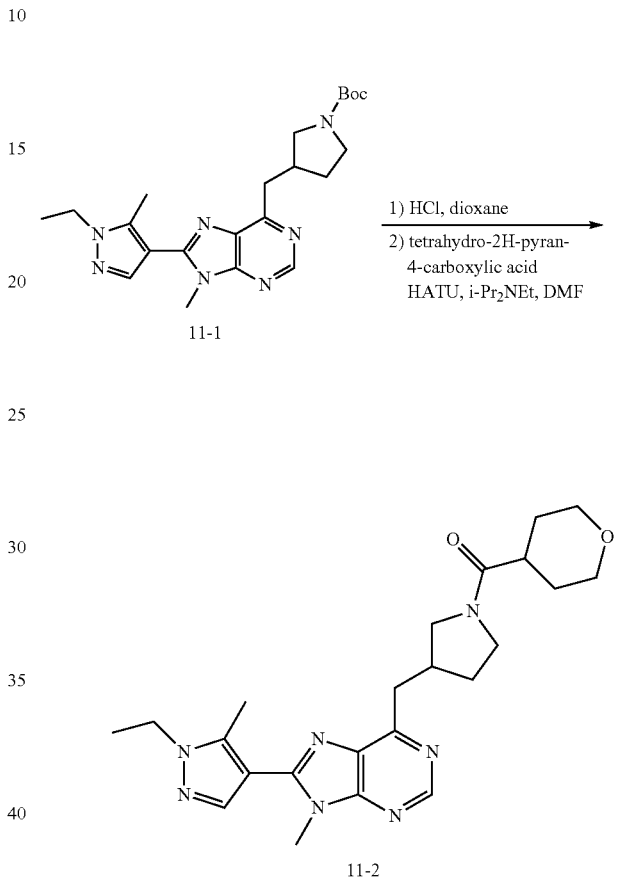

A solution of 11-1 (200 mg, 0.47 mmol) in 4 M HCl in dioxane (3 mL) was stirred for 1 h, then concentrated to dryness and redissolved in DMF (2 mL). The solution was treated with tetrahydro-2H-pyran-4-carboxylic acid (26 mg, 0.20 mmol), HATU (100 mg, 0.28 mmol) and i-Pr$_2$NEt (72 mg, 0.56 mmol), and finally stirred for 20 h. The reaction mixture was purified by reverse phase chromatography (water/MeCN with 10 mM NH$_4$HCO$_3$) to afford 11-2: $^1$H NMR (400 MHz, CDCl$_3$) δ 8.82 (s, 1H), 8.03 (s, 1H), 4.29 (q, J=7.6 Hz, 2H), 3.95-3.76 (m, 5H), 3.75-3.62 (m, 1H), 3.47-3.39 (m, 2H), 3.34-3.32 (m, 4H), 2.97-2.70 (m, 2H), 2.64 (s, 3H), 2.17-2.05 (m, 1H), 1.80-1.64 (m, 6H), 1.49 (t, J=7.6 Hz, 3H); MS (EI) Calc'd for C$_{23}$H$_{32}$N$_7$O$_2$ [M+H]$^+$, 438. found, 438.

Compound 11-3 included in the Table 11 below was prepared in an analogous fashion to that of compound 11-2 described in Example 22 illustrated above.

TABLE 11

| Compound | Structure | Compound Name | MS [M + H]+ |
|---|---|---|---|
| 11-1 | 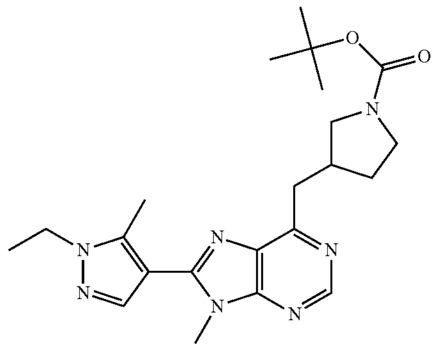 [SMILES: CCn1ncc(-c2nc3c(CC4CCN(C(=O)OC(C)(C)C)C4)ncnc3n2C)c1C] | tert-butyl 3-((8-(1-ethyl-5-methyl-1H-pyrazol-4-yl)-9-methyl-9H-purin-6-yl)methyl)pyrrolidine-1-carboxylate | Calc'd 426, found 426 |
| 11-2 | 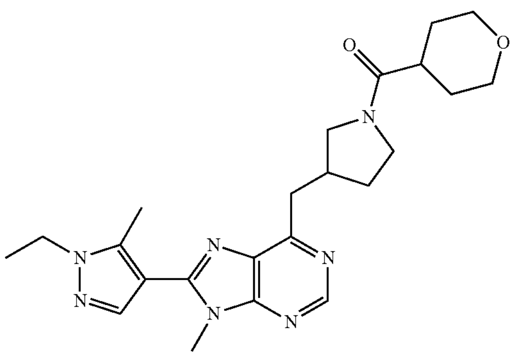 | (3-((8-(1-ethyl-5-methyl-1H-pyrazol-4-yl)-9-methyl-9H-purin-6-yl)methyl)pyrrolidin-1-yl)(tetrahydro-2H-pyran-4-yl)methanone | Calc'd 438, found 438 |
| 11-3 | 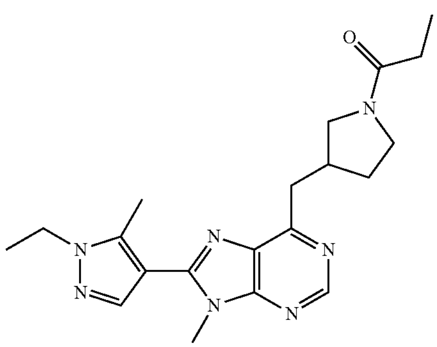 [SMILES: CCC(=O)N1CCC(Cc2ncnc3c2nc(-c2cnn(CC)c2C)n3C)C1] | 1-(3-((8-(1-ethyl-5-methyl-1H-pyrazol-4-yl)-9-methyl-9H-purin-6-yl)methyl)pyrrolidin-1-yl)propan-1-one | Calc'd 382, found 382 |

Compound Examples of Table 12

Example 23—Preparation of Compound 12-1

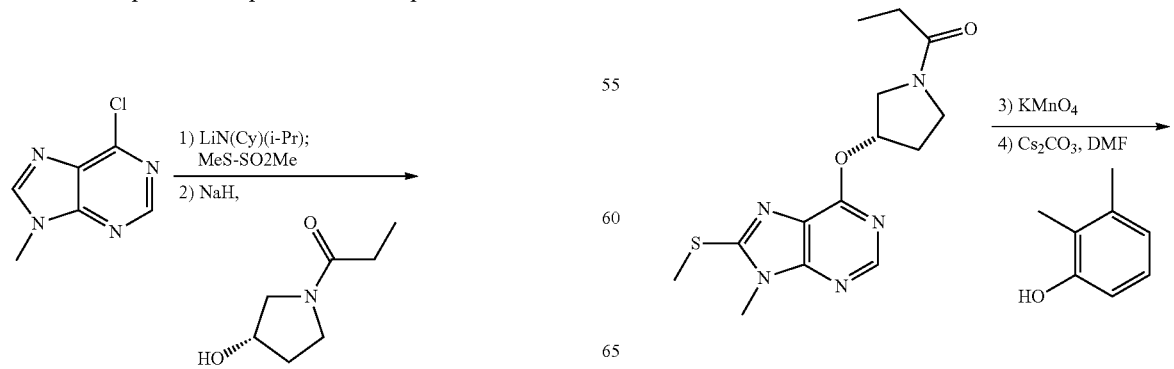

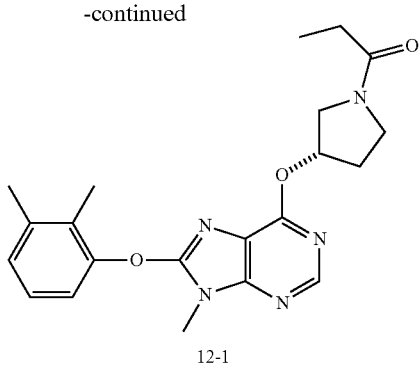

12-1

Steps 1 and 2: Preparation of (S)-1-(3-(9-methyl-8-(methylthio)-9H-purin-6-yloxy)pyrrolidin-1-yl)propan-1-one A mixture of N-isopropylcyclohexanamine (1.3 g, 8.9 mmol) and THF (30 mL) was cooled to −78° C., then n-BuLi (3.6 mL, 2.5 M, 8.9 mmol) was added dropwise at the same temperature over 15 min. A solution of 6-chloro-9-methyl-9H-purine (1.0 g, 5.9 mmol) in THF (10 mL) was added dropwise and stirred for 15 min, then S-methyl methanesulfonothioate (1.1 g, 8.9 mmol) was added and the reaction stirred at −78° C. for 1 hour. Aqueous NH$_4$Cl (30 mL) was added and the mixture was extracted with EtOAc (3×50 mL). The combined organic extracts were separated and dried over Na$_2$SO$_4$, filtered and concentrated to afford a solid. The solid was washed with ether to give 6-chloro-9-methyl-8-(methylthio)-9H-purine. MS (EI) Calc'd for $C_7H_8ClN_4S$ [M+H]$^+$, 215. found, 215.

A mixture of (S)-1-(3-hydroxypyrrolidin-1-yl)propan-1-one (400 mg, 2.79 mmol) in THF (20 mL) was treated with NaH (112 mg, 60%, 2.79 mmol) and stirred at room temperature for 10 min. 6-Chloro-9-methyl-8-(methylthio)-9H-purine (500 mg, 2.33 mmol) was added and the reaction mixture was stirred at room temperature for 15 hours. Water (20 mL) was added and the mixture was extracted with EtOAc (2×20 mL). The combined organic extracts were separated and dried over Na$_2$SO$_4$, filtered and concentrated. The residue was purified by column chromatography (EtOAc/hexane: 2:1) to give (S)-1-(3-((9-methyl-8-(methylthio)-9H-purin-6-yl)oxy)pyrrolidin-1-yl)propan-1-one. MS (EI) Calc'd for $C_{14}H_{20}N_5O_2S$ [M+H]$^+$, 322. found, 322.

Steps 3 and 4: Preparation of 12-1

A mixture of (S)-1-(3-((9-methyl-8-(methylthio)-9H-purin-6-yl)oxy)pyrrolidin-1-yl)propan-1-one (100 mg, 0.31 mmol), AcOH (5.0 mL) and water (2.0 mL) was cooled to 0° C., KMnO$_4$ (120 mg, 0.78 mmol) was then added and the reaction stirred at 0° C. for 3 hours. Water (10 mL) was added and H$_2$O$_2$ (30%, 0.2 mL) was added until the mixture became colorless. The mixture was extracted with DCM (3×20 mL). The combined organic extracts were dried with Na$_2$SO$_4$, filtered, concentrated, and the residue was purified by prep-TLC (silica gel, DCM/MeOH: 10:1) to give (S)-1-(3-((9-methyl-8-(methylsulfonyl)-9H-purin-6-yl)oxy)pyrrolidin-1-yl)propan-1-one. MS (EI) Calc'd for $C_{14}H_{20}N_5O_4S$ [M+H]$^+$, 354. found, 354.

A mixture of (S)-1-(3-((9-methyl-8-(methylsulfonyl)-9H-purin-6-yl)oxy)pyrrolidin-1-yl)propan-1-one (20 mg, 0.057 mmol), Cs$_2$CO$_3$ (37 mg, 0.11 mmol) and DMF (1.0 mL) was treated with 2,3-dimethylphenol (8 mg, 0.07 mmol). The reaction mixture was stirred at room temperature for 15 hours and the solvent was removed under reduced pressure. The residue was purified by prep-TLC (silica gel, DCM/MeOH: 10:1) to give 12-1. $^1$H NMR (400 MHz, CD$_3$OD) δ 8.45 (s, 1H), 7.23-7.10 (m, 3H), 5.91-5.82 (m, 1H), 3.90-3.49 (m, 7H), 2.40-2.25 (m, 7H), 2.18 (s, 3H), 1.10 (q, J=7.6 Hz, 3H). MS (EI) Calc'd for $C_{21}H_{26}N_5O_3$ [M+H]$^+$, 396. found, 396.

Compounds 12-2 to 12-4 were prepared in an analogous fashion as described for Example 23 (Compound 12-1).

TABLE 12

| Compound | Structure | Compound Name | MS [M + H]$^+$ |
|---|---|---|---|
| 12-1 | 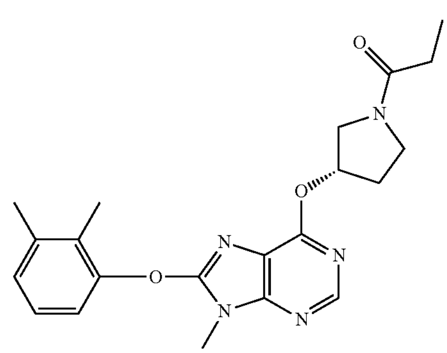 [SMILES: CCC(=O)N1CC[C@H](Oc2ncnc3c2nc(Oc2cccc(C)c2C)n3C)C1] | 8-(2,3-dimethylphenoxy)-9-methyl-6-{[(3S)-1-propanoylpyrrolidin-3-yl]oxy}-9H-purine | Calc'd 396, found 396 |

TABLE 12-continued

| Compound | Structure | Compound Name | MS [M + H]+ |
|---|---|---|---|
| 12-2 | 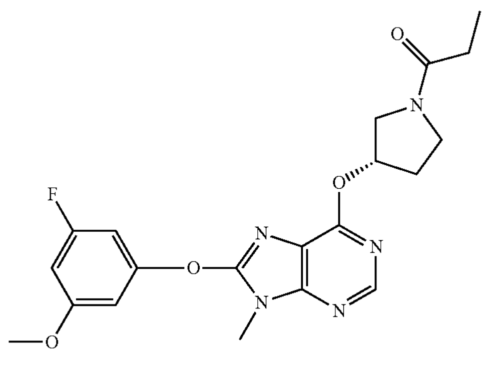 [SMILES: CCC(=O)N1CC[C@H](Oc2ncnc3c2nc(Oc2cc(F)cc(OC)c2)n3C)C1] | 8-(3-fluoro-5-methoxyphenoxy)-9-methyl-6-{[(3S)-1-propanoylpyrrolidin-3-yl]oxy}-9H-purine | Calc'd 416, found 416 |
| 12-3 | 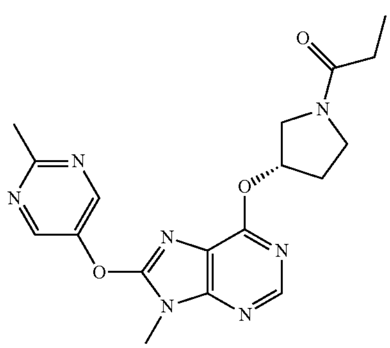 [SMILES: CCC(=O)N1CC[C@H](Oc2ncnc3c2nc(Oc2cnc(C)nc2)n3C)C1] | 9-methyl-8-[(2-methylpyrimidin-5-yl)oxy]-6-{[(3S)-1-propanoylpyrrolidin-3-yl]oxy}-9H-purine | Calc'd 384, found 384 |
| 12-4 | 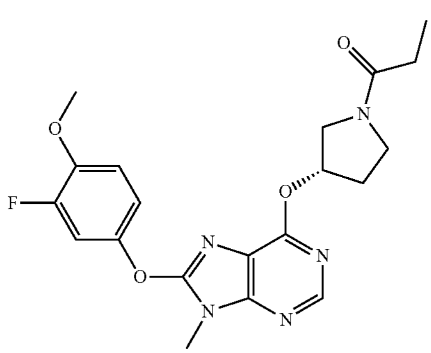 [SMILES: CCC(=O)N1CC[C@H](Oc2ncnc3c2nc(Oc2ccc(OC)c(F)c2)n3C)C1] | 8-(3-fluoro-4-methoxyphenoxy)-9-methyl-6-{[(3S)-1-propanoylpyrrolidin-3-yl]oxy}-9H-purine | Calc'd 416, found 416 |

Compound Examples of Table 13

Example 24—Preparation of 13-1

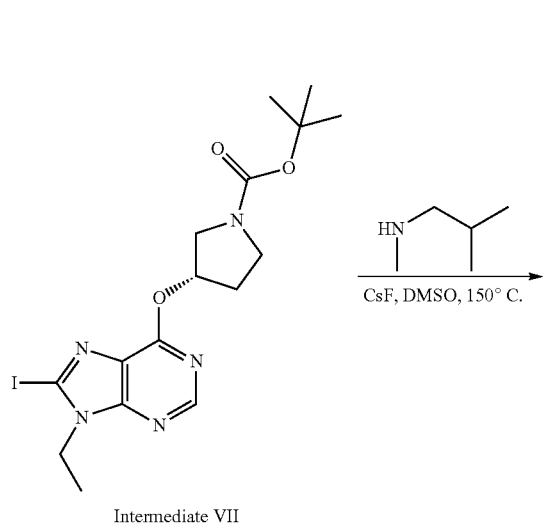

Intermediate VII 13-1

Example 25—Preparation of 13-7

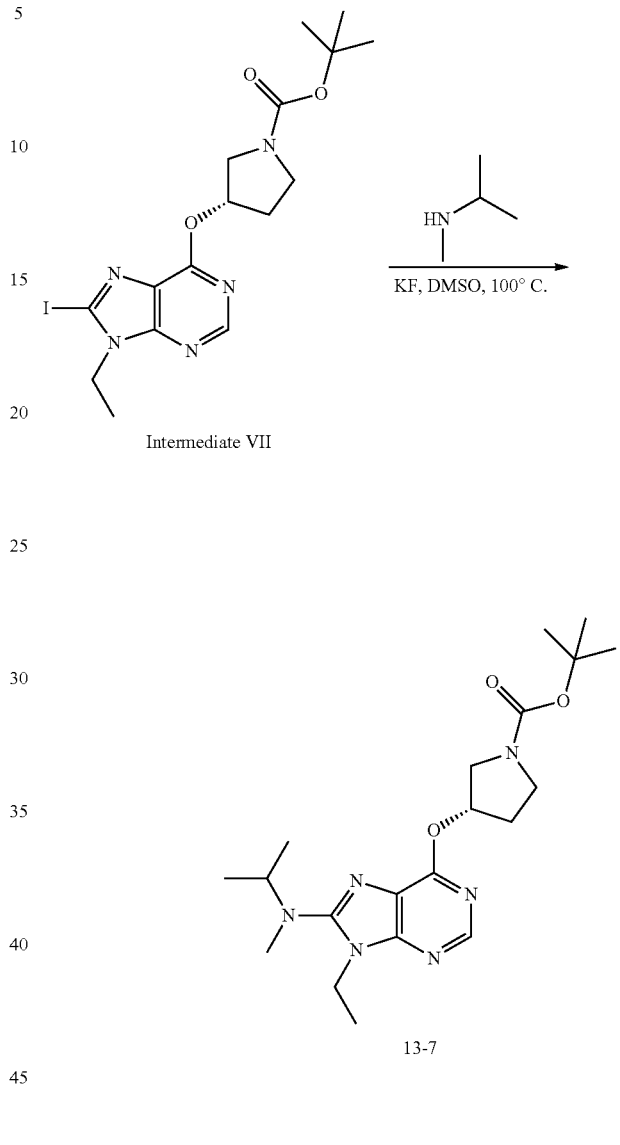

Intermediate VII 13-7

A sealed reaction vessel containing cesium fluoride (0.149 g, 0.98 mmol) was heated to 150° C. for 4 hours with stirring under high vacuum. The vial was cooled to ambient temperature under high vacuum, backfilled with argon and next was added a solution of N,2-dimethylpropan-1-amine (0.017 g, 0.20 mmol), (S)-tert-butyl 3-((9-ethyl-8-iodo-9H-purin-6-yl)oxy)pyrrolidine-1-carboxylate, Intermediate VII (0.030 g, 0.065 mmol) in DMSO (0.35 mL). The reaction was heated to 100° C. for 12 hours. The reaction was cooled, diluted to 1.0 mL with DMSO, and filtered. The filtrate was purified by reverse phase preparative HPLC to afford the TFA salt of 13-1. $^1$H NMR (500 MHz, DMSO-$d_6$) δ 8.35 (s, 1H), 5.71-5.68 (m, 1H), 4.17 (q, J=7.2 Hz, 2H), 3.67-3.60 (m, 1H), 3.47-3.33 (m, 4H), 3.18 (d, J=7.5 Hz, 2H), 3.02 (s, 3H), 2.26-2.11 (m, 1H), 2.01-1.96 (m, 1H), 1.50-1.20 (m, 9H), 1.33 (t, J=7.2 Hz, 3H), 0.87 (d, 6H). MS (EI) Calc'd. for $C_{21}H_{35}N_6O_3$ [M+H]$^+$, 419. found, 419.

To a reaction vessel were added (S)-tert-butyl 3-((9-ethyl-8-iodo-9H-purin-6-yl)oxy)pyrrolidine-1-carboxylate, Intermediate VII, (0.023 g, 0.050 mmol), N-methylpropan-2-amine (0.014 g, 0.20 mmol), potassium fluoride (0.030 g, 0.50 mmol) in DMSO (0.35 mL). The reaction was heated to 100° C. for 10 hours, cooled, diluted to 1.0 mL with DMSO, and filtered. The filtrate was purified by reverse phase preparative HPLC to afford the TFA salt of 13-7. $^1$H NMR (600 MHz, DMSO-$d_6$) δ 8.29 (s, 1H), 5.67 (m, 1H), 4.07 (q, J=7.2 Hz, 2H), 3.89-3.83 (m, 1H), 3.61 (m, 1H), 3.50-3.40 (m, 2H), 2.77 (s, 3H), 2.49-2.44 (m, 1H), 2.30-2.10 (m, 2H), 1.50-1.40 (m, 12H), 1.15 (d, J=6.6 Hz, 6H). MS ESI calc'd. for $C_{20}H_{33}N_6O_3$ [M+H]$^+$, 405. found, 405.

Compounds 13-2 to 13-6 and 13-8 were prepared in an analogous fashion as described for Example 25 using the corresponding amine.

TABLE 13

| Compound | Structure | Compound Name | MS [M + H]+ |
|---|---|---|---|
| 13-1 | 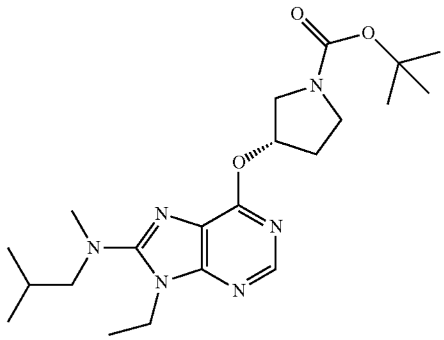 [SMILES: CCn1c(N(C)CC(C)C)nc2c(O[C@H]3CCN(C(=O)OC(C)(C)C)C3)ncnc21] | tert-butyl (3S)-3-({9-ethyl-8-[methyl(2-methylpropyl)amino]-9H-purin-6-yl}oxy)pyrrolidine-1-carboxylate | Calc'd 419, found 419 |
| 13-2 | 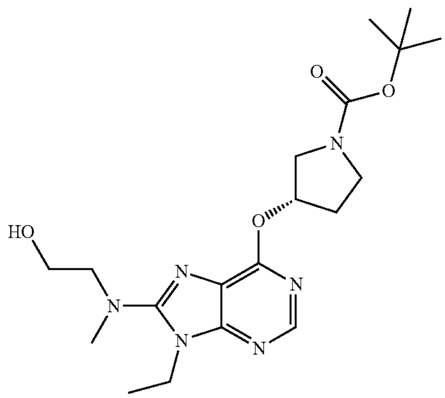 [SMILES: CCn1c(N(C)CCO)nc2c(O[C@H]3CCN(C(=O)OC(C)(C)C)C3)ncnc21] | tert-butyl (3S)-3-({9-ethyl-8-[(2-hydroxyethyl)(methyl)amino]-9H-purin-6-yl}oxy)pyrrolidine-1-carboxylate | Calc'd 407, found 407 |
| 13-3 | 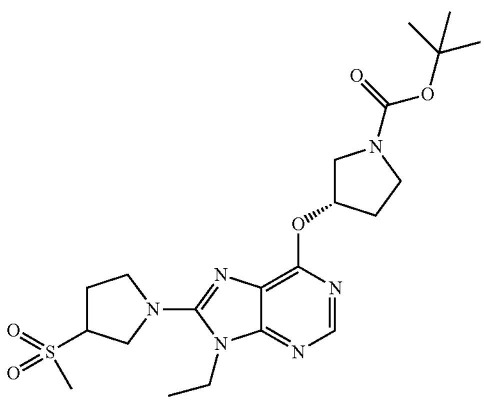 [SMILES: CCn1c(N2CCC(S(C)(=O)=O)C2)nc2c(O[C@H]3CCN(C(=O)OC(C)(C)C)C3)ncnc21] | tert-butyl (3S)-3-({9-ethyl-8-[3-(methylsulfonyl)pyrrolidin-1-yl]-9H-purin-6-yl}oxy)pyrrolidine-1-carboxylate | Calc'd 481, found 481 |
| 13-4 | 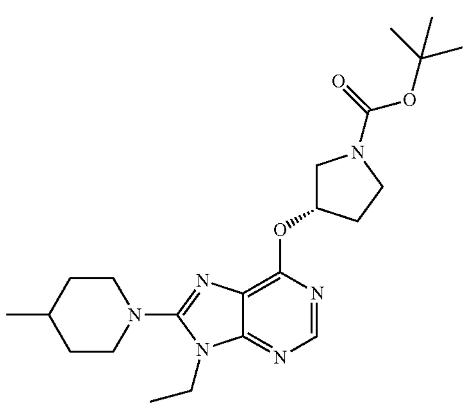 [SMILES: CCn1c(N2CCC(C)CC2)nc2c(O[C@H]3CCN(C(=O)OC(C)(C)C)C3)ncnc21] | tert-butyl (3S)-3-{[9-ethyl-8-(4-methylpiperidin-1-yl)-9H-purin-6-yl]oxy}pyrrolidine-1-carboxylate | Calc'd 431, found 431 |

TABLE 13-continued

| Compound | Structure | Compound Name | MS [M + H]⁺ |
|---|---|---|---|
| 13-5 | 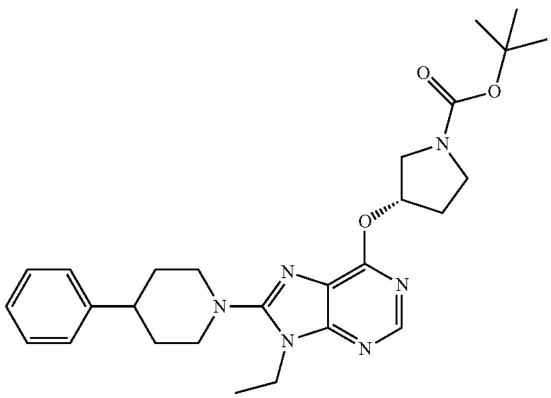 [SMILES: CCn1c(N2CCC(c3ccccc3)CC2)nc2c(O[C@H]3CCN(C(=O)OC(C)(C)C)C3)ncnc21] | tert-butyl (3S)-3-{[9-ethyl-8-(4-phenylpiperidin-1-yl)-9H-purin-6-yl]oxy}pyrrolidine-1-carboxylate | Calc'd 493, found 493 |
| 13-6 | 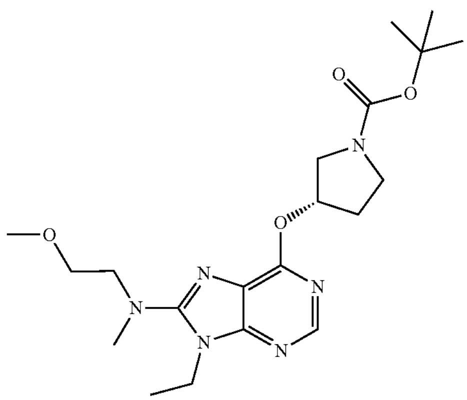 [SMILES: CCn1c(N(C)CCOC)nc2c(O[C@H]3CCN(C(=O)OC(C)(C)C)C3)ncnc21] | tert-butyl (3S)-3-({9-ethyl-8-[(2-methoxyethyl)(methyl)amino]-9H-purin-6-yl}oxy)pyrrolidine-1-carboxylate | Calc'd 421, found 421 |
| 13-7 | 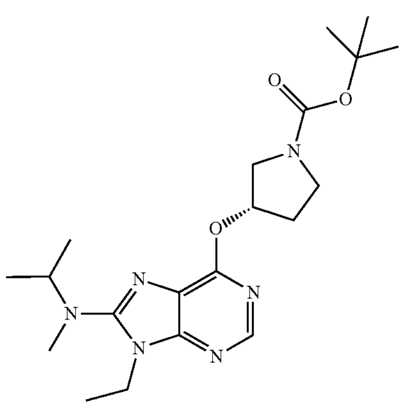 [SMILES: CCn1c(N(C)C(C)C)nc2c(O[C@H]3CCN(C(=O)OC(C)(C)C)C3)ncnc21] | tert-butyl (3S)-3-({9-ethyl-8-[methyl(1-methylethyl)amino]-9H-purin-6-yl}oxy)pyrrolidine-1-carboxylate | Calc'd 405, found 405 |

TABLE 13-continued

| Compound | Structure | Compound Name | MS [M + H]+ |
|---|---|---|---|
| 13-8 | 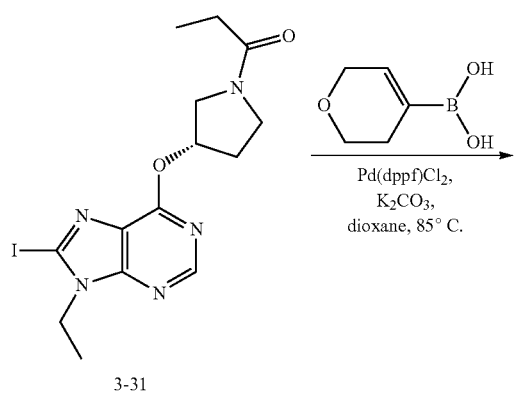 | tert-butyl (3S)-3-{[9-ethyl-8-(3-methylpyrrolidin-1-yl)-9H-purin-6-yl]oxy}pyrrolidine-1-carboxylate | Calc'd 417, found 417 |

Compound Examples of Table 14

Example 26—Preparation of Compound 14-1

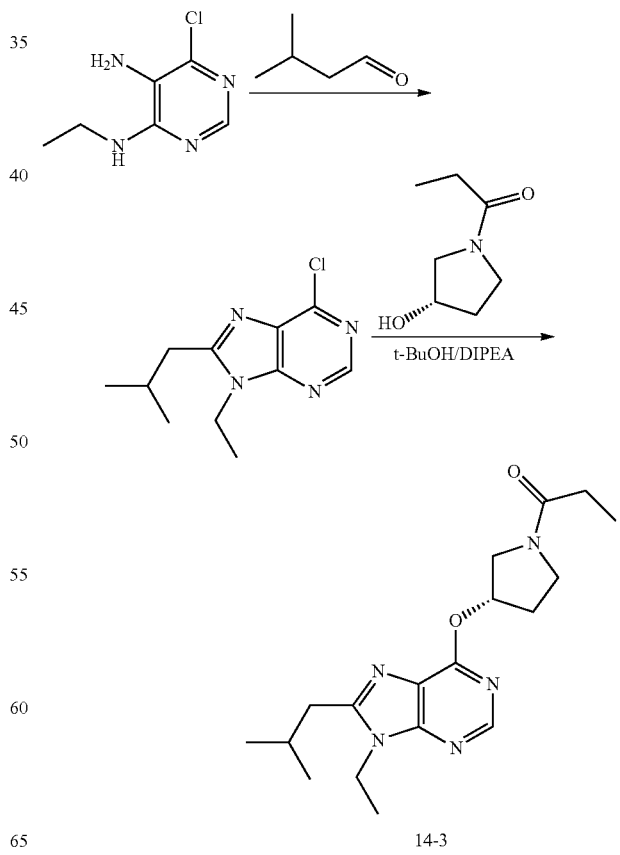

A mixture of compound 3-31 (15 mg, 0.12 mmol), 3,6-dihydro-2H-pyran-4-ylboronic acid (15 mg, 0.12 mmol), $K_2CO_3$ (21 mg, 0.15 mmol) and Pd(dppf)Cl$_2$ (15 mg, 0.02 mmol) in dioxane (3 mL) and water (1 mL) was heated to 85° C. for 16 h. After this time, the mixture was cooled to room temperature, the solvent was removed in vacuo, water (20 mL) and DCM (20 mL) were added, separated and the aqueous layer was extracted with DCM (2×30 mL). The organic layer was dried over Na$_2$SO$_4$ and concentrated. The residue was then purified by preparative reverse phase HPLC to provide 14-1 as a TFA salt. $^1$H NMR (400 MHz, CDCl$_3$) δ 8.52 (m, 1H), 6.33 (s, 1H), 5.93 (s, 1H), 4.41-4.37 (m, 4H), 3.99-3.96 (m, 3H), 3.87-3.77 (m, 2H), 3.72-3.62 (m, 1H), 2.72 (m, 2H), 2.52-2.43 (m, 1H), 2.38-2.27 (m, 3H), 1.52-1.47 (m, 3H), 1.19-1.14 (m, 3H). MS (EI) Calc'd for $C_{19}H_{26}N_5O_3$ [M+H]$^+$, 372. found, 372.

Example 27—Preparation of Compound 14-3

A mixture of 6-chloro-$N^4$-ethylpyrimidine-4,5-diamine described for the preparation of Intermediate IV (170 mg, 1.0 mmol) in DMF (1 mL) was treated with $FeCl_3$ hexahydrate (68 mg, 0.25 mmol), followed by 3-methylbutanal (190 mg, 2.0 mmol). The contents was heated to 80° C. for 16 h in a sealed vessel, then cooled to room temperature. The solvent was concentrated and the residue purified by chromatography on silica gel (10-30% EtOAc/hexanes) to furnish 6-chloro-9-ethyl-8-isobutyl-9H-purine as a white oil. MS (EI) Calc'd for $C_{11}H_{16}ClN_4$ [M+H]+, 239. found, 239.

To a solution of (S)-1-(3-hydroxypyrrolidin-1-yl)propan-1-one (34 mg, 0.24 mmol) in dry THF (2 mL) was added NaH (12 mg, 0.3 mmol, 60% in mineral oil) at 0° C. The mixture was stirred at this temperature for 10 min, then 6-chloro-9-ethyl-8-isobutyl-9H-purine (48 mg, 0.2 mmol) was added. The reaction mixture was then stirred at RT for 15 hr under a $N_2$ atmosphere. Water (20 mL) was added, and the mixture extracted with EtOAc (3×20 mL), the combined organic extracts was washed with brine (30 mL), dried over $Na_2SO_4$, filtered and concentrated. The residue was purified by chromatography on silica gel (eluting with 2:1 EtOAc/petroleum ether) to obtain 14-3. $^1H$ NMR (400 MHz, $CDCl_3$) δ 8.44-8.42 (m, 1H), 5.86 (s, 1H), 4.27-4.22 (m, 2H), 3.93-3.87 (m, 1H), 3.81-3.71 (m, 2H), 3.70-3.58 (m, 1H), 2.76-2.74 (m, 2H), 2.46-2.37 (m, 5H), 1.42-1.39 (m, 3H), 1.14-1.09 (m, 3H), 1.01-0.99 (m, 6H). MS (EI) Calc'd for $C_{18}H_{28}N_5O_2$ [M+H]$^+$, 346. found, 346.

Example 28—Preparation of Compound 14-5

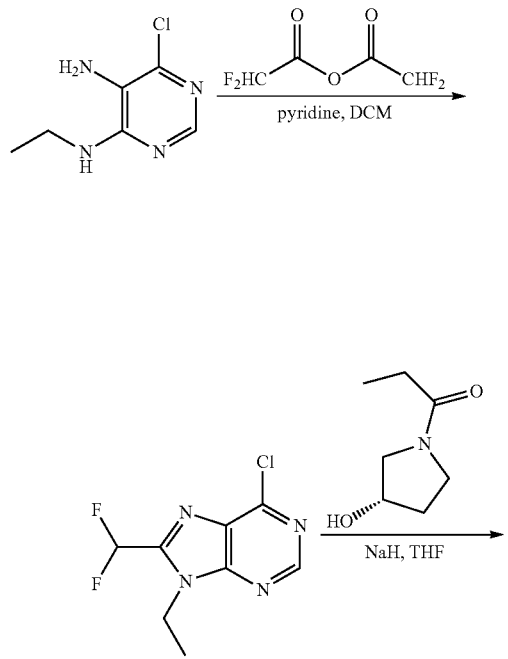

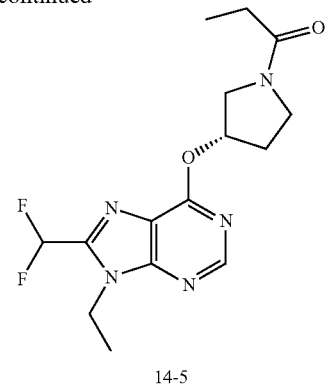

14-5

A mixture of 6-chloro-$N^4$-ethylpyrimidine-4,5-diamine described for the preparation of Intermediate IV (1.2 g, 7.0 mmol) in dry DCM (20 mL) and pyridine (13 mL, 140 mmol) was treated with difluoroacetic anhydride (2.4 g, 14 mmol). The reaction mixture was stirred for 16 h at room temperature. Another portion of difluoroacetic anhydride (2.4 g, 14 mmol) was added and the mixture was stirred for 4 h at room temperature. Water (20 mL) was added and the mixture was extracted with DCM (2×20 mL). The combined organic extract was dried over anhydrous sodium sulfate and concentrated under reduced pressure. The residue was purified chromatography on silica gel (eluting with 70/30 petroleum ether/EtOAc) to provide 6-chloro-8-(difluoromethyl)-9-ethyl-9H-purine as a white solid. MS (EI) Calc'd for $C_8H_8ClF_2N_4$ [M+H]$^+$, 233. found, 233.

To a solution of (S)-1-(3-hydroxypyrrolidin-1-yl)propan-1-one (38 mg, 0.26 mmol) in dry THF (2 mL) was added NaH (13 mg, 0.33 mmol, 60% on mineral) at 0° C. The mixture was stirred at this temperature for 10 min, then 6-chloro-8-(difluoromethyl)-9-ethyl-9H-purine (51 mg, 0.22 mmol) was added. The reaction mixture was then stirred for 15 h. Water (20 mL) was added, and the mixture was extracted with EtOAc (3×20 mL), the combined organic extract was washed with brine (30 mL), dried over $Na_2SO_4$, filtered and concentrated. The residue was purified by chromatography on silica gel (eluting with 2:1 petroleum ether/EtOAc) to afford 14-5. $^1H$ NMR (400 MHz, $CD_3OD$) δ 8.61 (s, 1H), 7.15 (t, J=52 Hz, 1H), 6.03-5.99 (m, 1H), 4.54-4.48 (m, 2H), 4.02-3.63 (m, 4H), 2.47-2.34 (m, 4H), 1.52-1.48 (m, 3H), 1.17-1.11 (m, 3H). MS (EI) Calc'd for $C_{15}H_{20}F_2N_5O_2$ [M+H]$^+$, 340. found, 340.

Compound 14-2 was prepared in an analogous fashion as described for Example 26 using cyclopropane boronic acid.

Compound 14-4 was prepared in an analogous fashion as described for Example 27.

Compounds 14-6 and 14-7 was prepared in an analogous fashion as described for Example 28, using trifluoroacetic anhydride.

TABLE 14

| Compound | Structure | Compound Name | MS [M + H]+ |
|---|---|---|---|
| 14-1 | 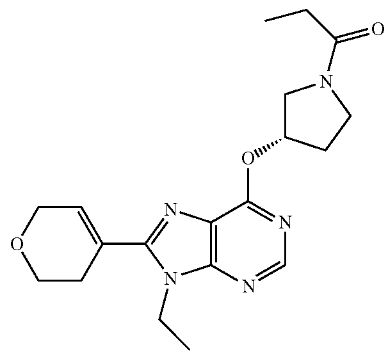 [SMILES: CCC(=O)N1CC[C@H](Oc2ncnc3c2nc(C2=CCOCC2)n3CC)C1] | 8-(3,6-dihydro-2H-pyran-4-yl)-9-ethyl-6-{[(3S)-1-propanoylpyrrolidin-3-yl]oxy}-9H-purine | Calc'd 372, found 372 |
| 14-2 | 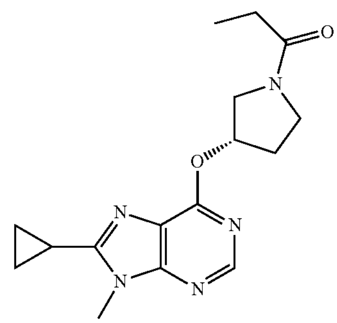 [SMILES: CCC(=O)N1CC[C@H](Oc2ncnc3c2nc(C2CC2)n3C)C1] | 8-cyclopropyl-9-methyl-6-{[(3S)-1-propanoylpyrrolidin-3-yl]oxy}-9H-purine | Calc'd 316, found 316 |
| 14-3 | 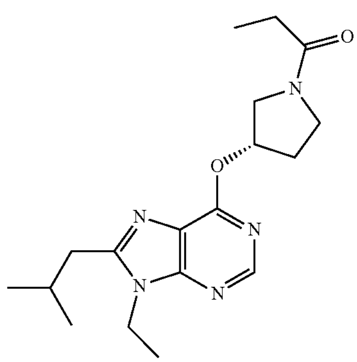 [SMILES: CCC(=O)N1CC[C@H](Oc2ncnc3c2nc(CC(C)C)n3CC)C1] | 9-ethyl-8-(2-methylpropyl)-6-{[(3S)-1-propanoylpyrrolidin-3-yl]oxy}-9H-purine | Calc'd 346, found 346 |
| 14-4 | 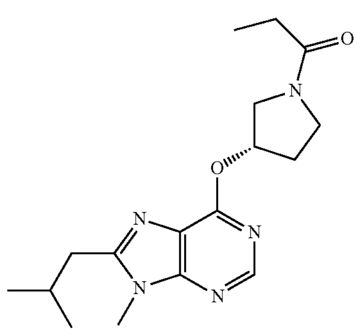 [SMILES: CCC(=O)N1CC[C@H](Oc2ncnc3c2nc(CC(C)C)n3C)C1] | 9-methyl-8-(2-methylpropyl)-6-{[(3S)-1-propanoylpyrrolidin-3-yl]oxy}-9H-purine | Calc'd 332, found 332 |

TABLE 14-continued

| Compound | Structure | Compound Name | MS [M + H]⁺ |
|---|---|---|---|
| 14-5 | 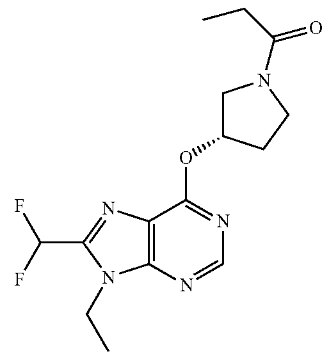 [SMILES: CCC(=O)N1CC[C@H](Oc2ncnc3c2nc(C(F)F)n3CC)C1] | 8-(difluoromethyl)-9-ethyl-6-{[(3S)-1-propanoylpyrrolidin-3-yl]oxy}-9H-purine | Calc'd 340, found 340 |
| 14-6 | 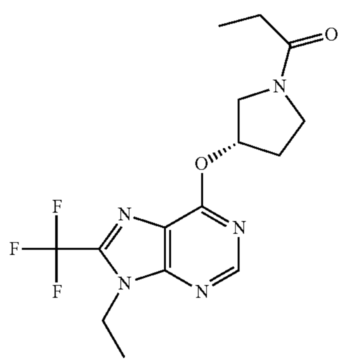 [SMILES: CCC(=O)N1CC[C@H](Oc2ncnc3c2nc(C(F)(F)F)n3CC)C1] | 9-ethyl-6-{[(3S)-1-propanoylpyrrolidin-3-yl]oxy}-8-(trifluoromethyl)-9H-purine | Calc'd 358, found 358 |
| 14-7 | 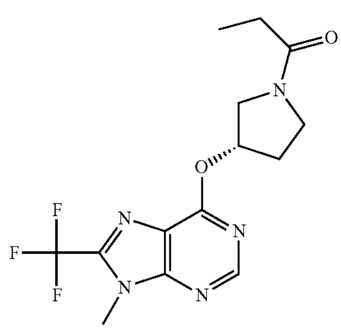 [SMILES: CCC(=O)N1CC[C@H](Oc2ncnc3c2nc(C(F)(F)F)n3C)C1] | 9-methyl-6-{[(3S)-1-propanoylpyrrolidin-3-yl]oxy}-8-(trifluoromethyl)-9H-purine | Calc'd 344, found 344 |

Compound Examples of Table 15

Example 29—Preparation of 15-1 and 15-2

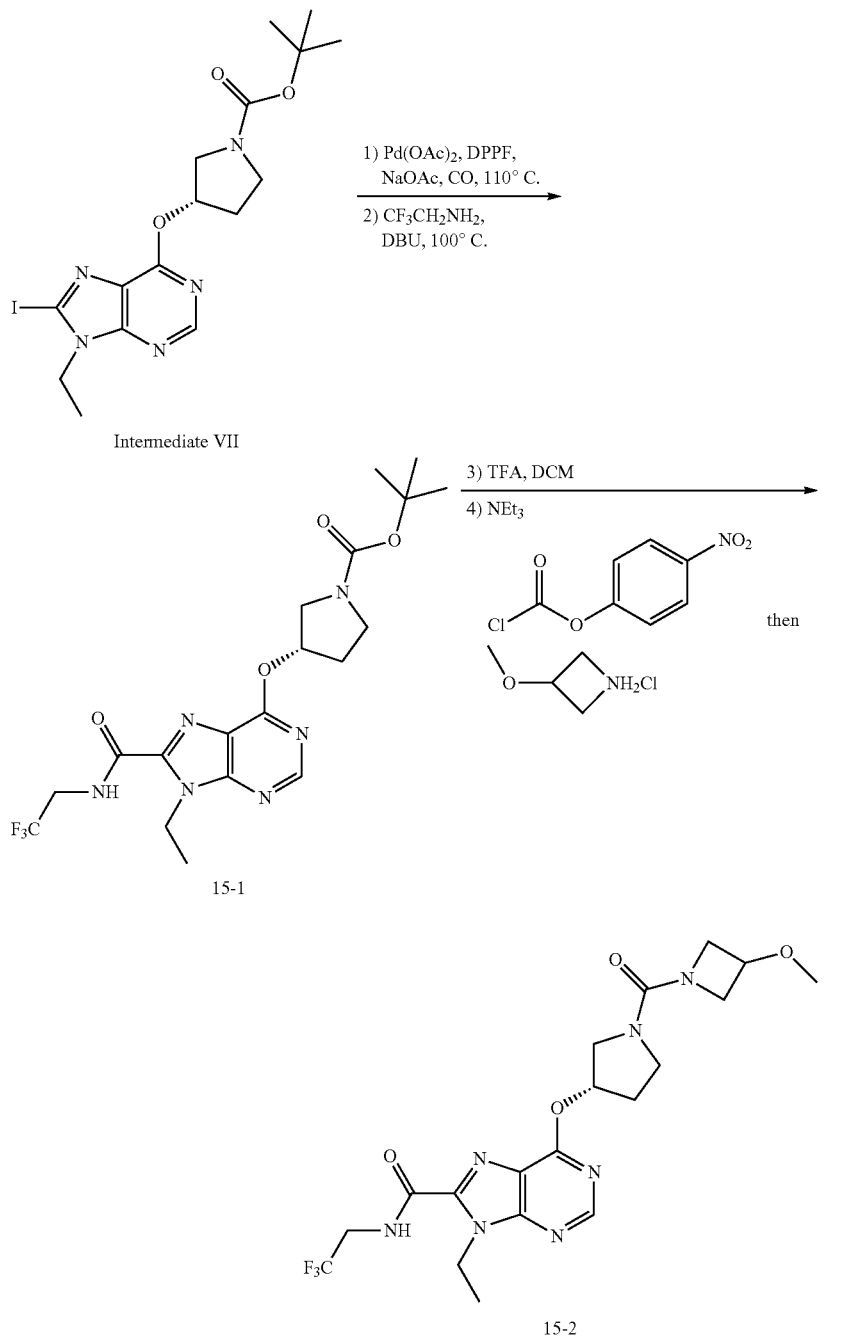

Steps 1 and 2: Preparation of 15-1

To a solution of Intermediate VII (1.6 g, 3.5 mmol) in EtOH (40 mL) were added 1,1'-bis(diphenylphosphino)ferrocene (190 mg, 0.35 mmol), palladium acetate (38 mg, 0.17 mmol) and sodium acetate (572 mg, 6.97 mmol). The reaction mixture was stirred for 24 h at 110° C. under carbon monoxide atmosphere (20 atm). The resulting mixture was concentrated and purified by silica gel column chromatography (10% EtOAc/petroleum ether) to provide (S)-ethyl 6-(1-(tert-butoxycarbonyl)pyrrolidin-3-yloxy)-9-ethyl-9H-purine-8-carboxylate.

To a solution of (S)-ethyl 6-(1-(tert-butoxycarbonyl)pyrrolidin-3-yloxy)-9-ethyl-9H-purine-8-carboxylate (650 mg, 1.6 mmol) in THF (15 mL) were added 2,2,2-trifluoroethanamine (20 mL) and 1,8-diazabicyclo[5.4.0]undec-7-ene (488 mg, 3.21 mmol). The mixture was stirred for 24 h at 100° C. and concentrated. The residue was purified by silica gel column chromatography (5-20% EtOAc/petroleum ether) to afford 15-1. MS (EI) calc'd for $C_{19}H_{26}F_3N_6O_4$ [M+H]$^+$, 459. found, 459.

Steps 3 and 4: Preparation of 15-2

To a solution of 15-1 (370 mg, 0.81 mmol) in DCM (10 mL) was added trifluoroacetic acid (2 mL) and stirred for 1 h at ambient temperature. The reaction mixture was concentrated under reduced pressure to give (S)-9-ethyl-6-(pyrrolidin-3-yloxy)-N-(2,2,2-trifluoroethyl)-9H-purine-8-carboxamide trifluoroacetic acid salt. The residue was dissolved in THF (15 mL) and treated with triethylamine (540 mg, 5.3 mmol) and 4-nitrophenyl carbonochloridate (140 mg, 0.67 mmol) at 0° C. The resulting solution was stirred at ambient temperature for 1 h followed by the addition of 3-methoxyazetidine hydrochloride (420 mg, 3.4 mmol). The mixture was stirred at 60° C. for 24 h, then concentrated and purified by reverse phase chromatography (MeCN/water with 10 mM aqueous NH$_4$HCO$_3$ modifier) to provide 15-2. $^1$H NMR (300 MHz, CDCl$_3$) δ 8.60 (s, 1H), 8.02 (s, 1H), 5.91 (s, 1H), 4.85 (q, J=7.2 Hz, 2H), 4.29-4.01 (m, 5H), 3.96-3.82 (m, 3H), 3.74-3.63 (m, 3H), 3.29 (s, 3H), 2.41-2.22 (m, 2H), 1.51 (t, J=7.2 Hz, 3H). MS (EI) calc'd for $C_{19}H_{25}F_3N_7O_4$ [M+H]$^+$, 472. found, 472.

Example 30—Preparation of 15-4

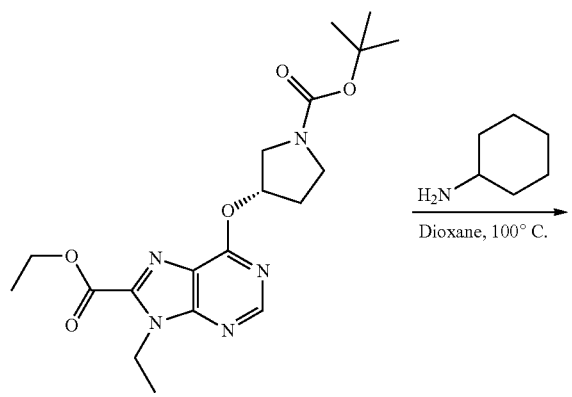

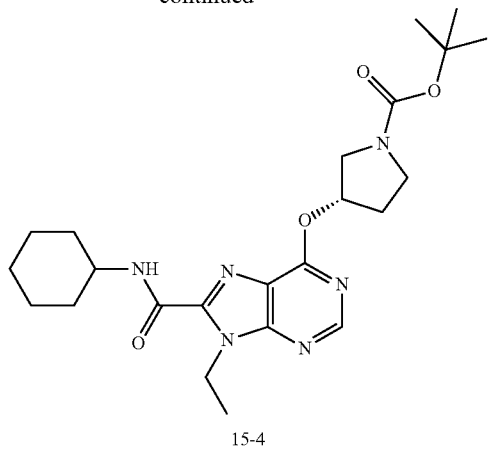

15-4

To a reaction vessel were added (S)-ethyl 6-(1-(tert-butoxycarbonyl)pyrrolidin-3-yloxy)-9-ethyl-9H-purine-8-carboxylate (prepared as described for the synthesis of 15-1; 0.030 g, 0.074 mmol), dioxane (0.5 mL), and cyclohexylamine (0.10 g, 1.0 mmol). The reaction vessel was sealed and warmed to 100° C. for 12 hours. The completed reaction was concentrated in vacuo, taken up in DMSO (1.0 mL) and purified by reverse phase HPLC (acetonitrile/water with 0.1% TFA modifier). The collected fractions were combined, diluted with EtOAc, and washed with a saturated sodium bicarbonate solution. The organic extracts were collected, dried over magnesium sulfate and filtered. The filtrate was concentrated to afford 15-4. $^1$H NMR (500 MHz, DMSO-d$_6$) δ 8.91 (d, J=8.4 Hz, 1H); 8.63 (s, 1H); 5.84 (d, J=14.1 Hz, 1H); 4.62 (q, J=7.1 Hz, 2H); 3.79-3.77 (m, 1H); 3.66-3.63 (m, 1H); 3.49-3.47 (m, 2H); 3.06-3.04 (m, 1H); 2.27-2.18 (m, 2H); 1.78-1.71 (m, 4H); 1.61-1.58 (m, 1H); 1.46-1.28 (m, 16H); 1.13-1.08 (m, 1H). MS (EI) Calc'd. for $C_{23}H_{35}N_6O_4$ [M+H]$^+$ 459. found 459.

Compounds 15-3 and 15-5 were prepared as described for 15-4 (Example 30) using the corresponding amine.

TABLE 15

| Compound | Structure | Compound Name | MS [M + H]$^+$ |
|---|---|---|---|
| 15-1 | 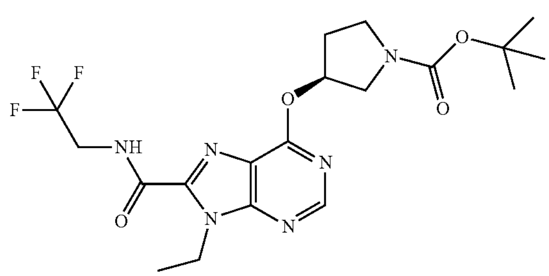 [SMILES: CCn1c(C(=O)NCC(F)(F)F)nc2c(O[C@H]3CCN(C(=O)OC(C)(C)C)C3)ncnc21] | tert-butyl (3S)-3-({9-ethyl-8-[(2,2,2-trifluoroethyl)carbamoyl]-9H-purin-6-yl}oxy)pyrrolidine-1-carboxylate | Calc'd 459, found 459 |

TABLE 15-continued

| Compound | Structure | Compound Name | MS [M + H]+ |
|---|---|---|---|
| 15-2 | 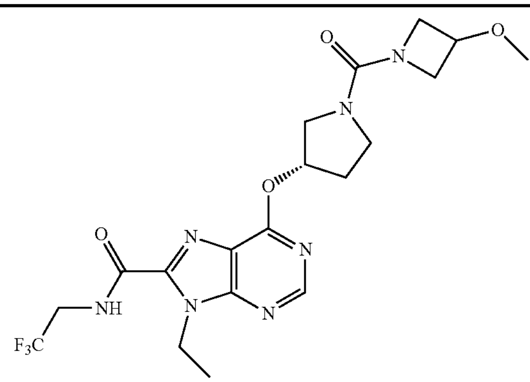 | (S)-9-ethyl-6-((1-(3-methoxyazetidine-1-carbonyl)pyrrolidin-3-yl)oxy)-N-(2,2,2-trifluoroethyl)-9H-purine-8-carboxamide | Calc'd 472, found 472 |
| 15-3 | 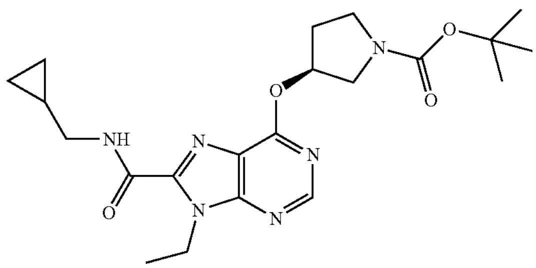 [SMILES: CCn1c(C(=O)NCC2CC2)nc2c(O[C@H]3CCN(C(=O)OC(C)(C)C)C3)ncnc21] | tert-butyl (3S)-3-({8-[(cyclopropylmethyl)carbamoyl]-9-ethyl-9H-purin-6-yl}oxy)pyrrolidine-1-carboxylate | Calc'd 431, found 431 |
| 15-4 | 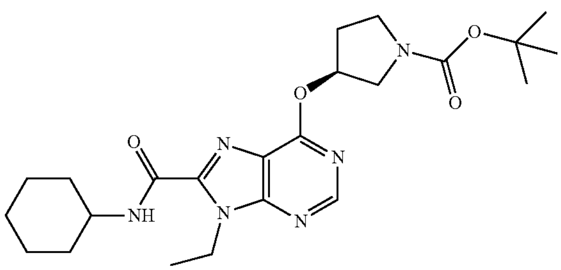 [SMILES: CCn1c(C(=O)NC2CCCCC2)nc2c(O[C@H]3CCN(C(=O)OC(C)(C)C)C3)ncnc21] | tert-butyl (3S)-3-{[8-(cyclohexylcarbamoyl)-9-ethyl-9H-purin-6-yl]oxy}pyrrolidine-1-carboxylate | Calc'd 459, found 459 |
| 15-5 | 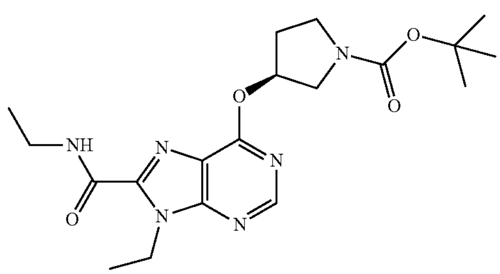 [SMILES: CCNC(=O)c1nc2c(O[C@H]3CCN(C(=O)OC(C)(C)C)C3)ncnc2n1CC] | tert-butyl (3S)-3-{[9-ethyl-8-(ethylcarbamoyl)-9H-purin-6-yl]oxy}pyrrolidine-1-carboxylate | Calc'd 405, found 405 |

HTRF PI3K Biochemical Assay to Measure Intrinsic Potency of Compound Inhibitors

The PI3-Kinase biochemical assays were developed to measure the intrinsic potency and compound dependent inhibition of the alpha, beta, delta, and gamma PI3K isoform enzymes. This assay was developed and further optimized from a kit produced by Upstate (Millipore catalog #33-047) and has been configured for HTS and SAR screening. Briefly, this procedure exploits the exquisite specificity and high affinity binding of enzyme reaction substrate phosphatidyl(3,4,5)triphosphate (PIP3) to the GRP1 pleckstrin homology (PH) domain to generate the signal. In the absence of PIP3, an HTRF (Homogeneous Time-Resolved Fluorescence energy transfer) complex is formed consisting of europium (Eu)-labeled anti-GST, GST tagged GRP1-PH domain, biotin-PIP3 and streptavidin conjugated APC. The native PIP3 produced by PI3-Kinase activity disrupts in a competitive manner the biotin-PIP3 from the PH domain, resulting in the loss of energy transfer (HTRF complex) and a decrease in the signal. The format of this assay is the same for all 4 isoforms of PI3K; the differences lie in the concentration of enzyme used to achieve robust assay window. The alpha, beta, and delta assays are run at 0.5, 1, and 0.3 nM enzymes and the gamma assay is run at 5 nM enzyme. The ATP concentration is 100 uM in the alpha, beta, and delta assays and 50 uM ATP in the gamma assay. All reactions are run at 5 uM PIP2.

Assay Protocol

Compounds are serially diluted (3-fold in 100% DMSO) across a 384-well polypropylene source plated from column 3 to column 12 and column 13 to column 22, to yield 10 concentration dose response for each test compound. Columns 1, 2, 23 and 24 contain either only DMSO or pharmacological known control inhibitor. Once titrations are made, 2.5 nL of the compounds on 384 well plates are reformatted and transferred by acoustic dispense in quadruplicates to a 1536 assay plate (Greiner) to assay across all four PI3K isoform enzymes.

The PI3-Kinase biochemical assay was optimized using the HTRF kit provided by Upstate (Millipore). The assay kit contains six reagents: 1) 4× Reaction Buffer; 2) native PIP2 (substrate); 3) Stop (EDTA); 4) Detection Mix A (Streptavidin-APC); 5) Detection Mix B (Eu-labeled Anti-GST plus GST-tagged PH-domain); 6) Detection Mix C. In addition, the following items were obtained or purchased; PI3Kinase (alpha 14-602, beta 14-603, gamma 14-558 and delta 14-604 from Upstate; Millipore), dithiothreitol (Sigma, D-5545), Adenosine-5' triphosphate (InVitrogen, Cat#AS001A), native PIP3 (PI(3,4,5)P3, diC8, H$^+$, CELLSIGNALS, INC. Cat #907) DMSO (Sigma, 472301).

PI3Kinase Reaction Buffer is prepared by dilution the stock 1:4 with de-ionized water. DTT, PIP2 and Biotin-PIP3 were added to 1536 assay plate at a final concentration of 5 mM, 5 mM and 25 nM on the day of use. Enzyme addition and compound pre-incubation are initiated by the addition of 1.25 ul of PI3K (at twice its final concentration) in the 1× reaction buffer to all wells using a BioRaptor. Plates are incubated at room temperature for 15 minutes. Reactions are initiated by addition of 1.25 ul of 2× substrate solution (PIP2 and ATP in 1× reaction buffer) using BioRaptor. Plates are incubated in humidified chamber at room temperature for one hour. Reactions are quenched by addition of 0.625 uL of stop solution to all wells using the BioRaptor. The quenched reactions are then processed to detect product formation by adding 0.625 uL of Detection Solution to all wells using the BioRaptor (Detection mix C, Detection Mix A, and Detection Mix B combined together in an 18:1:1 ratio prepared 2 hours prior to use). Following a one hour incubation in the dark, the HTRF signal is measured on the Envision plate reader set for 330 nm excitation and dual emission detection at 620 nM (Eu) and 665 nM (APC).

Data Analysis

The loss of the HTRF signal is due to the displacement of biotinylated-PIP3 from the PH domain by the PI3K-dependent conversion of PIP2 to PIP3. This loss of signal is nonlinear with respect to both increasing product and time. This non-linear detection will impact accuracy of $IC_{50}$ calculations; therefore, there is a need for a correction factor to obtain more accurate $IC_{50}$ values. This correction is derived from a PIP3 standard curve run in a separate assay plate. All data were calculated using the ratio of acceptor (APC) to donor (Europium) fluorescence in each well of the assay plate. The percent inhibition for each compound concentration was calculated as follows: % inhibition=100× (fluorescence ratio-CtrlB)/(CtrlA-CtrlB) where CtrlA=PI3Kinase reaction+known reference inhibitor and CtrlB=PI3K+DMSO. An $IC_{50}$ was then calculated fitting the % inhibition data to the equation: % inhibition=min+(Max−min)/1+([inhibitor]/$IC_{50}$)^n) where min is the % inhibition with inhibitor, max is the signal in DMSO control, and n is the Hill slope.

Biological Data

The following table tabulates the biological data disclosed for the instant invention. The biological data was collected using the methodology described above. For each compound, PI3Kdelta $IC_{50}$ values are listed along with the relative selectivity versus PI3K alpha, as well as the physical form of the compound dosed in this assay.

The determination of relative selectivity for a given compound is defined as the relative ratio of the (PI3K-alpha $IC_{50}$ value/PI3K-delta $IC_{50}$ value).

| Compound | Form Screened | PI3Kdelta $IC_{50}$ (nM) | Relative Selectivity versus PI3Kalpha |
|---|---|---|---|
| 1-1 | neutral | 4.3 | >10 |
| 1-2 | neutral | 2100 | >5 |
| 1-3 | TFA salt | 8.3 | >10 |
| 1-4 | TFA salt | 17 | >10 |
| 1-5 | TFA salt | 110 | |
| 1-6 | TFA salt | 14 | 4 |
| 1-7 | TFA salt | 340 | |
| 1-8 | TFA salt | 90 | |
| 1-9 | TFA salt | 28 | >10 |
| 1-10 | TFA salt | 300 | |
| 1-11 | TFA salt | 65 | |
| 1-12 | neutral | 610 | 3 |
| 1-13 | TFA salt | 2.6 | >10 |
| 1-14 | formic acid salt | 99 | >10 |
| 1-15 | formic acid salt | 30 | >10 |
| 1-16 | formic acid salt | 1200 | >9 |
| 1-17 | formic acid salt | 28 | >10 |
| 1-18 | formic acid salt | 98 | >10 |
| 1-19 | formic acid salt | 28 | >10 |
| 1-20 | formic acid salt | 65 | >10 |
| 1-21 | formic acid salt | 660 | >10 |
| 1-22 | formic acid salt | 210 | >10 |
| 1-23 | formic acid salt | 140 | >10 |
| 1-24 | formic acid salt | 4400 | >2 |
| 1-25 | formic acid salt | 330 | >10 |
| 1-26 | formic acid salt | 13 | >10 |
| 1-27 | formic acid salt | 590 | >10 |
| 1-28 | formic acid salt | 320 | >10 |
| 1-29 | formic acid salt | 35 | >10 |
| 1-30 | TFA salt | 1300 | 3 |
| 1-31 | neutral | 2100 | >5 |
| 1-32 | neutral | 1400 | >7 |
| 1-33 | neutral | 4.0 | >10 |
| 1-34 | TFA salt | 0.7 | >10 |
| 1-35 | TFA salt | 0.5 | >10 |
| 1-36 | TFA salt | 12 | >10 |
| 1-37 | TFA salt | 33 | >10 |
| 1-38 | TFA salt | 8.1 | >10 |
| 1-39 | TFA salt | 6.9 | >10 |
| 1-40 | neutral | 85 | >10 |
| 1-41 | neutral | 94 | >10 |
| 1-42 | neutral | 4600 | >2 |
| 1-43 | Neutral | 18 | >10 |
| 1-44 | Neutral | 3.3 | >10 |
| 1-45 | Neutral | 90 | >10 |
| 1-46 | Neutral | 3.7 | >10 |
| 1-47 | Neutral | 22 | >10 |
| 1-48 | Neutral | 4.0 | >10 |
| 1-49 | Neutral | 38 | >10 |
| 1-50 | Neutral | 37 | >10 |
| 1-51 | TFA salt | 15 | >10 |
| 2-1 | TFA salt | 68 | >10 |
| 2-2 | TFA salt | 9.4 | >10 |
| 2-3 | TFA salt | 28 | >10 |
| 2-4 | TFA salt | 22 | >10 |
| 2-5 | TFA salt | 77 | >10 |
| 2-6 | TFA salt | 31 | >10 |
| 2-7 | TFA salt | 17 | >10 |
| 2-8 | neutral | 4.3 | >10 |
| 2-9 | neutral | 1600 | 3 |
| 2-10 | TFA salt | 28 | >10 |
| 2-11 | TFA salt | 1100 | 2 |
| 2-12 | TFA salt | 960 | |
| 2-13 | TFA salt | 550 | |
| 2-14 | TFA salt | 800 | 1 |
| 2-15 | TFA salt | 38 | >10 |
| 2-16 | TFA salt | 6.3 | >10 |
| 2-17 | TFA salt | 12 | >10 |

| Compound | Form Screened | PI3Kdelta IC$_{50}$ (nM) | Relative Selectivity versus PI3Kalpha |
|---|---|---|---|
| 2-18 | TFA salt | 12 | |
| 2-19 | TFA salt | 480 | |
| 2-20 | TFA salt | 67 | |
| 2-21 | TFA salt | 110 | 1 |
| 2-22 | TFA salt | 19 | >10 |
| 2-23 | TFA salt | 12 | |
| 2-24 | neutral | 1.2 | >10 |
| 2-25 | TFA salt | 13 | >10 |
| 2-26 | TFA salt | 8.5 | >10 |
| 2-27 | neutral | 6.5 | >10 |
| 2-28 | neutral | 7.2 | >10 |
| 2-29 | neutral | 41 | 1 |
| 2-30 | neutral | 109 | |
| 2-31 | neutral | 30 | 5 |
| 2-32 | neutral | 4.7 | >10 |
| 2-33 | neutral | 3.0 | >10 |
| 2-34 | neutral | 130 | |
| 2-35 | neutral | 26 | >10 |
| 2-36 | neutral | 22 | >10 |
| 2-37 | neutral | 2.2 | >10 |
| 2-38 | neutral | 19 | 7 |
| 2-39 | neutral | 35 | >10 |
| 2-40 | neutral | 12 | 2 |
| 2-41 | neutral | 11 | 6 |
| 2-42 | neutral | 240 | 3 |
| 2-43 | neutral | 21 | 10 |
| 2-44 | neutral | 5.2 | 9 |
| 2-45 | neutral | 100 | |
| 2-46 | neutral | 5.3 | >10 |
| 2-47 | neutral | 860 | 1 |
| 2-48 | neutral | 3.6 | >10 |
| 2-49 | neutral | 68 | |
| 2-50 | neutral | 120 | 8 |
| 2-51 | TFA salt | 14 | >10 |
| 2-52 | TFA salt | 23 | >10 |
| 2-53 | TFA salt | 70 | |
| 2-54 | TFA salt | 210 | |
| 2-55 | TFA salt | 68 | |
| 2-56 | TFA salt | 25 | >10 |
| 2-57 | neutral | 7.2 | >10 |
| 2-58 | TFA salt | 3.7 | >10 |
| 2-59 | TFA salt | 150 | 2 |
| 2-60 | TFA salt | 79 | |
| 2-61 | TFA salt | 26 | >10 |
| 2-62 | TFA salt | 30 | >10 |
| 2-63 | TFA salt | 29 | 10 |
| 2-64 | TFA salt | 13 | >10 |
| 2-65 | TFA salt | 36 | >10 |
| 2-66 | TFA salt | 27 | >10 |
| 2-67 | TFA salt | 8.7 | >10 |
| 2-68 | TFA salt | 27 | >10 |
| 2-69 | TFA salt | 5.1 | >10 |
| 2-70 | TFA salt | 270 | |
| 2-71 | TFA salt | 15 | >10 |
| 2-72 | TFA salt | 16 | 9 |
| 2-73 | neutral | 5.4 | >10 |
| 2-74 | neutral | 88 | |
| 2-75 | neutral | 28 | 5 |
| 2-76 | neutral | 150 | |
| 2-77 | neutral | 10 | >10 |
| 2-78 | neutral | 74 | |
| 2-79 | neutral | 20 | >10 |
| 2-80 | neutral | 14 | 6 |
| 2-81 | neutral | 31 | 5 |
| 2-82 | neutral | 110 | |
| 2-83 | neutral | 1900 | |
| 2-84 | neutral | 23 | >10 |
| 2-85 | neutral | 76 | |
| 2-86 | neutral | 12 | >10 |
| 2-87 | TFA salt | 41 | >10 |
| 2-88 | TFA salt | 19 | >10 |
| 2-89 | TFA salt | 0.5 | >10 |
| 2-90 | TFA salt | 56 | >10 |
| 2-91 | TFA salt | 4.0 | >10 |
| 2-92 | TFA salt | 22 | >10 |
| 2-93 | TFA salt | 0.6 | >10 |
| 2-94 | TFA salt | 2.1 | >10 |
| 2-95 | TFA salt | 2.2 | >10 |
| 2-96 | TFA salt | 1.6 | >10 |
| 2-97 | TFA salt | 160 | >10 |
| 2-98 | Neutral | 2.8 | >10 |
| 2-99 | Neutral | 17 | >10 |
| 2-100 | Neutral | 17 | >10 |
| 2-101 | TFA salt | 39 | >10 |
| 2-102 | TFA salt | 70 | >10 |
| 2-103 | TFA salt | 25 | >10 |
| 2-104 | TFA salt | 88 | >10 |
| 2-105 | TFA salt | 7.0 | >10 |
| 2-106 | TFA salt | 13 | >10 |
| 2-107 | TFA salt | 2.8 | >10 |
| 2-108 | TFA salt | 1.5 | >10 |
| 2-109 | TFA salt | 3.0 | >10 |
| 2-110 | TFA salt | 1.2 | >10 |
| 2-111 | Neutral | 9.8 | >10 |
| 2-112 | Neutral | 50 | >10 |
| 2-113 | TFA salt | 5.8 | >10 |
| 2-114 | Neutral | 9.3 | >10 |
| 2-115 | Neutral | 41 | >10 |
| 2-116 | TFA salt | 4.4 | >10 |
| 2-117 | Neutral | 7.3 | >10 |
| 2-118 | Neutral | 4.1 | >10 |
| 2-119 | Neutral | 1.2 | >10 |
| 2-120 | Neutral | <1.0 | >10 |
| 2-121 | TFA salt | 13 | >10 |
| 2-122 | Neutral | 16 | >10 |
| 2-123 | Neutral | <1.0 | >10 |
| 2-124 | Neutral | 110 | >10 |
| 2-125 | Neutral | 3.0 | >10 |
| 2-126 | Neutral | 38 | >10 |
| 2-127 | Neutral | 1.0 | >10 |
| 2-128 | TFA salt | 12 | >10 |
| 2-129 | TFA salt | 1.3 | >10 |
| 2-130 | Neutral | 1.4 | >10 |
| 2-131 | Neutral | 46 | >10 |
| 2-132 | Neutral | 24 | >10 |
| 2-133 | Neutral | 1.0 | >10 |
| 2-134 | Neutral | 8.3 | >10 |
| 2-135 | Neutral | 5.2 | >10 |
| 2-136 | Neutral | 14 | >10 |
| 2-137 | Neutral | 6.3 | >10 |
| 2-138 | Neutral | 660 | >10 |
| 2-139 | Neutral | 170 | >10 |
| 2-140 | Neutral | 390 | >10 |
| 2-141 | Neutral | 8.7 | >10 |
| 2-142 | TFA salt | 9.3 | >10 |
| 2-143 | TFA salt | 1.0 | >10 |
| 2-144 | TFA salt | 20 | >10 |
| 2-145 | TFA salt | 3.0 | >10 |
| 2-146 | TFA salt | 3.4 | >10 |
| 2-147 | TFA salt | 14 | >10 |
| 3-1 | neutral | 7.2 | >10 |
| 3-2 | neutral | 99 | >10 |
| 3-3 | neutral | 19 | >10 |
| 3-4 | neutral | 120 | >10 |
| 3-5 | neutral | 44 | >10 |
| 3-6 | neutral | 7.8 | >10 |
| 3-7 | neutral | 37 | >10 |
| 3-8 | neutral | 66 | >10 |
| 3-9 | Neutral | 3.8 | >10 |
| 3-10 | Neutral | 23 | >10 |
| 3-11 | Neutral | 6.5 | >10 |
| 3-12 | TFA salt | 3.6 | >10 |
| 3-13 | Neutral | 24 | >10 |
| 3-14 | Neutral | 10 | >10 |
| 3-15 | Neutral | 5.7 | >10 |
| 3-16 | Neutral | 4.7 | >10 |
| 3-17 | Neutral | 16 | >10 |
| 3-18 | Neutral | 58 | >10 |
| 3-19 | Neutral | 130 | >10 |
| 3-20 | Neutral | 36 | >10 |

| Compound | Form Screened | PI3Kdelta IC$_{50}$ (nM) | Relative Selectivity versus PI3Kalpha | Compound | Form Screened | PI3Kdelta IC$_{50}$ (nM) | Relative Selectivity versus PI3Kalpha |
|---|---|---|---|---|---|---|---|
| 3-21 | TFA salt | 3.1 | >10 | 5-19 | TFA salt | 3.8 | >10 |
| 3-22 | Neutral | 23 | >10 | 5-20 | TFA salt | 7.3 | >10 |
| 3-23 | Neutral | <1.0 | >10 | 5-21 | TFA salt | 34 | >10 |
| 3-24 | Neutral | 2.2 | >10 | 5-22 | TFA salt | 5.7 | >10 |
| 3-25 | Neutral | <1.0 | >10 | 5-23 | TFA salt | 21 | >10 |
| 3-26 | Neutral | <1.0 | >10 | 5-24 | TFA salt | 10 | >10 |
| 3-27 | Neutral | 6.3 | >10 | 5-25 | TFA salt | 4.3 | >10 |
| 3-28 | Neutral | <1.0 | >10 | 5-26 | TFA salt | 14 | >10 |
| 3-29 | Neutral | 44 | >10 | 5-27 | TFA salt | 5.1 | >10 |
| 3-30 | Neutral | 4.3 | >10 | 5-28 | Neutral | <1.0 | >10 |
| 3-31 | Neutral | 140 | >10 | 6-1 | TFA salt | 270 | >10 |
| 3-32 | Neutral | 6.4 | >10 | 6-2 | TFA salt | 300 | >10 |
| 3-33 | Neutral | 10 | >10 | 6-3 | TFA salt | 3100 | |
| 3-34 | Neutral | 9.3 | >10 | 6-4 | TFA salt | 440 | |
| 3-35 | Neutral | 2.5 | >10 | 6-5 | Neutral | 380 | >10 |
| 3-36 | Neutral | 4.6 | >10 | 6-6 | Neutral | 28 | >10 |
| 3-37 | TFA salt | 8.4 | >10 | 7-1 | TFA salt | 21 | >10 |
| 3-38 | TFA salt | 2.0 | >10 | 7-2 | TFA salt | 5.2 | >10 |
| 3-39 | Neutral | 300 | >10 | 7-3 | TFA salt | 10 | >10 |
| 3-40 | Neutral | 2.4 | >10 | 7-4 | TFA salt | 12 | >10 |
| 3-41 | Neutral | <1.0 | >10 | 7-5 | TFA salt | 37 | >10 |
| 3-42 | Neutral | 2.4 | >10 | 7-6 | TFA salt | 30 | >10 |
| 3-43 | Neutral | 18 | >10 | 7-7 | TFA salt | 680 | >10 |
| 3-44 | Neutral | 1.1 | >10 | 7-8 | TFA salt | 17 | >10 |
| 3-45 | Neutral | 23 | >10 | 7-9 | TFA salt | 160 | >10 |
| 3-46 | Neutral | 20 | >10 | 7-10 | TFA salt | 128 | >10 |
| 3-47 | Neutral | 6.1 | >10 | 7-11 | TFA salt | 26 | >10 |
| 3-48 | TFA salt | 240 | >10 | 7-12 | TFA salt | 19 | >10 |
| 3-49 | TFA salt | <1.0 | >10 | 7-13 | TFA salt | 5.7 | >10 |
| 3-50 | TFA salt | 2.1 | >10 | 7-14 | TFA salt | 120 | >10 |
| 3-51 | TFA salt | <1.0 | >10 | 7-15 | TFA salt | 216 | >10 |
| 3-52 | TFA salt | 1.6 | >10 | 7-16 | Neutral | 85 | >10 |
| 3-53 | TFA salt | <1.0 | >10 | 7-17 | Neutral | 1.7 | >10 |
| 3-54 | TFA salt | <1.0 | >10 | 7-18 | Neutral | 4.1 | >10 |
| 3-55 | TFA salt | <1.0 | >10 | 7-19 | Neutral | 9.1 | >10 |
| 3-56 | TFA salt | <1.0 | >10 | 7-20 | TFA salt | 18 | >10 |
| 3-57 | TFA salt | <1.0 | >10 | 7-21 | TFA salt | 2.2 | >10 |
| 3-58 | TFA salt | 1.5 | >10 | 7-22 | TFA salt | 44 | >10 |
| 3-59 | TFA salt | <1.0 | >10 | 7-23 | TFA salt | 47 | >10 |
| 3-60 | TFA salt | <1.0 | >10 | 7-24 | TFA salt | 10 | >10 |
| 3-61 | Neutral | <1.0 | >10 | 7-25 | TFA salt | 11 | >10 |
| 3-62 | Neutral | 2.3 | >10 | 7-26 | TFA salt | 32 | >10 |
| 3-63 | Neutral | 380 | >10 | 7-27 | Neutral | 73 | >10 |
| 3-64 | Neutral | 1.3 | >10 | 8-1 | neutral | 220 | 9 |
| 3-65 | Neutral | 2.9 | >10 | 9-1 | neutral | 400 | |
| 3-66 | Neutral | 4.1 | >10 | 9-2 | neutral | 140 | |
| 3-67 | Neutral | 260 | >10 | 9-3 | TFA salt | 290 | 8 |
| 3-68 | Neutral | 2.6 | >10 | 9-4 | TFA salt | 120 | |
| 3-69 | Neutral | 850 | >10 | 9-5 | Neutral | 96 | >10 |
| 4-1 | TFA salt | 200 | | 9-6 | Neutral | 220 | >10 |
| 4-2 | TFA salt | 530 | | 9-7 | TFA salt | 330 | >10 |
| 4-3 | TFA salt | 1000 | | 9-8 | Neutral | 120 | >10 |
| 4-4 | TFA salt | 360 | | 9-9 | Neutral | 170 | >10 |
| 4-5 | TFA salt | 1500 | | 9-10 | Neutral | 150 | >10 |
| 4-6 | TFA salt | 220 | | 10-1 | neutral | 23 | >10 |
| 4-7 | TFA salt | 4600 | | 10-2 | neutral | 160 | 8 |
| 4-8 | Neutral | 170 | >10 | 10-3 | neutral | 18 | >10 |
| 5-1 | TFA salt | 230 | | 10-4 | neutral | 11 | >10 |
| 5-2 | TFA salt | 650 | | 10-5 | neutral | 960 | 5 |
| 5-3 | TFA salt | 9.2 | >10 | 10-6 | neutral | 210 | 5 |
| 5-4 | TFA salt | 4.7 | >10 | 10-7 | neutral | 3.8 | >10 |
| 5-5 | TFA salt | 630 | | 10-8 | neutral | 37 | >10 |
| 5-6 | TFA salt | 110 | 5 | 10-9 | neutral | 30 | >10 |
| 5-7 | TFA salt | 10 | >10 | 10-10 | neutral | 19 | >10 |
| 5-8 | Neutral | 19 | >10 | 10-11 | neutral | 25 | >10 |
| 5-9 | Neutral | 10 | >10 | 10-12 | neutral | 6.0 | >10 |
| 5-10 | Neutral | 28 | >10 | 10-13 | neutral | 5.5 | >10 |
| 5-11 | Neutral | 1.3 | >10 | 11-1 | neutral | 560 | >10 |
| 5-12 | Neutral | 46 | >10 | 11-2 | neutral | 290 | >10 |
| 5-13 | Neutral | 1.8 | >10 | 11-3 | neutral | 250 | >10 |
| 5-14 | Neutral | 5.9 | >10 | 12-1 | Neutral | 2400 | 4 |
| 5-15 | Neutral | 6.2 | >10 | 12-2 | Neutral | 110 | >10 |
| 5-16 | Neutral | 16 | >10 | 12-3 | Neutral | 380 | >10 |
| 5-17 | TFA salt | 32 | >10 | 12-4 | Neutral | 120 | >10 |
| 5-18 | TFA salt | 9.5 | >10 | 13-1 | TFA salt | 150 | >10 |

-continued

| Compound | Form Screened | PI3Kdelta IC$_{50}$ (nM) | Relative Selectivity versus PI3Kalpha |
|---|---|---|---|
| 13-2 | Neutral | 830 | >10 |
| 13-3 | Neutral | 700 | >10 |
| 13-4 | Neutral | 380 | >10 |
| 13-5 | Neutral | 120 | >10 |
| 13-6 | Neutral | 920 | >10 |
| 13-7 | Neutral | 580 | >10 |
| 13-8 | Neutral | 570 | >10 |
| 14-1 | Neutral | 93 | >10 |
| 14-2 | Neutral | 580 | >10 |
| 14-3 | Neutral | 240 | >10 |
| 14-4 | Neutral | 890 | >10 |
| 14-5 | Neutral | 100 | >10 |
| 14-6 | Neutral | 99 | >10 |
| 14-7 | Neutral | 430 | >10 |
| 15-1 | TFA salt | 31 | >10 |
| 15-2 | Neutral | 9.9 | >10 |
| 15-3 | Neutral | 150 | >10 |
| 15-4 | Neutral | 72 | >10 |
| 15-5 | Neutral | 310 | >10 |

The invention claimed is:

1. A compound of formula II or a pharmaceutically acceptable salt or thereof:

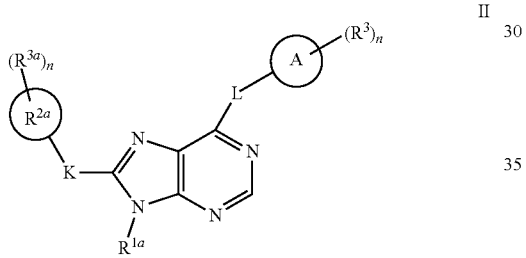

II $R^{1a}$ is selected from methyl, ethyl, propyl, butyl, pentyl, cyclopropyl, cyclobutyl, and cyclopentyl, wherein $R^{1a}$ is optionally substituted by 0, 1, 2, 3, or 4 groups independently selected from fluoro, chloro, methyl and amino;

$R^{2a}$ is selected from cyclopropyl, isobutyl, 2-methylpropyl, methyl, ethyl, iodo, pyridazinyl, pyrimidinyl, pyrazinyl, pyridinyl, pyrrolidinyl, piperidinyl, ethoxycarbonyl, cyclohexyl, phenyl, quinazolinyl, isoquinolinyl, pyrazolyl, imidazolyl, indolyl, indazolyl, thiazolyl, pyrazolo[1,5-a]pyrimidinyl, 3,6-dihydro-2H-pyranyl, 1H-pyrrolo[2,3-b]pyridinyl, cyclobutyl, 1H-pyrazolo[3,4-b]pyridinyl], pyrrolo[2,3-b]pyridinyl, benzimidazolyl, morpholinyl, 4,5,6,7,-tetrahydropyrazolo[1,5-a]pyridinyl, 5,6-dihydro-4H-pyrrolo[1,2-b]pyrazolyl, wherein $R^{2a}$ is substituted with 0, 1, 2, 3, or 4 $R^{3a}$ substituents;

n is 0, 1, 2, 3, or 4;

A is selected from pyrrolidinyl, piperidinyl, cyclobutyl, cyclohexyl, azaspiro [2.4]hept-2-yl, azabicyclo[2.2.1]heptanyl, azetidinyl, and cyclopentyl;

L is selected from O, S, SO$_2$, and —CH$_2$;

K is selected from a bond, NH, O, C(O), CH$_2$, N((C$_{1-5}$) alkyl)$_{1-2}$, —C(O)N(R$^b$)—(CH$_2$)$_m$, S, SO$_2$, and C$_{2-10}$ alkynylene;

$R^b$ is H or C$_{1-10}$ alkyl;

m is 0, 1, 2, or 3;

$R^{3a}$ is independently selected from: fluoro, chloro, methyl, ethyl, methoxy, pyrazolyl, hydroxyl, dimethylamino, morpholinyl, pyrrolidinyl, tert-butyl, methylsulfonyl, trifluoromethyl, phenyl, hydroxymethyl, cyclopropyl, imidazolyl, methylsulfonylamino, acetylamino, methylcarbonylamino, cyano, and amino, wherein $R^{3a}$ is each substituted with 0, 1, 2, 3, or 4 $R^{4a}$ substituents and each $R^{4a}$ is independently selected from: halogen, methyl, ethyl, hydroxy, and amino;

$R^3$ is independently selected from:

halogen,

C$_{1-10}$ alkyl(oxy)$_{0-1}$(carbonyl)$_{0-1}$C$_{0-10}$ alkyl,

C$_{2-10}$ alkenyl(oxy)$_{0-1}$(carbonyl)$_{0-1}$C$_{0-10}$ alkyl,

C$_{1-10}$ heteroalkyl(oxy)$_{0-1}$(carbonyl)$_{0-1}$C$_{0-10}$ alkyl, aryl C$_{0-10}$ alkyl(oxy)$_{0-1}$(carbonyl)$_{0-1}$C$_{0-10}$ alkyl, C$_{3-12}$ cycloalkylC$_{0-10}$ alkyl(oxy)$_{0-1}$(carbonyl)$_{0-1}$C$_{0-10}$ alkyl, heteroarylC$_{0-10}$ alkyl(oxy)$_{0-1}$(carbonyl)$_{0-1}$C$_{0-10}$ alkyl, (C$_{3-12}$)heterocycloalkyl C$_{0-10}$ alkyl(oxy)$_{0-1}$(carbonyl)$_{0-1}$C$_{0-10}$ alkyl, C$_{1-10}$ alkylamino(carbonyl)$_{0-1}$C$_{0-10}$ alkyl, (C$_{1-10}$)heteroalkylamino(carbonyl)$_{0-1}$C$_{0-10}$ alkyl, C$_{3-12}$ cycloalkyl C$_{0-10}$ alkylamino(carbonyl)$_{0-1}$C$_{0-10}$ alkyl, aryl C$_{0-10}$alkylamino(carbonyl)$_{0-1}$C$_{0-10}$ alkyl, heteroarylC$_{0-10}$alkylamino(carbonyl)$_{0-1}$C$_{0-10}$ alkyl, (C$_{3-12}$)heterocycloalkylC$_{0-10}$alkylamino(carbonyl)$_{0-1}$C$_{0-10}$ alkyl, C$_{1-10}$ alkyl(oxy)$_{0-1}$(carbonyl)$_{0-1}$aminoC$_{0-10}$ alkyl, C$_{1-10}$ heteroalkyl (oxy)$_{0-1}$(carbonyl)$_{0-1}$aminoC$_{0-10}$ alkyl, C$_{3-12}$ cycloalkyl C$_{0-10}$ alkyl (oxy)$_{0-1}$(carbonyl)$_{0-1}$aminoC$_{0-10}$ alkyl, aryl C$_{0-10}$ alkyl(oxy)$_{0-1}$(carbonyl)$_{0-1}$aminoC$_{0-10}$ alkyl, heteroaryl C$_{0-10}$ alkyl(oxy)$_{0-1}$(carbonyl)$_{0-1}$aminoC$_{0-10}$ alkyl, (C$_{3-12}$)heterocycloalkyl C$_{0-10}$ alkyl(oxy)$_{0-1}$(carbonyl)$_{0-1}$aminoC$_{0-10}$ alkyl, —CO$_2$(C$_{0-10}$ alkyl), —(C$_{0-10}$ alkyl)CO$_2$H, Oxo (=O), C$_{1-10}$alkylS(O)$_{1-2}$, heteroarylS(O)$_{1-2}$, arylS(O)$_{1-2}$, C$_{0-6}$ alkyl(amino)$_{0-1}$S(O)$_{1-2}$amino, C$_{1-10}$ heteroalkyl(amino)$_{0-1}$S(O)$_{1-2}$amino, (C$_{3-12}$)cycloalkyl(amino)$_{0-1}$S(O)$_{1-2}$amino, (C$_{3-12}$)cycloheteroalkyl(amino)$_{0-1}$S(O)$_{1-2}$amino, heteroaryl(amino)$_{0-1}$S(O)$_{1-2}$amino, C$_{1-10}$heteroalkylS(O)$_{1-2}$, (C$_{3-12}$)cycloalkylS(O)$_{1-2}$, (C$_{3-12}$)cycloheteroalkylS(O)$_{1-2}$, heteroarylS(O)$_{1-2}$, arylS(O)$_{1-2}$, —SO$_2$N(C$_{0-6}$ alkyl)$_{0-2}$, —SO$_2$CF$_3$, amino, (C$_{0-10}$ alkyl)$_{1-2}$ amino, hydroxy, (C$_{1-10}$ alkyl)OH, C$_{0-10}$ alkylalkoxy, cyano, C$_{1-6}$alkylcyano, and C$_{1-6}$ haloalkyl; wherein $R^3$ is each substituted with 0, 1, 2, 3, or 4 substituents, $R^4$;

$R^4$ is independently selected from:

halogen,

C$_{1-10}$ alkyl(oxy)$_{0-1}$(carbonyl)$_{0-1}$C$_{0-10}$ alkyl, aryl C$_{0-10}$ alkyl(oxy)$_{0-1}$(carbonyl)$_{0-1}$C$_{0-10}$ alkyl, C$_{3-12}$ cycloalkyl C$_{0-10}$ alkyl(oxy)$_{0-1}$ (carbonyl)$_{0-1}$C$_{0-10}$ alkyl, heteroaryl C$_{0-10}$ alkyl(oxy)$_{0-1}$(carbonyl)$_{0-1}$C$_{0-10}$ alkyl, C$_{3-12}$ heterocycloalkyl C$_{0-10}$ alkyl(oxy)$_{0-1}$(carbonyl)$_{0-1}$C$_{0-10}$ alkyl, C$_{1-10}$ alkyl (oxy)$_{0-1}$ (carbonyl)$_{0-1}$aminoC$_{0-10}$ alkyl, Oxo (=O), —SO$_2$C$_{1-6}$alkyl, amino, (C$_{0-10}$ alkyl)$_{1-2}$ amino, (C$_{1-10}$ alkyl)OH, C$_{1-10}$ alkoxy, cyano, and C$_{1-6}$ haloalkyl; wherein R$^4$ is substituted with 0, 1, 2, or 3 R$^5$;

R$^5$ is independently selected from hydroxy, (C$_{1-6}$)alkyl, (C$_{1-6}$)alkoxy, halogen, CO$_2$H, —(C$_{0-6}$)alkylCN, NO$_2$, trifluoromethoxy, trifluoroethoxy, trifluoromethyl, trifluoroethyl, oxo (O=), —O$_{(0-1)}$(C$_{1-10}$)haloalkyl, amino (C$_{1-6}$alkyl)$_{0-2}$ and NH$_2$; and R$^5$ is substituted with 0, 1, or 2 R$^6$ substituents; and R$^6$ is independently selected from hydroxy, methyl, halogen, oxo (O=) and NH$_2$.

2. A compound according to claim 1 or a pharmaceutically acceptable salt, or a stereoisomer thereof, wherein the compound is selected from:

tert-butyl-3-{[8-(1-ethyl-5-methyl-1H-pyrazol-4-yl)-9-methyl-9H-purin-6-yl]oxy}pyrrolidine-1-carboxylate;

8-(1-ethyl-5-methyl-1H-pyrazol-4-yl)-9-methyl-6-[pyrrolidin-3-yloxy]-9H-purine;

tert-butyl-3-{[9-ethyl-8-(2-methylpyrimidin-5-yl)-9H-purin-6-yl]oxy}pyrrolidine-1-carboxylate;

2-methylpropyl-3-{[8-(1-ethyl-5-methyl-1H-pyrazol-4-yl)-9-methyl-9H-purin-6-yl]oxy}pyrrolidine-1-carboxylate;

naphthalen-2-yl-3-{[8-(1-ethyl-5-methyl-1H-pyrazol-4-yl)-9-methyl-9H-purin-6-yl]oxy}pyrrolidine-1-carboxylate;

benzyl-3-{[8-(1-ethyl-5-methyl-1H-pyrazol-4-yl)-9-methyl-9H-purin-6-yl]oxy}pyrrolidine-1-carboxylate;

4-methylphenyl-3-{[8-(1-ethyl-5-methyl-1H-pyrazol-4-yl)-9-methyl-9H-purin-6-yl]oxy}pyrrolidine-1-carboxylate;

phenyl-3-{[8-(1-ethyl-5-methyl-1H-pyrazol-4-yl)-9-methyl-9H-purin-6-yl]oxy}pyrrolidine-1-carboxylate;

2,2-dimethylpropyl-3-{[8-(1-ethyl-5-methyl-1H-pyrazol-4-yl)-9-methyl-9H-purin-6-yl]oxy}pyrrolidine-1-carboxylate;

3-(trifluoromethyl)phenyl-3-{[8-(1-ethyl-5-methyl-1H-pyrazol-4-yl)-9-methyl-9H-purin-6-yl]oxy}pyrrolidine-1-carboxylate;

4-methoxyphenyl-3-{[8-(1-ethyl-5-methyl-1H-pyrazol-4-yl)-9-methyl-9H-purin-6-yl]oxy}pyrrolidine-1-carboxylate;

tert-butyl 4-{[8-(1-ethyl-5-methyl-1-pyrazol-3-yl)-9-methyl-9H-purin-6-yl]oxy}piperidine-1-carboxylate;

tert-butyl-3-{[8-(6-methoxy-5-methylpyridin-3-yl)-9-methyl-9H-purin-6-yl]oxy}pyrrolidine-1-carboxylate;

tert-butyl-3-{[9-methyl-8-(2-methylpyrimidin-5-yl)-9H-purin-6-yl]oxy}pyrrolidine-1-carboxylate;

tert-butyl-3-({9-methyl-8-[4-(1H-pyrazol-1-yl)phenyl]-9H-purin-6-yl}oxy)pyrrolidine-1-carboxylate;

tert-butyl-3-{[8-(1,3-dimethyl-1H-pyrazol-4-yl)-9-methyl-9H-purin-6-yl]oxy}pyrrolidine-1-carboxylate;

tert-butyl-3-{[8-(1,2-dimethyl-1H-imidazol-5-yl)-9-methyl-9H-purin-6-yl]oxy}pyrrolidine-1-carboxylate;

tert-butyl-3-{[8-(4-hydroxyphenyl)-9-methyl-9H-purin-6-yl]oxy}pyrrolidine-1-carboxylate;

tert-butyl-3-{[9-methyl-8-(1H-pyrazol-4-yl)-9H-purin-6-yl]oxy}pyrrolidine-1-carboxylate;

tert-butyl-3-({8-[6-(dimethylamino)pyridin-3-yl]-9-methyl-9H-purin-6-yl}oxy)pyrrolidine-1-carboxylate;

tert-butyl-3-{[9-methyl-8-(2-methyl-1H-indol-7-yl)-9H-purin-6-yl]oxy}pyrrolidine-1-carboxylate;

tert-butyl-3-[(9-methyl-8-pyrazolo[1,5-a]pyrimidin-3-yl-9H-purin-6-yl)oxy]pyrrolidine-1-carboxylate;

tert-butyl-3-({8-[4-(acetylamino)phenyl]-9-methyl-9H-purin-6-yl}oxy)pyrrolidine-1-carboxylate;

tert-butyl-3-{[9-methyl-8-(6-morpholin-4-ylpyridin-3-yl)-9H-purin-6-yl]oxy}pyrrolidine-1-carboxylate;

tert-butyl-3-({8-[4-(1H-imidazol-1-yl)phenyl]-9-methyl-9H-purin-6-yl}oxy)pyrrolidine-1-carboxylate;

tert-butyl-3-{[9-methyl-8-(3-methyl-1-pyrazol-4-yl)-9H-purin-6-yl]oxy}pyrrolidine-1-carboxylate;

tert-butyl-3-{[9-methyl-8-(6-pyrrolidin-1-ylpyridin-3-yl)-9H-purin-6-yl]oxy}pyrrolidine-1-carboxylate;

tert-butyl-3-[(8-isoquinolin-4-yl-9-methyl-9H-purin-6-yl)oxy]pyrrolidine-1-carboxylate;

tert-butyl-3-{[8-(1H-indazol-5-yl)-9-methyl-9H-purin-6-yl]oxy}pyrrolidine-1-carboxylate;

tert-butyl 4-((8-(1-ethyl-5-methyl-1H-pyrazol-4-yl)-9-methyl-9H-purin-6-yl)oxy)-2-methylpyrrolidine-1-carboxylate;

tert-butyl 3-((8-(3-methoxycyclobutyl)-9-methyl-9H-purin-6-yl)oxy)pyrrolidine-1-carboxylate;

tert-butyl 3-((9-methyl-8-(3-methyl-1H-pyrazolo[3,4-b]pyridin-5-yl)-9H-purin-6-yl)oxy)pyrrolidine-1-carboxylate;

tert-butyl-3-{[9-ethyl-8-(6-methoxy-5-methylpyridin-3-yl)-9H-purin-6-yl]oxy}pyrrolidine-1-carboxylate;

tert-butyl-3-{[8-(2-tert-butyl-1,3-thiazol-5-yl)-9-ethyl-9H-purin-6-yl]oxy}pyrrolidine-1-carboxylate;

methyl-3-{[8-(1-ethyl-5-methyl-1H-pyrazol-4-yl)-9-methyl-9H-purin-6-yl]oxy}pyrrolidine-1-carboxylate;

ethyl-3-{[8-(1-ethyl-5-methyl-1-pyrazol-4-yl)-9-methyl-9H-purin-6-yl]oxy}pyrrolidine-1-carboxylate;

1-methylethyl-3-{[8-(1-ethyl-5-methyl-1H-pyrazol-4-yl)-9-methyl-9H-purin-6-yl]oxy}pyrrolidine-1-carboxylate;

tert-butyl-3-{[8-(2-tert-butyl-1,3-thiazol-5-yl)-9-methyl-9H-purin-6-yl]oxy}pyrrolidine-1-carboxylate;

tert-butyl 3-((8-(1-ethyl-5-methyl-1H-pyrazol-4-yl)-9-methyl-9H-purin-6-yl)oxy)azetidine-1-carboxylate;

tert-butyl 3-((8-(1-ethyl-5-methyl-1H-pyrazol-4-yl)-9-methyl-9H-purin-6-yl)oxy)piperidine-1-carboxylate;

8-(1-ethyl-5-methyl-1H-pyrazol-4-yl)-9-methyl-6-{[1-(phenylcarbonyl)pyrrolidin-3-yl]oxy}-9H-purine;

6-{[1-(cyclopentylcarbonyl)pyrrolidin-3-yl]oxy}-8-(1-ethyl-5-methyl-1H-pyrazol-4-yl)-9-methyl-9H-purine;

8-(1-ethyl-5-methyl-1H-pyrazol-4-yl)-9-methyl-6-{[1-(naphthalen-2-ylcarbonyl)pyrrolidin-3-yl]oxy}-9H-purine;

6-{[1-(cyclohexylcarbonyl)pyrrolidin-3-yl]oxy}-8-(1-ethyl-5-methyl-1H-pyrazol-4-yl)-9-methyl-9H-purine;

8-(1-ethyl-5-methyl-1H-pyrazol-4-yl)-6-{[1-(methoxyacetyl)pyrrolidin-3-yl]oxy}-9-methyl-9H-purine;

8-(1-ethyl-5-methyl-1H-pyrazol-4-yl)-9-methyl-6-{[1-(tetrahydro-2H-pyran-4-ylacetyl)pyrrolidin-3-yl]oxy}-9H-purine;

8-(1-ethyl-5-methyl-1H-pyrazol-4-yl)-9-methyl-6-{[1-(1,3-oxazol-5-ylcarbonyl)pyrrolidin-3-yl]oxy}-9H-purine;

(3-((8-(1-ethyl-5-methyl-1H-pyrazol-4-yl)-9-methyl-9H-purin-6-yl)oxy)pyrrolidin-1-yl)(tetrahydro-2H-pyran-4-yl)methanone;

8-(1-ethyl-5-methyl-1H-pyrazol-4-yl)-9-methyl-6-({1-[(4-methyltetrahydro-2H-pyran-4-yl)carbonyl]pyrrolidin-3-yl}oxy)-9H-purine;

8-(1-ethyl-5-methyl-1H-pyrazol-3-yl)-9-methyl-6-{[1-(tetrahydro-2H-pyran-4-ylcarbonyl)piperidin-4-yl]oxy}-9H-purine;

8-(1-ethyl-5-methyl-1H-pyrazol-3-yl)-9-methyl-6-{[1-(phenylcarbonyl)piperidin-4-yl]oxy}-9H-purine;

6-{[1-(cyclopentylcarbonyl)piperidin-4-yl]oxy}-8-(1-ethyl-5-methyl-1H-pyrazol-3-yl)-9-methyl-9H-purine;

8-(1-ethyl-5-methyl-1H-pyrazol-3-yl)-9-methyl-6-[(1-propanoylpiperidin-4-yl)oxy]-9H-purine;

3-[3-{[8-(1-ethyl-5-methyl-1H-pyrazol-4-yl)-9-methyl-9H-purin-6-yl]oxy}pyrrolidin-1-yl]-3-oxopropanenitrile;

6-{[1-(cyclopropylcarbonyl)pyrrolidin-3-yl]oxy}-8-(1-ethyl-5-methyl-1H-pyrazol-4-yl)-9-methyl-9H-purine;

8-(1-ethyl-5-methyl-1H-pyrazol-4-yl)-9-methyl-6-{[1-(tetrahydrofuran-2-ylcarbonyl)pyrrolidin-3-yl]oxy}-9H-purine;

8-(1-ethyl-5-methyl-1H-pyrazol-4-yl)-9-methyl-6-(1-[(5-methylisoxazol-3-yl)carbonyl]pyrrolidin-3-yl}oxy)-9H-purine;

1-{2-[3-{[8-(1-ethyl-5-methyl-1H-pyrazol-4-yl)-9-methyl-9H-purin-6-yl]oxy}pyrrolidin-1-yl]-2-oxoethyl}pyrrolidin-2-one;

8-(1-ethyl-5-methyl-1H-pyrazol-4-yl)-9-methyl-6-{[1-(naphthalen-1-ylcarbonyl)pyrrolidin-3-yl]oxy}-9H-purine;

8-(1-ethyl-5-methyl-1H-pyrazol-4-yl)-9-methyl-6-{[1-{[4-(4-methylpiperazin-1-yl)phenyl]carbonyl}pyrrolidin-3-yl]oxy}-9H-purine;

8-(1-ethyl-5-methyl-1H-pyrazol-4-yl)-9-methyl-6-{[1-(pyridin-3-ylcarbonyl)pyrrolidin-3-yl]oxy}-9H-purine;

6-({1-[(2,2-dimethyltetrahydro-2H-pyran-4-yl)carbonyl]pyrrolidin-3-yl}oxy)-8-(1-ethyl-5-methyl-1H-pyrazol-4-yl)-9-methyl-9H-purine;

9-ethyl-8-(2-methylpyrimidin-5-yl)-6-{[1-propanoylpyrrolidin-3-yl]oxy}-9H-purine;

9-ethyl-8-(2-methylpyrimidin-5-yl)-6-{[1-(tetrahydro-2H-pyran-4-ylcarbonyl)pyrrolidin-3-yl]oxy}-9H-purine;

8-(1-ethyl-5-methyl-1H-pyrazol-4-yl)-9-methyl-6-({-1-[(2-methyl-1,3-oxazol-4-yl)carbonyl]pyrrolidin-3-yl}oxy)-9H-purine;

6-({1-[(2,5-dimethyl-1,3-oxazol-4-yl)carbonyl]pyrrolidin-3-yl}oxy)-8-(1-ethyl-5-methyl-1H-pyrazol-4-yl)-9-methyl-9H-purine;

8-(1-ethyl-5-methyl-1H-pyrazol-4-yl)-9-methyl-6-{[1-(1,2,5-oxadiazol-3-ylcarbonyl)pyrrolidin-3-yl]oxy}-9H-purine;

8-(1-ethyl-5-methyl-1H-pyrazol-4-yl)-9-methyl-6-{[1-{[3-(1-methylethyl)-1H-pyrazol-5-yl]carbonyl}pyrrolidin-3-yl]oxy}-9H-purine;

8-(1-ethyl-5-methyl-1H-pyrazol-4-yl)-9-methyl-6-{[1-{[1-(1-methylethyl)-1H-pyrazol-4-yl]carbonyl}pyrrolidin-3-yl]oxy}-9H-purine;

8-(1-ethyl-5-methyl-1H-pyrazol-4-yl)-6-{[1-(isoxazol-5-ylcarbonyl)pyrrolidin-3-yl]oxy}-9-methyl-9H-purine;

8-(1-ethyl-5-methyl-1H-pyrazol-4-yl)-9-methyl-6-{[1-(1H-pyrazol-5-ylcarbonyl)pyrrolidin-3-yl]oxy}-9H-purine;

8-(1-ethyl-5-methyl-1-pyrazol-4-yl)-9-methyl-6-{[1-(pyrazolo[1,5-a]pyridin-3-ylcarbonyl)pyrrolidin-3-yl]oxy}-9H-purine;

8-(1-ethyl-5-methyl-1H-pyrazol-4-yl)-9-methyl-6-({1-[(4-methyl-1,2,5-oxadiazol-3-yl)carbonyl]pyrrolidin-3-yl}oxy)-9H-purine;

8-(1-ethyl-5-methyl-1H-pyrazol-4-yl)-9-methyl-6-({1-[(1-methyl-1H-pyrazol-5-yl)carbonyl]pyrrolidin-3-yl}oxy)-9H-purine;

8-(1-ethyl-5-methyl-1H-pyrazol-4-yl)-9-methyl-6-({1-[(1-methyl-1H-pyrazol-3-yl)carbonyl]pyrrolidin-3-yl}oxy)-9H-purine;

6-({1-[(1,3-dimethyl-1H-pyrazol-5-yl)carbonyl]pyrrolidin-3-yl}oxy)-8-(1-ethyl-5-methyl-1H-pyrazol-4-yl)-9-methyl-9H-purine;

8-(1-ethyl-5-methyl-1H-pyrazol-4-yl)-9-methyl-6-({1-[(1-methyl-1H-imidazol-2-yl)carbonyl]pyrrolidin-3-yl}oxy)-9H-purine;

8-(1-ethyl-5-methyl-1H-pyrazol-4-yl)-9-methyl-6-{[1-(1H-1,2,3-triazol-4-ylcarbonyl)pyrrolidin-3-yl]oxy}-9H-purine;

8-(1-ethyl-5-methyl-1-pyrazol-4-yl)-9-methyl-6-{[1-(pyrazolo[1,5-a]pyrimidin-3-ylcarbonyl)pyrrolidin-3-yl]oxy}-9H-purine;

8-(1-ethyl-5-methyl-1H-pyrazol-4-yl)-9-methyl-6-{[1-(5,6,7,8-tetrahydro[1,2,4]triazolo[4,3-a]pyridin-3-ylcarbonyl)pyrrolidin-3-yl]oxy}-9H-purine;

8-(1-ethyl-5-methyl-1H-pyrazol-4-yl)-9-methyl-6-{[1-{[3-(trifluoromethyl)-1H-pyrazol-4-yl]carbonyl}pyrrolidin-3-yl]oxy}-9H-purine;

8-(1-ethyl-5-methyl-1H-pyrazol-4-yl)-9-methyl-6-({1-[(1-methyl-1H-1,2,3-triazol-4-yl)carbonyl]pyrrolidin-3-yl}oxy)-9H-purine;

8-(1-ethyl-5-methyl-1H-pyrazol-4-yl)-6-{[1-(imidazo[1,2-a]pyrimidin-2-ylcarbonyl)pyrrolidin-3-yl]oxy}-9-methyl-9H-purine;

8-(1-ethyl-5-methyl-1H-pyrazol-4-yl)-9-methyl-6-({1-[(5-methyl-1,2,3-thiadiazol-4-yl)carbonyl]pyrrolidin-3-yl}oxy)-9H-purine;

6-({1-[(7-chloro[1,2,4]triazolo[1,5-a]pyridin-2-yl)carbonyl]pyrrolidin-3-yl}oxy)-8-(1-ethyl-5-methyl-1H-pyrazol-4-yl)-9-methyl-9H-purine;

8-(1-ethyl-5-methyl-1H-pyrazol-4-yl)-9-methyl-6-({1-[(4-methyl-1H-pyrazol-5-yl)carbonyl]pyrrolidin-3-yl}oxy)-9H-purine;

5-{[3-{[8-(1-ethyl-5-methyl-1-pyrazol-4-yl)-9-methyl-9H-purin-6-yl]oxy}pyrrolidin-1-yl]carbonyl}-N,N-dimethyl-1,3,4-oxadiazol-2-amine;

2-(3-{[3-{[8-(1-ethyl-5-methyl-1-pyrazol-4-yl)-9-methyl-9H-purin-6-yl]oxy 1pyrrolidin-1-yl]carbonyl}-1,2,4-oxadiazol-5-yl)propan-2-ol;

8-(1-ethyl-5-methyl-1H-pyrazol-4-yl)-9-methyl-6-({1-[(3-methylisoxazol-4-yl)carbonyl]pyrrolidin-3-yl}oxy)-9H-purine;

8-(1-ethyl-5-methyl-1H-pyrazol-4-yl)-9-methyl-6-{[1-{[1-(1-methylethyl)-1H-pyrazol-5-yl]carbonyl}pyrrolidin-3-yl]oxy}-9H-purine;

8-(1-ethyl-5-methyl-1H-pyrazol-4-yl)-9-methyl-64 f 1-[(6-methylpyridin-3-yl)carbonyl]pyrrolidin-3-yl}oxy)-9H-purine;

8-(1-ethyl-5-methyl-1H-pyrazol-4-yl)-6-{[1-(4H-furo[3,2-b]pyrrol-5-ylcarbonyl)pyrrolidin-3-yl]oxy}-9-methyl-9H-purine;

8-(1-ethyl-5-methyl-1H-pyrazol-4-yl)-9-methyl-6-{[1-{[1-methyl-3-(trifluoromethyl)-1H-pyrazol-4-yl]carbonyl}pyrrolidin-3-yl]oxy}-9H-purine;

8-(1-ethyl-5-methyl-1H-pyrazol-4-yl)-9-methyl-6-({1-[(2-methylpyridin-4-yl)carbonyl]pyrrolidin-3-yl}oxy)-9H-purine;

8-(1-ethyl-5-methyl-1H-pyrazol-4-yl)-9-methyl-6-({1-[(5-methyl-1,3-oxazol-4-yl)carbonyl]pyrrolidin-3-yl}oxy)-9H-purine;

6-({1-[(2,4-dimethyl-1,3-oxazol-5-yl)carbonyl]pyrrolidin-3-yl}oxy)-8-(1-ethyl-5-methyl-1H-pyrazol-4-yl)-9-methyl-9H-purine;

6-({1-[(1,5-dimethyl-1H-pyrazol-3-yl)carbonyl]pyrrolidin-3-yl}oxy)-8-(1-ethyl-5-methyl-1H-pyrazol-4-yl)-9-methyl-9H-purine;

6-({1-[(5-cyclopropylisoxazol-4-yl)carbonyl]pyrrolidin-3-yl}oxy)-8-(1-ethyl-5-methyl-1H-pyrazol-4-yl)-9-methyl-9H-purine;

8-(1-ethyl-5-methyl-1H-pyrazol-4-yl)-9-methyl-6-{[1-{[1-methyl-3-(trifluoromethyl)-1H-pyrazol-5-yl]carbonyl}pyrrolidin-3-yl]oxy}-9H-purine;

4-{[3-{[8-(1-ethyl-5-methyl-1-pyrazol-4-yl)-9-methyl-9H-purin-6-yl]oxy}pyrrolidin-1-yl]carbonyl}-1-methylpyrrolidin-2-one;

8-(1-ethyl-5-methyl-1H-pyrazol-4-yl)-6-({1-[(1-ethyl-5-methyl-1H-pyrazol-4-yl)carbonyl]pyrrolidin-3-yl}oxy)-9-methyl-9H-purine;

8-(1-ethyl-5-methyl-1H-pyrazol-4-yl)-9-methyl-6-{[1-(pyridin-4-ylcarbonyl)pyrrolidin-3-yl]oxy}-9H-purine;

8-(1-ethyl-5-methyl-1H-pyrazol-4-yl)-9-methyl-64 (1-[(5-methylisoxazol-4-yl)carbonyl]pyrrolidin-3-yl)oxy)-9H-purine;

8-(1-ethyl-5-methyl-1H-pyrazol-4-yl)-9-methyl-6-{[1-(pyridin-2-ylcarbonyl)pyrrolidin-3-yl]oxy}-9H-purine;

8-(1-ethyl-5-methyl-1-pyrazol-4-yl)-9-methyl-6-({1-[(1-methyl-1H-pyrrol-2-yl)carbonyl]pyrrolidin-3-yl}oxy)-9H-purine;

6-({1-[(5-ethylisoxazol-4-yl)carbonyl]pyrrolidin-3-yl}oxy)-8-(1-ethyl-5-methyl-1H-pyrazol-4-yl)-9-methyl-9H-purine;

8-(1-ethyl-5-methyl-1H-pyrazol-4-yl)-9-methyl-6-({1-[(4-methylisoxazol-5-yl)carbonyl]pyrrolidin-3-yl}oxy)-9H-purine;

8-(1-ethyl-5-methyl-1H-pyrazol-4-yl)-6-{[1-(1H-imidazo[1,2-b]pyrazol-7-ylcarbonyl)pyrrolidin-3-yl]oxy}-9-methyl-9H-purine;

8-(1-ethyl-5-methyl-1H-pyrazol-4-yl)-9-methyl-6-({1-[(4-methyl-1,3-oxazol-5-yl)carbonyl]pyrrolidin-3-yl}oxy)-9H-purine;

8-(1-ethyl-5-methyl-1H-pyrazol-4-yl)-9-methyl-6-{[1-(1H-pyrazol-4-ylcarbonyl)pyrrolidin-3-yl]oxy}-9H-purine;

8-(1-ethyl-5-methyl-1H-pyrazol-4-yl)-9-methyl-6-({1-[(1-methyl-1H-imidazol-5-yl)carbonyl]pyrrolidin-3-yl}oxy)-9H-purine;

6-({1-[(3,5-dimethylisoxazol-4-yl)carbonyl]pyrrolidin-3-yl}oxy)-8-(1-ethyl-5-methyl-1H-pyrazol-4-yl)-9-methyl-9H-purine;

8-(1-ethyl-5-methyl-1H-pyrazol-4-yl)-9-methyl-6-({1-[(5-methyl-1H-pyrazol-3-yl)carbonyl]pyrrolidin-3-yl}oxy)-9H-purine;

6-({1-[(3-tert-butyl-1-methyl-1H-pyrazol-5-yl)carbonyl]pyrrolidin-3-yl}oxy)-8-(1-ethyl-5-methyl-1H-pyrazol-4-yl)-9-methyl-9H-purine;

4-{[3-{[8-(1-ethyl-5-methyl-1H-pyrazol-4-yl)-9-methyl-9H-purin-6-yl]oxy}pyrrolidin-1-yl]carbonyl}-1-(1-methylethyl)pyrrolidin-2-one;

8-(1-ethyl-5-methyl-1H-pyrazol-4-yl)-9-methyl-6-({1-[(1,3,5-trimethyl-1H-pyrazol-4-yl)carbonyl]pyrrolidin-3-yl}oxy)-9H-purine;

8-(1-ethyl-5-methyl-1H-pyrazol-4-yl)-9-methyl-6-({1-[(1,2,5-trimethyl-1H-pyrrol-3-yl)carbonyl]pyrrolidin-3-yl}oxy)-9H-purine;

8-(1-ethyl-5-methyl-1H-pyrazol-4-yl)-9-methyl-6-({1-[(1-methyl-1H-pyrazol-4-yl)carbonyl]pyrrolidin-3-yl}oxy)-9H-purine;

8-(1-ethyl-5-methyl-1H-pyrazol-4-yl)-9-methyl-6-({1-[(5-methyl-1,3,4-oxadiazol-2-yl)carbonyl]pyrrolidin-3-yl}oxy)-9H-purine;

2-(5-{[3-{[8-(1-ethyl-5-methyl-1H-pyrazol-4-yl)-9-methyl-9H-purin-6-yl]oxy}pyrrolidin-1-yl]carbonyl}-1,2,4-oxadiazol-3-yl)propan-2-ol;

8-(1-ethyl-5-methyl-1H-pyrazol-4-yl)-9-methyl-6-{[1-(1H-pyrrolo[3,2-b]pyridin-2-ylcarbonyl)pyrrolidin-3-yl]oxy}-9H-purine;

6-{[1-(6,7-dihydro-5H-pyrrolo[1,2-d]tetrazol-5-ylcarbonyl)pyrrolidin-3-yl]oxy}-8-(1-ethyl-5-methyl-1H-pyrazol-4-yl)-9-methyl-9H-purine;

6-{[1-(5,6-dihydro-4H-pyrrolo[1,2-b]pyrazol-2-ylcarbonyl)pyrrolidin-3-yl]oxy}-8-(1-ethyl-5-methyl-1H-pyrazol-4-yl)-9-methyl-9H-purine;

6-({1-[(2-ethyl-4-methyl-1,3-oxazol-5-yl)carbonyl]pyrrolidin-3-yl}oxy)-8-(1-ethyl-5-methyl-1H-pyrazol-4-yl)-9-methyl-9H-purine;

8-(1-ethyl-5-methyl-1H-pyrazol-4-yl)-9-methyl-6-{[1-{[5-(1-methylethy)isoxazol-4-yl]carbonyl}pyrrolidin-3-yl]oxy}-9H-purine;

8-(1-ethyl-5-methyl-1H-pyrazol-4-yl)-9-methyl-6-{[1-(1,3-oxazol-4-ylcarbonyl)pyrrolidin-3-yl]oxy}-9H-purine;

1-(3-((9-ethyl-8-(6-methoxy-5-methylpyridin-3-yl)-9H-purin-6-yl)oxy)pyrrolidin-1-yl)propan-1-one;

1-(3-((8-(1-ethyl-5-methyl-1H-pyrazol-4-yl)-9-methyl-9H-purin-6-yl)oxy)pyrrolidin-1-yl)ethanone;

1-(3-((8-(1-ethyl-5-methyl-1H-pyrazol-4-yl)-9-methyl-9H-purin-6-yl)oxy)pyrrolidin-1-yl)-2-methylpropan-1-one;

1-(3-((8-(1-ethyl-5-methyl-1H-pyrazol-4-yl)-9-methyl-9H-purin-6-yl)oxy)pyrrolidin-1-yl)-2,2-dimethylpropan-1-one;

1-(3-((9-ethyl-8-(1-ethyl-5-methyl-1H-pyrazol-4-yl)-9H-purin-6-yl)oxy)pyrrolidin-1-yl)propan-1-one;

1-(3-((8-(6-methoxy-5-methylpyridin-3-yl)-9-methyl-9H-purin-6-yl)oxy)pyrrolidin-1-yl)propan-1-one;

1-(3-((8-(2-(tert-butyl)thiazol-5-yl)-9-ethyl-9H-purin-6-yl)oxy)pyrrolidin-1-yl)propan-1-one;

1-(3-((8-(2-(tert-butyl)thiazol-5-yl)-9-methyl-9H-purin-6-yl)oxy)pyrrolidin-1-yl)propan-1-one;

1-(3-((9-cyclopropyl-8-(1-ethyl-5-methyl-1H-pyrazol-4-yl)-9H-purin-6-yl)oxy)pyrrolidin-1-yl)propan-1-one;

1-(3-((8-(1H-indazol-6-yl)-9-methyl-9H-purin-6-yl)oxy)pyrrolidin-1-yl)propan-1-one;

1-(3-((9-methyl-8-(6-(trifluoromethyl)pyridin-3-yl)-9H-purin-6-yl)oxy)pyrrolidin-1-yl)propan-1-one;

1-(3-((9-methyl-8-(1H-pyrrolo[2,3-b]pyridin-5-yl)-9H-purin-6-yl)oxy)pyrrolidin-1-yl)propan-1-one;

1-(3-((8-(1H-indol-6-yl)-9-methyl-9H-purin-6-yl)oxy)pyrrolidin-1-yl)propan-1-one;

1-(3-((8-(1H-indazol-5-yl)-9-methyl-9H-purin-6-yl)oxy)pyrrolidin-1-yl)propan-1-one;

1-(3-((8-(6-methoxy-5-(trifluoromethyl)pyridin-3-yl)-9-methyl-9H-purin-6-yl)oxy)pyrrolidin-1-yl)propan-1-one;

1-(3-((8-(1H-indol-5-yl)-9-methyl-9H-purin-6-yl)oxy)pyrrolidin-1-yl)propan-1-one;

1-(3-((9-methyl-8-(6-methylpyridin-3-yl)-9H-purin-6-yl)oxy)pyrrolidin-1-yl)propan-1-one;

8-(1-ethyl-5-methyl-1H-pyrazol-4-yl)-6-{[1-(ethylsulfonyl)pyrrolidin-3-yl]oxy}-9-methyl-9H-purine;
8-(1-ethyl-5-methyl-1H-pyrazol-4-yl)-9-methyl-6-({1-[(1-methylethyl)sulfonyl]pyrrolidin-3-yl}oxy)-9H-purine;
8-(1-ethyl-5-methyl-1H-pyrazol-4-yl)-9-methyl-6-({1-[(trifluoromethyl)sulfonyl]pyrrolidin-3-yl}oxy)-9H-purine;
8-(1-ethyl-5-methyl-1H-pyrazol-4-yl)-9-methyl-6-{[1-(phenylsulfonyl)pyrrolidin-3-yl]oxy}-9H-purine;
8-(1-ethyl-5-methyl-1H-pyrazol-4-yl)-9-methyl-6-({1-[(1-methyl-1H-imidazol-4-yl)sulfonyl]pyrrolidin-3-yl}oxy)-9H-purine;
8-(1-ethyl-5-methyl-1H-pyrazol-4-yl)-9-methyl-6-{[1-(naphthalen-2-ylsulfonyl)pyrrolidin-3-yl]oxy}-9H-purine;
6-{([1-(biphenyl-4-ylsulfonyl)pyrrolidin-3-yl]oxy}-8-(1-ethyl-5-methyl-1H-pyrazol-4-yl)-9-methyl-9H-purine;
N-cyclohexyl-3-{[8-(1-ethyl-5-methyl-1H-pyrazol-4-yl)-9-methyl-9H-purin-6-yl]oxy}pyrrolidine-1-carboxamide;
3-{[8-(1-ethyl-5-methyl-1H-pyrazol-4-yl)-9-methyl-9H-purin-6-yl]oxy}-N-(3-methylphenyl)pyrrolidine-1-carboxamide;
3-{[8-(1-ethyl-5-methyl-1H-pyrazol-4-yl)-9-methyl-9H-purin-6-yl]oxy}-N-(1-methylethyl)pyrrolidine-1-carboxamide;
3-{[8-(1-ethyl-5-methyl-1H-pyrazol-4-yl)-9-methyl-9H-purin-6-yl]oxy}-N-(1,1,3,3-tetramethylbutyl)pyrrolidine-1-carboxamide;
3-{[8-(1-ethyl-5-methyl-1H-pyrazol-4-yl)-9-methyl-9H-purin-6-yl]oxy 1-N-[(1R)-1-phenylethyl]pyrrolidine-1-carboxamide;
ethyl N-{[3-{[8-(1-ethyl-5-methyl-1H-pyrazol-4-yl)-9-methyl-9H-purin-6-yl]oxy}pyrrolidin-1-yl]carbonyl}alaninate;
N-ethyl-3-((8-(1-ethyl-5-methyl-1H-pyrazol-4-yl)-9-methyl-9H-purin-6-yl)oxy)pyrrolidine-1-carboxamide;
8-(1-ethyl-5-methyl-1H-pyrazol-4-yl)-9-methyl-6-[1-(1-phenylethyl)pyrrolidin-3-yl]oxy}-9H-purine;
6-{[1-(cyclohexylmethyl)pyrrolidin-3-yl]oxy}-8-(1-ethyl-5-methyl-1H-pyrazol-4-yl)-9-methyl-9H-purine;
4-{[3-{[8-(1-ethyl-5-methyl-1H-pyrazol-4-yl)-9-methyl-9H-purin-6-yl]oxy}pyrrolidin-1-yl]methyl}-N,N-dimethylaniline;
8-(1-ethyl-5-methyl-1H-pyrazol-4-yl)-9-methyl-6-{[1-(1H-pyrrol-2-ylmethyl)pyrrolidin-3-yl]oxy}-9H-purine;
8-(1-ethyl-5-methyl-1H-pyrazol-4-yl)-9-methyl-6-{[1-pyrimidin-2-ylpyrrolidin-3-yl]oxy}-9H-purine;
8-(1-ethyl-5-methyl-1H-pyrazol-4-yl)-9-methyl-6-{[1-(6-methylthieno[2,3-d]pyrimidin-4-yl)pyrrolidin-3-yl]oxy}-9H-purine;
8-(1-ethyl-5-methyl-1H-pyrazol-4-yl)-9-methyl-6-{[1-thieno[3,2-c]pyridin-4-ylpyrrolidin-3-yl]oxy}-9H-purine;
8-(1-ethyl-5-methyl-1H-pyrazol-4-yl)-9-methyl-6-{[1-thieno[3,2-d]pyrimidin-4-ylpyrrolidin-3-yl]oxy}-9H-purine;
8-(1-ethyl-5-methyl-1H-pyrazol-4-yl)-9-methyl-6-({1-[4-(trifluoromethyl)pyridin-2-yl]pyrrolidin-3-yl}oxy)-9H-purine;
8-[3-{[8-(1-ethyl-5-methyl-1H-pyrazol-4-yl)-9-methyl-9H-purin-6-yl]oxy 1pyrrolidin-1-yl][1,2,4]triazolo[4,3-a]pyrazine;
8-(1-ethyl-5-methyl-1H-pyrazol-4-yl)-9-methyl-6-{[1-pyridin-2-ylpyrrolidin-3-yl]oxy}-9H-purine;
1-[3-{[8-(1-ethyl-5-methyl-1H-pyrazol-4-yl)-9-methyl-9H-purin-6-yl]oxy}pyrrolidin-1-yl]phthalazine;
8-(1-ethyl-5-methyl-1H-pyrazol-4-yl)-9-methyl-6-({1-[6-(4-methyl-1H-pyrazol-1-yl)pyrimidin-4-yl]pyrrolidin-3-yl}oxy)-9H-purine;
8-(1-ethyl-5-methyl-1H-pyrazol-4-yl)-6-[1-(4-furan-2-ylpyrimidin-2-yl)pyrrolidin-3-yl]oxy}-9-methyl-9H-purine;
8-(1-ethyl-5-methyl-1H-pyrazol-4-yl)-9-methyl-6-{[1-(6-methylpyrazin-2-yl)pyrrolidin-3-yl]oxy}-9H-purine;
6-{[1-(5,6-dimethylthieno[2,3-d]pyrimidin-4-yl)pyrrolidin-3-yl]oxy}-8-(1-ethyl-5-methyl-1H-pyrazol-4-yl)-9-methyl-9H-purine;
8-(1-ethyl-5-methyl-1H-pyrazol-4-yl)-9-methyl-6-{[1-thieno[2,3-d]pyrimidin-4-ylpyrrolidin-3-yl]oxy}-9H-purine;
4-[3-{[8-(1-ethyl-5-methyl-1H-pyrazol-4-yl)-9-methyl-9H-purin-6-yl]oxy}pyrrolidin-1-yl]-1-methyl-1H-pyrazolo[3,4-d]pyrimidine;
8-(1-ethyl-5-methyl-1H-pyrazol-4-yl)-9-methyl-6-({1-[6-(1H-pyrazol-1-yl)pyrimidin-4-yl]pyrrolidin-3-yl}oxy)-9H-purine;
(3-((8-(1-ethyl-5-methyl-1H-pyrazol-4-yl)-9-methyl-9H-purin-6-yl)oxy)cyclopentyl)(morpholino)methanone;
tert-butyl [3-{[8-(1-ethyl-5-methyl-1H-pyrazol-4-yl)-9-methyl-9H-purin-6-yl]oxy}cyclopentyl]carbamate;
tert-butyl [3-{[8-(1-ethyl-5-methyl-1H-pyrazol-4-yl)-9-methyl-9H-purin-6-yl]oxy}cyclopentyl]carbamate;
N-[3-{[8-(1-ethyl-5-methyl-1H-pyrazol-4-yl)-9-methyl-9H-purin-6-yl]oxy}cyclopentyl]tetrahydro-2H-pyran-4-carboxamide;
1-[3-{[8-(1-ethyl-5-methyl-1H-pyrazol-4-yl)-9-methyl-9H-purin-6-yl]oxy}cyclopentyl]-1,3-dihydro-2H-imidazo[4,5-b]pyridin-2-one;
tert-butyl 3-((8-(1-ethyl-5-methyl-1H-pyrazol-4-yl)-9-methyl-9H-purin-6-yl)thio)pyrrolidine-1-carboxylate;
tert-butyl 3-((8-(1-ethyl-5-methyl-1H-pyrazol-4-yl)-9-methyl-9H-purin-6-yl)sulfonyl)pyrrolidine-1-carboxylate;
(3-((8-(1-ethyl-5-methyl-1H-pyrazol-4-yl)-9-methyl-9H-purin-6-yl)thio)pyrrolidin-1-yl)(tetrahydro-2H-pyran-4-yl)methanone;
1-(3-((8-(1-ethyl-5-methyl-1H-pyrazol-4-yl)-9-methyl-9H-purin-6-yl)thio)pyrrolidin-1-yl)propan-1-one;
(3-((8-(1-ethyl-5-methyl-1H-pyrazol-4-yl)-9-methyl-9H-purin-6-yl)sulfonyl)pyrrolidin-1-yl) (tetrahydro-2H-pyran-4-yl)methanone;
1-(3-((8-(1-ethyl-5-methyl-1H-pyrazol-4-yl)-9-methyl-9H-purin-6-yl)sulfonyl)pyrrolidin-1-yl)propan-1-one;
cyclopropyl(3-((8-(1-ethyl-5-methyl-1H-pyrazol-4-yl)-9-methyl-9H-purin-6-yl)thio)pyrrolidin-1-yl)methanone;
ethyl 3-((8-(1-ethyl-5-methyl-1H-pyrazol-4-yl)-9-methyl-9H-purin-6-yl)thio)pyrrolidine-1-carboxylate;
isobutyl 3-((8-(1-ethyl-5-methyl-1H-pyrazol-4-yl)-9-methyl-9H-purin-6-yl)thio)pyrrolidine-1-carboxylate;
(3-((8-(1-ethyl-5-methyl-1-pyrazol-4-yl)-9-methyl-9H-purin-6-yl)thio)pyrrolidin-1-yl)(1-methyl-1H-pyrazol-3-yl)methanone;
(3-((8-(1-ethyl-5-methyl-1-pyrazol-4-yl)-9-methyl-9H-purin-6-yl)thio)pyrrolidin-1-yl)(2-methyloxazol-4-yl)methanone;
8-(1-ethyl-5-methyl-1H-pyrazol-4-yl)-9-methyl-6-((1-(pyrimidin-4-yl)pyrrolidin-3-yl)thio)-9H-purine;
4-(3-((8-(1-ethyl-5-methyl-1H-pyrazol-4-yl)-9-methyl-9H-purin-6-yl)thio)pyrrolidin-1-yl)thieno[2,3-d]pyrimidine;

tert-butyl 3-((8-(1-ethyl-5-methyl-1H-pyrazol-4-yl)-9-methyl-9H-purin-6-yl)methyl)pyrrolidine-1-carboxylate;
(3-((8-(1-ethyl-5-methyl-1H-pyrazol-4-yl)-9-methyl-9H-purin-6-yl)methyl)pyrrolidin-1-yl)(tetrahydro-2H-pyran-4-yl)methanone;
1-(3-((8-(1-ethyl-5-methyl-1H-pyrazol-4-yl)-9-methyl-9H-purin-6-yl)methyl)pyrrolidin-1-yl)propan-1-one;
Ethyl 3-{[9-ethyl-8-(2-methylpyrimidin-5-yl)-9H-purin-6-yl]oxy}pyrrolidine-1-carboxylate;
Tert-butyl 3-{[9-ethyl-8-(2-methylpyrimidin-5-yl)-9H-purin-6-yl]oxy}-4-fluoropyrrolidine-1-carboxylate;
Benzyl 3-ethyl-4-{[9-ethyl-8-(2-methylpyrimidin-5-yl)-9H-purin-6-yl]oxy}pyrrolidine-1-carboxylate;
Tert-butyl 3-{[9-ethyl-8-(2-methylpyrimidin-5-yl)-9H-purin-6-yl]oxy}-4-hydroxypyrrolidine-1-carboxylate;
Tert-butyl 4-{[9-ethyl-8-(2-methylpyrimidin-5-yl)-9H-purin-6-yl]oxy}-3,3-difluoropyrrolidine-1-carboxylate;
Tert-butyl-3-{[9-ethyl-8-(2-methylpyrimidin-5-yl)-9H-purin-6-yl]oxy}-2-methylpyrrolidine-1-carboxylate;
2-(dimethylamino)ethyl-3-{[9-ethyl-8-(2-methylpyrimidin-5-yl)-9H-purin-6-yl]oxy}pyrrolidine-1-carboxylate;
2-(dimethylamino)propyl-3-{[9-ethyl-8-(2-methylpyrimidin-5-yl)-9H-purin-6-yl]oxy}pyrrolidine-1-carboxylate;
Tert-butyl-3-({8-[6-(difluoromethoxy)pyridin-3-yl]-9-ethyl-9H-purin-6-yl}oxy)pyrrolidine-1-carboxylate;
6-{[-1-(cyclopropylcarbonyl)-2-methylpyrrolidin-3-yl]oxy}-9-ethyl-8-(2-methylpyrimidin-5-yl)-9H-purine;
6-{[1-(cyclopropylcarbonyl)-4,4-difluoropyrrolidin-3-yl]oxy}-9-ethyl-8-(2-methylpyrimidin-5-yl)-9H-purine;
1-(cyclopropylcarbonyl)-4-{[9-ethyl-8-(2-methylpyrimidin-5-yl)-9H-purin-6-yl]oxy}pyrrolidin-3-01;
2-{[(3S)-3-{[9-ethyl-8-(2-methylpyrimidin-5-yl)-9H-purin-6-yl]oxy}pyrrolidin-1-yl]carbonyl}cyclopentanamine;
6-{[1-(azetidin-3-ylcarbonyl)pyrrolidin-3-yl]oxy}-9-ethyl-8-(2-methylpyrimidin-5-yl)-9H-purine;
2-{[3-{[9-ethyl-8-(2-methylpyrimidin-5-yl)-9H-purin-6-yl]oxy}pyrrolidin-1-yl]carbonyl}cyclopentanamine;
6-({1-[-1-azabicyclo[2.2.1]hept-3-ylcarbonyl]pyrrolidin-3-yl}oxy)-9-ethyl-8-(2-methylpyrimidin-5-yl)-9H-purine;
6-{[1-(cyclobutylcarbonyl)pyrrolidin-3-yl]oxy]-8-(1-ethyl-5-methyl-1H-pyrazol-4-yl)-9-methyl-9H-purine;
6-({1-[(3,3-difluorocyclobutyl)carbonyl]pyrrolidin-3-yl}oxy)-8-(1-ethyl-5-methyl-1H-pyrazol-4-yl)-9-methyl-9H-purine;
6-{[1-(cyclopropylcarbonyl)pyrrolidin-3-yl]oxy}-9-ethyl-8-(2-methylpyrimidin-5-yl)-9H-purine;
9-ethyl-6-({1-[(2-methylcyclopropyl)carbonyl]pyrrolidin-3-yl}oxy)-8-(2-methylpyrimidin-5-yl)-9H-purine;
9-ethyl-6-({1-[(1-methyl-1H-pyrazol-3-yl)carbonyl]pyrrolidin-3-yl}oxy)-8-(2-methylpyrimidin-5-yl)-9H-purine;
6-({1-[bicyclo[2.2.1]hept-2-ylcarbonyl]pyrrolidin-3-yl}oxy)-9-ethyl-8-(2-methylpyrimidin-5-yl)-9H-purine;
1-[3-{[9-ethyl-8-(2-methylpyrimidin-5-yl)-9H-purin-6-yl]oxy}pyrrolidin-1-yl]-3-methyl-1-oxobutan-2-amine;
1-{[3-{[9-ethyl-8-(2-methylpyrimidin-5-yl)-9H-purin-6-yl]oxy}pyrrolidin-1-yl]carbonyl}cyclobutanamine;
9-ethyl-8-(2-methylpyrimidin-5-yl)-6-{[1-(tetrahydrofuran-3-ylcarbonyl)pyrrolidin-3-yl]oxy}-9H-purine;
4-[3-{[9-ethyl-8-(2-methylpyrimidin-5-yl)-9H-purin-6-yl]oxy}pyrrolidin-1-yl]-2-methyl-4-oxobutan-2-amine;
6-{[1-(cyclopropylcarbonyl)-4-methoxypyrrolidin-3-yl]oxy}-9-ethyl-8-(2-methylpyrimidin-5-yl)-9H-purine;
9-ethyl-6-{[1-(3-methylbut-2-enoyl)pyrrolidin-3-yl]oxy}-8-(2-methylpyrimidin-5-yl)-9H-purine;
9-ethyl-6-({1-[(-methylcyclobutyl)carbonyl]pyrrolidin-3-yl}oxy)-8-(2-methylpyrimidin-5-yl)-9H-purine;
6-({1-[(2, 3-dimethylcyclopropyl)carbonyl]pyrrolidin-3-yl}oxy)-9-ethyl-8-(2-methylpyrimidin-5-yl)-9H-purine;
9-ethyl-8-(2-methylpyrimidin-5-yl)-6-{[spiro[2.4]hept-1-ylcarbonyl)pyrrolidin-3-yl]oxy}-9H-purine;
6-{[1-{[2-(difluoromethyl)cyclopropyl]carbonyl}pyrrolidin-3-yl]oxy}-9-ethyl-8-(2-methylpyrimidin-5-yl)-9H-purine;
6-({1-[(2,2-dimethylcyclopropyl)carbonyl]pyrrolidin-3-yl}oxy)-9-ethyl-8-(2-methylpyrimidin-5-yl)-9H-purine;
9-ethyl-6-({1-[(3-methylcyclobutyl)carbonyl]pyrrolidin-3-yl}oxy)-8-(2-methylpyrimidin-5-yl)-9H-purine;
{[(3S)-3-{[9-ethyl-8-(2-methylpyrimidin-5-yl)-9H-purin-6-yl]oxy}pyrrolidin-1-yl]carbonyl}cyclopropyl)methanol;
9-ethyl-6-{[1-{[2-(fluoromethyl)cyclopropyl]carbonyl}pyrrolidin-3-yl]oxy}-8-(2-methylpyrimidin-5-yl)-9H-purine;
9-ethyl-6-({(3S)-1-[(2-fluorocyclopropyl)carbonyl]pyrrolidin-3-yl}oxy)-8-(2-methylpyrimidin-5-yl)-9H-purine;
9-ethyl-8-(2-methylpyrimidin-5-yl)-6-1 [1-(1,3-oxazol-4-ylcarbonyl)pyrrolidin-3-yl]oxy}-9H-purine;
6-{[1-(cyclopropylcarbonyl)-4-fluoropyrrolidin-3-yl]oxy}-9-ethyl-8-(2-methylpyrimidin-5-yl)-9H-purine;
cyclopropyl(2-((9-ethyl-8-(2-methylpyrimidin-5-yl)-9H-purin-6-yl)oxy)-7-azabicyclo[2.2.1]heptan-7-yl)methanone;
6-{[1-(cyclopropylcarbonyl)-3-methylpyrrolidin-3-yl]oxy}-9-ethyl-8-(2-methylpyrimidin-5-yl)-9H-purine;
6-{[1-(cyclopropylcarbonyl)pyrrolidin-3-yl]oxy}-9-ethyl-8-[4-(trifluoromethoxy)phenyl]-9H-purine;
6-{[1-(cyclopropylcarbonyl)pyrrolidin-3-yl]oxy}-9-ethyl-8-(6-methoxypyridin-3-yl)-9H-purine;
6-{[1-(cyclopropylcarbonyl)pyrrolidin-3-yl]oxy}-9-ethyl-8-(2-methoxypyridin-4-yl)-9H-purine;
6-{[1-(cyclopropylcarbonyl)pyrrolidin-3-yl]oxy}-9-ethyl-8-[6-(trifluoromethyl)pyridin-3-yl]-9H-purine;
6-{[1-(cyclopropylcarbonyl)pyrrolidin-3-yl]oxy}-9-ethyl-8-[4-(trifluoromethyl)phenyl]-9H-purine;
6-{[1-(cyclopropylcarbonyl)pyrrolidin-3-yl]oxy}-8-[6-(difluoromethoxy)pyridin-3-yl]-9-ethyl-9H-purine;
3-fluoro-5-(9-methyl-6-{[1-propanoylpyrrolidin-3-yl]oxy}-9H-purin-8-yl)phenol;
9-methyl-8-(3-methyl-1H-pyrazolo[3,4-b]pyridin-5-yl)-6-{[1-propanoylpyrrolidin-3-yl]oxy}-9H-purine;
9-methyl-8-(1-phenyl-1H-pyrazol-4-yl)-6-{[1-propanoylpyrrolidin-3-yl]oxy}-9H-purine;
9-methyl-8-(5-methyl-1-phenyl-1H-pyrazol-4-yl)-6-{[1-propanoylpyrrolidin-3-yl]oxy}-9H-purine;
8-(1-ethyl-5-methyl-1-pyrazol-4-yl)-6-{[1-propanoylpyrrolidin-3-yl]oxy}-9H-purine;
N-[3-fluoro-5-(9-methyl-6-{[(3S)-1-propanoylpyrrolidin-3-yl]oxy}-9H-purin-8-yl)phenyl]methanesulfonamide;
5-(9-methyl-6-{[1-propanoylpyrrolidin-3-yl]oxy}-9H-purin-8-yl)pyridin-3-amine;

8-(1-tert-butyl-1H-pyrazol-4-yl)-9-methyl-6-{[1-propanoylpyrrolidin-3-yl]oxy}-9H-purine;
8-(6-chloropyridin-3-yl)-9-methyl-6-{[1-propanoylpyrrolidin-3-yl]oxy}-9H-purine;
8-(1-ethyl-5-methyl-1H-pyrazol-4-yl)-6-{[1-propanoylpyrrolidin-3-yl]oxy}-9-propyl-9H-purine;
8-(2-methylpyrimidin-5-yl)-6-{[1-propanoylpyrrolidin-3-yl]oxy}-9-propyl-9H-purine;
9-methyl-8-(2-methylpyrimidin-5-yl)-6-{[1-propanoylpyrrolidin-3-yl]oxy}-9H-purine;
9-(2,2-difluoroethyl)-8-(1-ethyl-5-methyl-1H-pyrazol-4-yl)-6-{[1-propanoylpyrrolidin-3-yl]oxy}-9H-purine;
8-(5,6-dihydro-4H-pyrrolo[1,2-b]pyrazol-3-yl)-9-methyl-6-{[1-propanoylpyrrolidin-3-yl]oxy}-9H-purine;
6-{([1-(cyclopropylcarbonyl)pyrrolidin-3-yl]oxy}-9-ethyl-8-(5-methyl-1-phenyl-1H-pyrazol-4-yl)-9H-purine;
6-{[1-(cyclopropylcarbonyl)pyrrolidin-3-yl]oxy}-9-ethyl-8-(3-fluoro-4-methoxyphenyl)-9H-purine;
6-{[1-(cyclopropylcarbonyl)pyrrolidin-3-yl]oxy}-9-ethyl-8-(1H-pyrrolo[2,3-b]pyridin-5-yl)-9H-purine;
6-{([1-(cyclopropylcarbonyl)pyrrolidin-3-yl]oxy}-9-ethyl-8-[6-methoxy-5-(trifluoromethyl)pyridin-3-yl]-9H-purine;
6-{[1-(cyclopropylcarbonyl)pyrrolidin-3-yl]oxy}-9-ethyl-8-(2-methoxypyrimidin-5-yl)-9H-purine;
8-(5-chloro-6-methoxypyridin-3-yl)-6-{[1-(cyclopropylcarbonyl)pyrrolidin-3-yl]oxy}-9-ethyl-9H-purine;
6-{[1-(cyclopropylcarbonyl)pyrrolidin-3-yl]oxy}-8-(2,4-dimethylpyrimidin-5-yl)-9-ethyl-9H-purine;
6-{[1-(cyclopropylcarbonyl)pyrrolidin-3-yl]oxy}-9-ethyl-8-(5-fluoro-6-methylpyridin-3-yl)-9H-purine;
8-iodo-9-methyl-6-{[1-propanoylpyrrolidin-3-yl]oxy}-9H-purine;
8-(3-fluoro-4-methoxyphenyl)-9-methyl-6-{[1-propanoylpyrrolidin-3-yl]oxy}-9H-purine;
8-(6-methoxypyridin-3-yl)-9-methyl-6-{[1-propanoylpyrrolidin-3-yl]oxy}-9H-purine;
8-(5-fluoro-6-methoxypyridin-3-yl)-9-methyl-6-{[1-propanoylpyrrolidin-3-yl]oxy}-9H-purine;
8-[4-methoxy-3-(trifluoromethyl)phenyl]-9-methyl-6-{[1-propanoylpyrrolidin-3-yl]oxy}-9H-purine;
8-(4-methoxy-3-methylphenyl)-9-methyl-6-{[1-propanoylpyrrolidin-3-yl]oxy}-9H-purine;
2-methoxy-5-(9-methyl-6-{[1-propanoylpyrrolidin-3-yl]oxy}-9H-purin-8-yl)pyridine-3-carbonitrile;
N-[2-methoxy-5-(9-methyl-6-{[1-propanoylpyrrolidin-3-yl]oxy}-9H-purin-8-yl)pyridin-3-yl]methanesulfonamide;
9-methyl-8-[4-(methylsulfonyl)phenyl]-6-{[1-propanoylpyrrolidin-3-yl]oxy}-9H-purine;
9-methyl-6-{[1-propanoylpyrrolidin-3-yl]oxy}-8-(4,5,6,7-tetrahydropyrazolo[1,5-a]pyridin-3-yl)-9H-purine;
N-[5-(6-{[1-(cyclopropylcarbonyl)pyrrolidin-3-yl]oxy}-9-ethyl-9H-purin-8-yl)-2-methoxypyridin-3-yl]methanesulfonamide;
5-(6-{[1-(cyclopropylcarbonyl)pyrrolidin-3-yl]oxy}-9-ethyl-9H-purin-8-yl)-2-methoxypyridine-3-carbonitrile;
6-{[1-(cyclopropylcarbonyl)pyrrolidin-3-yl]oxy}-9-ethyl-8-[2-(trifluoromethyl)pyrimidin-5-yl]-9H-purine;
5-(6-{[1-(cyclopropylcarbonyl)pyrrolidin-3-yl]oxy}-9-ethyl-9H-purin-8-yl)-3-(trifluoromethyl)pyridin-2-amine;
5-(6-{[1-(cyclopropylcarbonyl)pyrrolidin-3-yl]oxy}-9-ethyl-9H-purin-8-yl)-N,N-dimethylpyrimidin-2-amine;
6-{[1-(cyclopropylcarbonyl)-4-ethylpyrrolidin-3-yl]oxy}-9-ethyl-8-(2-methylpyrimidin-5-yl)-9H-purine;
6-{[1-(cyclopropylcarbonyl)pyrrolidin-3-yl]oxy}-9-ethyl-8-(5-methoxypyridin-2-yl)-9H-purine;
6-{[1-(cyclopropylcarbonyl)pyrrolidin-3-yl]oxy}-9-ethyl-8-(6-methoxy-5-methylpyridin-3-yl)-9H-purine;
9-ethyl-8-(6-methoxypyridin-3-yl)-6-{[1-(2-methylpropanoyl)pyrrolidin-3-yl]oxy}-9H-purine;
6-({1-[(3,3-difluorocyclobutyl)carbonyl]pyrrolidin-3-yl}oxy)-9-ethyl-8-(6-methoxypyridin-3-yl)-9H-purine;
9-ethyl-8-(6-methoxypyridin-3-yl)-6-{[1-(tetrahydro-2H-pyran-4-ylcarbonyl)pyrrolidin-3-yl]oxy}-9H-purine;
6-{[1-(cyclopropylcarbonyl)pyrrolidin-3-yl]oxy}-9-ethyl-8-(5-fluoro-6-methoxypyridin-3-yl)-9H-purine;
9-ethyl-8-(5-fluoro-6-methoxypyridin-3-yl)-6-{[1-(2-methylpropanoyl)pyrrolidin-3-yl]oxy 1-9H-purine;
6-({1-[(3,3-difluorocyclobutyl)carbonyl]pyrrolidin-3-yl}oxy)-9-ethyl-8-(5-fluoro-6-methoxypyridin-3-yl)-9H-purine;
9-ethyl-8-(5-fluoro-6-methoxypyridin-3-yl)-6-{[1-(tetrahydro-2H-pyran-4-ylcarbonyl)pyrrolidin-3-yl]oxy}-9H-purine;
9-ethyl-8-(5-fluoro-6-methoxypyridin-3-yl)-6-({1-[(1-methyl-1H-pyrazol-3-yl)carbonyl]pyrrolidin-3-yl}oxy)-9H-purine;
9-ethyl-8-(5-fluoro-6-methoxypyridin-3-yl)-6-({1-[(1-methyl-1H-imidazol-5-yl)carbonyl]pyrrolidin-3-yl}oxy)-9H-purine;
6-{[1-(cyclopropylcarbonyl)pyrrolidin-3-yl]oxy}-9-ethyl-8-(4,5,6,7-tetrahydropyrazolo[1,5-a]pyridin-3-yl)-9H-purine;
9-ethyl-6-{[1-(2-methylpropanoyl)pyrrolidin-3-yl]oxy}-8-(4,5,6,7-tetrahydropyrazolo[1,5-a]pyridin-3-yl)-9H-purine;
(3-((9-ethyl-8-(1-ethyl-5-methyl-1H-pyrazol-4-yl)-9H-purin-6-yl)oxy)pyrrolidin-1-yl)(tetrahydro-2H-pyran-4-yl)methanone;
6-{[1-(cyclopropylcarbonyl)-4,4-dimethylpyrrolidin-3-yl]oxy}-9-ethyl-8-(2-methylpyrimidin-5-yl)-9H-purine;
6-{[5-(cyclopropylcarbonyl)-5-azaspiro[2.4]hept-7-yl]oxy}-9-ethyl-8-(2-methylpyrimidin-5-yl)-9H-purine;
6-{[1-(cyclopropylcarbonyl)-4-methylpyrrolidin-3-yl]oxy}-9-ethyl-8-(2-methylpyrimidin-5-yl)-9H-purine;
Cyclopropyl([3-(difluoromethyl)-4-((9-ethyl-8-(2-methylpyrimidin-5-yl)-9H-purin-6-yl)oxy)pyrrolidin-1-yl)methanone;
Cyclopropyl(34(9-ethyl-8-(2-methylpyrimidin-5-yl)-9H-purin-6-yl)oxy)-4-(fluoromethyl)pyrrolidin-1-yl)methanone;
9-ethyl-6-((1-(ethylsulfonyl)pyrrolidin-3-yl)oxy)-8-(2-methylpyrimidin-5-yl)-9H-purine;
N-ethyl-3-{[9-ethyl-8-(2-methylpyrimidin-5-yl)-9H-purin-6-yl]oxy}pyrrolidine-1-carboxamide;
N-ethyl-3-{[9-ethyl-8-(2-methylpyrimidin-5-yl)-9H-purin-6-yl]oxy}-N-methylpyrrolidine-1-carboxamide;
N-cyclopropyl-3-{[9-ethyl-8-(2-methylpyrimidin-5-yl)-9H-purin-6-yl]oxy}-N-methylpyrrolidine-1-carboxamide;
6-{[1-(azetidin-1-ylcarbonyl)pyrrolidin-3-yl]oxy}-9-ethyl-8-(2-methylpyrimidin-5-yl)-9H-purine;
4-{[9-ethyl-8-(2-methylpyrimidin-5-yl)-9H-purin-6-yl]oxy}-N-methyl-N-phenylpiperidine-1-carboxamide;
9-ethyl-6-({1-[(3-methoxyazetidin-1-yl)carbonyl]pyrrolidin-3-yl}oxy)-8-(2-methylpyrimidin-5-yl)-9H-purine;

6-({1-[(3,3-difluoroazetidin-1-yl)carbonyl]pyrrolidin-3-yl}oxy)-9-ethyl-8-(2-methylpyrimidin-5-yl)-9H-purine;
9-ethyl-6-({(3S)-1-[(methylazetidin-1-yl)carbonyl]pyrrolidin-3-yl}oxy)-8-(2-methylpyrimidin-5-yl)-9H-purine;
3-{[9-ethyl-8-(2-methylpyrimidin-5-yl)-9H-purin-6-yl]oxy}-N-methyl-N-phenylpyrrolidine-1-carboxamide;
(1-{[3-{[9-ethyl-8-(2-methylpyrimidin-5-yl)-9H-purin-6-yl]oxy}pyrrolidin-1-yl]carbonyl}pyrrolidin-3-yl)methanol;
6-({1-[(3,3-dimethylpyrrolidin-1-yl)carbonyl]pyrrolidin-3-yl}oxy)-9-ethyl-8-(2-methylpyrimidin-5-yl)-9H-purine;
1-{[3-{[9-ethyl-8-(2-methylpyrimidin-5-yl)-9H-purin-6-yl]oxy}pyrrolidin-1-yl]carbonyl}-3-methylpyrrolidin-3-ol;
9-ethyl-6-({1-[(3-methoxy-3-methylazetidin-1-yl)carbonyl]pyrrolidin-3-yl}oxy)-8-(2-methylpyrimidin-5-yl)-9H-purine;
6-{[1-(3-azabicyclo[3.1.0]hex-3-ylcarbonyl)pyrrolidin-3-yl]oxy}-9-ethyl-8-(2-methylpyrimidin-5-yl)-9H-purine;
9-ethyl-8-(2-methylpyrimidin-5-yl)-6-{[1-(piperidin-1-ylcarbonyl)pyrrolidin-3-yl]oxy}-9H-purine;
6-({1-[(7-azabicyclo[2.2.1]hept-7-ylcarbonyl]pyrrolidin-3-yl}oxy)-9-ethyl-8-(2-methylpyrimidin-5-yl)-9H-purine;
1-{[3-{[9-ethyl-8-(2-methylpyrimidin-5-yl)-9H-purin-6-yl]oxy}pyrrolidin-1-yl]carbonyl}azetidin-3-ol;
6-({1-[(3,3-difluoropyrrolidin-1-yl)carbonyl]pyrrolidin-3-yl}oxy)-9-ethyl-8-(2-methylpyrimidin-5-yl)-9H-purine;
9-ethyl-6-({1-[(3-fluoroazetidin-1-yl)carbonyl]pyrrolidin-3-yl}oxy)-8-(2-methylpyrimidin-5-yl)-9H-purine;
(3((9-ethyl-8-(6-(trifluoromethyl)pyridin-3-yl)-9H-purin-6-yl)oxy)pyrrolidin-1-yl)(3-methoxyazetidin-1-yl)methanone;
8-(1-ethyl-5-methyl-1H-pyrazol-4-yl)-9-methyl-6-((1-propylpyrrolidin-3-yl)oxy)-9H-purine;
6-((1-benzyl-4,4-dimethylpyrrolidin-3-yl)oxy)-9-ethyl-8-(2-methylpyrimidin-5-yl)-9H-purine;
9-ethyl-6-{[1-(2-methylphenyl)pyrrolidin-3-yl]oxy}-8-(2-methylpyrimidin-5-yl)-9H-purine;
9-ethyl-8-(2-methylpyrimidin-5-yl)-6-{[1-pyridin-2-ylpyrrolidin-3-yl]oxy}-9H-purine;
9-ethyl-6-{[1-(4-methylpyridin-2-yl)pyrrolidin-3-yl]oxy}-8-(2-methylpyrimidin-5-yl)-9H-purine;
9-ethyl-8-(2-methylpyrimidin-5-yl)-6-{[1-phenylpyrrolidin-3-yl]oxy}-9H-purine;
9-ethyl-6-{[1-(4-fluorophenyl)pyrrolidin-3-yl]oxy}-8-(2-methylpyrimidin-5-yl)-9H-purine;
9-ethyl-6-{[1-(3-fluorophenyl)pyrrolidin-3-yl]oxy}-8-(2-methylpyrimidin-5-yl)-9H-purine;
9-ethyl-8-(2-methylpyrimidin-5-yl)-6-{[1-(1,3-thiazol-2-yl)pyrrolidin-3-yl]oxy}-9H-purine;
9-ethyl-8-(2-methylpyrimidin-5-yl)-6-{[1-pyrimidin-5-ylpyrrolidin-3-yl]oxy}-9H-purine;
9-ethyl-8-(2-methylpyrimidin-5-yl)-6-{[1-pyridin-3-ylpyrrolidin-3-yl]oxy}-9H-purine;
6-{[1-(1,2-benzisoxazol-6-yl)pyrrolidin-3-yl]oxy}-9-ethyl-8-(2-methylpyrimidin-5-yl)-9H-purine;
9-ethyl-8-(2-methylpyrimidin-5-yl)-6-{[1-pyrazin-2-ylpyrrolidin-3-yl]oxy}-9H-purine;
9-ethyl-8-(2-methylpyrimidin-5-yl)-6-{[1-pyridin-2-ylpiperidin-3-yl]oxy}-9H-purine;
tert-butyl (3-{[9-ethyl-8-(2-methylpyrimidin-5-yl)-9H-purin-6-yl]oxy}cyclobutyl)carbamate;
N-(4-{[9-ethyl-8-(2-methylpyrimidin-5-yl)-9H-purin-6-yl]oxy}cyclohexyl)propanamide;
N-(4-{[9-ethyl-8-(2-methylpyrimidin-5-yl)-9H-purin-6-yl]oxy}cyclohexyl) cyclopropanecarboxamide;
N-(3-{[9-ethyl-8-(2-methylpyrimidin-5-yl)-9H-purin-6-yl]oxy}cyclopentyl)tetrahydro-2H-pyran-4-carboxamide;
N-(3-{[9-ethyl-8-(2-methylpyrimidin-5-yl)-9H-purin-6-yl]oxy}cyclobutyl)ethanesulfonamide;
8-(2, 3-dimethylphenoxy)-9-methyl-6-{[1-propanoylpyrrolidin-3-yl]oxy}-9H-purine;
8-(3-fluoro-5-methoxyphenoxy)-9-methyl-6-{[1-propanoylpyrrolidin-3-yl]oxy}-9H-purine;
9-methyl-8-[(2-methylpyrimidin-5-yl)oxy]-6-{[1-propanoylpyrrolidin-3-yl]oxy}-9H-purine;
8-(3-fluoro-4-methoxyphenoxy)-9-methyl-6-{[1-propanoylpyrrolidin-3-yl]oxy}-9H-purine;
Tert-butyl-3-({9-ethyl-8-[methyl(2-methylpropyl)amino]-9H-purin-6-yl}oxy)pyrrolidine-1-carboxylate;
Tert-butyl-3-({9-ethyl-8-[(2-hydroxyethyl)(methyl)amino]-9H-purin-6-yl}oxy)pyrrolidine-1-carboxylate;
Tert-butyl-3-({9-ethyl-8-[3-(methylsulfonyl)pyrrolidin-1-yl]-9H-purin-6-yl}oxy)pyrrolidine-1-carboxylate;
Tert-butyl-3-{[9-ethyl-8-(4-methylpiperidin-1-yl)-9H-purin-6-yl]oxy}pyrrolidine-1-carboxylate;
Tert-butyl-3-{[9-ethyl-8-(4-phenylpiperidin-1-yl)-9H-purin-6-yl]oxy}pyrrolidine-1-carboxylate;
Tert-butyl-3-({9-ethyl-8-[(2-methoxyethyl)(methyl)amino]-9H-purin-6-yl}oxy)pyrrolidine-1-carboxylate;
Tert-butyl-3-({9-ethyl-8-[methyl(1-methylethyl)amino]-9H-purin-6-yl}oxy)pyrrolidine-1-carboxylate;
Tert-butyl-3-{[9-ethyl-8-(3-methylpyrrolidin-1-yl)-9H-purin-6-yl]oxy}pyrrolidine-1-carboxylate;
8-(3,6-dihydro-2H-pyran-4-yl)-9-ethyl-6-{[1-propanoylpyrrolidin-3-yl]oxy}-9H-purine;
8-cyclopropyl-9-methyl-6-{[1-propanoylpyrrolidin-3-yl]oxy}-9H-purine;
9-ethyl-8-(2-methylpropyl)-6-{[1-propanoylpyrrolidin-3-yl]oxy}-9H-purine;
9-methyl-8-(2-methylpropyl)-6-{[1-propanoylpyrrolidin-3-yl]oxy}-9H-purine;
8-(difluoromethyl)-9-ethyl-6-{[1-propanoylpyrrolidin-3-yl]oxy}-9H-purine;
9-ethyl-6-{[1-propanoylpyrrolidin-3-yl]oxy}-8-(trifluoromethyl)-9H-purine;
9-methyl-6-{[1-propanoylpyrrolidin-3-yl]oxy}-8-(trifluoromethyl)-9H-purine;
Tert-butyl-3-({9-ethyl-8-[(2,2,2-trifluoroethyl)carbamoyl]-9H-purin-6-yl}oxy)pyrrolidine-1-carboxylate;
9-ethyl-6-((1-(3-methoxyazetidine-1-carbonyl)pyrrolidin-3-yl)oxy)-N-(2,2,2-trifluoroethyl)-9H-purine-8-carboxamide;
Tert-butyl-3-({8-[(cyclopropylmethyl)carbamoyl]-9-ethyl-9H-purin-6-yl}oxy)pyrrolidine-1-carboxylate;
Tert-butyl-3-{[8-(cyclohexylcarbamoyl)-9-ethyl-9H-purin-6-yl]oxy}pyrrolidine-1-carboxylate; and
Tert-butyl-3-{[9-ethyl-8-(ethylcarbamoyl)-9H-purin-6-yl]oxy}pyrrolidine-1-carboxylate.

3. A compound according to claim 1, wherein K is a bond.

4. A compound according to claim 3, wherein L is O.

5. A compound according to claim 3, wherein L is selected from S and SO$_2$.

6. A compound according to claim 3, wherein L is CH$_2$.

7. A pharmaceutical composition comprising a compound of claim 1 or a pharmaceutically acceptable salt or stereoisomer thereof and a pharmaceutically acceptable carrier.

8. A pharmaceutical composition according to claim 7, further comprising one or more other therapeutic agents.

9. A compound according to claim 1 or a pharmaceutically acceptable salt or thereof, wherein $R^3$ is independently selected from: fluoro, chloro, methyl, ethyl, propyl, methoxy, pyrazolyl, thiazolyl, benzisoxazolyl, pyrazinyl, cyclopropyl, pyridinyl, hydroxy, oxo (=O), dimethylamino, morpholinyl, pyrrolidinyl, tert-butyl, trifluoromethyl, methoxymethyl, isobutylcarboxy, tert-butylcarboxy, phenylcarboxy, hydrogen, methylpropylcarboxy, ethoxycarbonyl, napthalenylcarboxy, benzylcarboxy, isobutylcarboxy, 2,2,-dimethylpropylcarboxy, methylcarboxy, ethylcarboxy, methylethylcarboxy, cyclopentylcarbonyl, cyclobutylcarbonyl, spiro[2.4]heptylcarbonyl, imidazolylcarbonyl, ethylcarbonyl, methylethylcarbonyl, propyloxycarbonyl, phenylcarbonyl, piperidinylcarbonyl, napthalenylcarbonyl, cyclohexylcarbonyl, methylcarbonyl, (tetrahydro-2H-pyran-4-ylmethyl)carbonyl, tetrahydro-2H-pyran-4-ylcarbonyl, oxazolylcarbonyl, pyridinylcarbonyl, cyclopropylcarbonyl, pyrrolidinylmethylcarbonyl, azetidinylcarbonyl, tetrahydropyranylcarbonyl, tetrahydropyranylcarbonylamino, cyclopropylaminocarbonyl, tetrahydrofuranylcarbonyl, isoxazolylcarbonyl, pyrazolo[1,5-a]pyridinylcarbonyl, triazolylcarbonyl, 1,2,3-triazolylcarbonyl, imidazo[1,2-a]pyrimidinylcarbonyl, thiadiazolylcarbonyl, 1,2,3-thiadiazolylcarbonyl, furo[3,2-b]pyrrolylcarbonyl, pyrazolylcarbonyl, pyrrolindinylcarbonyl, hydroxymethyl, fluoromethyl, pyrrolylcarbonyl, imidazo[1,2-b]pyrazolylcarbonyl, pyrrolo[3,2-b]pyridinylcarbonyl, pyrrolo[1,2-d]tetrazolylcarbonyl, oxadiazolylcarbonyl, 1,2,5-oxadiaxolylcarbonyl, 1,3,4-oxadiazolylcarbonyl, 1,2,4-oxadiazolylcarbonyl, pyrrolo[1,2-b]pyrazolylcarbonyl, ethylcarbonyl, ethylsulfonyl, methylsulfonyl, ethylsulfonylamino, methylsulfonylamino, (methylethyl)sulfonyl, phenylsulfonyl, imidazolylsulfonyl, naphthalenylsulfonyl, 5,6,7,8-tetrahydro[1,2,4]triazolo[4,3-a]pyridinylcarbonyl, [1,2,4]triazolo-[1,5-a]pyridinylcarbonyl, acetylamino, azabicyclo[3.1.0]hexylcarbonyl, azabicyclo[2.2.1]heptylcarbonyl, methylethylaminocarbonyl, cyclohexylaminocarbonyl, phenylaminocarbonyl, tetramethylbutylaminocarbonyl, benzylaminocarbonyl, ethylaminocarbonyl, methylcarbonylamino, bicyclo[2.2.1]heptylcarbonyl, phenyl, cyclohexylmethyl, phenylmethyl, 1-phenylethyl, pyrrolylmethyl, pyrimidinyl, thieno[2,3-d]pyrimidinyl, thieno[3,2-c]pyridinyl, difluoromethyl, [1,2,4]triazolo[4.3-a]pyrazinyl, phthalazinyl, pyrazolo[3,4-d]pyrimidinyl, morpholinylcarbonyl, tert-butylaminocarbonyl, tert-butyloxycarbonylamino, 2-methylpropylcarbonyl, (2-methylprop-1-ene)carbonyl, cyclopropylcarbonylamino, cyano, tetrahydro-2H-pyranylcarbonylamino, imidazo[4,5-b]pyridinyl, 1,3-dihydro-2H-imidazo[4,5-b]pyridinyl, amino, and isobutylcarbonyl; wherein $R^3$ is each substituted with 0, 1, 2, 3, or 4 substituents, $R^4$.

* * * * *